US012290231B2

(12) United States Patent
Shelton, IV et al.

(10) Patent No.: US 12,290,231 B2
(45) Date of Patent: May 6, 2025

(54) METHOD OF HUB COMMUNICATION, PROCESSING, STORAGE AND DISPLAY

(71) Applicant: Cilag GmbH International, Zug (CH)

(72) Inventors: Frederick E. Shelton, IV, Hillsboro, OH (US); David C. Yates, Morrow, OH (US); Eitan T. Wiener, Loveland, OH (US); Jeffrey L. Aldridge, Lebanon, OH (US); Jeffrey D. Messerly, Cincinnati, OH (US); Jason L. Harris, Lebanon, OH (US); Tamara Widenhouse, Clarksville, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/442,812

(22) Filed: Feb. 15, 2024

(65) Prior Publication Data
US 2024/0215800 A1 Jul. 4, 2024

Related U.S. Application Data

(63) Continuation of application No. 16/209,385, filed on Dec. 4, 2018, now Pat. No. 11,937,769.

(Continued)

(51) Int. Cl.
*A61B 1/06* (2006.01)
*A61B 1/00* (2006.01)
(Continued)

(52) U.S. Cl.
CPC .. *A61B 1/000094* (2022.02); *A61B 1/000096* (2022.02); *A61B 1/00045* (2013.01);
(Continued)

(58) Field of Classification Search
CPC ..... A61B 17/1155; A61B 34/20; A61B 34/32; A61B 34/71; A61B 90/35; A61B 90/361; A61B 1/00009; A61B 1/00045; A61B 1/051; A61B 1/0661; A61B 5/0066; A61B 5/0075; A61B 5/0261; A61B 6/5247; A61B 17/0682; A61B 17/072; A61B 17/1114; A61B 17/1285; A61B 17/320092; A61B 18/1442; A61B 18/1445;
(Continued)

(56) References Cited

U.S. PATENT DOCUMENTS 5,503,320 A 4/1996 Webster et al.
7,097,640 B2 8/2006 Wang et al.
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Julian W Woo

(57) ABSTRACT

A method including detecting a modular surgical device within bounds of a surgical operating room; connecting the modular surgical device to a surgical hub; connecting the surgical hub to a cloud-based system; transmitting surgical data associated with a surgical procedure being performed in the surgical operating room from the modular surgical device to the surgical hub; and transmitting the surgical data from the surgical hub to the cloud-based system.

20 Claims, 154 Drawing Sheets

Related U.S. Application Data

(60) Provisional application No. 62/773,778, filed on Nov. 30, 2018, provisional application No. 62/773,742, filed on Nov. 30, 2018, provisional application No. 62/773,728, filed on Nov. 30, 2018, provisional application No. 62/773,741, filed on Nov. 30, 2018, provisional application No. 62/750,539, filed on Oct. 25, 2018, provisional application No. 62/750,555, filed on Oct. 25, 2018, provisional application No. 62/750,529, filed on Oct. 25, 2018, provisional application No. 62/729,185, filed on Sep. 10, 2018, provisional application No. 62/729,177, filed on Sep. 10, 2018, provisional application No. 62/729,183, filed on Sep. 10, 2018, provisional application No. 62/729,191, filed on Sep. 10, 2018, provisional application No. 62/729,184, filed on Sep. 10, 2018, provisional application No. 62/729,195, filed on Sep. 10, 2018, provisional application No. 62/729,186, filed on Sep. 10, 2018, provisional application No. 62/729,182, filed on Sep. 10, 2018, provisional application No. 62/729,176, filed on Sep. 10, 2018, provisional application No. 62/721,994, filed on Aug. 23, 2018, provisional application No. 62/721,995, filed on Aug. 23, 2018, provisional application No. 62/721,999, filed on Aug. 23, 2018, provisional application No. 62/721,998, filed on Aug. 23, 2018, provisional application No. 62/721,996, filed on Aug. 23, 2018, provisional application No. 62/692,747, filed on Jun. 30, 2018, provisional application No. 62/692,748, filed on Jun. 30, 2018, provisional application No. 62/692,768, filed on Jun. 30, 2018, provisional application No. 62/691,262, filed on Jun. 28, 2018, provisional application No. 62/691,227, filed on Jun. 28, 2018, provisional application No. 62/691,230, filed on Jun. 28, 2018, provisional application No. 62/691,219, filed on Jun. 28, 2018, provisional application No. 62/691,257, filed on Jun. 28, 2018, provisional application No. 62/691,251, filed on Jun. 28, 2018, provisional application No. 62/691,228, filed on Jun. 28, 2018, provisional application No. 62/665,192, filed on May 1, 2018, provisional application No. 62/665,177, filed on May 1, 2018, provisional application No. 62/665,128, filed on May 1, 2018, provisional application No. 62/665,129, filed on May 1, 2018, provisional application No. 62/665,139, filed on May 1, 2018, provisional application No. 62/665,134, filed on May 1, 2018, provisional application No. 62/659,900, filed on Apr. 19, 2018, provisional application No. 62/650,887, filed on Mar. 30, 2018, provisional application No. 62/650,877, filed on Mar. 30, 2018, provisional application No. 62/650,898, filed on Mar. 30, 2018, provisional application No. 62/650,882, filed on Mar. 30, 2018, provisional application No. 62/649,327, filed on Mar. 28, 2018, provisional application No. 62/649,333, filed on Mar. 28, 2018, provisional application No. 62/649,296, filed on Mar. 28, 2018, provisional application No. 62/649,291, filed on Mar. 28, 2018, provisional application No. 62/649,309, filed on Mar. 28, 2018, provisional application No. 62/649,294, filed on Mar. 28, 2018, provisional application No. 62/649,307, filed on Mar. 28, 2018, provisional application No. 62/649,300, filed on Mar. 28, 2018, provisional application No. 62/648,315, filed on Mar. 28, 2018, provisional application No. 62/649,320, filed on Mar. 28, 2018, provisional application No. 62/649,302, filed on Mar. 28, 2018, provisional application No. 62/649,310, filed on Mar. 28, 2018, provisional application No. 62/649,313, filed on Mar. 28, 2018, provisional application No. 62/649,323, filed on Mar. 28, 2018, provisional application No. 62/611,339, filed on Dec. 28, 2017, provisional application No. 62/611,340, filed on Dec. 28, 2017, provisional application No. 62/611,341, filed on Dec. 28, 2017.

(51) Int. Cl.

| | | |
|---|---|---|
| *A61B 1/05* | (2006.01) | |
| *A61B 5/00* | (2006.01) | |
| *A61B 5/026* | (2006.01) | |
| *A61B 6/00* | (2024.01) | |
| *A61B 17/00* | (2006.01) | |
| *A61B 17/068* | (2006.01) | |
| *A61B 17/072* | (2006.01) | |
| *A61B 17/11* | (2006.01) | |
| *A61B 17/115* | (2006.01) | |
| *A61B 17/128* | (2006.01) | |
| *A61B 17/32* | (2006.01) | |
| *A61B 18/00* | (2006.01) | |
| *A61B 18/14* | (2006.01) | |
| *A61B 34/00* | (2016.01) | |
| *A61B 34/10* | (2016.01) | |
| *A61B 34/20* | (2016.01) | |
| *A61B 34/32* | (2016.01) | |
| *A61B 90/00* | (2016.01) | |
| *A61B 90/30* | (2016.01) | |
| *A61B 90/35* | (2016.01) | |
| *A61M 1/00* | (2006.01) | |
| *A61M 13/00* | (2006.01) | |
| *B25J 9/16* | (2006.01) | |
| *B25J 13/00* | (2006.01) | |
| *G06K 7/10* | (2006.01) | |
| *G06K 19/077* | (2006.01) | |
| *G16H 10/60* | (2018.01) | |
| *G16H 40/63* | (2018.01) | |
| *G16H 40/67* | (2018.01) | |
| *G16H 50/20* | (2018.01) | |
| *G16H 70/20* | (2018.01) | |
| *H01Q 1/22* | (2006.01) | |
| *H04L 9/40* | (2022.01) | |
| *H04L 67/10* | (2022.01) | |
| *H04L 67/12* | (2022.01) | |
| *H04N 5/272* | (2006.01) | |
| *H04N 7/18* | (2006.01) | |
| *H05K 1/02* | (2006.01) | |
| *H05K 1/18* | (2006.01) | |
| *A61B 34/30* | (2016.01) | |

(52) U.S. Cl.
CPC ............ *A61B 1/051* (2013.01); *A61B 1/0661* (2013.01); *A61B 5/0066* (2013.01); *A61B 5/0075* (2013.01); *A61B 5/0261* (2013.01); *A61B 6/5247* (2013.01); *A61B 17/0682* (2013.01); *A61B 17/072* (2013.01); *A61B 17/1114* (2013.01); *A61B 17/1155* (2013.01); *A61B 17/1285* (2013.01); *A61B 17/320092* (2013.01); *A61B 18/1442* (2013.01); *A61B 18/1445* (2013.01); *A61B 34/10* (2016.02); *A61B 34/20* (2016.02); *A61B 34/32* (2016.02); *A61B 34/71* (2016.02); *A61B 90/35* (2016.02); *A61B 90/361* (2016.02); *A61M 1/73*

(2021.05); *A61M 1/79* (2021.05); *B25J 9/1697* (2013.01); *B25J 13/006* (2013.01); *G06K 7/10316* (2013.01); *G06K 19/07749* (2013.01); *G16H 10/60* (2018.01); *G16H 40/63* (2018.01); *G16H 40/67* (2018.01); *G16H 50/20* (2018.01); *G16H 70/20* (2018.01); *H01Q 1/22* (2013.01); *H04L 63/1416* (2013.01); *H04L 67/10* (2013.01); *H04L 67/12* (2013.01); *H04N 5/272* (2013.01); *H04N 7/183* (2013.01); *H05K 1/028* (2013.01); *H05K 1/189* (2013.01); *A61B 2017/00022* (2013.01); *A61B 2017/00026* (2013.01); *A61B 2017/0003* (2013.01); *A61B 2017/00039* (2013.01); *A61B 2017/00044* (2013.01); *A61B 2017/00057* (2013.01); *A61B 2017/00061* (2013.01); *A61B 2017/00075* (2013.01); *A61B 2017/00084* (2013.01); *A61B 2017/00097* (2013.01); *A61B 2017/00106* (2013.01); *A61B 2017/0011* (2013.01); *A61B 2017/00115* (2013.01); *A61B 2017/00119* (2013.01); *A61B 2017/00199* (2013.01); *A61B 2017/00203* (2013.01); *A61B 2017/00221* (2013.01); *A61B 2017/00398* (2013.01); *A61B 2017/00402* (2013.01); *A61B 2017/00734* (2013.01); *A61B 2017/00809* (2013.01); *A61B 2017/00818* (2013.01); *A61B 2017/07257* (2013.01); *A61B 2017/07271* (2013.01); *A61B 2017/07278* (2013.01); *A61B 2017/07285* (2013.01); *A61B 2017/1132* (2013.01); *A61B 2017/32007* (2017.08); *A61B 2017/320074* (2017.08); *A61B 2017/320084* (2013.01); *A61B 2017/320095* (2017.08); *A61B 2017/320097* (2017.08); *A61B 2018/00541* (2013.01); *A61B 2018/00589* (2013.01); *A61B 2018/00595* (2013.01); *A61B 2018/00601* (2013.01); *A61B 2018/00607* (2013.01); *A61B 2018/0063* (2013.01); *A61B 2018/00642* (2013.01); *A61B 2018/00684* (2013.01); *A61B 2018/00791* (2013.01); *A61B 2018/00827* (2013.01); *A61B 2018/00875* (2013.01); *A61B 2018/00892* (2013.01); *A61B 2018/00988* (2013.01); *A61B 2018/00994* (2013.01); *A61B 2034/2055* (2016.02); *A61B 2034/2057* (2016.02); *A61B 34/30* (2016.02); *A61B 2034/301* (2016.02); *A61B 2034/305* (2016.02); *A61B 2090/309* (2016.02); *A61B 2217/005* (2013.01); *A61B 2217/007* (2013.01); *A61B 2218/002* (2013.01); *A61B 2218/007* (2013.01); *A61B 2218/008* (2013.01); *A61M 1/80* (2021.05); *A61M 13/003* (2013.01); *A61M 2205/3306* (2013.01); *A61M 2205/3327* (2013.01); *A61M 2205/3331* (2013.01); *A61M 2205/3365* (2013.01); *A61M 2205/3368* (2013.01); *G05B 2219/40174* (2013.01); *G05B 2219/45119* (2013.01)

(58) Field of Classification Search
CPC .... A61B 2034/2055; A61B 2034/2057; A61B 34/30; A61B 2034/301; A61B 2034/305; A61B 2090/309; A61B 2017/32007; A61B 2017/320074; A61B 2017/320095; A61B 2017/320097; A61B 2017/00022; A61B 2017/00026; A61B 2017/0003; A61B 2017/00039; A61B 2017/00044; A61B 2017/00057; A61B 2017/00061; A61B 2017/00075; A61B 2017/00084; A61B 2017/00097; A61B 2017/00106; A61B 2017/0011; A61B 2017/00115; A61B 2017/00119; A61B 2017/00199; A61B 2017/00203; A61B 2017/00221; A61B 2017/00398; A61B 2017/00402; A61B 2017/00734; A61B 2017/00809; A61B 2017/00818; A61B 2017/07257; A61B 2017/07271; A61B 2017/07278; A61B 2017/07285; A61B 2017/1132; A61B 2017/320084; A61B 2018/00541; A61B 2018/00589; A61B 2018/00595; A61B 2018/00601; A61B 2018/00607; A61B 2018/0063; A61B 2018/00642; A61B 2018/00684; A61B 2018/00791; A61B 2018/00827; A61B 2018/00875; A61B 2018/00892; A61B 2018/00988; A61B 2018/00994; A61B 2217/005; A61B 2217/007; A61B 2218/002; A61B 2218/007; A61B 2218/008; A61B 2034/2059; A61B 2034/2048; A61B 2034/254; A61B 2034/258; A61B 2034/256; A61B 2090/502; A61B 2090/372; A61B 6/464; A61B 6/486; A61B 6/547; A61B 34/37; A61B 2090/376; A61B 2090/365; A61B 90/98; A61B 90/96; A61B 18/1206; A61B 2090/061; A61B 2018/1253; A61B 2018/126; A61B 1/00006; A61B 2090/064; A61B 2090/066; A61B 2017/00973; A61B 2017/00207; A61B 2017/00128; A61B 2017/0046; A61B 2017/00473; A61B 2090/0811; A61B 2090/0804; A61B 2017/07235; A61B 2090/0809; A61B 2017/07228; A61B 90/90; A61B 17/07207; A61B 2017/00017; A61B 34/25; A61B 17/0206; A61B 2034/105; A61B 2017/00225; A61M 1/0025; A61M 1/0056; A61M 1/0066; A61M 13/003; A61M 2205/3306; A61M 2205/3327; A61M 2205/3331; A61M 2205/3365; A61M 2205/3368; G16H 40/67; G16H 10/60; G16H 50/20; G16H 40/63; G16H 70/20; G16H 20/40; G16H 40/20; B25J 9/1697; B25J 13/006; G06K 7/10316; G06K 19/07749; H01Q 1/22; H04L 63/1416; H04L 67/10; H04L 67/12; H04L 63/0442; H04L 2463/121; H04L 63/123; H04L 63/0428; H04N 5/272; H04N 7/183; H05K 1/028; H05K 1/189; G05B 2219/40174; G05B 2219/45119

See application file for complete search history.

(56) References Cited

U.S. PATENT DOCUMENTS

| | | |
|---|---|---|
| 7,317,955 B2 | 1/2008 | McGreevy |
| 7,982,776 B2 | 7/2011 | Dunki-Jacobs et al. |
| 7,995,045 B2 | 8/2011 | Dunki-Jacobs |
| 8,262,560 B2 | 9/2012 | Whitman |
| 8,960,520 B2 | 2/2015 | McCuen |
| 9,011,427 B2 | 4/2015 | Price et al. |
| 9,060,775 B2 | 6/2015 | Wiener et al. |
| 9,123,155 B2 | 9/2015 | Cunningham et al. |
| 9,345,481 B2 | 5/2016 | Hall et al. |
| 9,566,708 B2 | 2/2017 | Kurnianto |
| 9,993,305 B2 | 6/2018 | Andersson |

(56) References Cited

U.S. PATENT DOCUMENTS

| | | |
|---|---|---|
| 10,095,942 B2 | 10/2018 | Mentese et al. |
| 10,098,527 B2 | 10/2018 | Weisenburgh, II et al. |
| 10,595,887 B2 | 3/2020 | Shelton, IV et al. |
| 10,624,691 B2 | 4/2020 | Wiener et al. |
| 10,695,081 B2 | 6/2020 | Shelton, IV et al. |
| 10,743,872 B2 | 8/2020 | Leimbach et al. |
| 10,755,813 B2 | 8/2020 | Shelton, IV et al. |
| 10,758,310 B2 | 9/2020 | Shelton, IV et al. |
| 10,772,651 B2 | 9/2020 | Shelton, IV et al. |
| 10,849,697 B2 | 12/2020 | Yates et al. |
| 10,881,399 B2 | 1/2021 | Shelton, IV et al. |
| 10,892,899 B2 | 1/2021 | Shelton, IV et al. |
| 10,892,995 B2 | 1/2021 | Shelton, IV et al. |
| 10,898,622 B2 | 1/2021 | Shelton, IV et al. |
| 10,932,772 B2 | 3/2021 | Shelton, IV et al. |
| 10,932,806 B2 | 3/2021 | Shelton, IV et al. |
| 10,932,872 B2 | 3/2021 | Shelton, IV et al. |
| 10,943,454 B2 | 3/2021 | Shelton, IV et al. |
| 10,944,728 B2 | 3/2021 | Wiener et al. |
| 10,959,744 B2 | 3/2021 | Shelton, IV et al. |
| 10,966,791 B2 | 4/2021 | Harris et al. |
| 10,980,560 B2 | 4/2021 | Shelton, IV et al. |
| 10,987,178 B2 | 4/2021 | Shelton, IV et al. |
| 11,013,563 B2 | 5/2021 | Shelton, IV et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,045,197 B2 | 6/2021 | Shelton, IV et al. |
| 11,045,591 B2 | 6/2021 | Shelton, IV et al. |
| 11,051,836 B2 | 7/2021 | Shelton, IV et al. |
| 11,051,876 B2 | 7/2021 | Shelton, IV et al. |
| 11,056,244 B2 | 7/2021 | Shelton, IV et al. |
| 11,058,498 B2 | 7/2021 | Shelton, IV et al. |
| 11,069,012 B2 | 7/2021 | Shelton, IV et al. |
| 11,071,560 B2 | 7/2021 | Deck et al. |
| 11,076,921 B2 | 8/2021 | Shelton, IV et al. |
| 11,096,693 B2 | 8/2021 | Shelton, IV et al. |
| 11,100,631 B2 | 8/2021 | Yates et al. |
| 11,103,268 B2 | 8/2021 | Shelton, IV et al. |
| 11,109,866 B2 | 9/2021 | Shelton, IV et al. |
| 11,109,878 B2 | 9/2021 | Shelton, IV et al. |
| 11,114,195 B2 | 9/2021 | Shelton, IV et al. |
| 11,123,070 B2 | 9/2021 | Shelton, IV et al. |
| 11,129,636 B2 | 9/2021 | Shelton, IV et al. |
| 11,132,462 B2 | 9/2021 | Shelton, IV et al. |
| 11,141,160 B2 | 10/2021 | Shelton, IV et al. |
| 11,147,607 B2 | 10/2021 | Yates et al. |
| 11,160,605 B2 | 11/2021 | Shelton, IV et al. |
| 11,166,772 B2 | 11/2021 | Shelton, IV et al. |
| 11,166,775 B2 * | 11/2021 | Gilhooley .............. A61B 34/32 |
| 11,179,175 B2 | 11/2021 | Houser et al. |
| 11,179,208 B2 | 11/2021 | Yates et al. |
| 11,202,570 B2 | 12/2021 | Shelton, IV et al. |
| 11,207,090 B2 | 12/2021 | Shelton, IV et al. |
| 11,213,359 B2 | 1/2022 | Shelton, IV et al. |
| 11,229,436 B2 | 1/2022 | Shelton, IV et al. |
| 11,234,756 B2 | 2/2022 | Shelton, IV et al. |
| 11,253,315 B2 | 2/2022 | Yates et al. |
| 11,257,589 B2 | 2/2022 | Shelton, IV et al. |
| 11,266,468 B2 | 3/2022 | Shelton, IV et al. |
| 11,273,001 B2 | 3/2022 | Shelton, IV et al. |
| 11,278,281 B2 | 3/2022 | Shelton, IV et al. |
| 11,284,936 B2 | 3/2022 | Shelton, IV et al. |
| 11,291,465 B2 | 4/2022 | Parihar et al. |
| 11,291,495 B2 | 4/2022 | Yates et al. |
| 11,291,510 B2 | 4/2022 | Shelton, IV et al. |
| 11,298,128 B2 | 4/2022 | Messerly et al. |
| 11,304,699 B2 | 4/2022 | Shelton, IV et al. |
| 11,304,720 B2 | 4/2022 | Kimball et al. |
| 11,304,745 B2 | 4/2022 | Shelton, IV et al. |
| 11,304,763 B2 | 4/2022 | Shelton, IV et al. |
| 11,308,075 B2 | 4/2022 | Shelton, IV et al. |
| 11,311,306 B2 | 4/2022 | Shelton, IV et al. |
| 11,311,342 B2 | 4/2022 | Parihar et al. |
| 11,317,919 B2 | 5/2022 | Shelton, IV et al. |
| 11,317,937 B2 | 5/2022 | Nott et al. |
| 11,364,075 B2 | 6/2022 | Yates et al. |
| 11,376,002 B2 | 7/2022 | Shelton, IV et al. |
| 11,389,164 B2 | 7/2022 | Yates et al. |
| 11,406,390 B2 | 8/2022 | Shelton, IV et al. |
| 11,410,259 B2 | 8/2022 | Harris et al. |
| 11,413,042 B2 | 8/2022 | Shelton, IV et al. |
| 11,419,630 B2 | 8/2022 | Yates et al. |
| 11,419,667 B2 | 8/2022 | Messerly et al. |
| 11,423,007 B2 | 8/2022 | Shelton, IV et al. |
| 11,432,885 B2 | 9/2022 | Shelton, IV et al. |
| 11,446,052 B2 | 9/2022 | Shelton, IV et al. |
| 11,464,535 B2 | 10/2022 | Shelton, IV et al. |
| 11,464,559 B2 | 10/2022 | Nott et al. |
| 11,504,192 B2 | 11/2022 | Shelton, IV et al. |
| 11,510,741 B2 | 11/2022 | Shelton, IV et al. |
| 11,529,187 B2 | 12/2022 | Shelton, IV et al. |
| 11,540,855 B2 | 1/2023 | Messerly et al. |
| 11,559,307 B2 | 1/2023 | Shelton, IV et al. |
| 11,559,308 B2 | 1/2023 | Yates et al. |
| 11,564,703 B2 | 1/2023 | Shelton, IV et al. |
| 11,564,756 B2 | 1/2023 | Shelton, IV et al. |
| 11,571,234 B2 | 2/2023 | Nott et al. |
| 11,576,677 B2 | 2/2023 | Shelton, IV et al. |
| 11,589,888 B2 | 2/2023 | Shelton, IV et al. |
| 11,602,366 B2 | 3/2023 | Shelton, IV et al. |
| 11,602,393 B2 | 3/2023 | Shelton, IV et al. |
| 11,607,239 B2 | 3/2023 | Swensgard et al. |
| 11,612,408 B2 | 3/2023 | Yates et al. |
| 11,612,444 B2 | 3/2023 | Shelton, IV et al. |
| 11,633,237 B2 | 4/2023 | Shelton, IV et al. |
| 11,648,022 B2 | 5/2023 | Shelton, IV |
| 11,659,023 B2 | 5/2023 | Shelton, IV et al. |
| 11,666,331 B2 | 6/2023 | Shelton, IV et al. |
| 11,672,605 B2 | 6/2023 | Messerly et al. |
| 11,678,881 B2 | 6/2023 | Yates et al. |
| 11,696,760 B2 | 7/2023 | Shelton, IV et al. |
| 11,696,778 B2 | 7/2023 | Shelton, IV et al. |
| 11,759,224 B2 | 9/2023 | Shelton, IV et al. |
| 11,771,487 B2 | 10/2023 | Shelton, IV et al. |
| 11,786,245 B2 | 10/2023 | Shelton, IV |
| 11,793,537 B2 | 10/2023 | Shelton, IV et al. |
| 11,801,098 B2 | 10/2023 | Stokes et al. |
| 11,819,231 B2 | 11/2023 | Shelton, IV et al. |
| 11,832,899 B2 | 12/2023 | Shelton, IV et al. |
| 11,844,579 B2 | 12/2023 | Shelton, IV et al. |
| 11,857,152 B2 | 1/2024 | Shelton, IV et al. |
| 11,864,728 B2 | 1/2024 | Shelton, IV et al. |
| 11,871,901 B2 | 1/2024 | Shelton, IV et al. |
| 11,896,322 B2 | 2/2024 | Yates et al. |
| 11,896,443 B2 | 2/2024 | Shelton, IV et al. |
| 2008/0058593 A1 | 3/2008 | Gu et al. |
| 2009/0046146 A1 | 2/2009 | Hoyt |
| 2011/0306840 A1 | 12/2011 | Allen et al. |
| 2014/0263552 A1 | 9/2014 | Hall et al. |
| 2015/0317899 A1 | 11/2015 | Dumbauld et al. |
| 2019/0125320 A1 | 5/2019 | Shelton, IV et al. |
| 2019/0125336 A1 | 5/2019 | Deck et al. |
| 2019/0125361 A1 | 5/2019 | Shelton, IV et al. |
| 2019/0125432 A1 | 5/2019 | Shelton, IV et al. |
| 2019/0125476 A1 | 5/2019 | Shelton, IV et al. |
| 2019/0200844 A1 | 7/2019 | Shelton, IV et al. |
| 2019/0200906 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200987 A1 | 7/2019 | Shelton, IV et al. |
| 2019/0200997 A1 | 7/2019 | Shelton, IV et al. |
| 2019/0201021 A1 | 7/2019 | Shelton, IV et al. |
| 2019/0201034 A1 | 7/2019 | Shelton, IV et al. |
| 2019/0201039 A1 | 7/2019 | Widenhouse et al. |
| 2019/0201042 A1 | 7/2019 | Nott et al. |
| 2019/0201045 A1 | 7/2019 | Yates et al. |
| 2019/0201087 A1 | 7/2019 | Shelton, IV et al. |
| 2019/0201090 A1 | 7/2019 | Shelton, IV et al. |
| 2019/0201102 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |

(56) References Cited

U.S. PATENT DOCUMENTS

| | | |
|---|---|---|
| 2019/0201118 A1 | 7/2019 | Shelton, IV et al. |
| 2019/0201130 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201146 A1 | 7/2019 | Shelton, IV et al. |
| 2019/0201594 A1 | 7/2019 | Shelton, IV et al. |
| 2019/0205567 A1 | 7/2019 | Shelton, IV et al. |
| 2019/0206555 A1 | 7/2019 | Morgan et al. |
| 2019/0206561 A1 | 7/2019 | Shelton, IV et al. |
| 2019/0206564 A1 | 7/2019 | Shelton, IV et al. |
| 2019/0206569 A1 | 7/2019 | Shelton, IV et al. |

OTHER PUBLICATIONS

IEEE Std 802.3-2012 (Revision of IEEE Std 802.3-2008, published Dec. 28, 2012.

\* cited by examiner

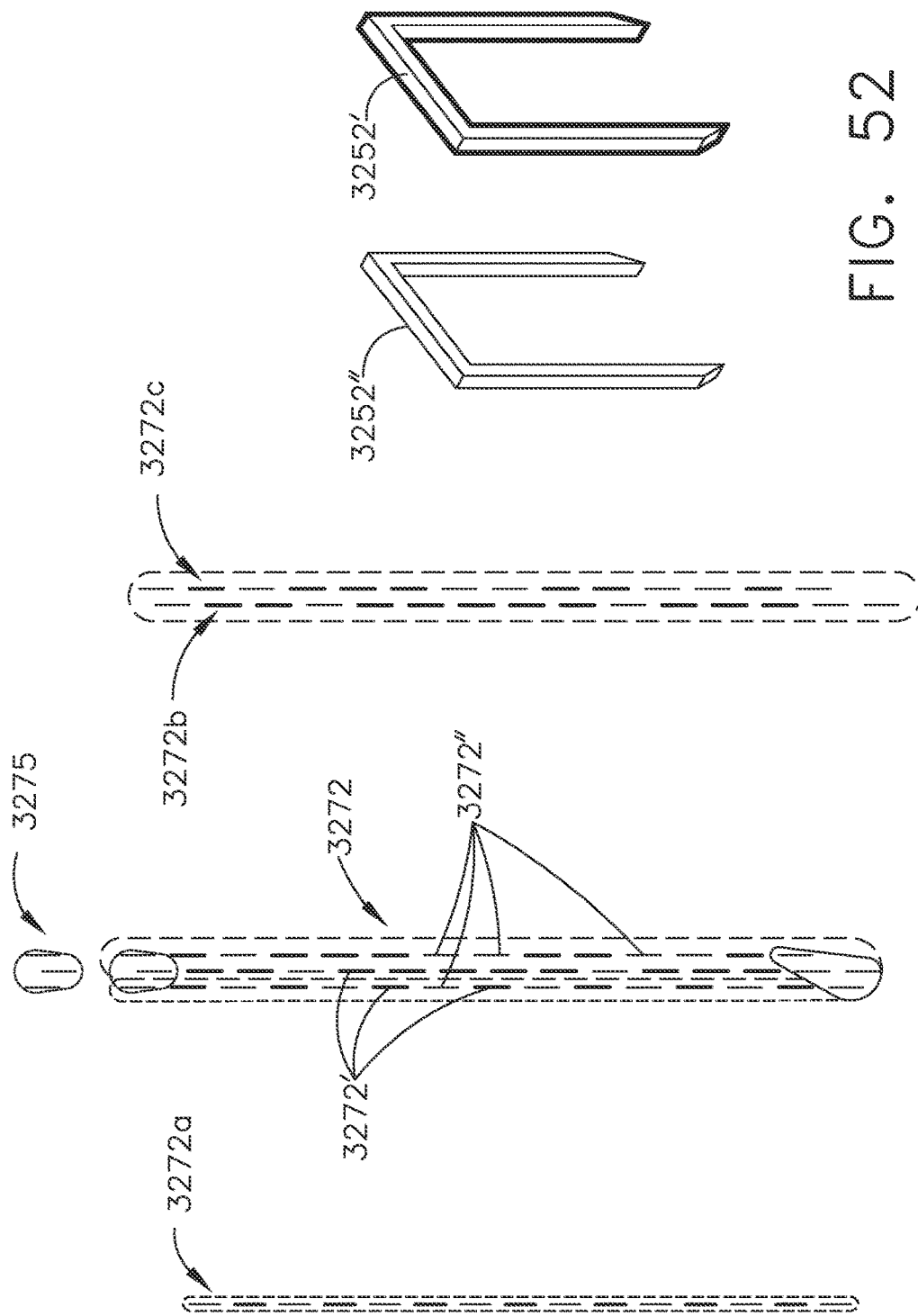

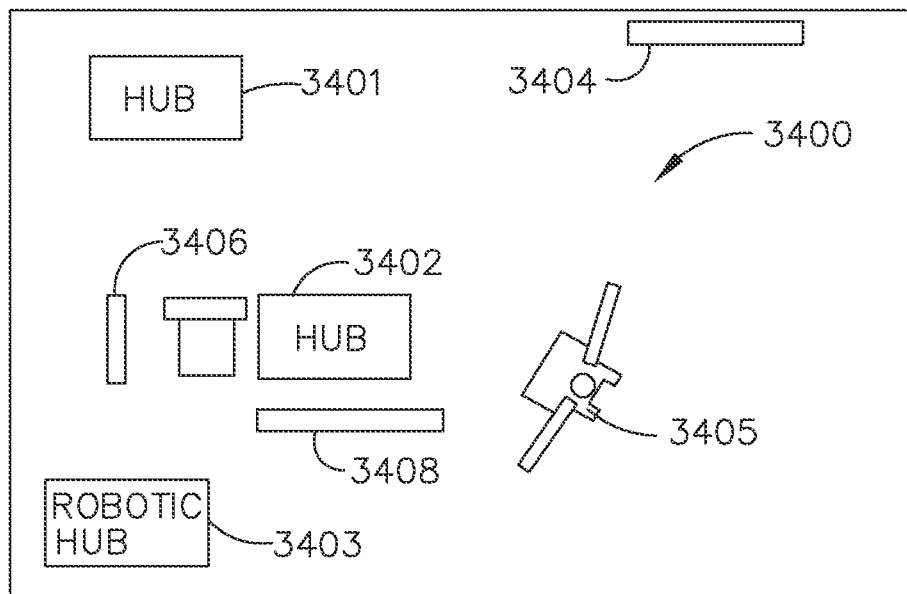
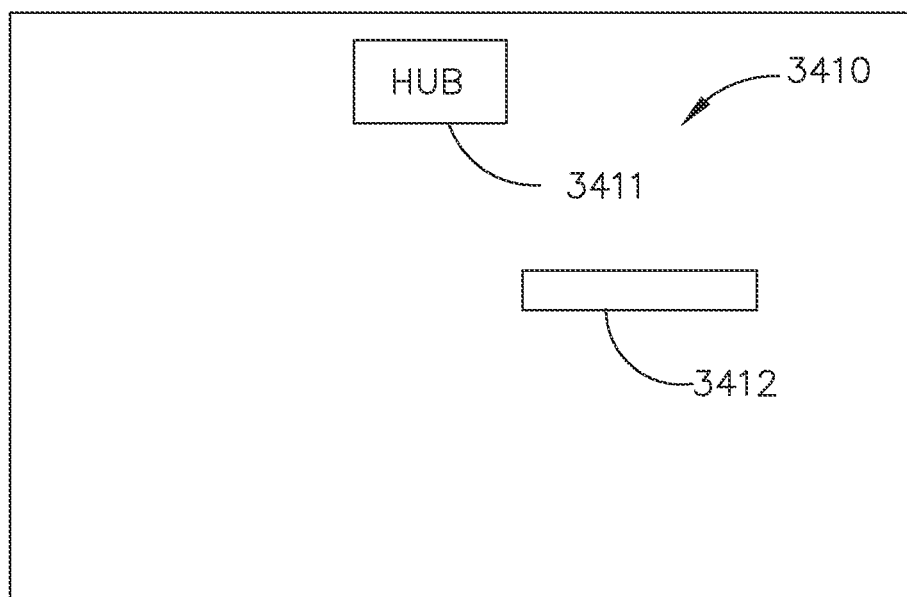
FIG. 56

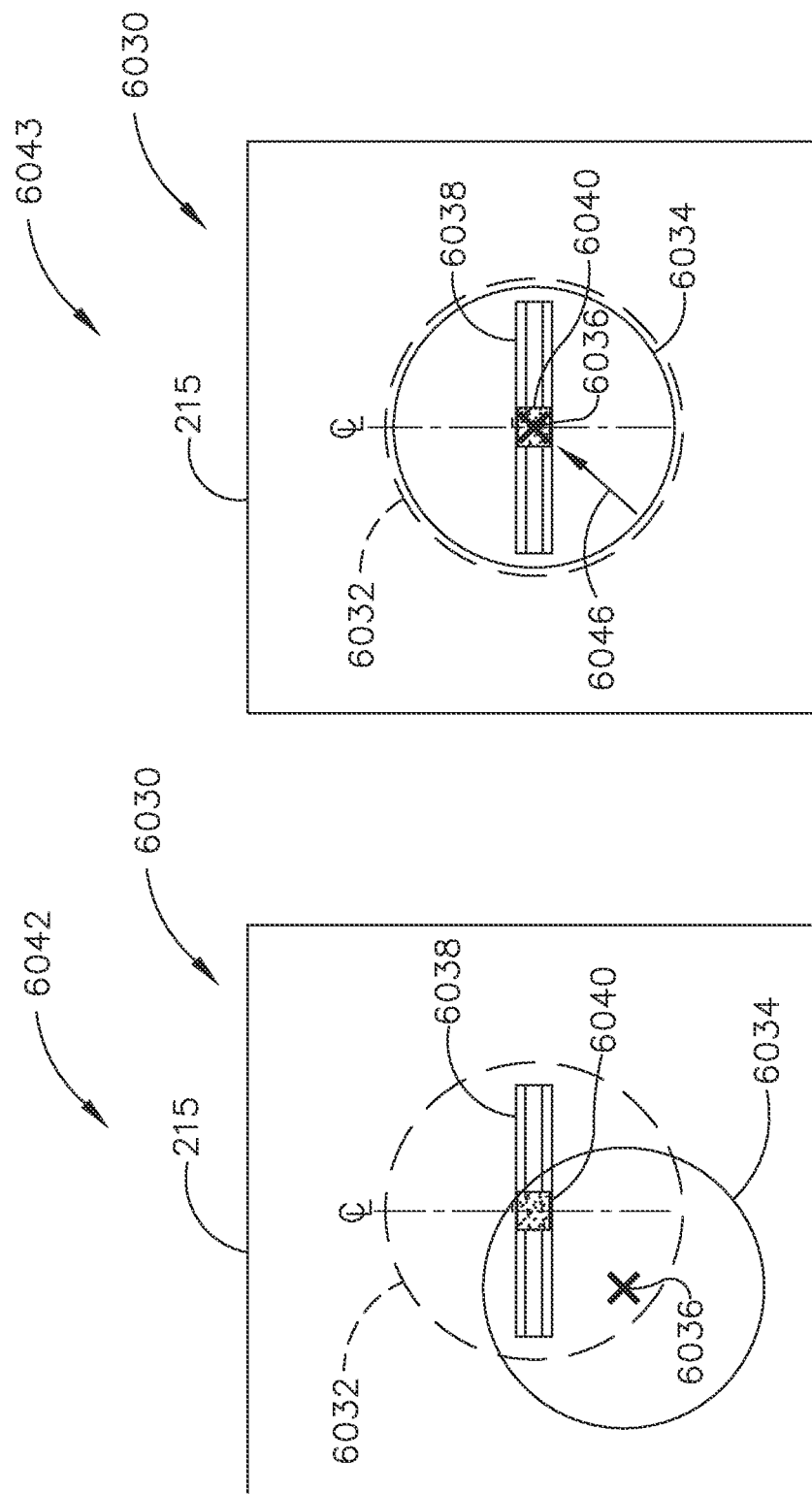

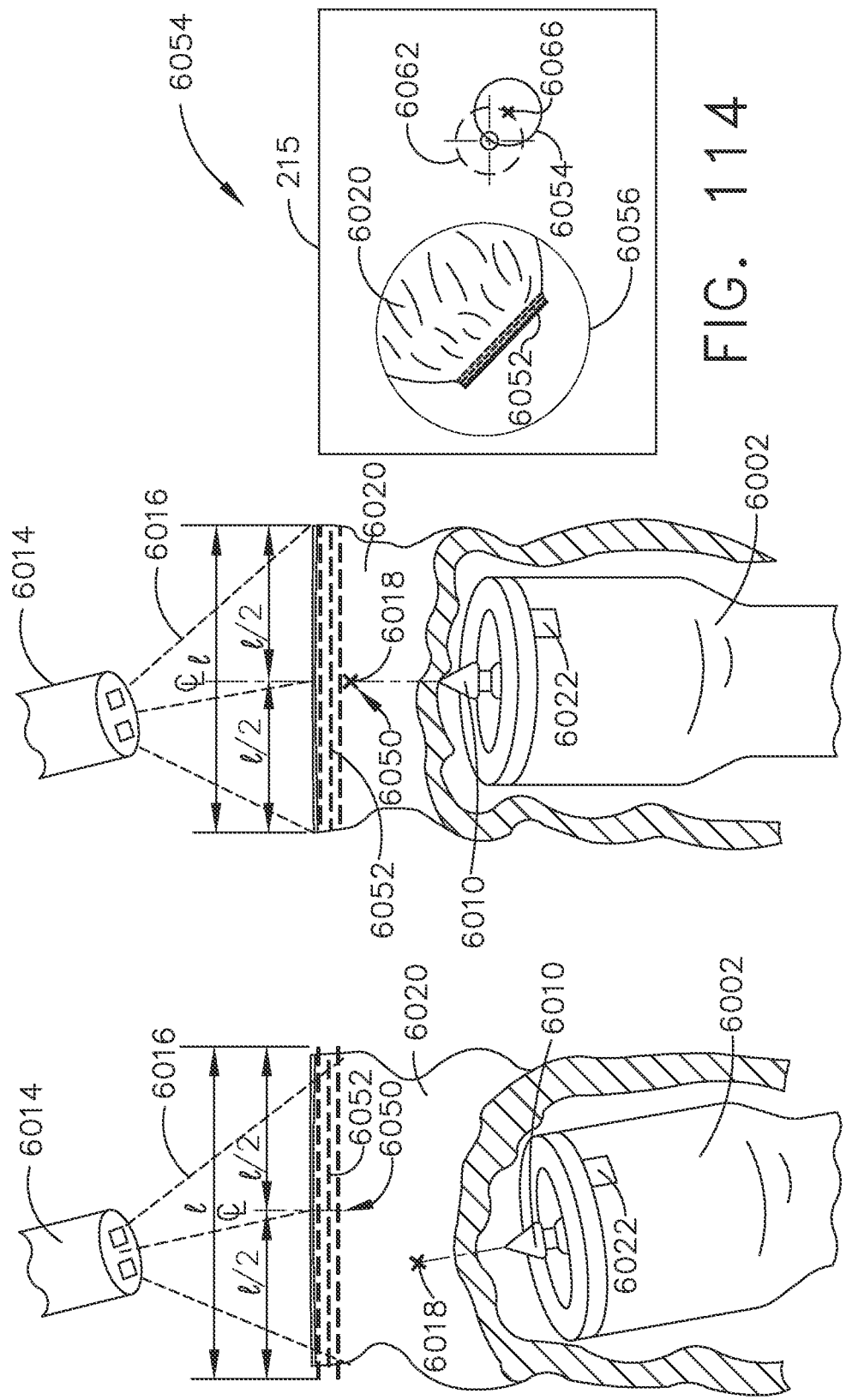

THRESHOLD TO 100%
COMPLETE CREEP
STABILITY METER

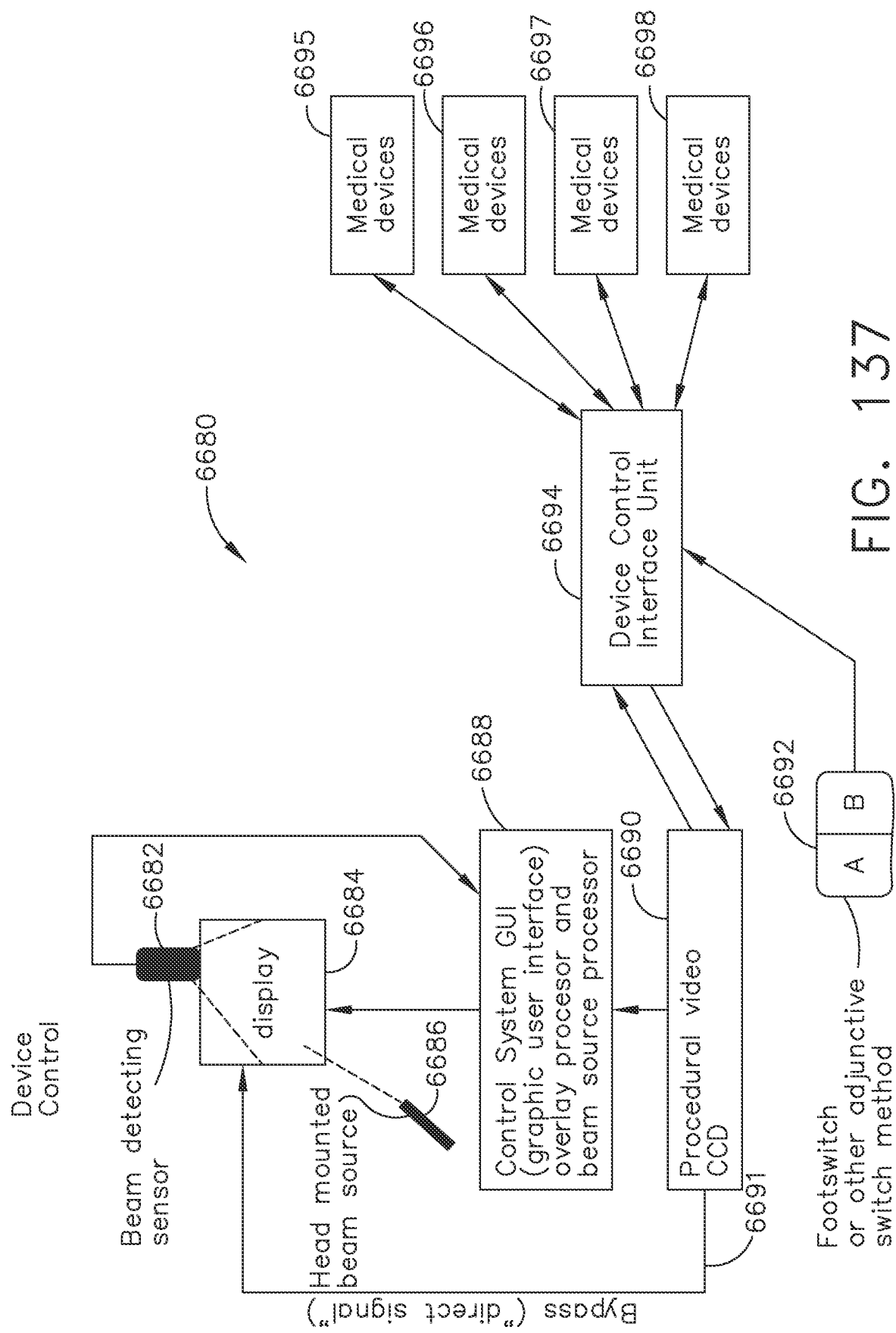

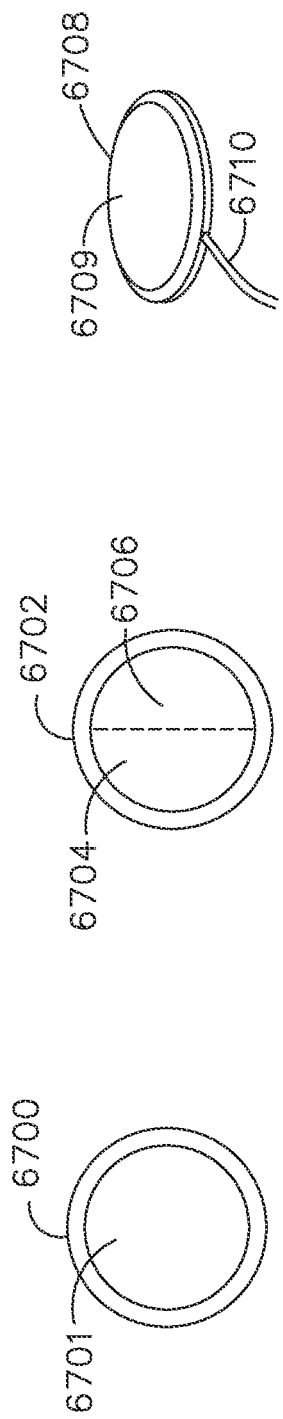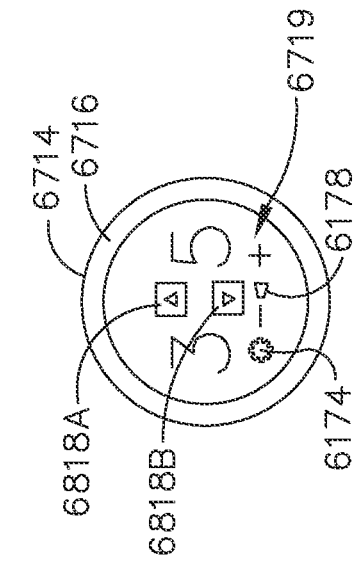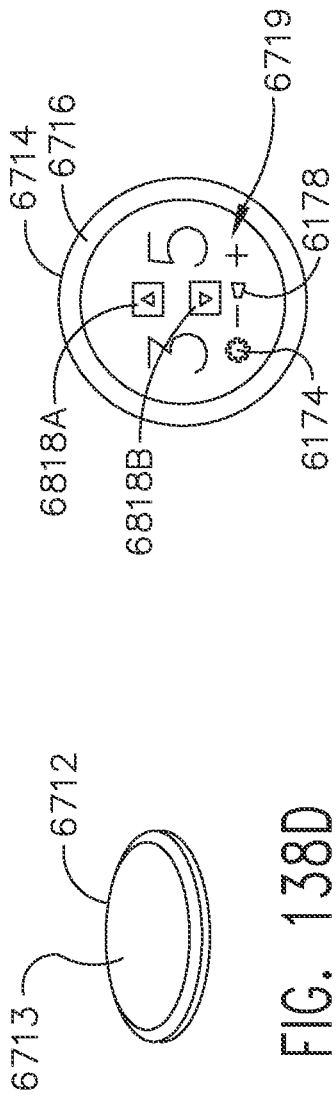

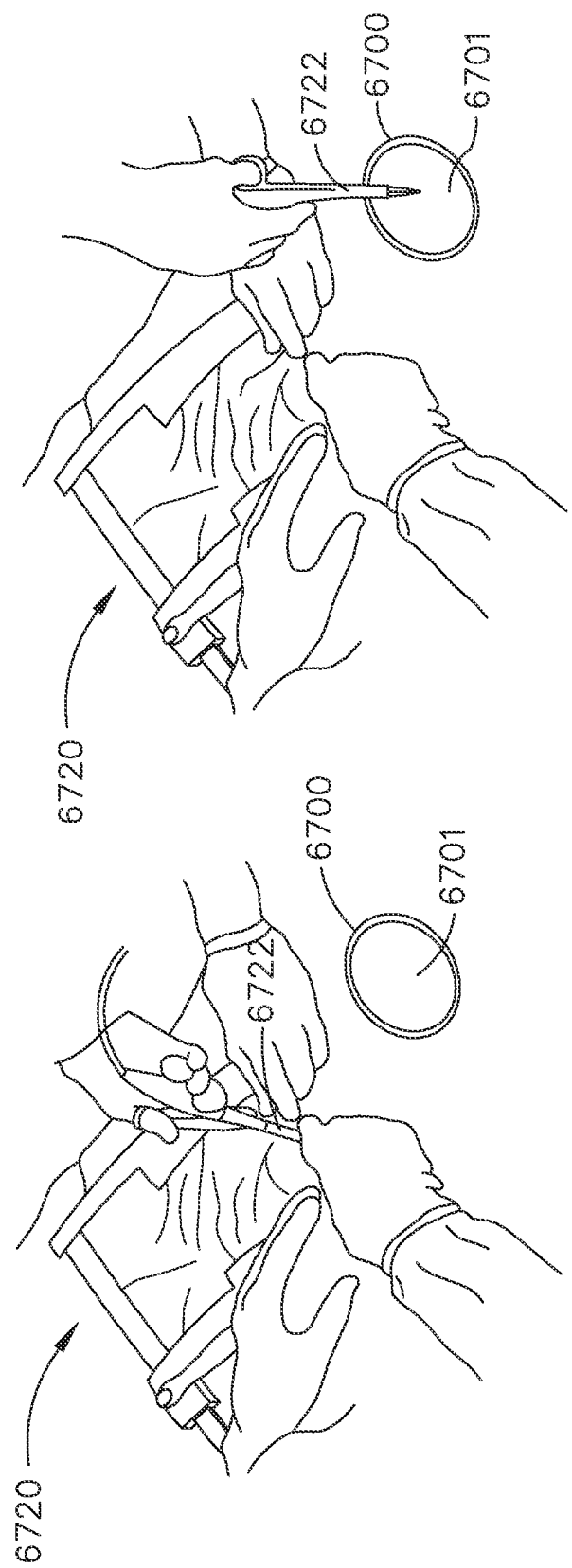

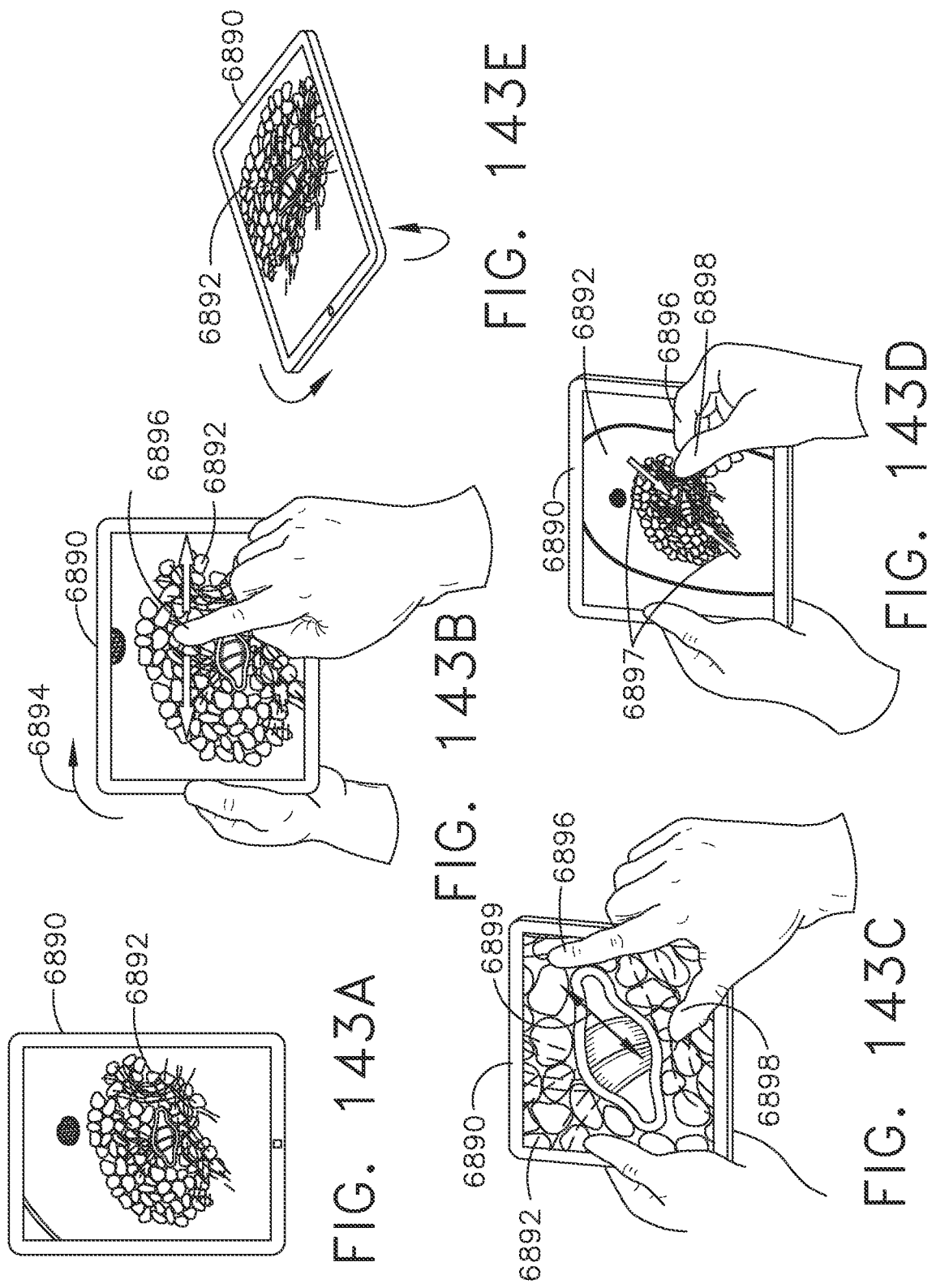

METHOD OF HUB COMMUNICATION, PROCESSING, STORAGE AND DISPLAY

CROSS-REFERENCE TO RELATED APPLICATIONS

The present application claims priority under 35 U.S.C. § 120 to U.S. patent application Ser. No. 16/209,385, titled METHOD OF HUB COMMUNICATION, PROCESSING, STORAGE AND DISPLAY, filed Dec. 4, 2018, now U.S. Patent Application Publication No. 2019/0200844, the disclosure of which is herein incorporated by reference in its entirety.

U.S. patent application Ser. No. 16/209,385 claims priority under 35 U.S.C. § 119(e) to U.S. Provisional Patent Application No. 62/773,778, titled METHOD FOR ADAPTIVE CONTROL SCHEMES FOR SURGICAL NETWORK CONTROL AND INTERACTION, filed Nov. 30, 2018, to U.S. Provisional Patent Application No. 62/773,728, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Nov. 30, 2018, to U.S. Provisional Patent Application No. 62/773,741, titled METHOD FOR FACILITY DATA COLLECTION AND INTERPRETATION, filed Nov. 30, 2018, and to U.S. Provisional Patent Application No. 62/773,742, titled METHOD FOR CIRCULAR STAPLER CONTROL ALGORITHM ADJUSTMENT BASED ON SITUATIONAL AWARENESS, filed Nov. 30, 2018, the disclosure of each of which is herein incorporated by reference in its entirety.

U.S. patent application Ser. No. 16/209,385 claims priority under 35 U.S.C. § 119(e) to U.S. Provisional Patent Application No. 62/750,529, titled METHOD FOR OPERATING A POWERED ARTICULATING MULTI-CLIP APPLIER, filed Oct. 25, 2018, to U.S. Provisional Patent Application No. 62/750,539, titled SURGICAL CLIP APPLIER, filed Oct. 25, 2018, and to U.S. Provisional Patent Application No. 62/750,555, titled SURGICAL CLIP APPLIER, filed Oct. 25, 2018, the disclosure of each of which is herein incorporated by reference in its entirety.

U.S. patent application Ser. No. 16/209,385 also claims priority under 35 U.S.C. § 119(e) to U.S. Provisional Patent Application No. 62/729,183, titled CONTROL FOR A SURGICAL NETWORK OR SURGICAL NETWORK CONNECTED DEVICE THAT ADJUSTS ITS FUNCTION BASED ON A SENSED SITUATION OR USAGE, filed Sep. 10, 2018, to U.S. Provisional Patent Application No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION, filed Sep. 10, 2018, to U.S. Provisional Patent Application No. 62/729,176, titled INDIRECT COMMAND AND CONTROL OF A FIRST OPERATING ROOM SYSTEM THROUGH THE USE OF A SECOND OPERATING ROOM SYSTEM WITHIN A STERILE FIELD WHERE THE SECOND OPERATING ROOM SYSTEM HAS PRIMARY AND SECONDARY OPERATING MODES, filed Sep. 10, 2018, to U.S. Provisional Patent Application No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING, filed Sep. 10, 2018, to U.S. Provisional Patent Application No. 62/729,184, titled POWERED SURGICAL TOOL WITH A PREDEFINED ADJUSTABLE CONTROL ALGORITHM FOR CONTROLLING AT LEAST ONE END EFFECTOR PARAMETER AND A MEANS FOR LIMITING THE ADJUSTMENT, filed Sep. 10, 2018, to U.S. Provisional Patent Application No. 62/729,182, titled SENSING THE PATIENT POSITION AND CONTACT UTILIZING THE MONO-POLAR RETURN PAD ELECTRODE TO PROVIDE SITUATIONAL AWARENESS TO THE HUB, filed Sep. 10, 2018, to U.S. Provisional Patent Application No. 62/729,191, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, filed Sep. 10, 2018, to U.S. Provisional Patent Application No. 62/729,195, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Sep. 10, 2018, and to U.S. Provisional Patent Application No. 62/729,186, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES, filed Sep. 10, 2018, the disclosure of each of which is herein incorporated by reference in its entirety.

U.S. patent application Ser. No. 16/209,385 also claims priority under 35 U.S.C. § 119(e) to U.S. Provisional Patent Application No. 62/721,995, titled CONTROLLING AN ULTRASONIC SURGICAL INSTRUMENT ACCORDING TO TISSUE LOCATION, filed Aug. 23, 2018, to U.S. Provisional Patent Application No. 62/721,998, titled SITUATIONAL AWARENESS OF ELECTROSURGICAL SYSTEMS, filed Aug. 23, 2018, to U.S. Provisional Patent Application No. 62/721,999, titled INTERRUPTION OF ENERGY DUE TO INADVERTENT CAPACITIVE COUPLING, filed Aug. 23, 2018, to U.S. Provisional Patent Application No. 62/721,994, titled BIPOLAR COMBINATION DEVICE THAT AUTOMATICALLY ADJUSTS PRESSURE BASED ON ENERGY MODALITY, filed Aug. 23, 2018, and to U.S. Provisional Patent Application No. 62/721,996, titled RADIO FREQUENCY ENERGY DEVICE FOR DELIVERING COMBINED ELECTRICAL SIGNALS, filed Aug. 23, 2018, the disclosure of each of which is herein incorporated by reference in its entirety.

U.S. patent application Ser. No. 16/209,385 also claims priority under 35 U.S.C. § 119(e) to U.S. Provisional Patent Application No. 62/692,747, titled SMART ACTIVATION OF AN ENERGY DEVICE BY ANOTHER DEVICE, filed on Jun. 30, 2018, to U.S. Provisional Patent Application No. 62/692,748, titled SMART ENERGY ARCHITECTURE, filed on Jun. 30, 2018, and to U.S. Provisional Patent Application No. 62/692,768, titled SMART ENERGY DEVICES, filed on Jun. 30, 2018, the disclosure of each of which is herein incorporated by reference in its entirety.

U.S. patent application Ser. No. 16/209,385 also claims priority under 35 U.S.C. § 119(e) to U.S. Provisional Patent Application No. 62/691,228, titled METHOD OF USING REINFORCED FLEX CIRCUITS WITH MULTIPLE SENSORS WITH ELECTROSURGICAL DEVICES, filed Jun. 28, 2018, to U.S. Provisional Patent Application No. 62/691,227, titled CONTROLLING A SURGICAL INSTRUMENT ACCORDING TO SENSED CLOSURE PARAMETERS, filed Jun. 28, 2018, to U.S. Provisional Patent Application No. 62/691,230, titled SURGICAL INSTRUMENT HAVING A FLEXIBLE ELECTRODE, filed Jun. 28, 2018, to U.S. Provisional Patent Application No. 62/691,219, titled SURGICAL EVACUATION SENSING AND MOTOR CONTROL, filed Jun. 28, 2018, to U.S. Provisional Patent Application No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM, filed Jun. 28, 2018, to U.S. Provisional Patent Application No. 62/691, 262, titled SURGICAL EVACUATION SYSTEM WITH A COMMUNICATION CIRCUIT FOR COMMUNICATION BETWEEN A FILTER AND A SMOKE EVACUATION DEVICE, filed Jun. 28, 2018, and to U.S. Provisional Patent Application No. 62/691,251, titled DUAL IN-SERIES LARGE AND SMALL DROPLET FILTERS, filed Jun. 28, 2018, the disclosure of each of which is herein incorporated by reference in its entirety.

U.S. patent application Ser. No. 16/209,385 claims priority under 35 U.S.C. § 119(e) to U.S. Provisional Patent Application No. 62/665,129, titled SURGICAL SUTURING SYSTEMS, filed May 1, 2018, to U.S. Provisional Patent Application No. 62/665,139, titled SURGICAL INSTRUMENTS COMPRISING CONTROL SYSTEMS, filed May 1, 2018, to U.S. Provisional Patent Application No. 62/665,177, titled SURGICAL INSTRUMENTS COMPRISING HANDLE ARRANGEMENTS, filed May 1, 2018, to U.S. Provisional Patent Application No. 62/665, 128, titled MODULAR SURGICAL INSTRUMENTS, filed May 1, 2018, to U.S. Provisional Patent Application No. 62/665,192, titled SURGICAL DISSECTORS, filed May 1, 2018, and to U.S. Provisional Patent Application No. 62/665,134, titled SURGICAL CLIP APPLIER, filed May 1, 2018, the disclosure of each of which is herein incorporated by reference in its entirety.

U.S. patent application Ser. No. 16/209,385 also claims priority under 35 U.S.C. § 119(e) to U.S. Provisional Patent Application No. 62/659,900, titled METHOD OF HUB COMMUNICATION, filed on Apr. 19, 2018, the disclosure of which is herein incorporated by reference in its entirety.

U.S. patent application Ser. No. 16/209,385 also claims priority under 35 U.S.C. § 119(e) to U.S. Provisional Patent Application No. 62/650,898, filed on Mar. 30, 2018, titled CAPACITIVE COUPLED RETURN PATH PAD WITH SEPARABLE ARRAY ELEMENTS, to U.S. Provisional Patent Application No. 62/650,887, titled SURGICAL SYSTEMS WITH OPTIMIZED SENSING CAPABILITIES, filed Mar. 30, 2018, to U.S. Provisional Patent Application No. 62/650,882, titled SMOKE EVACUATION MODULE FOR INTERACTIVE SURGICAL PLATFORM, filed Mar. 30, 2018, and to U.S. Provisional Patent Application No. 62/650,877, titled SURGICAL SMOKE EVACUATION SENSING AND CONTROLS, filed Mar. 30, 2018, the disclosure of each of which is herein incorporated by reference in its entirety.

U.S. patent application Ser. No. 16/209,385 also claims the benefit of priority under 35 U.S.C. § 119(e) to U.S. Provisional Patent Application No. 62/649,302, titled INTERACTIVE SURGICAL SYSTEMS WITH ENCRYPTED COMMUNICATION CAPABILITIES, filed Mar. 28, 2018, to U.S. Provisional Patent Application No. 62/649,294, titled DATA STRIPPING METHOD TO INTERROGATE PATIENT RECORDS AND CREATE ANONYMIZED RECORD, filed Mar. 28, 2018, to U.S. Provisional Patent Application No. 62/649,300, titled SURGICAL HUB SITUATIONAL AWARENESS, filed Mar. 28, 2018, to U.S. Provisional Patent Application No. 62/649, 309, titled SURGICAL HUB SPATIAL AWARENESS TO DETERMINE DEVICES IN OPERATING THEATER, filed Mar. 28, 2018, to U.S. Provisional Patent Application No. 62/649,310, titled COMPUTER IMPLEMENTED INTERACTIVE SURGICAL SYSTEMS, filed Mar. 28, 2018, to U.S. Provisional Patent Application No. 62/649, 291, titled USE OF LASER LIGHT AND RED-GREEN-BLUE COLORATION TO DETERMINE PROPERTIES OF BACK SCATTERED LIGHT, filed Mar. 28, 2018, to U.S. Provisional Patent Application No. 62/649,296, titled ADAPTIVE CONTROL PROGRAM UPDATES FOR SURGICAL DEVICES, filed Mar. 28, 2018, to U.S. Provisional Patent Application No. 62/649,333, titled CLOUD-BASED MEDICAL ANALYTICS FOR CUSTOMIZATION AND RECOMMENDATIONS TO A USER, filed Mar. 28, 2018, to U.S. Provisional Patent Application No. 62/649,327, titled CLOUD-BASED MEDICAL ANALYTICS FOR SECURITY AND AUTHENTICATION TRENDS AND REACTIVE MEASURES, filed Mar. 28, 2018, to U.S. Provisional Patent Application No. 62/649,315, titled DATA HANDLING AND PRIORITIZATION IN A CLOUD ANALYTICS NETWORK, filed Mar. 28, 2018, to U.S. Provisional Patent Application No. 62/649,313, titled CLOUD INTERFACE FOR COUPLED SURGICAL DEVICES, filed Mar. 28, 2018, to U.S. Provisional Patent Application No. 62/649,320, titled DRIVE ARRANGEMENTS FOR ROBOT-ASSISTED SURGICAL PLATFORMS, filed Mar. 28, 2018, to U.S. Provisional Patent Application No. 62/649, 307, titled AUTOMATIC TOOL ADJUSTMENTS FOR ROBOT-ASSISTED SURGICAL PLATFORMS, filed Mar. 28, 2018, and to U.S. Provisional Patent Application No. 62/649,323, titled SENSING ARRANGEMENTS FOR ROBOT-ASSISTED SURGICAL PLATFORMS, filed Mar. 28, 2018, the disclosure of each of which is herein incorporated by reference in its entirety.

U.S. patent application Ser. No. 16/209,385 also claims the benefit of priority under 35 U.S.C. § 119(e) to U.S. Provisional Patent Application No. 62/611,341, titled INTERACTIVE SURGICAL PLATFORM, filed Dec. 28, 2017, to U.S. Provisional Patent Application No. 62/611, 340, titled CLOUD-BASED MEDICAL ANALYTICS, filed Dec. 28, 2017, and to U.S. Provisional Patent Application No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to various surgical systems. Surgical procedures are typically performed in surgical operating theaters or rooms in a healthcare facility such as, for example, a hospital. A sterile field is typically created around the patient. The sterile field may include the scrubbed team members, who are properly attired, and all furniture and fixtures in the area. Various surgical devices and systems are utilized in performance of a surgical procedure.

Furthermore, in the Digital and Information Age, medical systems and facilities are often slower to implement systems or procedures utilizing newer and improved technologies due to patient safety and a general desire for maintaining traditional practices. However, often times medical systems and facilities may lack communication and shared knowledge with other neighboring or similarly situated facilities as a result. To improve patient practices, it would be desirable to find ways to help interconnect medical systems and facilities better.

SUMMARY

In one aspect the present disclosure provides a method, comprising: detecting a modular surgical device within bounds of a surgical operating room; connecting the modular surgical device to a surgical hub; connecting the surgical hub to a cloud-based system; transmitting surgical data associated with a surgical procedure being performed in the surgical operating room from the modular surgical device to the surgical hub; and transmitting the surgical data from the surgical hub to the cloud-based system.

In another aspect the present disclosure provides a method, comprising: detecting a medical imaging device within bounds of a surgical operating room; connecting the medical imaging device to a surgical hub including an imaging module; transmitting a livestream of a surgical site in the surgical operating room from the medical imaging device to the imaging module; capturing, by the imaging module, at least one image frame from the livestream; deriving information relevant to the surgical site from data extracted from the at least one image frame; transmitting the information from the surgical hub to the medical imaging device; and overlaying the information onto the livestream.

In another aspect the present disclosure provides a method, comprising: detecting a modular surgical device within bounds of a surgical operating room; connecting the modular surgical device to a surgical hub; transmitting a livestream of a surgical site in the surgical operating room to an imaging module of the surgical hub; capturing, by the imaging module, at least one image frame from the livestream; and assessing a surgical activity performed by an end effector of the modular surgical device at the surgical site from data extracted from the at least one image frame.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 51 illustrates three rows of staples deployed on one side of a tissue stapled and cut by a surgical stapler, in accordance with at least one aspect of the present disclosure.

FIG. 52 illustrates a non-anodized staple and an anodized staple, in accordance with at least one aspect of the present disclosure.

FIG. 56 illustrates an interaction between two surgical hubs in different operating rooms ("OR1" and "OR3"), in accordance with at least one aspect of the present disclosure.

FIG. 84I illustrates a logic flow diagram of a process for determining a patient status according to pulse oximeter, blood pressure monitor, and/or EKG monitor perioperative data, in accordance with at least one aspect of the present disclosure.

FIG. 107 illustrates an anvil trocar of a circular stapler that is not aligned with a staple overlap portion of a linear staple line created by a double-stapling technique;

Figure 109:
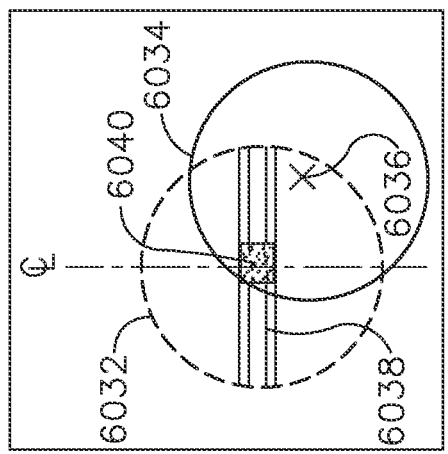
FIGS. 107-109 illustrate a process of aligning an anvil trocar of a circular stapler to a staple overlap portion of a linear staple line created by a double-stapling technique, in accordance with at least one aspect of the present disclosure, where.
Figure 108:
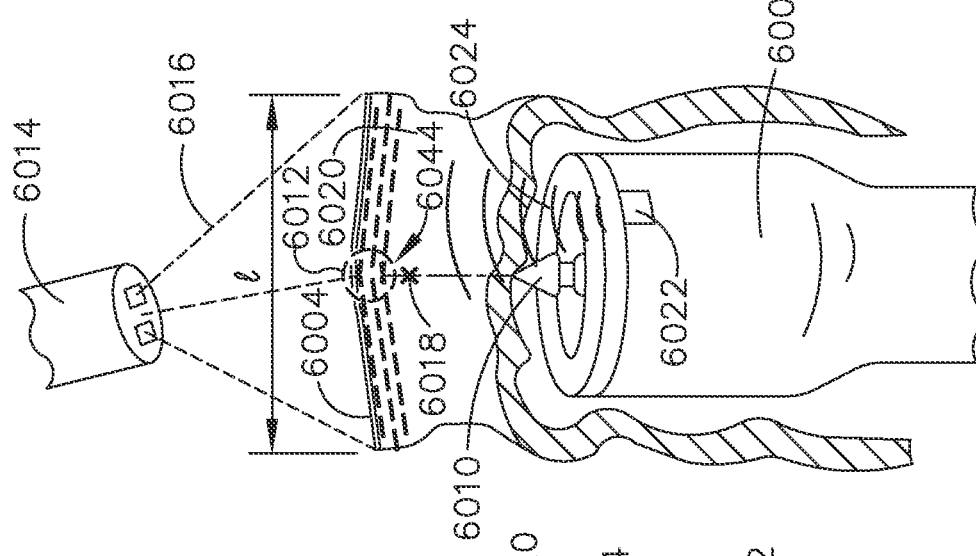
Figure 107:
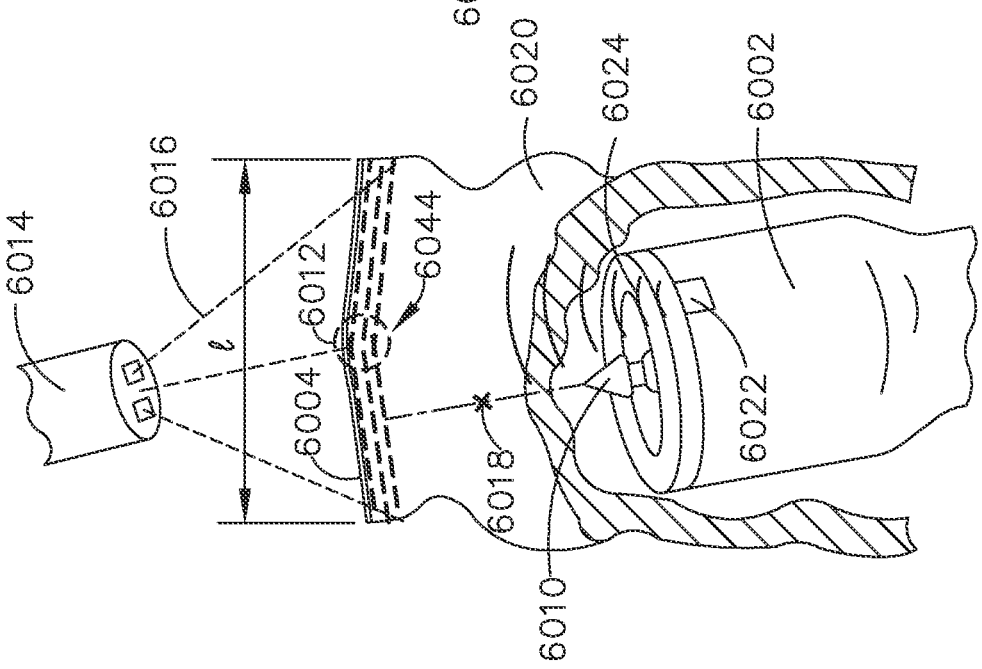

FIG. 108 illustrates an anvil trocar of a circular stapler that is aligned with the center of the staple overlap portion of the linear staple line created by a double-stapling technique; and FIG. 109 illustrates a centering tool displayed on a surgical hub display showing a staple overlap portion of a linear staple line created by a double-stapling technique to be cut out by a circular stapler, where the anvil trocar is not aligned with the staple overlap portion of the double staple line as shown in FIG. 107.

FIGS. 110 and 111 illustrate a before image and an after image of a centering tool, in accordance with at least one aspect of the present disclosure, where:

FIG. 110 illustrates an image of a projected cut path of an anvil trocar and circular knife before alignment with the target alignment ring circumscribing the image of the linear staple line over the image of the staple overlap portion presented on a surgical hub display; and FIG. 111 illustrates an image of a projected cut path of an anvil trocar and circular knife after alignment with the target alignment ring circumscribing the image of the linear staple line over the image of the staple overlap portion presented on a surgical hub display.

FIGS. 112-114 illustrate a process of aligning an anvil trocar of a circular stapler to a center of a linear staple line, in accordance with at least one aspect of the present disclosure, where:

FIG. 112 illustrates the anvil trocar out of alignment with the center of the linear staple line;

FIG. 113 illustrates the anvil trocar in alignment with the center of the linear staple line; and FIG. 114 illustrates a centering tool displayed on a surgical hub display of a linear staple line, where the anvil trocar is not aligned with the staple overlap portion of the double staple line as shown in FIG. 112.

Figures 115, 116, 117:
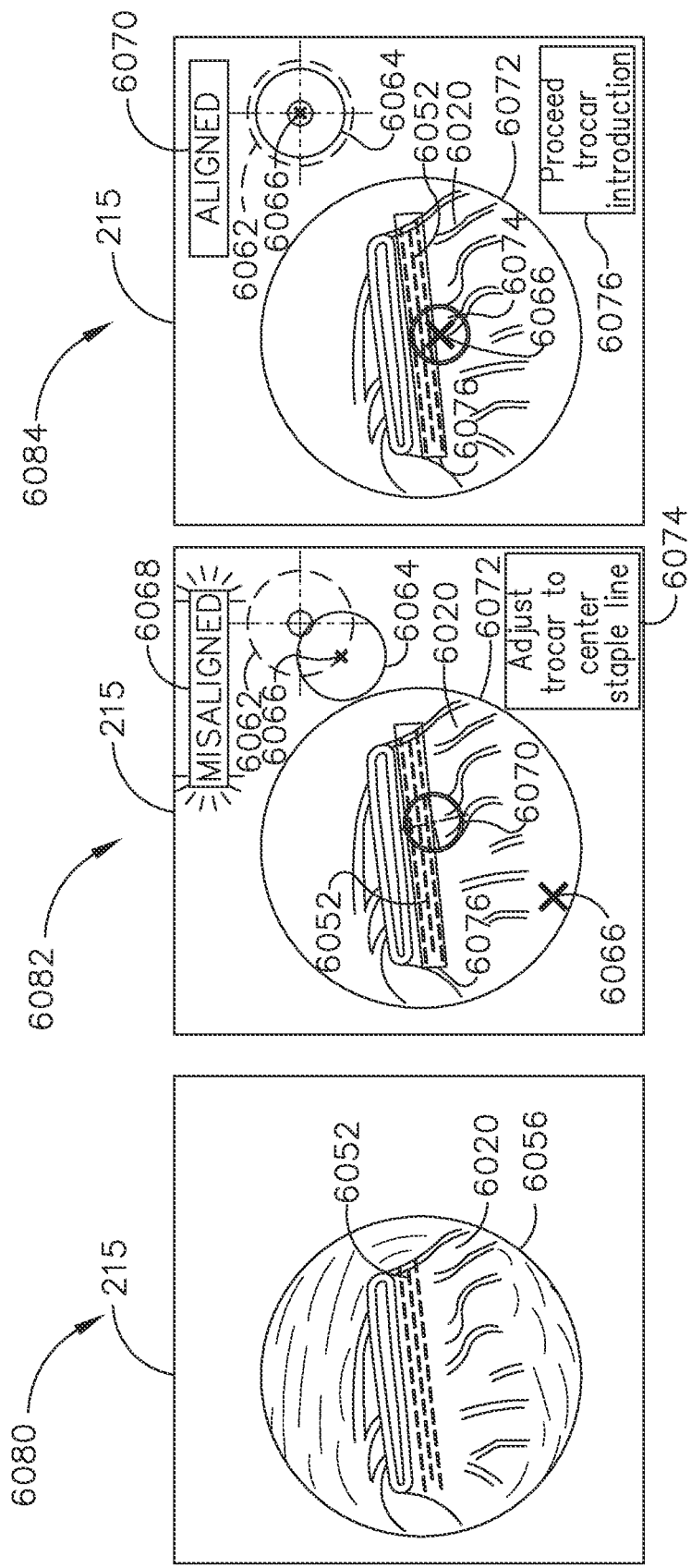

FIG. 115 is an image of a standard reticle field view of a linear staple line transection of a surgical as viewed through a laparoscope displayed on the surgical hub display, in accordance with at least one aspect of the present disclosure.

FIG. 116 is an image of a laser-assisted reticle field of view of the surgical site shown in FIG. 115 before the anvil trocar and circular knife of the circular stapler are aligned to the center of the linear staple line, in accordance with at least one aspect of the present disclosure.

FIG. 117 is an image of a laser-assisted reticle field of view of the surgical site shown in FIG. 116 after the anvil trocar and circular knife of the circular stapler are aligned to the center of the linear staple line, in accordance with at least one aspect of the present disclosure.

Figure 118:
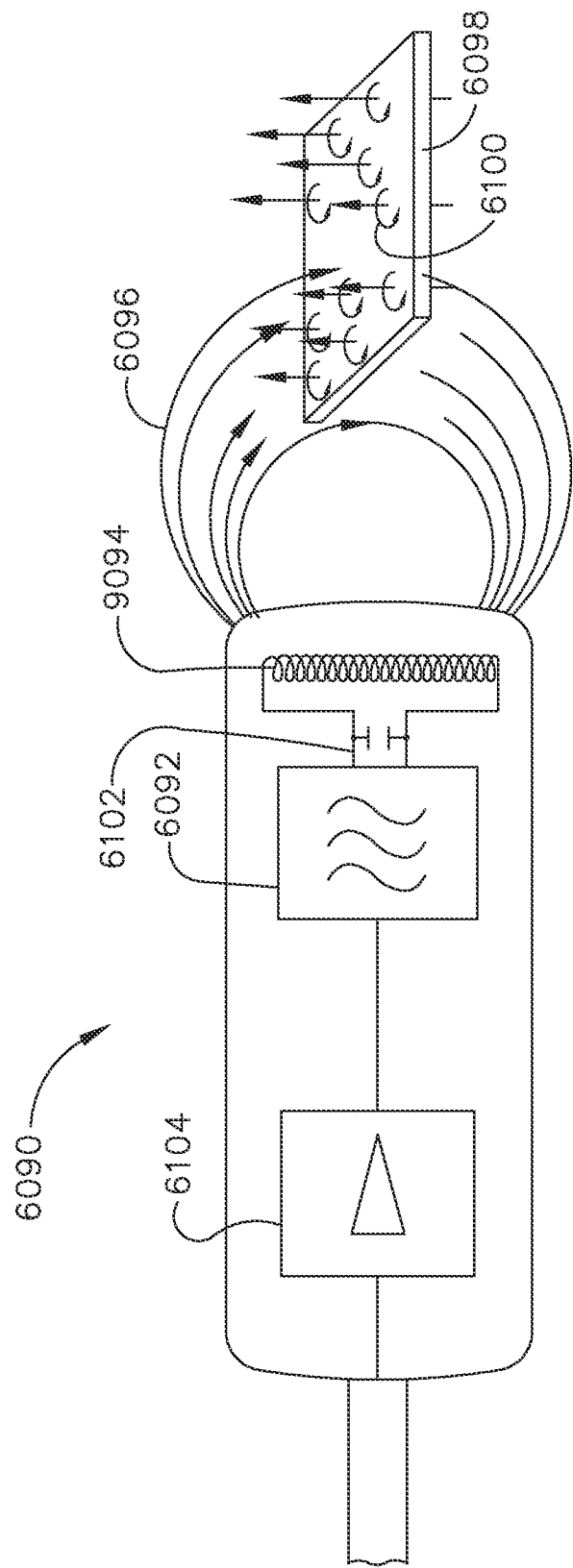

FIG. 118 illustrates a non-contact inductive sensor implementation of a non-contact sensor to determine an anvil trocar location relative to the center of a staple line transection, in accordance with at least one aspect of the present disclosure.

Figure 119:
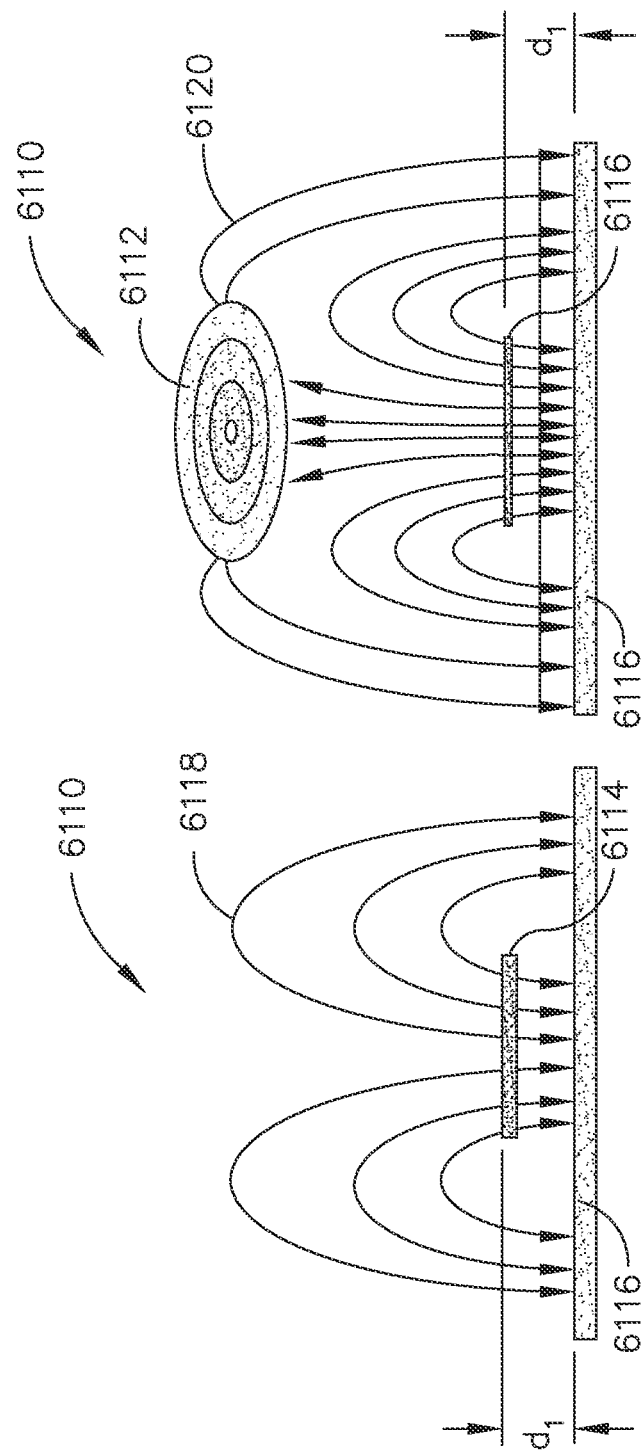

FIGS. 119A and 119B illustrate one aspect of a non-contact capacitive sensor implementation of the non-contact sensor to determine an anvil trocar location relative to the center of a staple line transection, in accordance with at least one aspect of the present disclosure, where:

FIG. 119A shows the non-contact capacitive sensor without a nearby metal target; and FIG. 119B shows the non-contact capacitive sensor near a metal target.

Figure 120:
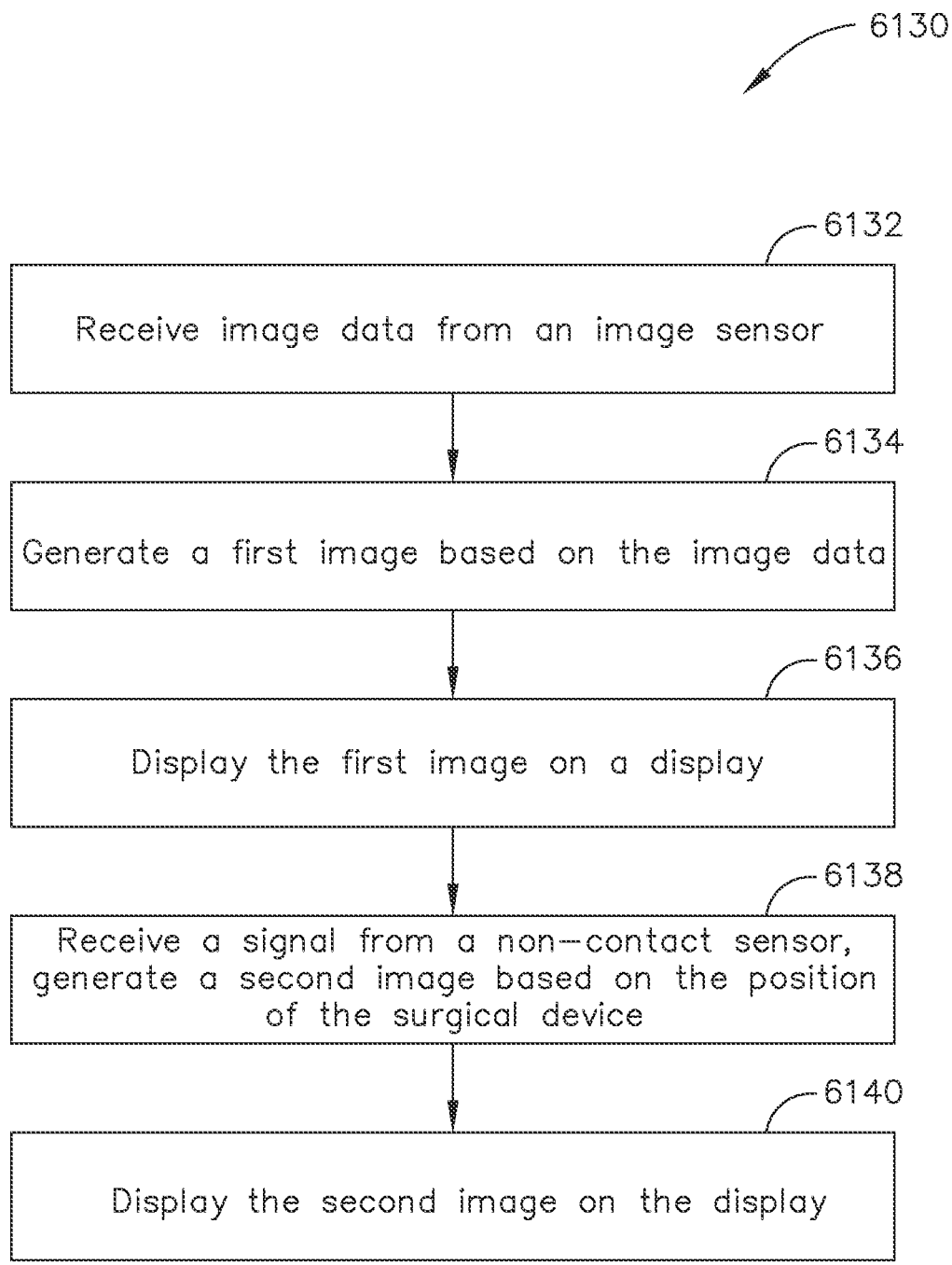

FIG. 120 is a logic flow diagram of a process depicting a control program or a logic configuration for aligning a surgical instrument, in accordance with at least one aspect of the present disclosure.

Figure 121:
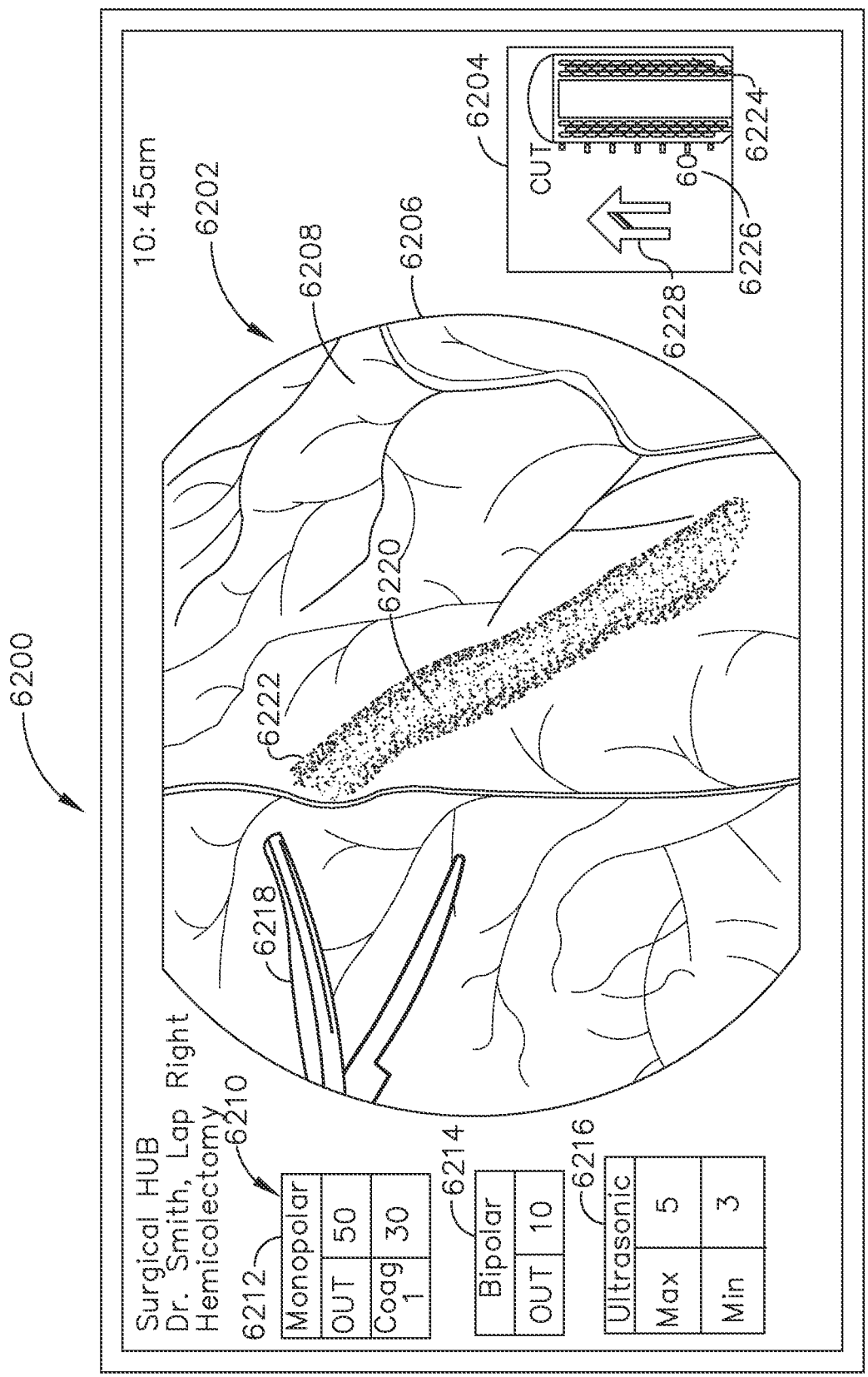

FIG. 121 illustrates a primary display of the surgical hub comprising a global and local display, in accordance with at least one aspect of the present disclosure.

Figure 122:
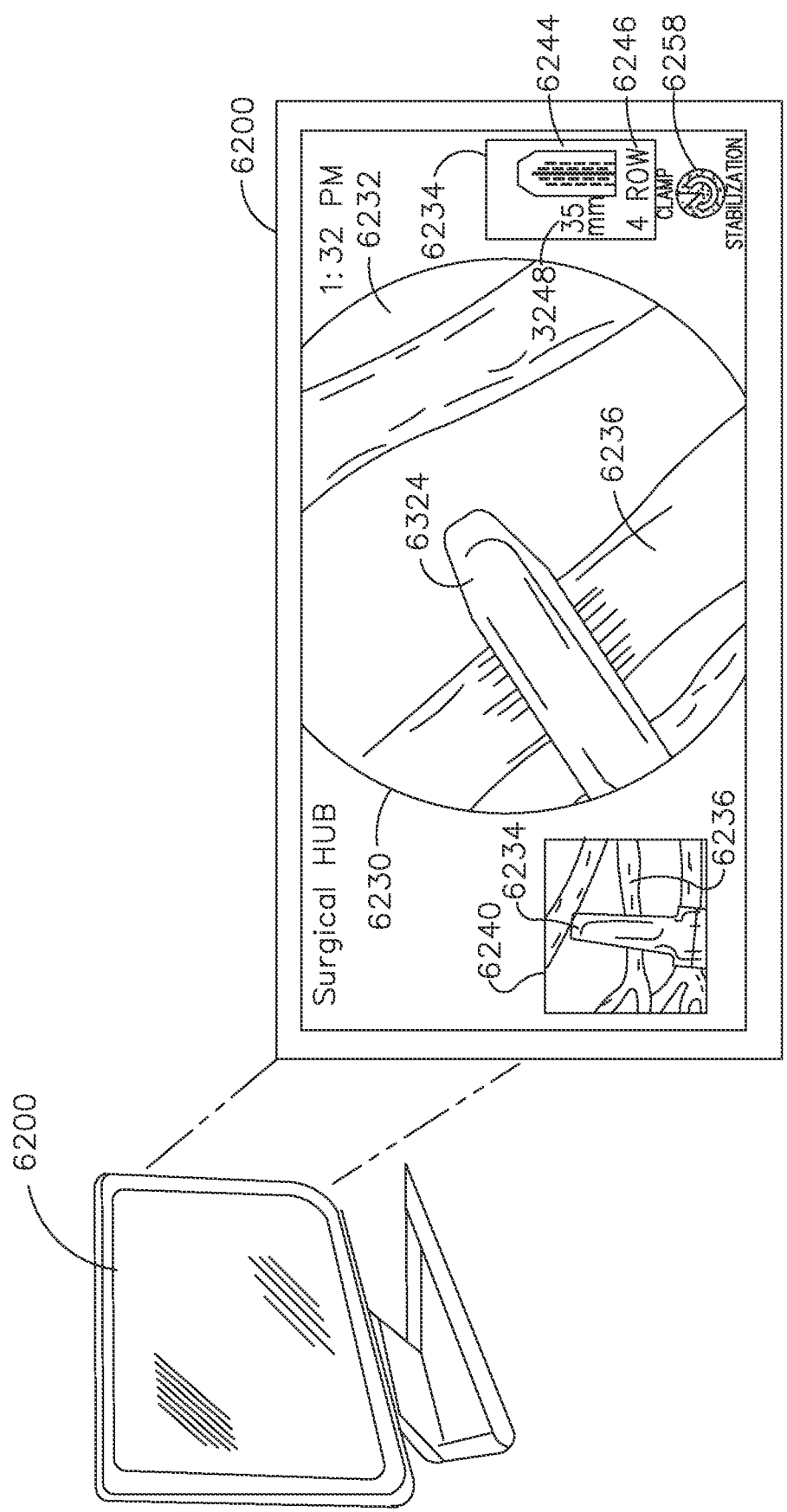

FIG. 122 illustrates a primary display of the surgical hub, in accordance with at least one aspect of the present disclosure.

Figure 123:
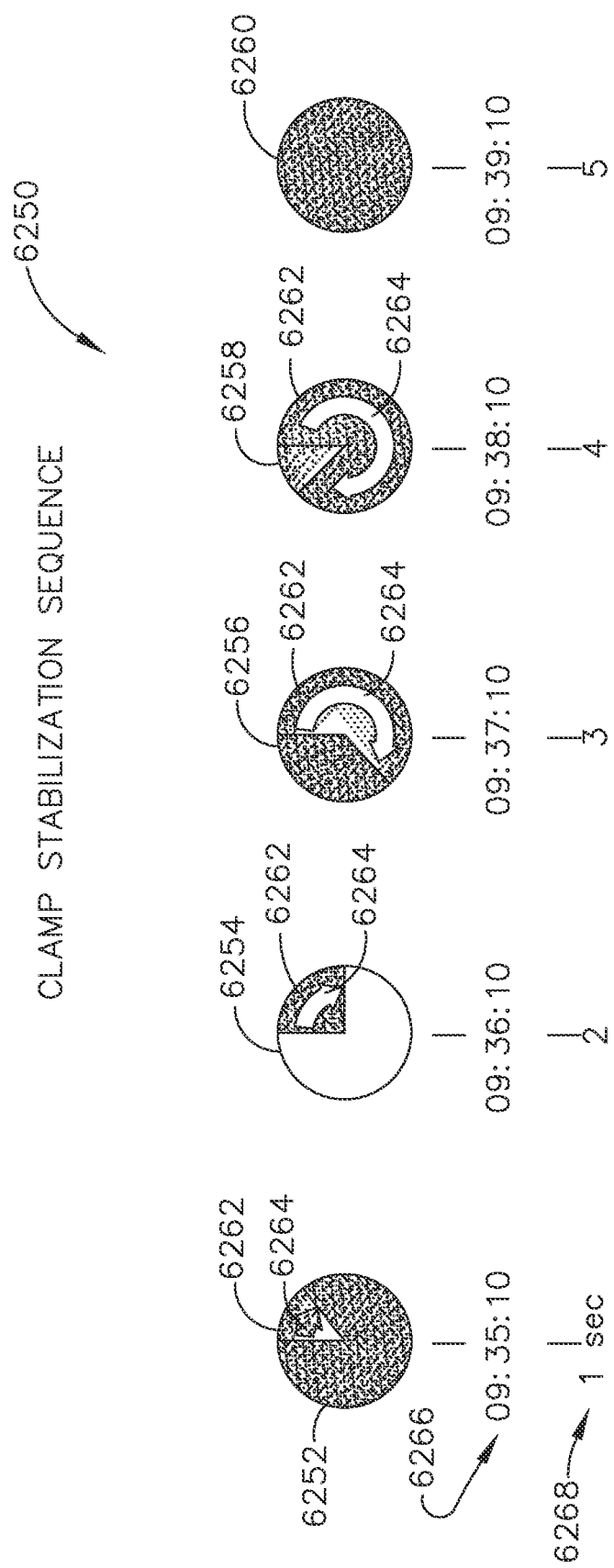

FIG. 123 illustrates a clamp stabilization sequence over a five second period, in accordance with at least one aspect of the present disclosure.

Figure 124:
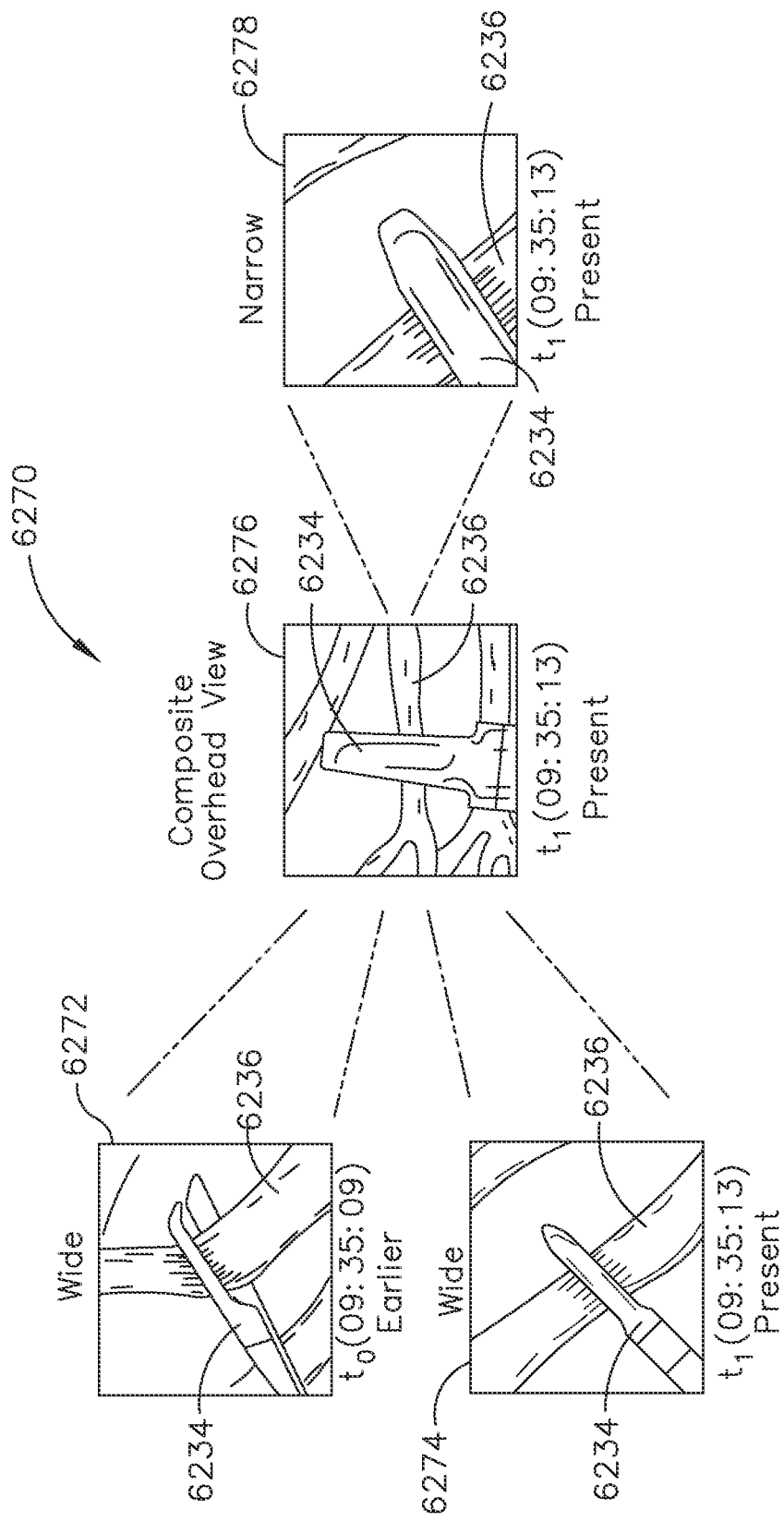

FIG. 124 illustrates a diagram of four separate wide angle view images of a surgical site at four separate times during the procedure, in accordance with at least one aspect of the present disclosure.

Figure 125:
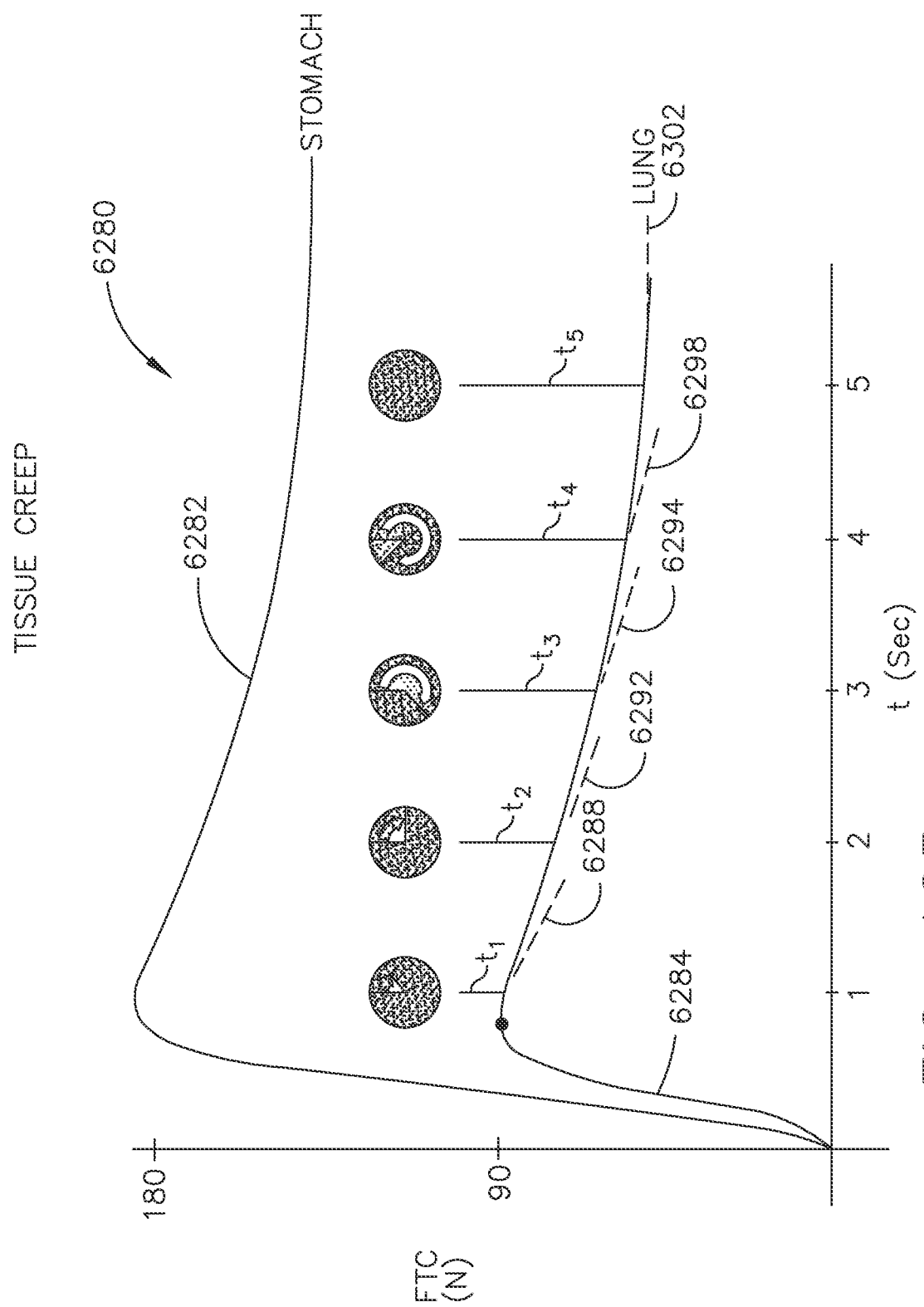

FIG. 125 is a graph of tissue creep clamp stabilization curves for two tissue types, in accordance with at least one aspect of the present disclosure.

Figure 126:
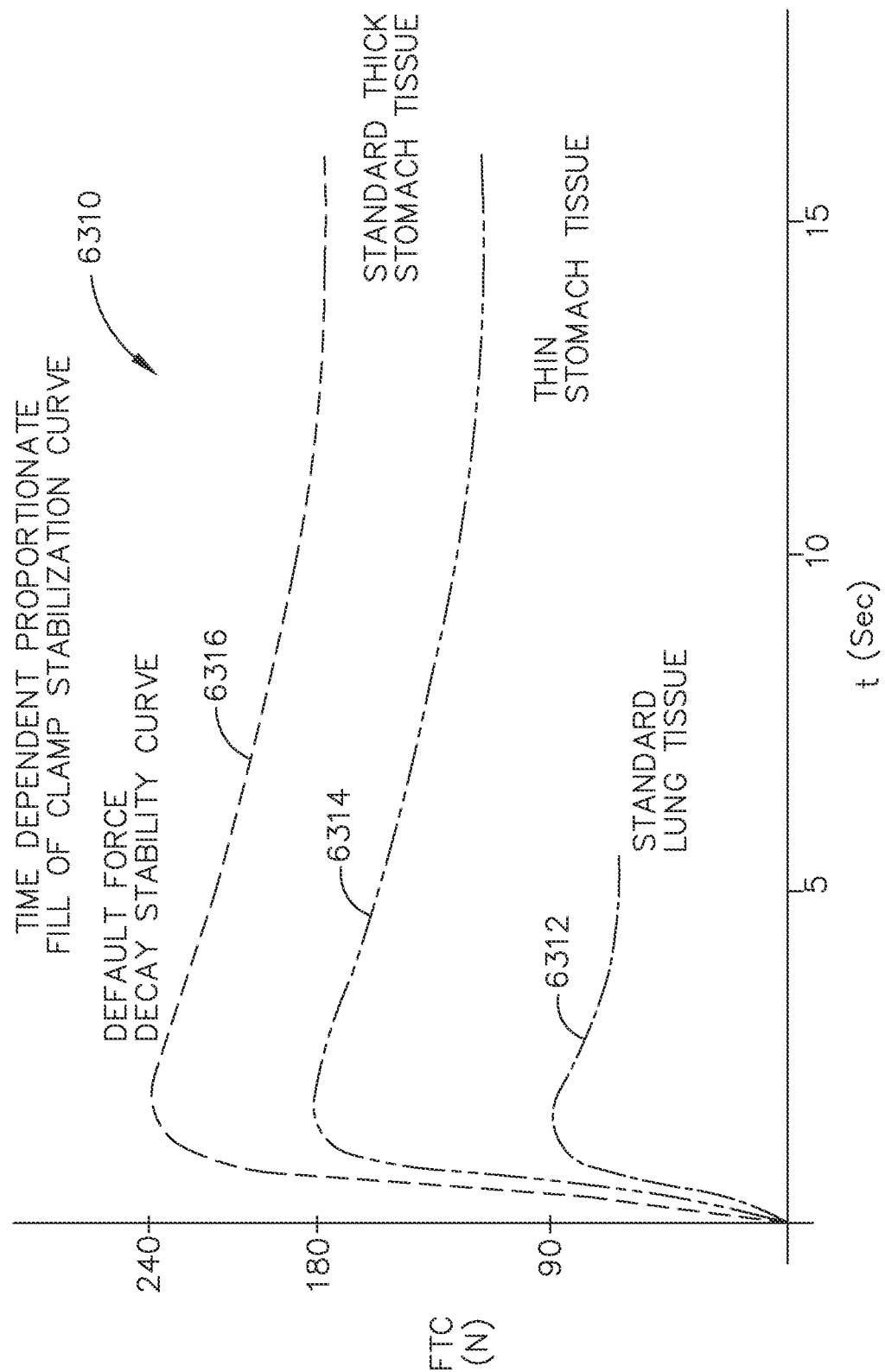

FIG. 126 is a graph of time dependent proportionate fill of a clamp force stabilization curve, in accordance with at least one aspect of the present disclosure.

Figure 127:
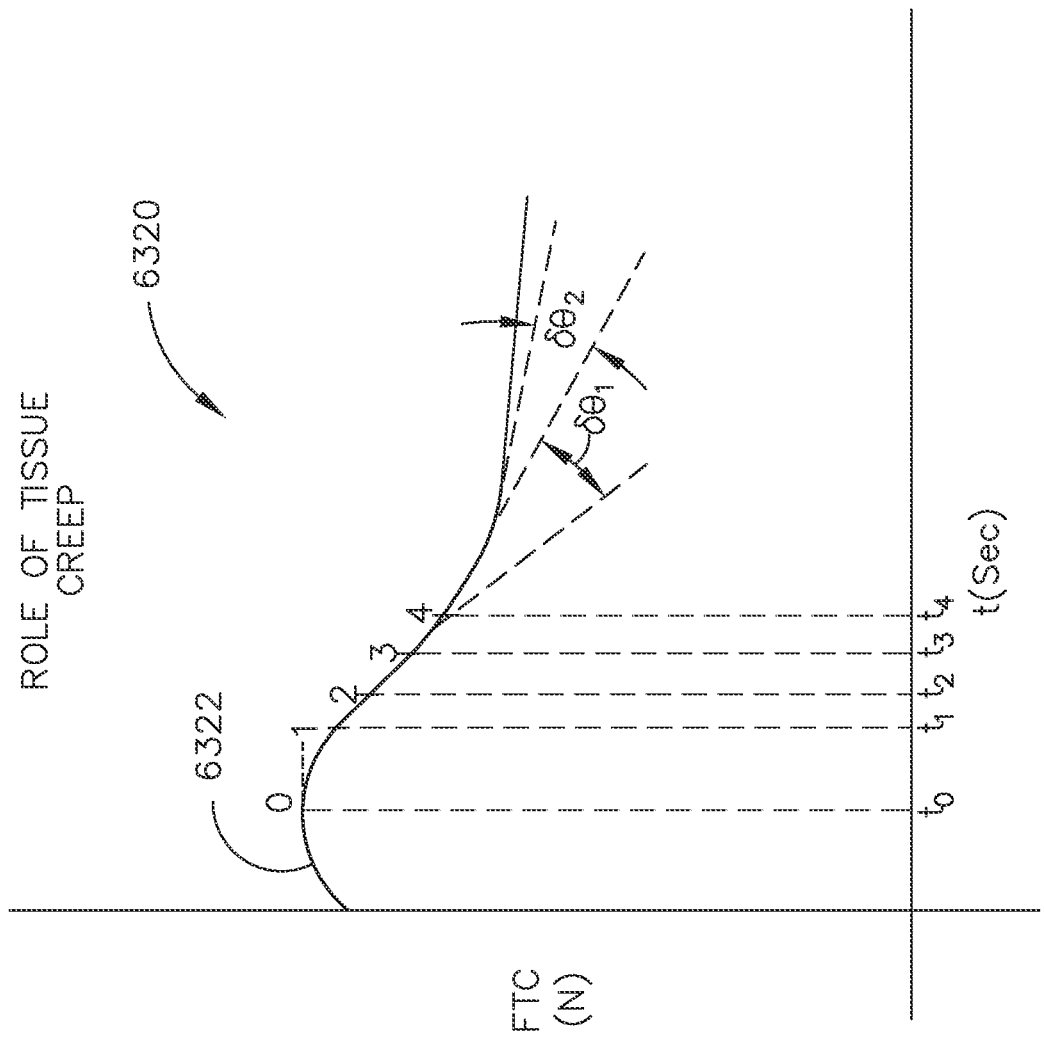

FIG. 127 is a graph of the role of tissue creep in the clamp force stabilization curve, in accordance with at least one aspect of the present disclosure.

Figure 128A:
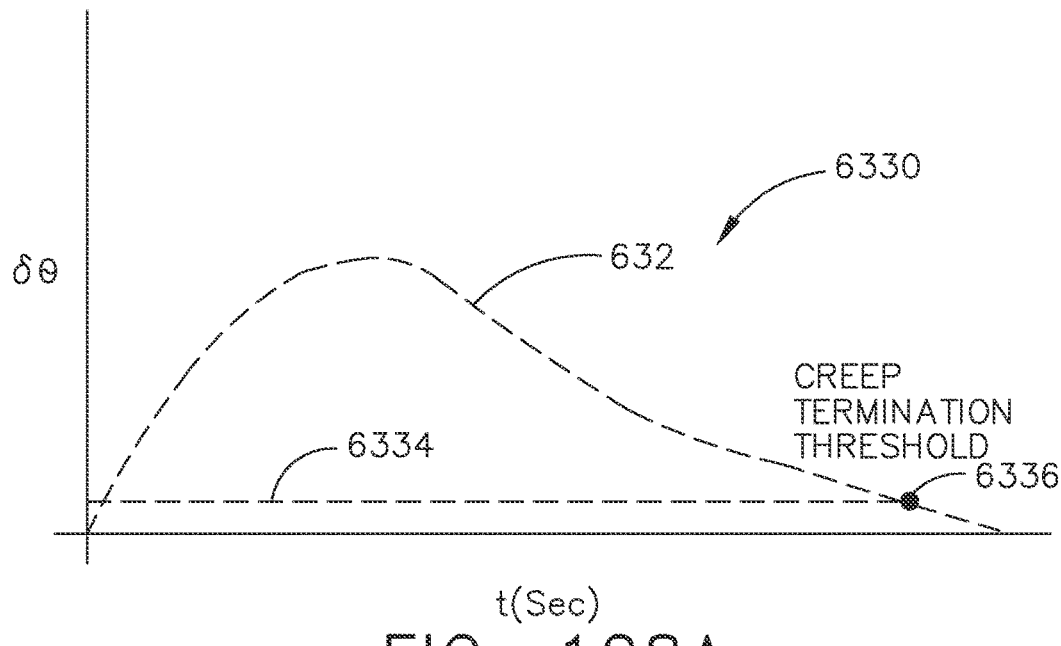
Figure 128B:
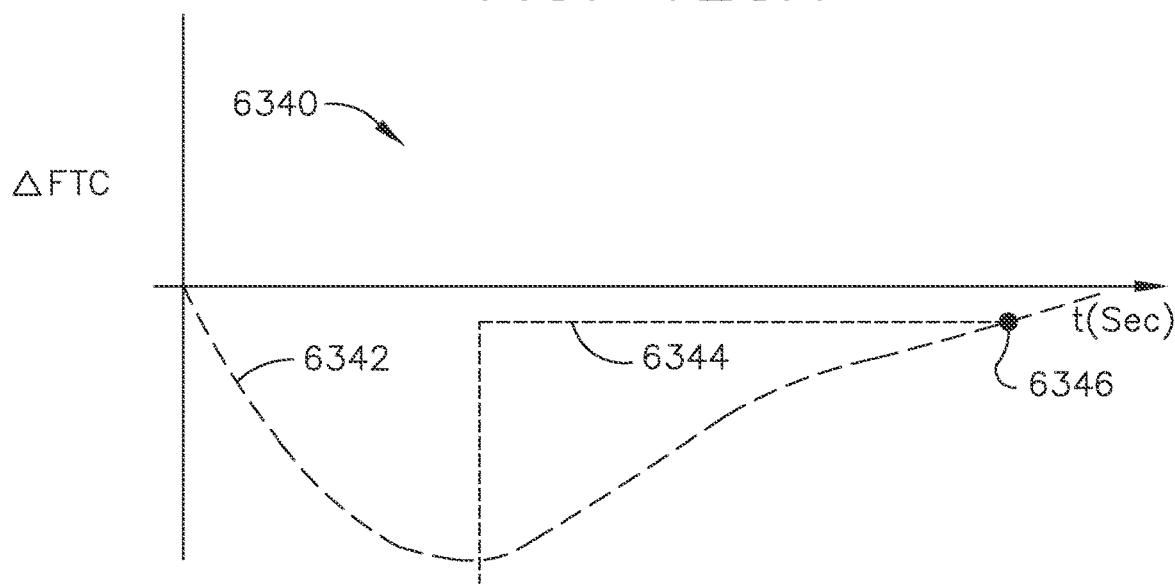

FIGS. 128A and 128B illustrate two graphs for determining when the clamped tissue has reached creep stability, in accordance with at least one aspect of the present disclosure, where:

FIG. 128A illustrates a curve that represents a vector tangent angle $d\theta$ as a function of time: and FIG. 128B illustrates a curve that represents change in force-to-close (AFTC) as a function of time.

Figure 129:
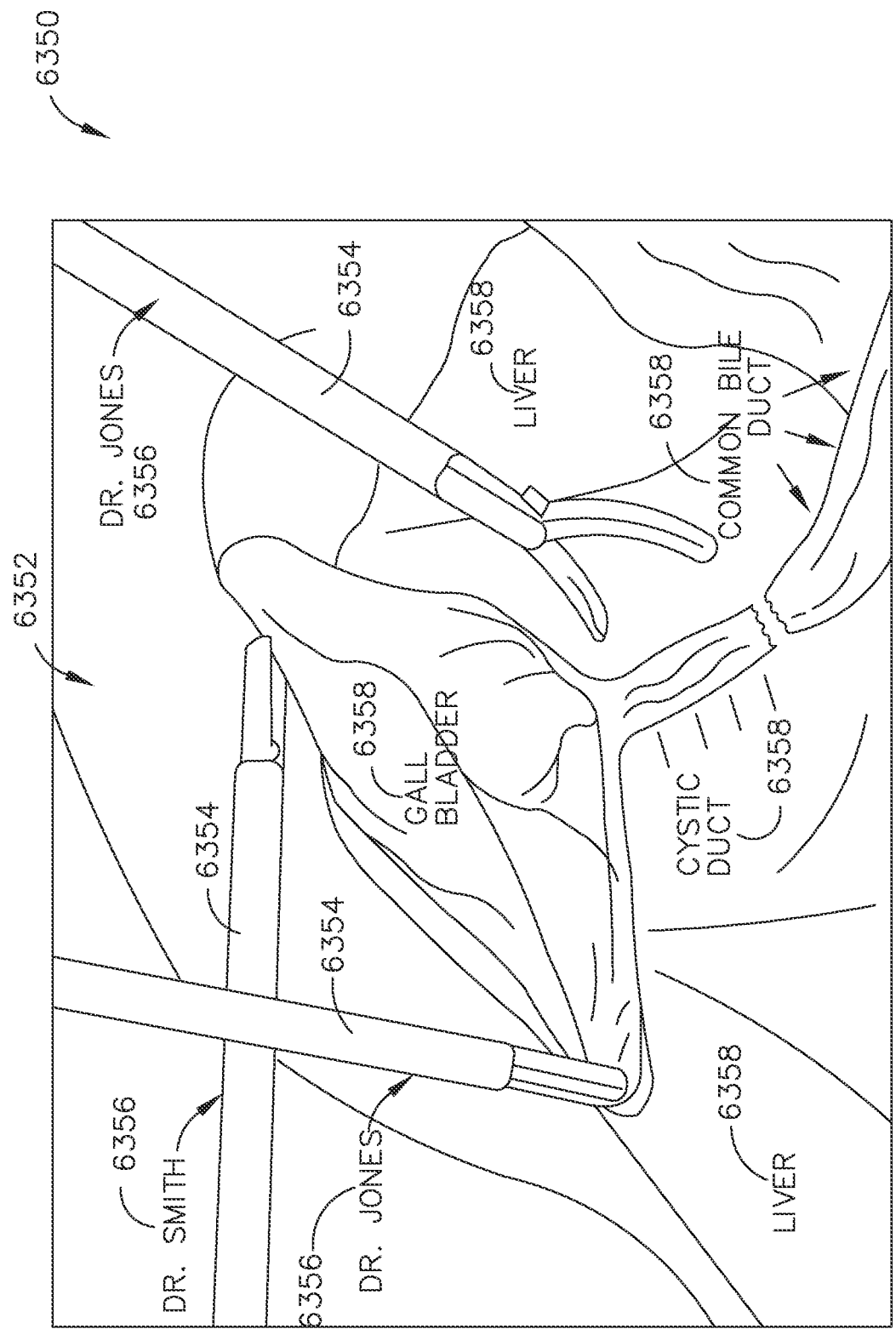

FIG. 129 illustrates an example of an augmented video image of a pre-operative video image augmented with data identifying displayed elements, in accordance with at least one aspect of the present disclosure.

Figure 130:
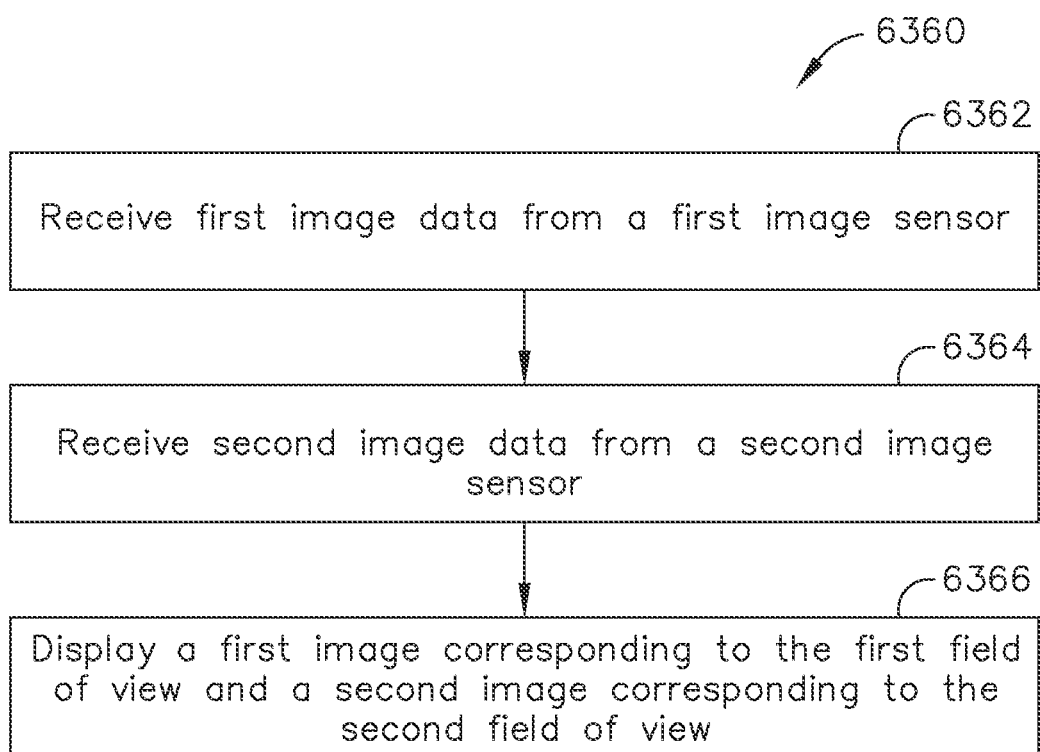

FIG. 130 is a logic flow diagram of a process depicting a control program or a logic configuration to display images, in accordance with at least one aspect of the present disclosure.

Figure 131:
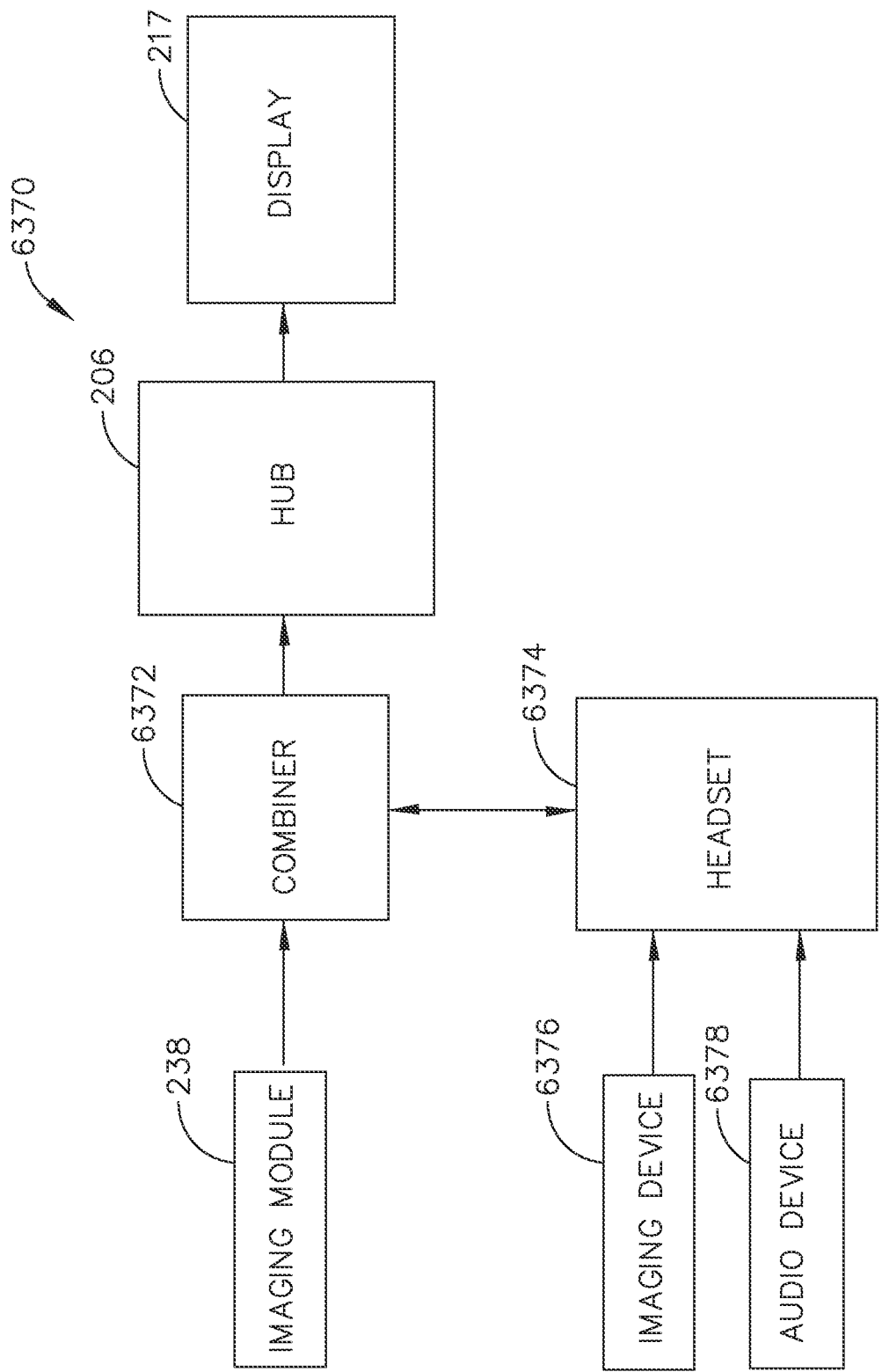

FIG. 131 illustrates a communication system comprising an intermediate signal combiner positioned in the communication path between an imaging module and a surgical hub display, in accordance with at least one aspect of the present disclosure.

Figure 132:
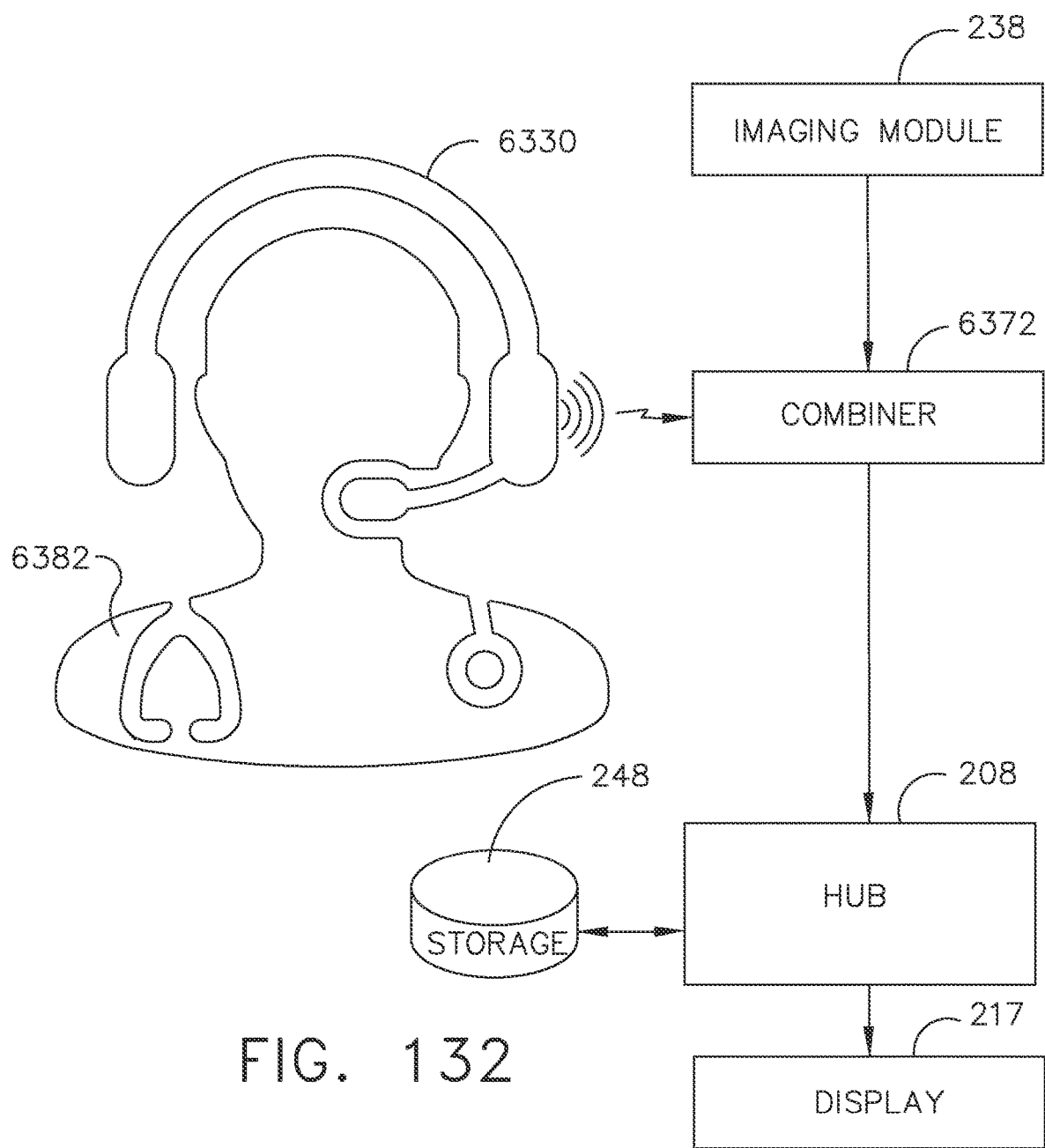

FIG. 132 illustrates an independent interactive headset worn by a surgeon to communicate data to the surgical hub, according to one aspect of the present disclosure.

Figure 133:
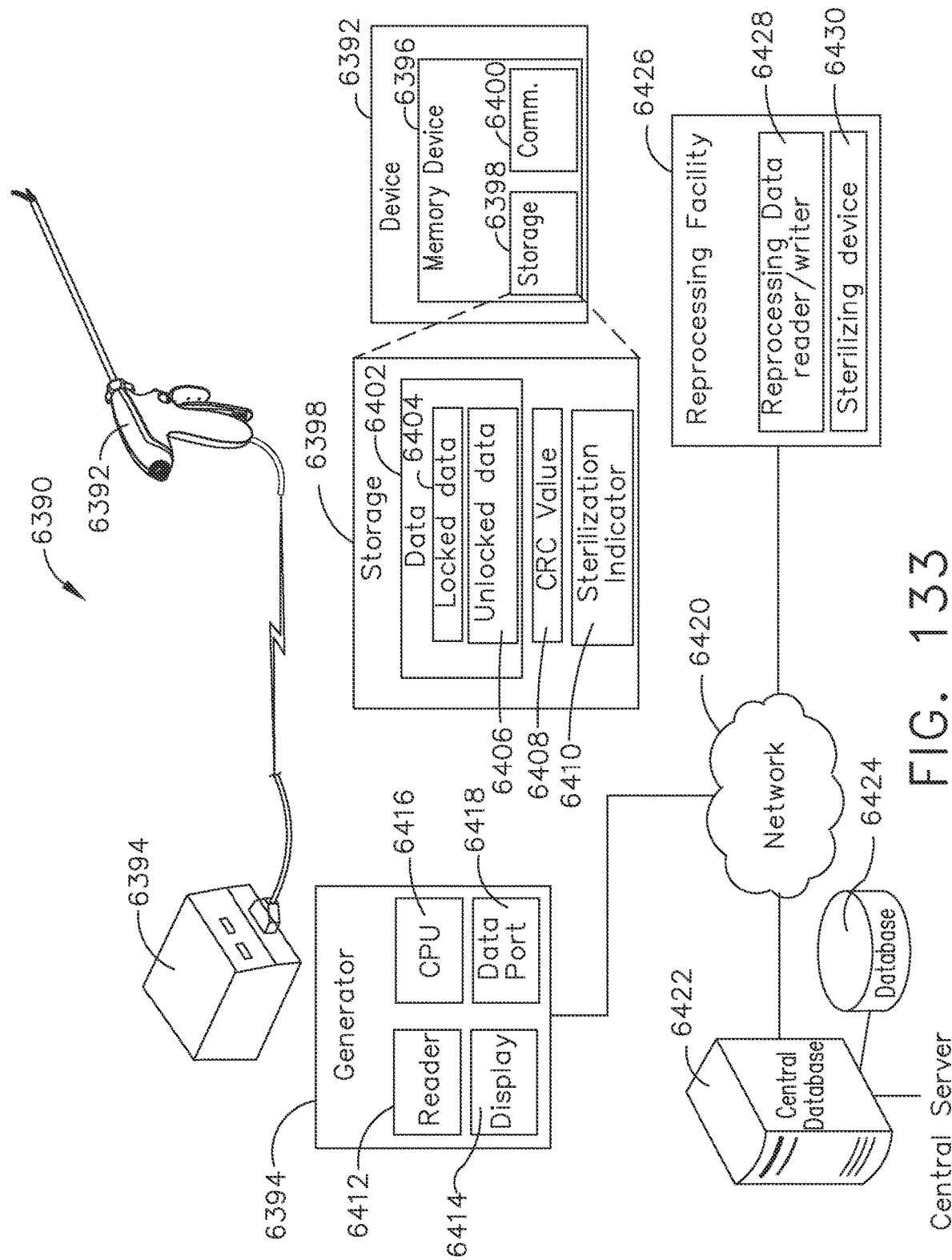

FIG. 133 illustrates a method for controlling the usage of a device, in accordance with at least one aspect of the present disclosure, in accordance with at least one aspect of the present disclosure.

Figure 134:
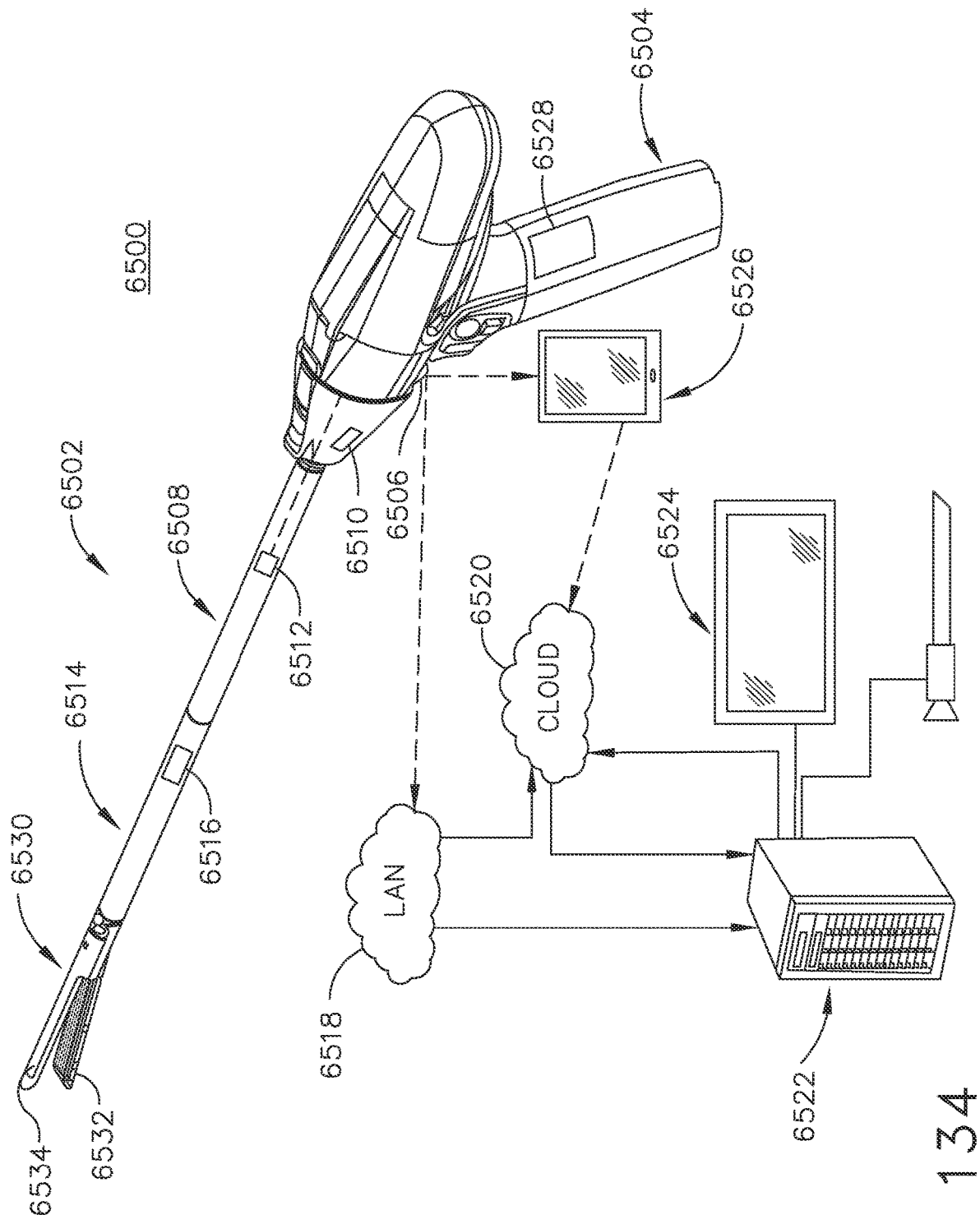

FIG. 134 illustrates a surgical system that includes a handle having a controller and a motor, an adapter releasably coupled to the handle, and a loading unit releasably coupled to the adapter, in accordance with at least one aspect of the present disclosure.

Figure 135:
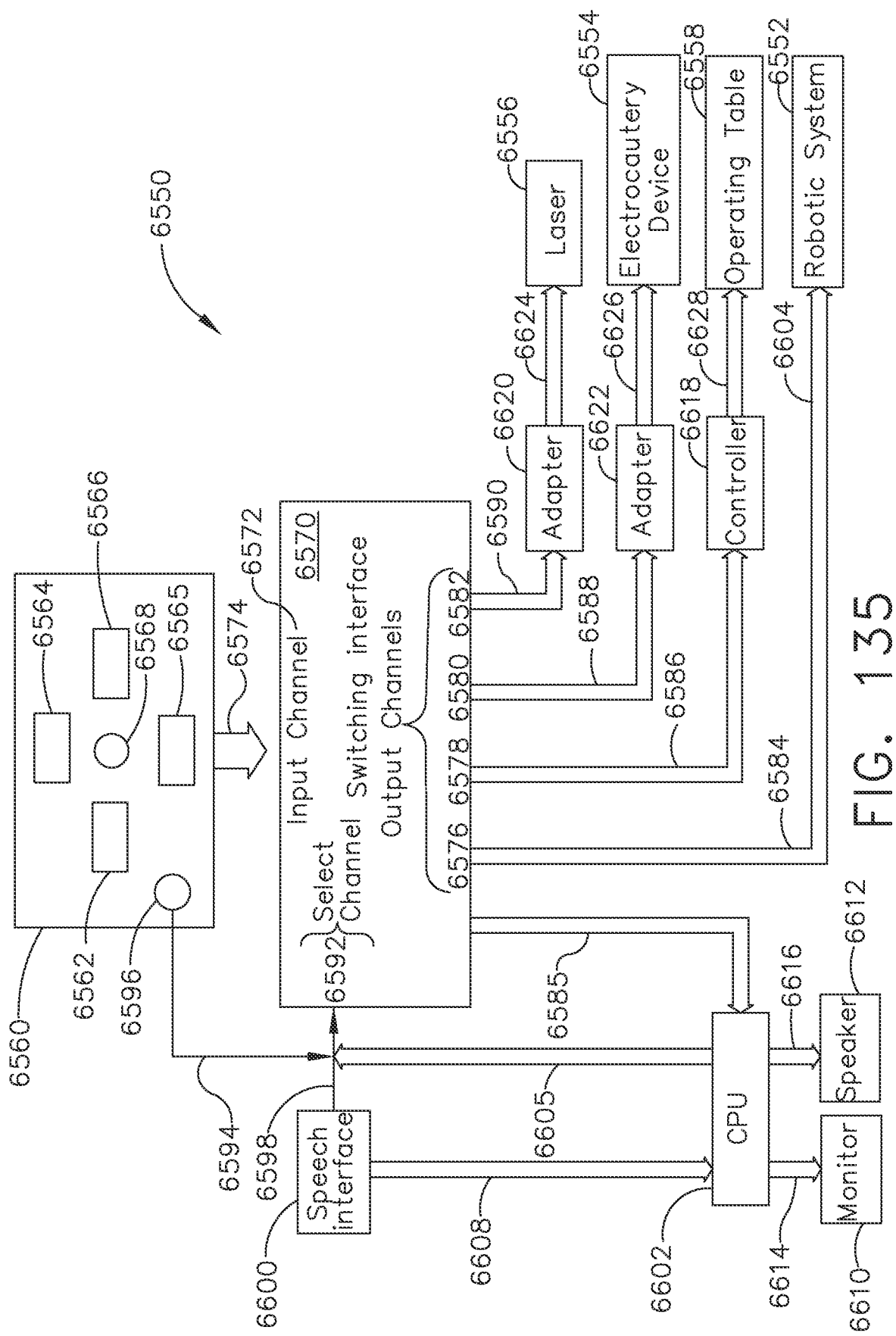

FIG. 135 illustrates a verbal Automated Endoscopic System for Optimal Positioning (AESOP) camera positioning system, in accordance with at least one aspect of the present disclosure.

Figure 136:
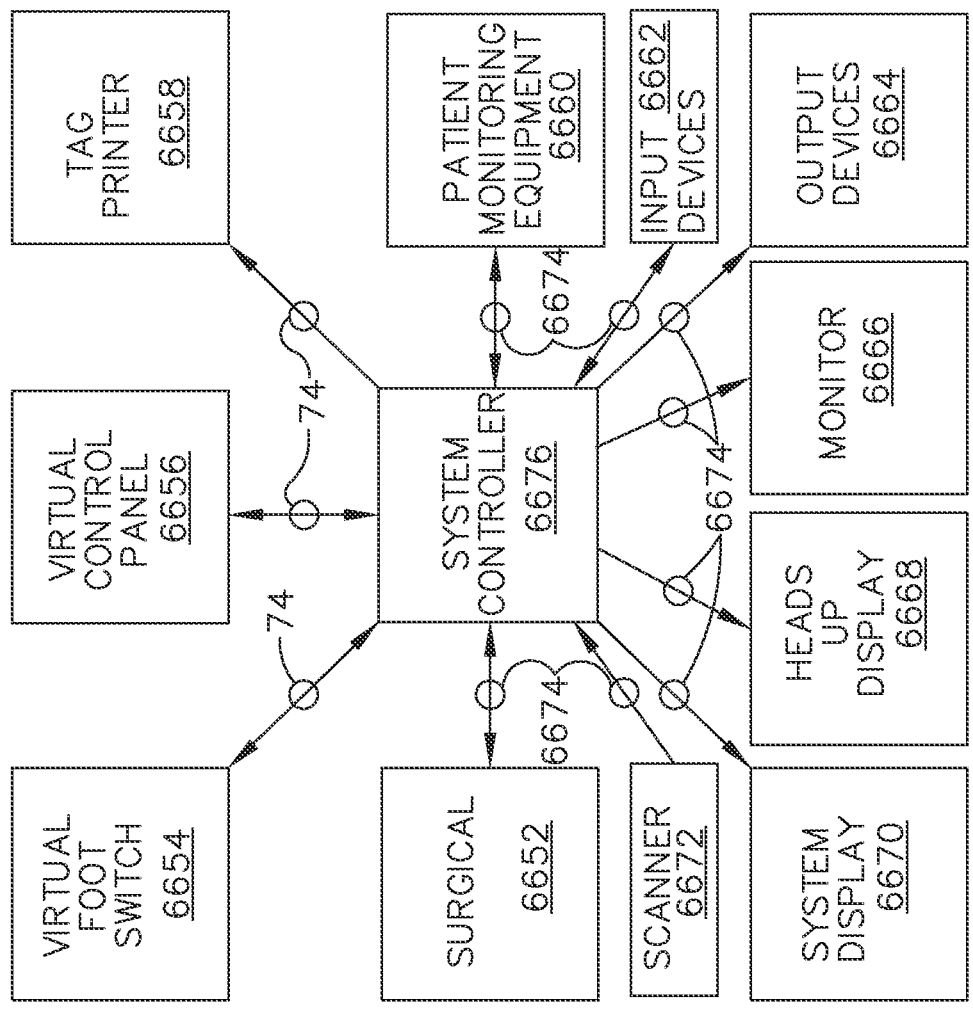

FIG. 136 illustrates a multi-functional surgical control system and switching interface for virtual operating room integration, in accordance with at least one aspect of the present disclosure.

FIG. 137 illustrates a diagram of a beam source and combined beam detector system utilized as a device control mechanism in an operating theater, in accordance with at least one aspect of the present disclosure.

FIGS. 138A-E illustrate various types of sterile field control and data input consoles, in accordance with at least one aspect of the present disclosure, where:

FIG. 138A illustrates a single zone sterile field control and data input console;

FIG. 138B illustrates a multi zone sterile field control and data input console;

FIG. 138C illustrates a tethered sterile field control and data input console;

FIG. 138D illustrates a battery operated sterile field control and data input console; and FIG. 138E illustrates a battery operated sterile field control and data input console.

FIGS. 139A-139B illustrate a sterile field console in use in a sterile field during a surgical procedure, in accordance with at least one aspect of the present disclosure, where:

FIG. 139A shows the sterile field console positioned in the sterile field near two surgeons engaged in an operation; and FIG. 139B shows one of the surgeons tapping the touchscreen of the sterile field console.

Figure 140:
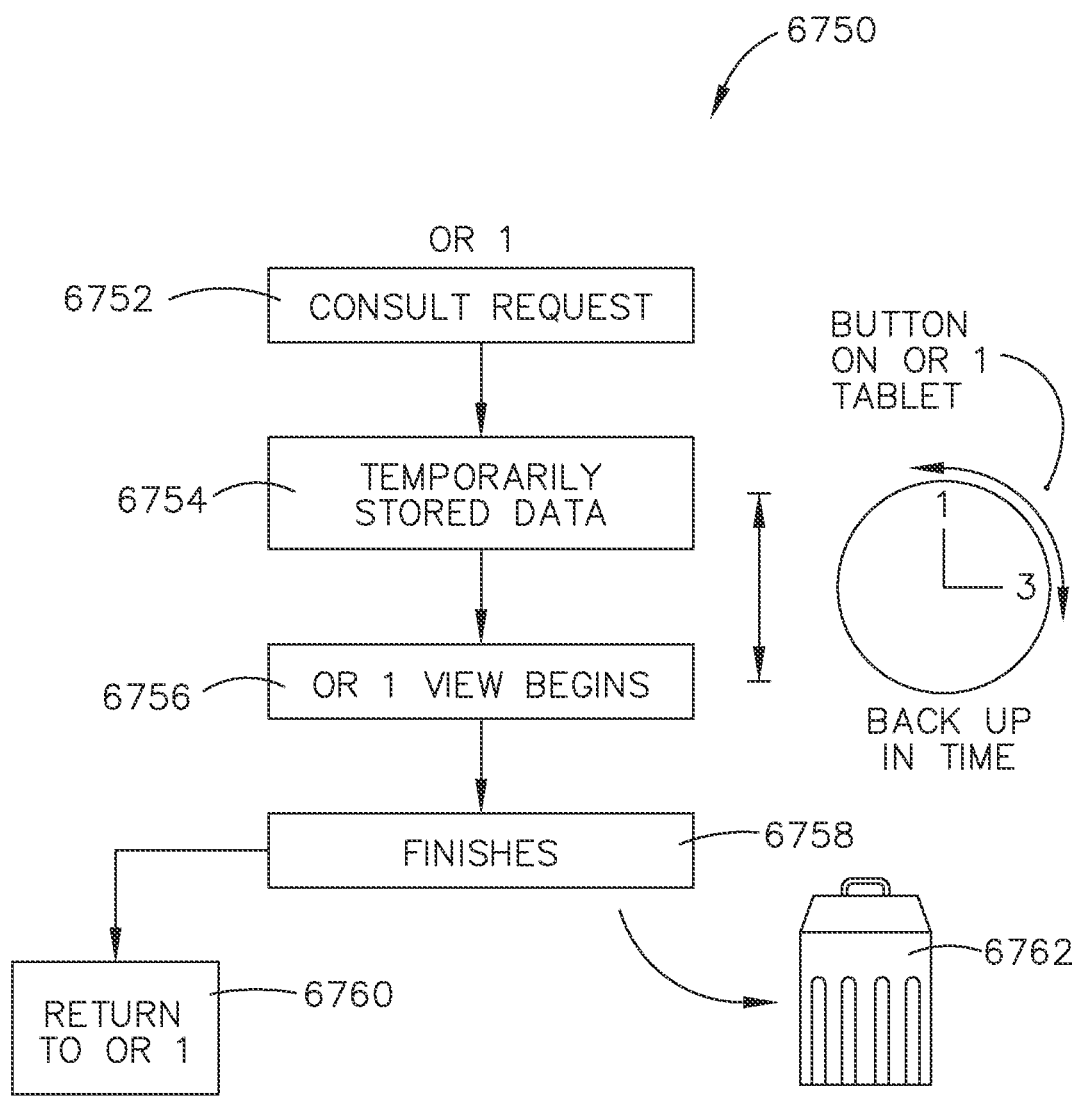

FIG. 140 illustrates a process for accepting consult feeds from another operating room, in accordance with at least one aspect of the present disclosure.

Figure 141:
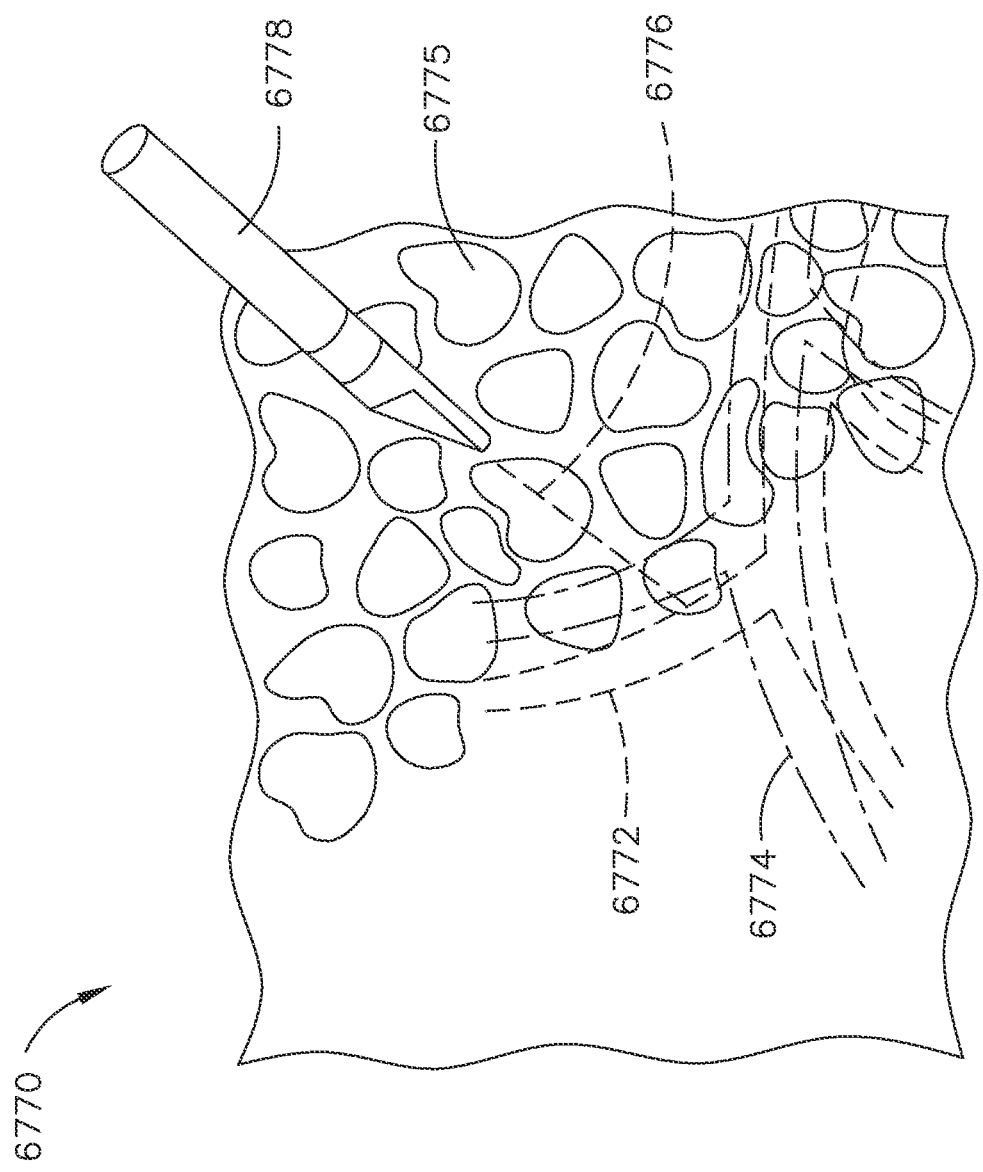

FIG. 141 illustrates a standard technique for estimating vessel path and depth and device trajectory, in accordance with at least one aspect of the present disclosure.

Figure 142A:
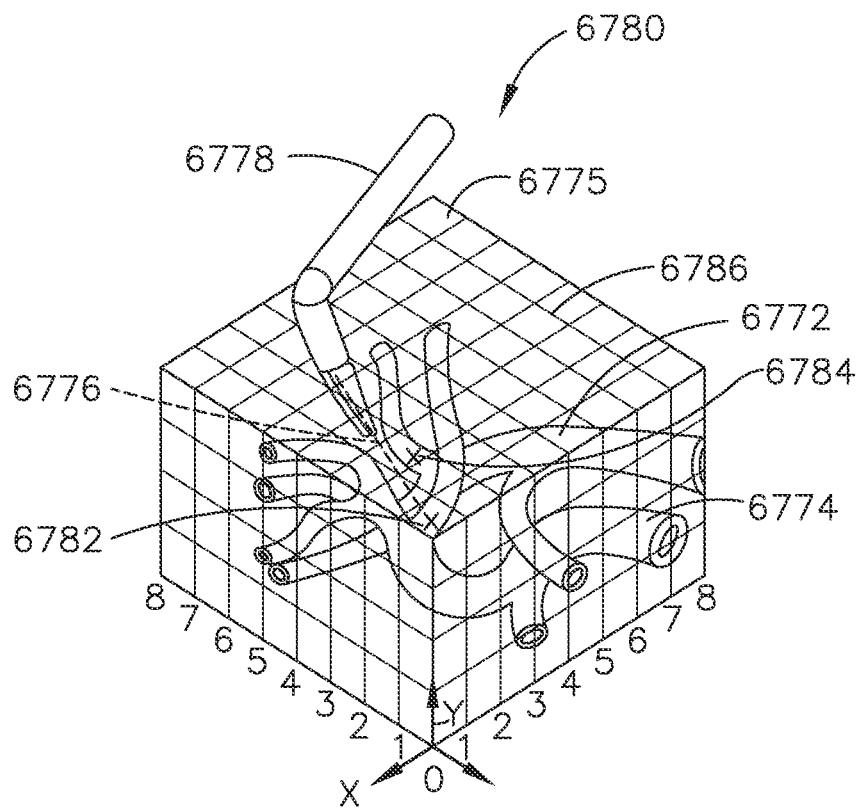
Figure 142B:
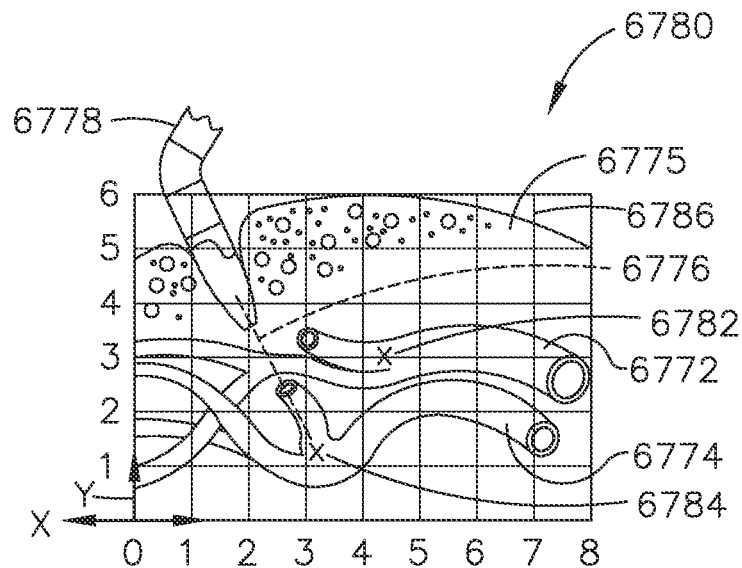
Figure 142C:
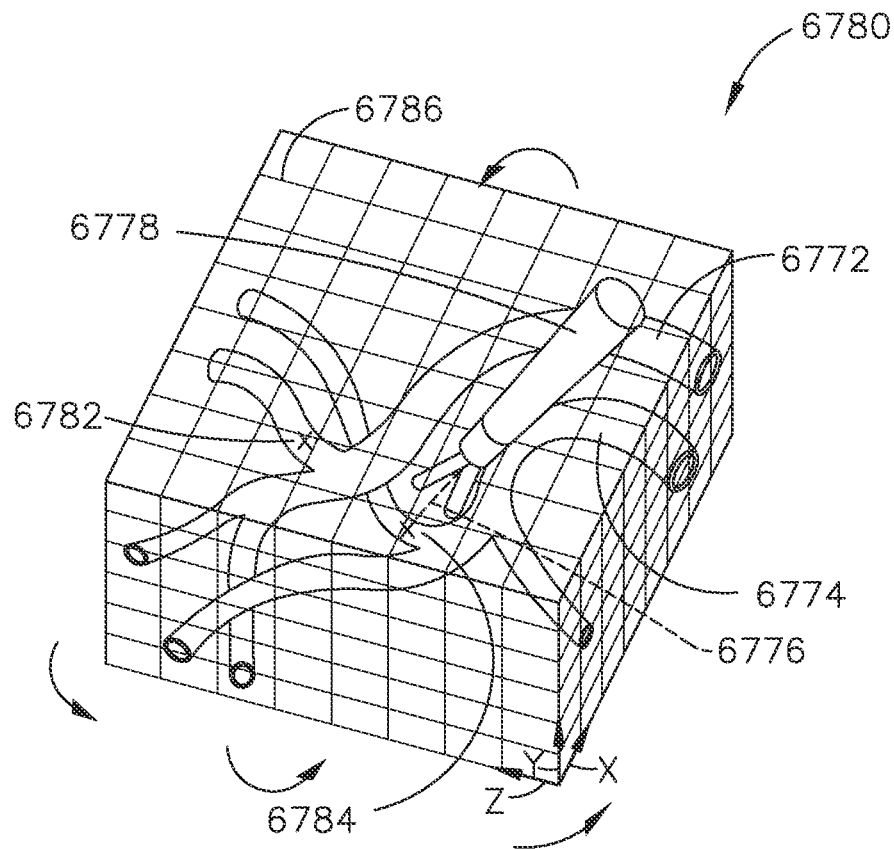

FIGS. 142A-142D illustrate multiple real time views of images of a virtual anatomical detail for dissection, in accordance with at least one aspect of the present disclosure, where:

FIG. 142A is a perspective view of the virtual anatomical detail;

FIG. 142B is a side view of the virtual anatomical detail;

FIG. 142C is a perspective view of the virtual anatomical detail; and

Figure 142D:
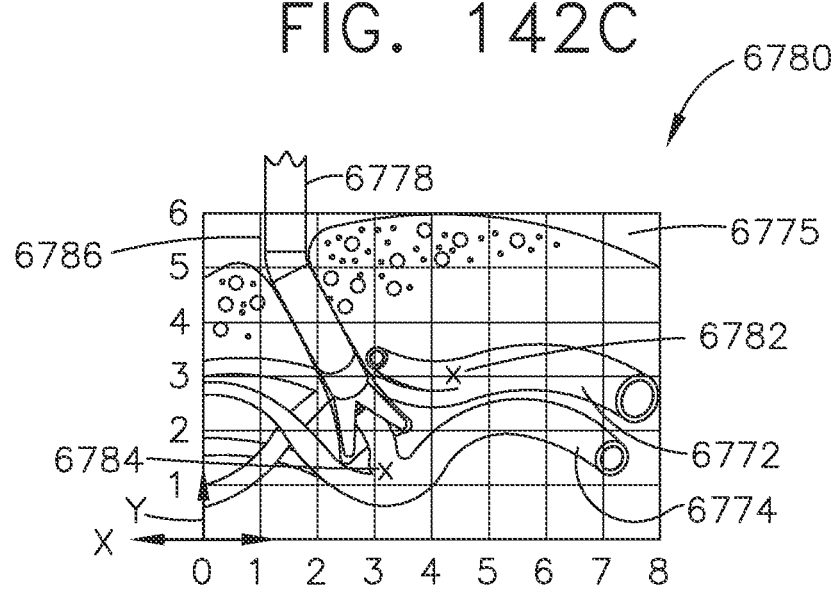

FIG. 142D is a side view of the virtual anatomical detail.

FIGS. 143A-143E illustrate a touchscreen display that may be used within the sterile field, in accordance with at least one aspect of the present disclosure, where:

FIG. 143A illustrates an image of a surgical site displayed on a touchscreen display in portrait mode;

FIG. 143B shows the touchscreen display rotated in landscape mode and the surgeon uses his index finger to scroll the image in the direction of the arrows;

FIG. 143C shows the surgeon using his index finger and thumb to pinch open the image in the direction of the arrows to zoom in;

FIG. 143D shows the surgeon using his index finger and thumb to pinch close the image in the direction of the arrows to zoom out; and FIG. 143E shows the touchscreen display rotated in two directions indicated by arrows to enable the surgeon to view the image in different orientations.

Figure 144:
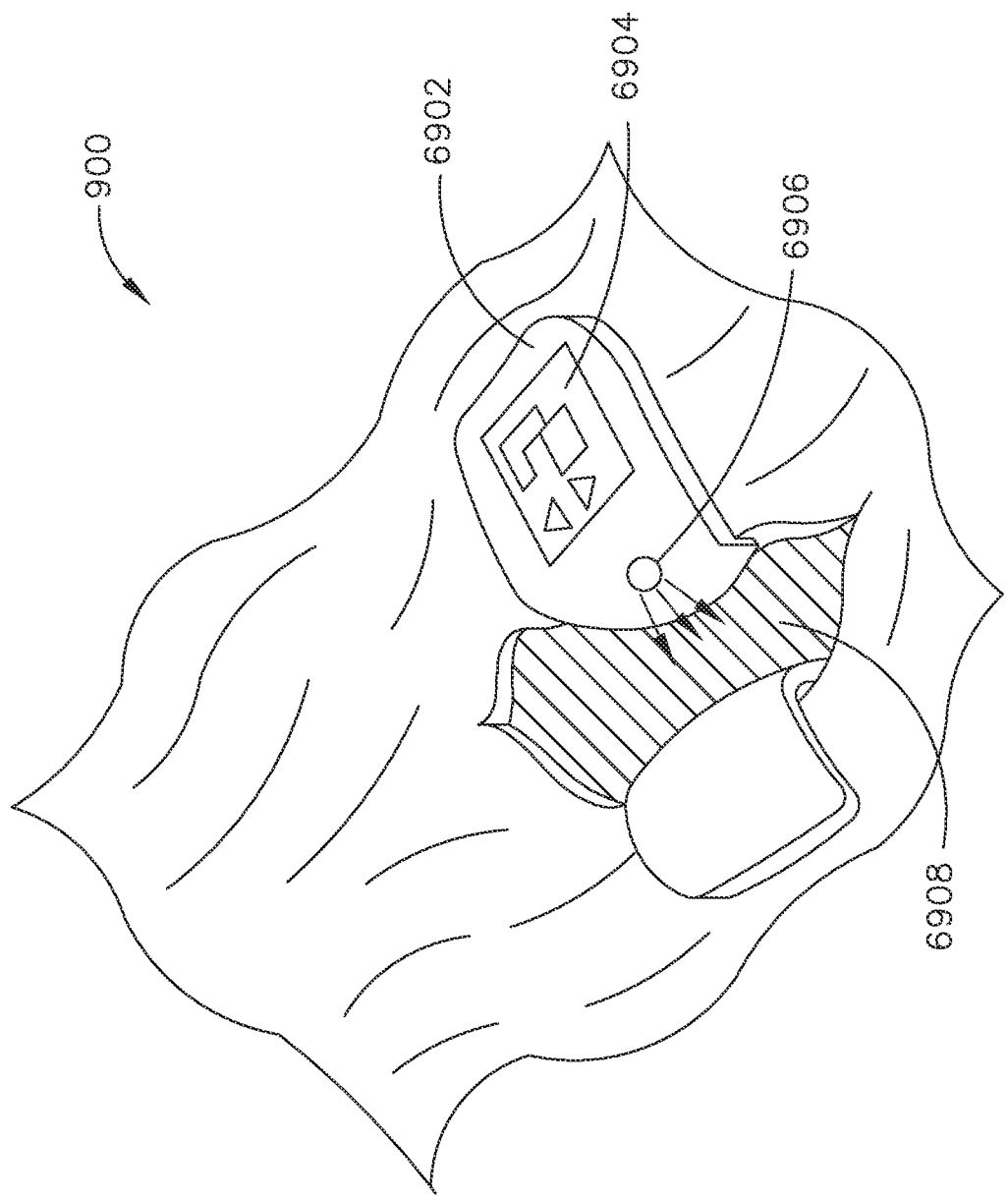

FIG. 144 illustrates a surgical site employing a smart retractor comprising a direct interface control to a surgical hub, in accordance with at least one aspect of the present disclosure.

Figure 145:
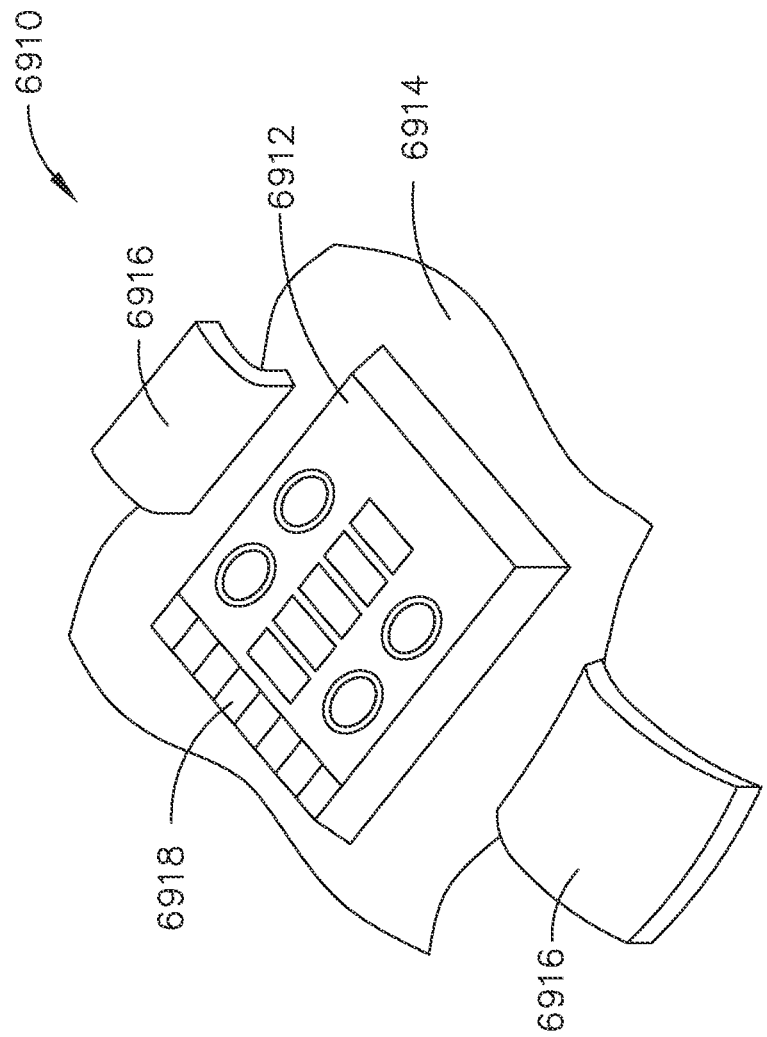

FIG. 145 illustrates a surgical site with a smart flexible sticker display attached to the body of a patient, in accordance with at least one aspect of the present disclosure.

Figure 146:
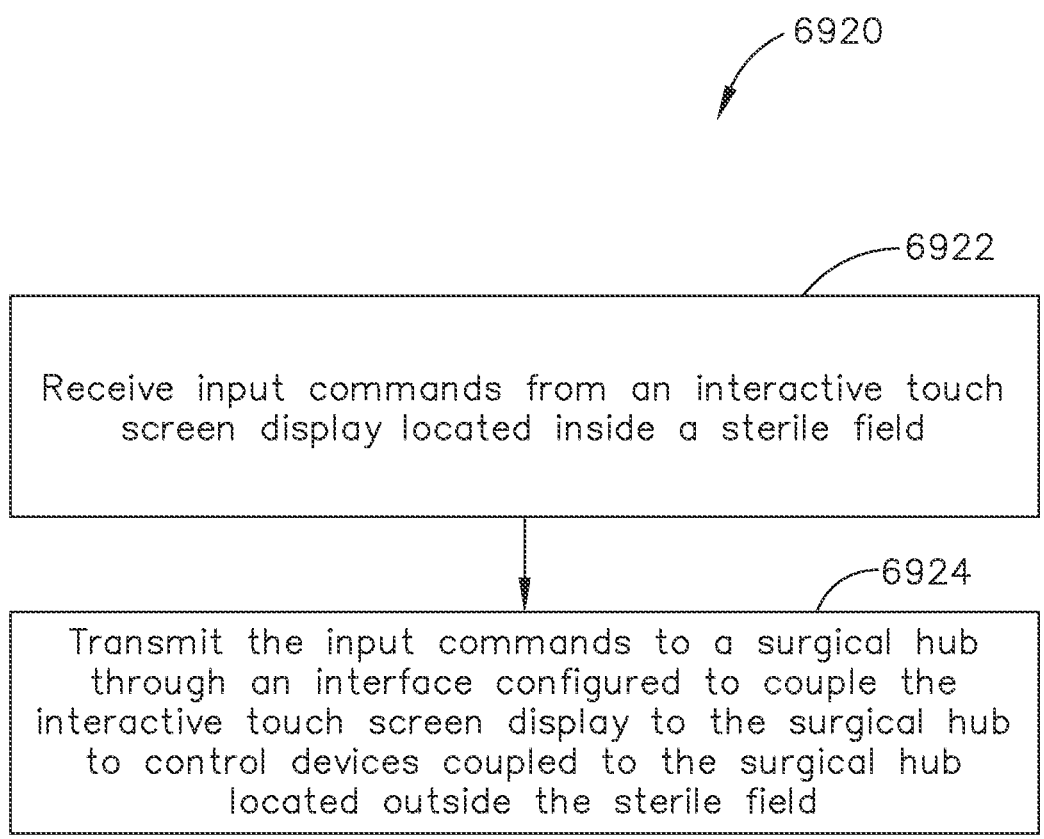

FIG. 146 is a logic flow diagram of a process depicting a control program or a logic configuration to communicate from inside a sterile field to a device located outside the sterile field, in accordance with at least one aspect of the present disclosure.

Figure 147:
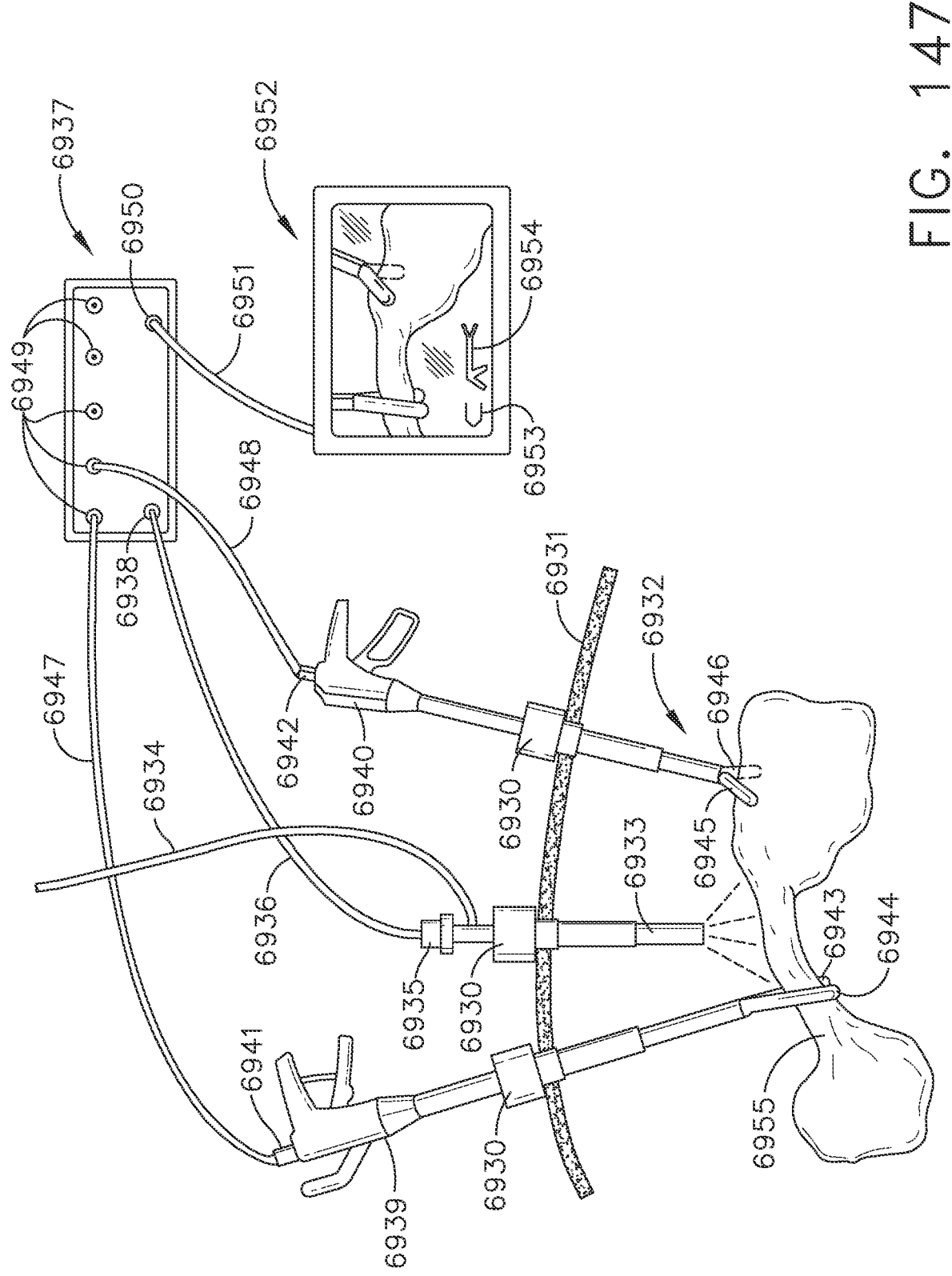

FIG. 147 illustrates a system for performing surgery, in accordance with at least one aspect of the present disclosure.

Figure 148:
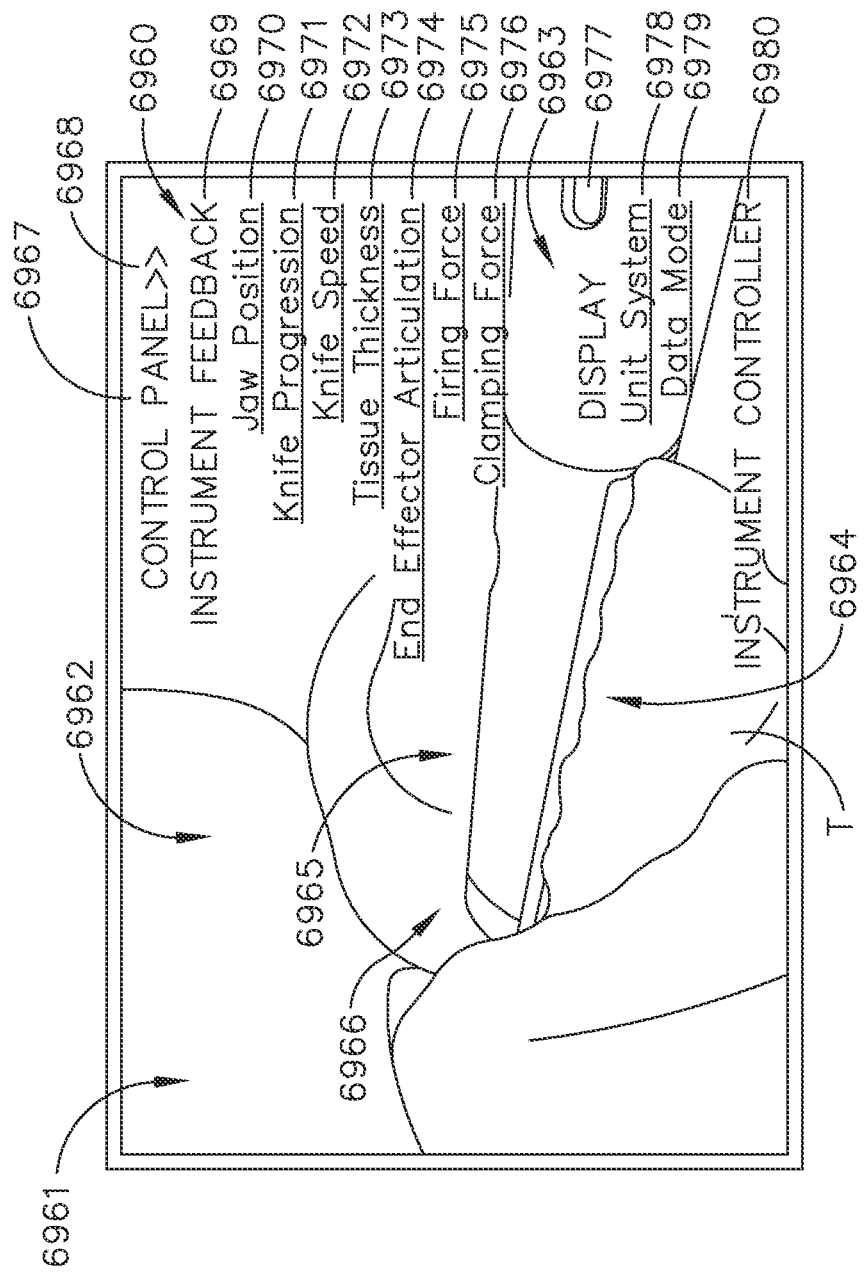

FIG. 148 illustrates a second layer of information overlaying a first layer of information, in accordance with at least one aspect of the present disclosure.

Figure 149:
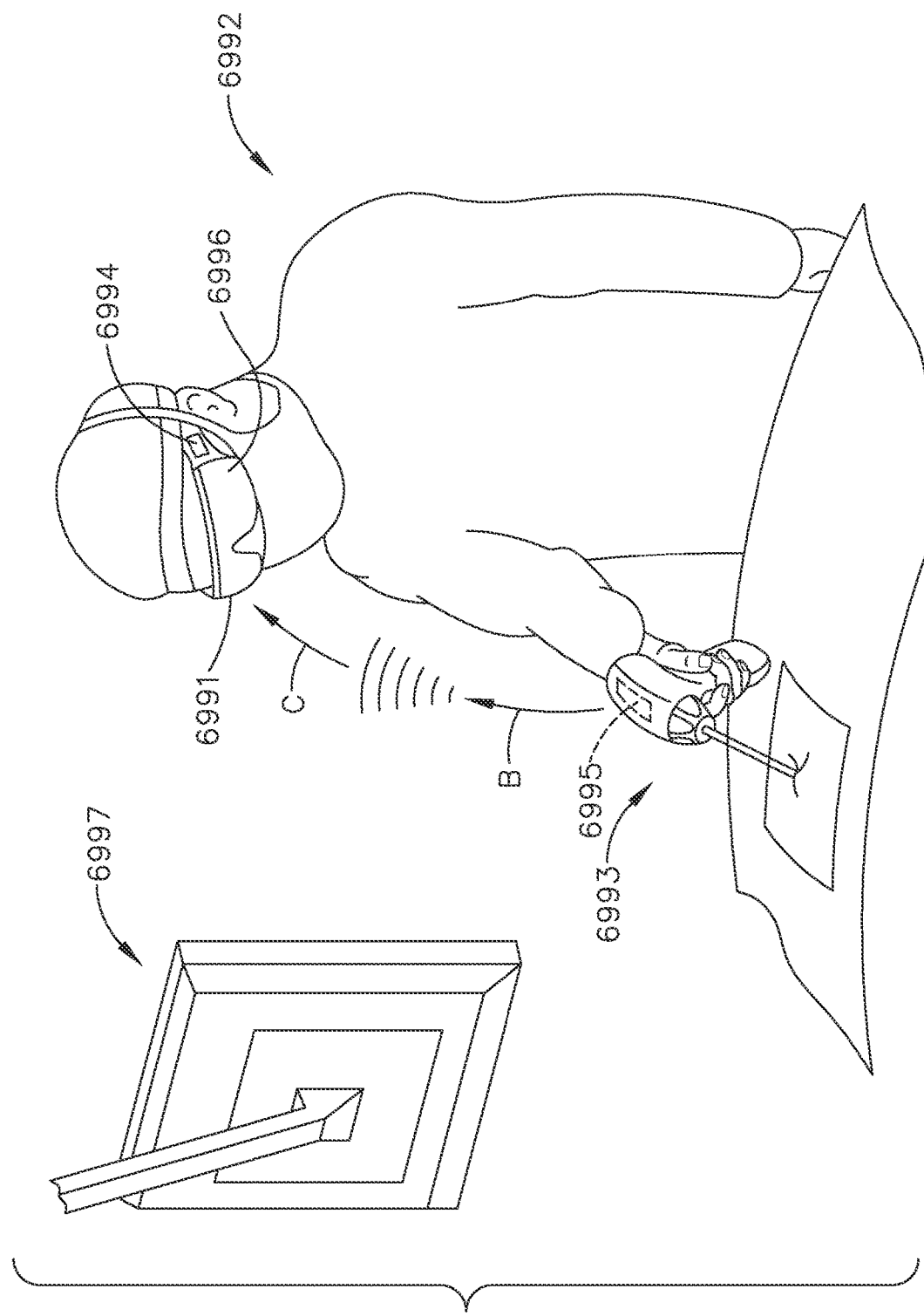

FIG. 149 depicts a perspective view of a surgeon using a surgical instrument that includes a handle assembly housing and a wireless circuit board during a surgical procedure, with the surgeon wearing a set of safety glasses, in accordance with at least one aspect of the present disclosure.

Figure 150:
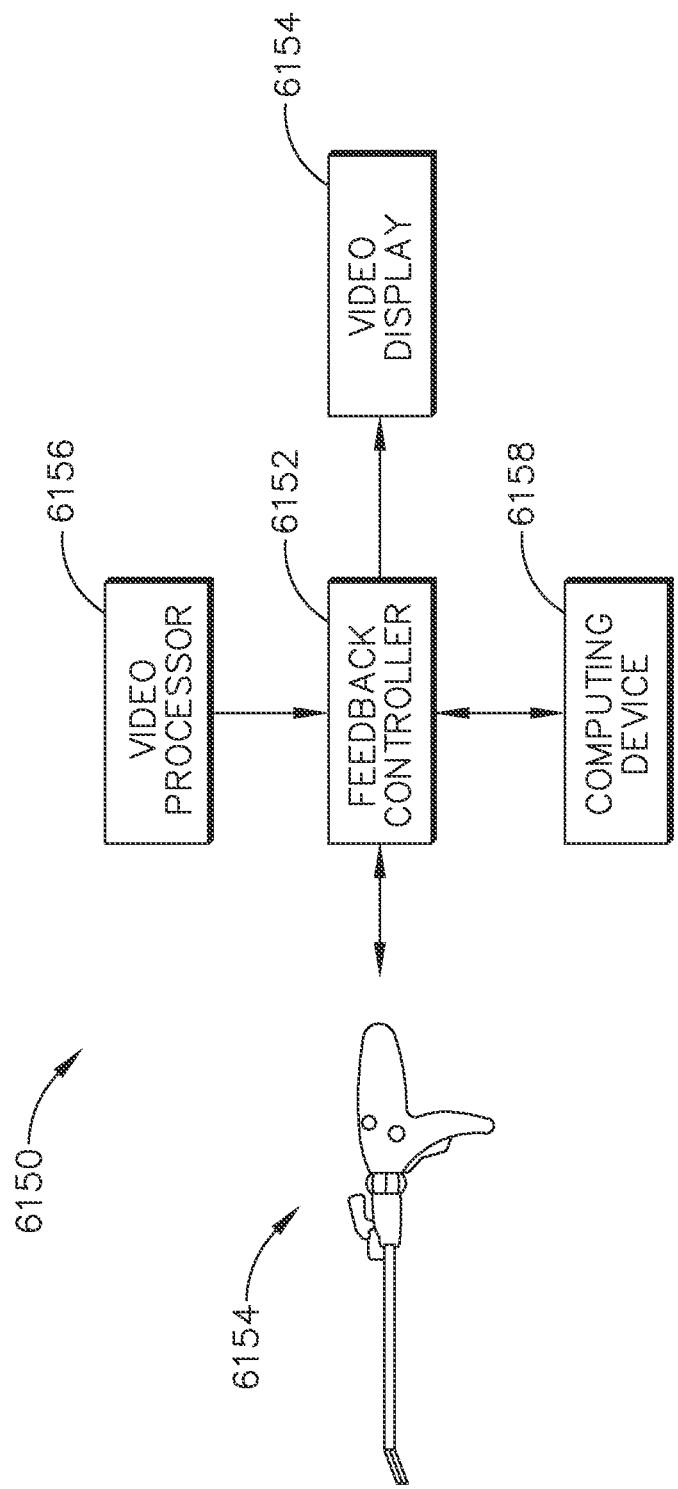

FIG. 150 is a schematic diagram of a feedback control system for controlling a surgical instrument, in accordance with at least one aspect of the present disclosure.

Figure 151:
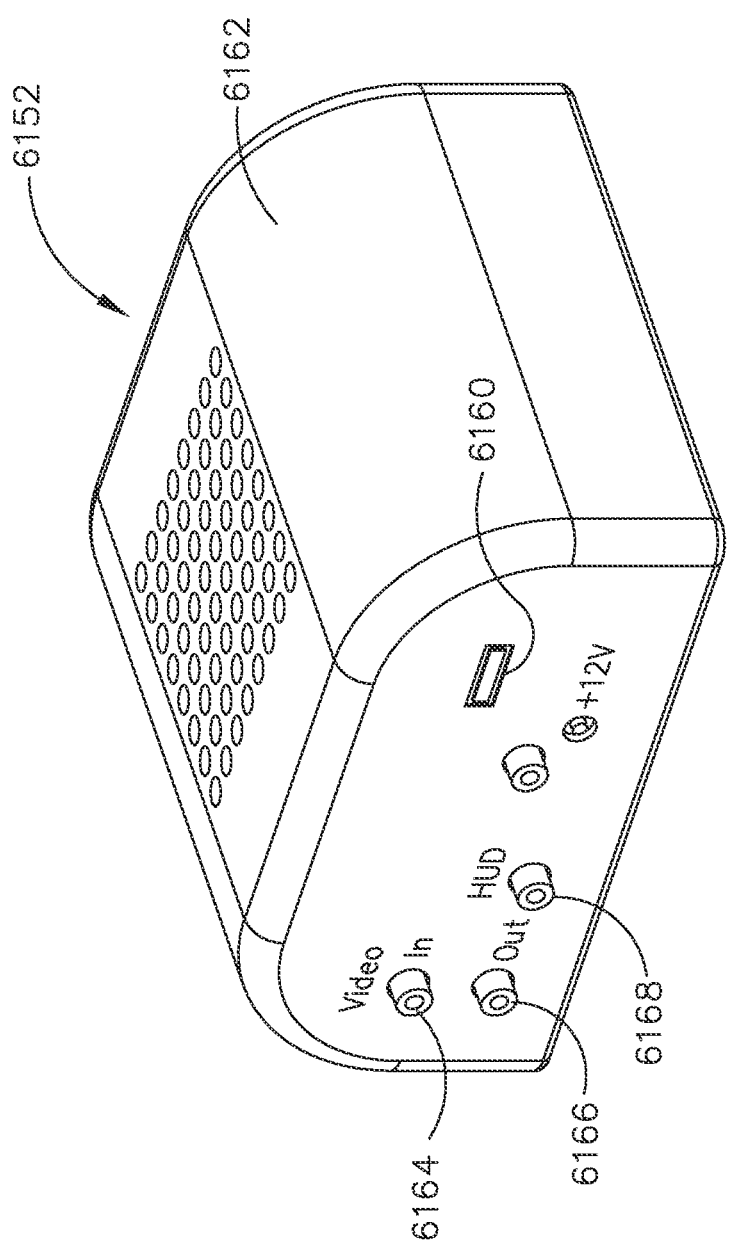

FIG. 151 illustrates a feedback controller that includes an on-screen display module and a heads up display (HUD) module, in accordance with at least one aspect of the present disclosure.

DESCRIPTION

Applicant of the present application owns the following U.S. patent applications, filed on Dec. 4, 2018, the disclosure of each of which is herein incorporated by reference in its entirety:

U.S. patent application Ser. No. 16/209,395, titled METHOD OF HUB COMMUNICATION, now U.S. Pat. No. 11,659,023;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL, now U.S. Pat. No. 11,559,307;

U.S. patent application Ser. No. 16/209,416, titled METHOD OF HUB COMMUNICATION, PROCESSING, DISPLAY, AND CLOUD ANALYTICS, now U.S. Pat. No. 11,576,677;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Pat. No. 11,389,164;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser. No. 16/209,447, titled METHOD FOR SMOKE EVACUATION FOR SURGICAL HUB, now U.S. Patent Application Publication No. 2019/0201045;

U.S. patent application Ser. No. 16/209,453, titled METHOD FOR CONTROLLING SMART ENERGY DEVICES, now U.S. Pat. No. 11,589,888;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,465, titled METHOD FOR ADAPTIVE CONTROL SCHEMES FOR SURGICAL NETWORK CONTROL AND INTERACTION, now U.S. Pat. No. 11,559,308;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Pat. No. 11,871,901;

U.S. patent application Ser. No. 16/209,490, titled METHOD FOR FACILITY DATA COLLECTION AND INTERPRETATION, now U.S. Patent Application Publication No. 2019/0206564; and U.S. patent application Ser. No. 16/209,465, titled METHOD FOR CIRCULAR STAPLER CONTROL ALGORITHM ADJUSTMENT BASED ON SITUATIONAL AWARENESS, now U.S. Pat. No. 11,304,699.

Applicant of the present application owns the following U.S. patent applications, filed on Nov. 6, 2018, the disclosure of each of which is herein incorporated by reference in its entirety:

U.S. patent application Ser. No. 16/182,224, titled SURGICAL NETWORK, INSTRUMENT, AND CLOUD RESPONSES BASED ON VALIDATION OF RECEIVED DATASET AND AUTHENTICATION OF ITS SOURCE AND INTEGRITY, now U.S. Pat. No. 11,308,075;

U.S. patent application Ser. No. 16/182,230, titled SURGICAL SYSTEM FOR PRESENTING INFORMATION INTERPRETED FROM EXTERNAL DATA, now U.S. Patent Application Publication No. 2019/0200980;

U.S. patent application Ser. No. 16/182,233, titled SURGICAL SYSTEMS WITH AUTONOMOUSLY ADJUSTABLE CONTROL PROGRAMS, now U.S. Pat. No. 11,832,899;

U.S. patent application Ser. No. 16/182,239, titled ADJUSTMENT OF DEVICE CONTROL PROGRAMS BASED ON STRATIFIED CONTEXTUAL DATA IN ADDITION TO THE DATA, now U.S. Pat. No. 11,423,007;

U.S. patent application Ser. No. 16/182,243, titled SURGICAL HUB AND MODULAR DEVICE RESPONSE ADJUSTMENT BASED ON SITUATIONAL AWARENESS, now U.S. Pat. No. 11,273,001;

U.S. patent application Ser. No. 16/182,248, titled DETECTION AND ESCALATION OF SECURITY RESPONSES OF SURGICAL INSTRUMENTS TO INCREASING SEVERITY THREATS, now U.S. Pat. No. 10,943,454;

U.S. patent application Ser. No. 16/182,251, titled INTERACTIVE SURGICAL SYSTEM, now U.S. Pat. No. 11,278,281;

U.S. patent application Ser. No. 16/182,260, titled AUTOMATED DATA SCALING, ALIGNMENT, AND ORGANIZING BASED ON PREDEFINED PARAMETERS WITHIN SURGICAL NETWORKS, now U.S. Pat. No. 11,056,244;

U.S. patent application Ser. No. 16/182,267, titled SENSING THE PATIENT POSITION AND CONTACT UTILIZING THE MONO-POLAR RETURN PAD ELECTRODE TO PROVIDE SITUATIONAL AWARENESS TO THE HUB, now U.S. Patent Application Publication No. 2019/0201128;

U.S. patent application Ser. No. 16/182,249, titled POWERED SURGICAL TOOL WITH PREDEFINED ADJUSTABLE CONTROL ALGORITHM FOR CONTROLLING END EFFECTOR PARAMETER, now U.S. Pat. No. 11,234,756;

U.S. patent application Ser. No. 16/182,246, titled ADJUSTMENTS BASED ON AIRBORNE PARTICLE PROPERTIES, now U.S. Pat. No. 11,844,579;

U.S. patent application Ser. No. 16/182,256, titled ADJUSTMENT OF A SURGICAL DEVICE FUNCTION BASED ON SITUATIONAL AWARENESS, now U.S. Pat. No. 11,612,444;

U.S. patent application Ser. No. 16/182,242, titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES, now U.S. Pat. No. 11,257,589;

U.S. patent application Ser. No. 16/182,255, titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES, now U.S. Pat. No. 11,633,237;

U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE, now U.S. Pat. No. 11,304,763;

U.S. patent application Ser. No. 16/182,278, titled COMMUNICATION OF DATA WHERE A SURGICAL NETWORK IS USING CONTEXT OF THE DATA AND REQUIREMENTS OF A RECEIVING SYSTEM/USER TO INFLUENCE INCLUSION OR LINKAGE OF DATA AND METADATA TO ESTABLISH CONTINUITY, now U.S. Patent Application Publication No. 2019/0201130;

U.S. patent application Ser. No. 16/182,290, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, now U.S. Patent Application Publication No. 2019/0201102;

U.S. patent application Ser. No. 16/182,232, titled CONTROL OF A SURGICAL SYSTEM THROUGH A SURGICAL BARRIER, now U.S. Patent Application Publication No. 2019/0201158;

U.S. patent application Ser. No. 16/182,227, titled SURGICAL NETWORK DETERMINATION OF PRIORITIZATION OF COMMUNICATION, INTERACTION, OR PROCESSING BASED ON SYSTEM OR DEVICE NEEDS, now U.S. Pat. No. 10,892,995;

U.S. patent application Ser. No. 16/182,231, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES, now U.S. Pat. No. 10,758,310;

U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING, now U.S. Pat. No. 11,096,693;

U.S. patent application Ser. No. 16/182,234, titled STAPLING DEVICE WITH BOTH COMPULSORY AND DISCRETIONARY LOCKOUTS BASED ON SENSED PARAMETERS, now U.S. Patent Application Publication No. 2019/0200997;

U.S. patent application Ser. No. 16/182,240, titled POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING, now U.S. Patent Application Publication No. 2019/0201034;

U.S. patent application Ser. No. 16/182,235, titled VARIATION OF RADIO FREQUENCY AND ULTRASONIC POWER LEVEL IN COOPERATION WITH VARYING CLAMP ARM PRESSURE TO ACHIEVE PREDEFINED HEAT FLUX OR POWER APPLIED TO TISSUE, now U.S. Pat. No. 11,446,052; and U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, now U.S. Pat. No. 11,419,667.

Applicant of the present application owns the following U.S. patent applications that were filed on Oct. 26, 2018, the disclosure of each of which is herein incorporated by reference in its entirety:

U.S. patent application Ser. No. 16/172,303, titled METHOD FOR OPERATING A POWERED ARTICULATING MULTI-CLIP APPLIER, now U.S. Patent Application Publication No. 2019/0125361;

U.S. patent application Ser. No. 16/172,130, titled CLIP APPLIER COMPRISING INTERCHANGEABLE CLIP RELOADS, now U.S. Pat. No. 11,406,390;

U.S. patent application Ser. No. 16/172,066, titled CLIP APPLIER COMPRISING A MOVABLE CLIP MAGAZINE, now U.S. Pat. No. 11,045,197;

U.S. patent application Ser. No. 16/172,078, titled CLIP APPLIER COMPRISING A ROTATABLE CLIP MAGAZINE, now U.S. Pat. No. 11,123,070;

U.S. patent application Ser. No. 16/172,087, titled CLIP APPLIER COMPRISING CLIP ADVANCING SYSTEMS, now U.S. Pat. No. 11,026,687;

U.S. patent application Ser. No. 16/172,094, titled CLIP APPLIER COMPRISING A CLIP CRIMPING SYSTEM, now U.S. Pat. No. 11,317,919;

U.S. patent application Ser. No. 16/172,128, titled CLIP APPLIER COMPRISING A RECIPROCATING CLIP ADVANCING MEMBER, now U.S. Pat. No. 11,413,042;

U.S. patent application Ser. No. 16/172,168, titled CLIP APPLIER COMPRISING A MOTOR CONTROLLER, now U.S. Pat. No. 11,141,160;

U.S. patent application Ser. No. 16/172,164, titled SURGICAL SYSTEM COMPRISING A SURGICAL TOOL AND A SURGICAL HUB, now U.S. Pat. No. 11,229,436;

U.S. patent application Ser. No. 16/172,328, titled METHOD OF HUB COMMUNICATION WITH SURGICAL INSTRUMENT SYSTEMS, now U.S. Pat. No. 11,504,192;

U.S. patent application Ser. No. 16/172,280, titled METHOD FOR PRODUCING A SURGICAL INSTRUMENT COMPRISING A SMART ELECTRICAL SYSTEM, now U.S. Pat. No. 11,510,741;

U.S. patent application Ser. No. 16/172,219, titled METHOD OF HUB COMMUNICATION WITH SURGICAL INSTRUMENT SYSTEMS, now U.S. Pat. No. 11,219,510;

U.S. patent application Ser. No. 16/172,248, titled METHOD OF HUB COMMUNICATION WITH SURGICAL INSTRUMENT SYSTEMS, now U.S. Pat. No. 11,311,342;

U.S. patent application Ser. No. 16/172,198, titled METHOD OF HUB COMMUNICATION WITH SURGICAL INSTRUMENT SYSTEMS, now U.S. Pat. No. 11,564,756; and U.S. patent application Ser. No. 16/172,155, titled METHOD OF HUB COMMUNICATION WITH SURGICAL INSTRUMENT SYSTEMS, now U.S. Pat. No. 11,801,098.

Applicant of the present application owns the following U.S. patent applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR, now U.S. Patent Application Publication No. 2019/0201073;

U.S. patent application Ser. No. 16/115,205, titled TEMPERATURE CONTROL OF ULTRASONIC END EFFECTOR AND CONTROL SYSTEM THEREFOR, now U.S. Patent Application Publication No. 2019/0201036;

U.S. patent application Ser. No. 16/115,233, titled RADIO FREQUENCY ENERGY DEVICE FOR DELIVERING COMBINED ELECTRICAL SIGNALS, now U.S. Patent Application Publication No. 2019/0201091;

U.S. patent application Ser. No. 16/115,208, titled CONTROLLING AN ULTRASONIC SURGICAL INSTRUMENT ACCORDING TO TISSUE LOCATION, now U.S. Patent Application Publication No. 2019/0201037;

U.S. patent application Ser. No. 16/115,220, titled CONTROLLING ACTIVATION OF AN ULTRASONIC SURGICAL INSTRUMENT ACCORDING TO THE PRESENCE OF TISSUE, now U.S. Patent Application Publication No. 2019/0201040;

U.S. patent application Ser. No. 16/115,232, titled DETERMINING TISSUE COMPOSITION VIA AN ULTRASONIC SYSTEM, now U.S. Patent Application Publication No. 2019/0201038;

U.S. patent application Ser. No. 16/115,239, titled DETERMINING THE STATE OF AN ULTRASONIC ELECTROMECHANICAL SYSTEM ACCORDING TO FREQUENCY SHIFT, now U.S. Patent Application Publication No. 2019/0201042;

U.S. patent application Ser. No. 16/115,247, titled DETERMINING THE STATE OF AN ULTRASONIC END EFFECTOR, now U.S. Patent Application Publication No. 2019/0274716;

U.S. patent application Ser. No. 16/115,211, titled SITUATIONAL AWARENESS OF ELECTROSURGICAL SYSTEMS, now U.S. Patent Application Publication No. 2019/0201039;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT, now U.S. Patent Application Publication No. 2019/0201075;

U.S. patent application Ser. No. 16/115,240, titled DETECTION OF END EFFECTOR EMERSION IN LIQUID, now U.S. Patent Application Publication No. 2019/0201043;

U.S. patent application Ser. No. 16/115,249, titled INTERRUPTION OF ENERGY DUE TO INADVERTENT CAPACITIVE COUPLING, now U.S. Patent Application Publication No. 2019/0201077;

U.S. patent application Ser. No. 16/115,256, titled INCREASING RADIO FREQUENCY TO CREATE PAD-LESS MONOPOLAR LOOP, now U.S. Patent Application Publication No. 2019/0201092;

U.S. patent application Ser. No. 16/115,223, titled BIPOLAR COMBINATION DEVICE THAT AUTOMATICALLY ADJUSTS PRESSURE BASED ON ENERGY MODALITY, now U.S. Patent Application Publication No. 2019/0201074; and U.S. patent application Ser. No. 16/115,238, titled ACTIVATION OF ENERGY DEVICES, now U.S. Patent Application Publication No. 2019/0201041.

Applicant of the present application owns the following U.S. patent applications, filed on Aug. 24, 2018, the disclosure of each of which is herein incorporated by reference in its entirety:

U.S. patent application Ser. No. 16/112,129, titled SURGICAL SUTURING INSTRUMENT CONFIGURED TO MANIPULATE TISSUE USING MECHANICAL AND ELECTRICAL POWER, now U.S. Patent Application Publication No. 2019/0125431;

U.S. patent application Ser. No. 16/112,155, titled SURGICAL SUTURING INSTRUMENT COMPRISING A CAPTURE WIDTH WHICH IS LARGER THAN TROCAR DIAMETER, now U.S. Patent Application Publication No. 2019/0125335;

U.S. patent application Ser. No. 16/112,168, titled SURGICAL SUTURING INSTRUMENT COMPRISING A NON-CIRCULAR NEEDLE, now U.S. Patent Application Publication No. 2019/0125336;

U.S. patent application Ser. No. 16/112,180, titled ELECTRICAL POWER OUTPUT CONTROL BASED ON MECHANICAL FORCES, now U.S. Patent Application Publication No. 2019/0125432;

U.S. patent application Ser. No. 16/112,193, titled REACTIVE ALGORITHM FOR SURGICAL SYSTEM, now U.S. Pat. No. 10,932,806;

U.S. patent application Ser. No. 16/112,099, titled SURGICAL INSTRUMENT COMPRISING AN ADAPTIVE ELECTRICAL SYSTEM, now U.S. Patent Application Publication No. 2019/0125378;

U.S. patent application Ser. No. 16/112,112, titled CONTROL SYSTEM ARRANGEMENTS FOR A MODULAR SURGICAL INSTRUMENT, now U.S. Patent Application Publication No. 2019/0125320;

U.S. patent application Ser. No. 16/112,119, titled ADAPTIVE CONTROL PROGRAMS FOR A SURGICAL SYSTEM COMPRISING MORE THAN ONE TYPE OF CARTRIDGE, now U.S. Patent Application Publication No. 2019/0125338;

U.S. patent application Ser. No. 16/112,097, titled SURGICAL INSTRUMENT SYSTEMS COMPRISING BATTERY ARRANGEMENTS, now U.S. Patent Application Publication No. 2019/0125377;

U.S. patent application Ser. No. 16/112,109, titled SURGICAL INSTRUMENT SYSTEMS COMPRISING HANDLE ARRANGEMENTS, now U.S. Patent Application Publication No. 2019/0125388;

U.S. patent application Ser. No. 16/112,114, titled SURGICAL INSTRUMENT SYSTEMS COMPRISING FEEDBACK MECHANISMS, now U.S. Pat. No. 10,980,560;

U.S. patent application Ser. No. 16/112,117, titled SURGICAL INSTRUMENT SYSTEMS COMPRISING LOCKOUT MECHANISMS, now U.S. Patent Application Publication No. 2019/0125476;

U.S. patent application Ser. No. 16/112,095, titled SURGICAL INSTRUMENTS COMPRISING A LOCKABLE END EFFECTOR SOCKET, now U.S. Patent Application Publication No. 2019/0125387;

U.S. patent application Ser. No. 16/112,121, titled SURGICAL INSTRUMENTS COMPRISING A SHIFTING MECHANISM, now U.S. Patent Application Publication No. 2019/0125389;

U.S. patent application Ser. No. 16/112,151, titled SURGICAL INSTRUMENTS COMPRISING A SYSTEM FOR ARTICULATION AND ROTATION COMPENSATION, now U.S. Pat. No. 10,772,651;

U.S. patent application Ser. No. 16/112,154, titled SURGICAL INSTRUMENTS COMPRISING A BIASED SHIFTING MECHANISM, now U.S. Patent Application Publication No. 2019/0125321;

U.S. patent application Ser. No. 16/112,226, titled SURGICAL INSTRUMENTS COMPRISING AN ARTICULATION DRIVE THAT PROVIDES FOR HIGH ARTICULATION ANGLES, now U.S. Patent Application Publication No. 2019/0125379;

U.S. patent application Ser. No. 16/112,062, titled SURGICAL DISSECTORS AND MANUFACTURING TECHNIQUES, now U.S. Pat. No. 10,959,744;

U.S. patent application Ser. No. 16/112,098, titled SURGICAL DISSECTORS CONFIGURED TO APPLY MECHANICAL AND ELECTRICAL ENERGY, now U.S. Patent Application Publication No. 2019/0125430;

U.S. patent application Ser. No. 16/112,237, titled SURGICAL CLIP APPLIER CONFIGURED TO STORE CLIPS IN A STORED STATE, now U.S. Patent Application Publication No. 2019/0125347;

U.S. patent application Ser. No. 16/112,245, titled SURGICAL CLIP APPLIER COMPRISING AN EMPTY CLIP CARTRIDGE LOCKOUT, now U.S. Patent Application Publication No. 2019/0125352;

U.S. patent application Ser. No. 16/112,249, titled SURGICAL CLIP APPLIER COMPRISING AN AUTOMATIC CLIP FEEDING SYSTEM, now U.S. Patent Application Publication No. 2019/0125353;

U.S. patent application Ser. No. 16/112,253, titled SURGICAL CLIP APPLIER COMPRISING ADAPTIVE FIRING CONTROL, now U.S. Patent Application Publication No. 2019/0125348; and U.S. patent application Ser. No. 16/112,257, titled SURGICAL CLIP APPLIER COMPRISING ADAPTIVE CONTROL IN RESPONSE TO A STRAIN GAUGE CIRCUIT, now U.S. Patent Application Publication No. 2019/0125354.

Applicant of the present application owns the following U.S. patent applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS, now U.S. Patent Application Publication No. 2019/0201090;

U.S. patent application Ser. No. 16/024,057, titled CONTROLLING A SURGICAL INSTRUMENT ACCORDING TO SENSED CLOSURE PARAMETERS, now U.S. Pat. No. 10,695,081;

U.S. patent application Ser. No. 16/024,067, titled SYSTEMS FOR ADJUSTING END EFFECTOR PARAMETERS BASED ON PERIOPERATIVE INFORMATION, now U.S. Pat. No. 10,595,887;

U.S. patent application Ser. No. 16/024,075, titled SAFETY SYSTEMS FOR SMART POWERED SURGICAL STAPLING, now U.S. Patent Application Publication No. 2019/0201146;

U.S. patent application Ser. No. 16/024,083, titled SAFETY SYSTEMS FOR SMART POWERED SURGICAL STAPLING, now U.S. Patent Application Publication No. 2019/0200984;

U.S. patent application Ser. No. 16/024,094, titled SURGICAL SYSTEMS FOR DETECTING END EFFECTOR TISSUE DISTRIBUTION IRREGULARITIES, now U.S. Patent Application Publication No. 2019/0201020;

U.S. patent application Ser. No. 16/024,138, titled SYSTEMS FOR DETECTING PROXIMITY OF SURGICAL END EFFECTOR TO CANCEROUS TISSUE, now U.S. Patent Application Publication No. 2019/0200985;

U.S. patent application Ser. No. 16/024,150, titled SURGICAL INSTRUMENT CARTRIDGE SENSOR ASSEMBLIES, now U.S. Patent Application Publication No. 2019/0200986;

U.S. patent application Ser. No. 16/024,160, titled VARIABLE OUTPUT CARTRIDGE SENSOR ASSEMBLY, now U.S. Patent Application Publication No. 2019/0200987;

U.S. patent application Ser. No. 16/024,124, titled SURGICAL INSTRUMENT HAVING A FLEXIBLE ELECTRODE, now U.S. Patent Application Publication No. 2019/0201079;

U.S. patent application Ser. No. 16/024,132, titled SURGICAL INSTRUMENT HAVING A FLEXIBLE CIRCUIT, now U.S. Patent Application Publication No. 2019/0201021;

U.S. patent application Ser. No. 16/024,141, titled SURGICAL INSTRUMENT WITH A TISSUE MARKING ASSEMBLY, now U.S. Patent Application Publication No. 2019/0201159;

U.S. patent application Ser. No. 16/024,162, titled SURGICAL SYSTEMS WITH PRIORITIZED DATA TRANSMISSION CAPABILITIES, now U.S. Patent Application Publication No. 2019/0200988;

U.S. patent application Ser. No. 16/024,066, titled SURGICAL EVACUATION SENSING AND MOTOR CONTROL, now U.S. Patent Application Publication No. 2019/0201082;

U.S. patent application Ser. No. 16/024,096, titled SURGICAL EVACUATION SENSOR ARRANGEMENTS, now U.S. Patent Application Publication No. 2019/0201083;

U.S. patent application Ser. No. 16/024,116, titled SURGICAL EVACUATION FLOW PATHS, now U.S. Patent Application Publication No. 2019/0201084;

U.S. patent application Ser. No. 16/024,149, titled SURGICAL EVACUATION SENSING AND GENERATOR CONTROL, now U.S. Patent Application Publication No. 2019/0201085;

U.S. patent application Ser. No. 16/024,180, titled SURGICAL EVACUATION SENSING AND DISPLAY, now U.S. Patent Application Publication No. 2019/0201086;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM, now U.S. Pat. No. 10,755,813;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM, now U.S. Patent Application Publication No. 2019/0201087;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE, now U.S. Pat. No. 10,898,622; and U.S. patent application Ser. No. 16/024,273, titled DUAL IN-SERIES LARGE AND SMALL DROPLET FILTERS, now U.S. Patent Application Publication No. 2019/0201597.

Applicant of the present application owns the following U.S. patent applications, filed on Mar. 29, 2018, the disclosure of each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES, now U.S. Pat. No. 10,944,728;

U.S. patent application Ser. No. 15/940,648, titled INTERACTIVE SURGICAL SYSTEMS WITH CONDITION HANDLING OF DEVICES AND DATA CAPABILITIES, now U.S. Patent Application Publication No. 2019/0206004;

U.S. patent application Ser. No. 15/940,656, titled SURGICAL HUB COORDINATION OF CONTROL AND COMMUNICATION OF OPERATING ROOM DEVICES, now U.S. Patent Application Publication No. 2019/0201141;

U.S. patent application Ser. No. 15/940,666, titled SPATIAL AWARENESS OF SURGICAL HUBS IN OPERATING ROOMS, now U.S. Patent Application Publication No. 2019/0206551;

U.S. patent application Ser. No. 15/940,670, titled COOPERATIVE UTILIZATION OF DATA DERIVED FROM SECONDARY SOURCES BY INTELLIGENT SURGICAL HUBS, now U.S. Patent Application Publication No. 2019/0201116;

U.S. patent application Ser. No. 15/940,677, titled SURGICAL HUB CONTROL ARRANGEMENTS, now U.S. Pat. No. 10,987,178;

U.S. patent application Ser. No. 15/940,632, titled DATA STRIPPING METHOD TO INTERROGATE PATIENT RECORDS AND CREATE ANONYMIZED RECORD, now U.S. Patent Application Publication No. 2019/0205566;

U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS, now U.S. Patent Application Publication No. 2019/0200863;

U.S. patent application Ser. No. 15/940,645, titled SELF DESCRIBING DATA PACKETS GENERATED AT AN ISSUING INSTRUMENT, now U.S. Pat. No. 10,892,899;

U.S. patent application Ser. No. 15/940,649, titled DATA PAIRING TO INTERCONNECT A DEVICE MEASURED PARAMETER WITH AN OUTCOME, now U.S. Patent Application Publication No. 2019/0205567;

U.S. patent application Ser. No. 15/940,654, titled SURGICAL HUB SITUATIONAL AWARENESS, now U.S. Patent Application Publication No. 2019/0201140;

U.S. patent application Ser. No. 15/940,663, titled SURGICAL SYSTEM DISTRIBUTED PROCESSING, now U.S. Patent Application Publication No. 2019/0201033;

U.S. patent application Ser. No. 15/940,668, titled AGGREGATION AND REPORTING OF SURGICAL HUB DATA, now U.S. Patent Application Publication No. 2019/0201115;

U.S. patent application Ser. No. 15/940,671, titled SURGICAL HUB SPATIAL AWARENESS TO DETERMINE DEVICES IN OPERATING THEATER, now U.S. Patent Application Publication No. 2019/0201104;

U.S. patent application Ser. No. 15/940,686, titled DISPLAY OF ALIGNMENT OF STAPLE CARTRIDGE TO PRIOR LINEAR STAPLE LINE, now U.S. Patent Application Publication No. 2019/0201105;

U.S. patent application Ser. No. 15/940,700, titled STERILE FIELD INTERACTIVE CONTROL DISPLAYS, now U.S. Patent Application Publication No. 2019/0205001;

U.S. patent application Ser. No. 15/940,629, titled COMPUTER IMPLEMENTED INTERACTIVE SURGICAL SYSTEMS, now U.S. Patent Application Publication No. 2019/0201112;

U.S. patent application Ser. No. 15/940,704, titled USE OF LASER LIGHT AND RED-GREEN-BLUE COLORATION TO DETERMINE PROPERTIES OF BACK SCATTERED LIGHT, now U.S. Patent Application Publication No. 2019/0206050;

U.S. patent application Ser. No. 15/940,722, titled CHARACTERIZATION OF TISSUE IRREGULARITIES THROUGH THE USE OF MONO-CHROMATIC LIGHT REFRACTIVITY, now U.S. Patent Application Publication No. 2019/0200905;

U.S. patent application Ser. No. 15/940,742, titled DUAL CMOS ARRAY IMAGING, now U.S. Patent Application Publication No. 2019/0200906;

U.S. patent application Ser. No. 15/940,636, titled ADAPTIVE CONTROL PROGRAM UPDATES FOR SURGICAL DEVICES, now U.S. Patent Application Publication No. 2019/0206003;

U.S. patent application Ser. No. 15/940,653, titled ADAPTIVE CONTROL PROGRAM UPDATES FOR SURGICAL HUBS, now U.S. Patent Application Publication No. 2019/0201114;

U.S. patent application Ser. No. 15/940,660, titled CLOUD-BASED MEDICAL ANALYTICS FOR CUSTOMIZATION AND RECOMMENDATIONS TO A USER, now U.S. Patent Application Publication No. 2019/0206555;

U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET, now U.S. Pat. No. 10,932,872;

U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION, now U.S. Pat. No. 10,966,791;

U.S. patent application Ser. No. 15/940,634, titled CLOUD-BASED MEDICAL ANALYTICS FOR SECURITY AND AUTHENTICATION TRENDS AND REACTIVE MEASURES, now U.S. Patent Application Publication No. 2019/0201138;

U.S. patent application Ser. No. 15/940,706, titled DATA HANDLING AND PRIORITIZATION IN A CLOUD ANALYTICS NETWORK, now U.S. Patent Application Publication No. 2019/0206561;

U.S. patent application Ser. No. 15/940,675, titled CLOUD INTERFACE FOR COUPLED SURGICAL DEVICES, now U.S. Pat. No. 10,849,697;

U.S. patent application Ser. No. 15/940,627, titled DRIVE ARRANGEMENTS FOR ROBOT-ASSISTED SURGICAL PLATFORMS, now U.S. Pat. No. 11,013,563;

U.S. patent application Ser. No. 15/940,637, titled COMMUNICATION ARRANGEMENTS FOR ROBOT-ASSISTED SURGICAL PLATFORMS, now U.S. Patent Application Publication No. 2019/0201139;

U.S. patent application Ser. No. 15/940,642, titled CONTROLS FOR ROBOT-ASSISTED SURGICAL PLATFORMS, now U.S. Patent Application Publication No. 2019/0201113;

U.S. patent application Ser. No. 15/940,676, titled AUTOMATIC TOOL ADJUSTMENTS FOR ROBOT-ASSISTED SURGICAL PLATFORMS, now U.S. Patent Application Publication No. 2019/0201142;

U.S. patent application Ser. No. 15/940,680, titled CONTROLLERS FOR ROBOT-ASSISTED SURGICAL PLATFORMS, now U.S. Patent Application Publication No. 2019/0201135;

U.S. patent application Ser. No. 15/940,683, titled COOPERATIVE SURGICAL ACTIONS FOR ROBOT-ASSISTED SURGICAL PLATFORMS, now U.S. Patent Application Publication No. 2019/0201145;

U.S. patent application Ser. No. 15/940,690, titled DISPLAY ARRANGEMENTS FOR ROBOT-ASSISTED SURGICAL PLATFORMS, now U.S. Patent Application Publication No. 2019/0201118; and U.S. patent application Ser. No. 15/940,711, titled SENSING ARRANGEMENTS FOR ROBOT-ASSISTED SURGICAL PLATFORMS, now U.S. Patent Application Publication No. 2019/0201120.

Applicant of the present application owns the following U.S. Provisional patent applications, filed on Mar. 8, 2018, the disclosure of each of which is herein incorporated by reference in its entirety:

U.S. Provisional Patent Application No. 62/640,417, titled TEMPERATURE CONTROL IN ULTRASONIC DEVICE AND CONTROL SYSTEM THEREFOR; and U.S. Provisional Patent Application No. 62/640,415, titled ESTIMATING STATE OF ULTRASONIC END EFFECTOR AND CONTROL SYSTEM THEREFOR.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Aspects of the present disclosure are presented for a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more surgical devices that are used to conduct medical procedures on patients. The surgical hubs provide a wide array of functionality to improve the outcomes of medical procedures. The data generated by the various surgical devices and medical hubs about the patient and the medical procedure may be transmitted to the cloud-based medical analytics system. This data may then be aggregated with similar data gathered from many other surgical hubs and surgical devices located at other medical facilities. Various patterns and correlations may be found through the cloud-based analytics system analyzing the collected data. Improvements in the techniques used to generate the data may be generated as a result, and these improvements may then be disseminated to the various surgical hubs and surgical devices. Due to the interconnectedness of all of the aforementioned components, improvements in medical procedures and practices may be found that otherwise may not be found if the many components were not so interconnected. Various examples of structures and functions of these various components will be described in more detail in the following description.

Figure 1:
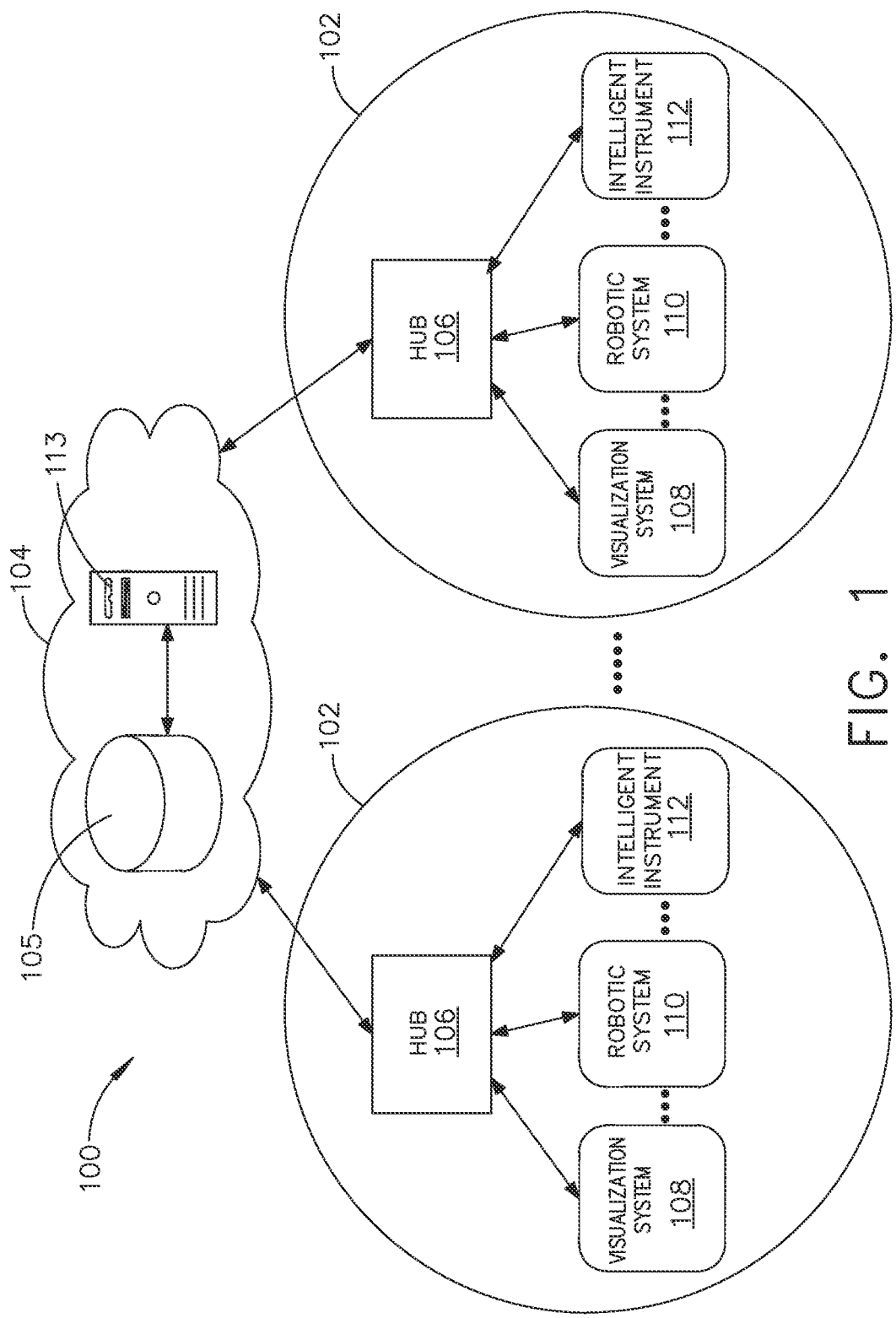
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
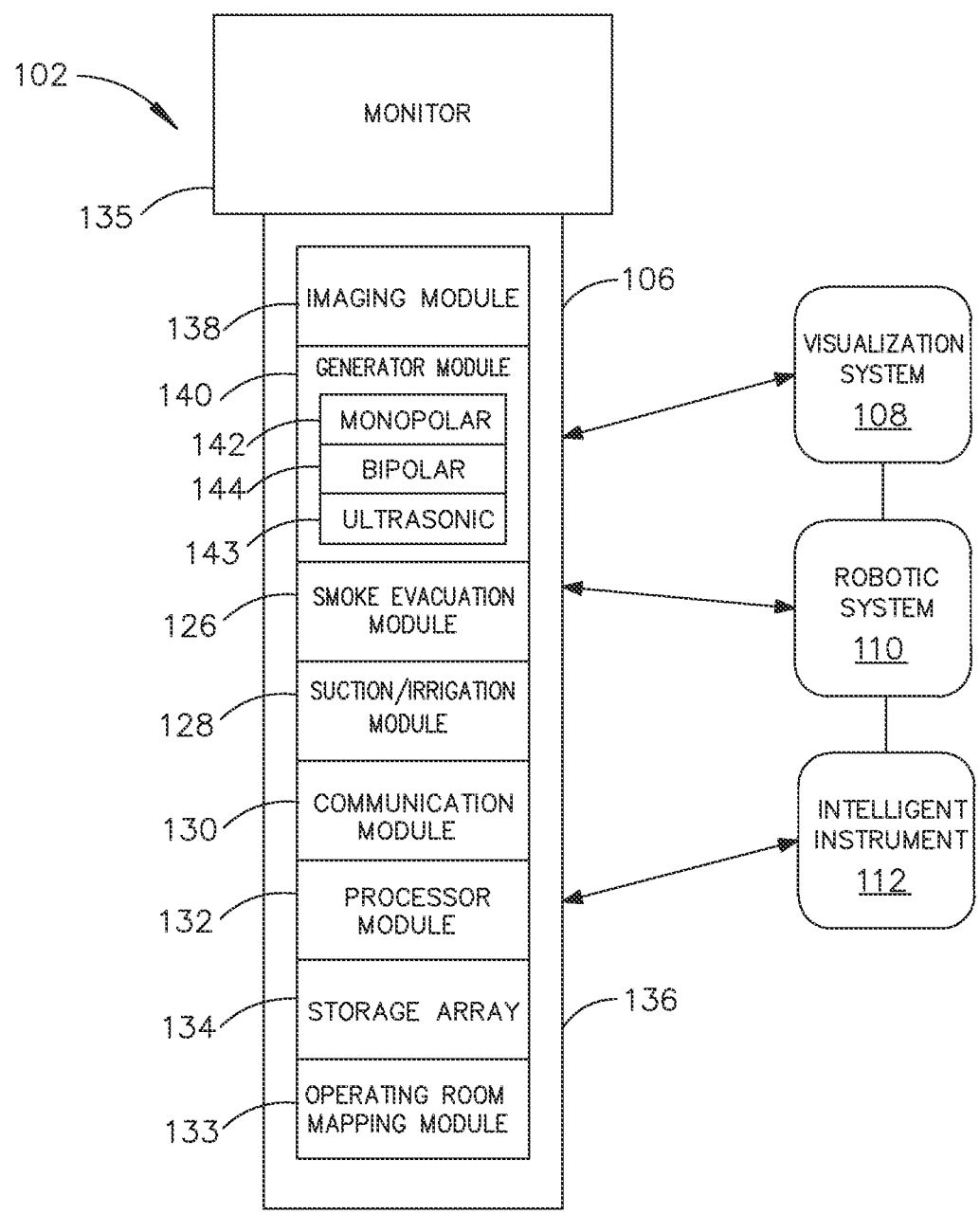
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater." i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
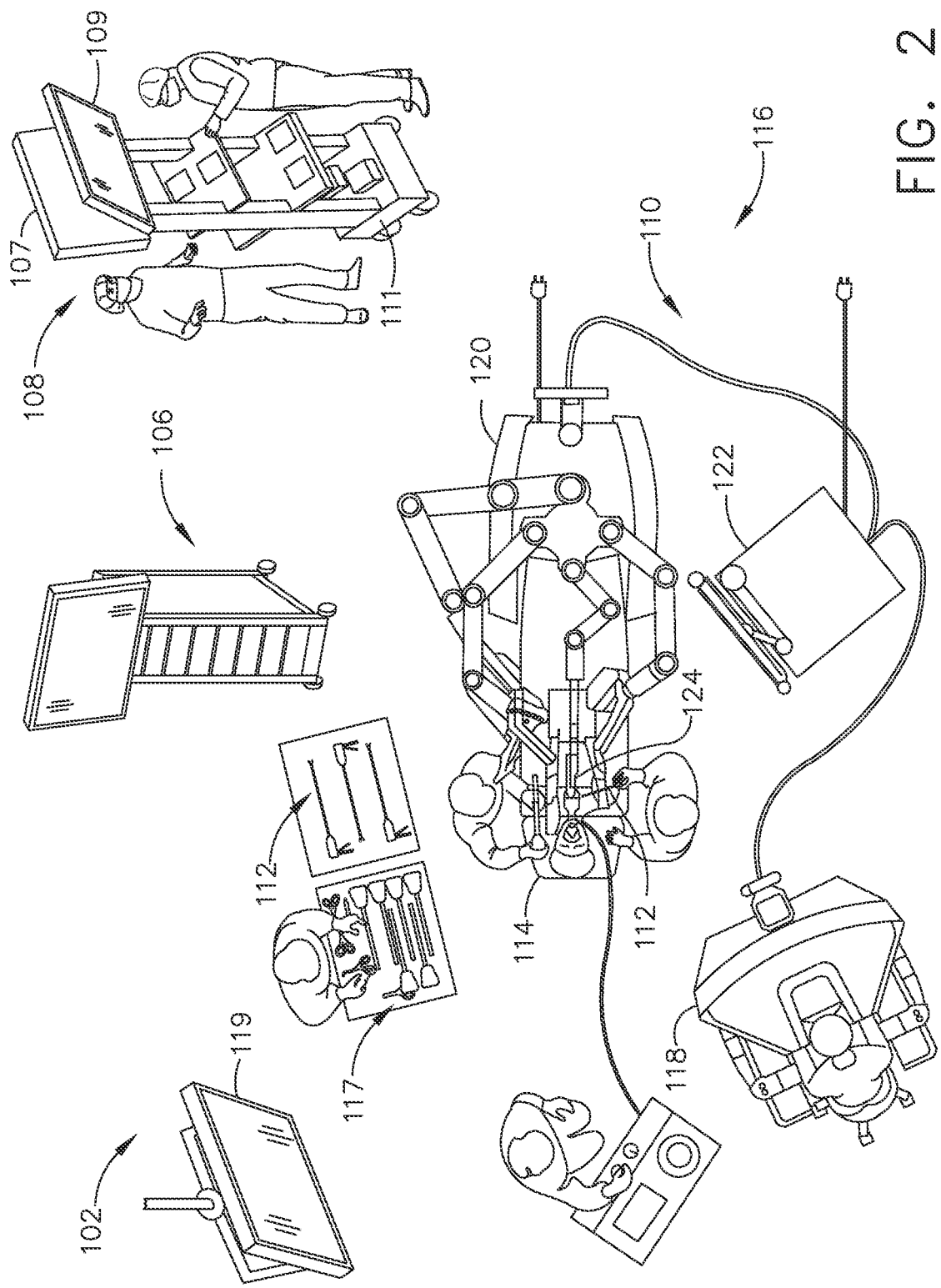
FIG. 2 is a surgical system being used to perform a surgical procedure in an operating room, in accordance with at least one aspect of the present disclosure.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
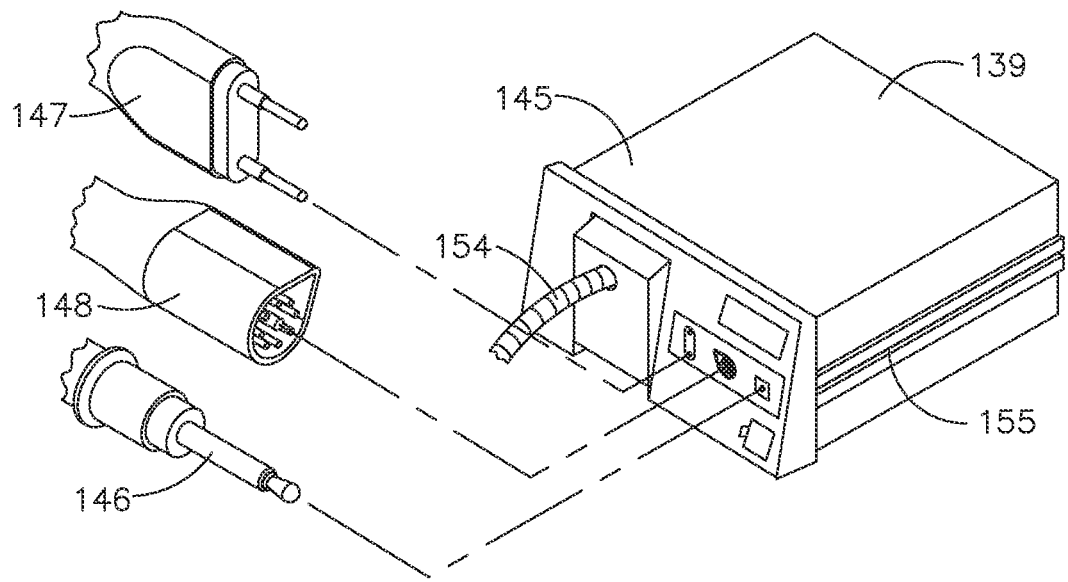
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
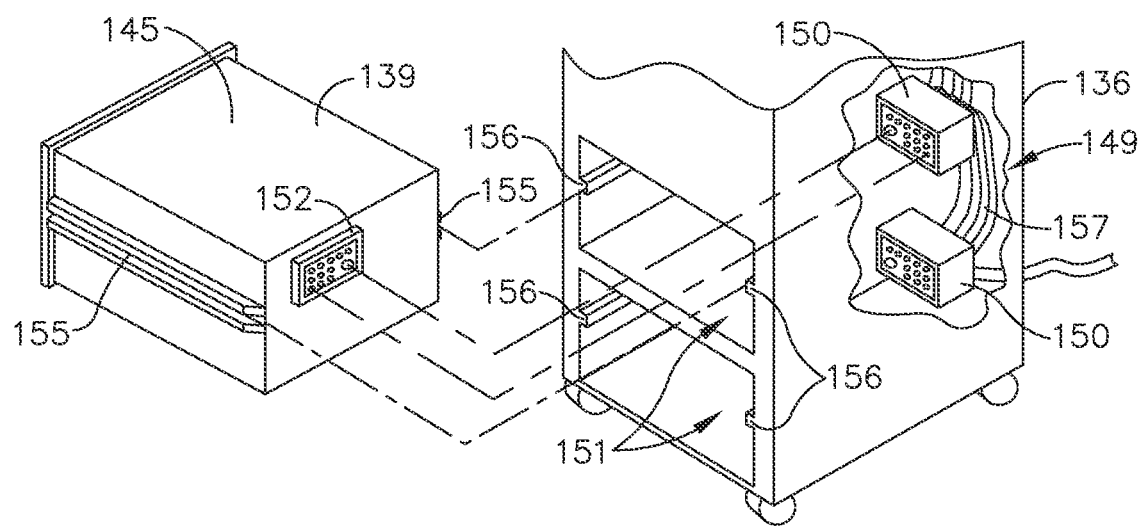
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
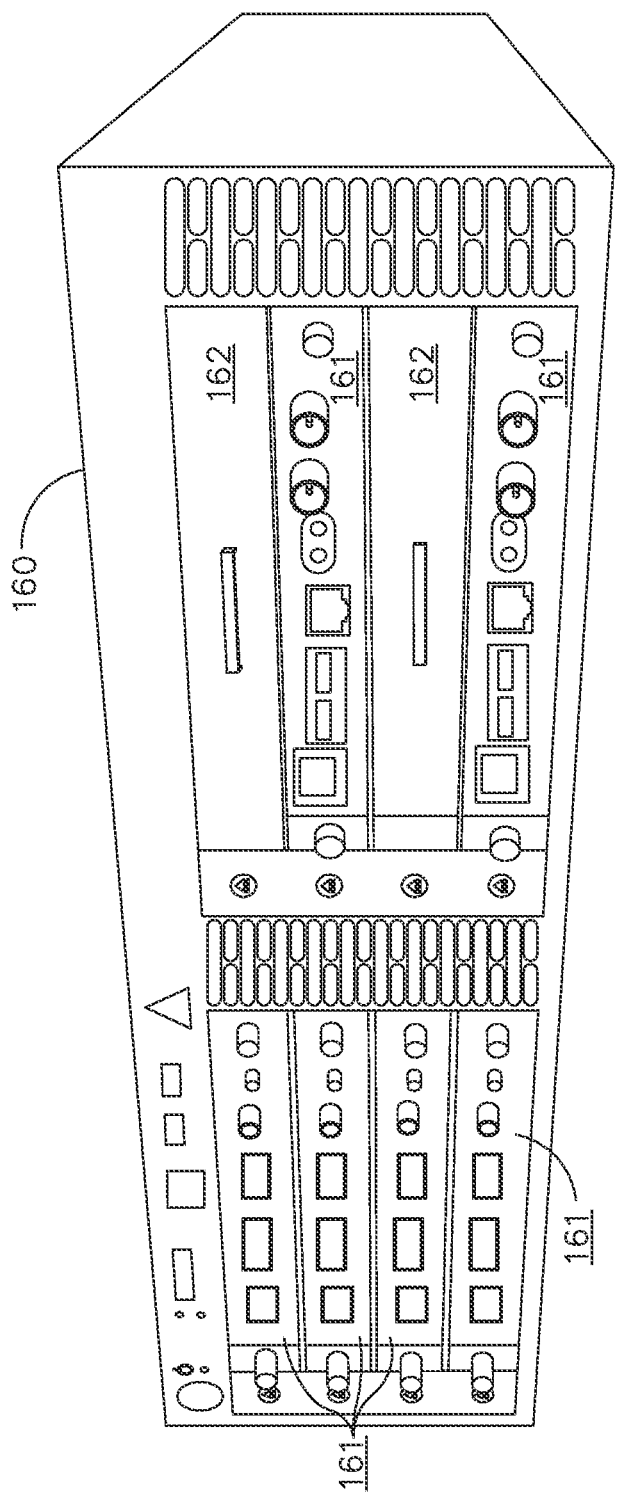
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
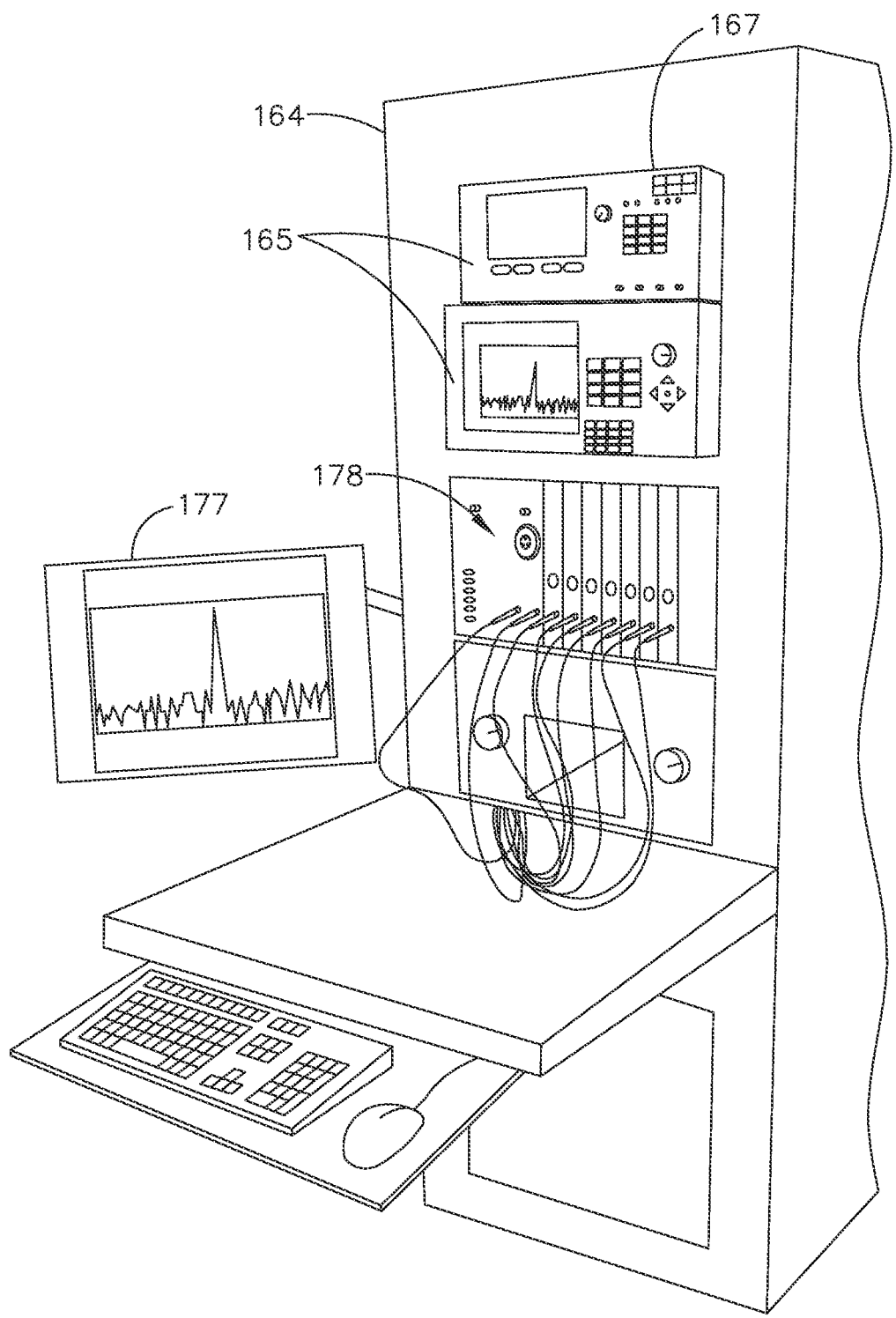
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Pat. No. 10,098,527, titled SYSTEM FOR PERFORMING A MINIMALLY INVASIVE SURGICAL PROCEDURE, which issued on Oct. 16, 2018, each of which is herein incorporated by reference in its entirety.

Figure 8:
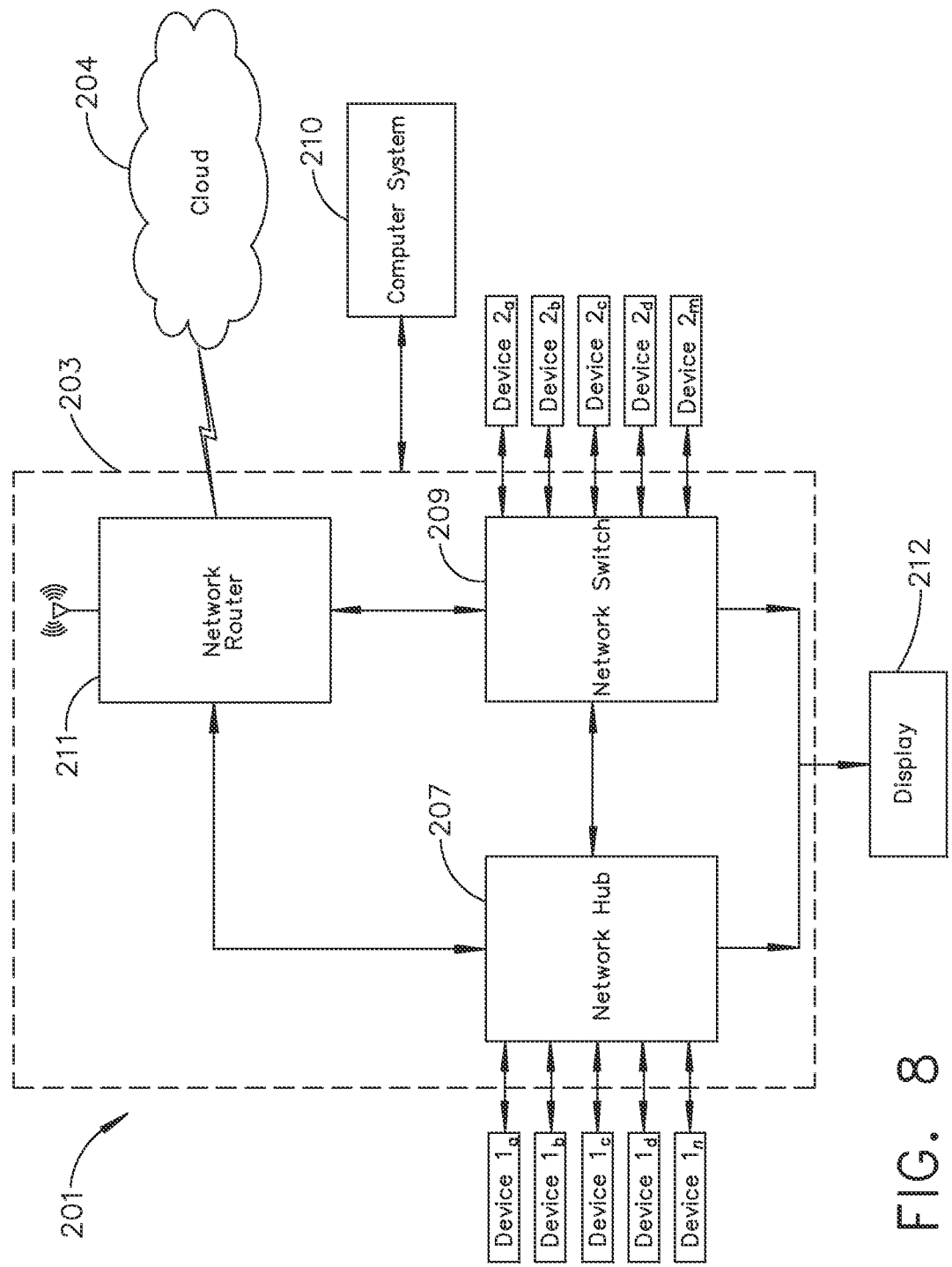
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1*a*-1*n* located in the operating theater may be coupled to the modular communication hub 203. The network hub 207 and/or the network switch 209 may be coupled to a network router 211 to connect the devices 1*a*-1*n* to the cloud 204 or the local computer system 210. Data associated with the devices 1*a*-1*n* may be transferred to cloud-based computers via the router for remote data processing and manipulation. Data associated with the devices 1*a*-1*n* may also be transferred to the local computer system 210 for local data processing and manipulation. Modular devices 2*a*-2*m* located in the same operating theater also may be coupled to a network switch 209. The network switch 209 may be coupled to the network hub 207 and/or the network router 211 to connect to the devices 2*a*-2*m* to the cloud 204. Data associated with the devices 2*a*-2*n* may be transferred to the cloud 204 via the network router 211 for data processing and manipulation. Data associated with the devices 2*a*-2*m* may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services-such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHZ) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
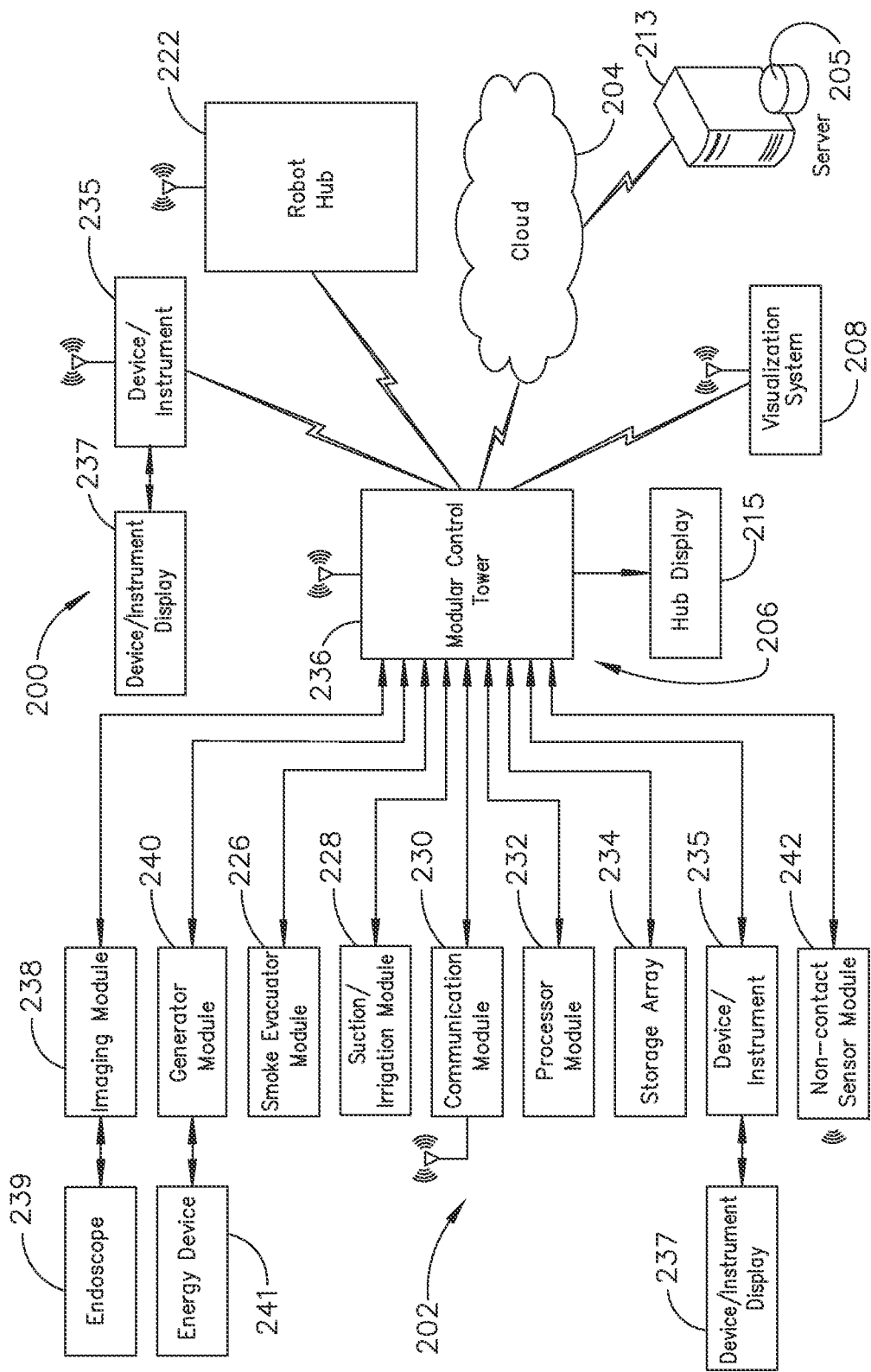
FIG. 9 illustrates a computer-implemented interactive surgical system, in accordance with at least one aspect of the present disclosure.
Figure 10:
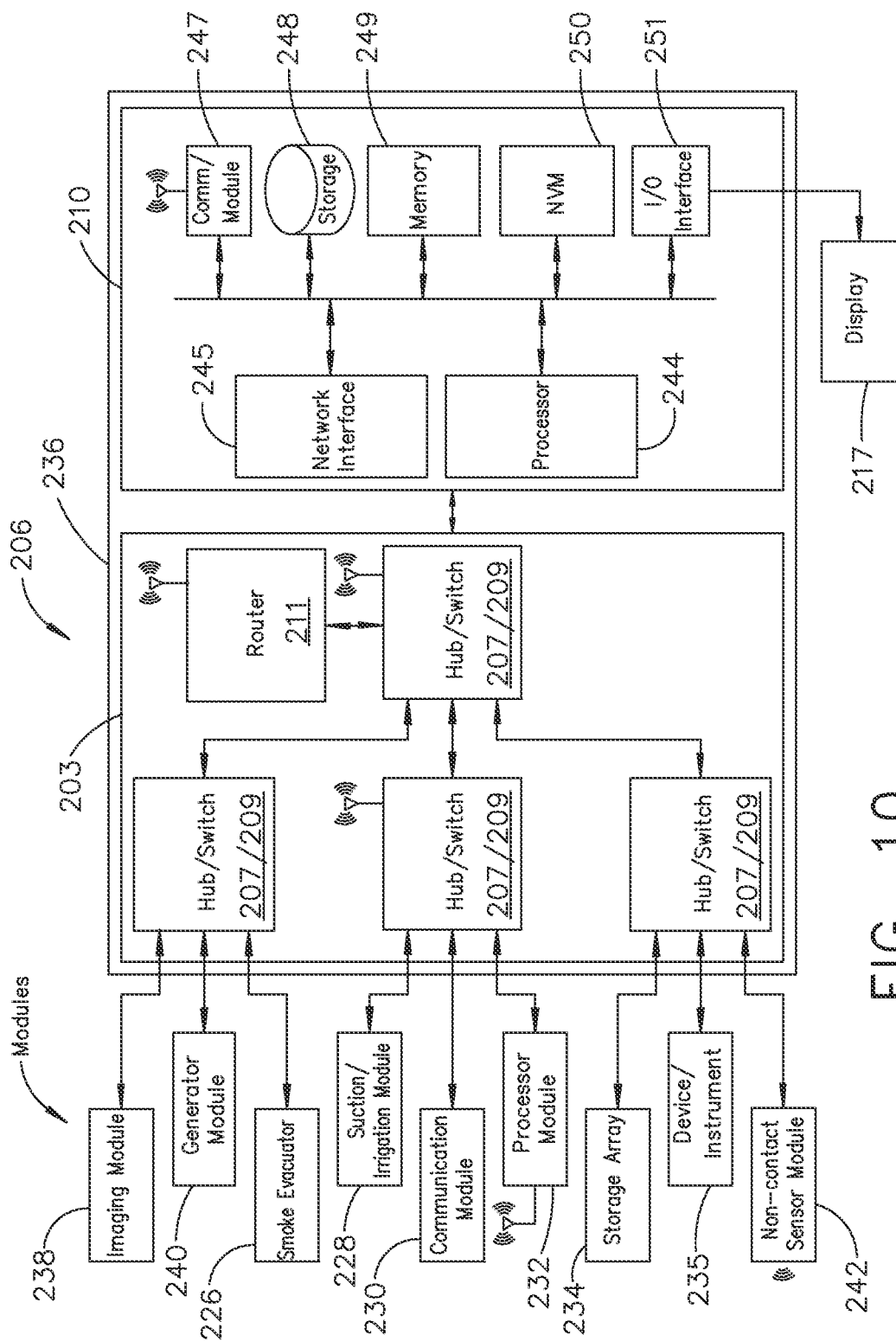
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with Stellaris Ware® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
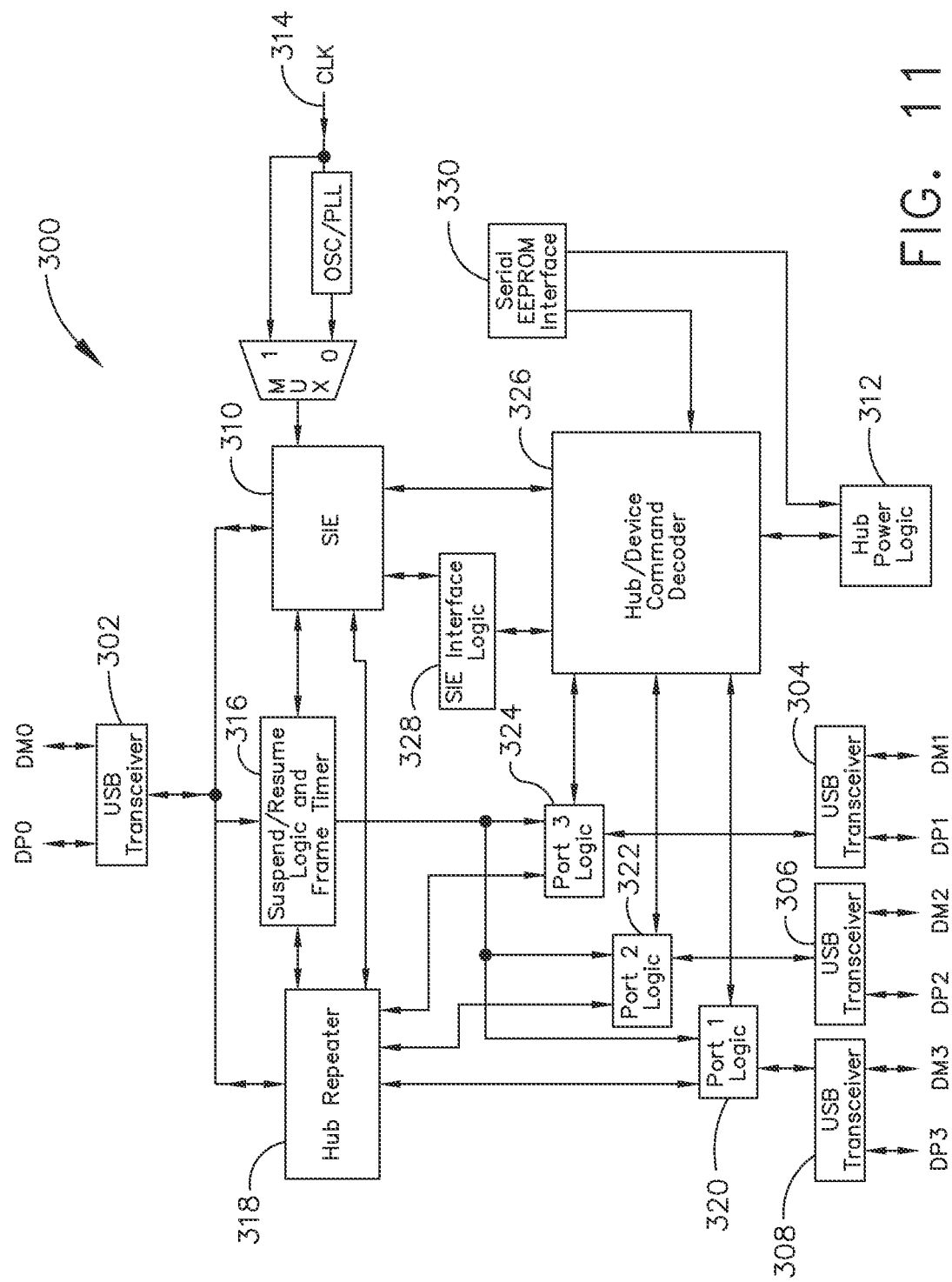
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, according to one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
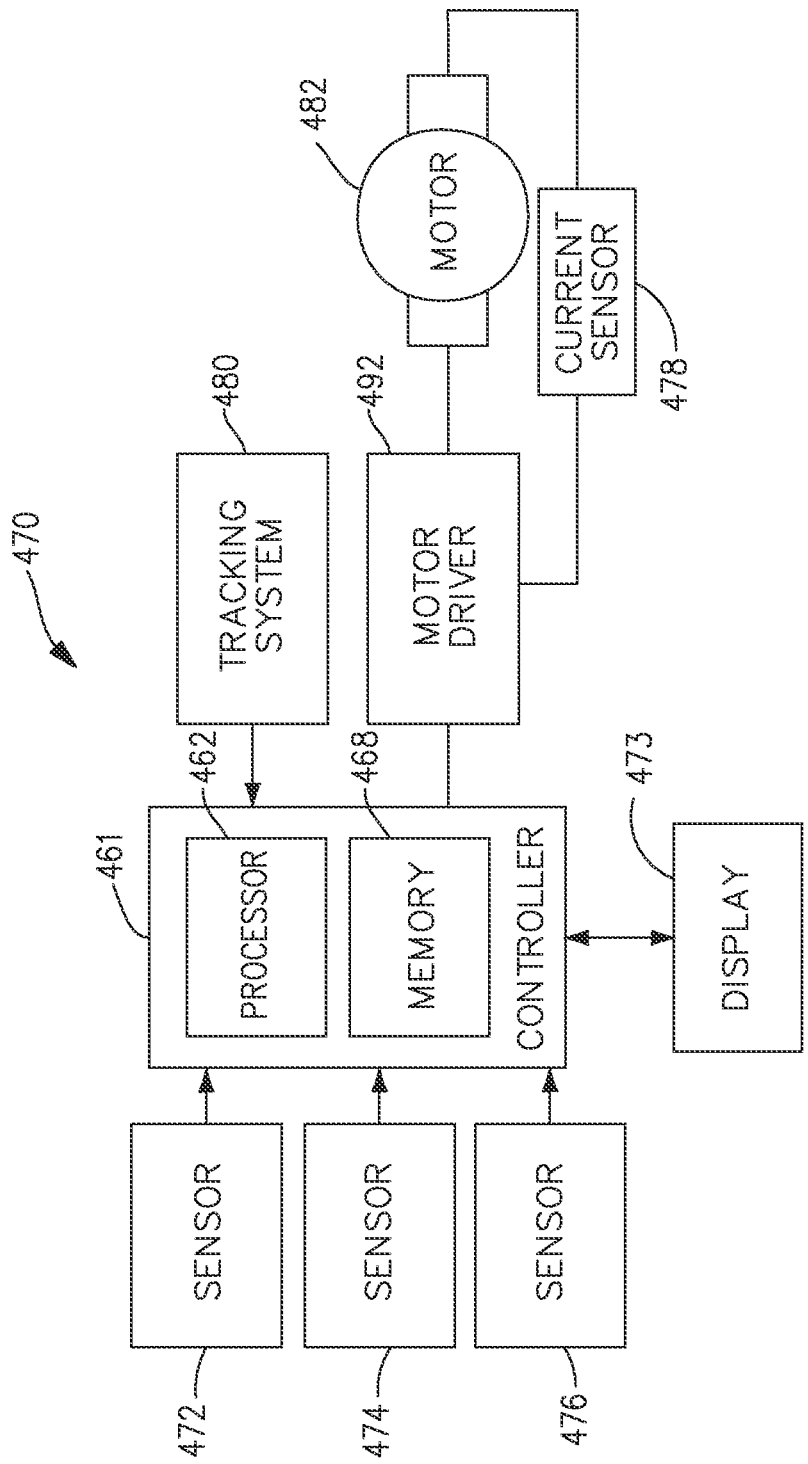
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with Stellaris Ware® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. Pat. No. 10,881,399, titled TECHNIQUES FOR ADAPTIVE CONTROL OF MOTOR VELOCITY OF A SURGICAL STAPLING AND CUTTING INSTRUMENT, which issued on Jan. 5, 2021, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue.

The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
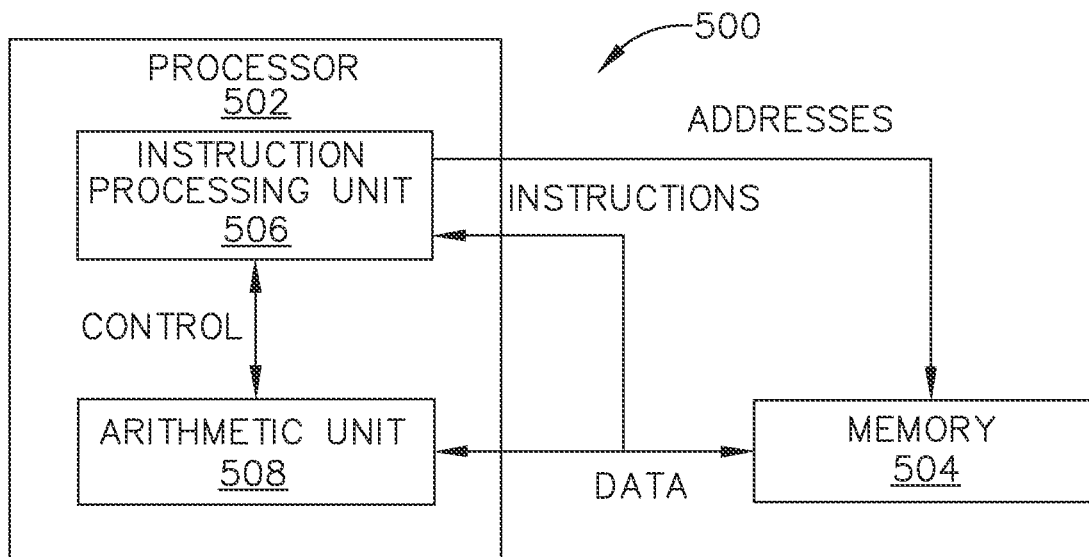
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
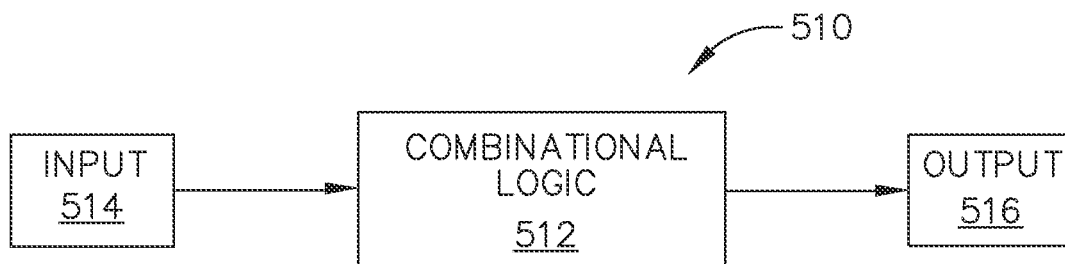
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
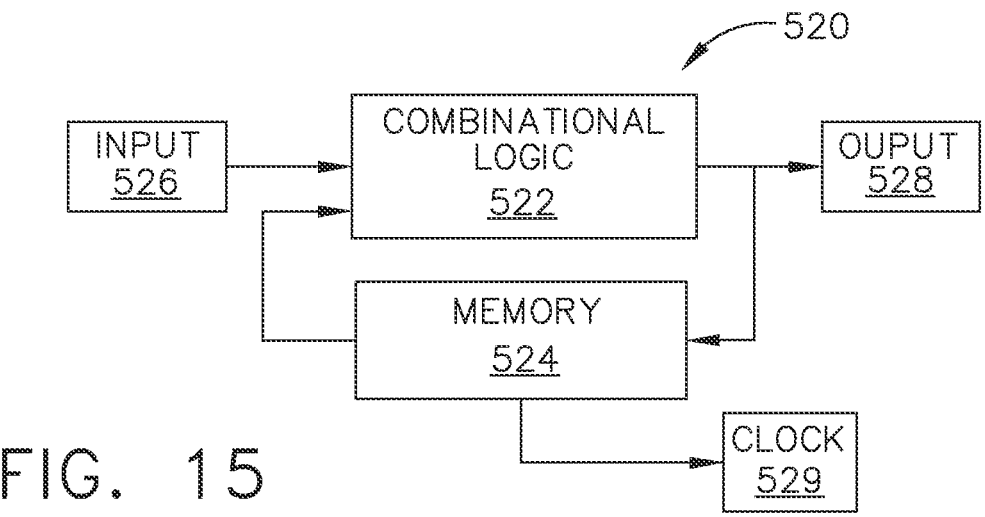
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
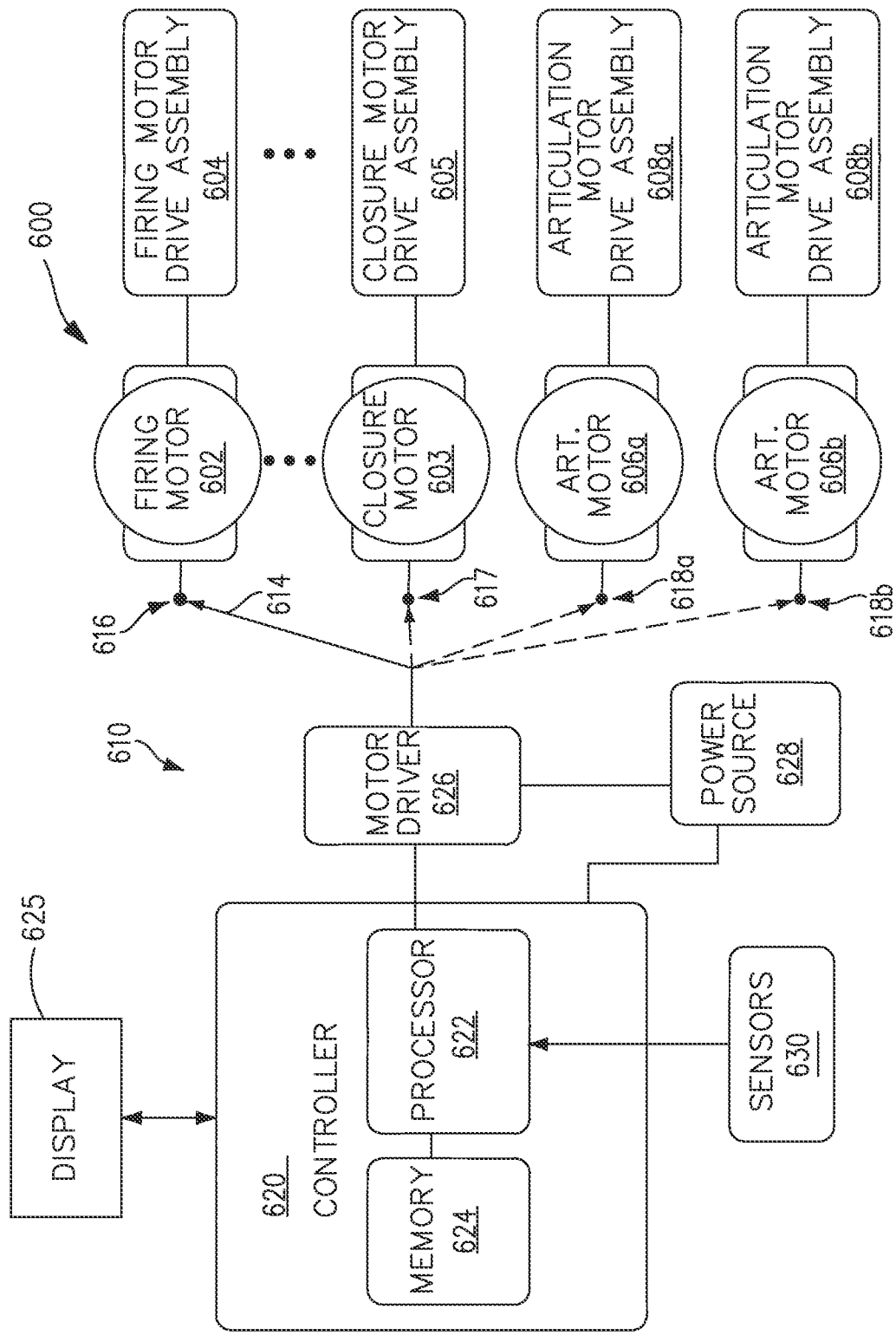
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore, the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
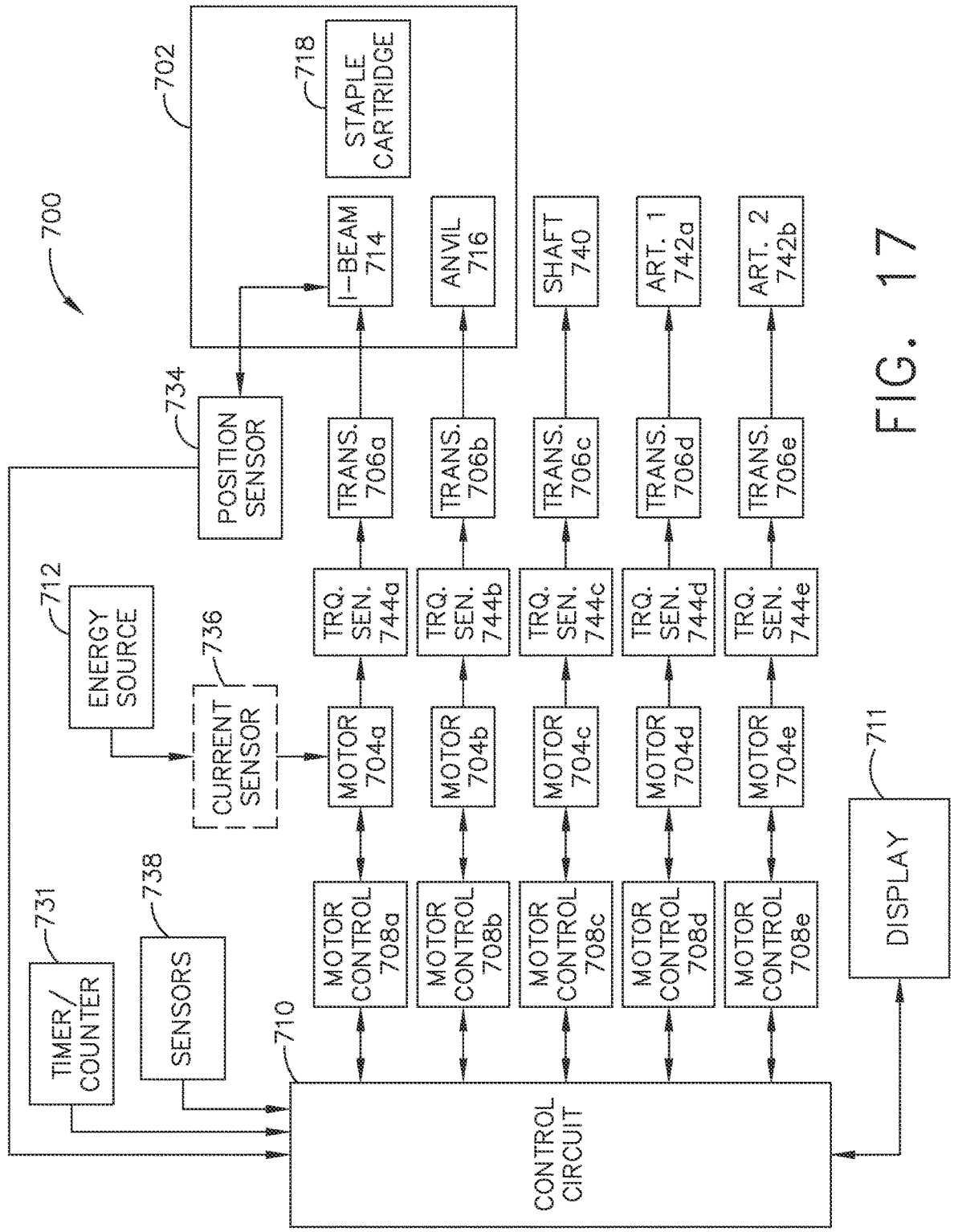
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the I-beam 714. The transmission 706a comprises movable mechanical elements such as rotating elements and a firing member to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the I-beam 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. Pat. No. 10,932,772, titled METHODS FOR CLOSED LOOP VELOCITY CONTROL TECHNIQUES FOR ROBOTIC SURGICAL INSTRUMENT, which issued on Mar. 2, 2021, which is herein incorporated by reference in its entirety.

Figure 18:
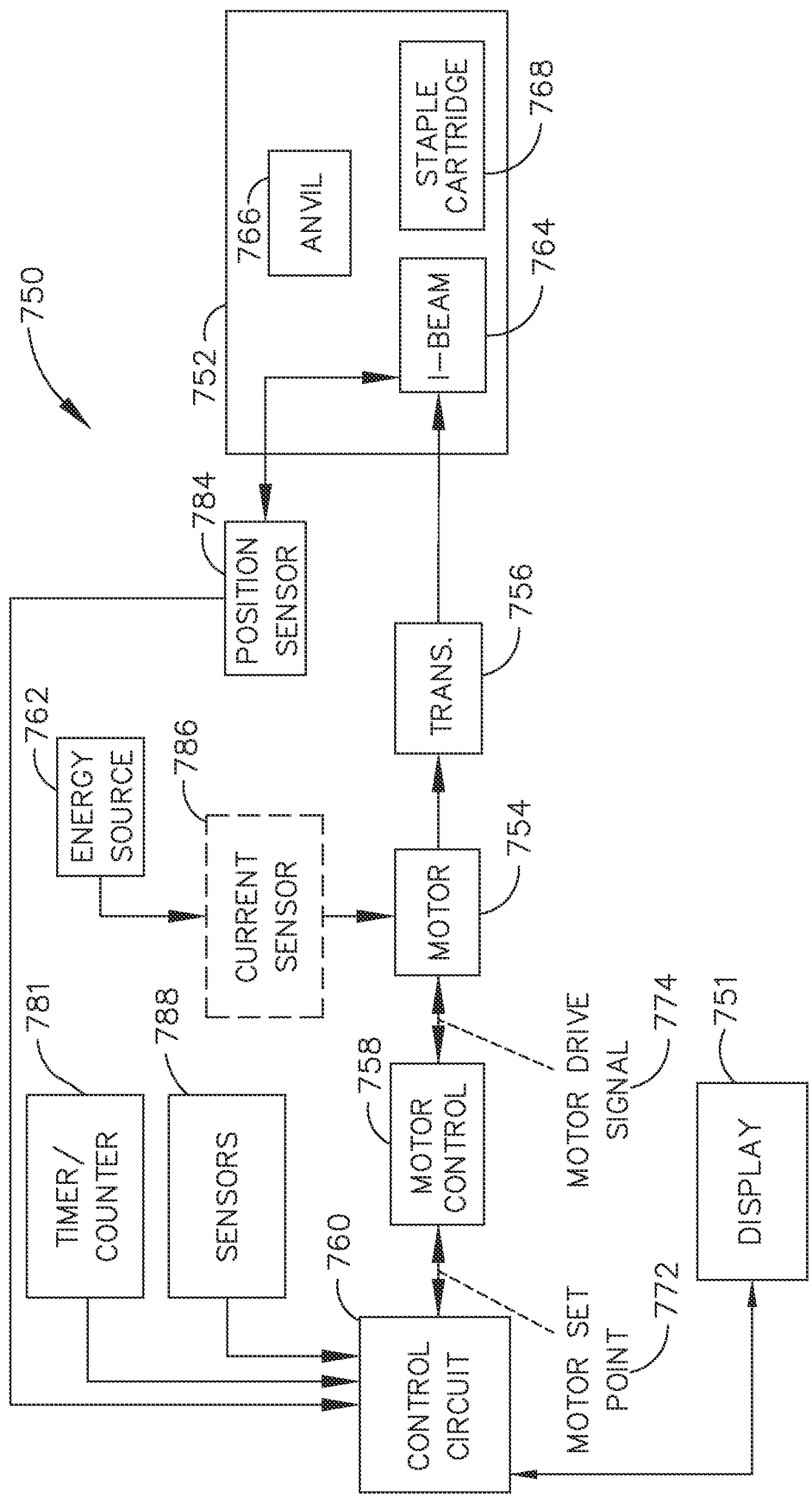
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member according to one aspect of this disclosure. In one aspect, the surgical instrument 750 is programmed to control the distal translation of a displacement member such as the I-beam 764. The surgical instrument 750 comprises an end effector 752 that may comprise an anvil 766, an I-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. Pat. No. 10,743,872, titled SYSTEM AND METHODS FOR CONTROLLING A DISPLAY OF A SURGICAL INSTRUMENT, which issued on Aug. 18, 2020, which is herein incorporated by reference in its entirety.

Figure 19:
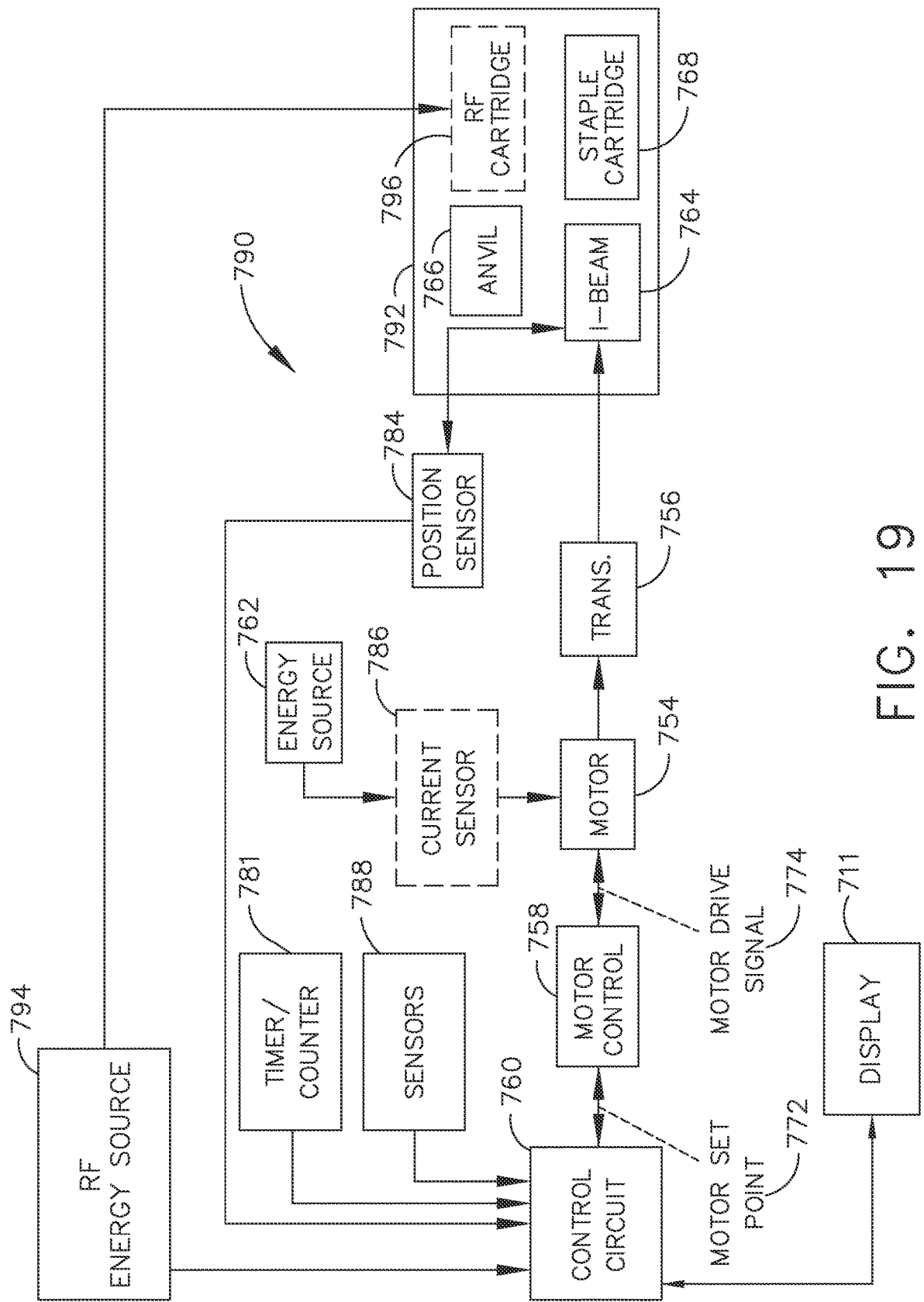
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line).

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly-owned U.S. Pat. No. 10,881,399, titled TECHNIQUES FOR ADAPTIVE CONTROL OF MOTOR VELOCITY OF A SURGICAL STAPLING AND CUTTING INSTRUMENT, which issued on Jan. 5, 2021, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the I-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. Patent Application Publication No. 2019/0000478, titled SURGICAL SYSTEM COUPLABLE WITH STAPLE CARTRIDGE AND RADIO FREQUENCY CARTRIDGE, AND METHOD OF USING SAME, which published on Jan. 3, 2019, which is herein incorporated by reference in its entirety.

Generator Hardware

Figure 20:
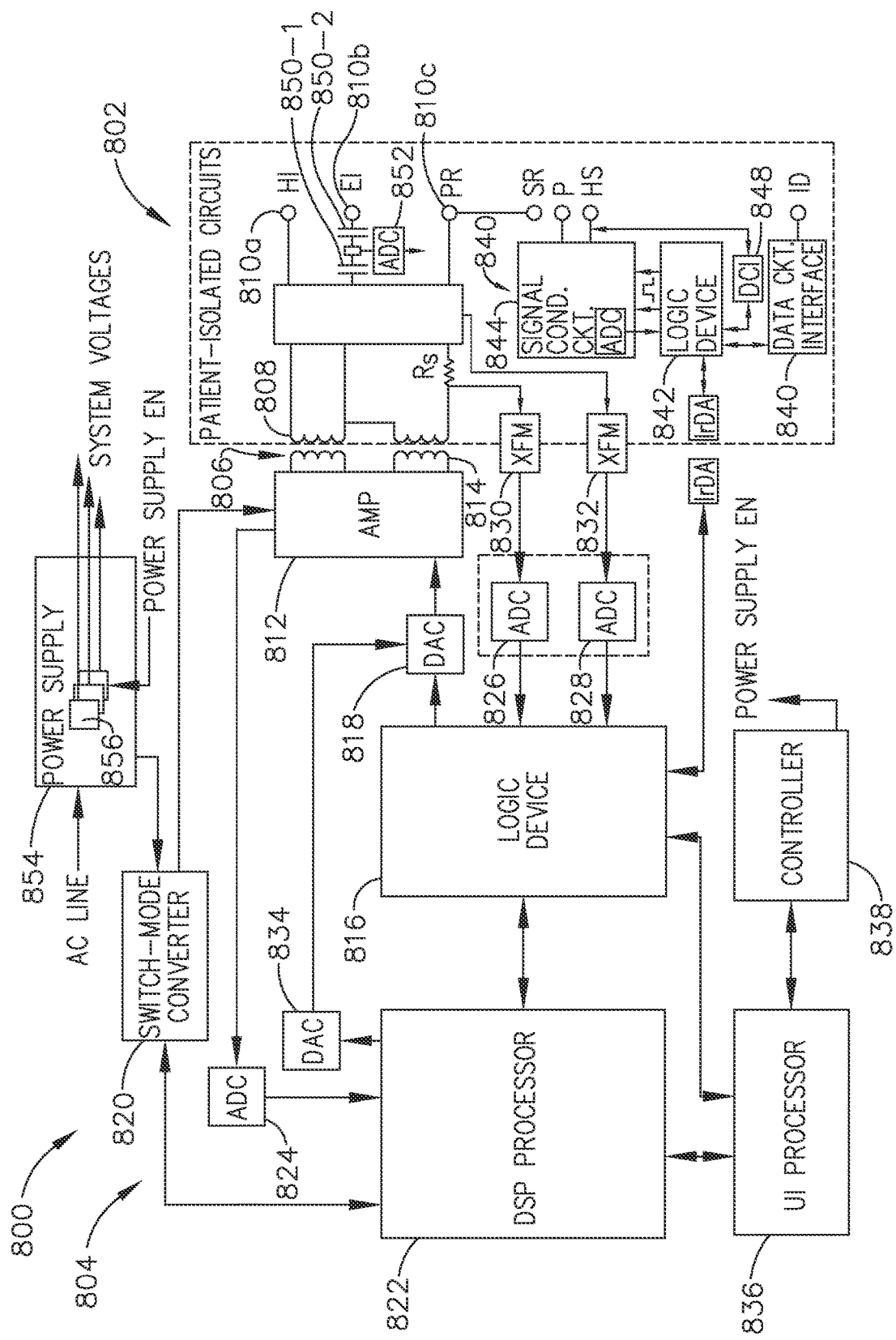
FIG. 20 is a simplified block diagram of a generator configured to provide inductorless tuning, among other benefits, in accordance with at least one aspect of the present disclosure.

FIG. 20 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810*a*, 810*b*, 810*c* for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810*a*, 810*c* may output an ultrasonic drive signal (e.g., a 420V root-mean-square (RMS) drive signal) to an ultrasonic surgical instrument, and drive signal outputs 810*b*, 810*c* may output an RF electrosurgical drive signal (e.g., a 100V RMS drive signal) to an RF electrosurgical instrument, with the drive signal output 810*b* corresponding to the center tap of the power transformer 806.

In certain forms, the ultrasonic and electrosurgical drive signals may be provided simultaneously to distinct surgical instruments and/or to a single surgical instrument, such as the multifunction surgical instrument, having the capability to deliver both ultrasonic and electrosurgical energy to tissue. It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue, while the electrosurgical RF energy may be employed for vessel sealing.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, MA, for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy.

The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, California, for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In one form, the instrument interface circuit 840 may comprise a first data circuit interface 846 to enable information exchange between the logic circuit 842 (or other element of the instrument interface circuit 840) and a first data circuit disposed in or otherwise associated with a surgical instrument. In certain forms, for example, a first data circuit may be disposed in a cable integrally attached to a surgical instrument handpiece or in an adaptor for interfacing a specific surgical instrument type or model with the generator 800. The first data circuit may be implemented in any suitable manner and may communicate with the generator according to any suitable protocol, including, for example, as described herein with respect to the first data circuit. In certain forms, the first data circuit may comprise a non-volatile storage device, such as an EEPROM device. In certain forms, the first data circuit interface 846 may be implemented separately from the logic circuit 842 and comprise suitable circuitry (e.g., discrete logic devices, a processor) to enable communication between the logic circuit 842 and the first data circuit. In other forms, the first data circuit interface 846 may be integral with the logic circuit 842.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810b to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

Figure 21:
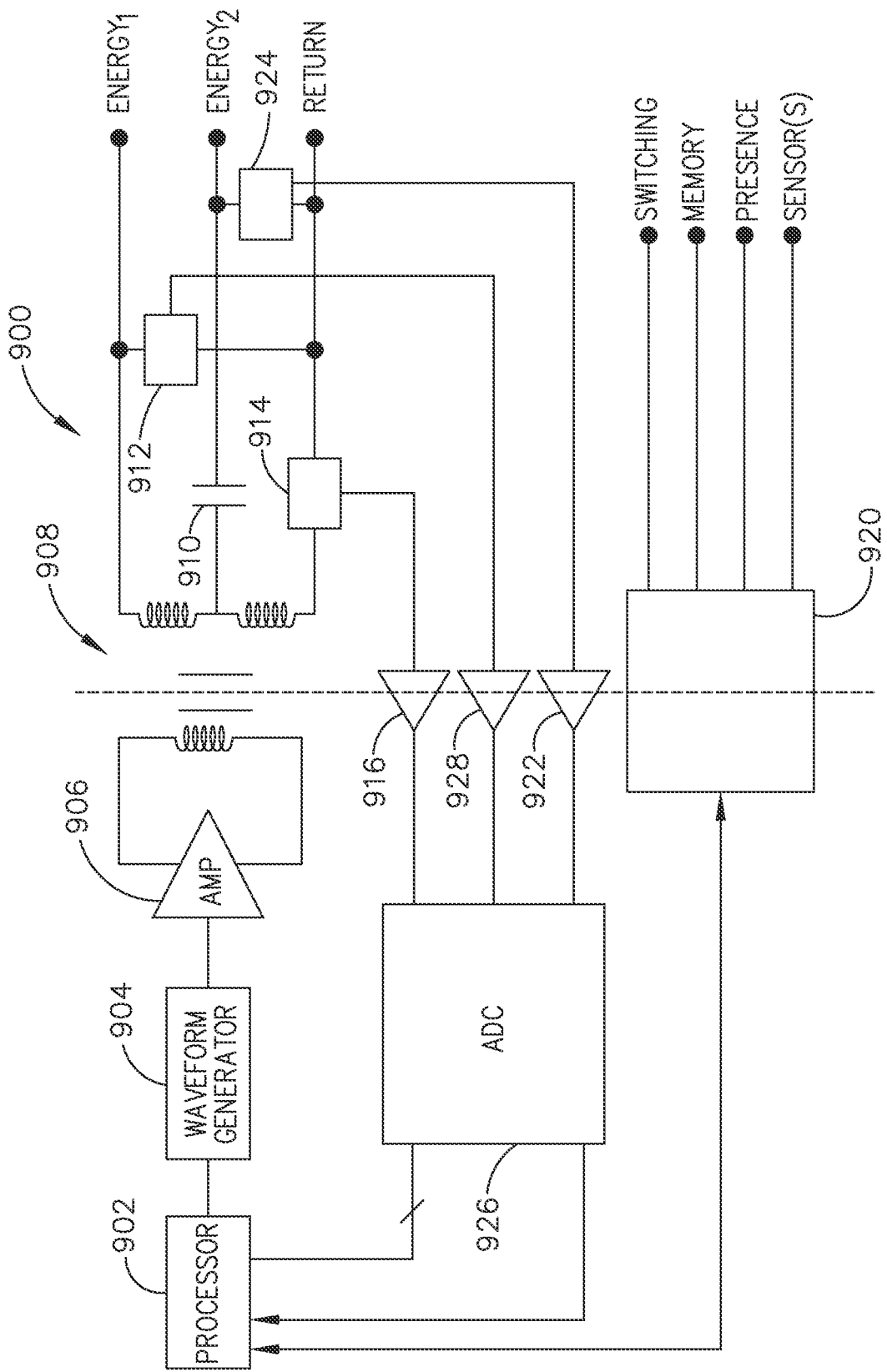
FIG. 21 illustrates an example of a generator, which is one form of the generator of FIG. 20, in accordance with at least one aspect of the present disclosure.

FIG. 21 illustrates an example of a generator 900, which is one form of the generator 800 (FIG. 20). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 21. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Pat. No. 10,624,691, titled TECHNIQUES FOR OPERATING GENERATOR FOR DIGITALLY GENERATING ELECTRICAL SIGNAL WAVEFORMS AND SURGICAL INSTRUMENTS, which issued on Apr. 21, 2020, which is herein incorporated by reference in its entirety.

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions-all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; an SoC may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with Stellaris Ware® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIGS. 3 and 9, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Long Distance Communication and Condition Handling of Devices and Data

Surgical procedures are performed by different surgeons at different locations, some with much less experience than others. For a given surgical procedure, there are many parameters that can be varied to attempt to realize a desired outcome. For example, for a given surgical procedure which utilizes energy supplied by a generator, the surgeon often relies on experience alone for determining which mode of energy to utilize, which level of output power to utilize, the duration of the application of the energy, etc., in order to attempt to realize the desired outcome. To increase the likelihood of realizing desired outcomes for a plurality of different surgical procedures, each surgeon should be provided with best practice recommendations which are based on important relationships identified within large, accurate data sets of information associated with multiple surgical procedures performed in multiple locations over time. However, there are many ways that such data sets can be rendered compromised, inaccurate, and/or unsecure, thereby calling into question the applicability of the best practice recommendations derived therefrom. For example, for data sent from a source to a cloud-based system, the data can be lost while in transit to the cloud-based system, the data can be corrupted while in transit to the cloud-based system, the confidentiality of the data can be comprised while in transit to the cloud-based system, and/or the content of the data can be altered while in transit to the cloud-based system.

A plurality of operating rooms located in multiple locations can each be equipped with a surgical hub. When a given surgical procedure is performed in a given operating room, the surgical hub can receive data associated with the surgical procedure and communicate the data to a cloud-based system. Over time, the cloud-based system will receive large data sets of information associated with the surgeries. The data can be communicated from the surgical hubs to the cloud-based system in a manner which allows for the cloud-based system to (1) verify the authenticity of the communicated data, (2) authenticate each of the respective surgical hubs which communicated the data, and (3) trace the paths the data followed from the respective surgical hubs to the cloud-based system.

Accordingly, in one aspect, the present disclosure provides a surgical hub for transmitting generator data associated with a surgical procedure to a cloud-based system communicatively coupled to a plurality of surgical hubs. The surgical hub comprises a processor and a memory coupled to the processor. The memory stores instructions executable by the processor to receive data from a generator, encrypt the data, generate a message authentication code (MAC) based on the data, generate a datagram comprising the encrypted data, the generated MAC, a source identifier, and a destination identifier, and transmit the datagram to a cloud-based system. The data is structured into a data packet comprising at least two of the following fields: a field that indicates the source of the data, a unique time stamp, a field indicating an energy mode of the generator, a field indicating the power output of the generator, and a field indicating a duration of the power output of the generator. The datagram allows for the cloud-based system to decrypt the encrypted data of the transmitted datagram, verify integrity of the data based on the MAC, authenticate the surgical hub as the source of the datagram, and validate a transmission path followed by the datagram between the surgical hub and the cloud-based system.

In various aspects, the present disclosure provides a control circuit to transmit generator data associated with a surgical procedure to a cloud-based system communicatively coupled to a plurality of surgical hubs, as described above. In various aspects, the present disclosure provides a non-transitory computer-readable medium storing computer-readable instructions which, when executed, causes a machine to transmit generator data associated with a surgical procedure to a cloud-based system communicatively coupled to a plurality of surgical hubs, as described above.

In another aspect, the present disclosure provides a cloud-based system communicatively coupled to a plurality of surgical hubs. Each surgical hub is configured to transmit generator data associated with a surgical procedure to the cloud-based system. The cloud-based system comprises a processor and a memory coupled to the processor. The memory stores instructions executable by the processor to receive a datagram generated by a surgical hub, decrypt the encrypted generator data of the received datagram, verify integrity of the generator data based on the MAC, authenticate the surgical hub as the source of the datagram, and validate a transmission path followed by the datagram between the surgical hub and the cloud-based system. The datagram comprises generator data captured from a generator associated with the surgical hub, a MAC generated by the surgical hub based on the generator data, a source identifier, and a destination identifier. The generator data has been encrypted by the surgical hub. The encrypted generator data has been structured into a data packet comprising at least two of the following fields: a field that indicates the source of the data, a unique time stamp, a field indicating an energy mode, a field indicating power output, and a field indicating a duration of applied power.

In various aspects, the present disclosure provides a control circuit to transmit generator data associated with a surgical procedure to the cloud-based system. In various aspects, the present disclosure provides a non-transitory computer-readable medium storing computer-readable instructions which, when executed, causes a machine to transmit generator data associated with a surgical procedure to the cloud-based system.

In another aspect, the present disclosure provides a method, comprising capturing data from a combination generator of a surgical hub during a surgical procedure, wherein the combination generator is configured to supply two or more different modes of energy. Encrypting the captured generator data, generating a MAC based on the captured generator data, generating a datagram comprising the encrypted generator data, the MAC, a source identifier, and a destination identifier, and communicating the datagram from the surgical hub to a cloud-based system. The datagram allows for the cloud-based system to authenticate integrity of the communicated generator data, authenticate the surgical hub as a source of the datagram, and determine a communication path followed by the datagram between the surgical hub and the cloud-based system.

By sending captured generator data from a plurality of different surgical hubs to a cloud-based system, the cloud-based system is able to quickly build large data sets of information associated with multiple surgical procedures performed in multiple locations over time. Furthermore, due to the composition of the respective datagrams, for a given datagram, the cloud-based system is able to determine whether the datagram was originally sent by one of the surgical hubs (source validation), thereby providing an indication that the generator data received at the cloud-based system is legitimate data. For the given datagram, the cloud-based system is also able to determine whether the generator data received at the cloud-based system is identical to the generator data sent by the given surgical hub (data integrity), thereby allowing for the authenticity of the received generator data to be verified. Additionally, for the given datagram, the cloud-based system is also able to re-trace the communication path followed by the datagram, thereby allowing for enhanced troubleshooting if a datagram received by the cloud-based system was originally sent from a device other than the surgical hubs and/or if the content of the datagram was altered while in transit to the cloud-based system. Notably, the present disclosure references generator data in particular. Here, the present disclosure should not be limited as being able to process only generator data. For example, the surgical hub 206 and/or the cloud-based system 205 may process data received from any component (e.g., imaging module 238, generator module 240, smoke evacuator module 226, suction/irrigation module 228, communication module 230, processor module 232, storage array 234, smart device/instrument 235, non-contact sensor module 242, robot hub 222, a non-robotic surgical hub 206, wireless smart device/instrument 235, visualization system 208) of the surgical system 202 that is coupled to the surgical hub 206 and/or data from any devices (e.g., endoscope 239, energy device 241) coupled to/through such components (e.g., see FIGS. 9-10), in a similar manner as discussed herein.

Unfortunately, the outcome of a surgical procedure is not always optimal. For example, a failure event such as a surgical device failure, an unwanted tissue perforation, an unwanted post-operative bleeding, or the like can occur. The occurrence of a failure event can be attributed to any of a variety of different people and devices, including one or more surgeons, one or more devices associated with the surgery, a condition of the patient, and combinations thereof. When a given failure event occurs, it is not always clear regarding who or what caused the failure event or how the occurrence of the failure event can be mitigated in connection with a future surgery.

During a given surgical procedure, a large amount of data associated with the surgical procedure can be generated and captured. All of the captured data can be communicated to a surgical hub, and the captured data can be time-stamped either before or after being received at the surgical hub. When a failure event associated with the surgical procedure is detected and/or identified, it can be determined which of the captured data is associated with the failure event and/or which of the captured data is not associated with the failure event. In making this determination, the failure event can be defined to include a period of time prior to the detection/identification of the failure event. Once the determination is made regarding the captured data associated with the failure event, the surgical hub can separate the captured data associated with the failure event from all other captured data, and the captured data can be separated based on tagging, flagging, or the like. The captured data associated with the failure event can then be chronologized based on the time-stamping and the defined time period applicable to the failure event. The chronologized captured data can then be communicated to a cloud-based system on a prioritized basis for analysis, where the prioritized basis is relative to the captured data which is not associated with the failure event. Whether or not the analysis identifies a device associated with the surgical procedure as the causation of the failure event, the surgical hub can tag the device for removal of the device from future use, further analysis of the device, and/or to return the device to the manufacturer.

When a given surgical procedure is performed, a large amount of data associated with the surgical procedure can be generated and captured. All of the captured data can be communicated to a surgical hub, where the information can be stripped of all "personal" associations. The captured data can be time-stamped before being received at the surgical hub, after being received at the surgical hub, before being stripped of the "personal" associations, or after being stripped of the "personal" associations. The surgical hub can communicate the stripped data to the cloud-based system for subsequent analysis. Over time, the cloud-based system will receive large data sets of information associated with the surgeries.

Accordingly, in one aspect, the present disclosure provides a surgical hub for prioritizing surgical data associated with a surgical procedure to a cloud-based system communicatively coupled to a plurality of surgical hubs. The surgical hub comprises a processor and a memory coupled to the processor. The memory stores instructions executable by the processor to capture surgical data, wherein the surgical data comprises data associated with a surgical device, time-stamp the captured surgical data, identify a failure event, identify a time period associated with the failure event, isolate failure event surgical data from surgical data not associated with the failure event based on the identified time period, chronologize the failure event surgical data by time-stamp, encrypt the chronologized failure event surgical data, generate a datagram comprising the encrypted failure event surgical data, and transmit the datagram to a cloud-based system. The datagram is structured to include a field which includes a flag that prioritizes the encrypted failure event surgical data over other encrypted data of the datagram. The datagram allows for the cloud-based system to decrypt the encrypted failure event surgical data, focus analysis on the failure event surgical data rather than surgical data not associated with the failure event, and flag the surgical device associated with the failure event for at least one of the following: removal from an operating room, return to a manufacturer, or future inoperability in the cloud-based system.

In various aspects, the present disclosure provides a control circuit to prioritize surgical data associated with a surgical procedure to a cloud-based system communicatively coupled to a plurality of surgical hubs. In various aspects, the present disclosure provides a non-transitory computer-readable medium storing computer-readable instructions which, when executed, causes a machine to prioritize surgical data associated with a surgical procedure to a cloud-based system communicatively coupled to a plurality of surgical hubs.

In another aspect, the present disclosure provides a method, comprising capturing data during a surgical procedure, communicating the captured data to a surgical hub, time-stamping the captured data, identifying a failure event associated with the surgical procedure, determining which of the captured data is associated with the failure event, separating the captured data associated with the failure event from all other captured data, chronologizing the captured data associated with the failure event, and communicating the chronologized captured data to a cloud-based system on a prioritized basis.

By capturing the large amount of data associated with the surgical procedure, and with having the captured data time-stamped, the portion of the captured data which is relevant to the detected/identified failure event can be more easily isolated from all of the other captured data, thereby allowing for a more focused subsequent analysis on just the relevant captured data. The data associated with the failure event can then be chronologized (this requires less processing power than chronologizing all of the captured data), thereby allowing for the events leading up to the detection/identification of the failure event to be more easily considered during the subsequent analysis of the failure event. The chronologized data can then be communicated to the cloud-based system (this requires less communication resources than communicating all of the captured data at the same time) on a prioritized basis, thereby allowing for the focused subsequent analysis of the fault event to be performed by the cloud-based system in a more time-sensitive manner.

To help ensure that the best practice recommendations are developed based on accurate data, it would be desirable to ensure that the generator data received at the cloud-based system is the same as the generator data communicated to the cloud-based system. Also, to help to be able to determine the cause of a failure event as quickly as possible, it would be desirable to ensure that surgical data associated with the failure event is communicated to the cloud-based system in a prioritized manner (relative to surgical data not associated with the failure event) so that analysis of the surgical data can be performed in an expedited manner.

Aspects of a system and method for communicating data associated with a surgical procedure are described herein. As shown in FIG. 9, various aspects of the computer implemented interactive surgical system 200 includes a device/instrument 235, a generator module 240, a modular control tower 236, and a cloud-based system 205. As shown in FIG. 10, the device/instrument 235, the generator module 240, and the modular control tower 236 are components/portions of a surgical hub 206.

Figure 22:
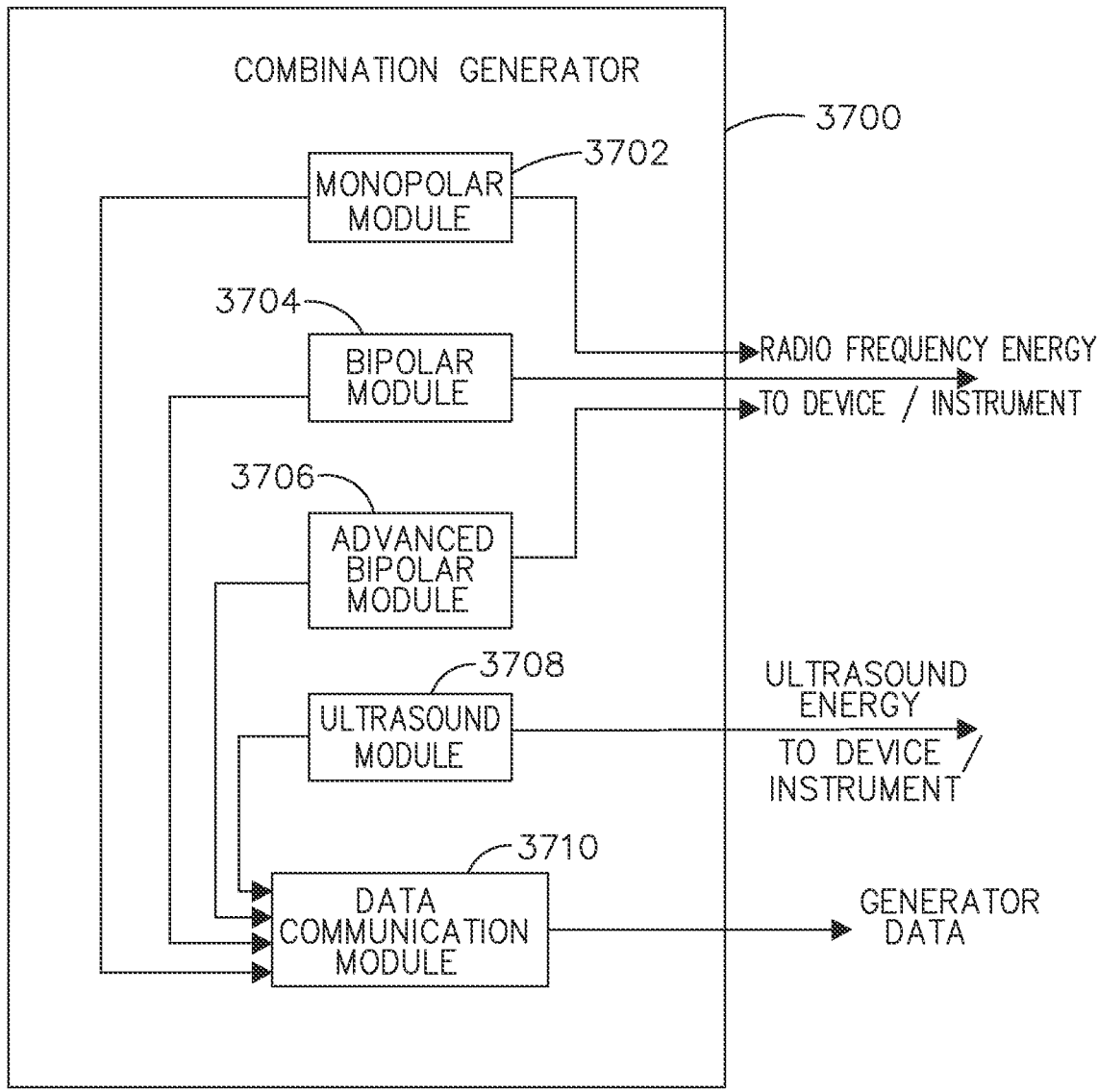
FIG. 22 illustrates a combination generator, in accordance with at least one aspect of the present disclosure.

In various aspects, the generator module 240 of the surgical hub 206 can supply radio-frequency energy such as monopolar radio-frequency energy, bipolar radio-frequency energy, and advanced bipolar energy and/or ultrasonic energy to a device/instrument 235 for use in a surgical procedure. Thus, the generator module 240 may be referred to as a combination generator. An example of such a combination generator is shown in FIG. 22, where the combination generator 3700 is shown as including a monopolar module 3702, a bipolar module 3704, an advanced bipolar module 3706, and an ultrasound module 3708. When utilized during a surgical procedure, the respective energy modules (e.g., 3702, 3704, 3706, and/or 3708) of the combination generator 3700 can provide generator data such as type of energy supplied to the device instrument (e.g., radio-frequency energy, ultrasound energy, radio-frequency energy and ultrasound energy), type of radio-frequency energy (e.g., monoplar, bipolar, advanced bipolar), frequency, power output, duration, etc., to the data communication module 3710 of the combination generator 3700.

Figure 23:
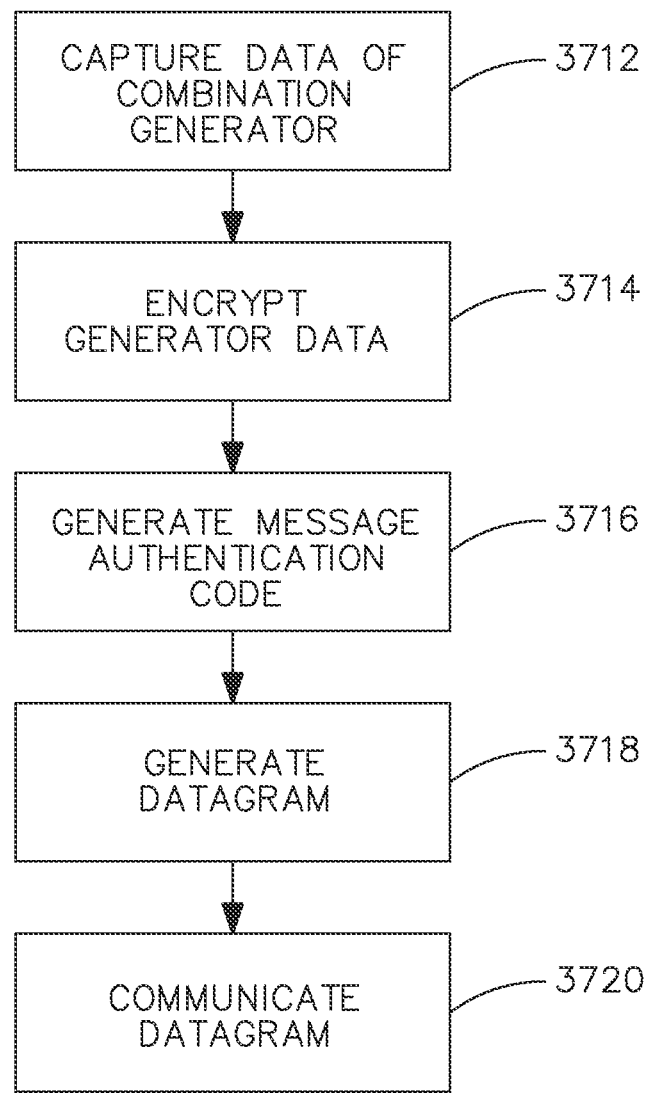
FIG. 23 illustrates a method of capturing data from a combination generator and communicating the captured generator data to a cloud-based system, in accordance with at least one aspect of the present disclosure.

FIG. 23 illustrates various aspects of a method of capturing data from a combination generator 3700 and communicating the captured generator data to a cloud-based system 205. Notably, as discussed herein, the present disclosure should not be limited to processing generator data. As such, the method of FIG. 23 similarly extends to other types of data received from other components coupled to the surgical hub 206 (e.g., imaging module data, smoke evacuator data, suction/irrigation data, device/instrument data). The method comprises (1) capturing 3712 data from a combination generator 3700 of a surgical hub 206 during a surgical procedure, wherein the combination generator 3700 is configured to supply two or more different modes of energy; (2) encrypting 3714 the captured generator data; (3) generating 3716 a MAC based on the captured generator data; (4) generating 3718 a datagram comprising the encrypted generator data, the MAC, a source identifier, and a destination identifier; and (5) communicating 3720 the datagram from the surgical hub 206 to a cloud-based system 205, wherein the datagram allows for the cloud-based system 205 to (i) authenticate integrity of the communicated generator data, (ii) authenticate the surgical hub as a source of the datagram, and (iii) determine a communication path followed by the datagram between the surgical hub 206 and the cloud-based system 205.

More specifically, once the generator data is received at the data communication module 3710 of the combination generator 3700, the generator data can be communicated to the modular communication hub 203 of the surgical hub 206 for subsequent communication to the cloud-based system 205. The data communication module 3710 can communicate the generator data to the modular communication hub 203 serially over a single communication line or in parallel over a plurality of communication lines, and such communication can be performed in real time or near real time. Alternatively, such communication can be performed in batches.

Figure 24:
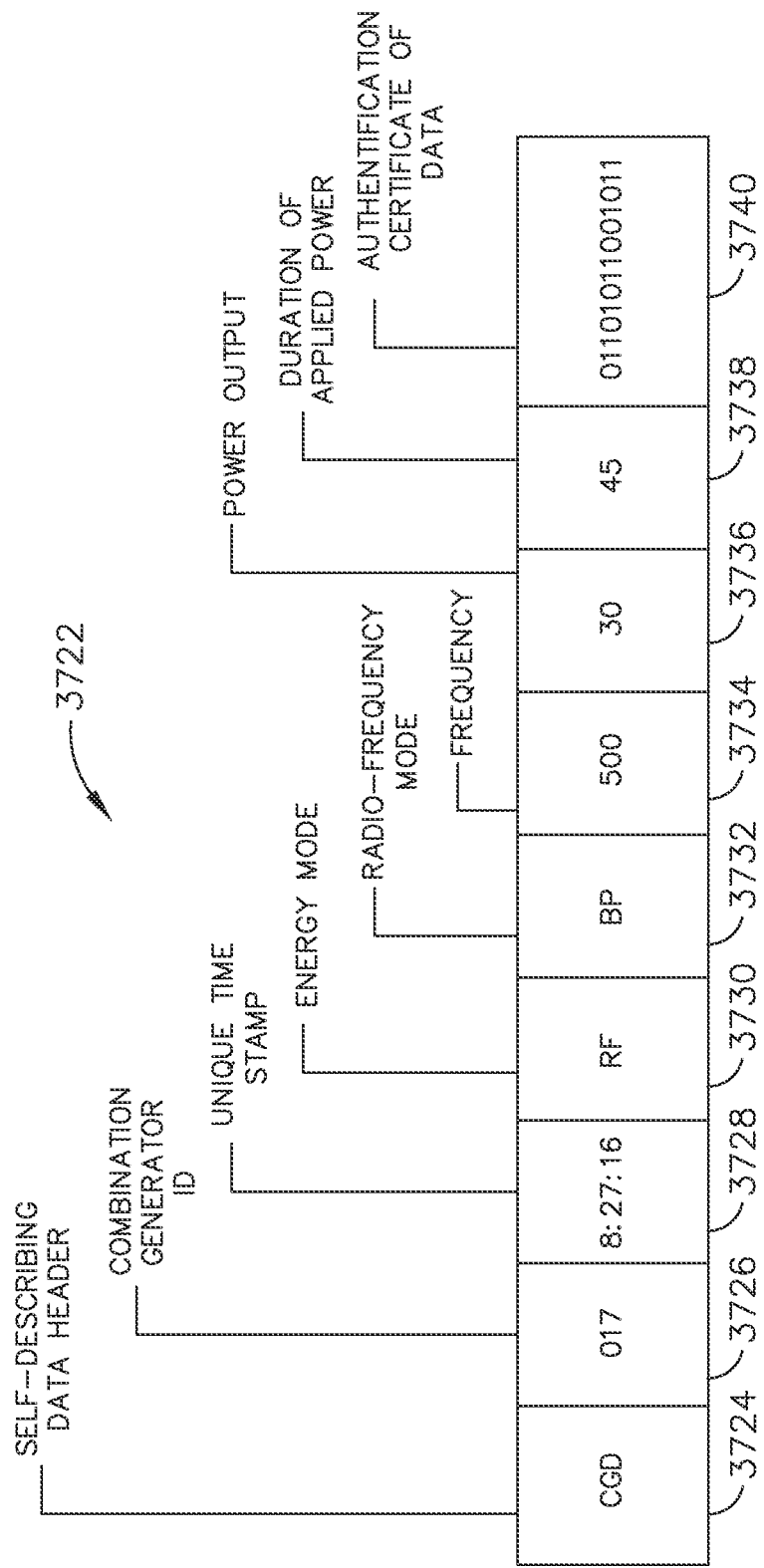
FIG. 24 illustrates a data packet of combination generator data, in accordance with at least one aspect of the present disclosure.

According to various aspects, prior to communicating the generator data to the modular communication hub 203, a component of the combination generator 3700 (e.g., the data communication module 3710) can organize the generator data into data packets. An example of such a data packet is shown in FIG. 24, where the data packet 3722 includes a preamble 3724 or self-describing data header which defines what the data is (e.g., combination generator data—CGD) and fields which indicate where the generator data came from [e.g., combination generator ID number 3726—(e.g., 017), a unique time stamp 3728 (e.g., 08:27:16), the energy mode utilized 3730 (e.g., RF, U, RF+U), the type of radio-frequency energy or radio frequency mode 3732 (e.g., MP, BP, ABP), the frequency 3734 (e.g., 500 Khz), the power output 3736 (e.g., 30 watts), the duration of applied power 3738 (e.g., 45 milliseconds), and an authentication/identification certificate of the data point 3740 (e.g., 01101011001011). The example data packet 3722 may be considered a self-describing data packet, and the combination generator 3700 and other intelligent devices (e.g., the surgical hub 206) can use the self-describing data packets to minimize data size and data-handling resources. Again, as discussed herein, the present disclosure should not be limited to processing generator data received from a combination generator 3700. As such, the data packet 3722 of FIG. 24 similarly extends to other types of data received from other components coupled to the surgical hub 206. In one aspect, the data packet 3722 may comprise data associated with endoscope 239 (e.g., image data) received from a component of the imaging module 238. In another aspect, the data packet 3722 may comprises data associated with an evacuation system (e.g., pressures, particle counts, flow rates, motor speeds) received from a component of the smoke evacuator module 226. In yet another aspect, the data packet 3722 may comprise data associated with a device/instrument (e.g., temperature sensor data, firing data, sealing data) received from a component of the device/instrument 235. In various other aspects, the data packet 3722 may similarly comprise data received from other components coupled to the surgical hub 206 (e.g., suction/irrigation module 228, non-contact sensor module 242)

Additionally, the data communication module 3710 can compress the generator data and/or encrypt the generator data prior to communicating the generator data to the modular communication hub 203. The specific method of compressing and/or encrypting can be the same as or different from the compressing and/or encrypting which may be performed by the surgical hub 206 as described in more detail below.

The modular communication hub 203 can receive the generator data communicated from the combination generator 3700 (e.g., via the data communication module 3710), and the generator data can be subsequently communicated to the cloud-based system 205 (e.g., through the Internet). According to various aspects, the modular communication hub 203 can receive the generator data through a hub/switch 207/209 of the modular communication hub 203 (See FIG. 10), and the generator data can be communicated to the cloud-based system 205 by a router 211 of the modular communication hub 203 (See FIG. 10). The generator data may be communicated in real time, near real time, or in batches to the cloud-based system 205 or may be stored at the surgical hub 206 prior to being communicated to the cloud-based system 205. The generator data can be stored, for example, at the storage array 234 or at the memory 249 of the computer system 210 of the surgical hub 206.

In various aspects, for instances where the generator data received at the modular communication hub 203 is not encrypted, prior to the received generator data being communicated to the cloud-based system 205, the generator data is encrypted to help ensure the confidentiality of the generator data, either while it is being stored at the surgical hub 206 or while it is being transmitted to the cloud 204 using the Internet or other computer networks. According to various aspects, a component of the surgical hub 206 utilizes an encryption algorithm to convert the generator data from a readable version to an encoded version, thereby forming the encrypted generator data. The component of the surgical hub 206 which utilizes/executes the encryption algorithm can be, for example, the processor module 232, the processor 244 of the computer system 210, and/or combinations thereof. The utilized/executed encryption algorithm can be a symmetric encryption algorithm and/or an asymmetric encryption algorithm.

Using a symmetric encryption algorithm, the surgical hub 206 would encrypt the generator data using a shared secret (e.g., private key, passphrase, password). In such an aspect, a recipient of the encrypted generator data (e.g., cloud-based system 205) would then decrypt the encrypted generator data using the same shared secret. In such an aspect, the surgical hub 206 and the recipient would need access to and/or knowledge of the same shared secret. In one aspect, a shared secret can be generated/chosen by the surgical hub 206 and securely delivered (e.g., physically) to the recipient before encrypted communications to the recipient.

Alternatively, using an asymmetric encryption algorithm, the surgical hub 206 would encrypt the generator data using a public key associated with a recipient (e.g., cloud-based system 205). This public key could be received by the surgical hub 206 from a certificate authority that issues a digital certificate certifying the public key as owned by the recipient. The certificate authority can be any entity trusted by the surgical hub 206 and the recipient. In such an aspect, the recipient of the encrypted generator data would then decrypt the encrypted generator data using a private key (i.e., known only by the recipient) paired to the public key used by the surgical hub 206 to encrypt the generator data. Notably, in such an aspect, the encrypted generator data can only be decrypted using the recipient's private key.

According to aspects of the present disclosure, components (e.g., surgical device/instrument 235, energy device 241, endoscope 239) of the surgical system 202 are associated with unique identifiers, which can be in the form of serial numbers. As such, according to various aspects of the present disclosure, when a component is coupled to a surgical hub 206, the component may establish a shared secret with the surgical hub 206 using the unique identifier of the coupled component as the shared secret. Further, in such an aspect, the component may derive a checksum value by applying a checksum function/algorithm to the unique identifier and/or other data being communicated to the surgical hub 206. Here, the checksum function/algorithm is configured to output a significantly different checksum value if there is a modification to the underlying data.

In one aspect, the component may initially encrypt the unique identifier of a coupled component using a public key associated with the surgical hub (e.g., received by the component from the surgical hub 206 upon/after connection) and communicate the encrypted unique identifier to the surgical hub 206. In other aspects, the component may encrypt the unique identifier and the derived checksum value of a coupled component using a public key associated with the surgical hub 206 and communicate the encrypted unique identifier and linked/associated checksum value to the surgical hub 206.

In yet other aspects, the component may encrypt the unique identifier and a checksum function/algorithm using a public key associated with the surgical hub 206 and communicate the encrypted unique identifier and the checksum function/algorithm to the surgical hub 206. In such aspects, the surgical hub 206 would then decrypt the encrypted unique identifier or the encrypted unique identifier and the linked/associated checksum value or the encrypted unique identifier and the checksum function/algorithm using a private key (i.e., known only by the surgical hub 206) paired to the public key used by the component to encrypt the unique identifier.

Since the encrypted unique identifier can only be decrypted using the surgical hub's 206 private key and the private key is only known by the surgical hub, this is a secure way to communicate a shared secret (e.g., the unique identifier of the coupled component) to the surgical hub 206. Further, in aspects where a checksum value is linked to/associated with the unique identifier, the surgical hub 206 may apply the same checksum function/algorithm to the decrypted unique identifier to generate a validating checksum value. If the validating checksum value matches the decrypted checksum value, the integrity of the decrypted unique identifier is further verified. Further, in such aspects, with a shared secret established, the component can encrypt future communications to the surgical hub 206, and the surgical hub 206 can decrypt the future communications from the component using the shared secret (e.g., the unique identifier of the coupled component). Here, according to various aspects, a checksum value may be derived for and communicated with each communication between the component and the surgical hub 206 (e.g., the checksum value based on the communicated data or at least a designated portion thereof). Here, a checksum function/algorithm (e.g., known by the surgical hub 206 and/or component or communicated when establishing the shared secret between the surgical hub 206 and the component as described above) may be used to generate validating checksum values for comparison with communicated checksum values to further verify the integrity of communicated data in each communication.

Notably, asymmetric encryption algorithms may be complex and may require significant computational resources to execute each communication. As such, establishing the unique identifier of the coupled component as the shared secret is not only quicker (e.g., no need to generate a shared secret using a pseudorandom key generator) but also increases computational efficiency (e.g., enables the execution of faster, less complex symmetric encryption algorithms) for all subsequent communications. In various aspects, this established shared secret may be utilized by the component and surgical hub 206 until the component is decoupled from the surgical hub (e.g., surgical procedure ended).

According to other aspects of the present disclosure, components (e.g., surgical device/instrument 235, energy device 241, endoscope 239) of the surgical system 202 may comprise sub-components (e.g., handle, shaft, end effector, cartridge) each associated with its own unique identifier. As such, according to various aspects of the present disclosure, when a component is coupled to the surgical hub 206, the component may establish a shared secret with the surgical hub 206 using a unique compilation/string (e.g., ordered or random) of the unique identifiers associated with the sub-components that combine to form the coupled component. In one aspect, the component may initially encrypt the unique compilation/string of the coupled component using a public key associated with the surgical hub 206 and communicate the encrypted unique compilation/string to the surgical hub 206. In such an aspect, the surgical hub 206 would then decrypt the encrypted unique compilation/string using a private key (i.e., known only by the surgical hub 206) paired to the public key used by the component to encrypt the unique compilation/string. Since the encrypted unique compilation/string can only be decrypted using the surgical hub's 206 private key and the private key is only known by the surgical hub 206, this is a secure way to communicate a shared secret (e.g., the unique compilation/string of the coupled component) to the surgical hub 206. Further, in such an aspect, with a shared secret established, the component can encrypt future communications to the surgical hub 206, and the surgical hub 206 can decrypt the future communications from the component using the shared secret (e.g., the unique compilation/string of the coupled component).

Again, asymmetric encryption algorithms may be complex and may require significant computational resources to execute each communication. As such, establishing the unique compilation/string of the coupled component (i.e., readily combinable by the component) as the shared secret is not only quicker (e.g., no need to generate a shared secret using a pseudorandom key generator) but also increases computational efficiency (e.g., enables the execution of faster, less complex symmetric encryption algorithms) for all subsequent communications. In various aspects, this established shared secret may be utilized by the component and surgical hub 206 until the component is decoupled from the surgical hub 206 (e.g., surgical procedure ended). Furthermore, in such an aspect, since various sub-components may be reusable (e.g., handle, shaft, end effector) while other sub-components may not be reusable (e.g., end effector, cartridge) each new combination of sub-components that combine to form the coupled component provide a unique compilation/string usable as a shared secret for component communications to the surgical hub 206.

According to further aspects of the present disclosure, components (e.g., surgical device/instrument 235, energy device 241, endoscope 239) of the surgical system 202 are associated with unique identifiers. As such, according to various aspects of the present disclosure, when a component is coupled to the surgical hub 206, the surgical hub 206 may establish a shared secret with a recipient (e.g., cloud-based system 205) using the unique identifier of the coupled component. In one aspect, the surgical hub 206 may initially encrypt the unique identifier of a coupled component using a public key associated with the recipient and communicate the encrypted unique identifier to the recipient. In such an aspect, the recipient would then decrypt the encrypted unique identifier using a private key (i.e., known only by the recipient) paired to the public key used by the surgical hub 206 to encrypt the unique identifier. Since the encrypted unique identifier can only be decrypted using the recipient's private key and the private key is only known by the recipient, this is a secure way to communicate a shared secret (e.g., the unique identifier of the coupled component) to the recipient (e.g., cloud-based system). Further in such an aspect, with a shared secret established, the surgical hub 206 can encrypt future communications to the recipient (e.g., cloud-based system 205), and the recipient can decrypt the future communications from the surgical hub 206 using the shared secret (e.g., the unique identifier of the coupled component).

Notably, asymmetric encryption algorithms may be complex and may require significant computational resources to execute each communication. As such, establishing the unique identifier of the coupled component (i.e., already available to the surgical hub 206) as the shared secret is not only quicker (e.g., no need to generate a shared secret using a pseudorandom key generator) but also increases computational efficiency by, for example, enabling the execution of faster, less complex symmetric encryption algorithms for all subsequent communications. In various aspects, this established shared secret may be utilized by the surgical hub 206 until the component is decoupled from the surgical hub (e.g., surgical procedure ended).

According to yet further aspects of the present disclosure, components (e.g., surgical device/instrument 235, energy device 241, endoscope 239) of the surgical system 202 may comprise sub-components (e.g., handle, shaft, end effector, cartridge) each associated with its own unique identifier. As such, according to various aspects of the present disclosure, when a component is coupled to the surgical hub 206, the surgical hub 206 may establish a shared secret with a recipient (e.g., cloud-based system 205) using a unique compilation/string (e.g., ordered or random) of the unique identifiers associated with the sub-components that combine to form the coupled component.

In one aspect, the surgical hub 206 may initially encrypt the unique compilation/string of the coupled component using a public key associated with the recipient and communicate the encrypted unique compilation/string to the recipient. In such an aspect, the recipient would then decrypt the encrypted unique compilation/string using a private key (i.e., known only by the recipient) paired to the public key used by the surgical hub 206 to encrypt the unique compilation/string. Since the encrypted unique compilation/string can only be decrypted using the recipient's private key and the private key is only known by the recipient, this is a secure way to communicate a shared secret (e.g., the unique compilation/string of the coupled component) to the recipient. With a shared secret established, the surgical hub 206 can encrypt future communications to the recipient (e.g., cloud-based system 205), and the recipient can decrypt the future communications from the surgical hub 206 using the shared secret (e.g., the unique compilation/string of the coupled component). Again, asymmetric encryption algorithms may be complex and may require significant computational resources to execute each communication. As such, establishing the unique compilation/string of the coupled component (i.e., readily combinable by the surgical hub 206) as the shared secret is not only quicker (e.g., no need to generate a shared secret using a pseudorandom key generator) but also increases computational efficiency (e.g., enables the execution of faster, less complex symmetric encryption algorithms) for all subsequent communications.

In various aspects, this established shared secret may be utilized by the surgical hub 206 until the component is decoupled from the surgical hub (e.g., surgical procedure ended). Furthermore, in such an aspect, since various sub-components may be reusable (e.g., handle, shaft, end effector) while other sub-components may not be reusable (e.g., end effector, cartridge) each new combination of sub-components that combine to form the coupled component provide a unique compilation/string usable as a shared secret for surgical hub 206 communications to the recipient.

Figure 25:
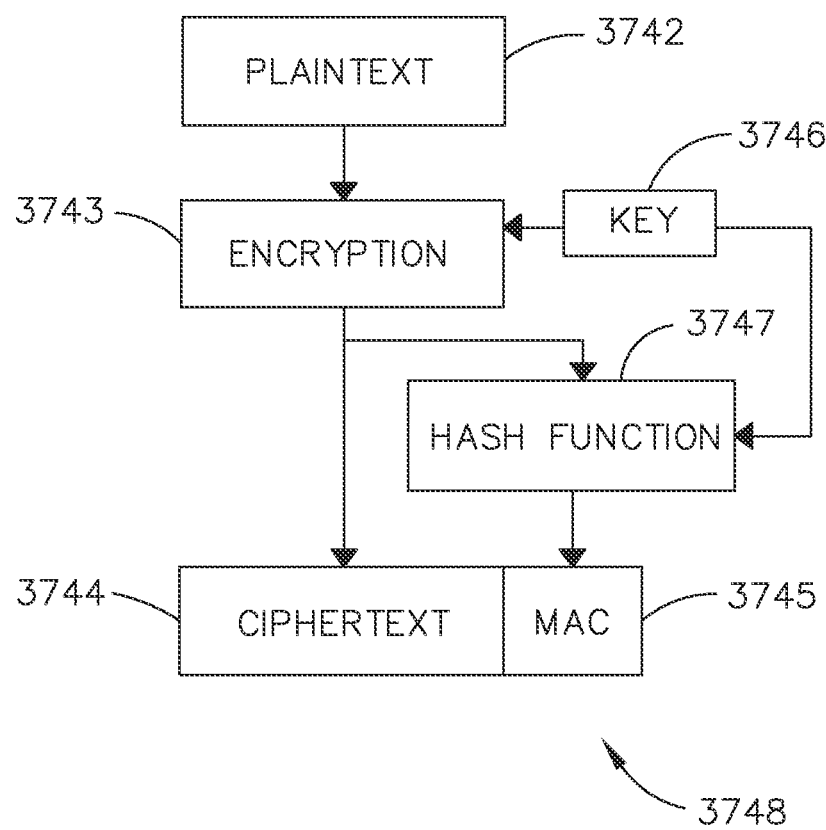
FIG. 25 illustrates an encryption algorithm, in accordance with at least one aspect of the present disclosure.

In some aspects, an encrypt-then-MAC (EtM) approach may be utilized to produce the encrypted generator data. An example of this approach is shown in FIG. 25, where the non-encrypted generator data (i.e., the plaintext 3742, e.g., data packet 3722) is first encrypted 3743 (e.g., via key 3746) to produce a ciphertext 3744 (i.e., the encrypted generator data), then a MAC 3745 is produced based on the resulting ciphertext 3744, the key 3746, and a MAC algorithm (e.g., a hash function 3747). More specifically, the ciphertext 3744 is processed through the MAC algorithm using the key 3746. In one aspect similar to symmetric encryption discussed herein, the key 3746 is a secret key accessible/known by the surgical hub 206 and the recipient (e.g., cloud-based system 205). In such an aspect, the secret key is a shared secret associated with/chosen by the surgical hub 206, a shared secret associated with/chosen by the recipient, or a key selected via a pseudorandom key generator. For this approach, as shown generally at 3748, the encrypted generator data (i.e., the ciphertext 3744) and the MAC 3745 would be communicated together to the cloud-based system 205.

Figure 26:
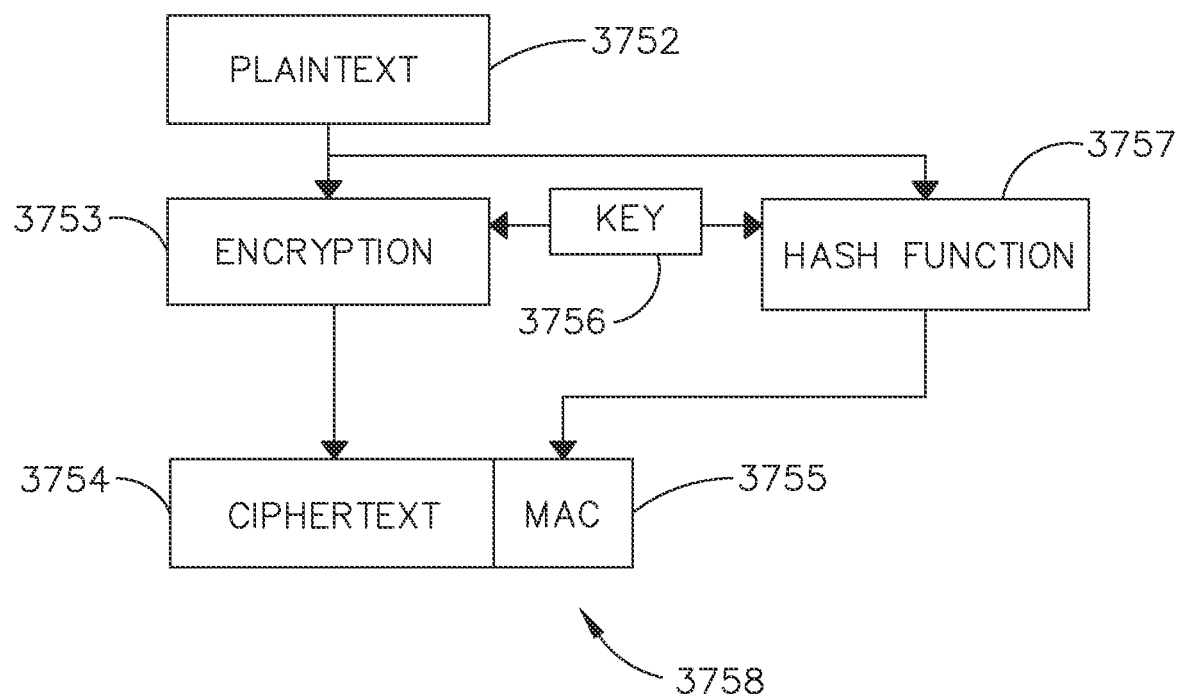
FIG. 26 illustrates another encryption algorithm, in accordance with at least one aspect of the present disclosure.

In other aspects, an encrypt-and-MAC (E&M) approach may be utilized to produce the encrypted generator data. An example of this approach is shown in FIG. 26, where the MAC 3755 is produced based on the non-encrypted generator data (i.e., the plaintext 3752, e.g., data packet 3722), a key 3756, and a MAC algorithm (e.g., a hash function 3757). More specifically, the plaintext 3752 is processed through the MAC algorithm using the key 3756. In one aspect similar to symmetric encryption discussed herein, the key 3756 is a secret key accessible/known by the surgical hub 206 and the recipient (e.g., cloud-based system 205). In such an aspect, the secret key is a shared secret associated with/chosen by the surgical hub 206, a shared secret associated with/chosen by the recipient, or a key selected via a pseudorandom key generator. Further, in such an aspect, the non-encrypted generator data (i.e., the plaintext 3752, e.g., data packet 3722) is encrypted 3753 (e.g., via key 3756) to produce a ciphertext 3754. For this approach, as shown generally at 3758, the MAC 3755 (i.e., produced based on the non-encrypted generator data) and the encrypted generator data (i.e., the ciphertext 3754) would be communicated together to the cloud-based system 205.

Figure 27:
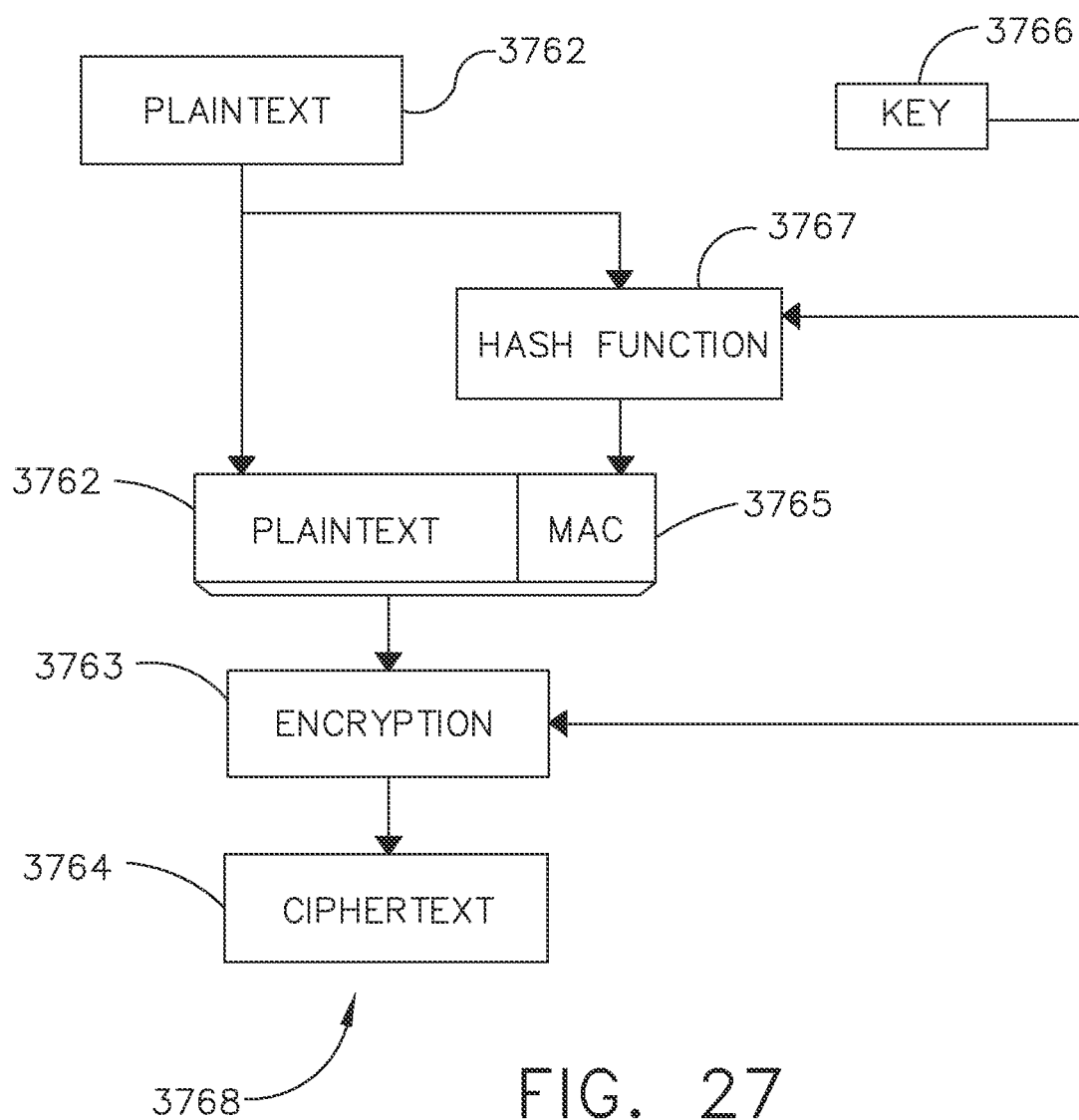
FIG. 27 illustrates yet another encryption algorithm, in accordance with at least one aspect of the present disclosure.

In yet other aspects, a MAC-then-encrypt (MtE) approach may be utilized to produce the encrypted generator data. An example of this approach is shown in FIG. 27, where the MAC 3765 is produced based on the non-encrypted generator data (i.e., the plaintext 3762), a key 3766, and a MAC algorithm (e.g., a hash function 3767). More specifically, the plaintext 3762 is processed through the MAC algorithm using the key 3766. In one aspect similar to symmetric encryption discussed herein, the key 3766 is a secret key accessible/known by the surgical hub 206 and the recipient (e.g., cloud-based system 205). In such an aspect, the secret key is a shared secret associated with/chosen by the surgical hub 206, a shared secret associated with/chosen by the recipient, or a key selected via a pseudorandom key generator. Next, the non-encrypted generator data (i.e., the plaintext 3762) and the MAC 3765 are together encrypted 3763 (e.g., via key 3766) to produce a ciphertext 3764 based on both. For this approach, as shown generally at 3768, the ciphertext 3764 (i.e., which includes the encrypted generator data and the encrypted MAC 3765) would be communicated to the cloud-based system 205.

In alternative aspects, the key used to encrypt the non-encrypted generator data (e.g., FIG. 25 and FIG. 26) or the non-encrypted generator data and the MAC (e.g., FIG. 27) may be different from the key (e.g., keys 3746, 3756, 3766) used to produce the MAC. For example, the key used to encrypt the non-encrypted generator data (e.g., FIG. 25 and FIG. 26) or the non-encrypted generator data and the MAC (e.g., FIG. 27) may be a different shared secret or a public key associated with the recipient.

In lieu of utilizing the MAC to provide for a subsequent assurance of data integrity to the cloud-based system 205, according to other aspects, the surgical hub 206 can utilize a digital signature to allow the cloud-based system 205 to subsequently authenticate integrity of the communicated generator data. For example, the processor module 232 and/or the processor 244 of the computer system 210 can utilize one or more algorithms to generate a digital signature associated with the generator data, and the cloud-based system 205 can utilize an algorithm to determine the authenticity of the received generator data. The algorithms utilized by the processor module 232 and/or the processor 244 of the computer system 210 can include: (1) a key generation algorithm that selects a private key uniformly at random from a set of possible private keys, where the key generation algorithm outputs the private key and a corresponding public key; and (2) a signing algorithm that, given the generator data and a private key, produces a digital signature associated with the generator data. The cloud-based system 205 can utilize a signature verifying algorithm that, given the received generator data, public key, and digital signature, can accept the received generator data as authentic if the digital signature is determined to be authentic or consider the generator data to be compromised or altered if the digital signature is not determined to be authentic.

According to other aspects of the present disclosure, the surgical hub 206 can utilize a commercial authentication program (e.g., Secure Hash Algorithm, SHA-2 comprising SHA-256) to provide for a subsequent assurance of data integrity of the communicated generator data to the cloud-based system 205.

After the generator data has been encrypted (e.g., via EtM, E&M, MtE), a component of the surgical hub 206 can communicate the encrypted generator data to the cloud-based system 205. The component of the surgical hub 206 which communicates the encrypted generator data to the cloud-based system 205 can be, for example, the processor module 232, a hub/switch 207/209 of the modular communication hub 203, the router 211 of the modular communication hub 203, the communication module 247 of the computer system 210, etc.

Figure 28:
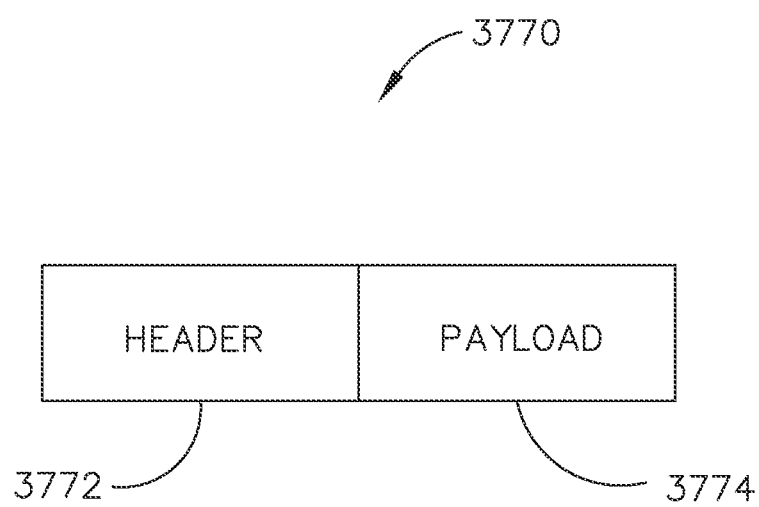
FIG. 28 illustrates a high-level representation of a datagram, in accordance with at least one aspect of the present disclosure.
Figure 29:
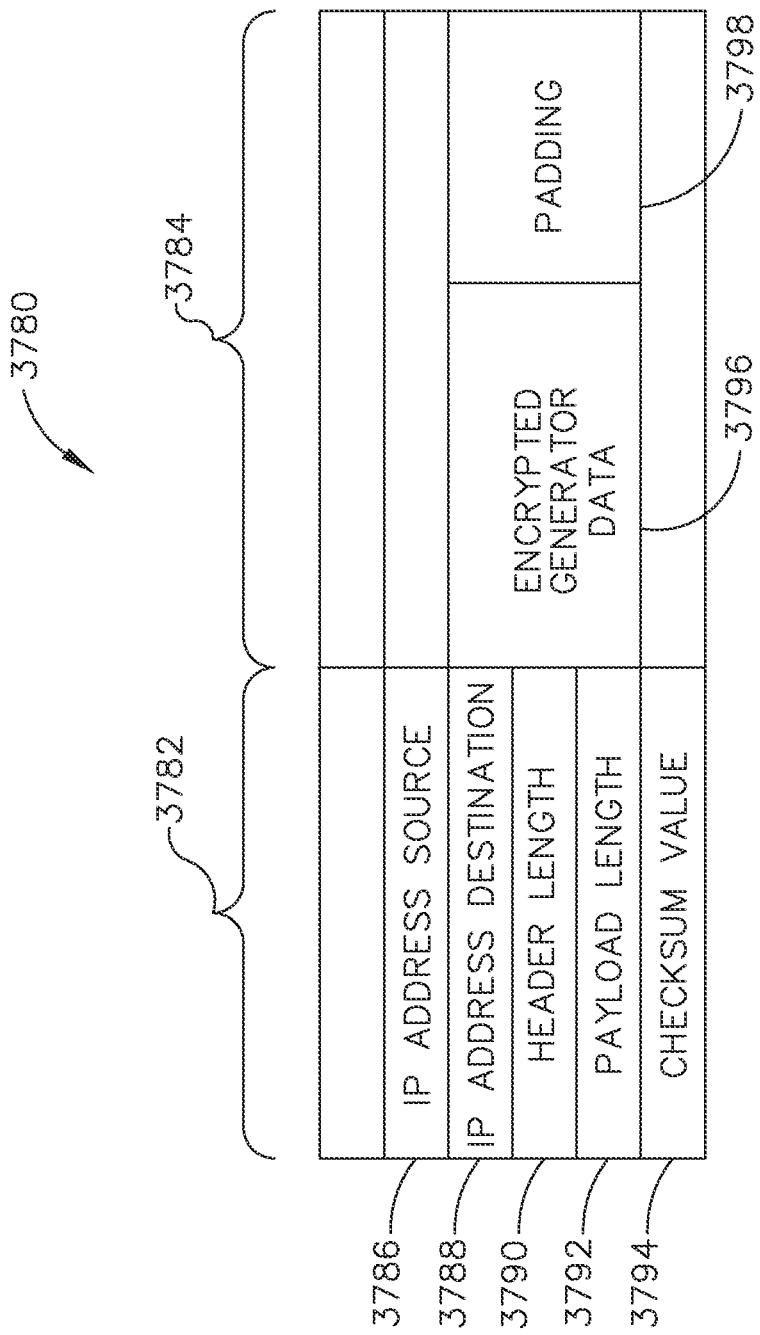
FIG. 29 illustrates a more detailed representation of the datagram of FIG. 28, in accordance with at least one aspect of the present disclosure.

According to various aspects, the communication of the encrypted generator data through the Internet can follow an IP which: (1) defines datagrams that encapsulate the encrypted generator data to be delivered and/or (2) defines addressing methods that are used to label the datagram with source and destination information. A high-level representation of an example datagram 3770 is shown in FIG. 28, where the datagram 3770 includes a header 3772 and a payload 3774, and in other aspects also may include a trailer (not shown). A more detailed representation of an example datagram 3780 is shown in FIG. 29, where the header 3782 can include fields for information such as, for example, the IP address of the source 3786 which is sending the datagram (e.g., the router 211 of the modular communication hub 203), the IP address of the destination 3788 which is to receive the datagram (e.g., the cloud 204 and/or the remote server 213 associated with the cloud-based system 205), a type of service designation (not shown), a header length 3790, a payload length 3792, and a checksum value 3794. In such an aspect, the surgical hub 206 may further apply a checksum function/algorithm to the non-encrypted generator data (i.e., the plaintext 3742, e.g., data packet 3722) or at least a portion of the non-encrypted generator data (e.g., combination generator ID 3726) to derive the checksum value 3794. Here, the checksum function/algorithm is configured to output a significantly different checksum value if there is any modification (e.g., even a slight change) to the underlying data (e.g., generator data). After decryption of the encrypted generator data by its recipient (e.g., cloud-based system 205), the recipient may apply the same checksum function/algorithm to the decrypted generator data to generate a validating checksum value. If the validating checksum value matches the checksum value 3794 (i.e., stored in the header 3782 of the received datagram 3780), the integrity of the received generator data is further verified. The payload 3784 may include the encrypted generator data 3796 and can also include padding 3798 if the encrypted generator data 3796 is less than a specified payload length. Notably, the communicated encrypted generator data 3796 may comprise a MAC as discussed in FIGS. 25, 26, and 27 above (e.g., references 3748, 3758, and 3768, respectively). In some aspects, the header 3782 can further include a specific path the datagram is to follow when the datagram is communicated from the surgical hub 206 to the cloud-based system 205 (e.g., from IP address of the source, to IP address of at least one intermediate network component (e.g., specified routers, specified servers), to IP address of the destination).

According to various aspects, prior to the generator data being encrypted, the generator data can be time-stamped (if not already time-stamped by the combination generator 3700) and/or the generator data can be compressed (if not already compressed by the combination generator 3700). Time-stamping allows for the cloud-based system 205 to correlate the generator data with other data (e.g., stripped patient data) which may be communicated to the cloud-based system 205. The compression allows for a smaller representation of the generator data to be subsequently encrypted and communicated to the cloud-based system 205. For the compression, a component of the surgical hub 206 can utilize a compression algorithm to convert a representation of the generator data to a smaller representation of the generator data, thereby allowing for a more efficient and economical encryption of the generator data (e.g., less data to encrypt utilizes less processing resources) and a more efficient and economical communication of the encrypted generator data (e.g., smaller representations of the generator data within the payload of the datagrams (e.g., FIGS. 28 and 29) allow for more generator data to be included in a given datagram, for more generator data to be communicated within a given time period, and/or for generator data to be communicated with fewer communication resources). The component of the surgical hub 206 which utilizes/executes the compression algorithm can be, for example, the processor module 232, the processor 244 of the computer system, and/or combinations thereof. The utilized/executed compression algorithm can be a lossless compression algorithm or a lossy compression algorithm.

Once the generator data and the MAC for a given datagram has been received at the cloud-based system 205 (e.g., FIG. 25, reference 3748; FIG. 26, reference 3758; and FIG. 27, reference 3768), the cloud-based system 205 can decrypt the encrypted generator data from the payload of the communicated datagram to realize the communicated generator data.

In one aspect, referring back to FIG. 25, the recipient (e.g., cloud-based system 205) may, similar to the surgical hub 206, process the ciphertext 3744 through the same MAC algorithm using the same known/accessible secret key to produce an authenticating MAC. If the received MAC 3745 matches this authenticating MAC, the recipient (e.g., cloud-based system 205) may safely assume that the ciphertext 3744 has not been altered and is from the surgical hub 206. The recipient (e.g., cloud-based system 205) may then decrypt the ciphertext 3744 (e.g., via key 3746) to realize the plaintext 3742 (e.g., data packet comprising generator data).

In another aspect, referring back to FIG. 26, the recipient (e.g., cloud-based system 205) may decrypt the ciphertext 3754 (e.g., via key 3756) to realize the plaintext 3752 (e.g., data packet comprising generator data). Next, similar to the surgical hub 206, the recipient (e.g., cloud-based system 205) may process the plaintext 3752 through the same MAC algorithm using the same known/accessible secret key to produce an authenticating MAC. If the received MAC 3755 matches this authenticating MAC, the recipient (e.g., cloud-based system 205) may safely assume that the plaintext 3752 has not been altered and is from the surgical hub 206.

In yet another aspect, referring back to FIG. 27, the recipient (e.g., cloud-based system 205) may decrypt the ciphertext 3764 (e.g., via key 3766) to realize the plaintext 3762 (e.g., data packet comprising generator data) and the MAC 3765. Next, similar to the surgical hub 206, the recipient (e.g., cloud-based system 205) may process the plaintext 3762 through the same MAC algorithm using the same known/accessible secret key to produce an authenticating MAC. If the received MAC 3765 matches this authenticating MAC, the recipient (e.g., cloud-based system 205) may safely assume that the plaintext 3762 has not been altered and is from the surgical hub 206.

In alternative aspects, the key used to encrypt the non-encrypted generator data (e.g., FIG. 25 and FIG. 26) or the non-encrypted generator data and the MAC (e.g., FIG. 27) may be different from the key (e.g., keys 3746, 3756, 3766) used to produce the MAC. For example, the key used to encrypt the non-encrypted generator data (e.g., FIG. 25 and FIG. 26) or the non-encrypted generator data and the MAC (e.g., FIG. 27) may be a different shared secret or a public key associated with the recipient. In such aspects, referring to FIG. 25, the recipient (e.g., cloud-based system 205) may, after verifying the authenticating MAC via key 3746 (described above), then decrypt the ciphertext 3744 (e.g., via the different shared secret or private key associated with the recipient) to realize the plaintext 3742 (e.g., data packet comprising generator data). In such aspects, referring to FIG. 26, the recipient may decrypt the ciphertext 3754 (e.g., via the different shared secret or private key associated with the recipient) to realize the plaintext 3752 (e.g., data packet comprising generator data), then verify the authenticating MAC via key 3756 (described above). In such aspects, referring to FIG. 27, the recipient may decrypt the ciphertext 3764 (e.g., via the different shared secret or private key associated with the recipient) to realize the plaintext 3762 (e.g., data packet comprising generator data) and the MAC 3765, then verify the authenticating MAC via key 3766 (described above).

In sum, referring to FIGS. 25-27, if an authenticating MAC, as determined/calculated by the cloud-based system 205, is the same as the MAC which was received with the datagram, the cloud-based system 205 can have confidence that the received generator data is authentic (i.e., it is the same as the generator data which was communicated by the surgical hub 206) and that the data integrity of the communicated generator data has not been compromised or altered. As described above, the recipient may further apply the plaintext 3742, 3752, 3762, or at least a portion thereof to the same checksum function/algorithm (i.e., used by the surgical hub 206) to generate a validating checksum value to further verify the integrity of the generator data based on the checksum value stored in the header of the communicated datagram.

Additionally, based on the decrypted datagram, the IP address of the source (e.g., FIG. 29, reference 3786) which originally communicated the datagram to the cloud-based system 205 can be determined from the header of the communicated datagram. If the determined source is a recognized source, the cloud-based system 205 can have confidence that the generator data originated from a trusted source, thereby providing source authentication and even more assurance of the data integrity of the generator data. Furthermore, since each router the datagram passed through in route to the cloud-based system 205 includes its IP address with its forwarded communication, the cloud-based system 205 is able to trace back the path followed by the datagram and identify each router which handled the datagram. The ability to identify the respective routers can be helpful in instances where the content of the datagram received at the cloud-based system 205 is not the same as the content of the datagram as originally communicated by the surgical hub 206. For aspects where the communication path was pre-specified and included in the header of the communicated datagram, the ability to identify the respective routers can allow for path validation and provide additional confidence of the authenticity of the received generator data.

Furthermore, according to various aspects, after authenticating the received generator data, the cloud-based system 205 can communicate a message (e.g., a handshake or similar message) to the surgical hub 206 via the Internet or another communication network, confirming/guaranteeing that the datagram communicated from the surgical hub 206 was received intact by the cloud-based system 205, thereby effectively closing the loop for that particular datagram.

Aspects of the above-described communication method, and/or variations thereof, can also be employed to communicate data other than generator data to the cloud-based system 205 and/or to communicate generator data and/or other data from the surgical hub 206 to systems and/or devices other than the cloud-based system 205. For example, according to various aspects, the generator data and/or other data can be communicated from the surgical hub 206 to a hand-held surgical device/instrument (e.g., wireless device/instrument), to a robotic interface of a surgical device/instrument (e.g., robot hub 222) and/or to other servers, including servers (e.g., similar to server 213) associated with other cloud-based systems (e.g., similar to cloud-based system 205) in accordance with the above-described communication method. For example, in certain instances, an EEPROM chip of a given surgical instrument can initially be provided with merely an electronic chip device ID. Upon connection of the given surgical instrument to the combination generator 3700, data can be downloaded from the cloud-based system 205 to the surgical hub 206 and subsequently to the EEPROM of the surgical instrument in accordance with the above-described communication method.

In addition to communicating generator data to the cloud-based system 205, the surgical hub 206 can also utilize the above-described method of communication, and/or variations thereof, to communicate data other than generator data to the cloud-based system 205. For example, the surgical hub 206 can also communicate other information associated with the surgical procedure to the cloud-based system 205. Such other information can include, for example, the type of surgical procedure being performed, the name of the facility where the surgical procedure is being performed, the location of the facility where the surgical procedure is being performed, an identification of the operating room within the facility where the surgical procedure is being performed, the name of the surgeon performing the surgical procedure, the age of the patient, and data associated with the condition of the patient (e.g., blood pressure, heart rate, current medications). According to various aspects, such other information may be stripped of all information which could identify the specific surgery, the patient, or the surgeon, so that the information is essentially anonymized for further processing and analysis by the cloud-based system 205. In other words, the stripped data is not correlated to a specific surgery, patient, or surgeon. The stripped information can be communicated to the cloud-based system 205 either together with or distinct from the communicated generator data.

For instances where the stripped/other data is to be communicated apart from the generator data, the stripped/other data can be time-stamped, compressed, and/or encrypted in a manner identical to or different from that described above regarding the generator data, and the surgical hub 206 may be programmed/configured to generate a datagram which includes the encrypted stripped/other information in lieu of the encrypted generator data. The datagram can then be communicated from the surgical hub 206 through the Internet to the cloud-based system 205 following an IP which: (1) defines datagrams that encapsulate the encrypted stripped/other data to be delivered, and (2) defines addressing methods that are used to label the datagram with source and destination information.

Figure 30:
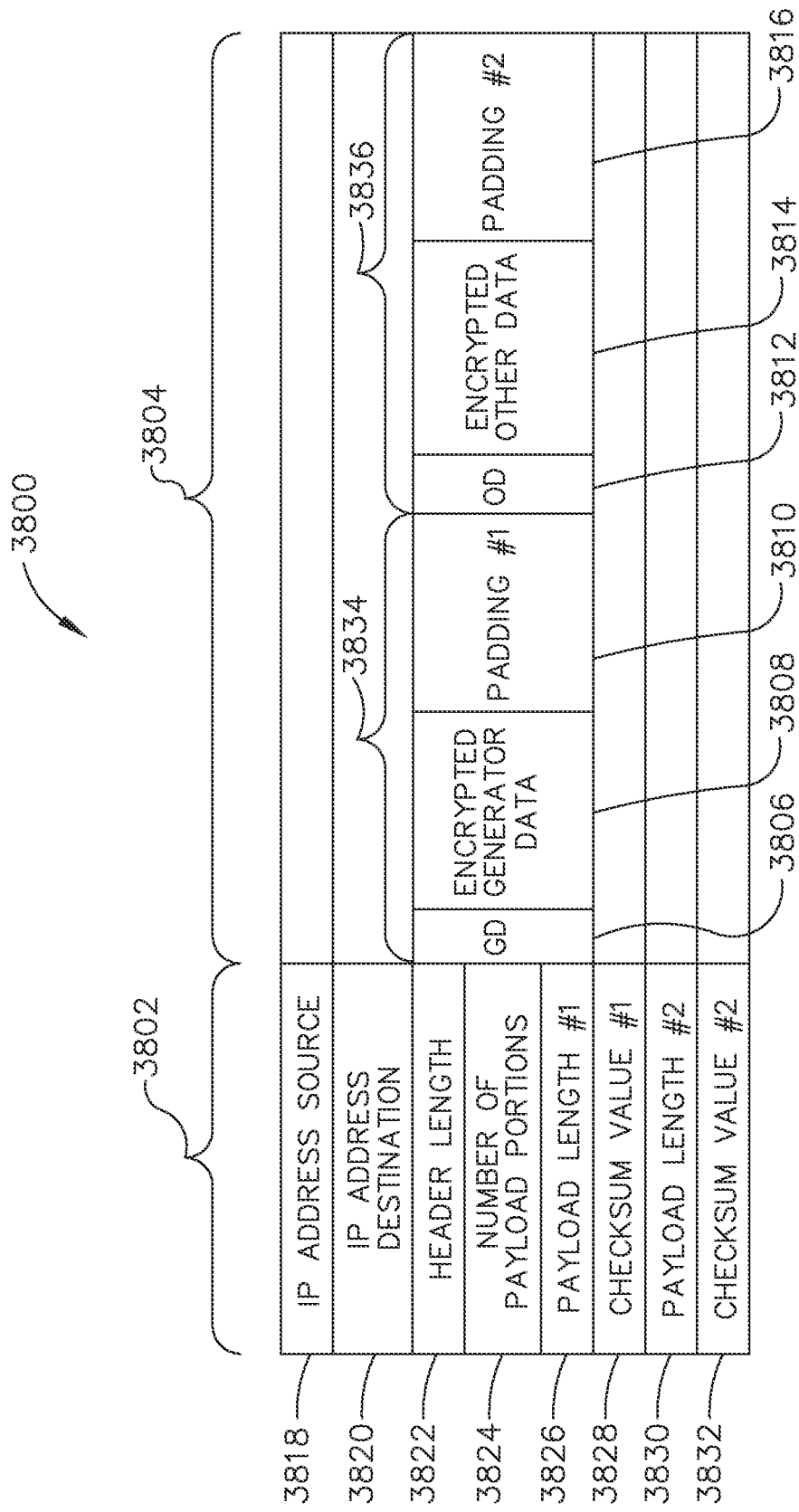
FIG. 30 illustrates another representation of the datagram of FIG. 28, in accordance with at least one aspect of the present disclosure.

For instances where the stripped/other information is to be communicated with the generator data, the stripped/other data can be time-stamped, compressed, and/or encrypted in a manner identical to or different from that described above regarding the generator data, and the surgical hub 206 may be programmed/configured to generate a datagram which includes both the encrypted generator data and the encrypted stripped/other information. An example of such a datagram in shown in FIG. 30, where the payload 3804 of the datagram 3800 is divided into two or more distinct payload data portions (e.g., one for the encrypted generator data 3834, one for the encrypted stripped/other information 3836), with each portion having an identifying bit (e.g., generator data (GD) 3806, other data (OD) 3812), the associated encrypted data 3808, 3814, and the associated padding 3810, 3816, if needed, respectively. Further, as shown in FIG. 30, the header 3802 may be the same as (e.g., IP address source 3818, IP address destination 3820, header length 3822) or different from the header 3782 described with reference to the datagram 3780 shown in FIG. 29. For example, the header 3802 may be different in that the header 3802 further includes a field designating the number of payload data portions 3824 (e.g., 2) included in the payload 3804 of the datagram 3800. The header 3802 can also be different in that it can include fields designating the payload length 3826, 3830 and the checksum value 3828, 2832 for each payload data portion 3834, 3836, respectively. Although only two payload data portions are shown in FIG. 30, it will be appreciated that the payload 3804 of the datagram 3800 may include any quantity/number of payload data portions (e.g., 1, 2, 3, 4, 5), where each payload data portion includes data associated with a different aspect of the surgical procedure. The datagram 3800 can then be communicated from the surgical hub 206 through the Internet to the cloud-based system 205 following an IP which: (1) defines datagrams that encapsulate the encrypted generator data and the encrypted stripped/other data to be delivered, and (2) defines addressing methods that are used to label the datagram with source and destination information.

As set forth above, it is an unfortunate reality that the outcomes of all surgical procedures are not always optimal and/or successful. For instances where a failure event is detected and/or identified, a variation of the above-described communication methods can be utilized to isolate surgical data which is associated with the failure event (e.g., failure event surgical data) from surgical data which is not associated with the failure event (e.g., non-failure event surgical data) and communicate the surgical data which is associated with the failure event (e.g., failure event data) from the surgical hub 206 to the cloud-based system 205 on a prioritized basis for analysis. According to one aspect of the present disclosure, failure event surgical data is communicated from the surgical hub 206 to the cloud-based system 205 on a prioritized basis relative to non-failure event surgical data.

Figure 31:
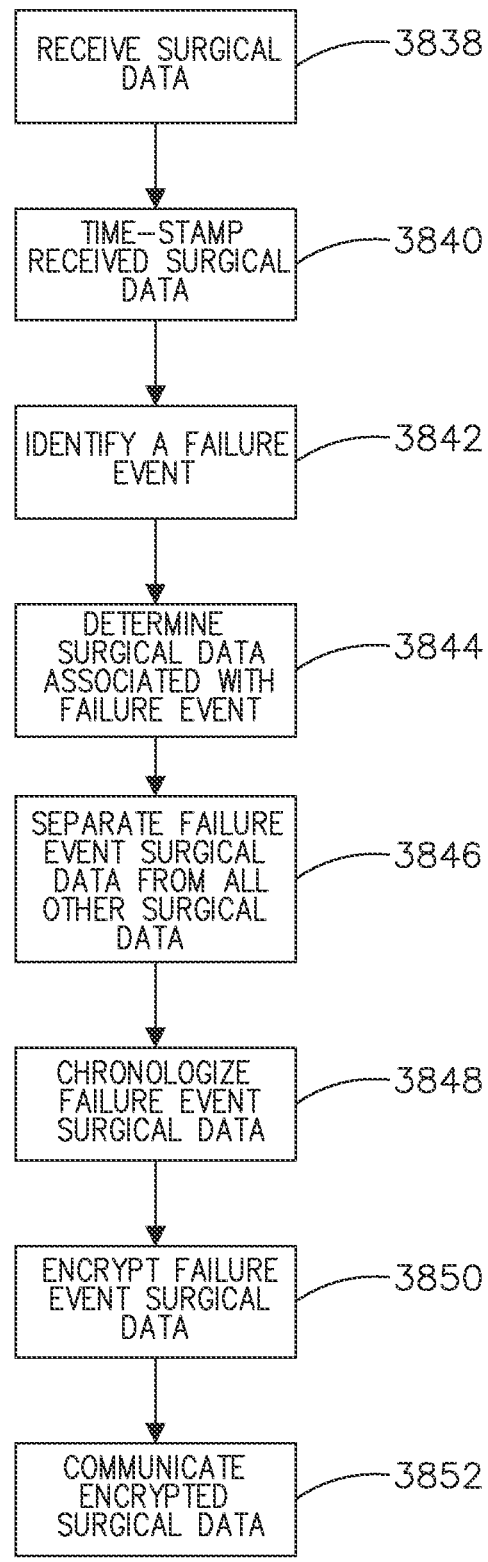
FIG. 31 illustrates a method of identifying surgical data associated with a failure event and communicating the identified surgical data to a cloud-based system on a prioritized basis, in accordance with at least one aspect of the present disclosure.

FIG. 31 illustrates various aspects of a system-implemented method of identifying surgical data associated with a failure event (e.g., failure event surgical data) and communicating the identified surgical data to a cloud-based system 205 on a prioritized basis. The method comprises (1) receiving 3838 surgical data at a surgical hub 206, wherein the surgical data is associated with a surgical procedure; (2) time-stamping 3840 the surgical data; (3) identifying 3842 a failure event associated with the surgical procedure; (4) determining 3844 which of the surgical data is associated with the failure event (e.g., failure event surgical data); (5) separating 3846 the surgical data associated with the failure event from all other surgical data (e.g., non-failure event surgical data) received at the surgical hub 206; (6) chronologizing 3848 the surgical data associated with the failure event; (7) encrypting 3850 the surgical data associated with the failure event; and (8) communicating 3852 the encrypted surgical data to a cloud-based system 205 on a prioritized basis.

More specifically, various surgical data can be captured during a surgical procedure and the captured surgical data, as well as other surgical data associated with the surgical procedure, can be communicated to the surgical hub 206. The surgical data can include, for example, data associated with a surgical device/instrument (e.g., FIG. 9, surgical device/instrument 235) utilized during the surgery, data associated with the patient, data associated with the facility where the surgical procedure was performed, and data associated with the surgeon. Either prior to or subsequent to the surgical data being communicated to and received by the surgical hub 206, the surgical data can be time-stamped and/or stripped of all information which could identify the specific surgery, the patient, or the surgeon, so that the information is essentially anonymized for further processing and analysis by the cloud-based system 205.

Once a failure event has been detected and/or identified (e.g., which can be either during or after the surgical procedure), the surgical hub 206 can determine which of the surgical data is associated with the failure event (e.g., failure event surgical data) and which of the surgical data is not associated with the surgical event (e.g., non-failure event surgical data). According to one aspect of the present disclosure, a failure event can include, for example, a detection of one or more misfired staples during a stapling portion of a surgical procedure. For example, in one aspect, referring to FIG. 9, an endoscope 239 may take snapshots while a surgical device/instrument 235 comprising an end effector including a staple cartridge performs a stapling portion of a surgical procedure. In such an aspect, an imaging module 238 may compare the snapshots to stored images and/or images downloaded from the cloud-based system 205 that convey correctly fired staples to detect a misfired staple and/or evidence of a misfired staple (e.g., a leak). In another aspect, the imaging module 238 may analyze the snapshots themselves to detect a misfired staple and/or evidence of a misfired staple. In one alternative aspect, the surgical hub 206 may communicate the snapshots to the cloud-based system 205, and a component of the cloud-based system 205 may perform the various imaging module functions described above to detect a misfired staple and/or evidence of a misfired staple and to report the detection to the surgical hub 206. According to another aspect of the present disclosure, a failure event can include a detection of a tissue temperature which is below the expected temperature during a tissue-sealing portion of a surgical procedure and/or a visual indication of excessive bleeding or oozing following a surgical procedure (e.g., FIG. 9, via endoscope 239). For example, in one aspect, referring to FIG. 9, the surgical device/instrument 235 may comprise an end effector, including a temperature sensor and the surgical hub 206, and/or the cloud-based system may compare at least one temperature detected by the temperature sensor (e.g., during a tissue-sealing portion of a surgical procedure) to a stored temperature and/or a range of temperatures expected and/or associated with that surgical procedure to detect an inadequate/low sealing temperature. In another aspect, an endoscope 239 may take snapshots during a surgical procedure. In such an aspect, an imaging module 238 may compare the snapshots to stored images and/or images downloaded from the cloud-based system 205 that convey tissue correctly sealed at expected temperatures to detect evidence of an improper/insufficient sealing temperature (e.g., charring, oozing/bleeding). Further, in such an aspect, the imaging module 238 may analyze the snapshots themselves to detect evidence of an improper/insufficient sealing temperature (e.g., charring, oozing/bleeding). In one alternative aspect, the surgical hub 206 may communicate the snapshots to the cloud-based system 205, and a component of the cloud-based system 205 may perform the various imaging module functions described above to detect evidence of an improper/insufficient sealing temperature and to report the detection to the surgical hub 206. According to the various aspects described above, in response to the detected and/or identified failure event, the surgical hub 206 may download a program from the cloud-based system 205 for execution by the surgical device/instrument 235 that corrects the detected issue (i.e., program that alters surgical device/instrument parameters to prevent misfired staples, program that alters surgical device/instrument parameters to ensure correct sealing temperature).

In some aspects, a failure event is deemed to cover a certain time period, and all surgical data associated with that certain time period can be deemed to be associated with the failure event.

After the surgical data associated with the failure event has been identified, the identified surgical data (e.g., failure event surgical data) can be separated or isolated from all of the other surgical data associated with the surgical procedure (e.g., non-failure event surgical data). The separation can be realized, for example, by tagging or flagging the identified surgical data, by storing the identified surgical data apart from all of the other surgical data associated with the surgical procedure, or by storing only the other surgical data while continuing to process the identified surgical data for subsequent prioritized communication to the cloud-based system 205. According to various aspects, the tagging or flagging of the identified surgical data can occur during the communication process when the datagram is generated as described in more detail below.

The time-stamping of all of the surgical data (e.g., either before or after the surgical data is received at the surgical hub) can be utilized by a component of the surgical hub 206 to chronologize the identified surgical data associated with the failure event. The component of the surgical hub 206 which utilizes the time-stamping to chronologize the identified surgical data can be, for example, the processor module 232, the processor 244 of the computer system 210, and/or combinations thereof. By chronologizing the identified surgical data, the cloud-based system 205 and/or other interested parties can subsequently better understand the conditions which were present leading up to the occurrence of the failure event and possibly pinpoint the exact cause of the failure event, thereby providing the knowledge to potentially mitigate a similar failure event from occurring during a similar surgical procedure performed at a future date.

Once the identified surgical data has been chronologized, the chronologized surgical data may be encrypted in a manner similar to that described above with respect to the encryption of the generator data. Thus, the identified surgical data can be encrypted to help ensure the confidentiality of the identified surgical data, either while it is being stored at the surgical hub 206 or while it is being transmitted to the cloud-based system 205 using the Internet or other computer networks. According to various aspects, a component of the surgical hub 206 utilizes an encryption algorithm to convert the identified surgical data from a readable version to an encoded version, thereby forming the encrypted surgical data associated with the failure event (e.g., FIGS. 25-27). The component of the surgical hub which utilizes the encryption algorithm can be, for example, the processor module 232, the processor 244 of the computer system 210, and/or combinations thereof. The utilized encryption algorithm can be a symmetric encryption algorithm or an asymmetric encryption algorithm.

Figure 32:
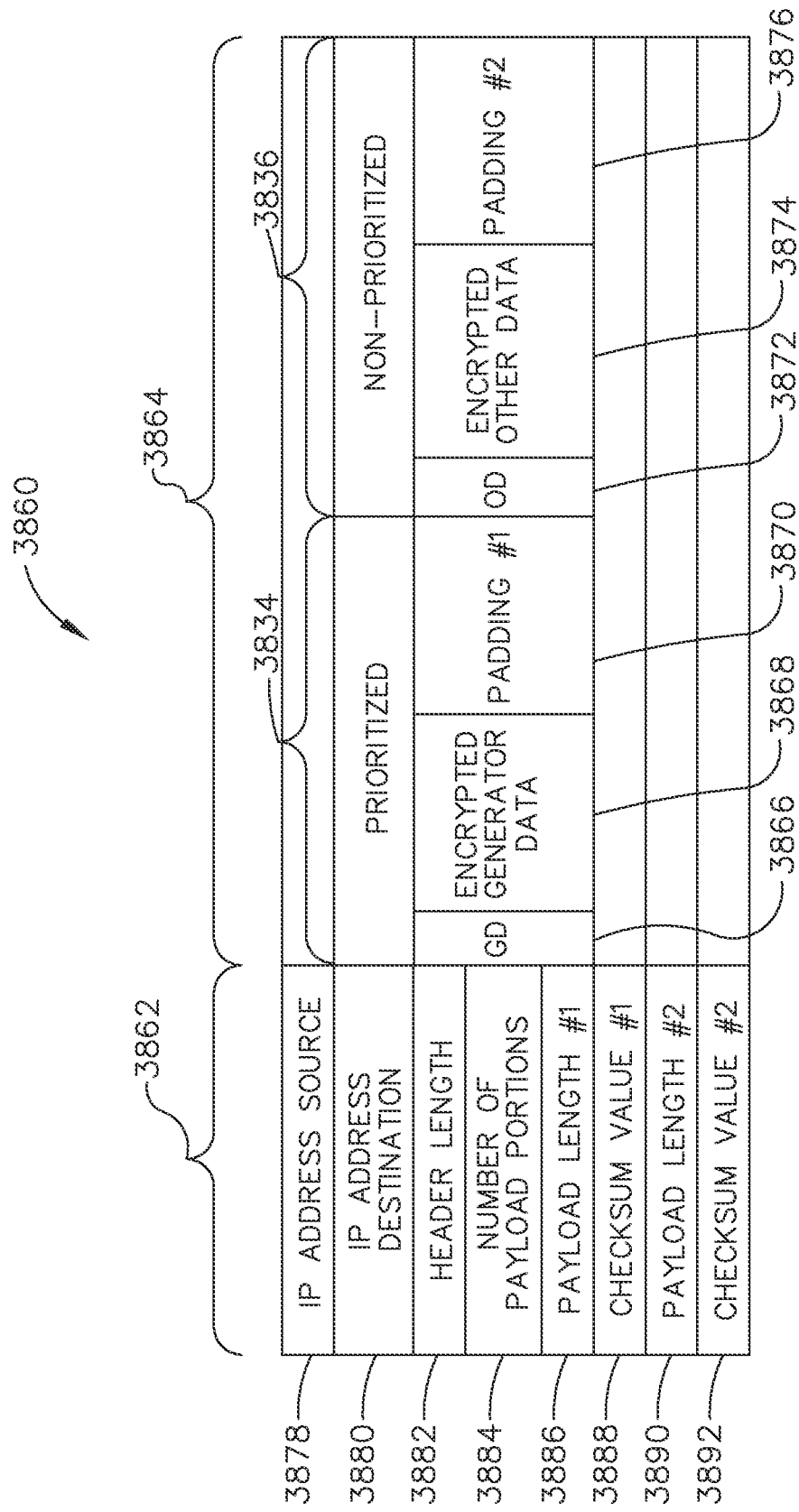
FIG. 32 illustrates yet another representation of the datagram of FIG. 28, in accordance with at least one aspect of the present disclosure.

After the identified surgical data has been encrypted, a component of the surgical hub can communicate the encrypted surgical data associated with the failure event (e.g., encrypted failure event surgical data) to the cloud-based system 205. The component of the surgical hub which communicates the encrypted surgical data to the cloud-based system 205 can be, for example, the processor module 232, a hub/switch 207/209 of the modular communication hub 203, the router 211 of the modular communication hub 203, or the communication module 247 of the computer system 210. According to various aspects, the communication of the encrypted surgical data (e.g., encrypted failure event surgical data) through the Internet can follow an IP which: (1) defines datagrams that encapsulate the encrypted surgical data to be delivered, and (2) defines addressing methods that are used to label the datagram with source and destination information. The datagram can be similar to the datagram shown in FIG. 29 or the datagram shown in FIG. 30, but can be different in that either the header or the payload of the datagram can include a field which includes a flag or a tag which identifies the encrypted surgical data (e.g., encrypted failure event surgical data) as being prioritized relative to other non-prioritized surgical data (e.g., encrypted non-failure event surgical data). An example of such a datagram is shown in FIG. 32, where the payload 3864 of the datagram 3860 includes a field which indicates (e.g., a prioritized designation 3834) that the payload 3864 includes prioritized surgical data (e.g., combination generator data 3868). According to various aspects, the payload 3864 of the datagram 3860 can also include non-flagged/non-tagged/non-prioritized surgical data 3836 (e.g., other surgical data 3874) as shown in FIG. 32.

According to various aspects, prior to the identified surgical data (e.g., failure event surgical data) being encrypted, the identified surgical data can be compressed (if not already compressed by the source(s) of the relevant surgical data). The compression allows for a smaller representation of the surgical data associated with the failure event to be subsequently encrypted and communicated to the cloud-based system 205. For the compression, a component of the surgical hub 206 can utilize a compression algorithm to convert a representation of the identified surgical data to a smaller representation of the identified surgical data, thereby allowing for a more efficient and economical encryption of the identified surgical data (less data to encrypt utilizes less processing resources) and a more efficient and economical communication of the encrypted surgical data (smaller representations of the surgical data within the payload of the datagrams allow for more identified surgical data to be included in a given datagram, for more identified surgical data to be communicated within a given time period, and/or for identified surgical data to be communicated with fewer communication resources). The component of the surgical hub 206 which utilizes the compression algorithm can be, for example, the processor module 232, the processor 244 of the computer system 210, and/or combinations thereof. The utilized compression algorithm can be a lossless compression algorithm or a lossy compression algorithm.

In instances where other non-prioritized surgical data (e.g., non-failure event surgical data) is to be communicated with prioritized surgical data (e.g., failure event surgical data), the other non-prioritized surgical data can be time-stamped, compressed, and/or encrypted in a manner identical to or different from that described above regarding the surgical data identified as associated with a failure event (e.g., failure event surgical data), and the surgical hub 206 may be programmed/configured to generate a datagram which includes both the encrypted prioritized surgical data (e.g., encrypted failure event surgical data) and the encrypted other non-prioritized surgical data (e.g., encrypted non-failure event surgical data). For example, in light of FIG. 32, the payload 3864 of the datagram 3860 may be divided into two or more distinct payload data portions (e.g., one for the prioritized surgical data 3834, one for the non-prioritized surgical data 3836), with each portion having an identifying bit (e.g., generator data (GD) 3866, other data (OD) 3872), the associated encrypted data (e.g., encrypted prioritized surgical data 3868, encrypted non-prioritized surgical data 3874), and the associated padding 3870, 3876, if needed, respectively. Further, similar to FIG. 30, the header 3862 may be the same as (e.g., IP address source 3878, IP address destination 3880, header length 3882) or different from the header 3782 described with reference to the datagram 3780 shown in FIG. 29. For example, the header 3862 may be different in that the header 3862 further includes a field designating the number of payload data portions 3884 (e.g., 2) included in the payload 3864 of the datagram 3860. The header 3862 can also be different in that it can include fields designating the payload length 3886, 3890 and the checksum value 3888, 2892 for each payload data portion 3834, 3836, respectively. Although only two payload data portions are shown in FIG. 32, it will be appreciated that the payload 3864 of the datagram 3860 may include any quantity/number of payload data portions (e.g., 1, 2, 3, 4, 5), where each payload data portion includes data associated with a different aspect of the surgical procedure. The datagram 3860 can then be communicated from the surgical hub 206 through the Internet to the cloud-based system 205 following an IP which: (1) defines datagrams that encapsulate the encrypted generator data and the encrypted stripped/other data to be delivered, and (2) defines addressing methods that are used to label the datagram with source and destination information.

In some aspects, once a failure event associated with a surgical procedure has been identified, the surgical hub 206 and/or the cloud-based system 205 can subsequently flag or tag a surgical device/instrument 235 which was utilized during the surgical procedure for inoperability and/or removal. For example, in one aspect, information (e.g., serial number, ID) associated with the surgical device/instrument 235 and stored at the surgical hub 206 and/or the cloud-based system 205 can be utilized to effectively block the surgical device/instrument 235 from being used again (e.g., blacklisted). In another aspect, information (e.g., serial number, ID) associated with the surgical device/instrument can initiate the printing of a shipping slip and shipping instructions for returning the surgical device/instrument 235 back to a manufacturer or other designated party so that a thorough analysis/inspection of the surgical device/instrument 235 can be performed (e.g., to determine the cause of the failure). According to various aspects described herein, once the cause of a failure is determined (e.g., via the surgical hub 206 and/or the cloud-based system 205), the surgical hub 206 may download a program from the cloud-based system 205 for execution by the surgical device/instrument 235 that corrects the determined cause of the failure (i.e., program that alters surgical device/instrument parameters to prevent the failure from occurring again).

According to some aspects, the surgical hub 206 and/or the cloud-based system 205 can also provide/display a reminder (e.g., via hub display 215 and/or surgical device/instrument display 237) to administrators, staff, and/or other personnel to physically remove the surgical device/instrument 235 from the operating room (e.g., if detected as still present in the operating room) and/or to send the surgical device/instrument 235 to the manufacturer or the other designated party. In one aspect, the reminder may be set up to be provided/displayed periodically until an administrator can remove the flag or tag of the surgical device/instrument 235 from the surgical hub 206 and/or the cloud-based system 205. According to various aspects, an administrator may remove the flag or tag once the administrator can confirm (e.g., system tracking of the surgical device/instrument 235 via its serial number/ID) that the surgical device/instrument 235 has been received by the manufacturer or the other designated party. By using the above-described method to flag and/or track surgical data associated with a failure event, a closed loop control of the surgical data associated with the failure event and/or with a surgical device/instrument 235 can be realized. Additionally, in view of the above, it will be appreciated that the surgical hub 206 can be utilized to effectively manage the utilization (or non-utilization) of surgical devices/instruments 235 which have or potentially could be utilized during a surgical procedure.

In various aspects of the present disclosure, the surgical hub 206 and/or cloud-based system 205 may want to control which components (e.g., surgical device/instrument 235, energy device 241) are being utilized in its interactive surgical system 100/200 to perform surgical procedures (e.g., to minimize future failure events, to avoid the use of unauthorized or knock-off components).

As such, in various aspects of the present disclosure, since an interactive surgical system 100 may comprise a plurality of surgical hubs 106, a cloud-based system 105 and/or each surgical hub 106 of the interactive surgical system 100 may want to track component-surgical hub combinations utilized over time. In one aspect, upon/after a component (See FIG. 9, e.g., surgical device/instrument 235, energy device 241) is connected to/used with a particular surgical hub 106 (e.g., surgical device/instrument 235 wired/wirelessly connected to the particular surgical hub 106, energy device 241 connected to the particular surgical hub 106 via generator module 240), the particular surgical hub 106 may communicate a record/block of that connection/use (e.g., linking respective unique identifiers of the connected devices) to the cloud-based system 105 and/or to the other surgical hubs 106 in the interactive surgical system 100. For example, upon/after the connection/use of an energy device 241, a particular surgical hub 106 may communicate a record/block (e.g., linking a unique identifier of the energy device 241 to a unique identifier of a generator module 240 to a unique identifier of the particular surgical hub 106) to the cloud-based system 105 and/or other surgical hubs 106 in the interactive surgical system 100. In such an aspect, if this is the first time the component (e.g., energy device) is connected to/used with a surgical hub 106 in the interactive surgical system 100, the cloud-based system 105 and/or each surgical hub 106 of the interactive surgical system 100 may store the record/block as a genesis record/block. In such an aspect, the genesis record/block stored at the cloud-based system 105 and/or each surgical hub 106 may comprise a time stamp. However, in such an aspect, if this is not the first time the component (e.g., energy device 241) has been connected to/used with a surgical hub 106 in the interactive surgical system 100, the cloud-based system 105 and/or each surgical hub 106 of the interactive surgical system may store the record/block as a new record/block in a chain of record/blocks associated with the component. In such an aspect, the new record/block may comprise a cryptographic hash of the most recently communicated record/block stored at the cloud-based system 105 and/or each surgical hub 106, the communicated linkage data, and a time stamp. In such an aspect, each cryptographic hash links each new record/block (e.g., each use of the component) to its prior record/block to form a chain confirming the integrity of each prior record/block(s) back to an original genesis record/block (e.g., first use of the component). According to such an aspect, this blockchain of records/blocks may be developed at the cloud-based system 105 and/or each surgical hub 106 of the interactive surgical system 100 to permanently and verifiably tie usage of a particular component to one or more than one surgical hub 106 in the interactive surgical system 100 over time. Here, according to another aspect, this approach may be similarly applied to sub-components (e.g., handle, shaft, end effector, cartridge) of a component when/after the component is connected to/used with a particular surgical hub 106 of an interactive surgical system 100.

According to various aspects of the present disclosure, the cloud-based system 105 and/or each surgical hub 106 may utilize such records/blocks to trace usage of a particular component and/or a sub-component back to its initial usage in the interactive surgical system 100. For example, if a particular component (e.g., surgical device/instrument 235) is flagged/tagged as related to a failure event, the cloud-based system 105 and/or a surgical hub 106 may analyze such records/blocks to determine whether past usage of that component and/or a sub-component of that component contributed to or caused the failure event (e.g., overused). In one example, the cloud-based system 105 may determine that a sub-component (e.g., end effector) of that component may actually be contributing/causing the failure event and then tag/flag that component for inoperability and/or removal based on the determination.

According to another aspect, the cloud-based system 205 and/or surgical hub 206 may control which components (e.g., surgical device/instrument 235, energy device 241) are being utilized in an interactive surgical system 200 to perform surgical procedures by authenticating the component and/or its supplier/manufacturer. In one aspect, the supplier/manufacturer of a component may associate a serial number and a source ID with the component. In such an aspect, the supplier/manufacturer may create/generate a private key for the serial number, encrypt the serial number with the private key, and store the encrypted serial number and the source ID on an electronic chip (e.g., memory) in the component prior to shipment to a surgical site. Here, upon/after connection of the component to a surgical hub 206, the surgical hub 206 may read the encrypted serial number and the source ID from the electronic chip. In response, the surgical hub 206 may send a message (i.e., comprising the encrypted serial number) to a server of the supplier/manufacturer associated with the source ID (e.g., directly or via the cloud-based system 205). In such an aspect, the surgical hub 206 may encrypt the message using a public key associated with that supplier/manufacturer. In response, the surgical hub 206 may receive a message (i.e., comprising the private key the supplier/manufacturer generated for/associated with that encrypted serial number) from the supplier/manufacturer server (e.g., directly or via the cloud-based system 205). In such an aspect, the supplier/manufacturer server may encrypt the message using a public key associated with the surgical hub 206. Further, in such an aspect, the surgical hub 206 may then decrypt the message (e.g., using a private key paired to the public key used to encrypt the message) to reveal the private key associated with the encrypted serial number. The surgical hub 206 may then decrypt the encrypted serial number, using that private key, to reveal the serial number. Further, in such an aspect, the surgical hub 206 may then compare the decrypted serial number to a comprehensive list of authorized serial numbers (e.g., stored at the surgical hub 206 and/or the cloud-based system and/or downloaded from the cloud-based system, e.g., received separately from the supplier/manufacturer) and permit use of the connected component if the decrypted serial number matches an authorized serial number. Initially, such a process permits the surgical hub 206 to authenticate the supplier/manufacturer. In particular, the surgical hub 206 encrypted the message comprising the encrypted serial number using a public key associated with the supplier/manufacturer. As such, receiving a response message (i.e., comprising the private key) authenticates the supplier/manufacturer to the surgical hub 206 (i.e., otherwise the supplier/manufacturer would not have access to the private key paired to the public key used by the surgical hub 206 to encrypt the message, and the supplier/manufacturer would not have been able to associate the encrypted serial number received in the message to its already generated private key). Furthermore, such a process permits the surgical hub 206 to authenticate the connected component/device itself. In particular, the supplier/manufacturer (e.g., just authenticated) encrypted the serial number of the component using the delivered private key. Upon secure receipt of the private key, the surgical hub 206 is able to decrypt the encrypted serial number (i.e., read from the connected component), which authenticates the component and/or its association with the supplier/manufacturer (i.e., only that private key as received from that supplier/manufacturer would decrypt the encrypted serial number). Nonetheless, the surgical hub 206 further verifies the component as authentic (e.g., compares the decrypted serial number to a comprehensive list of authorized serial numbers received separately from the supplier/manufacturer). Notably, such aspects as described above can alternatively be performed by the cloud-based system 205 and/or a combination of the cloud-based system 205 and the surgical hub 206 to control which components (e.g., surgical device/instrument 235, energy device 241) are being utilized in an interactive surgical system 200 (e.g., to perform surgical procedures) by authenticating the component and/or its supplier/manufacturer. In one aspect, such described approaches may prevent the use of knock-off component(s) within the interactive surgical system 200 and ensure the safety and well-being of surgical patients.

According to another aspect, the electronic chip of a component (e.g., surgical device/instrument 235, energy device 241) may store (e.g., in memory) data associated with usage of that component (i.e., usage data, e.g., number of uses with a limited use device, number of uses remaining, firing algorithms executed, designation as a single-use component). In such an aspect, the surgical hub 206 and/or the cloud-based system 205, upon/after connection of the component to the interactive surgical system, may read such usage data from the memory of a component and write back at least a portion of that usage data for storage (e.g., in memory 249) at the surgical hub 206 and/or for storage at the cloud-based system 205 (e.g., individually and/or under a blockchain approach discussed herein). According to such an aspect, the surgical hub 206 and/or the cloud-based system 205, upon/after a subsequent connection of that component to the interactive surgical system, may again read such usage data and compare that usage to previously stored usage data. Here, if a discrepancy exists or if a predetermined/authorized usage has been met, the surgical hub 206 and/or the cloud-based system 205 may prevent use of that component (e.g., blacklisted, rendered inoperable, flagged for removal) on the interactive surgical system 200. In various aspects, such an approach prevents bypass of the encryption chip systems. If the component's electronic chip/memory has been tampered with (e.g., memory reset, number of uses altered, firing algorithms altered, single-use device designated as a multi-use device), a discrepancy will exist, and the component's use will be controlled/prevented.

Additional details are disclosed in U.S. Pat. No. 10,624,691, titled TECHNIQUES FOR OPERATING GENERATOR FOR DIGITALLY GENERATING ELECTRICAL SIGNAL WAVEFORMS AND SURGICAL INSTRUMENTS, which issued on Apr. 21, 2020, which is incorporated herein by reference in its entirety.

Surgical Hub Coordination of Device Pairing in an Operating Room

One of the functions of the surgical hub 106 is to pair (also referred to herein as "connect" or "couple") with other components of the surgical system 102 to control, gather information from, or coordinate interactions between the components of the surgical system 102. Since the operating rooms of a hospital are likely in close physical proximity to one another, a surgical hub 106 of a surgical system 102 may unknowingly pair with components of a surgical system 102 in a neighboring operating room, which would significantly interfere with the functions of the surgical hub 106. For example, the surgical hub 106 may unintentionally activate a surgical instrument in a different operating room or record information from a different ongoing surgical procedure in a neighboring operating room.

Aspects of the present disclosure present a solution, wherein a surgical hub 106 only pairs with detected devices of the surgical system 102 that are located within the bounds of its operating room.

Furthermore, the surgical hub 106 relies on its knowledge of the location of other components of the surgical system 102 within its operating room in making decisions about, for example, which surgical instruments should be paired with one another or activated. A change in the position of the surgical hub 106 or another component of the surgical system 102 can be problematic.

Aspects of the present disclosure further present a solution wherein the surgical hub 106 is configured to reevaluate or redetermine the bounds of its operating room upon detecting that the surgical hub 106 has been moved. Aspects of the present disclosure further present a solution wherein the surgical hub 106 is configured to redetermine the bounds of its operating room upon detection of a potential device of the surgical system 102, which can be an indication that the surgical hub 106 has been moved.

In various aspects, a surgical hub 106 is used with a surgical system 102 in a surgical procedure performed in an operating room. The surgical hub 106 comprises a control circuit configured to determine the bounds of the operating room, determine devices of the surgical system 102 located within the bounds of the operating room, and pair the surgical hub 106 with the devices of the surgical system 102 located within the bounds of the operating room.

In one aspect, the control circuit is configured to determine the bounds of the operating room after activation of the surgical hub 106. In one aspect, the surgical hub 106 includes a communication circuit configured to detect and pair with the devices of the surgical system located within the bounds of the operating room. In one aspect, the control circuit is configured to redetermine the bounds of the operating room after a potential device of the surgical system 102 is detected. In one aspect, the control circuit is configured to periodically determine the bounds of the operating room.

In one aspect, the surgical hub 106 comprises an operating room mapping circuit that includes a plurality of non-contact sensors configured to measure the bounds of the operating room.

In various aspects, the surgical hub 106 includes a processor and a memory coupled to the processor. The memory stores instructions executable by the processor to pair the surgical hub with devices of the surgical system 102 located within the bounds of the operating room, as described above. In various aspects, the present disclosure provides a non-transitory computer-readable medium storing computer-readable instructions which, when executed, cause a machine to pair the surgical hub 106 with devices of the surgical system 102 located within the bounds of the operating room, as described above.

Figure 35:
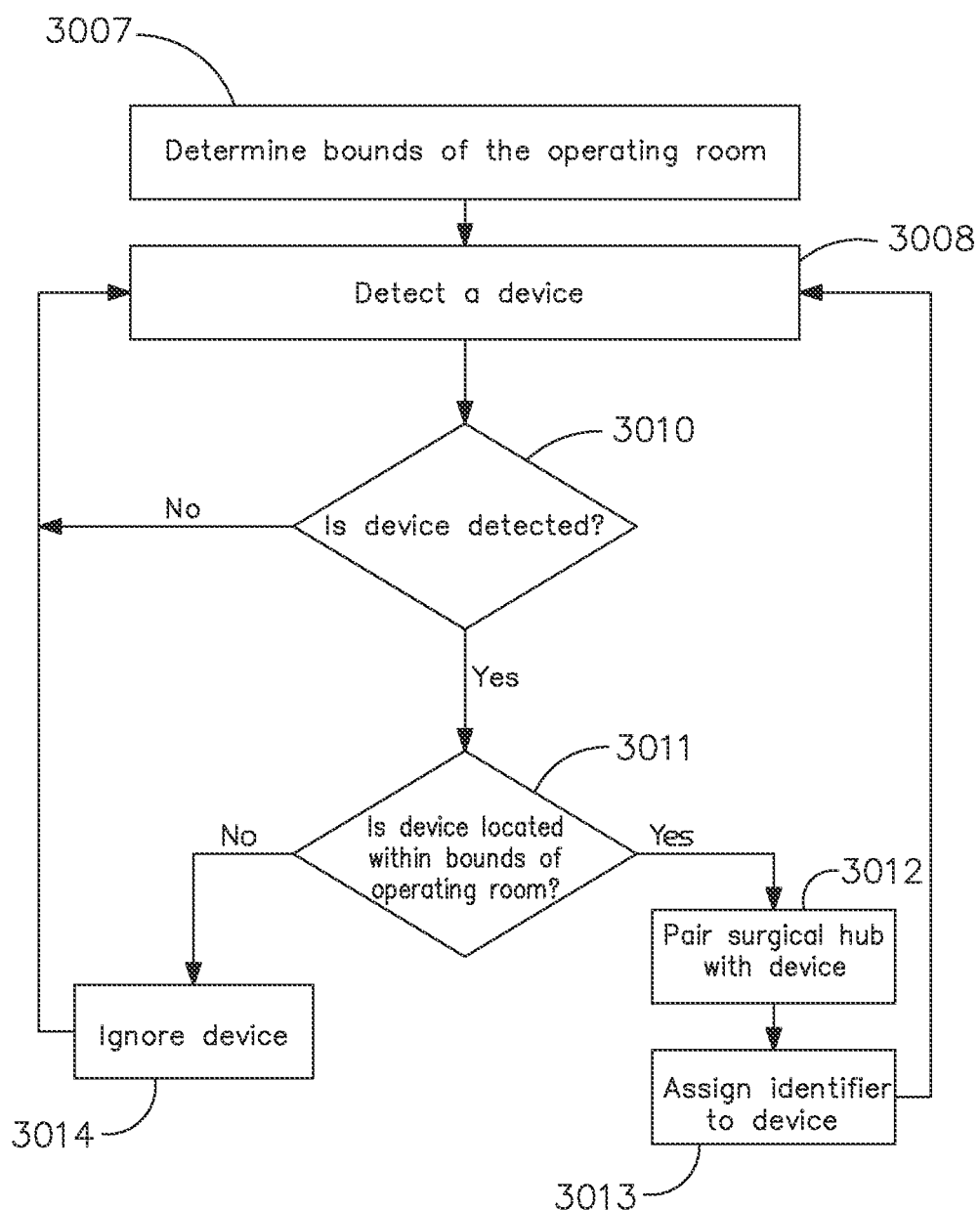
FIG. 35 is a logic flow diagram of a process depicting a control program or a logic configuration for surgical hub pairing with surgical devices of a surgical system that are located within the bounds of an operating room, in accordance with at least one aspect of the present disclosure.
Figure 36:
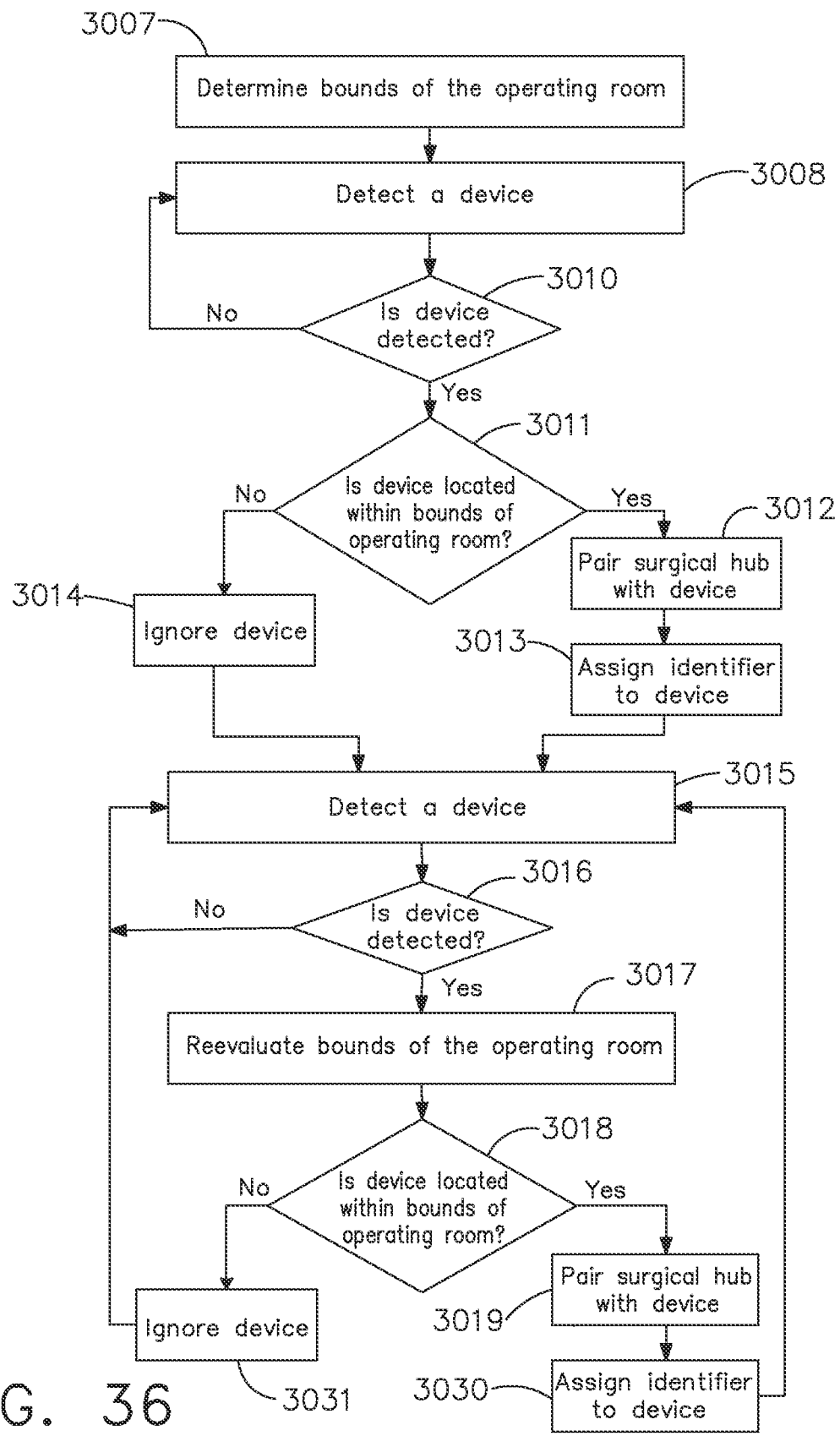
FIG. 36 is a logic flow diagram of a process depicting a control program or a logic configuration for selectively forming and severing connections between devices of a surgical system, in accordance with at least one aspect of the present disclosure.

FIGS. 35 and 36 are logic flow diagrams of processes depicting control programs or logic configurations for pairing the surgical hub 106 with devices of the surgical system 102 located within the bounds of the operating room, as described above.

The surgical hub 106 performs a wide range of functions that requires short- and long-range communication, such as assisting in a surgical procedure, coordinating between devices of the surgical system 102, and gathering and transmitting data to the cloud 104. To properly perform its functions, the surgical hub 106 is equipped with a communication module 130 capable of short-range communication with other devices of the surgical system 102. The communication module 130 is also capable of long-range communication with the cloud 104.

The surgical hub 106 is also equipped with an operating-room mapping module 133 which is capable of identifying the bounds of an operating room, and identifying devices of the surgical system 102 within the operating room. The surgical hub 106 is configured to identify the bounds of an operating room, and only pair with or connect to potential devices of the surgical system 102 that are detected within the operating room.

In one aspect, the pairing comprises establishing a communication link or pathway. In another aspect, the pairing comprises establishing a control link or pathway.

Figure 37:
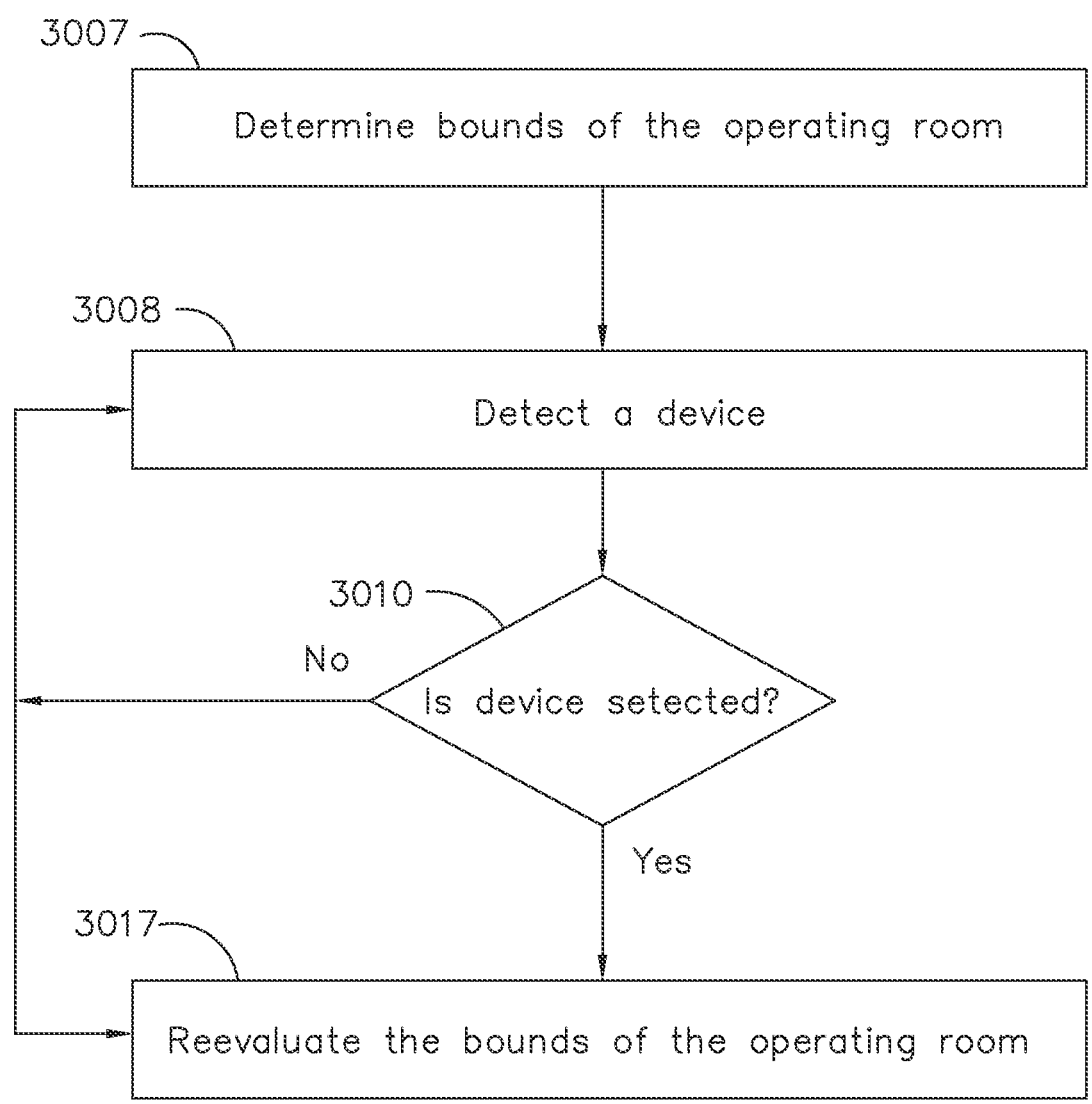
FIG. 37 is a logic flow diagram of a process depicting a control program or a logic configuration for selectively reevaluating the bounds of an operating room after detecting a new device, in accordance with at least one aspect of the present disclosure.
Figure 38:
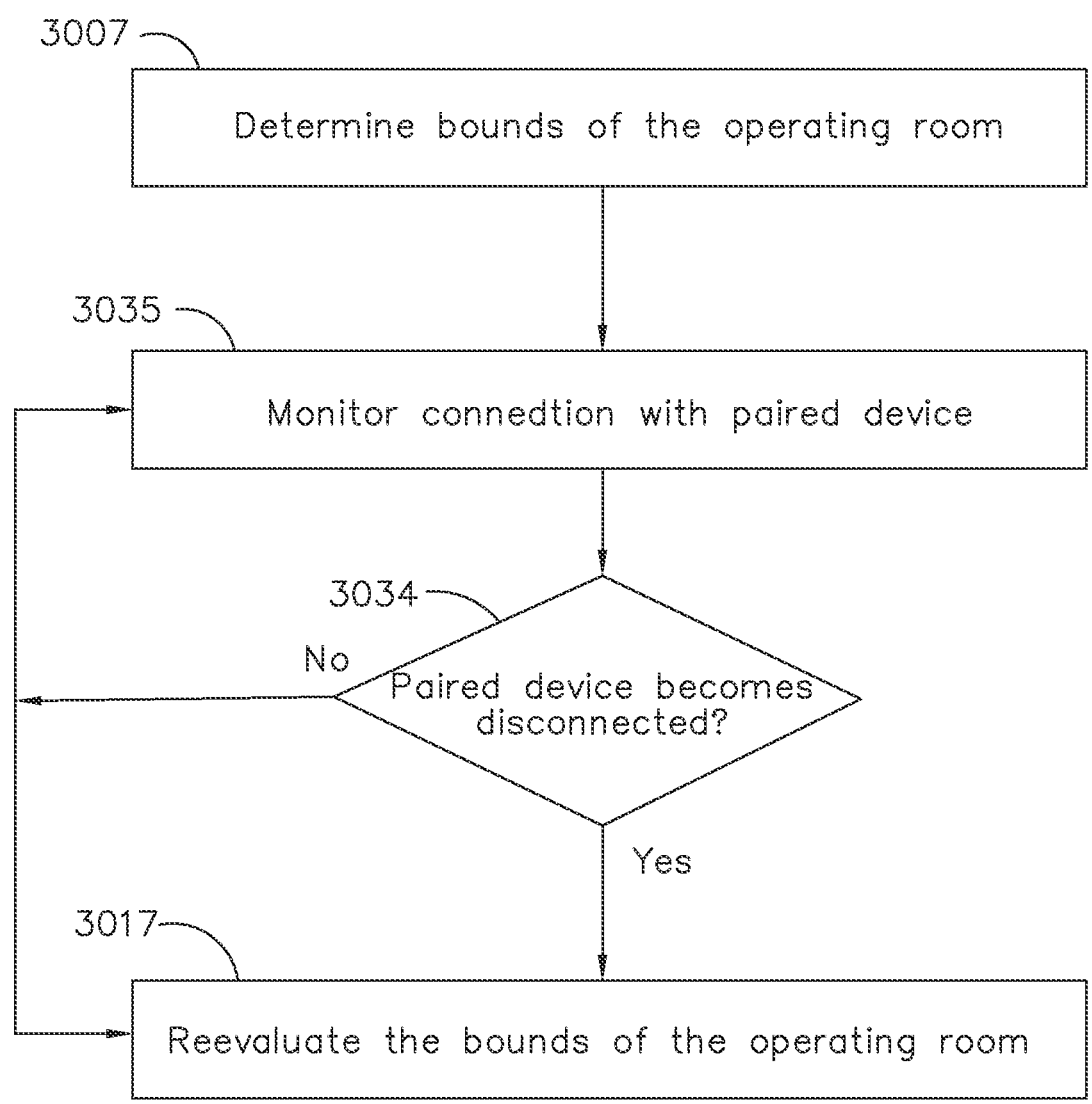
FIG. 38 is a logic flow diagram of a process depicting a control program or a logic configuration for selectively reevaluating the bounds of an operating room after disconnection of a paired device, in accordance with at least one aspect of the present disclosure.
Figure 39:
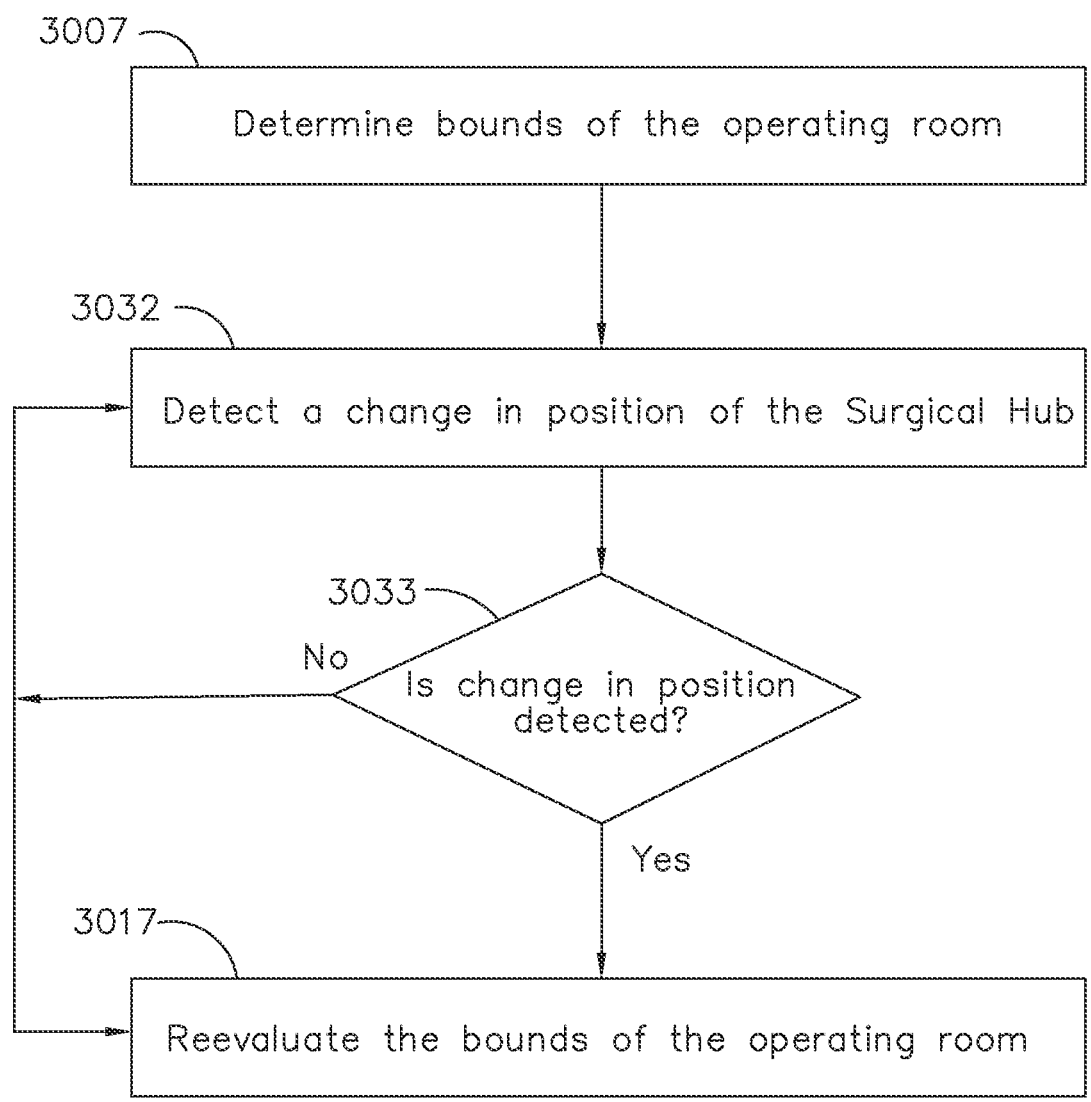
FIG. 39 is a logic flow diagram of a process depicting a control program or a logic configuration for reevaluating the bounds of an operating room by a surgical hub after detecting a change in the position of the surgical hub, in accordance with at least one aspect of the present disclosure.

An initial mapping or evaluation of the bounds of the operating room takes place during an initial activation of the surgical hub 106. Furthermore, the surgical hub 106 is configured to maintain spatial awareness during operation by periodically mapping its operating room, which can be helpful in determining if the surgical hub 106 has been moved. The reevaluation 3017 can be performed periodically or it can be triggered by an event such as observing a change in the devices of the surgical system 102 that are deemed within the operating room. In one aspect, the change is detection 3010 of a new device that was not previously deemed as within the bounds of the operating room, as illustrated in FIG. 37. In another aspect, the change is a disappearance, disconnection, or un-pairing of a paired device that was previously deemed as residing within the operating room, as illustrated in FIG. 38. The surgical hub 106 may continuously monitor 3035 the connection with paired devices to detect 3034 the disappearance, disconnection, or un-pairing of a paired device.

In other aspects, reevaluation triggering events can be, for example, changes in surgeons' positions, instrument exchanges, or sensing of a new set of tasks being performed by the surgical hub 106.

In one aspect, the evaluation of the bounds of the room by the surgical hub 106 is accomplished by activation of a sensor array of the operating-room mapping module 133 within the surgical hub 106 which enables it to detect the walls of the operating room.

Other components of the surgical system 102 can be made to be spatially aware in the same, or a similar, manner as the surgical hub 106. For example, a robotic hub 122 may also be equipped with an operating-room mapping module 133.

The spatial awareness of the surgical hub 106 and its ability to map an operating room for potential components of the surgical system 102 allows the surgical hub 106 to make autonomous decisions about whether to include or exclude such potential components as part of the surgical system 102, which relieves the surgical staff from dealing with such tasks. Furthermore, the surgical hub 106 is configured to make inferences about, for example, the type of surgical procedure to be performed in the operating room based on information gathered prior to, during, and/or after the performance of the surgical procedure. Examples of gathered information include the types of devices that are brought into the operating room, time of introduction of such devices into the operating room, and/or the devices sequence of activation.

In one aspect, the surgical hub 106 employs the operating-room mapping module 133 to determine the bounds of the surgical theater (e.g., a fixed, mobile, or temporary operating room or space) using either ultrasonic or laser non-contact measurement devices.

Figure 34:
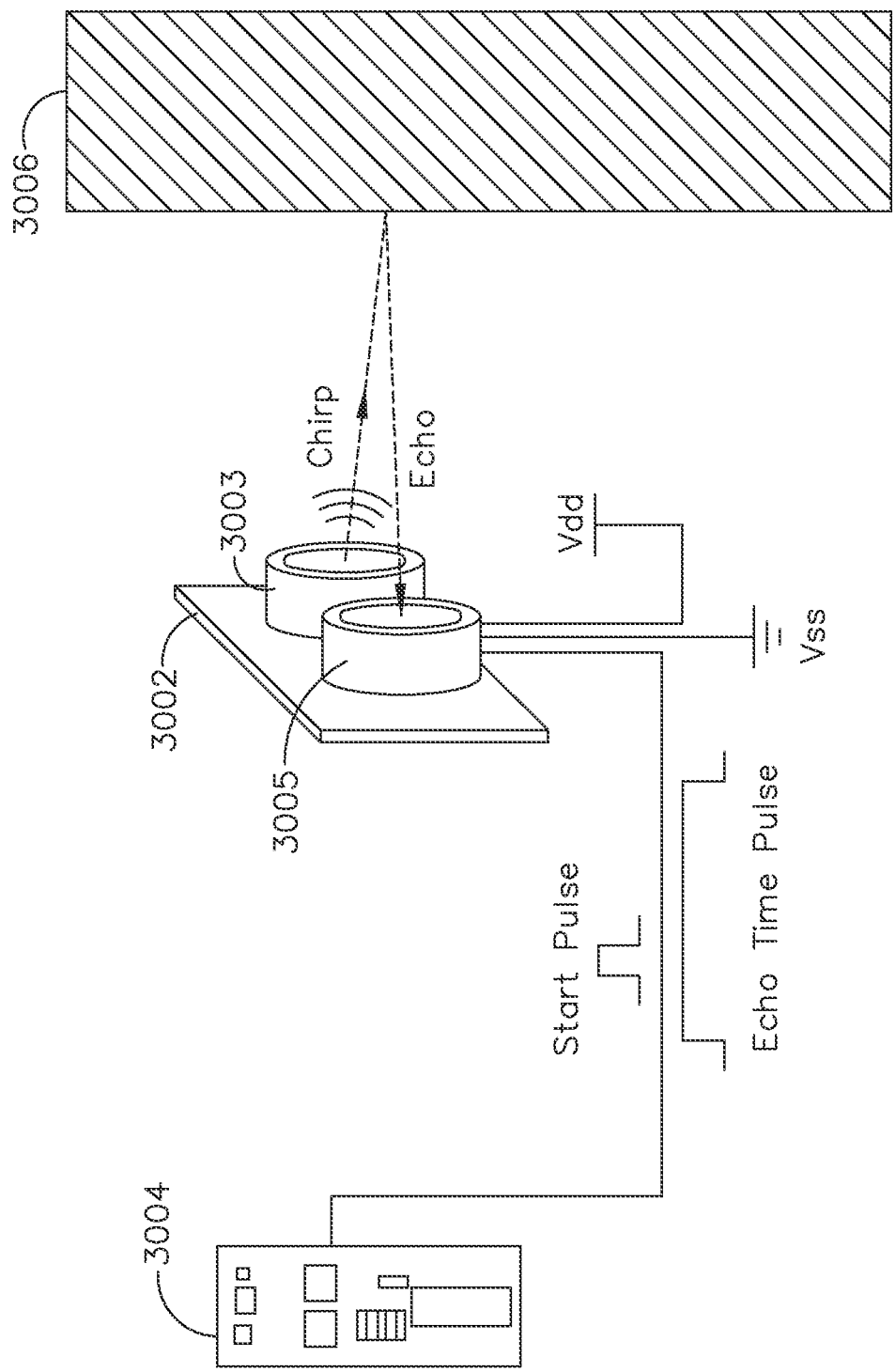
FIG. 34 illustrates ultrasonic pinging of an operating room wall to determine a distance between a surgical hub and the operating room wall, in accordance with at least one aspect of the present disclosure.

Referring to FIG. 34, ultrasound based non-contact sensors 3002 can be employed to scan the operating theater by transmitting a burst of ultrasound and receiving the echo when it bounces off a perimeter wall 3006 of an operating theater to determine the size of the operating theater and to adjust Bluetooth pairing distance limits. In one example, the non-contact sensors 3002 can be Ping ultrasonic distance sensors, as illustrated in FIG. 34.

FIG. 34 shows how an ultrasonic sensor 3002 sends a brief chirp with its ultrasonic speaker 3003 and makes it possible for a micro-controller 3004 of the operating-room mapping module 133 to measure how long the echo takes to return to the ultrasonic sensor's ultrasonic microphone 3005. The micro-controller 3004 has to send the ultrasonic sensor 3002 a pulse to begin the measurement. The ultrasonic sensor 3002 then waits long enough for the micro-controller program to start a pulse input command. Then, at about the same time the ultrasonic sensor 3002 chirps a 40 kHz tone, it sends a high signal to the micro-controller 3004. When the ultrasonic sensor 3002 detects the echo with its ultrasonic microphone 3005, it changes that high signal back to low. The micro-controller's pulse input command measures the time between the high and low changes and stores its measurement in a variable. This value can be used along with the speed of sound in air to calculate the distance between the surgical hub 106 and the operating-room wall 3006.

Figure 33:
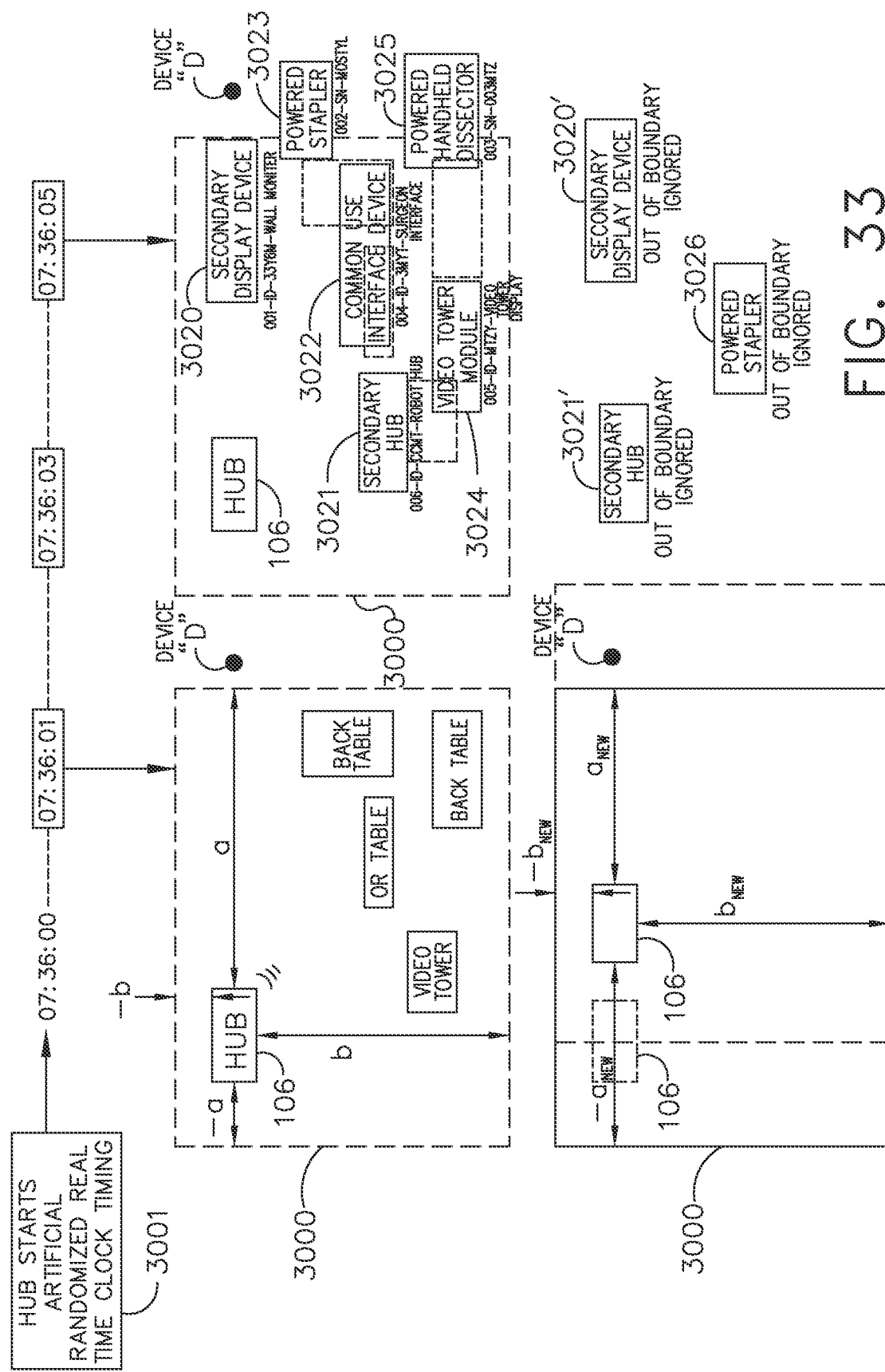
FIG. 33 illustrates a partial artificial timeline of a surgical procedure performed in an operating room via a surgical system, in accordance with at least one aspect of the present disclosure.

In one example, as illustrated in FIG. 33, a surgical hub 106 can be equipped with four ultrasonic sensors 3002, wherein each of the four ultrasonic sensors is configured to assess the distance between the surgical hub 106 and a wall of the operating room 3000. A surgical hub 106 can be equipped with more or less than four ultrasonic sensors 3002 to determine the bounds of an operating room.

Other distance sensors can be employed by the operating-room mapping module 133 to determine the bounds of an operating room. In one example, the operating-room mapping module 133 can be equipped with one or more photoelectric sensors that can be employed to assess the bounds of an operating room. In one example, suitable laser distance sensors can also be employed to assess the bounds of an operating room. Laser-based non-contact sensors may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits.

Referring to the top left corner of FIG. 33, a surgical hub 106 is brought into an operating room 3000. The surgical hub 106 is activated at the beginning of the set-up that occurs prior to the surgical procedure. In the example of FIG. 33, the set-up starts at an actual time of 11:31:14 (EST) based on a real-time clock. However, at the stated procedure set-up start time, the surgical hub 106 starts 3001 an artificial randomized real-time clock timing scheme at artificial real time 07:36:00 to protect private patient information.

At artificial real time 07:36:01, the operating-room mapping module 133 employs the ultrasonic distance sensors to ultrasonically ping the room (e.g., sends out a burst of ultrasound and listens for the echo when it bounces off the perimeter walls of the operating room as described above) to verify the size of the operating room and to adjust pairing distance limits.

At artificial real time 07:36:03, the data is stripped and time-stamped. At artificial real time 07:36:05, the surgical hub 106 begins pairing devices located only within the operating room 3000 as verified using ultrasonic distance sensors 3002 of the operating-room mapping module 133. The top right corner of FIG. 33 illustrates several example devices that are within the bounds of the operating room 3000 and are paired with the surgical hub 106, including a secondary display device 3020, a secondary hub 3021, a common interface device 3022, a powered stapler 3023, a video tower module 3024, and a powered handheld dissector 3025. On the other hand, secondary hub 3021', secondary display device 3020', and powered stapler 3026 are all outside the bounds of the operating room 3000 and, accordingly, are not paired with the surgical hub 106.

In addition to establishing a communication link with the devices of the surgical system 102 that are within the operating room, the surgical hub 106 also assigns a unique identification and communication sequence or number to each of the devices. The unique sequence may include the device's name and a time stamp of when the communication was first established. Other suitable device information may also be incorporated into the unique sequence of the device.

As illustrated in the top left corner of FIG. 33, the surgical hub 106 has determined that the operating room 3000 bounds are at distances a, −a, b, and −b from the surgical hub 106. Since Device "D" is outside the determined bounds of its operating room 3000, the surgical hub 106 will not pair with the Device "D." FIG. 35 is an example algorithm illustrating how the surgical hub 106 only pairs with devices within the bounds of its operating room. After activation, the surgical hub 106 determines 3007 bounds of the operating room using the operating-room mapping module 133, as described above. After the initial determination, the surgical hub 106 continuously searches for or detects 3008 devices within a pairing range. If a device is detected 3010, the surgical hub 106 then determines 3011 whether the detected device is within the bounds of the operating room. The surgical hub 106 pairs 3012 with the device if it is determined that the device is within the bounds of the operating room. In certain instances, the surgical hub 106 will also assign 3013 an identifier to the device. If, however, the surgical hub 106 determines that the detected device is outside the bounds of the operating room, the surgical hub 106 will ignore 3014 the device.

Referring to FIG. 36, after an initial determination of the bounds of the room, and after an initial pairing of devices located within such bounds, the surgical hub 106 continues to detect 3015 new devices that become available for pairing. If a new device is detected 3016, the surgical hub 106 is configured to reevaluate 3017 the bounds of the operating room prior to pairing with the new device. If the new device is determined 3018 to be within the newly determined bounds of the operating room, then the surgical hub 106 pairs with the device 3019 and assigns 3030 a unique identifier to the new device. If, however, the surgical hub 106 determines that the new device is outside the newly determined bounds of the operating room, the surgical hub 106 will ignore 3031 the device.

For pairing, the operating-room mapping module 133 contains a compass and integrated Bluetooth transceiver. Other communication mechanisms, which are not significantly affected by the hospital environment or geographical location, can be employed. Bluetooth Low Energy (BLE) beacon technology can currently achieve indoor distance measurements with accuracy of about 1-2 meters, with improved accuracy in closer proximities (within 0-6 meters). To improve the accuracy of the distance measurements, a compass is used with the BLE. The operating-room mapping module 133 utilizes the BLE and the compass to determine where modules are located in relation to the patient. For example, two modules facing each other (detected by compass) with greater than one meter distance between them may clearly indicate that the modules are on opposite sides of the patient. The more "Hub"-enabled modules that reside in the operating room, the greater the achievable accuracy becomes due to triangulation techniques.

In the situations where multiple surgical hubs 106, modules, and/or other peripherals are present in the same operating room, as illustrated in the top right corner of FIG. 33, the operating-room mapping module 133 is configured to map the physical location of each module that resides within the operating room. This information could be used by the user interface to display a virtual map of the room, enabling the user to more easily identify which modules are present and enabled, as well as their current status. In one aspect, the mapping data collected by surgical hubs 106 are uploaded to the cloud 104, where the data are analyzed for identifying how an operating room is physically setup, for example.

The surgical hub 106 is configured to determine a device's location by assessing transmission radio signal strength and direction. For Bluetooth protocols, the Received Signal Strength Indication (RSSI) is a measurement of the received radio signal strength. In one aspect, the devices of the surgical system 102 can be equipped with USB Bluetooth dongles. The surgical hub 106 may scan the USB Bluetooth beacons to get distance information. In another aspect, multiple high-gain antennas on a Bluetooth access point with variable attenuators can produce more accurate results than RSSI measurements. In one aspect, the hub is configured to determine the location of a device by measuring the signal strength from multiple antennas. Alternatively, in some examples, the surgical hub 106 can be equipped with one or more motion sensor devices configured to detect a change in the position of the surgical hub 106.

Referring to the bottom left corner of FIG. 33, the surgical hub 106 has been moved from its original position, which is depicted in dashed lines, to a new position closer to the device "D," which is still outside the bounds of the operating room 3000. The surgical hub 106 in its new position, and based on the previously determined bounds of the operating room, would naturally conclude that the device "D" is a potential component of the surgical system 102. However, the introduction of a new device is a triggering event for reevaluation 3017 of the bounds of the operating room, as illustrated in the example algorithm of FIGS. 35, 37. After performing the reevaluation, the surgical hub 106 determines that the operating room bounds have changed. Based on the new bounds, at distances $a_{new}$, $-a_{new}$, $b_{new}$, and $-b_{new}$, the surgical hub 106 concludes that it has been moved and that the Device "D" is outside the newly determined bounds of its operating room. Accordingly, the surgical hub 106 will still not pair with the Device "D."

In one aspect, one or more of the processes depicted in FIGS. 35-39 can be executed by a control circuit of a surgical hub 106, as depicted in FIG. 10 (processor 244). In another aspect, one or more of the processes depicted in FIGS. 35-39 can be executed by a cloud computing system 104, as depicted in FIG. 1. In yet another aspect, one or more of the processes depicted in FIGS. 35-39 can be executed by at least one of the aforementioned cloud computing systems 104 and/or a control circuit of a surgical hub 106 in combination with a control circuit of a modular device, such as the microcontroller 461 of the surgical instrument depicted in FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18-19, or the controller 838 of the generator 800 depicted in FIG. 20.

Spatial Awareness of Surgical Hubs in Operating Rooms

During a surgical procedure, a surgical instrument such as an ultrasonic or an RF surgical instrument can be coupled to a generator module 140 of the surgical hub 106. In addition, a separate surgical instrument controller such as a foot, or hand, switch or activation device can be used by an operator of the surgical instrument to activate the energy flow from the generator to the surgical instrument. Multiple surgical instrument controllers and multiple surgical instruments can be used concurrently in an operating room. Pressing or activating the wrong surgical instrument controller can lead to undesirable consequences. Aspects of the present disclosure present a solution in which the surgical hub 106 coordinates the pairing of surgical instrument controllers and surgical instruments to ensure patient and operator safety.

Aspects of the present disclosure are presented for a surgical hub 106 configured to establish and sever pairings between components of the surgical system 102 within the bounds of the operating room to coordinate flow of information and control actions between such components. The surgical hub 106 can be configured to establish a pairing between a surgical instrument controller and a surgical instrument that reside within the bounds of an operating room of surgical hub 106.

In various aspects, the surgical hub 106 can be configured to establish and sever pairings between components of the surgical system 102 based on operator request or situational and/or spatial awareness. The hub situational awareness is described in greater detail below in connection with FIG. 86.

Aspects of the present disclosure are presented for a surgical hub for use with a surgical system in a surgical procedure performed in an operating room. The surgical hub includes a control circuit that selectively forms and severs pairings between devices of the surgical system. In one aspect, the hub includes a control circuit is configured to pair the hub with a first device of the surgical system, assign a first identifier to the first device, pair the hub with a second device of the surgical system, assign a second identifier to the second device, and selectively pair the first device with the second device. In one aspect, the surgical hub includes a storage medium, wherein the control circuit is configured to store a record indicative of the pairing between the first device and the second device in the storage medium. In one aspect, the pairing between the first device and the second device defines a communication pathway therebetween. In one aspect, the pairing between the first device and the second device defines a control pathway for transmitting control actions from the second device to the first device.

Further to the above, in one aspect, the control circuit is further configured to pair the hub with a third device of the surgical system, assign a third identifier to the third device, sever the pairing between the first device and the second device, and selectively pair the first device with the third device. In one aspect, the control circuit is further configured to store a record indicative of the pairing between the first device and the third device in the storage medium. In one aspect, the pairing between the first device and the third device defines a communication pathway therebetween. In one aspect, the pairing between the first device and the third device defines a control pathway for transmitting control actions from the third device to the first device.

Figure 40:
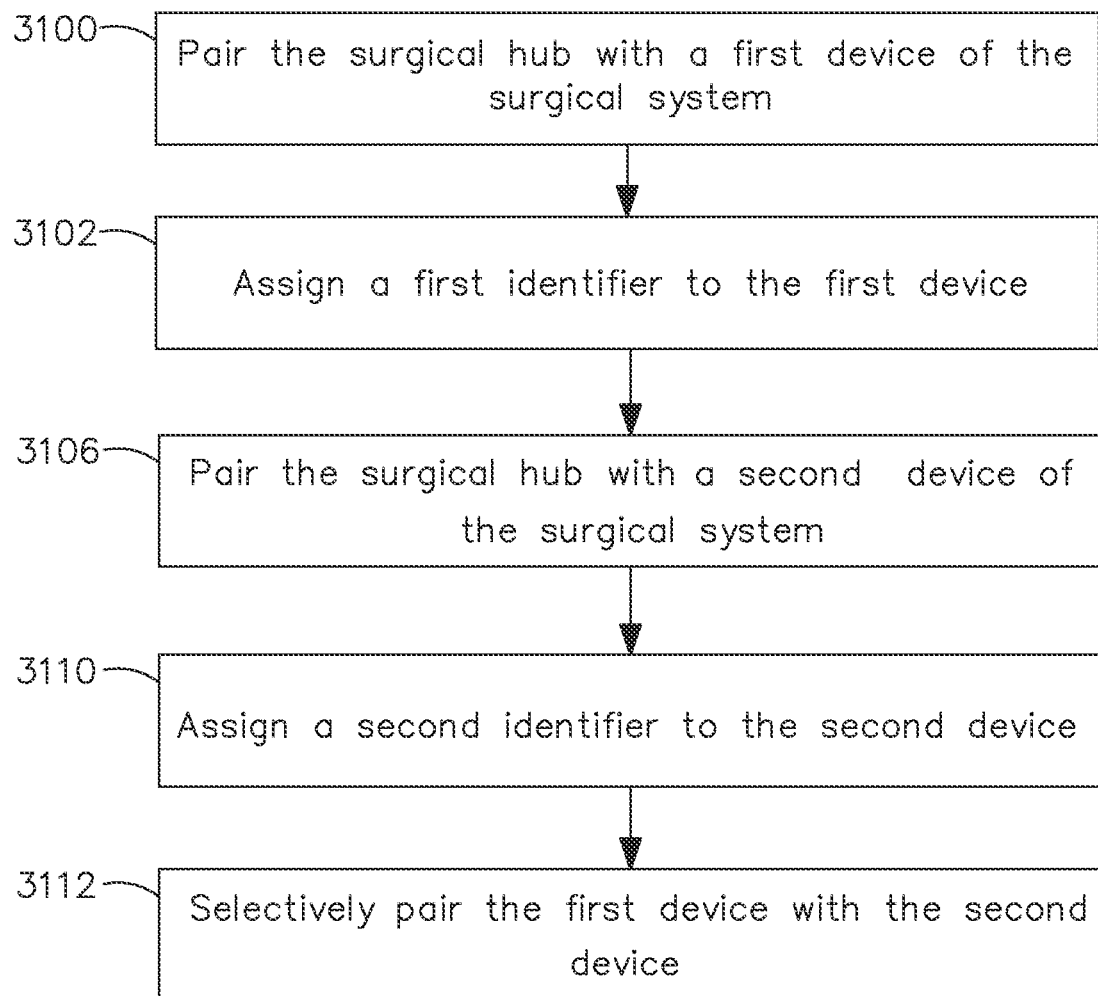
FIG. 40 is a logic flow diagram of a process depicting a control program or a logic configuration for selectively forming connections between devices of a surgical system, in accordance with at least one aspect of the present disclosure.
Figure 41:
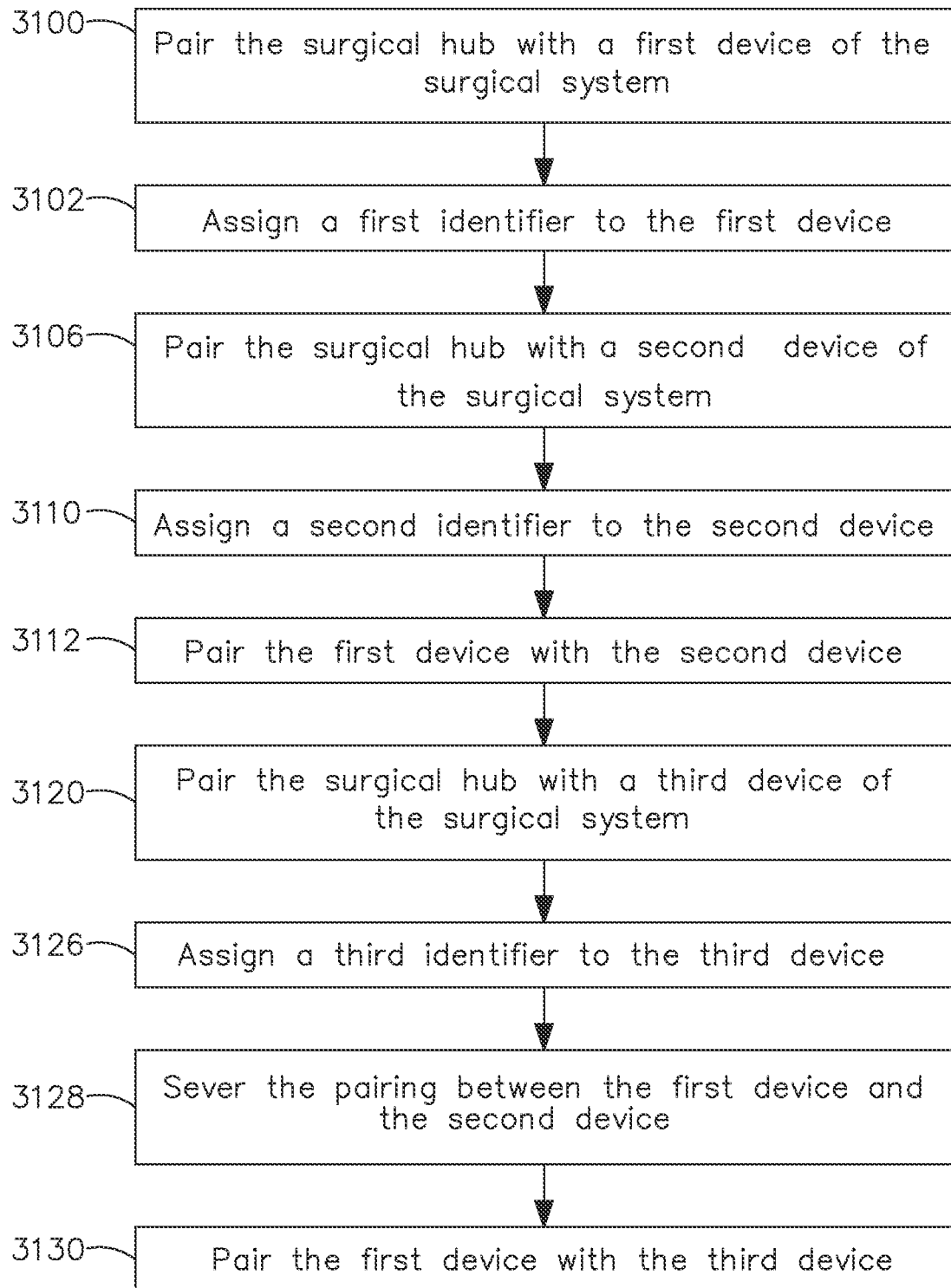
FIG. 41 is a logic flow diagram of a process depicting a control program or a logic configuration for selectively forming and severing connections between devices of a surgical system, in accordance with at least one aspect of the present disclosure.

In various aspects, the surgical hub includes a processor and a memory coupled to the processor. The memory stores instructions executable by the processor to selectively form and sever pairings between the devices of the surgical system, as described above. In various aspects, the present disclosure provides a non-transitory computer-readable medium storing computer-readable instructions which, when executed, cause a machine to selectively form and sever pairings between the devices of the surgical system, as described above. FIGS. 40 and 41 are logic flow diagrams of processes depicting control programs or logic configurations for selectively forming and severing pairings between the devices of the surgical system, as described above.

In one aspect, the surgical hub 106 establishes a first pairing with a surgical instrument and a second pairing with the surgical instrument controller. The surgical hub 106 then links the pairings together allowing the surgical instrument and the surgical instrument controller to operate with one another. In another aspect, the surgical hub 106 may sever an existing communication link between a surgical instrument and a surgical instrument controller, then link the surgical instrument to another surgical instrument controller that is linked to the surgical hub 106.

In one aspect, the surgical instrument controller is paired to two sources. First, the surgical instrument controller is paired to the surgical hub 106, which includes the generator module 140, for control of its activation. Second, the surgical instrument controller is also paired to a specific surgical instrument to prevent inadvertent activation of the wrong surgical instrument.

Figure 42:
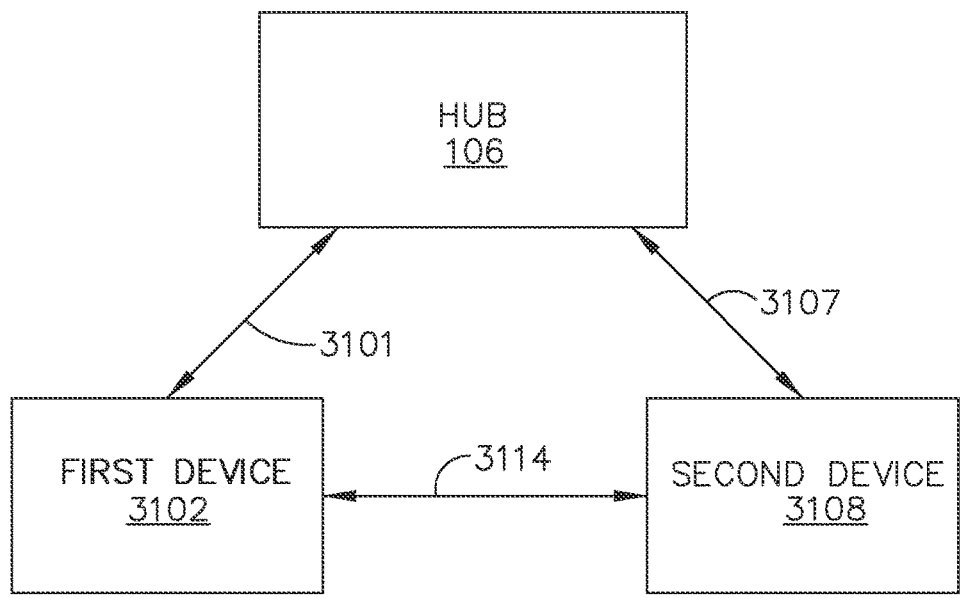
FIG. 42 illustrates a surgical hub pairing a first device and a second device of a surgical system in an operating room, in accordance with at least one aspect of the present disclosure.

Referring to FIGS. 40 and 42, the surgical hub 106 may cause the communication module 130 to pair 3100 or establish a first communication link 3101 with a first device 3102 of the surgical system 102, which can be a first surgical instrument. Then, the hub may assign 3104 a first identification number to the first device 3102. This is a unique identification and communication sequence or number that may include the device's name and a time stamp of when the communication was first established.

In addition, the surgical hub 106 may then cause the communication module 130 to pair 3106 or establish a second communication link 3107 with a second device 3108 of the surgical system 102, which can be a surgical instrument controller. The surgical hub 106 then assigns 3110 a second identification number to the second device 3108.

In various aspects, the steps of pairing a surgical hub 106 with a device may include detecting the presence of a new device, determining that the new device is within bounds of the operating room, as described above in greater detail, and only pairing with the new device if the new device is located within the bounds of the operating room.

The surgical hub 106 may then pair 3112 or authorize a communication link 3114 to be established between the first device 3102 and the second device 3108, as illustrated in FIG. 42. A record indicative of the communication link 3114 is stored by the surgical hub 106 in the storage array 134. In one aspect, the communication link 3114 is established through the surgical hub 106. In another aspect, as illustrated in FIG. 42, the communication link 3114 is a direct link between the first device 3102 and the second device 3108.

Figure 43:
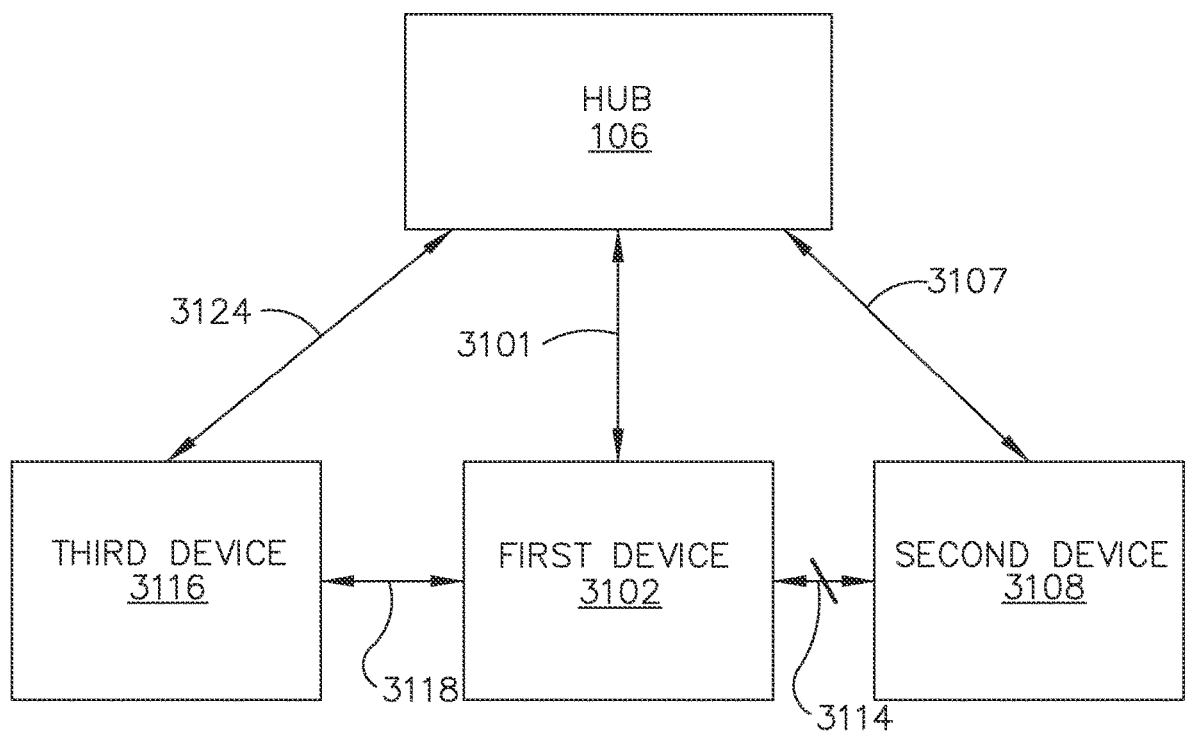
FIG. 43 illustrates a surgical hub unpairing a first device and a second device of a surgical system in an operating room, and pairing the first device with a third device in the operating room, in accordance with at least one aspect of the present disclosure.

Referring to FIGS. 41 and 43, the surgical hub 106 may then detect and pair 3120 or establish a third communication link 3124 with a third device 3116 of the surgical system 102, which can be another surgical instrument controller, for example. The surgical hub 106 may then assign 3126 a third identification number to the third device 3116.

In certain aspects, as illustrated in FIG. 43, the surgical hub 106 may then pair 3130 or authorize a communication link 3118 to be established between the first device 3102 and the third device 3116, while causing the communication link 3114 to be severed 3128, as illustrated in FIG. 43. A record indicative of the formation of the communication link 3118 and severing of the communication link 3114 is stored by the surgical hub 106 in the storage array 134. In one aspect, the communication link 3118 is established through the surgical hub 106. In another aspect, as illustrated in FIG. 43, the communication link 3118 is a direct link between the first device 3102 and the third device 3116.

As described above, the surgical hub 106 can manage an indirect communication between devices of the surgical system 102. For example, in situations where the first device 3102 is a surgical instrument and the second device 3108 is a surgical instrument controller, an output of the surgical instrument controller can be transmitted through the communication link 3107 to the surgical hub 106, which may then transmit the output to the surgical instrument through the communication link 3101.

In making a decision to connect or sever a connection between devices of the surgical system 102, the surgical hub 106 may rely on perioperative data received or generated by the surgical hub 106. Perioperative data includes operator input, hub-situational awareness, hub-spatial awareness, and/or cloud data. For example, a request can be transmitted to the surgical hub 106 from an operator user-interface to assign a surgical instrument controller to a surgical instrument. If the surgical hub 106 determines that the surgical instrument controller is already connected to another surgical instrument, the surgical hub 106 may sever the connection and establish a new connection per the operator's request.

In certain examples, the surgical hub 106 may establish a first communication link between the visualization system 108 and the primary display 119 to transmit an image, or other information, from the visualization system 108, which resides outside the sterile field, to the primary display 119, which is located within the sterile field. The surgical hub 106 may then sever the first communication link and establish a second communication link between a robotic hub 122 and the primary display 119 to transmit another image, or other information, from the robotic hub 122 to the primary display 119, for example. The ability of the surgical hub 106 to assign and reassign the primary display 119 to different components of the surgical system 102 allows the surgical hub 106 to manage the information flow within the operating room, particularly between components inside the sterile field and outside the sterile field, without physically moving these components.

In another example that involves the hub-situational awareness, the surgical hub 106 may selectively connect or disconnect devices of the surgical system 102 within an operating room based on the type of surgical procedure being performed or based on a determination of an upcoming step of the surgical procedure that requires the devices to be connected or disconnected. The hub situational awareness is described in greater detail below in connection with FIG. 86.

Figure 44:
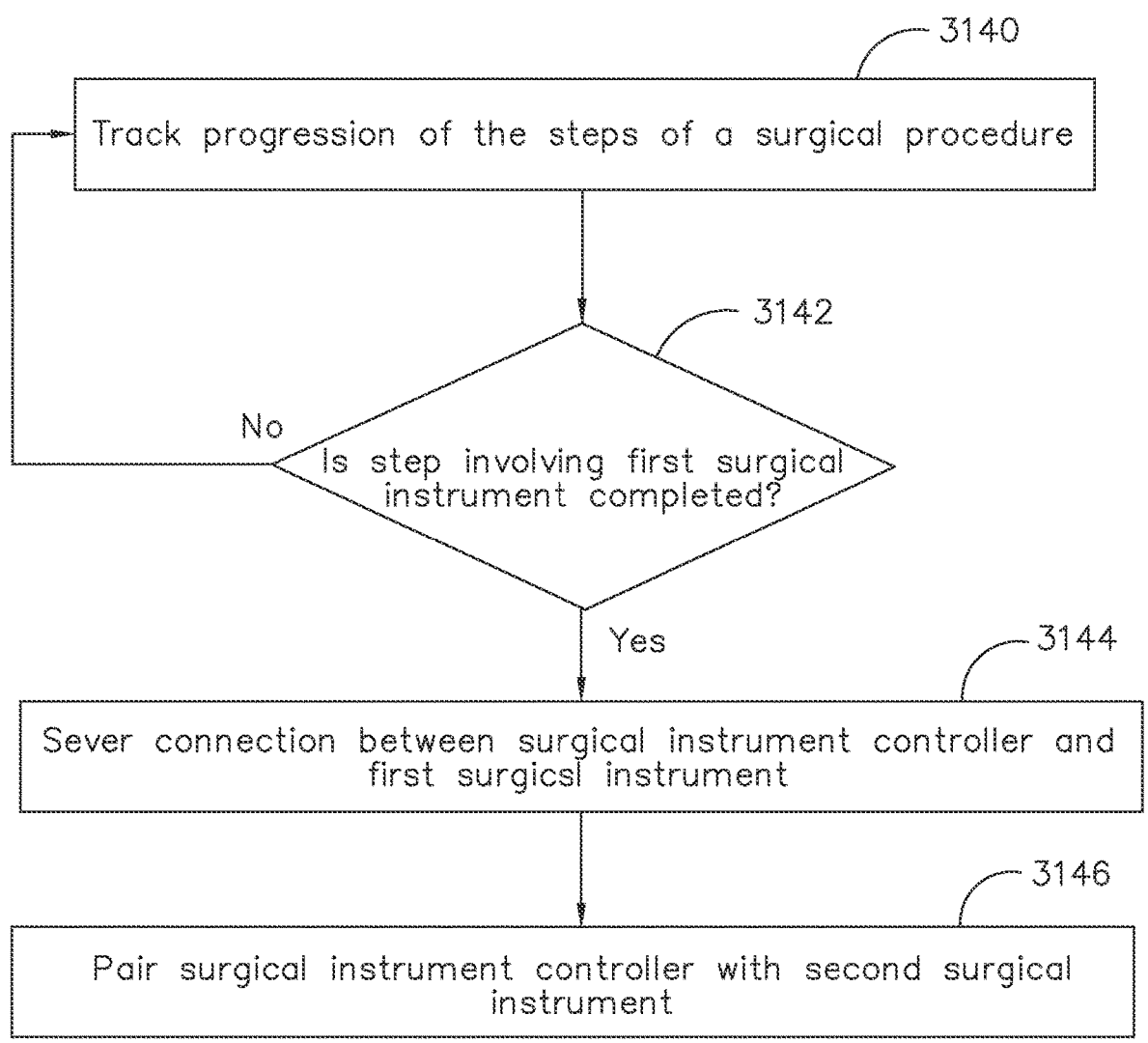
FIG. 44 is a logic flow diagram of a process depicting a control program or a logic configuration for forming an severing connections between devices of a surgical system in an operating room during a surgical procedure based on progression of the steps of the surgical procedure, in accordance with at least one aspect of the present disclosure.

Referring to FIG. 44, the surgical hub 106 may track 3140 the progression of surgical steps in a surgical procedure and may coordinate pairing and unpairing of the devices of the surgical system 102 based upon such progression. For example, the surgical hub 106 may determine that a first surgical step requires use of a first surgical instrument, while a second surgical step, occurring after completion of the first surgical step, requires use of a second surgical instrument. Accordingly, the surgical hub 106 may assign a surgical instrument controller to the first surgical instrument for the duration of the first surgical step. After detecting completion 3142 of the first surgical step, the surgical hub 106 may cause the communication link between the first surgical instrument and the surgical instrument controller to be severed 3144. The surgical hub 106 may then assign the surgical instrument controller to the second surgical instrument by pairing 3146 or authorizing the establishment of a communication link between the surgical instrument controller and the second surgical instrument.

Various other examples of the hub-situational awareness, which can influence the decision to connect or disconnect devices of the surgical system 102, are described in greater detail below in connection with FIG. 86.

In certain aspects, the surgical hub 106 may utilize its spatial awareness capabilities, as described in greater detail elsewhere herein, to track progression of the surgical steps of a surgical procedure and autonomously reassign a surgical instrument controller from one surgical instrument to another surgical instrument within the operating room of the surgical hub 106. In one aspect, the surgical hub 106 uses Bluetooth pairing and compass information to determine the physical position of the components of the surgical system 102.

In the example illustrated in FIG. 2, the surgical hub 106 is paired with a first surgical instrument held by a surgical operator at the operating table and a second surgical instrument positioned on a side tray. A surgical instrument controller can be selectively paired with either the first surgical instrument or the second surgical instrument. Utilizing the Bluetooth pairing and compass information, the surgical hub 106 autonomously assigns the surgical instrument controller to the first surgical instrument because of its proximity to the patient.

After completion of the surgical step that involved using the first surgical instrument, the first surgical instrument may be returned to the side tray or otherwise moved away from the patient. Detecting a change in the position of the first surgical instrument, the surgical hub 106 may sever the communication link between the first surgical instrument and the surgical instrument controller to protect against unintended activation of the first surgical instrument by the surgical instrument controller. The surgical hub 106 may also reassign the surgical instrument controller to another surgical instrument if the surgical hub 106 detects that it has been moved to a new position at the operating table.

In various aspects, devices of the surgical system 102 are equipped with an easy hand-off operation mode that would allow one user to give activation control of a device they currently control to another surgical instrument controller within reach of another operator. In one aspect, the devices are equipped to accomplish the hand-off through a predetermined activation sequence of the devices that causes the devices that are activated in the predetermined activation sequence to pair with one another.

In one aspect, the activation sequence is accomplished by powering on the devices to be paired with one another in a particular order. In another aspect, the activation sequence is accomplished by powering on the devices to be paired with one another within a predetermined time period. In one aspect, the activation sequence is accomplished by activating communication components, such as Bluetooth, of the devices to be paired with one another in a particular order. In another aspect, the activation sequence is accomplished by activating communication components, such as Bluetooth, of the devices to be paired within one another within a predetermined time period.

Alternatively, the hand-off can also be accomplished by a selection of a device through one of the surgical-operator input devices. After the selection is completed, the next activation by another controller would allow the new controller to take control.

In various aspects, the surgical hub 106 can be configured to directly identify components of the surgical system 102 as they are brought into an operating room. In one aspect, the devices of the surgical system 102 can be equipped with an identifier recognizable by the surgical hub 106, such as, for example, a bar code or an RFID tag. NFC can also be employed. The surgical hub 106 can be equipped with a suitable reader or scanner for detecting the devices brought into the operating room.

The surgical hub 106 can also be configured to check and/or update various control programs of the devices of the surgical system 102. Upon detecting and establishing a communication link of a device of the surgical system 102, the surgical hub 106 may check if its control program is up to date. If the surgical hub 106 determines that a later version of the control program is available, the surgical hub 106 may download the latest version from the cloud 104 and may update the device to the latest version. The surgical hub 106 may issue a sequential identification and communication number to each paired or connected device.

Cooperative Utilization of Data Derived from Secondary Sources by Intelligent Surgical Hubs In a surgical procedure, the attention of a surgical operator must be focused on the tasks at hand. Receiving information from multiple sources, such as, for example, multiple displays, although helpful, can also be distracting. The imaging module 138 of the surgical hub 106 is configured to intelligently gather, analyze, organize/package, and disseminate relevant information to the surgical operator in a manner that minimizes distractions.

Aspects of the present disclosure are presented for cooperative utilization of data derived from multiple sources, such as, for example, an imaging module 138 of the surgical hub 106. In one aspect, the imaging module 138 is configured to overlay data derived from one or more sources onto a livestream destined for the primary display 119, for example. In one aspect, the overlaid data can be derived from one or more frames acquired by the imaging module 138. The imaging module 138 may commandeer image frames on their way for display on a local display such as, for example, the primary display 119. The imaging module 138 also comprises an image processor that may preform an array of local image processing on the commandeered images.

Furthermore, a surgical procedure generally includes a number of surgical tasks which can be performed by one or more surgical instruments guided by a surgical operator or a surgical robot, for example. Success or failure of a surgical procedure depends on the success or failure of each of the surgical tasks. Without relevant data on the individual surgical tasks, determining the reason for a failed surgical procedure is a question of probability.

Aspects of the present disclosure are presented for capturing one or more frames of a livestream of a surgical procedure for further processing and/or pairing with other data. The frames may be captured at the completion of a surgical task (also referred to elsewhere herein as "surgical step") to assess whether the surgical task was completed successfully. Furthermore, the frames, and the paired data, can be uploaded to the cloud for further analysis.

In one aspect, one or more captured images are used to identify at least one previously completed surgical task to evaluate the outcome of the surgical task. In one aspect, the surgical task is a tissue-stapling task. In another aspect, the surgical task is an advanced energy transection.

Figure 45:
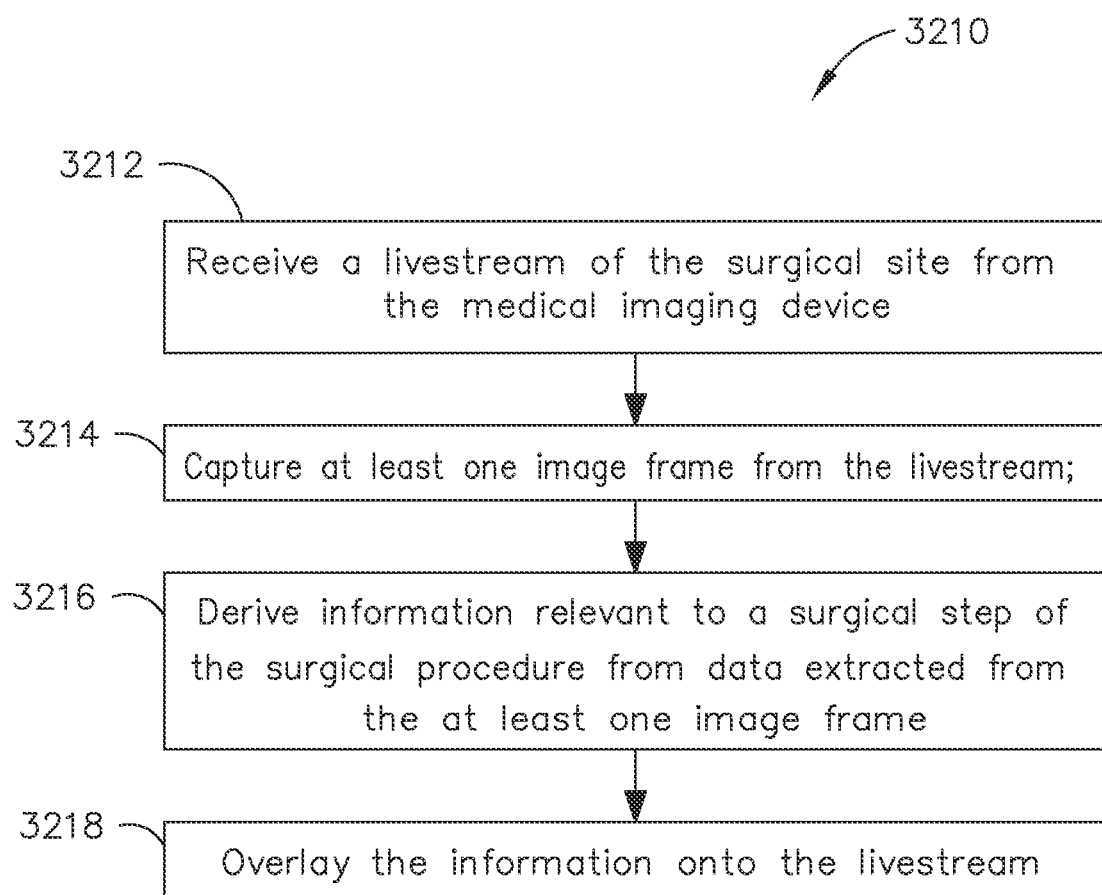
FIG. 45 is a logic flow diagram of a process depicting a control program or a logic configuration for overlaying information derived from one or more still frames of a livestream of a remote surgical site onto the livestream, in accordance with at least one aspect of the present disclosure.

FIG. 45 is a logic flow diagram of a process 3210 depicting a control program or a logic configuration for overlaying information derived from one or more still frames of a livestream of a remote surgical site onto the livestream. The process 3210 includes receiving 3212 a livestream of a remote surgical site from a medical imaging device 124, for example, capturing 3214 at least one image frame of a surgical step of the surgical procedure from the livestream, deriving 3216 information relevant to the surgical step from data extracted from the at least one image frame, and overlaying 3218 the information onto the livestream.

In one aspect, the still frames can be of a surgical step performed at the remote surgical site. The still frames can be analyzed for information regarding completion of the surgical step. In one aspect, the surgical step comprises stapling tissue at the surgical site. In another aspect, the surgical task comprises applying energy to tissue at the surgical site.

Figure 46:
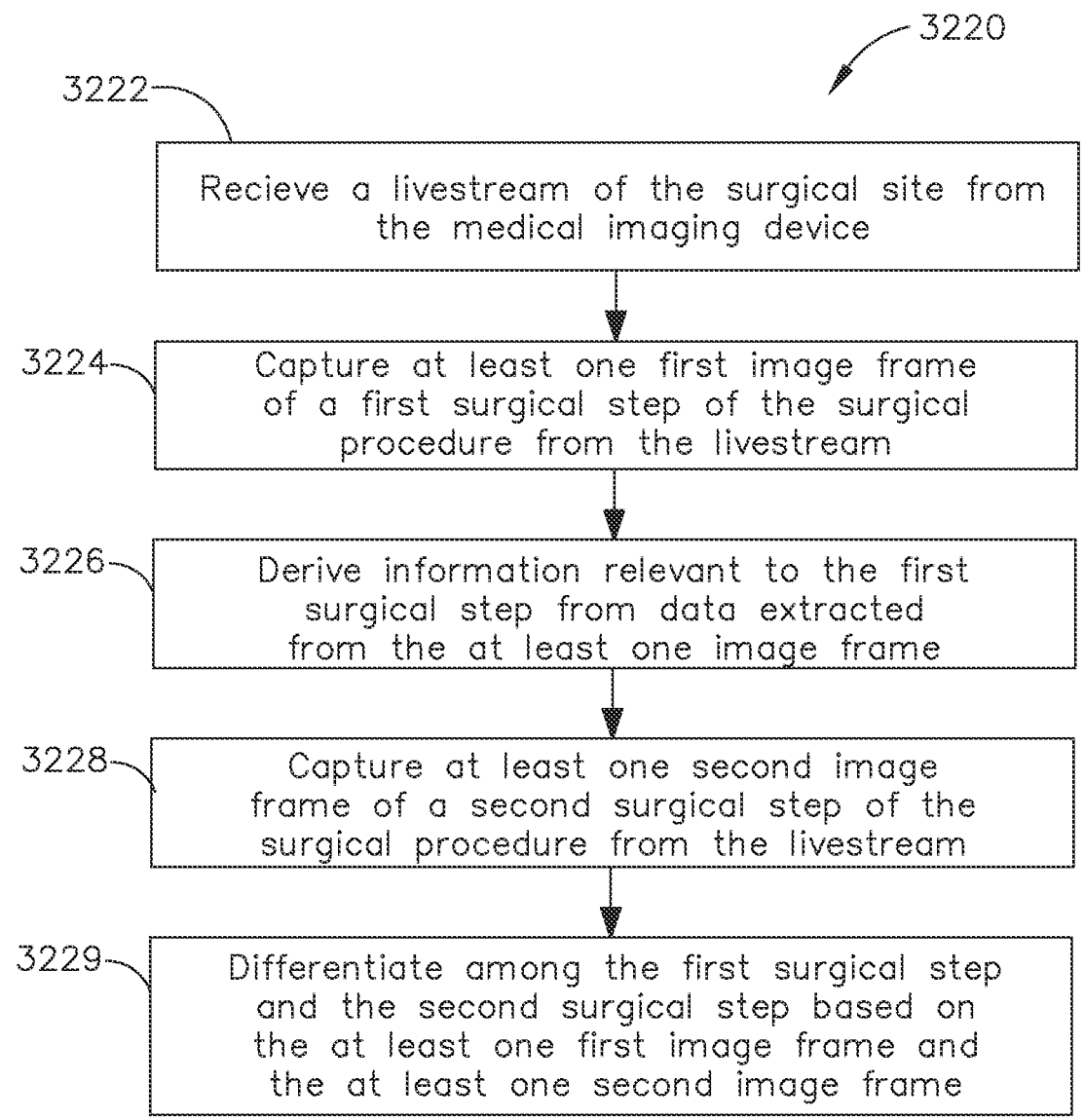
FIG. 46 is a logic flow diagram of a process depicting a control program or a logic configuration for differentiating among surgical steps of a surgical procedure, in accordance with at least one aspect of the present disclosure.

FIG. 46 is a logic flow diagram of a process 3220 depicting a control program or a logic configuration for differentiating among surgical steps of a surgical procedure. The process 3220 includes receiving 3222 a livestream of a surgical site from a medical imaging device 124, for example, capturing 3224 at least one first image frame of a first surgical step of the surgical procedure from the livestream, deriving 3226 information relevant to the first surgical step from data extracted from the at least one image frame, capturing 3228 at least one second image frame of a second surgical step of the surgical procedure from the livestream, and differentiating 3229 among the first surgical step and the second surgical step based on the at least one first image frame and the at least one second image frame.

Figure 47:
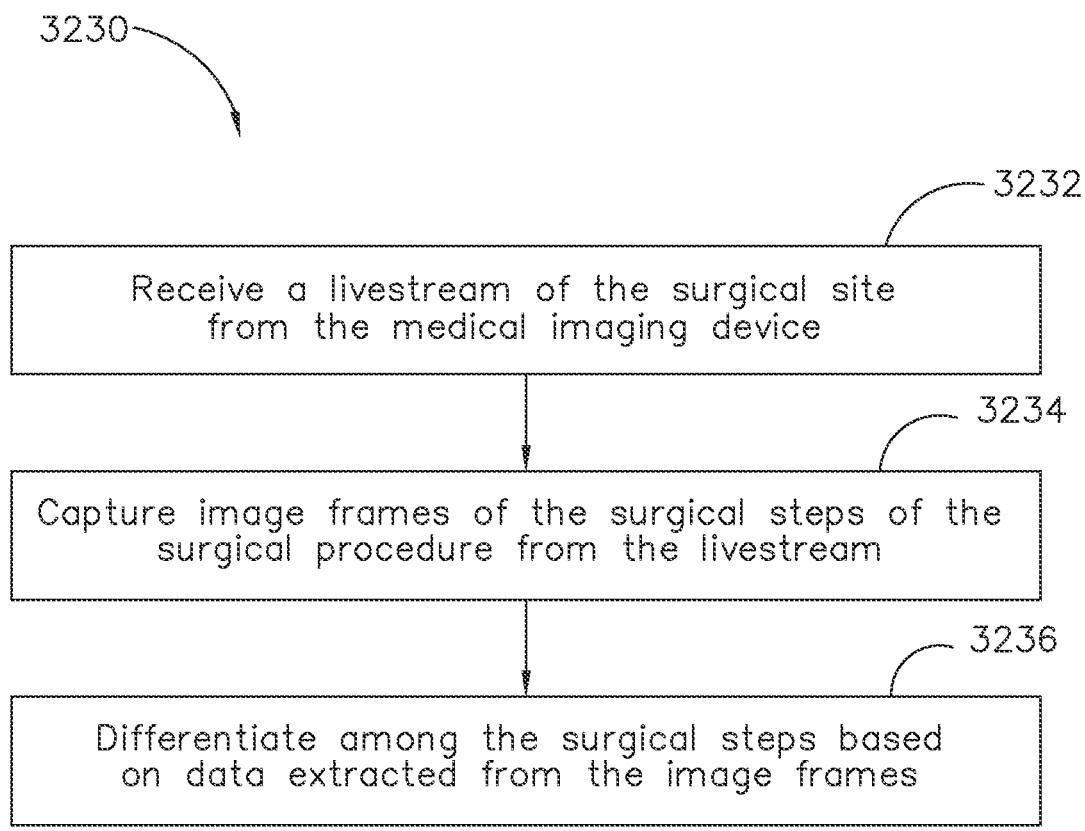
FIG. 47 is a logic flow diagram of a process 3230 depicting a control program or a logic configuration for differentiating among surgical steps of a surgical procedure, in accordance with at least one aspect of the present disclosure.

FIG. 47 is a logic flow diagram of a process 3230 depicting a control program or a logic configuration for differentiating among surgical steps of a surgical procedure. The process 3232 includes receiving 3232 a livestream of the surgical site from a medical imaging device 124, for example, capturing 3234 image frames of the surgical steps of the surgical procedure from the livestream and differentiating 3236 among the surgical steps based on data extracted from the image frames.

Figure 48:
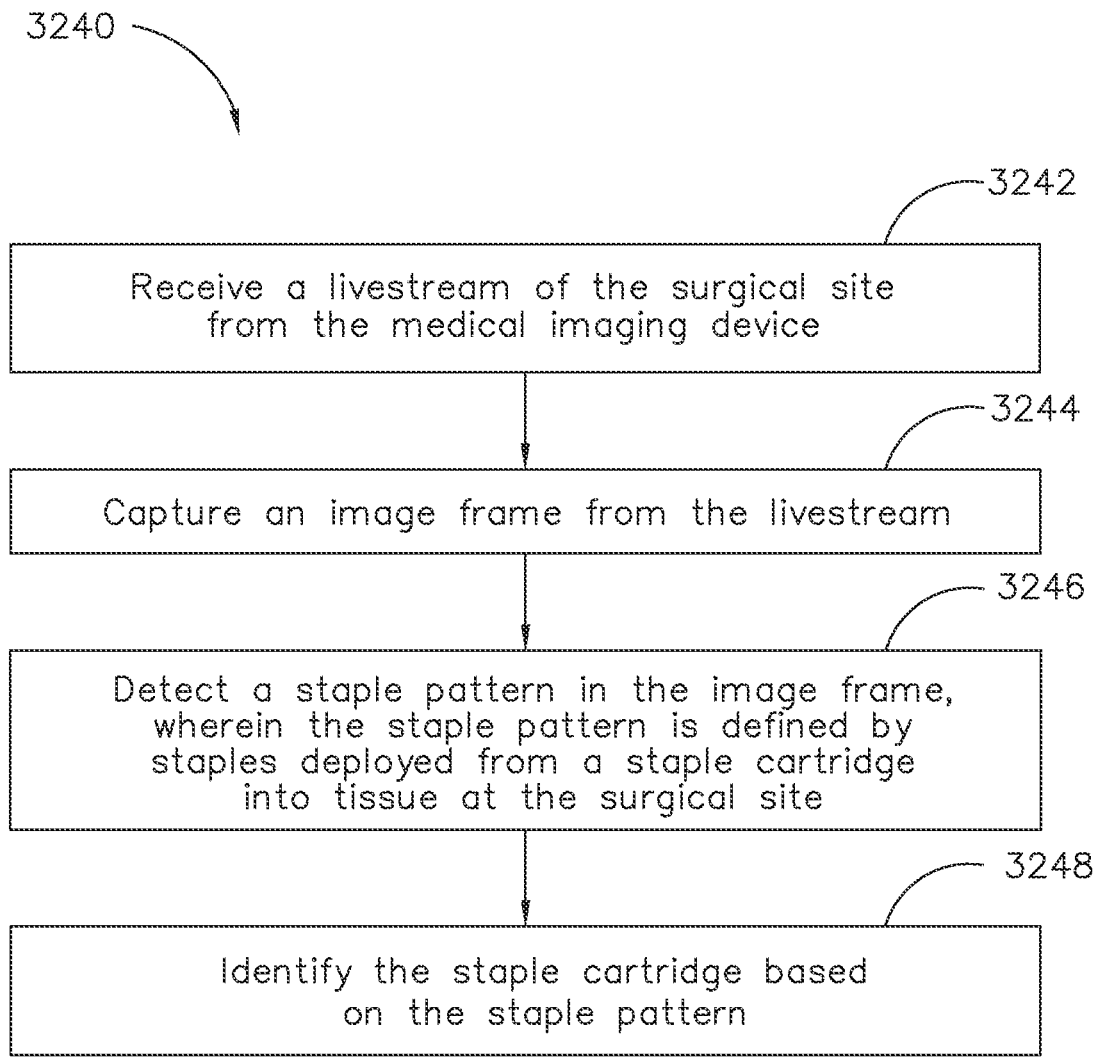
FIG. 48 is a logic flow diagram of a process 3240 depicting a control program or a logic configuration for identifying a staple cartridge from information derived from one or more still frames of staples deployed from the staple cartridge into tissue, in accordance with at least one aspect of the present disclosure.

FIG. 48 is a logic flow diagram of a process 3240 depicting a control program or a logic configuration for identifying a staple cartridge from information derived from one or more still frames of staples deployed from the staple cartridge into tissue. The process 3240 includes receiving 3242 a livestream of the surgical site from medical imaging device 124, for example, capturing 3244 an image frame from the livestream, detecting 3246 a staple pattern in the image frame, wherein the staple pattern is defined by staples deployed from a staple cartridge into tissue at the surgical site. The process 3240 further includes identifying 3248 the staple cartridge based on the staple pattern.

In various aspects, one or more of the steps of the processes 3210, 3220, 3230, 3240 can be executed by a control circuit of an imaging module of a surgical hub, as depicted in FIGS. 3, 9, 10. In certain examples, the control circuit may include a processor and a memory coupled to the processor, wherein the memory stores instructions executable by the processor to perform one or more of the steps of the processes 3210, 3220, 3230, 3240. In certain examples, a non-transitory computer-readable medium stores computer-readable instructions which, when executed, cause a machine to perform one or more of the steps of the processes 3210, 3220, 3230, 3240. For economy, the following description of the processes 3210, 3220, 3230, 3240 will be described as being executed by the control circuit of an imaging module of a surgical hub; however, it should be understood that the execution of the processes 3210, 3220, 3230, 3240 can be accomplished by any of the aforementioned examples.

Figure 49:
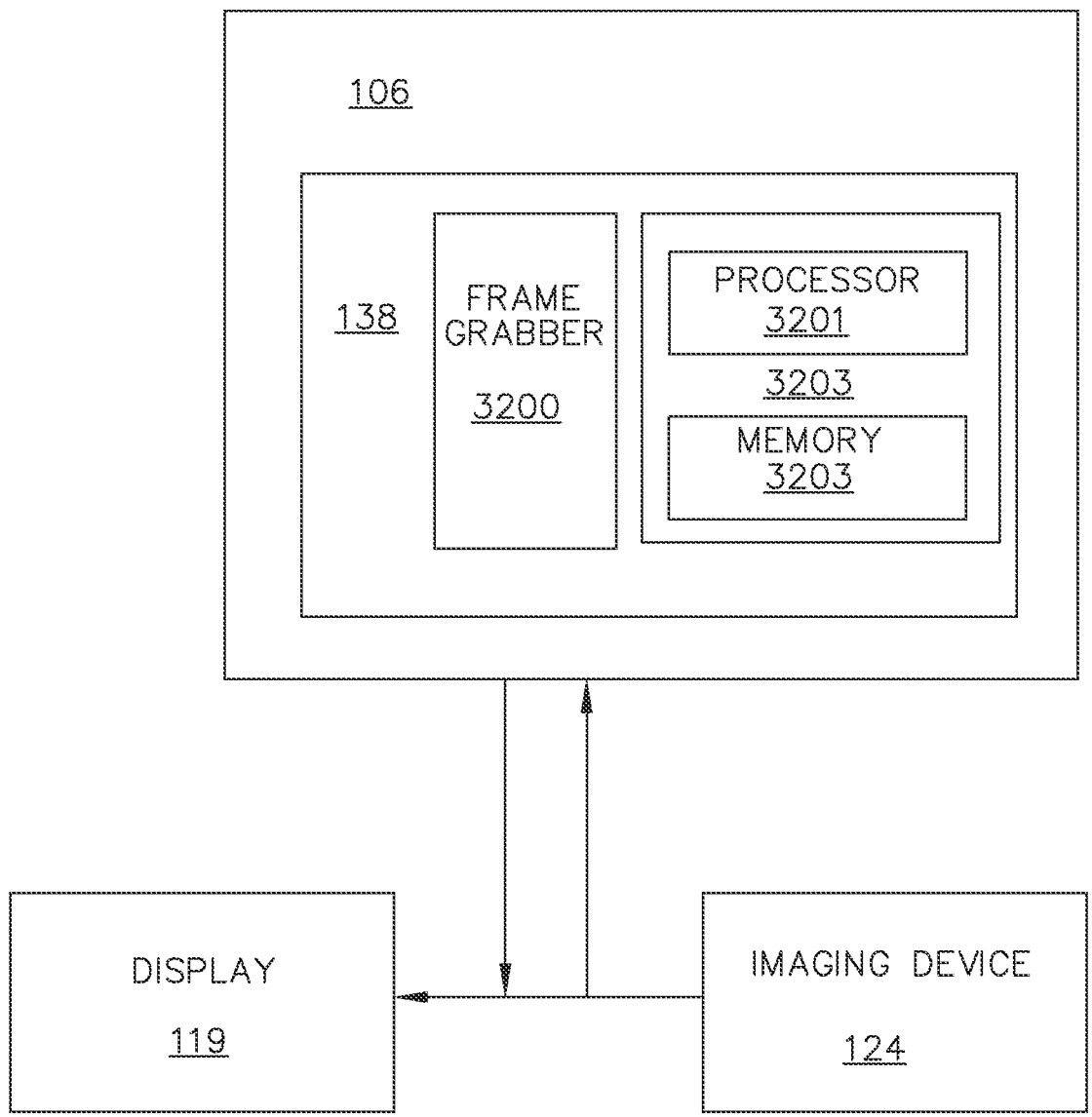
FIG. 49 is a partial view of a surgical system in an operating room, the surgical system including a surgical hub that has an imaging module in communication with an imaging device at a remote surgical site, in accordance with at least one aspect of the present disclosure.

Referring to FIGS. 34 and 49, a surgical hub 106 is in communication with a medical imaging device 124 located at a remote surgical site during a surgical procedure. The imaging module 138 receives a livestream of the remote surgical site transmitted by the imaging device 124 to a primary display 119, for example, in accordance with steps 3212, 3222, 3232, 3242.

Further to the above, the imaging module 138 of the surgical hub 106 includes a frame grabber 3200. The frame grabber 3200 is configured to capture (i.e., "grabs") individual, digital still frames from the livestream transmitted by the imaging device 124, for example, to a primary display 119, for example, during a surgical procedure, in accordance with steps 3214, 3224, 3234, 3244. The captured still frames are stored and processed by a computer platform 3203 (FIG. 49) of the imaging module 138 to derive information about the surgical procedure. Processing of the captured frames may include performance of simple operations, such as histogram calculations, 2D filtering, and arithmetic operations on arrays of pixels to the performance of more complex tasks, such as object detection, 3D filtering, and the like.

In one aspect, the derived information can be overlaid onto the livestream. In one aspect, the still frames and/or the information resulting from processing the still frames can be communicated to a cloud 104 for data aggregation and further analysis.

In various aspects, the frame grabber 3200 may include a digital video decoder and a memory for storing the acquired still frames, such as, for example, a frame buffer. The frame grabber 3200 may also include a bus interface through which a processor can control the acquisition and access the data and a general purpose I/O for triggering image acquisition or controlling external equipment.

As described above, the imaging device 124 can be in the form of an endoscope, including a camera and a light source positioned at a remote surgical site, and configured to provide a livestream of the remote surgical site at the primary display 119, for example.

In various aspects, image recognition algorithms can be implemented to identify features or objects in still frames of a surgical site that are captured by the frame grabber 3200. Useful information pertaining to the surgical steps associated with the captured frames can be derived from the identified features. For example, identification of staples in the captured frames indicates that a tissue-stapling surgical step has been performed at the surgical site. The type, color, arrangement, and size of the identified staples can also be used to derive useful information regarding the staple cartridge and the surgical instrument employed to deploy the staples. As described above, such information can be overlaid on a livestream directed to a primary display 119 in the operating room.

The image recognition algorithms can be performed at least in part locally by the computer platform 3203 (FIG. 49) of the imaging module 138. In certain instances, the image recognition algorithms can be performed at least in part by the processor module 132 of the surgical hub 106. An image database can be utilized in performance of the image recognition algorithms and can be stored in a memory 3202 of the computer platform 3203. Alternatively, the imaging database can be stored in the storage array 134 (FIG. 3) of the surgical hub 106. The image database can be updated from the cloud 104.

An example image recognition algorithm that can be executed by the computer platform 3203 may include a key points-based comparison and a region-based color comparison. The algorithm includes: receiving an input at a processing device, such as, for example, the computer platform 3203; the input, including data related to a still frame of a remote surgical site; performing a retrieving step, including retrieving an image from an image database and, until the image is either accepted or rejected, designating the image as a candidate image; performing an image recognition step, including using the processing device to perform an image recognition algorithm on the still frame and candidate images in order to obtain an image recognition algorithm output; and performing a comparison step, including: if the image recognition algorithm output is within a pre-selected range, accepting the candidate image as the still frame and if the image recognition algorithm output is not within the pre-selected range, rejecting the candidate image and repeating the retrieving, image recognition, and comparison steps.

Figure 50:
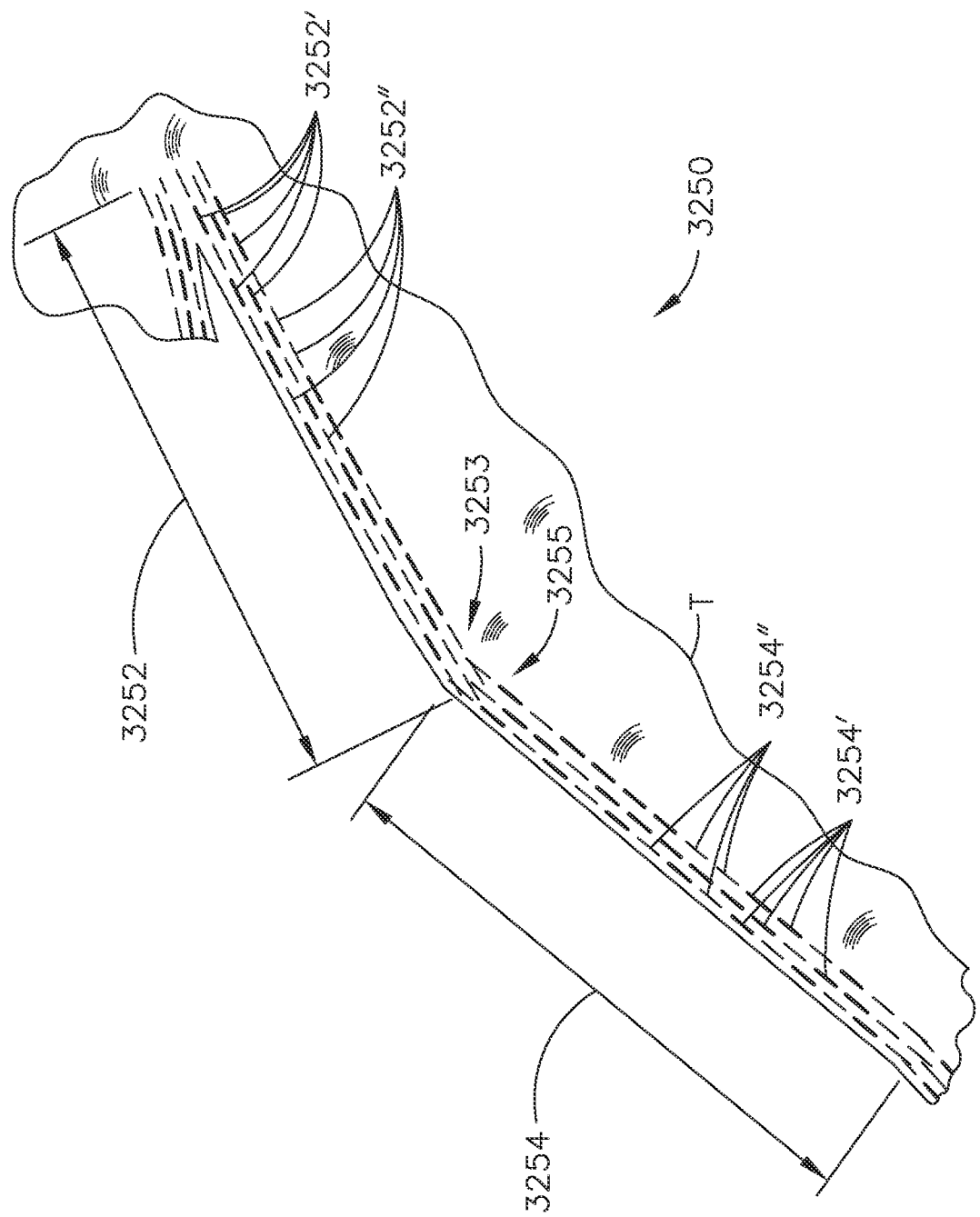
FIG. 50 illustrates a partial view of stapled tissue that received a first staple firing and a second staple firing arranged end-to-end, in accordance with at least one aspect of the present disclosure.

Referring to FIGS. 50-52, in one example, a surgical step involves stapling and cutting tissue. FIG. 50 depicts a still frame 3250 of a stapled and cut tissue T. A staple deployment 3252 includes staples 3252', 3252" from a first staple cartridge. A second staple deployment 3254 includes staples 3254', 3254" from a second staple cartridge. A proximal portion 3253 of the staple deployment 3252 overlaps with a distal portion 3255 of the staple deployment 3254. Six rows of staples were deployed in each deployment. Tissue T was cut between the third and fourth rows of each deployment, but only one side of the stapled tissue T is fully shown.

In various aspects, the imaging module 138 identifies one or more of the staples 3252, 3252", 3254', 3254" in the still frame 3250, which were absent in a previous still frame captured by the frame grabber 3200. The imaging module 138 then concludes that a surgical stapling and cutting instrument has been used at the surgical site.

In the example of FIG. 50, the staple deployment 3252 includes two different staples 3252', 3252". Likewise, the staple deployment 3254 includes two different staples 3254', 3254". For brevity, the following description focuses on the staples 3252, 3252", but is equally applicable to the staples 3254', 3254". The staples 3252', 3252" are arranged in a predetermined pattern or sequence that forms a unique identifier corresponding to the staple cartridge that housed the staples 3252', 3252". The unique pattern can be in a single row or multiple rows of the staples 3250. In one example, the unique pattern can be achieved by alternating the staples 3252', 3252" at a predetermined arrangement.

In one aspect, multiple patterns can be detected in a firing of staples. Each pattern can be associated with a unique characteristic of the staples, the staple cartridge that housed the staples, and/or the surgical instrument that was employed to fire the staple. For example, a firing of staples may include patterns that represent staple form, staple size, and/or location of the firing.

In the example, of FIG. 50, the imaging module 138 may identify a unique pattern of the staples 3252 from the still frame 3250. A database storing staple patterns and corresponding identification numbers of staple cartridges can then be explored to determine an identification number of a staple cartridge that housed the staples 3252.

The patterns of the example of FIG. 50 are based on only two different staples; however, other aspects may include three or more different staples. The different staples can be coated with different coatings, which can be applied to the staples by one or more of the following methods: anodizing, dying, electro-coating, photoluminescent coating, application of nitrides, methyl methacylate, painting, powder coating, coating with paraffins, oil stains or phosphor coatings, the use of hydroxyapatite, polymers, titanium oxinitrides, zinc sulfides, carbides, etc. It should be noted that, while the listed coatings are fairly specific as disclosed herein, other coatings known in the art to distinguish the staple are within the contemplated scope of the present disclosure.

In the example of FIGS. 50-52, the staples 3252' are anodized staples, while the staples 3252" are non-anodized staples. In one aspect, the different staples may comprise two or more different colors. Different metal staples may comprise magnetic or radioactive staple markers that differentiate them from unmarked staples.

FIG. 51 illustrates a staple deployment 3272 deployed into tissue from a staple cartridge via a surgical instrument. Only three staple rows 3272a, 3272b, 3272c are depicted in FIG. 51. The rows 3272a, 3272b, 3272c are arranged between a medial line, where the tissue was cut, and a lateral line at the tissue edge. For clarity, the inner row 3272a of staples is redrawn separately to the left and the outer two rows 3272b, 3272c are redrawn separately to the right. A proximal end 3273 and a distal end portion of the staple deployment 3272 are also redrawn in FIG. 51 for clarity.

The staple deployment 3272 includes two different staples 3272', 3272" that are arranged in predetermined patterns that serve various functions. For example, the inner row 3272a comprises a pattern of alternating staples 3272'. 3272", which defines a metric for distance measurements in the surgical field. In other words, the pattern of the inner row 3272a acts as a ruler for measuring distances, which can be helpful in accurately determining the position of a leak, for example. The outer rows 3272b, 3272c define a pattern that represents an identification number of the staple cartridge that housed the staples 3272', 3272".

Furthermore, unique patterns at the ends of the staple deployment 3272 identify the proximal end portion 3273 and distal end portion 3275. In the example of FIG. 51, a unique arrangement of three staples 3272″ identifies the distal end 3275, while a unique arrangement of four staples 3272″ identifies the proximal end 3273. Identification of the proximal and distal ends of a staple deployment allows the imaging module 128 to distinguish between different staple deployments within a captured frame, which can be useful in pointing the source of a leak, for example.

In various aspects, the imaging module 138 may detect a sealed tissue in a still frame of a remote surgical site captured by the frame grabber 3200. Detection of the sealed tissue can be indicative of a surgical step that involves applying therapeutic energy to tissue.

Sealing tissue can be accomplished by the application of energy, such as electrical energy, for example, to tissue captured or clamped within an end effector of a surgical instrument in order to cause thermal effects within the tissue. Various mono-polar and bi-polar RF surgical instruments and harmonic surgical instruments have been developed for such purposes. In general, the delivery of energy to captured tissue can elevate the temperature of the tissue and, as a result, the energy can at least partially denature proteins within the tissue. Such proteins, like collagen, for example, can be denatured into a proteinaceous amalgam that intermixes and fuses, or seals, together as the proteins renature.

Accordingly, sealed tissue has a distinct color and/or shape that can be detected by the imaging module 138 using image recognition algorithms, for example. In addition, smoke detection at the surgical site can indicate that therapeutic energy application to the tissue is in progress.

Further to the above, the imaging module 138 of the surgical hub 106 is capable of differentiating between surgical steps of a surgical procedure based on the captured frames. As described above, a still frame that comprises fired staples is indicative of a surgical step involving tissue stapling, while a still frame that comprises a sealed tissue is indicative of a surgical step involving energy application to tissue.

In one aspect, the surgical hub 106 may selectively overlay information relevant to a previously completed surgical task onto the livestream. For example, the overlaid information may comprise image data from a still frame of the surgical site captured during the previously completed surgical task. Furthermore, guided by common landmark locations at the surgical site, the imaging module 138 can interlace one image frame to another to establish and detect surgical locations and relationship data of a previously completed surgical task.

In one example, the surgical hub 106 is configured to overlay information regarding a potential leak in a tissue treated by stapling or application of therapeutic energy in a previously completed surgical task. The potential leak can be spotted by the imaging module 138 during the processing of a still frame of the tissue. The surgical operator can be alerted about the leak by overlaying information about the potential leak onto the livestream.

In various aspects, still frames of an end effector of a surgical instrument at a surgical site can be used to identify the surgical instrument. For example, the end effector may include an identification number that can be recognized by the imaging module 138 during image processing of the still frame. Accordingly, the still frames captured by the imaging module 138 may be used to identify a surgical instrument utilized in a surgical step of a surgical procedure. The still frames may also include useful information regarding the performance of the surgical instrument. All such information can be uploaded to the cloud 104 for data aggregation and further analysis.

In various examples, the surgical hub 106 may also selectively overlay information relevant to a current or upcoming surgical task, such as an anatomical location or a surgical instrument suitable for the surgical task.

The imaging module 138 may employ various images and edge detection techniques to track a surgical site where a surgical instrument was used to complete a surgical task. Success or failure of the surgical task can then be assessed. For example, a surgical instrument can be employed to seal and/or cut tissue at the surgical site. A still frame of the surgical site can be stored in the memory 3202 or the storage array 134 of the surgical hub 106, for example, upon completion of the surgical task.

In the following surgical step, the quality of the seal can be tested via different mechanisms. To ensure that the testing is accurately applied to the treated tissue, the stored still frame of the surgical site is overlaid onto the livestream in search of a match. Once a match is found, the testing can take place. One or more additional still frames can be taken during the testing, which can be later analyzed by the imaging module 138 of the surgical hub 106. The testing mechanisms include bubble detection, bleeding detection, dye detection (where a dye is employed at the surgical site), and/or burst stretch detection (where a localized strain is applied adjacent to an anastomosis site), for example.

The imaging module 138 may capture still frames of the response of the treated tissue to these tests, which can be stored in the memory 3202 or the storage array 134 of the surgical hub 106, for example. The still frames can be stored alone or in combination with other data, such as, for example, data from the surgical instrument that performed the tissue treatment. The paired data can also be uploaded to the cloud 104 for additional analysis and/or pairing.

In various aspects, the still frames captured by the frame grabber 3200 can be processed locally, paired with other data, and can also be transmitted to the cloud 104. The size of the processed and/or transmitted data will depend on the number of captured frames. In various aspects, the rate at which the frame grabber 3200 captures the still frames from the livestream can be varied in an effort to reduce the size of the data without sacrificing quality.

In one aspect, the frame-capturing rate may depend on the type of surgical task being performed. Certain surgical tasks may need a higher number of still frames than others for an evaluation of success or failure. The frame-capturing rate can be scalded to accommodate such needs.

In one aspect, the frame-capturing rate is dependent upon the detected motion of the imaging device 124. In use, an imaging device 124 may target one surgical site for a period of time. Observing no or minor changes in the still frames captured while the imaging device 124 is not being moved, the imaging module 138 may reduce the frame-capturing rate of the frame grabber 3200. If the situation changes, however, where frequent motion is detected, the imaging module 138 may respond by increasing the frame-capturing rate of the frame grabber 3200. In other words, the imaging module 138 may be configured to correlate the frame-capturing rate of the frame grabber 3200 with the detected degree of motion of the imaging device 124.

For additional efficiency, only portions of the still frames, where motion is detected, need to be stored, processed, and/or transmitted to the cloud 104. The imaging module 138 can be configured to select the portions of the still frames where motion is detected. In one example, motion detection can be achieved by comparing a still frame to a previously captured still frame. If movement is detected, the imaging module 138 may cause the frame grabber 3200 to increase the frame-capturing rate, but only the portions where motion is detected are stored, processed, and/or transmitted to the cloud 104.

In another aspect, the data size can be managed by scaling the resolution of the captured information based on the area of the screen where the focal point is or where end effectors are located, for example. The remainder of the screen could be captured at a lower resolution.

In one aspect, the corners of the screen and the edges could generally be captured at a lower resolution. The resolution, however, can be scalded up if an event of significance is observed.

During a surgical procedure, the surgical hub 106 can be connected to various operating-room monitoring devices, such as, for example, heart rate monitors and insufflation pumps. Data collected from these devices can improve the situational awareness of the surgical hub 106. The hub situational awareness is described in greater detail below in connection with FIG. 86.

In one example, the surgical hub 106 can be configured to utilize patient data received from a heart rate monitor connected along with data regarding the location of the surgical site to assess proximity of the surgical site to sensory nerves. An increase in the patient's heart rate, when combined with anatomical data indicating that the surgical site is in a region high in sensory nerves, can be construed as an indication of sensory nerve proximity. Anatomical data can be available to the surgical hub 106 through accessing patient records (e.g., an EMR database containing patient records).

The surgical hub 106 may be configured to determine the type of surgical procedure being performed on a patient from data received from one or more of the operating-room monitoring devices, such as, for example, heart rate monitors and insufflation pumps. Abdominal surgical procedures generally require insufflation of the abdomen, while insufflation is not required in theoretic surgery. The surgical hub 106 can be configured to determine whether a surgical procedure is an abdominal or a thoracic surgical procedure by detecting whether the insufflation pump is active. In one aspect, the surgical hub 106 may be configured to monitor insufflation pressure on the output side of the insufflation pump in order to determine whether the surgical procedure being performed is one that requires insufflation.

The surgical hub 106 may also gather information from other secondary devices in the operating room to assess, for example, whether the surgical procedure is a vascular or avascular procedure.

The surgical hub 106 may also monitor AC current supply to one or more of its components to assess whether a component is active. In one example, the surgical hub 106 is configured to monitor AC current supply to the generator module to assess whether the generator is active, which can be an indication that the surgical procedure being performed is one that requires application of energy to seal tissue.

In various aspects, secondary devices in the operating room that are incapable of communication with the surgical hub 106 can be equipped with communication interface devices (communication modules) that can facilitate pairing of these devices with the surgical hub 106. In one aspect, the communication interface devices may be configured to be bridging elements, which would allow them two-way communication between the surgical hub 106 and such devices.

In one aspect, the surgical hub 106 can be configured to control one or more operational parameters of a secondary device through a communication interface device. For example, the surgical hub 106 can be configured to increase or decrease the insufflation pressure through a communication interface device coupled to an insufflation device.

In one aspect, the communication interface device can be configured to engage with an interface port of the device. In another aspect, the communication interface device may comprise an overlay or other interface that directly interacts with a control panel of the secondary device. In other aspects, the secondary devices, such as, for example, the heart rate monitor and/or the insufflation devices, can be equipped with integrated communication modules that allow them to pair with the hub for two-way communication therewith.

In one aspect, the surgical hub 106 can also be connected through a communication interface device, for example, to muscle pads that are connected to the neuro-stim detection devices to improve resolution of a nerve-sensing device.

Furthermore, the surgical hub 106 can also be configured to manage operating room supplies. Different surgical procedures require different supplies. For example, two different surgical procedures may require different sets of surgical instruments. Certain surgical procedures may involve using a robotic system, while others may not. Furthermore, two different surgical procedures may require staple cartridges that are different in number, type, and/or size. Accordingly, the supplies brought into the operating room can provide clues as to the nature of the surgical procedure that will be performed.

In various aspects, the surgical hub 106 can be integrated with an operating room supplies scanner to identify items pulled into the operating room and introduced into the sterile field. The surgical hub 106 may utilize data from the operating room supplies scanner, along with data from the devices of the surgical system 102 that are paired with the surgical hub 106, to autonomously determine the type of surgical procedure that will be performed. In one example, the surgical hub 106 may record a list of serial numbers of the smart cartridge that are going to be used in the surgical procedure. During the surgical procedure, the surgical hub 106 may gradually remove the staples that have been fired, based on information collected from the staple cartridge chips. In one aspect, the surgical hub 106 is configured to make sure that all the items are accounted for at the end of the procedure.

Surgical Hub Control Arrangements

In a surgical procedure, a second surgical hub may be brought into an operating room already under the control of a first surgical hub. The second surgical hub can be, for example, a surgical robotic hub brought into the operating room as a part of a robotic system. Without coordination between the first and second surgical hubs, the robotic surgical hub will attempt to pair with all the other components of the surgical system 102 that are within the operating room. The confusion arising from the competition between two hubs in a single operating room can lead to undesirable consequences. Also, sorting out the instrument distribution between the hubs during the surgical procedure can be time consuming.

Aspects of the present disclosure are presented for a surgical hub for use with a surgical system in a surgical procedure performed in an operating room. A control circuit of the surgical hub is configured to determine the bounds of the operating room and establish a control arrangement with a detected surgical hub located within the bounds of the operating room.

In one aspect, the control arrangement is a peer-to-peer arrangement. In another aspect, the control arrangement is a master-slave arrangement. In one aspect, the control circuit is configured to select one of a master mode of operation or a slave mode of operation in the master-slave arrangement. In one aspect, the control circuit is configured to surrender control of at least one surgical instrument to the detected surgical hub in the slave mode of operation.

In one aspect, the surgical hub includes an operating room mapping circuit that includes a plurality of non-contact sensors configured to measure the bounds of the operating room.

In various aspects, the surgical hub includes a processor and a memory coupled to the processor. The memory stores instructions executable by the processor to coordinate a control arrangement between surgical hubs, as described above. In various aspects, the present disclosure provides a non-transitory computer-readable medium storing computer-readable instructions which, when executed, cause a machine to coordinate a control arrangement between surgical hubs, as described above.

Aspects of the present disclosure are presented for a surgical system comprising two independent surgical hubs that are configured to interact with one another. Each of the hubs has their own linked surgical devices and the control designation of and distribution of where data is recorded and processed. This interaction causes one or both hubs to change how they were behaving before the interaction. In one aspect, the change involves a redistribution of devices previously assigned to each of the hubs. In another aspect, the change involves establishing a master-slave arrangement between the hubs. In yet another aspect, the change can be a change in the location of the processing shared between the hubs.

Figure 53:
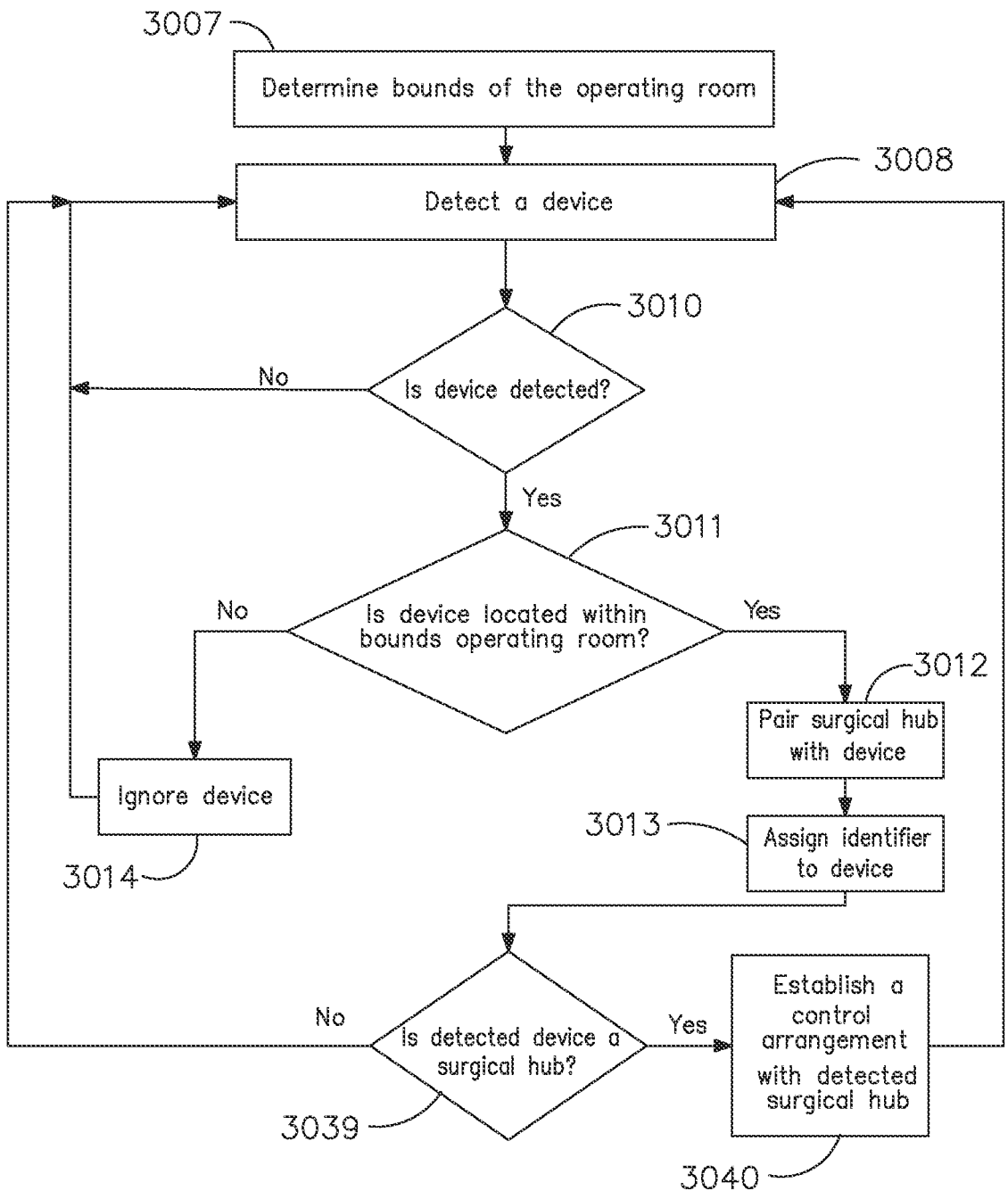
FIG. 53 is a logic flow diagram of a process depicting a control program or a logic configuration for coordinating a control arrangement between surgical hubs, in accordance with at least one aspect of the present disclosure.

FIG. 53 is a logic flow diagram of a process depicting a control program or a logic configuration for coordinating a control arrangement between surgical hubs. The process of FIG. 53 is similar in many respects to the process of FIG. 35 except that the process of FIG. 53 addresses detection of a surgical hub by another surgical hub. As illustrated in FIG. 53, the surgical hub 106 determines 3007 the bounds of the operating room. After the initial determination, the surgical hub 106 continuously searches for or detects 3008 devices within a pairing range. If a device is detected 3010, and if the detected device is located 3011 within the bounds of the operating room, the surgical hub 106 pairs 3012 with the device and assigns 3013 an identifier to the device. If through an initial interaction, as described below in greater detail, the surgical hub 106 determines 3039 that the device is another surgical hub, a control arrangement is established 3040 therebetween.

Figure 54:
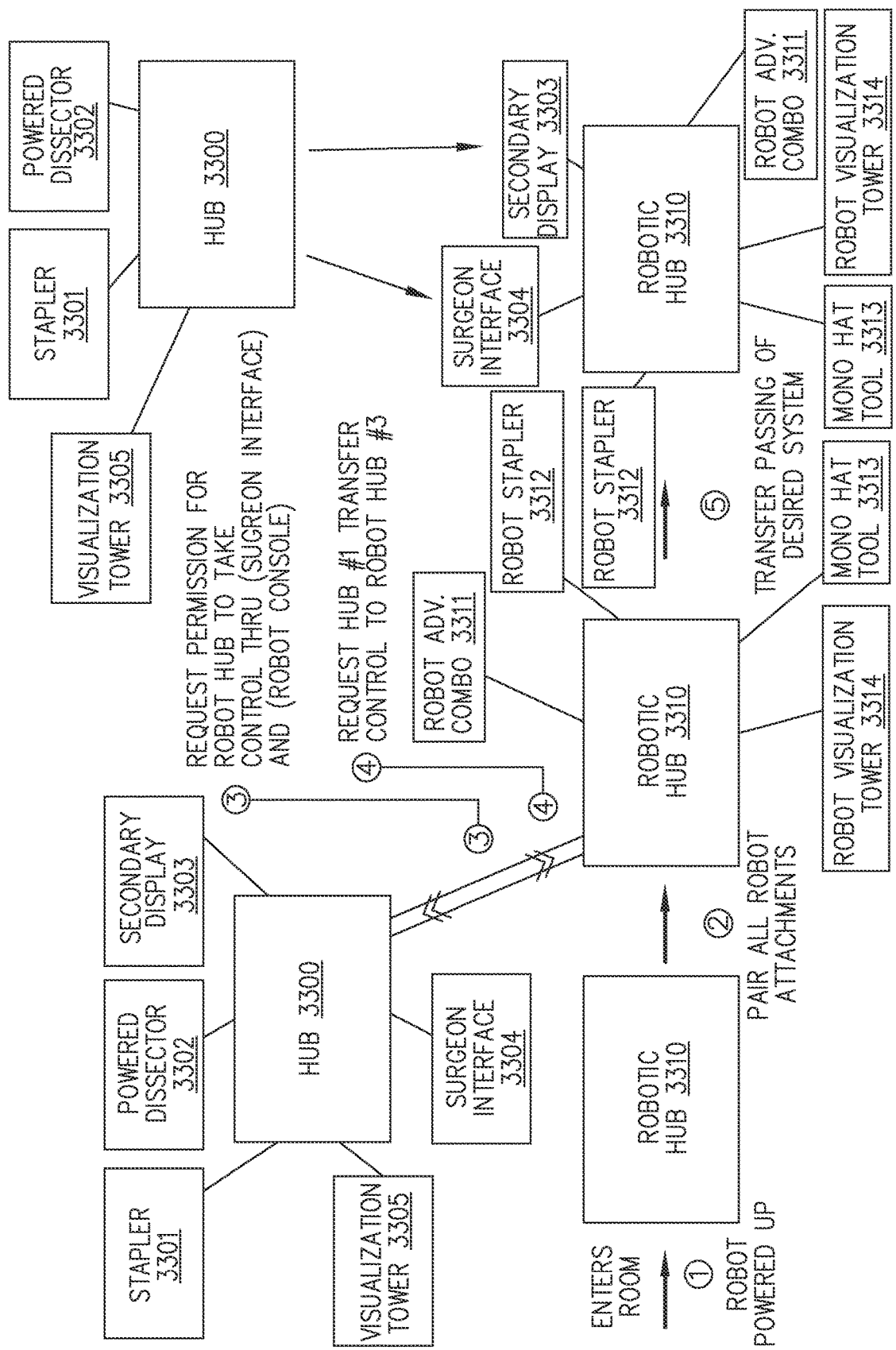
FIG. 54 illustrates an interaction between two surgical hubs in an operating room, in accordance with at least one aspect of the present disclosure.

Referring to FIG. 54, a robotic surgical hub 3300 enters an operating room already occupied by a surgical hub 3300. The robotic surgical hub 3310 and the surgical hub 3300 are similar in many respects to other surgical hubs described in greater detail elsewhere herein, such as, for example, the surgical hubs 106. For example, the robotic surgical hub 3310 includes non-contact sensors configured to measure the bounds of the operating room, as described in greater detail elsewhere herein in connection with FIGS. 33, 34.

As the robotic surgical hub 3310 is powered up, it determines the bounds of the operating room and begins to pair with other components of the surgical system 102 that are located within the bounds of the operating room. The robotic surgical hub 3310 pairs with a robotic advanced energy tool 3311, a robotic stapler 3312, a monopolar energy tool 3313, and a robotic visualization tower 3314, which are all located within the bounds of the operating room. The surgical hub 3300 is already paired with a handheld stapler 3301, a handheld powered dissector 3302, a secondary display 3303, a surgeon interface 3304, and a visualization tower 3305. Since the handheld stapler 3301, the handheld powered dissector 3302, the secondary display 3303, the surgeon interface 3304, and the visualization tower 3305 are already paired with the surgical hub 3300, such devices cannot pair with another surgical hub without permission from the surgical hub 3300.

Further to the above, the robotic surgical hub 3310 detects and/or is detected by the surgical hub 3300. A communication link is established between the communication modules of the surgical hubs 3300, 3310. The surgical hubs 3300, 3310 then determine the nature of their interaction by determining a control arrangement therebetween. In one aspect, the control arrangement can be a master-slave arrangement. In another aspect, the control arrangement can be a peer-to-peer arrangement.

In the example of FIG. 54, a master-slave arrangement is established. The surgical hubs 3300, 3310 request permission from a surgical operator for the robotic surgical hub 3310 to take control of the operating room from the surgical hub 3300. The permission can be requested through a surgeon interface or console 3304. Once permission is granted, the robotic surgical hub 3310 requests the surgical hub 3300 to transfer control to the robotic surgical hub 3310.

Alternatively, the surgical hubs 3300, 3310 can negotiate the nature of their interaction without external input based on previously gathered data. For example, the surgical hubs 3300, 3310 may collectively determine that the next surgical task requires use of a robotic system. Such determination may cause the surgical hub 3300 to autonomously surrender control of the operating room to the robotic surgical hub 3310. Upon completion of the surgical task, the robotic surgical hub 3310 may then autonomously return the control of the operating room to surgical hub 3300.

The outcome of the interaction between the surgical hubs 3300, 3310 is illustrated on the right of FIG. 54. The surgical hub 3300 has transferred control to the robotic surgical hub 3310, which has also taken control of the surgeon interface 3304 and the secondary display 3303 from the surgical hub 3300. The robotic surgical hub 3310 assigns new identification numbers to the newly transferred devices. The surgical hub 3300 retains control the handheld stapler 3301, the handheld powered dissector 3302, and visualization tower 3305. In addition, the surgical hub 3300 performs a supporting role, wherein the processing and storage capabilities of the surgical hub 3300 are now available to the robotic surgical hub 3310.

Figure 55:
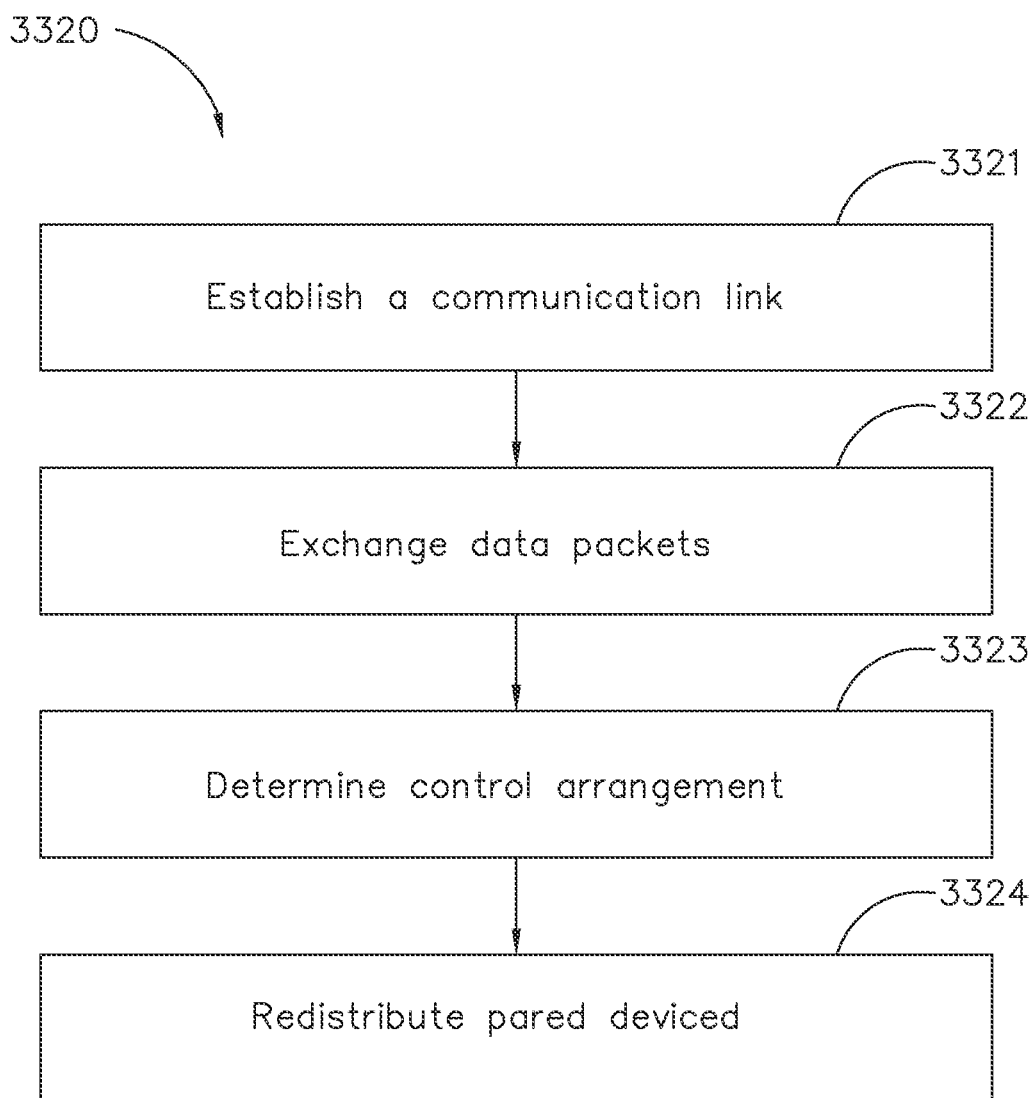
FIG. 55 is a logic flow diagram of a process depicting a control program or a logic configuration for coordinating a control arrangement between surgical hubs, in accordance with at least one aspect of the present disclosure.

FIG. 55 is a logic flow diagram of a process depicting a control program or a logic configuration for coordinating a control arrangement between surgical hubs. In various aspects, two independent surgical hubs will interact with one another in a predetermined manner to assess the nature of their relationship. In one example, after establishing 3321 a communication link, the surgical hubs exchange 3322 data packets. A data packet may include type, identification number, and/or status of a surgical hub. A data packet may further include a record of devices under control of the surgical hub and/or any limited communication connections, such as data ports for other secondary operating room devices.

The control arrangement between the surgical hubs is then determined 3323 based on input from a surgical operator or autonomously between the surgical hubs. The surgical hubs may store instructions as to how to determine a control arrangement therebetween. The control arrangement between two surgical hubs may depend on the type of surgical procedure being performed. The control arrangement between two surgical hubs may depend on their types, identification information, and/or status. The control arrangement between two surgical hubs may depend on the devices paired with the surgical hubs. The surgical hubs then redistribute 3324 the devices of the surgical system 102 therebetween based upon the determined control arrangement.

In the master-slave arrangement, the record communication can be unidirectional from the slave hub to the master hub. The master hub may also require the slave hub to hand-off some of its wireless devices to consolidate communication pathways. In one aspect, the slave hub can be relegated to a relay configuration with the master hub originating all commands and recording all data. The slave hub can remain linked to the master hub for a distributed sub-processing of the master hub commands, records, and/or controls. Such interaction expands the processing capacity of the dual linked hubs beyond the capabilities of the master hub by itself.

In a peer-to-peer arrangement, each surgical hub may retain control of its devices. In one aspect, the surgical hubs may cooperate in controlling a surgical instrument. In one aspect, an operator of the surgical instrument may designate the surgical hub that will control the surgical instrument at the time of its use.

Referring generally to FIGS. 56-61, the interaction between surgical hubs can be extended beyond the bounds of the operating room. In various aspects, surgical hubs in separate operating rooms may interact with one another within predefined limits. Depending on their relative proximity, surgical hubs in separate operating rooms may interact through any suitable wired or wireless data communication network such as Bluetooth and WiFi. As used here, a "data communication network" represents any number of physical, virtual, or logical components, including hardware, software, firmware, and/or processing logic configured to support data communication between an originating component and a destination component, where data communication is carried out in accordance with one or more designated communication protocols over one or more designated communication media.

In various aspects, a first surgical operator in a first operating room may wish to consult a second surgical operator in a second operating room, such as in case of an emergency. A temporary communication link may be established between the surgical hubs of the first and second operating room to facilitate the consult while the first and second surgical operators remain in their respective operating rooms.

The surgical operator being consulted can be presented with a consult request through the surgical hub in his/her operating room. If the surgical operator accepts, he/she will have access to all the data compiled by the surgical hub requesting the consult. The surgical operator may access all previously stored data, including a full history of the procedure. In addition, a livestream of the surgical site at the requesting operating room can be transmitted through the surgical hubs to a display at the receiving operating room.

When a consult request begins, the receiving surgical hub begins to record all received information in a temporarily storage location, which can be a dedicated portion of the storage array of the surgical hub. At the end of the consult, the temporary storage location is purged from all the information. In one aspect, during a consult, the surgical hub records all accessible data, including blood pressure, ventilation data, oxygen stats, generator settings and uses, and all patient electronic data. The recorded data will likely be more than the data stored by the surgical hub during normal operation, which is helpful in providing the surgical operator being consulted with as much information as possible for the consult.

Referring to FIG. 56, a non-limiting example of an interaction between surgical hubs in different operating rooms is depicted. FIG. 56 depicts an operating room OR 1 that includes a surgical system 3400 supporting a thoracic segmentectomy and a second operating room OR 3 that includes a surgical system 3410 supporting a colorectal procedure. The surgical system 3400 includes surgical hub 3401, surgical hub 3402, and robotic surgical hub 3403. The surgical system 3400 further includes a personal interface 3406, a primary display 3408, and secondary displays 3404, 3405. The surgical system 3410 includes a surgical hub 3411 and a secondary display 3412. For clarity, several components of the surgical systems 3400, 3410 are removed.

In the example of FIG. 56, the surgical operator of OR 3 is requesting a consult from the surgical operator of OR 1. A surgical hub 3411 of the OR 3 transmits the consult request to one of the surgical hubs of the OR 1, such as the surgical hub 3401. In OR 1, the surgical hub 3401 presents the request at a personal interface 3406 held by the surgical operator. The consult is regarding selecting an optimal location of a colon transection. The surgical operator of OR 1, through a personal interface 3406, recommends an optimal location for the transection site that avoids a highly vascular section of the colon. The recommendation is transmitted in real time through the surgical hubs 3401, 3411. Accordingly, the surgical operator is able to respond to the consult request in real time without having to leave the sterile field of his own operating room. The surgical operator requesting the consult also did not have to leave the sterile field of OR 3.

If the surgical hub 3401 is not in communication with the personal interface 3406, it may relay the message to another surgical hub such as, for example, the surgical hub 3402 or the robotic surgical hub 3403. Alternatively, the surgical hub 3401 may request control of the personal interface 3406 from another surgical hub.

Figure 57:
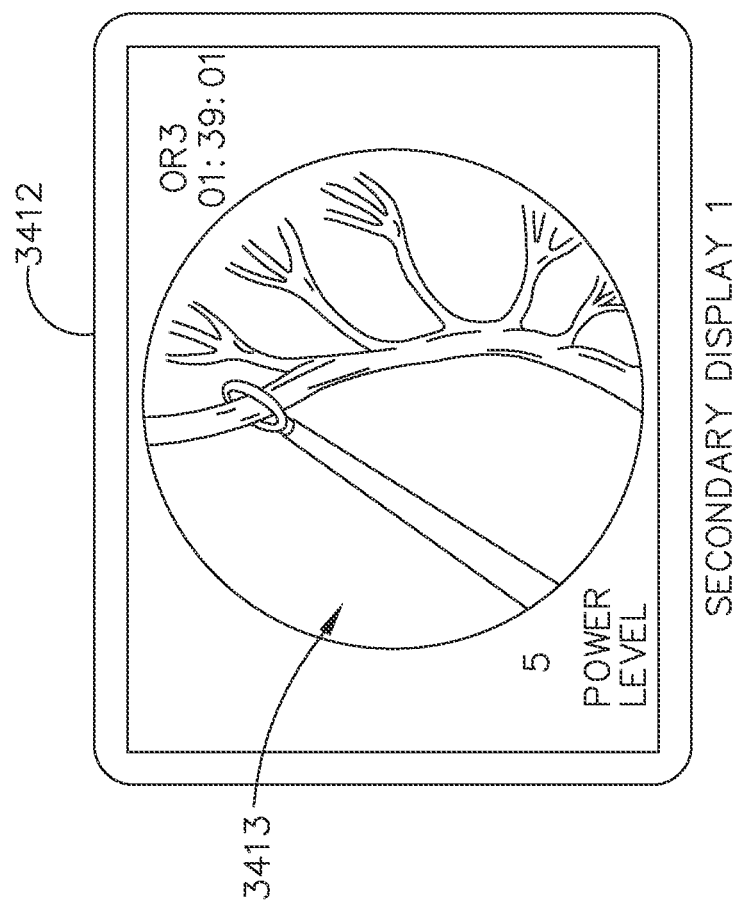
FIG. 57 illustrates a secondary display in an operating room ("OR3") showing a surgical site in a colorectal procedure, in accordance with at least one aspect of the present disclosure.
Figure 58:
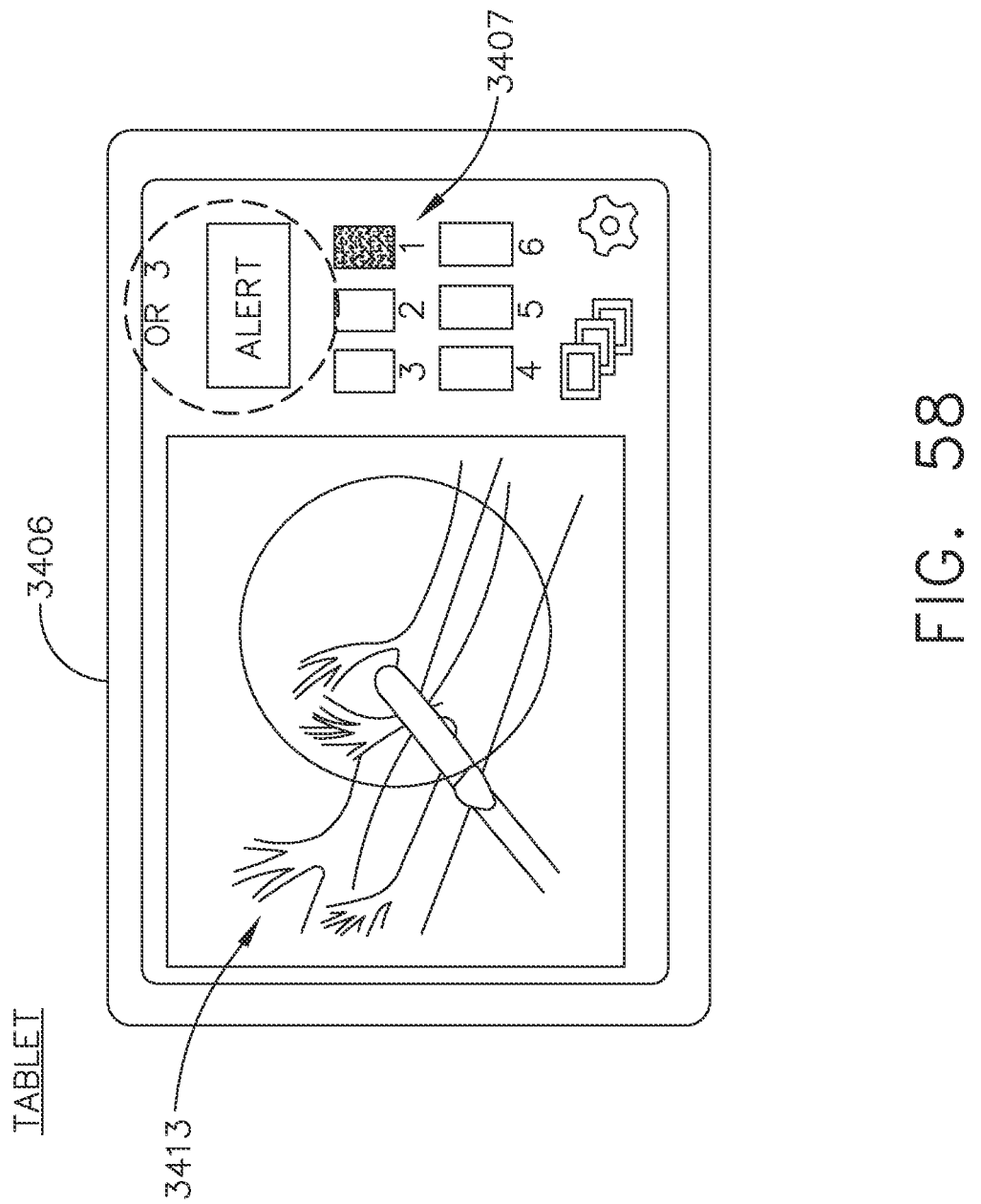
FIG. 58 illustrates a personal interface or tablet in OR1 displaying the surgical site of OR3, in accordance with at least one aspect of the present disclosure.

In any event, if the surgical operator of OR 1 decides to accept the consult request, a livestream, or frames, of a surgical site 3413 of the colorectal procedure of OR 3 is transmitted to OR 1 through a connection established between the surgical hubs 3401, 3411, for example. FIG. 57 illustrates a livestream of the surgical site 3413 displayed on a secondary display of OR 3. The surgical hubs 3401, 3411 cooperate to transmit the livestream of the surgical site of OR 3 to the personal interface 3406 of the OR 1, as illustrated in FIG. 58.

Figure 59:
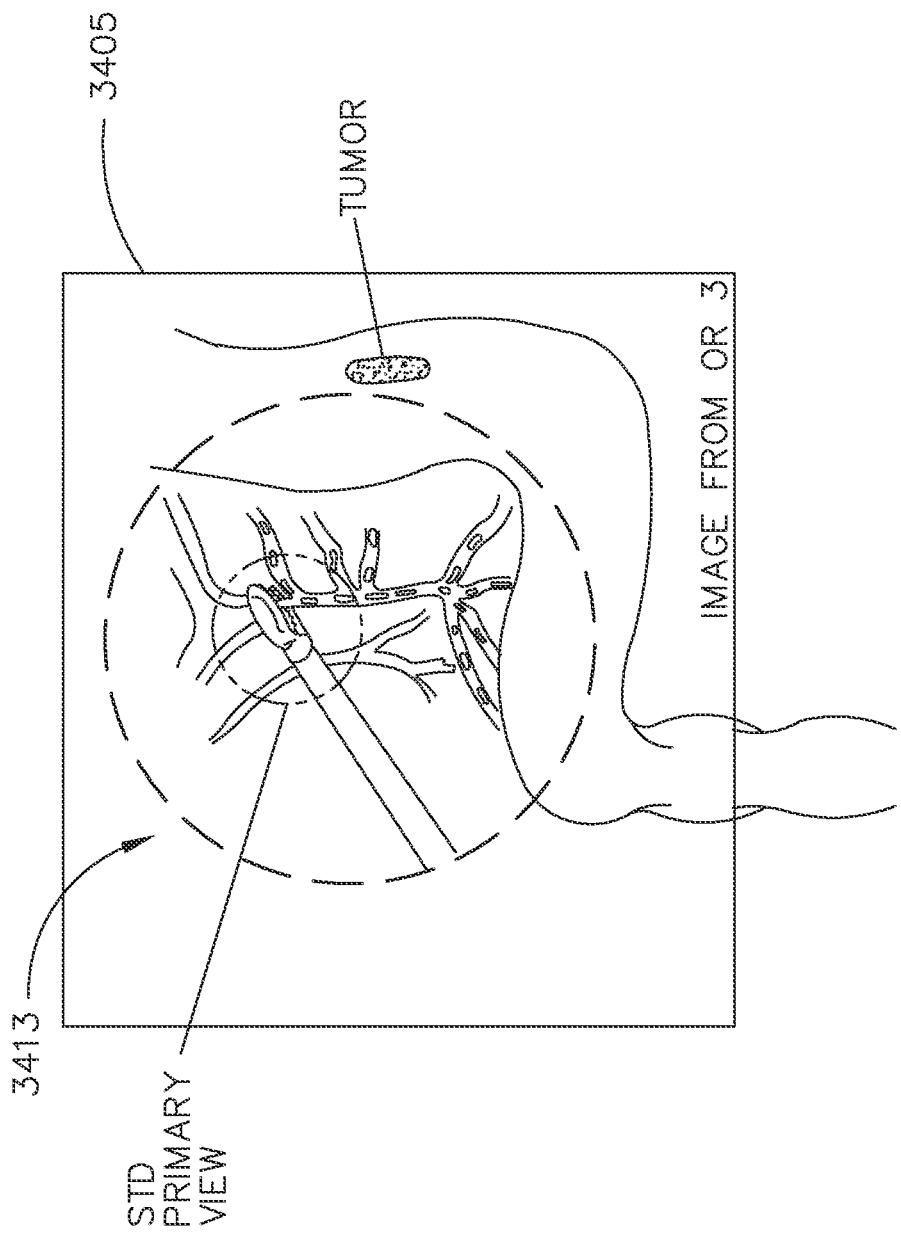
FIG. 59 illustrates an expanded view of the surgical site of OR3 displayed on a primary display of OR1, in accordance with at least one aspect of the present disclosure.
Figure 60:
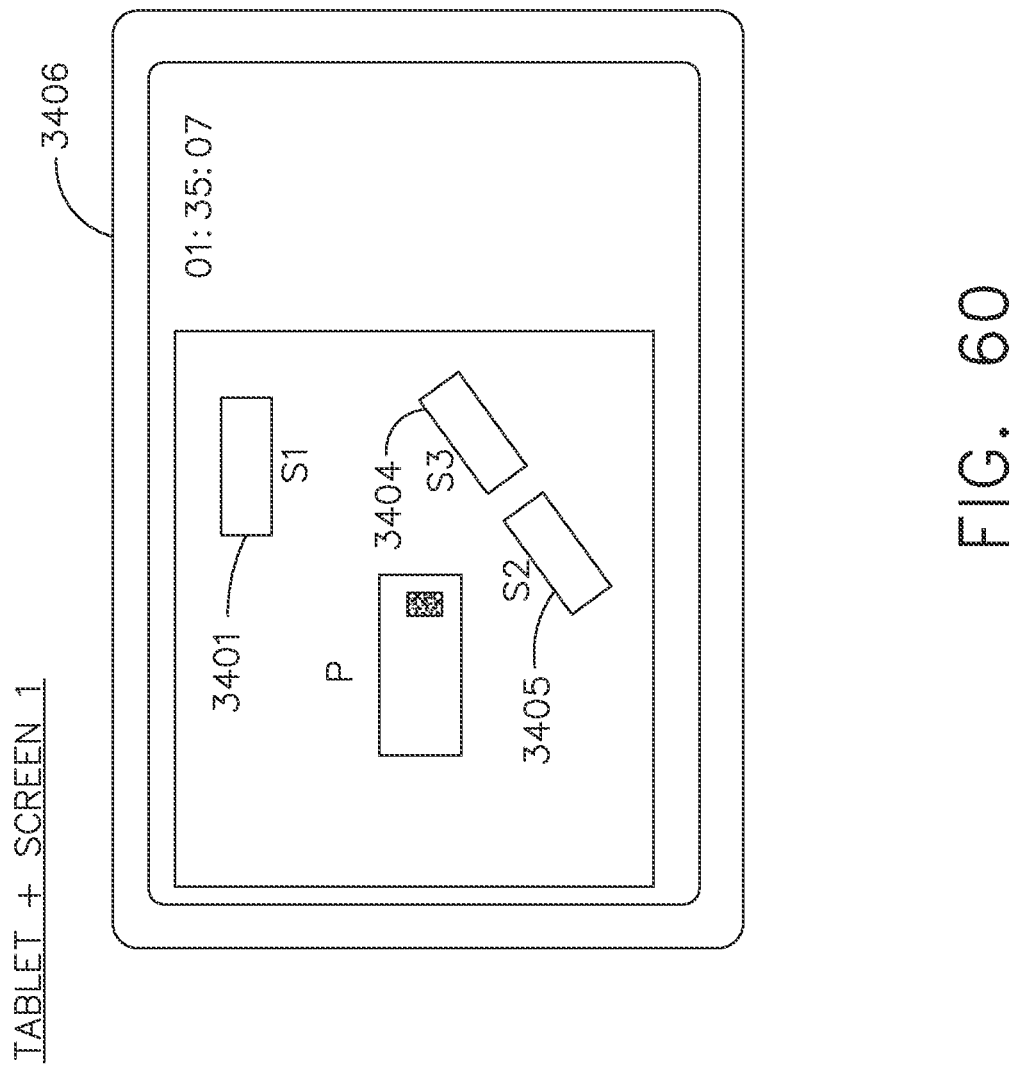
FIG. 60 illustrates a personal interface or tablet displaying a layout of OR1 that shows available displays, in accordance with at least one aspect of the present disclosure.
Figure 61:
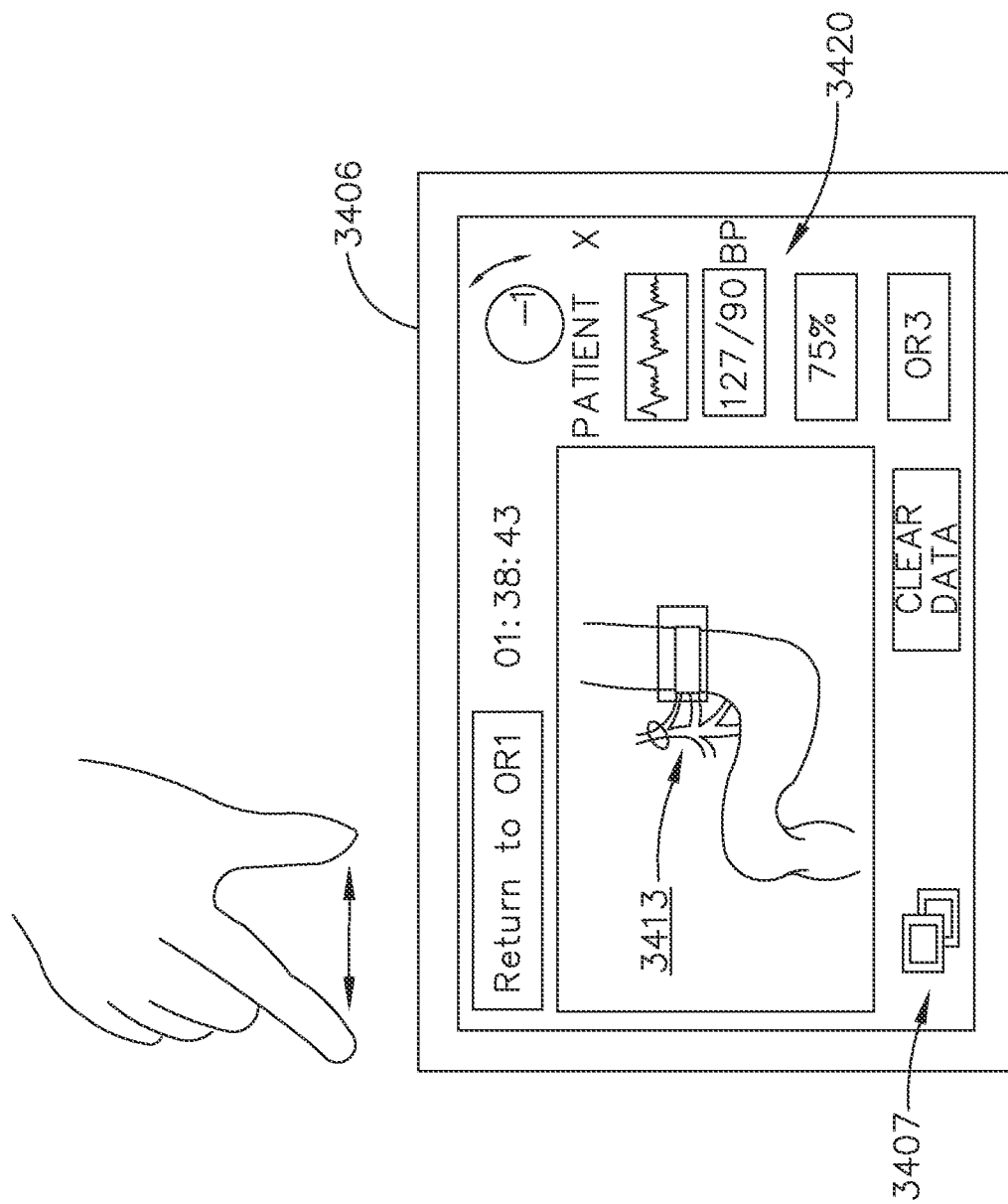
FIG. 61 illustrates a recommendation of a transection location of a surgical site of OR3 made by a surgical operator in OR1 via a personal interface or tablet in OR1, in accordance with at least one aspect of the present disclosure.

Referring to FIGS. 59-61, the surgical operator may expand the laparoscopic livestream from OR 3 onto the primary display 3405 in OR 1, for example, through the controls of the personal interface 3406. The personal interface 3406 allows the surgical operator to select a destination for the livestream by presenting the surgical operator with icons that represent the displays that are available in OR 1, as illustrated in FIG. 60. Other navigation controls 3407 are available to the surgical operator through the personal interface 3406, as illustrated in FIG. 61. For example, the personal interface 3406 includes navigation controls for adjusting the livestream of the surgical site of OR 3 in OR 1 by the surgical operator moving his or her fingers on the livestream displayed on the personal interface 3406. To visualize the high vasculature regions, the consulted surgical operator may change the view of the livestream from OR 3 through the personal interface 3406 to an advanced imaging screen. The surgical operator may then manipulate the image in multiple planes to see the vascularization using a wide-angle multi-spectral view, for example.

As illustrated in FIG. 61, the surgical operator also has access to an array of relevant information 3420, such as, for example, heart rate, blood pressure, ventilation data, oxygen stats, generator settings and uses, and all patient electronic data of the patient in OR 3.

Data Management and Collection

In one aspect the surgical hub provides data storage capabilities. The data storage includes creation and use of self-describing data including identification features, management of redundant data sets, and storage of the data in a manner of paired data sets which can be grouped by surgery but not necessarily keyed to actual surgical dates and surgeons to maintain data anonymity. The following description incorporates by reference all of the "hub" and "cloud" analytics system hardware and software processing techniques to implement the specific data management and collection techniques described hereinbelow, as incorporated by reference herein. FIGS. 62-80 will be described in the context of the interactive surgical system 100 environment including a surgical hub 106, 206 described in connection FIGS. 1-11 and intelligent instruments and generators described in connection with FIGS. 12-21.

Electronic Medical Record (EMR) Interaction

Figure 62:
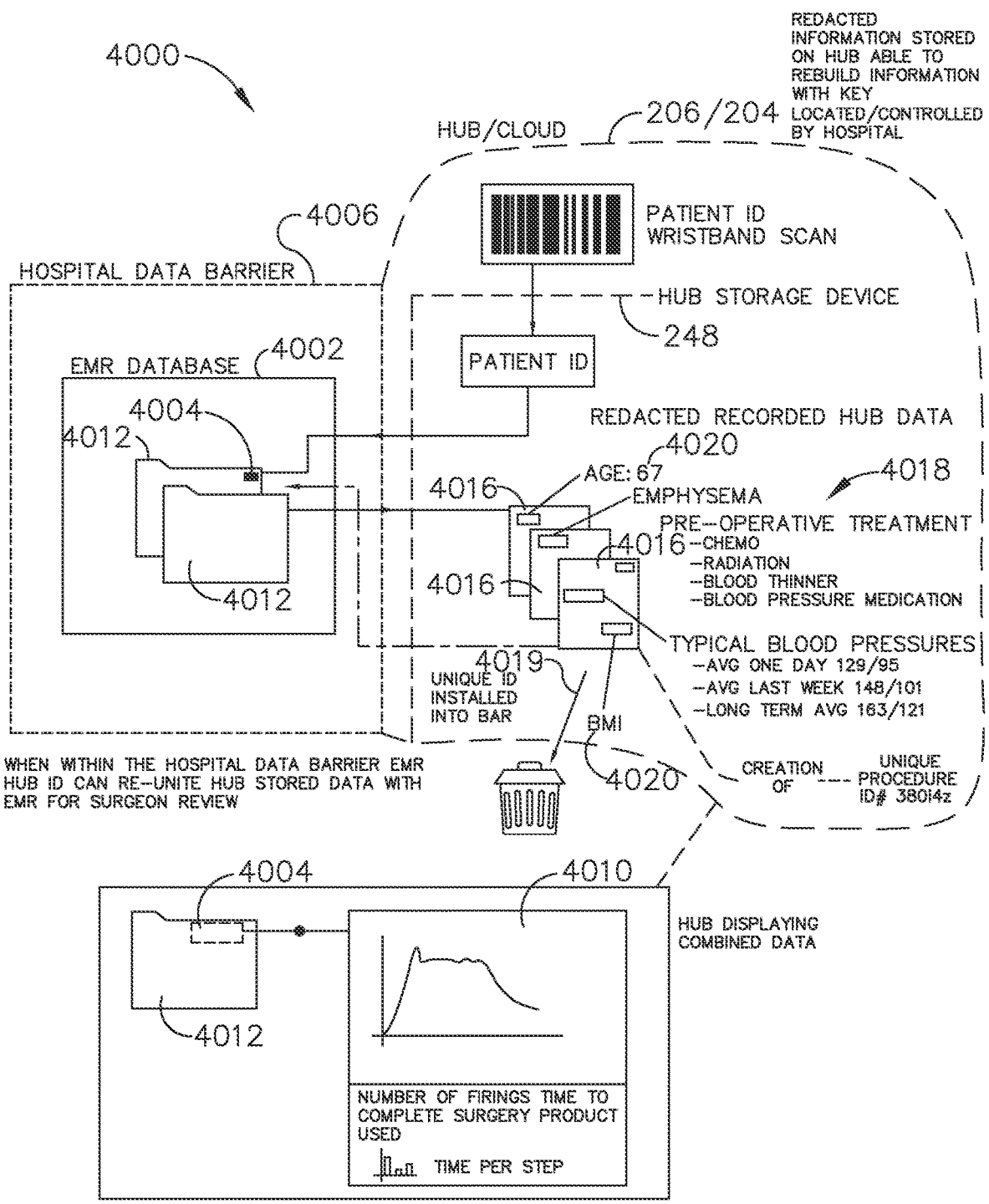
FIG. 62 is a diagram illustrating a technique for interacting with a patient Electronic Medical Record (EMR) database, in accordance with at least one aspect of the present disclosure.

FIG. 62 is a diagram 4000 illustrating a technique for interacting with a patient Electronic Medical Record (EMR) database 4002, according to one aspect of the present disclosure. In one aspect, the present disclosure provides a method of embedding a key 4004 within the EMR database 4002 located within the hospital or medical facility. A data barrier 4006 is provided to preserve patient data privacy and allows the reintegration of stripped and isolated data pairs, as described hereinbelow, from the surgical hub 106, 206 or the cloud 104, 204, to be reassembled. A schematic diagram of the surgical hub 206 is described generally in FIGS. 1-11 and in particular in FIGS. 9-10. Therefore, in the description of FIG. 62, the reader is guided to FIG. 1-11 and in particular FIGS. 9-10 for any implementation details of the surgical hub 206 that may be omitted here for conciseness and clarity of disclosure. Returning to FIG. 62, the method allows the users full access to all the data collected during a surgical procedure and patient information stored in the form of electronic medical records 4012. The reassembled data can be displayed on a monitor 4010 coupled to the surgical hub 206 or secondary monitors but is not permanently stored on any surgical hub storage device 248. The reassembled data is temporarily stored in a storage device 248 located either in the surgical hub 206 or the cloud 204 and is deleted at the end of its use and overwritten to insure it cannot be recovered. The key 4004 in the EMR database 4002 is used to reintegrate anonymized hub data back into full integrated patient electronic medical records 4012 data.

As shown in FIG. 62, the EMR database 4002 is located within the hospital data barrier 4006. The EMR database 4002 may be configured for storing, retrieving, and managing associative arrays, or other data structures known today as a dictionary or hash. Dictionaries contain a collection of objects, or records, which in turn have many different fields within them, each containing data. The patient electronic medical records 4012 may be stored and retrieved using a key 4004 that uniquely identifies the patient electronic medical record 4012, and is used to quickly find the data within the EMR database 4002. The key-value EMR database 4002 system treats the data as a single opaque collection which may have different fields for every record.

Information from the EMR database 4002 may be transmitted to the surgical hub 206 and the patient electronic medical records 4012 data is redacted and stripped before it is sent to an analytics system based either on the hub 206 or the cloud 204. An anonymous data file 4016 is created by redacting personal patient data and stripping relevant patient data 4018 from the patient electronic medical record 4012. As used herein, the redaction process includes deleting or removing personal patient information from the patient electronic medical record 4012 to create a redacted record that includes only anonymous patient data. A redacted record is a record from which sensitive patient information has been expunged. Un-redacted data may be deleted 4019. The relevant patient data 4018 may be referred to herein as stripped/extracted data 4018. The relevant patient data 4018 is used by the surgical hub 206 or cloud 204 processing engines for analytic purposes and may be stored on the storage device 248 of the surgical hub 206 or may be stored on the cloud 204 based analytics system storage device 205. The surgical hub anonymous data file 4016 can be rebuilt using a key 4004 stored in the EMR database 4002 to reintegrate the surgical hub anonymous data file 4016 back into a fully integrated patient electronic medical record 4012. The relevant patient data 4018 that is used in analytic processes may include information such as the patient's diagnoses of emphysema, pre-operative treatment (e.g., chemotherapy, radiation, blood thinner, blood pressure medication, etc.), typical blood pressures, or any data that alone cannot be used to ascertain the identity of the patient. Data 4020 to be redacted includes personal information removed from the patient electronic medical record 4012, may include age, employer, body mass index (BMI), or any data that can be used to ascertain the identify of the patient. The surgical hub 206 creates a unique anonymous procedure ID number (e.g., 380i4z), for example, as described in FIG. 63. Within the EMR database 4002 located in the hospital data barrier 4006, the surgical hub 206 can reunite the data in the anonymous data file 4016 stored on the surgical hub 206 storage device 248 with the data in the patient electronic medical record 4012 stored on the EMR database 4002 for surgeon review. The surgical hub 206 displays the combined patient electronic medical record 4012 on a display or monitor 4010 coupled to the surgical hub 206. Ultimately, un-redacted data is deleted 4019 from the surgical hub 206 storage 248.

Creation of a Hospital Data Barrier, Inside which the Data from Hubs can be Compared Using Non-Anonymized Data and Outside of which the Data has to be Stripped In one aspect, the present disclosure provides a surgical hub 206 as described in FIGS. 9 and 10, for example, where the surgical hub 206 comprises a processor 244; and a memory 249 coupled to the processor 244. The memory 249 stores instructions executable by the processor 244 to interrogate a surgical instrument 235, retrieve a first data set from the surgical instrument 235, interrogate a medical imaging device 238, retrieve a second data set from the medical imaging device 238, associate the first and second data sets by a key, and transmit the associated first and second data sets to a remote network, e.g., the cloud 204, outside of the surgical hub 206. The surgical instrument 235 is a first source of patient data and the first data set is associated with a surgical procedure. The medical imaging device 238 is a second source of patient data and the second data set is associated with an outcome of the surgical procedure. The first and second data records are uniquely identified by the key.

In another aspect, the surgical hub 206 provides a memory 249 storing instructions executable by the processor 244 to retrieve the first data set using the key, anonymize the first data set, retrieve the second data set using the key, anonymize the second data set, pair the anonymized first and second data sets, and determine success rate of surgical procedures grouped by the surgical procedure based on the anonymized paired first and second data sets.

In another aspect, the surgical hub 206 provides a memory 249 storing instructions executable by the processor 244 to retrieve the anonymized first data set, retrieve the anonymized second data set, and reintegrate the anonymized first and second data sets using the key.

In another aspect, the first and second data sets define first and second data payloads in respective first and second data packets.

In various aspects, the present disclosure provides a control circuit to associate the first and second data sets by a key as described above. In various aspects, the present disclosure provides a non-transitory computer readable medium storing computer readable instructions which, when executed, causes a machine to associate the first and second data sets by a key as described above.

During a surgical procedure it would be desirable to monitor data associated with the surgical procedure to enable configuration and operation of instruments used during the procedure to improve surgical outcomes. The technical challenge is to retrieve the data in a manner that maintains the anonymity of the patient to maintain privacy of the data associated with the patient. The data may be used for conglomeration with other data without individualizing the data.

One solution provides a surgical hub 206 to interrogate an electronic medical records database 4002 for patient electronic medical records 4012 data, strip out desirable or relevant patient data 4018 from the patient electronic medical record 4012, and redact any personal information that could be used to identify the patient. The redaction technique removes any information that could be used to correlate the stripped relevant patient data 4018 to a specific patient, surgery, or time. The surgical hub 206 and the instruments 235 coupled to the surgical hub 206 can then be configured and operated based on the stripped relevant patient data 4018.

As disclosed in connection with FIG. 62, extracting (or stripping) relevant patient data 4018 from a patient electronic medical record 4012 while redacting any information that can be used to correlate the patient with the surgery or a scheduled time of the surgery enables the relevant patient data 4018 to be anonymized. The anonymous data file 4016 can then be sent to the cloud 204 for aggregation, processing, and manipulation. The anonymous data file 4016 can be used to configure the surgical instrument 235, or any of the modules shown in FIGS. 9 and 10 or the surgical hub 206 during the surgery based on the extracted anonymous data file 4016.

In one aspect, a hospital data barrier 4006 is created such that inside the data barrier 4006 data from various surgical hubs 206 can be compared using non-anonymized unredacted data and outside the data barrier 4006 data from various surgical hubs 206 are stripped to maintain anonymity and protect the privacy of the patient and the surgeon. This aspect is discussed further in connection with FIG. 66.

In one aspect, the data from a surgical hub 206 can be exchanged between surgical hubs 206 (e.g., hub-to-hub, switch-to-switch, or router-to-router) to provide in-hospital analysis and display of the data. FIG. 1 shows an example of multiple hubs 106 in communication which each other and with the cloud 104. This aspect also is discussed further in connection with FIG. 66.

In another aspect, an artificial time measure is substituted for a real time clock for all information stored internally within an instrument 235, a robot located in a robot hub 222, a surgical hub 206, and/or hospital computer equipment. The anonymized data, which may include anonymized patient and surgeon data, is transmitted to the server 213 in the cloud 204 and it is stored in the cloud storage device 205 coupled to the server 213. The substitution of an artificial real time clock enables anonymizing the patient data and surgeon data while maintaining data continuity. In one aspect, the instrument 235, robot hub 222, surgical hub 206, and/or the cloud 204 are configured to obscure patient identification (ID) while maintaining data continuity. This aspect is discussed further in connection with FIG. 63.

Within the surgical hub 206, a local decipher key 4004 allows information retrieved from the surgical hub 206 itself to reinstate the real-time information from the anonymized data set located in the anonymous data file 4016. The data stored on the hub 206 or the cloud 204, however, cannot be reinstated to real-time information from the anonymized data set in the anonymous data file 4016. The key 4004 is held locally in the surgical hub 206 computer/storage device 248 in an encrypted format. The surgical hub 206 network processor ID is part of the decryption mechanism such that if the key 4004 and data is removed, the anonymized data set in the anonymous data file 4016 cannot be restored without being on the original surgical hub 206 computer/storage device 248.

Figure 63:
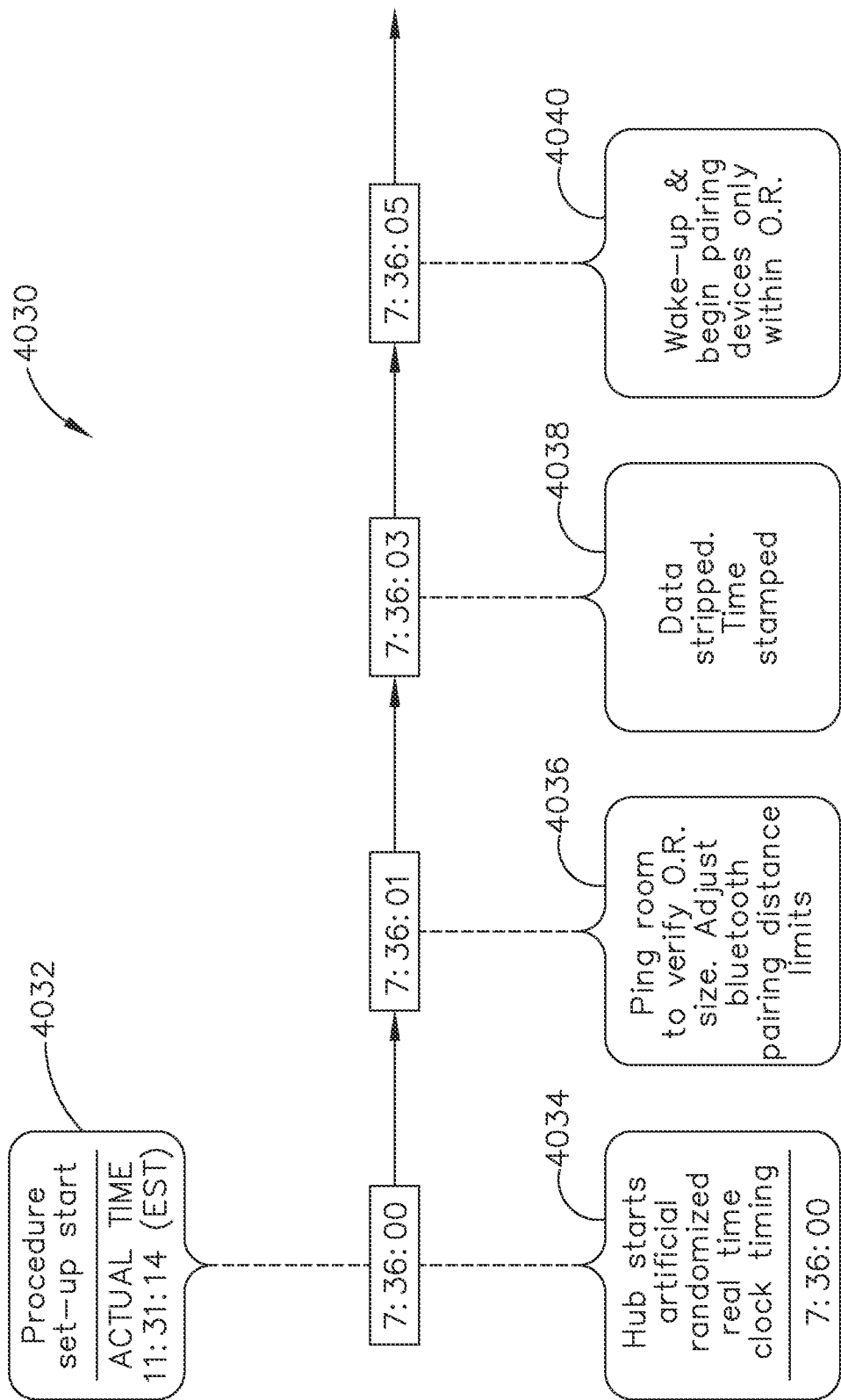
FIG. 63 illustrates a process of anonymizing a surgical procedure by substituting an artificial time measure for a real time clock for all information stored internally within the instrument, robot, surgical hub, and/or hospital computer equipment, in accordance with at least one aspect of the present disclosure.

Substituting Artificial Time Measure for Real Time Clock for all Internally Stored Information and Sent to the Cloud as a Means to Anonymizing the Patient and Surgeon Data FIG. 63 illustrates a process 4030 of anonymizing a surgical procedure by substituting an artificial time measure for a real time clock for all information stored internally within the instrument, robot, surgical hub, and/or hospital computer equipment, according to one aspect of the present disclosure. As shown in FIG. 63, the surgical procedure set-up start time 4032 was scheduled to begin at an actual time of 11:31:14 (EST) based on a real time clock. At the stated procedure set-up start time 4032, the surgical hub 206 starts 4034 an artificial randomized real time clock timing scheme at artificial real time at 07:36:00. The surgical hub 206 then ultrasonically pings 4036 the operating theater (e.g., sends out a burst of ultrasound and listens for the echo when it bounces off the perimeter walls of an operating theater (e.g., a fixed, mobile, temporary, or field the operating room) as described in connection with FIG. 64 to verify the size of the operating theater and to adjust short range wireless, e.g., Bluetooth, pairing distance limits at artificial real time 07:36:01. At artificial real time 07:36:03, the surgical hub 206 strips 4038 the relevant data and applies a time stamp to the stripped data. At artificial real time 07:36:05, the surgical hub 206 wakes up and begins pairing 4040 only devices located within the operating theater as verified using the ultrasonic pinging 4036 process.

Figure 64:
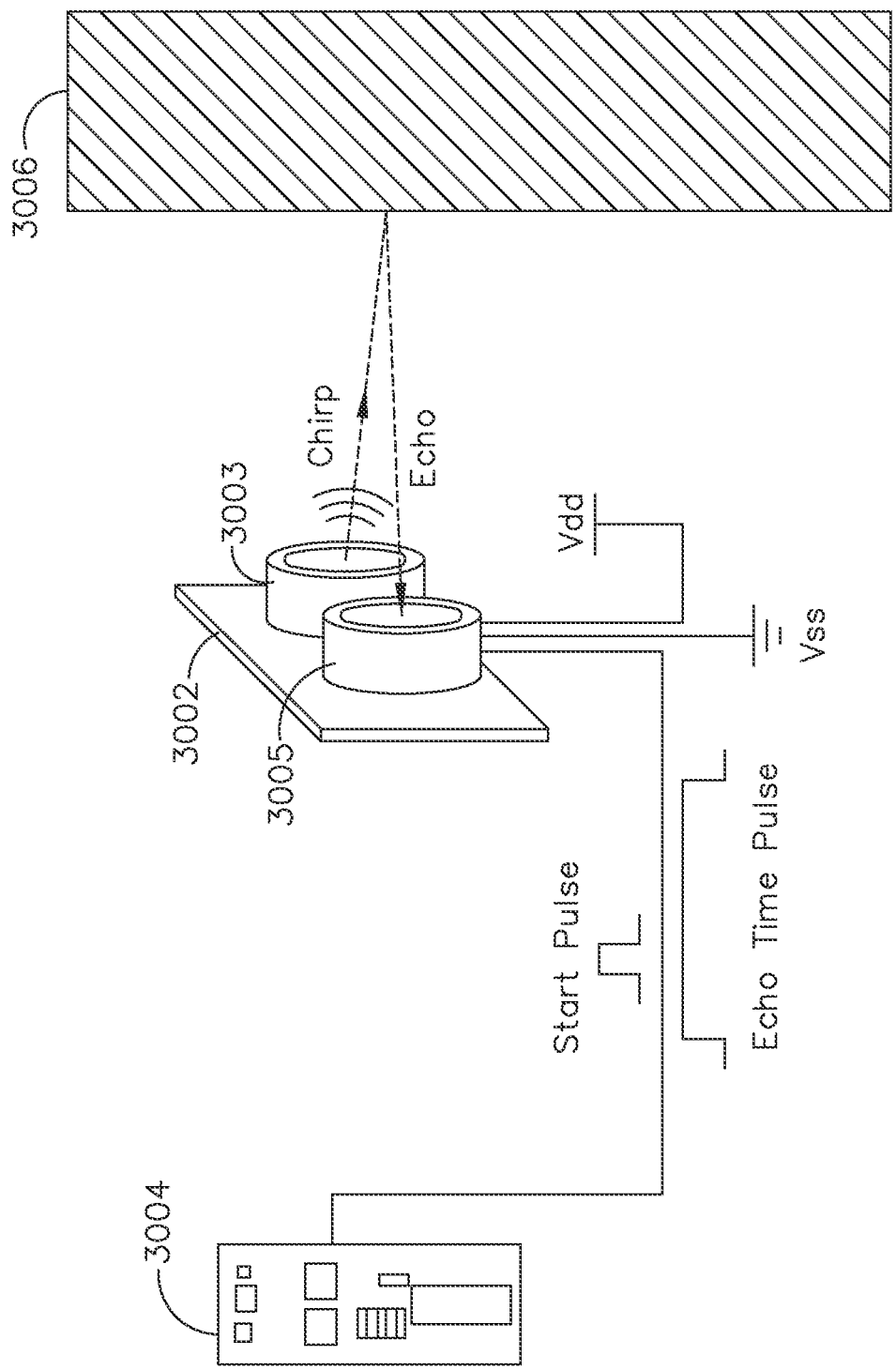
FIG. 64 illustrates ultrasonic pinging of an operating room wall to determine a distance between a surgical hub and the operating room wall, in accordance with at least one aspect of the present disclosure.

FIG. 64 illustrates ultrasonic pinging of an operating room wall to determine a distance between a surgical hub and the operating room wall, in accordance with at least one aspect of the present disclosure. With reference also to FIG. 2, the spatial awareness of the surgical hub 206 and its ability to map an operating room for potential components of the surgical system allows the surgical hub 206 to make autonomous decisions about whether to include or exclude such potential components as part of the surgical system, which relieves the surgical staff from dealing with such tasks. Furthermore, the surgical hub 206 is configured to make inferences about, for example, the type of surgical procedure to be performed in the operating room based on information gathered prior to, during, and/or after the performance of the surgical procedure. Examples of gathered information include the types of devices that are brought into the operating room, time of introduction of such devices into the operating room, and/or the devices sequence of activation.

In one aspect, the surgical hub 206 employs the operating-room mapping module, such as, for example, the non-contact sensor module 242 to determine the bounds of the surgical theater (e.g., a fixed, mobile, or temporary operating room or space) using either ultrasonic or laser non-contact measurement devices.

Referring now to FIG. 64, ultrasound based non-contact sensors 3002 can be employed to scan the operating theater by transmitting a burst of ultrasound and receiving the echo when it bounces off a perimeter wall 3006 of an operating theater to determine the size of the operating theater and to adjust short range wireless, e.g., Bluetooth, pairing distance limits. In one example, the non-contact sensors 3002 can be Ping ultrasonic distance sensors, as illustrated in FIG. 64.

FIG. 64 shows how an ultrasonic sensor 3002 sends a brief chirp with its ultrasonic speaker 3003 and makes it possible for a micro-controller 3004 of the operating-room mapping module to measure how long the echo takes to return to the ultrasonic sensor's ultrasonic microphone 3005. The micro-controller 3004 has to send the ultrasonic sensor 3002 a pulse to begin the measurement. The ultrasonic sensor 3002 then waits long enough for the micro-controller program to start a pulse input command. Then, at about the same time the ultrasonic sensor 3002 chirps a 40 kHz tone, it sends a high signal to the micro-controller 3004. When the ultrasonic sensor 3002 detects the echo with its ultrasonic microphone 3005, it changes that high signal back to low. The micro-controller's pulse input command measures the time between the high and low changes, and stores it measurement in a variable. This value can be used along with the speed of sound in air to calculate the distance between the surgical hub 106 and the operating-room wall 3006.

In one example, a surgical hub 206 can be equipped with four ultrasonic sensors 3002, wherein each of the four ultrasonic sensors is configured to assess the distance between the surgical hub 206 and a wall of the operating room 3000. A surgical hub 206 can be equipped with more or less than four ultrasonic sensors 3002 to determine the bounds of an operating room.

Other distance sensors can be employed by the operating-room mapping module to determine the bounds of an operating room. In one example, the operating-room mapping module can be equipped with one or more photoelectric sensors that can be employed to assess the bounds of an operating room. In one example, suitable laser distance sensors can also be employed to assess the bounds of an operating room. Laser based non-contact sensors may scan the operating theater by transmitting laser light pulses, receiving laser light pulses that bounce off the perimeter walls of the operating theater, and comparing the phase of the transmitted pulse to the received pulse to determine the size of the operating theater and to adjust short range wireless, e.g., Bluetooth, pairing distance limits.

Stripping Out Data from Images and Connected Smart Instrument Data to Allow Conglomeration but not Individualization In one aspect, the present disclosure provides a data stripping method which interrogates the electronic patient records provided, extracts the relevant portions to configure and operate the surgical hub and instruments coupled to the surgical hub, while anonymizing the surgery, patient, and all identifying parameters to maintain patient privacy.

With reference now back to FIG. 63 and also to FIGS. 1-11 to show interaction with an interactive surgical system 100 environment including a surgical hub 106, 206, once the size of the operating theater has been verified and Bluetooth pairing is complete, based on artificial real time, the computer processor 244 of the surgical hub 206 begins stripping 4038 data received from the modules coupled to the surgical hub 206. In one example, the processor 244 begins stripping 4083 images received from the imaging module 238 and connected smart instruments 235, for example. Stripping 4038 the data allows conglomeration of the data but not individualization of the data. This enables stripping 4038 the data identifier, linking the data, and monitoring an event while maintaining patient privacy by anonymizing the data.

With reference to FIGS. 1-64, in one aspect, a data stripping 4038 method is provided. In accordance with the data stripping 4038 method, the surgical hub 206 processor 244 interrogates the patient records stored in the surgical hub database 238 and extracts the relevant portions of the patient records to configure and operate the surgical hub 206 and its instruments 235, robots, and other modular devices, e.g., modules. The data stripping 4038 method anonymizes the surgical procedure, patient, and all identifying parameters associated with the surgical procedure. Stripping 4038 the data on the fly ensures that at no time the data is correlated to a specific patient, surgical procedure, surgeon, time or other possible identifier that can be used to correlate the data.

The data may be stripped 4038 for compilation of the base information at a remote cloud 204 database storage device 205 coupled to the remote server 213. The data stored in the database storage device 248 can be used in advanced cloud based analytics, as described in U.S. Provisional Patent Application Ser. No. 62/611,340, filed Dec. 28, 2017, titled CLOUD-BASED MEDICAL ANALYTICS, which is incorporated herein by reference in its entirety. A copy of the information with data links intact also can be stored into the patient EMR database 4002 (FIG. 62). For example, the surgical hub 206 may import patient tissue irregularities or co-morbidities to add to an existing data set stored in the database 248. The data may be stripped 4038 before the surgery and/or may be stripped 4038 as the data is transmitted to the cloud 204 database storage device 205 coupled to the remote server 213.

Figure 65:
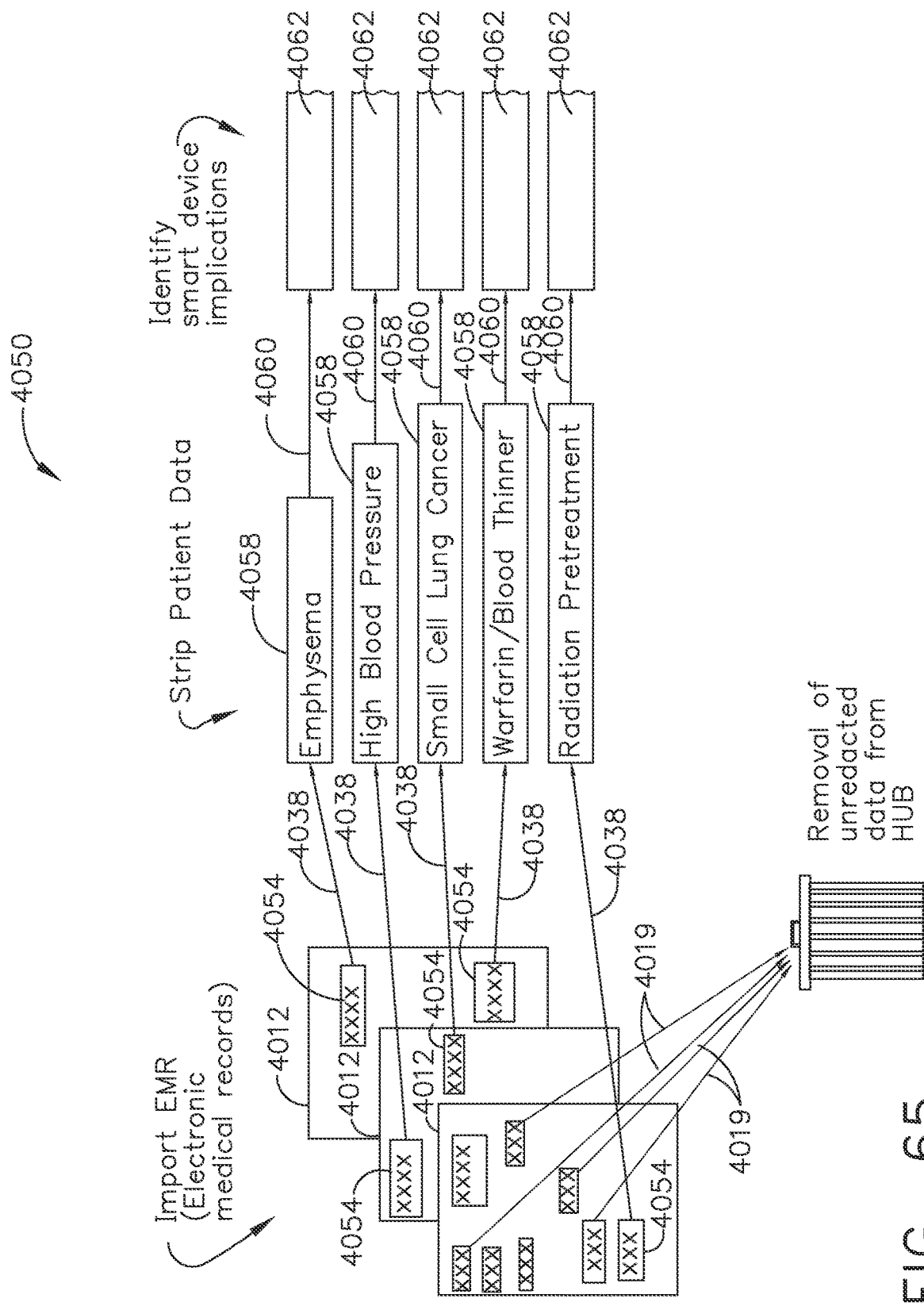
FIG. 65 illustrates a diagram depicting the process of importing patient data stored in an Electronic Medical Record (EMR) database, stripping the patient data, and identifying smart device implications, in accordance with at least one aspect of the present disclosure.

With continued reference to FIGS. 1-11 and 62-64, FIG. 65 is a diagram 4050 depicting the process of importing patient electronic medical records 4012 containing surgical procedure and relevant patient data 4018 stored in the EMR database 4002, stripping 4038 the relevant patient data 4018 from the imported medical records 4012, and identifying 4060 smart device implications 4062, or inferences, according to one aspect of the present disclosure. As shown in FIG. 65, the patient electronic medical records 4012, containing information stored in the patient EMR database 4002, are retrieved from the EMR database 4002, imported into the surgical hub 206, and stored in the surgical hub 206 storage device 248. Un-redacted data is removed or deleted 4019 from the patient electronic medical records 4012 before they are stored in the surgical hub 206 storage device 248 as an anonymous data file 4016 (FIG. 62). The relevant patient data 4018 is then stripped 4038 from the medical records 4012 to remove the desired relevant patient data 4018 and delete 4019 un-redacted data to maintain patient anonymity. In the illustrated example, the stripped data 4058 includes emphysema, high blood pressure, small lung cancer, warfarin/blood thinner, and/or radiation pretreatment. The stripped data 4058 is employed to identify 4060 smart device implications while maintaining patient anonymity as described hereinbelow.

Although the surgical procedure data and relevant patient data 4018 is described as being imported from patient electronic medical records 4012 stored in the EMR database 4002, in various aspects, the surgical procedure data and relevant patient data 4018 may be retrieved from a modular device coupled to the surgical hub 206 before being stored in the EMR database 4002. For example, the surgical hub 206 may interrogate the module to retrieve the surgical procedure data and relevant patient data 4018 from the module. As described herein, a module includes an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242, among other modules as illustrated in FIGS. 3 and 8-10.

For example, the anonymized stripped data 4058 may be employed to identify 4060 catastrophic failures of instruments, and other smart devices, and may initiate an automatic archive process and submission of data for further implications analysis. For example, the implication of detecting a counterfeit component or adapter on an original equipment manufacturer (OEM) device would be to initiate documentation of the component and recording of the results and outcome of its use. For example, the surgical hub 206 may execute situational awareness algorithms as described in connection FIG. 86. In one aspect, the surgical hub 206 may initially receive or identify a variety of implications 4062 that are derived from anonymized stripped data 4058. The surgical hub 206 is configured to control the instruments 235, or other modules, so that they operate correspondingly to the derived implications 4062. In one example, the surgical hub 206 control logic identifies that (i) lung tissue may be more fragile than normal (e.g., due to emphysema), (ii) hemostasis issues are more likely (e.g., due to high blood pressure and/or the patient being on a blood thinner, such as warfarin), (iii) cancer may be more aggressive (e.g., due to the target of the procedure being a small cell lung cancer), and (iv) lung tissue may be stiffer and more prone to fracture (e.g., due to the patient having received a radiation pretreatment). The control logic or processor 244 of the surgical hub 206 then interprets how this data impacts the instruments 235, or other modules, so that the instruments 235 are operated consistently with the data and then communicates the corresponding adjustments to each of the instruments 235.

In one example relating to a stapler type of surgical instrument 235, based on the implications 4062 identified 4060 from the anonymized stripped data 4058, the control logic or processor 244 of the surgical hub 206 may (i) notify the stapler to adjust the compression rate threshold parameter, (ii) adjust the surgical hub 206 visualization threshold value to quantify the bleeding and internal parameters, (iii) notify the combo generator module 240 of the lung tissue and vessel tissue types so that the power and generator module 240 control algorithms are adjusted accordingly, (iv) notify the imaging module 238 of the aggressive cancer tag to adjust the margin ranges accordingly, (v) notify the stapler of the margin parameter adjustment needed (the margin parameter corresponds to the distance or amount of tissue around the cancer that will be excised), and (vi) notify the stapler that the tissue is potentially fragile. Furthermore, the anonymized stripped data 4058, upon which the implications 40602 are based, is identified by the surgical hub 206 and is fed into the situational awareness algorithm (see FIG. 86). Examples include, without limitations, thoracic lung resection, e.g., segmentectomy, among others.

Figure 66:
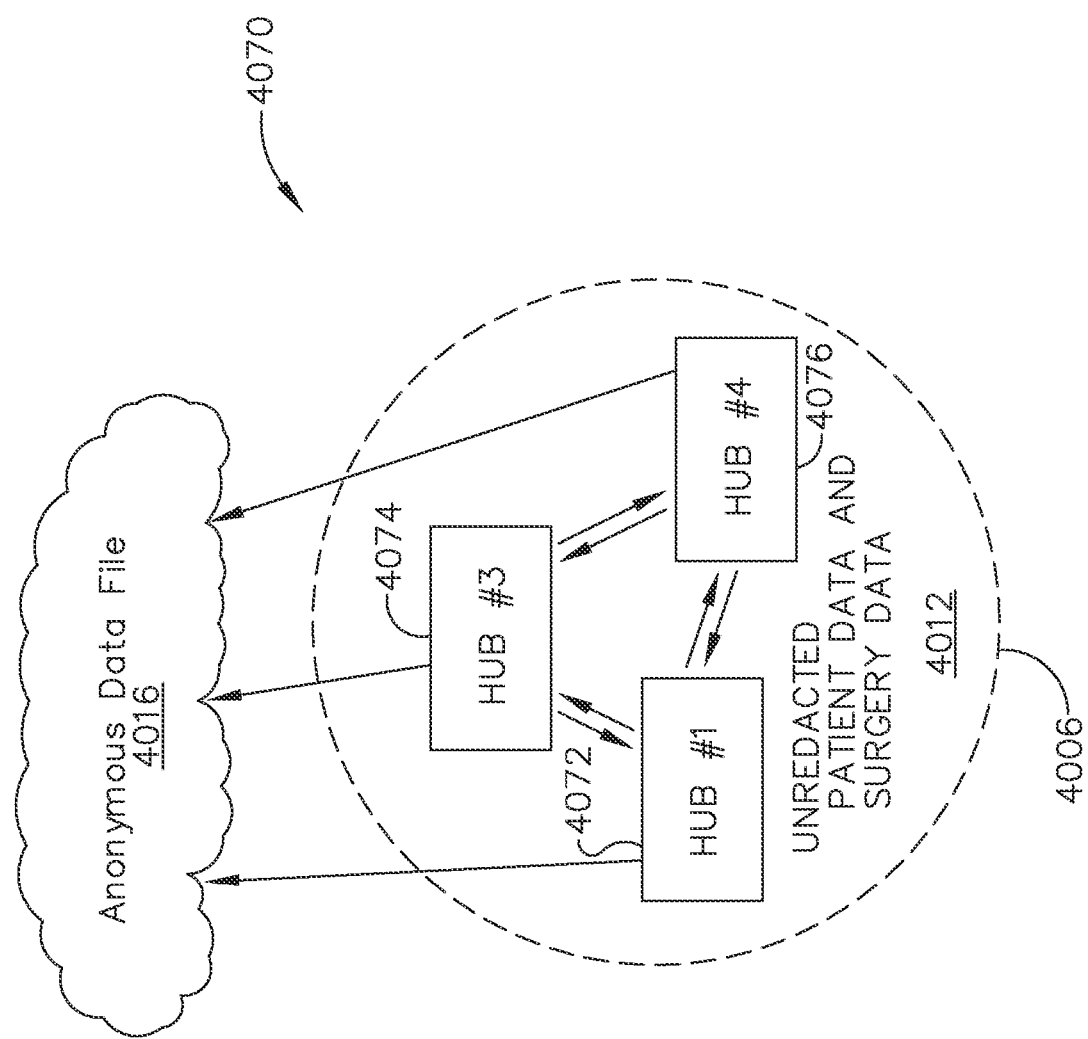
FIG. 66 illustrates the application of cloud based analytics to redacted and stripped patient data and independent data pairs, in accordance with at least one aspect of the present disclosure.

FIG. 66 is a diagram 4070 illustrating the application of cloud based analytics to un-redacted data, stripped relevant patient data 4018, and independent data pairs, according to one aspect of the present disclosure. As shown, multiple surgical hubs Hub #1 4072, Hub #3 4074, and Hub #4 4076 are located within the hospital data barrier 4006 (see also FIG. 62). The un-redacted patient electronic medical record 4012 including patient data and surgery related data may be used and exchanged between the surgical hubs: Hub #1 4072, Hub #3 4074, and Hub #4 4076 located within the hospital data barrier 4006. Prior to transmitting the un-redacted patient electronic medical record 4012 containing patient data and surgery related data outside the hospital data barrier 4006, however, the patient electronic medical record 4012 patient data is redacted and stripped to create an anonymous data file 4016 containing anonymized information for further analysis and processing of the redacted/stripped data by a cloud based analytic processes in the cloud 204.

Figure 67:
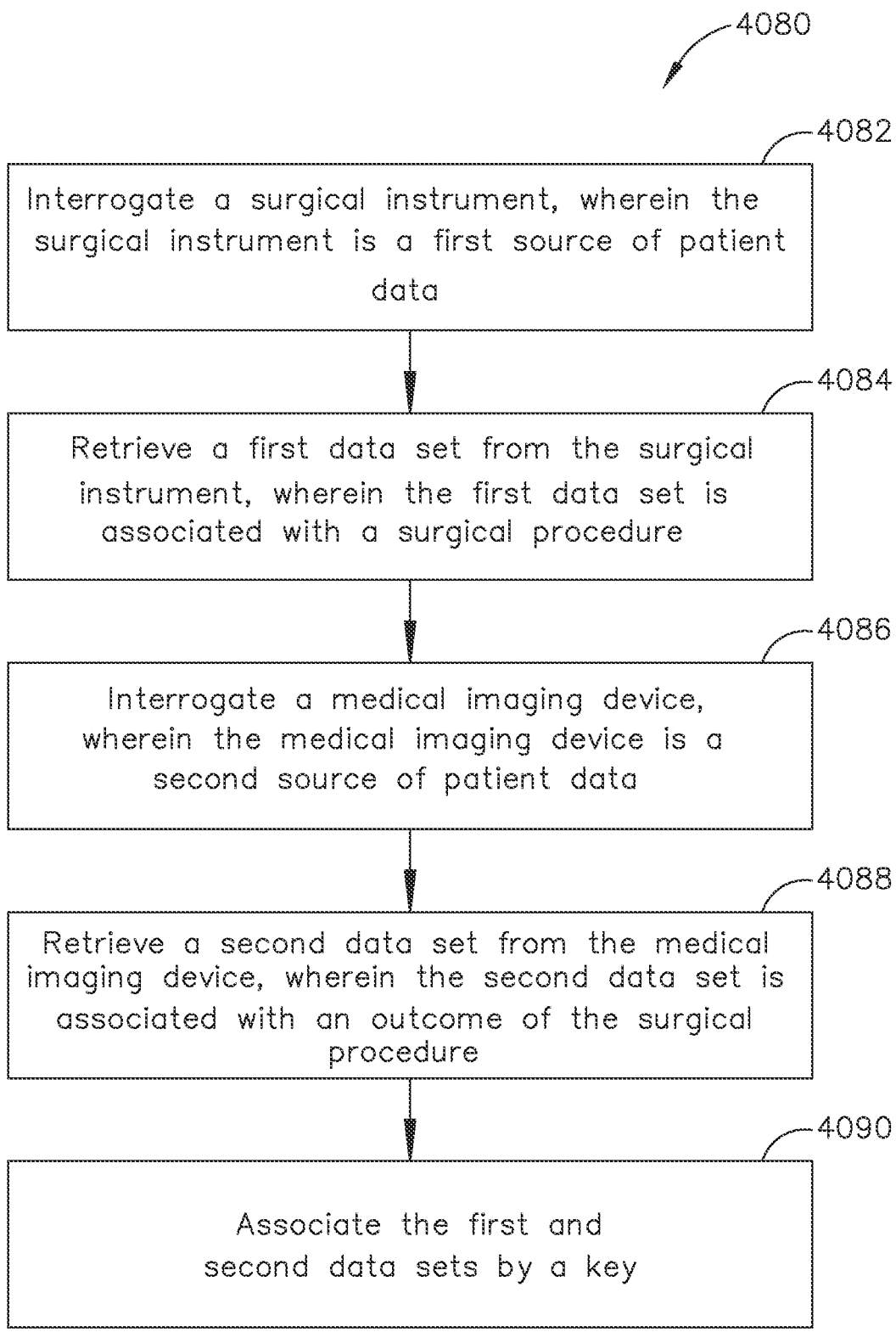
FIG. 67 is a logic flow diagram of a process depicting a control program or a logic configuration for associating patient data sets from first and second sources of data, in accordance with at least one aspect of the present disclosure.

FIG. 67 is a logic flow diagram 4080 of a process depicting a control program or a logic configuration for associating patient data sets from first and second sources of data, according to one aspect of the present disclosure. With reference to FIG. 67 and with reference also to FIGS. 1-11 to show interaction with an interactive surgical system 100 environment including a surgical hub 106, 206, in one aspect, the present disclosure provides a surgical hub 206, comprising a processor 244; and a memory 249 coupled to the processor 244. The memory 249 stores instructions executable by the processor 244 to interrogate 4082 a surgical instrument 235, retrieve 4084 a first data set from the surgical instrument 235, interrogate 4086 a medical imaging device 238, retrieve 4088 a second data set from the medical imaging device 238, associate 4090 the first and second data sets by a key, and transmit the associated first and second data sets to a remote network outside of the surgical hub 206. The surgical instrument 235 is a first source of patient data and the first data set is associated with a surgical procedure. The medical imaging device 238 is a second source of patient data and the second data set is associated with an outcome of the surgical procedure. The first and second data records are uniquely identified by the key.

In another aspect, the surgical hub 206 provides a memory 249 storing instructions executable by the processor 244 to retrieve the first data set using the key, anonymize the first data set, retrieve the second data set using the key, anonymize the second data set, pair the anonymized first and second data sets, and determine success rate of surgical procedures grouped by the surgical procedure based on the anonymized paired first and second data sets.

In another aspect, the surgical hub 206 provides a memory 249 storing instructions executable by the processor 244 to retrieve the anonymized first data set, retrieve the anonymized second data set, and reintegrate the anonymized first and second data sets using the key.

Figure 68:
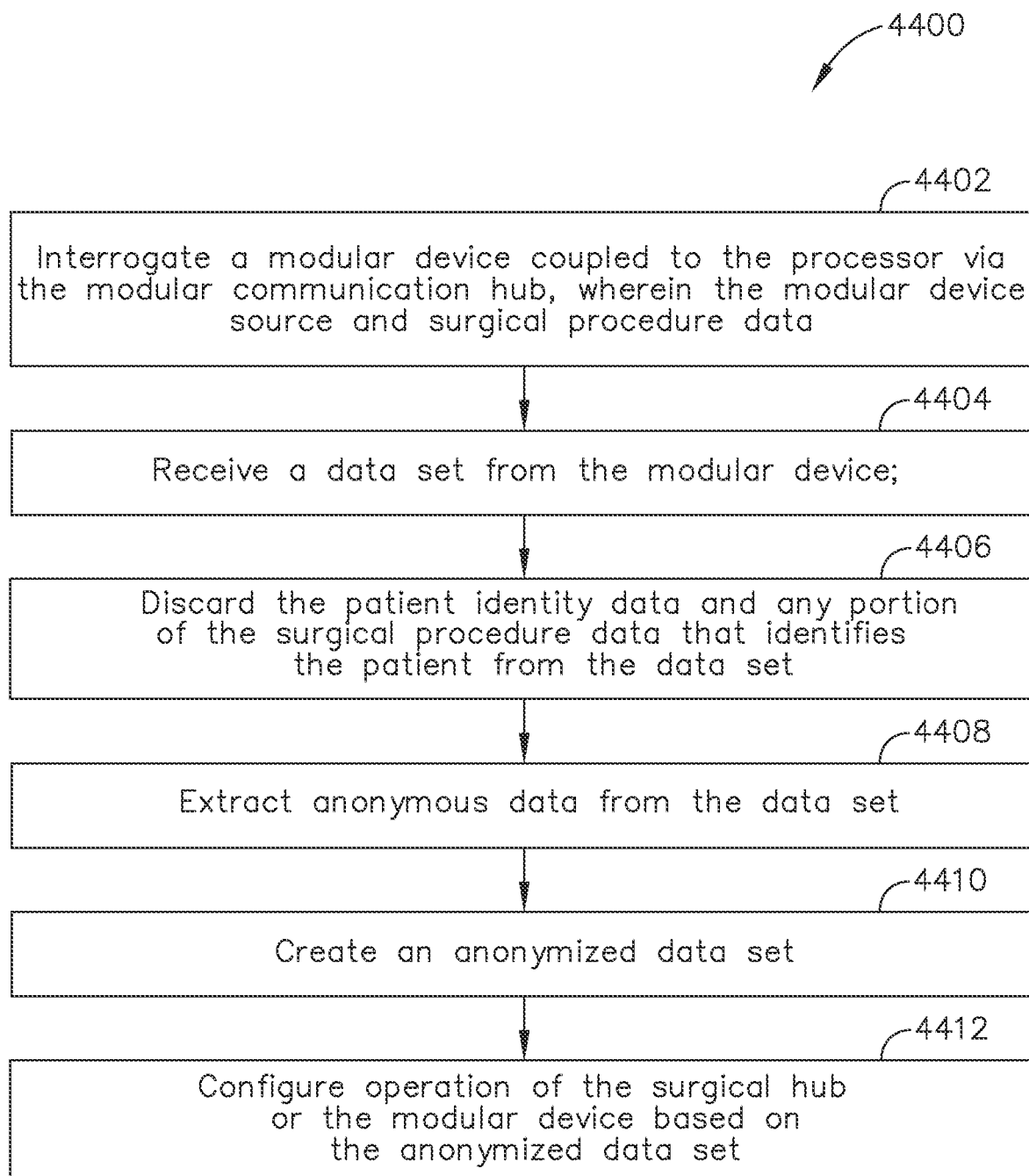
FIG. 68 is a logic flow diagram of a process depicting a control program or a logic configuration for stripping data to extract relevant portions of the data to configure and operate the surgical hub and modules (e.g., instruments) coupled to the surgical hub, in accordance with at least one aspect of the present disclosure.

FIG. 68 is a logic flow diagram of a process 4400 depicting a control program or a logic configuration for stripping data to extract relevant portions of the data to configure and operate the surgical hub 206 and modules (e.g., instruments 235) coupled to the surgical hub 206, according to one aspect of the present disclosure. With reference to FIG. 68 and with reference also to FIGS. 1-11 to show interaction with an interactive surgical system 100 environment including a surgical hub 106, 206, in one aspect, the surgical hub 206 may be configured to interrogate a module coupled to surgical hub 206 for data, and strip the data to extract relevant portions of the data to configure and operate the surgical hub 206 and modules (e.g., instruments 235) coupled to the surgical hub 206 and anonymize the surgery, patient, and other parameters that can be used to identify the patient to maintain patient privacy. According to the process 4400, in one aspect the present disclosure provides a surgical hub 206 including a processor 244, a modular communication hub 203 coupled to the processor 244, where the modular communication hub 203 is configured to connect modular devices located in one or more operating theaters to the surgical hub 206. The processor 244 is coupled to a memory 249, where the memory 249 stores instructions executable by the processor 244 to cause the processor to interrogate 4402 a modular device coupled to the processor 244 via the modular communication hub 203. The modular device is a source of data sets that include patient identity data and surgical procedure data. The processor 244 receives 4404 a data set from the modular device. The processor 244 discards 4406 the patient identity data and any portion of the surgical procedure data that identifies the patient from the data set. The processor 244 extracts 4408 anonymous data from the data set and creates 4410 an anonymized data set. The processor 244 configures 4412 the operation of the surgical hub 206 or the modular device based on the anonymized data set.

In another aspect, where the anonymized data set includes catastrophic failure of a modular device, the memory 249 stores instructions executable by the processor 244 to initiate automatic archiving and submission of data for implications analysis based on the catastrophic failure of the modular device. In another aspect, the memory 249 stores instructions executable by the processor 244 to detect counterfeit component information from the anonymized data set. In another aspect, the memory 249 stores instructions executable by the processor 244 to derive implications of the modular device from the anonymized data set and the memory 249 stores instructions executable by the processor 244 to configure the modular device to operate based on the derived implications or to configure the surgical hub based on the derived implications. In another aspect, the memory 249 stores instructions executable by the processor 244 to conglomerate the anonymized data. In another aspect, the memory 249 stores instructions executable by the processor 244 to extract the anonymized data prior to storing the received data in a storage device coupled to the surgical hub. In another aspect, the memory 249 stores instructions executable by the processor to transmit the anonymized data to a remote network outside of the surgical hub, compile the anonymized data at the remote network, and store a copy of the data set from the modular device in a patient electronic medical records database.

Storage of Data Creation and Use of Self-Describing Data Including Identification Features In one aspect, the present disclosure provides self-describing data packets generated at the issuing instrument and including identifiers for all devices that handled the packet. The self description allows the processor to interpret the data in the self-describing packet without knowing the data type in advance prior to receipt of the self-describing packet. The data applies to every data point or data string and includes the type of data, the source of the self-describing packet, the device identification that generated the packet, the units, the time of generation of the packet, and an authentication that the data contained in the packet is unaltered. When the processor (in the device or the surgical hub) receives an unexpected packet and verifies the source of the packet, the processor alters the collection techniques to be ready for any subsequent packets from that source.

With reference also to FIGS. 1-11 to show interaction with an interactive surgical system 100 environment including a surgical hub 106, 206, during a surgical procedure being performed in a surgical hub 206 environment, the size and quantity of data being generated by surgical devices 235 coupled to the surgical hub 206 can become quite large. Also, data exchanged between the surgical devices 235 and/or the surgical hub 206 can become quite large.

One solution provides a techniques for minimizing the size of the data and handling the data within a surgical hub 206 by generating a self-describing packet. The self-describing packet is initially assembled by the instrument 235 that generated it. The packet is then ordered and encrypted b generating an encryption certificate which is unique for each data packet. The data is then communicated from the instrument 235 via encrypted wired or wireless protocols and stored on the surgical hub 206 for processing and transmission to the cloud 204 analytics engine. Each self-describing data packet includes an identifier to identify the specific instrument that generated it and the time it was generated. A surgical hub 206 identifier is added to the packet when the packet is received by the surgical hub 206.

In one aspect, the present disclosure provides a surgical hub 206 comprising a processor 244 and a memory 249 coupled to the processor 244. The memory 249 storing instructions executable by the processor 244 to receive a first data packet from a first source, receive a second data packet from a second source, associate the first and second data packets, and generate a third data packet comprising the first and second data payloads. The first data packet comprises a first preamble, a first data payload, a source of the first data payload, and a first encryption certificate. The first preamble defines the first data payload and the first encryption certificate verifies the authenticity of the first data packet. The second data packet comprises a second preamble, a second data payload, a source of the second data payload, and a second encryption certificate. The second preamble defines the second data payload and the second encryption certificate verifies the authenticity of the second data packet.

In another aspect, the memory 249 stores instructions executable by the processor 244 to determine that a data payload is from a new source, verify the new source of the data payload, and alter a data collection process at the surgical hub to receive subsequent data packets from the new source.

In another aspect, the memory 249 stores instructions executable by the processor 244 to associate the first and second data packets based on a key. In another aspect, the memory 249 stores instructions executable by the processor 244 to anonymize the data payload of the third data packet. In another aspect, the memory 249 stores instructions executable by the processor 244 to receive an anonymized third data packet and reintegrate the anonymized third data packet into the first and second data packets using the key.

In various aspects, the present disclosure provides a control circuit to receive and process data packets as described above. In various aspects, the present disclosure provides a non-transitory computer-readable medium storing computer readable instructions, which when executed, causes a machine to receive and process data packets as described above.

In other aspects, the present disclosure a method of generating a data packet comprising self-describing data. In one aspect, a surgical instrument includes a processor and a memory coupled to the processor, a control circuit, and/or a computer-readable medium configured to generate a data packet comprising a preamble, a data payload, a source of the data payload, and an encryption certificate. The preamble defines the data payload and the encryption certificate verifies the authenticity of the data packet. In various aspects, the data packet may be generated by any module coupled to the surgical hub. Self-describing data packets minimize data size and data handing in the surgical hub.

In one aspect, the present disclosure provides a self-describing data packet generated at an issuing device (e.g., instrument, tool, robot). The self-describing data packet comprises identifiers for all devices that handle the data packet along a communication path; a self description to enable a processor to interpret that data contained in the data packet without having been told in advance of receipt of the data packet along a path; data for every data point or data string; and type of data, source of data, device IDs that generated the data, units of the data, time of generation, and authentication that the data packet is unaltered. In another aspect, when a processor receives a data packet from an unexpected source and verifies the source of the data, the processor alters the data collection technique to prepare for any subsequent data packets from the source.

In the creation and use of a data packet comprising self-describing data, the surgical hub includes identification features. The hub and intelligent devices use self-describing data packets to minimize data size and data handling. In a surgical hub that generates large volumes of data, the self-describing data packets minimize data size and data handling, thus saving time and enabling the operating theater to run more efficiently.

Figure 69:
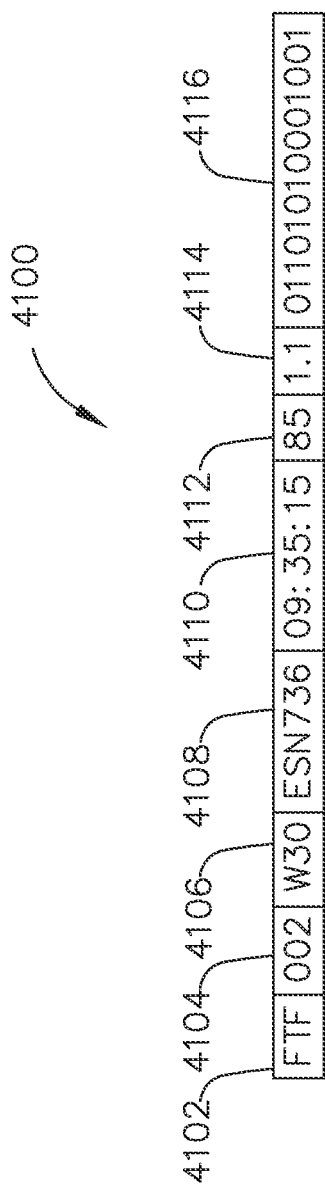
FIG. 69 illustrates a self-describing data packet comprising self-describing data, in accordance with at least one aspect of the present disclosure.

FIG. 69 illustrates a self-describing data packet 4100 comprising self-describing data, according to one aspect of the present disclosure. With reference also to FIGS. 1-11 to show interaction with an interactive surgical system 100 environment including a surgical hub 106, 206, in one aspect, self-describing data packets 4100 as shown in FIG. 69 are generated at an issuing instrument 235, or device or module located in or in communication with the operating theater, and include identifiers for all devices 235 that handle the packet along a communication path. The self description allows a processor 244 to interpret the data payload of the packet 4100 without having advance knowledge of the definition of the data payload prior to receiving the self-describing data packet 4100. The processor 244 can interpret the data payload by parsing an incoming self-describing packet 4100 as it is received and identifying the data payload without being notified in advance that the self-describing packet 4100 was received. The data is for every data point or data string. The data payload includes type of data, source of data, device IDs that generated the data, data units, time when data was generated, and an authentication that the self-describing data packet 4100 is unaltered. Once the processor 244, which may be located either in the device or the surgical hub 206, receives an unexpected self-describing data packet 4100 and verifies the source of the self-describing data packet 4100, the processor 244 alters the data collection means to be ready for any subsequent self-describing data packets 4100 from that source. In one example, the information contained in a self-describing packet 4100 may be recorded during the first firing 4172 in the lung tumor resection surgical procedure described in connection with FIGS. 71-75.

The self-describing data packet 4100 includes not only the data but a preamble which defines what the data is and where the data came from as well as an encryption certificate verifying the authenticity of each data packet 4100. As shown in FIG. 69, the data packet 4100 may comprise a self-describing data header 4102 (e.g., force-to-fire [FTF], force-to-close [FTC], energy amplitude, energy frequency, energy pulse width, speed of firing, and the like), a device ID 4104 (e.g., 002), a shaft ID 4106 (e.g., W30), a cartridge ID 4108 (e.g., ESN736), a unique time stamp 4110 (e.g., 09:35:15), a force-to-fire value 4112 (e.g., 85) when the self-describing data header 4102 includes FTF (force-to-fire), otherwise, this position in the data packet 4100 includes the value of force-to-close, energy amplitude, energy frequency, energy pulse width, speed of firing, and the like. The data packet 4100, further includes tissue thickness value 4114 (e.g., 1.1 mm), and an identification certificate of data value 4116 (e.g., 01101010001001) that is unique for each data packet 4100. Once the self-describing data packet 4100 is received by another instrument 235, surgical hub 206, cloud 204, etc., the receiver parses the self-describing data header 4102 and based on its value knows what data type is contained in the self-describing data packet 4100. TABLE 1 below lists the value of the self-describing data header 4102 and the corresponding data value.

TABLE 1

| Self-Describing Data Header (4102) | Data Type |
| --- | --- |
| FTF | Force To Fire (N) |
| FTC | Force To Close (N) |
| EA | Energy Amplitude (J) |
| EF | Energy Frequency (Hz) |
| EPW | Energy Pulse Width (Sec) |
| SOF | Speed Of Firing (mm/sec) |

Each self-describing data packet 4100 comprising self-describing data is initially assembled by the instrument 235, device, or module that generated the self-describing data packet 4100. Subsequently, the self-describing data packet 4100 comprising self-describing data is ordered and encrypted to generate an encryption certificate. The encryption certificate is unique for each self-describing data packet 4100. That data is then communicated via encrypted wired or wireless protocols and stored on the surgical hub 206 for processing and transmission to the cloud 204 analytics engine.

Each self-describing data packet 4100 comprising self-describing data includes a device ID 4104 to identify the specific instrument 235 that generated the self-describing data packet 4100, a time stamp 4110 to indicate the time that the data packet 4100 was generated, and when the self-describing data packet 4100 is received by the surgical hub 206. The surgical hub 206 ID also may be added to the self-describing data packet 4100.

Each of the self-describing data packets 4100 comprising self-describing data may include a packet wrapper that defines the beginning of the data packet 4100 and the end of the data packet 4100 including any identifiers necessary to forecast the number and order of the bits in the self-describing data packet.

The surgical hub 206 also manages redundant data sets. As the device 235 functions and interconnects with other surgical hubs 206, multiple sets of the same data may be created and stored on various devices 235. Accordingly, the surgical hub 206 manages multiple images of redundant data as well as anonymization and security of data. The surgical hub 206 also provides temporary visualization and communication, incident management, peer-to-peer processing or distributed processing, and storage backup and protection of data.

Figure 70:
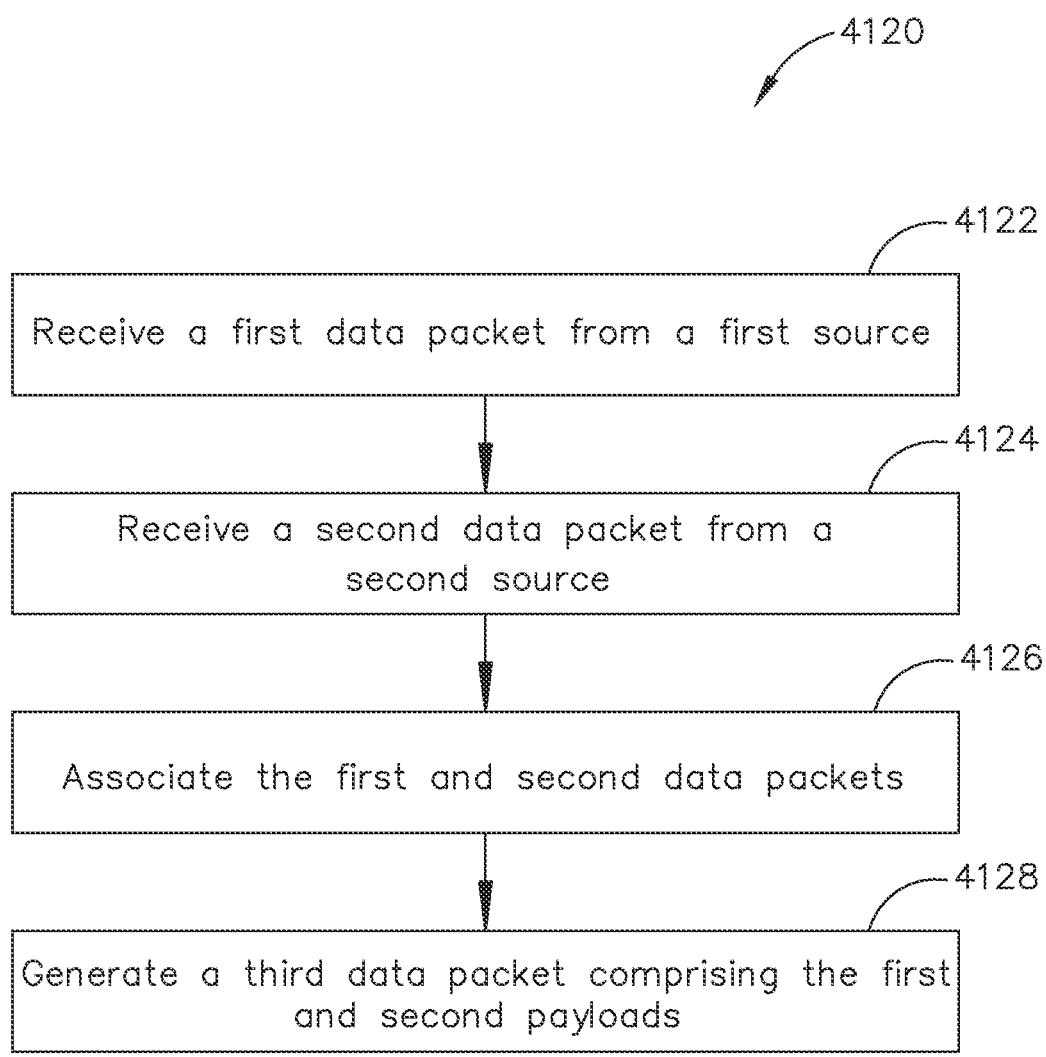
FIG. 70 is a logic flow diagram of a process depicting a control program or a logic configuration for using data packets comprising self-describing data, in accordance with at least one aspect of the present disclosure.

FIG. 70 is a logic flow diagram 4120 of a process depicting a control program or a logic configuration for using data packets comprising self-describing data, according to one aspect of the present disclosure. With reference to FIGS. 1-69, in one aspect, the present disclosure provides a surgical hub 206 comprising a processor 244 and a memory 249 coupled to the processor 244. The memory 249 storing instructions executable by the processor 244 to receive a first data packet from a first source, receive a second data packet from a second source, associate the first and second data packets, and generate a third data packet comprising the first and second data payloads. The first data packet comprises a first preamble, a first data payload, a source of the first data payload, and a first encryption certificate. The first preamble defines the first data payload and the first encryption certificate verifies the authenticity of the first data packet. The second data packet comprises a second preamble, a second data payload, a source of the second data payload, and a second encryption certificate. The second preamble defines the second data payload and the second encryption certificate verifies the authenticity of the second data packet.

In another aspect, the memory 249 stores instructions executable by the processor 244 to determine that a data payload is from a new source, verify the new source of the data payload, and alter a data collection process at the surgical hub to receive subsequent data packets from the new source.

In another aspect, the memory 249 stores instructions executable by the processor 244 to associate the first and second data packets based on a key. In another aspect, the memory 249 stores instructions executable by the processor 244 to anonymize the data payload of the third data packet. In another aspect, the memory 244 stores instructions executable by the processor 244 to receive an anonymized third data packet and reintegrate the anonymized third data packet into the first and second data packets using the key.

Figure 71:
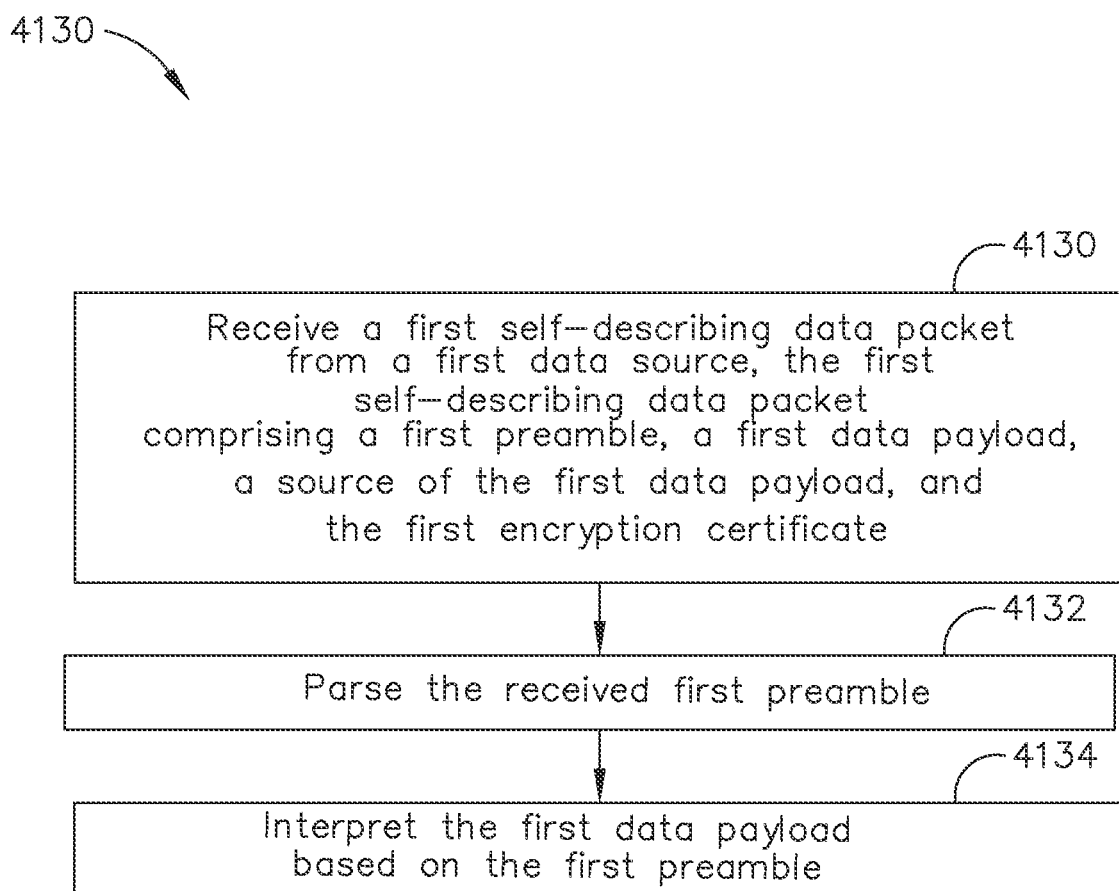
FIG. 71 is a logic flow diagram of a process depicting a control program or a logic configuration for using data packets comprising self-describing data, in accordance with at least one aspect of the present disclosure.

FIG. 71 is a logic flow diagram 4130 of a process depicting a control program or a logic configuration for using data packets comprising self-describing data, according to one aspect of the present disclosure. With reference to FIG. 71 and with reference also to FIGS. 1-11 to show interaction with an interactive surgical system 100 environment including a surgical hub 106, 206, in one aspect, the present disclosure provides a surgical hub 206 comprising a processor 244 and a memory 249 coupled to the processor 244. The memory 249 storing instructions executable by the processor 244 to receive 4132 a first self-describing data packet from a first data source, the first self-describing data packet comprising a first preamble, a first data payload, a source of the first data payload, and a first encryption certificate. The first preamble defines the first data payload and the first encryption certificate verifies the authenticity of the first data packet. The memory 249 storing instructions executable by the processor 244 to parse 4134 the received first preamble and interpret 4136 the first data payload based on the first preamble.

In various aspects, the memory 249 stores instructions executable by the processor 244 to receive a second self-describing data packet from a second data source, the second self-describing data packet comprising a second preamble, a second data payload, a source of the second data payload, and a second encryption certificate. The second preamble defines the second data payload and the second encryption certificate verifies the authenticity of the second data packet. The memory 249 storing instructions executable by the processor 244 to parse the received second preamble, interpret the second data payload based on the second preamble, associate the first and second self-describing data packets, and generate a third self-describing data packet comprising the first and second data payloads. In one aspect, the memory stores instructions executable by the processor to anonymize the data payload of the third self-describing data packet.

In various aspects, the memory stores instructions executable by the processor to determine that a data payload was generated by a new data source, verify the new data source of the data payload, and alter a data collection process at the surgical hub to receive subsequent data packets from the new data source. In one aspect, the memory stores instructions executable by the processor to associate the first and second self-describing data packets based on a key. In another aspect, the memory stores instructions executable by the processor to receive an anonymized third self-describing data packet and reintegrate the anonymized third self-describing data packet into the first and second self-describing data packets using the key.

Storage of the Data in a Manner of Paired Data Sets which can be Grouped by Surgery but not Necessarily Keyed to Actual Surgical Dates and Surgeons In one aspect, the present disclosure provides a data pairing method that allows a surgical hub to interconnect a device measured parameter with a surgical outcome. The data pair includes all the relevant surgical data or patient qualifiers without any patient identifier data. The data pair is generated at two separate and distinct times. The disclosure further provides configuring and storing the data in such a manner as to be able to rebuild a chronological series of events or merely a series of coupled but unconstrained data sets. The disclosure further provides storing data in an encrypted form and having predefined backup and mirroring to the cloud.

To determine the success or failure of a surgical procedure, data stored in a surgical instrument should be correlated with the outcome of the surgical procedure while simultaneously anonymizing the data to protect the privacy of the patient. One solution is to pair data associated with a surgical procedure, as recorded by the surgical instrument during the surgical procedure, with data assessing the efficacy of the procedure. The data is paired without identifiers associated with surgery, patient, or time to preserve anonymity. The paired data is generated at two separate and distinct times.

In one aspect, the present disclosure provides a surgical hub configured to communicate with a surgical instrument. The surgical hub comprises a processor and a memory coupled to the processor. The memory storing instructions executable by the processor to receive a first data set associated with a surgical procedure, receive a second data set associated with the efficacy of the surgical procedure, anonymize the first and second data sets by removing information that identifies a patient, a surgery, or a scheduled time of the surgery, and store the first and second anonymized data sets to generate a data pair grouped by surgery. The first data set is generated at a first time, the second data set is generated at a second time, and the second time is separate and distinct from the first time.

In another aspect, the memory stores instructions executable by the processor to reconstruct a series of chronological events based on the data pair. In another aspect, the memory stores instructions executable by the processor to reconstruct a series of coupled but unconstrained data sets based on the data pair. In another aspect, the memory stores instructions executable by the processor to encrypt the data pair, define a backup format for the data pair, and mirror the data pair to a cloud storage device.

In various aspects, the present disclosure provides a control circuit to receive and process data sets as described above. In various aspects, the present disclosure provides a non-transitory computer-readable medium storing computer readable instructions, which when executed, causes a machine to receive and process data sets as described above.

Storage of paired anonymous data enables the hospital or surgeon to use the data pairs locally to link to specific surgeries or to store the data pairs to analyze overall trends without extracting specific events in chronological manner.

In one aspect, the surgical hub provides user defined storage and configuration of data. Storage of the data may be made in a manner of paired data sets which can be grouped by surgery, but not necessarily keyed to actual surgical dates and surgeons. This technique provides data anonymity with regard to the patient and surgeon.

In one aspect, the present disclosure provides a data pairing method. The data pairing method comprises enabling a surgical hub to interconnect a device measured parameter with an outcome, wherein a data pair includes all the relevant tissue or patient qualifiers without any of the identifiers, wherein the data pair is generated at two distinct and separate times. In another aspect, the present disclosure provides a data configuration that includes whether the data is stored in such a manner as to enable rebuilding a chronological series of events or merely a series of coupled but unconstrained data sets. In another aspect, the data may be stored in an encrypted form. The stored data may comprise a predefined backup and mirroring to the cloud.

The data may be encrypted locally to the device. The data backup may be automatic to an integrated load secondary storage device. The device and/or the surgical hub may be configured to maintain the time of storage of the data and compile and transmit the data to another location for storage, e.g., another surgical hub or a cloud storage device. The data may be grouped together and keyed for transmission to the cloud analytics location. A cloud based analytics system is described in commonly-owned U.S. Provisional Patent Application Ser. No. 62/611,340, filed Dec. 28, 2017, titled CLOUD-BASED MEDICAL ANALYTICS, which is incorporated herein by reference in its entirety.

In another aspect, the hub provides user selectable options for storing the data. In one technique, the hub enables the hospital or the surgeon to select if the data should be stored in such a manner that it could be used locally in a surgical hub to link to specific surgeries. In another technique, the surgical hub enables the data to be stored as data pairs so that overall trends can be analyzed without specific events extracted in a chronological manner.

Figure 72:
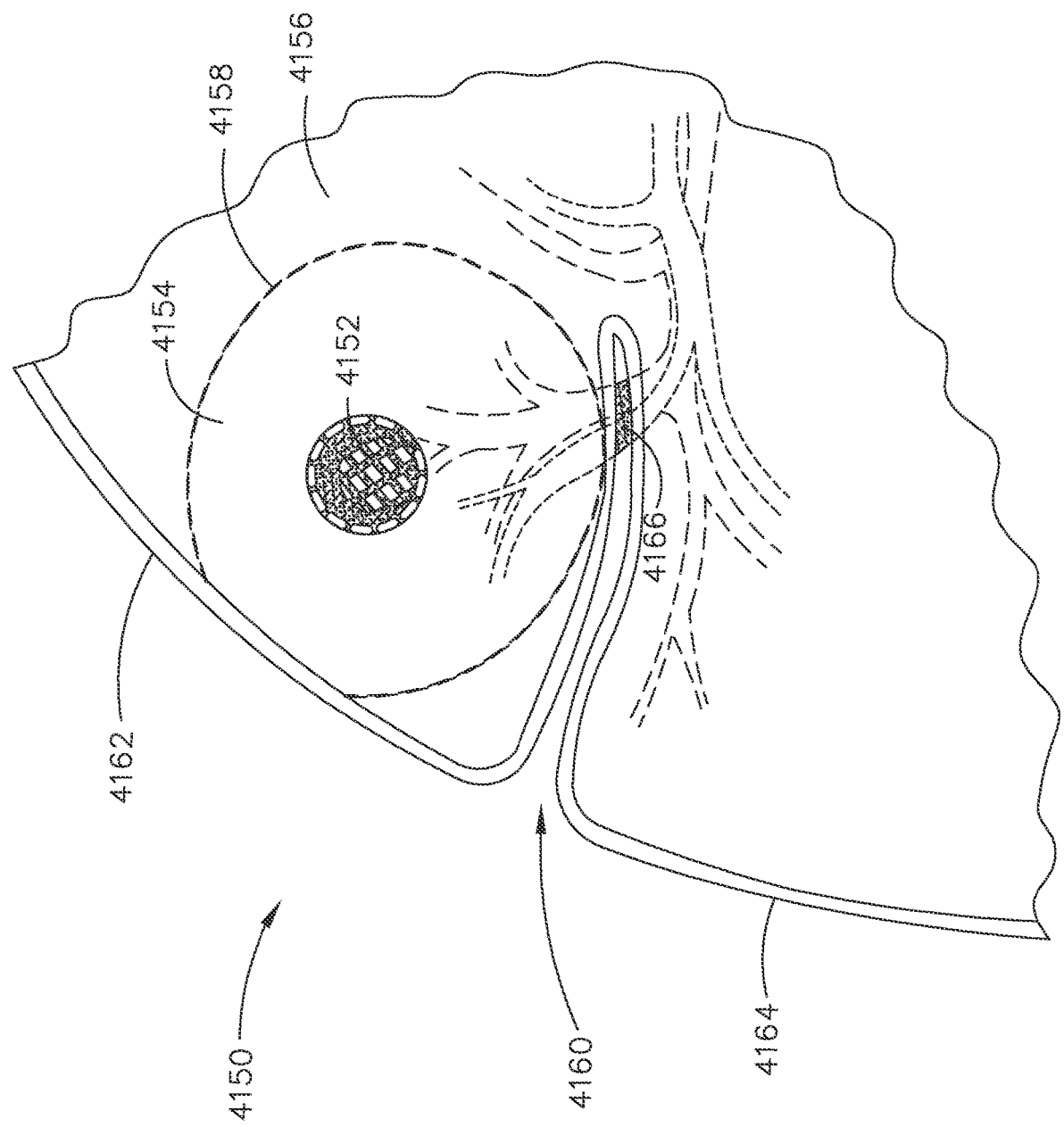
FIG. 72 is a diagram of a tumor embedded in the right superior posterior lobe of the right lung, in accordance with at least one aspect of the present disclosure.
Figure 78:
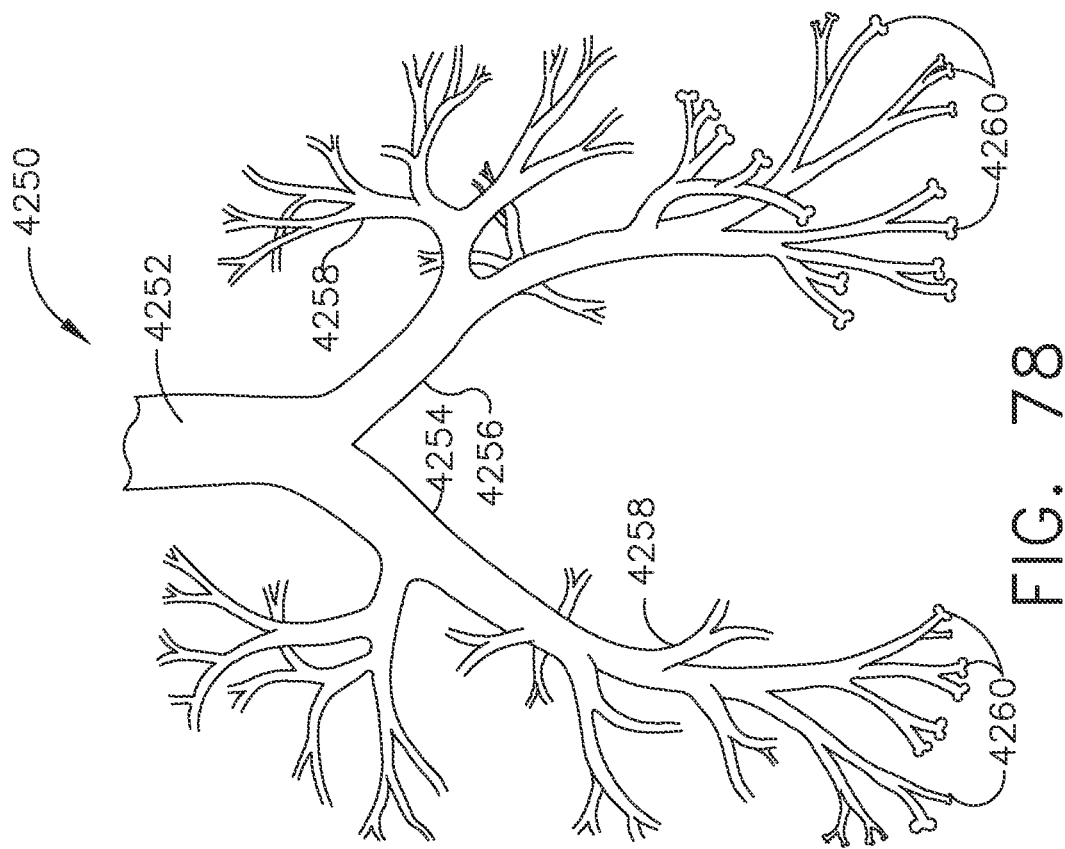
FIG. 78 is a diagram of the bronchial tree including the trachea and bronchi of the lung.
Figure 77:
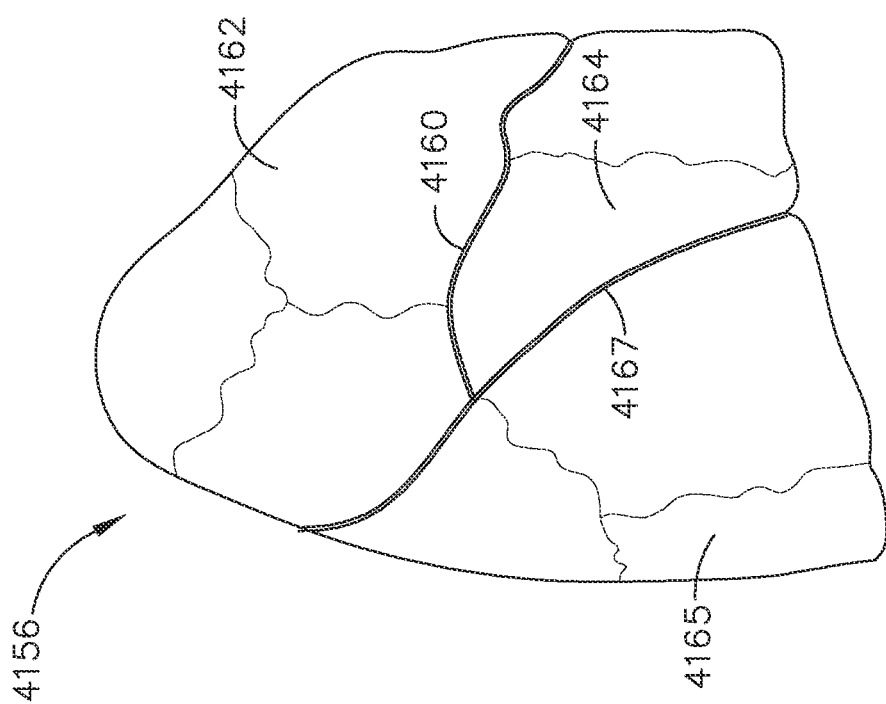
FIG. 77 is a diagram of the right lung.

FIG. 72 is a diagram 4150 of a tumor 4152 embedded in the right superior posterior lobe 4154 of the right lung 4156, according to one aspect of the present disclosure. To remove the tumor 4152, the surgeon cuts around the tumor 4152 along the perimeter generally designated as a margin 4158. A fissure 4160 separates the upper lobe 4162 and the middle lobe 4164 of the right lung 4156. In order to cut out the tumor 4152 about the margin 4158, the surgeon must cut the bronchial vessels 4166 leading to and from the middle lobe 4164 and the upper lobe 4162 of the right lung 4156. The bronchial vessels 4166 must be sealed and cut using a device such as a surgical stapler, electrosurgical instrument, ultrasonic instrument, a combo electrosurgical/ultrasonic instrument, and/or a combo stapler/electrosurgical device generally represented herein as the instrument/device 235 coupled to the surgical hub 206. The device 235 is configured to record data as described above, which is formed as a data packet, encrypted, stored, and/or transmitted to a remote data storage device 105 and processed by the server 113 in the cloud 104. FIGS. 77 and 78 are diagrams that illustrate the right lung 4156 and the bronchial tree 4250 embedded within the parenchyma tissue of the lung.

In one aspect, the data packet may be in the form of the self-describing data 4100 described in connection with FIGS. 69-71. The self-describing data packet 4100 will contain the information recorded by the device 235 during the procedure. Such information may include, for example, a self-describing data header 4102 (e.g., force-to-fire [FTF], force-to-close [FTC], energy amplitude, energy frequency, energy pulse width, speed of firing, and the like) based on the particular variable. The device ID 4104 (e.g., 002) of the instrument/device 235 used in the procedure including components of the instrument/device 235 such as the shaft ID 4106 (e.g., W30) and the cartridge ID 4108 (e.g., ESN736). The self-describing packet 4100 also records a unique time stamp 4110 (e.g., 09:35:15) and procedural variables such as a force-to-fire value 4112 (e.g., 85) when the self-describing data header 4102 includes FTF (force-to-fire), otherwise, this position in the data packet 4100 includes the value of force-to-close (FTC), energy amplitude, energy frequency, energy pulse width, speed of firing, and the like, as shown in TABLE 1, for example. The data packet 4100, further may include tissue thickness value 4114 (e.g., 1.1 mm), which in this example refers to the thickness of the bronchial vessel 4166 exposed in the fissure 4160 that were sealed and cut. Finally, each self-describing packet 4100 includes an identification certificate of data value 4116 (e.g., 01101010001001) that uniquely identifies each data packet 4100 transmitted by the device/instrument 235 to the surgical hub 206, further transmitted from the surgical hub 206 to the cloud 204 and stored on the storage device 205 coupled to the server 213, and/or further transmitted to the robot hub 222 and stored.

The data transmitted by way of a self-describing data packet 4100 is sampled by the instrument device 235 at a predetermined sample rate. Each sample is formed into a self-describing data packet 4100 which is transmitted to the surgical hub 206 and eventually is transmitted from the surgical hub 206 to the cloud 204. The samples may be stored locally in the instrument device 235 prior to packetizing or may be transmitted on the fly. The predetermined sampling rate and transmission rate are dictated by communication traffic in the surgical hub 206 and may be adjusted dynamically to accommodate current bandwidth limitations. Accordingly, in one aspect, the instrument device 235 may record all the samples taken during surgery and at the end of the procedure packetize each sample into a self-describing packet 4100 and transmit the self-describing packet 4100 to the surgical hub 206. In another aspect, the sampled data may be packetized as it is recorded and transmitted to the surgical hub 206 on the fly.

Figure 73:
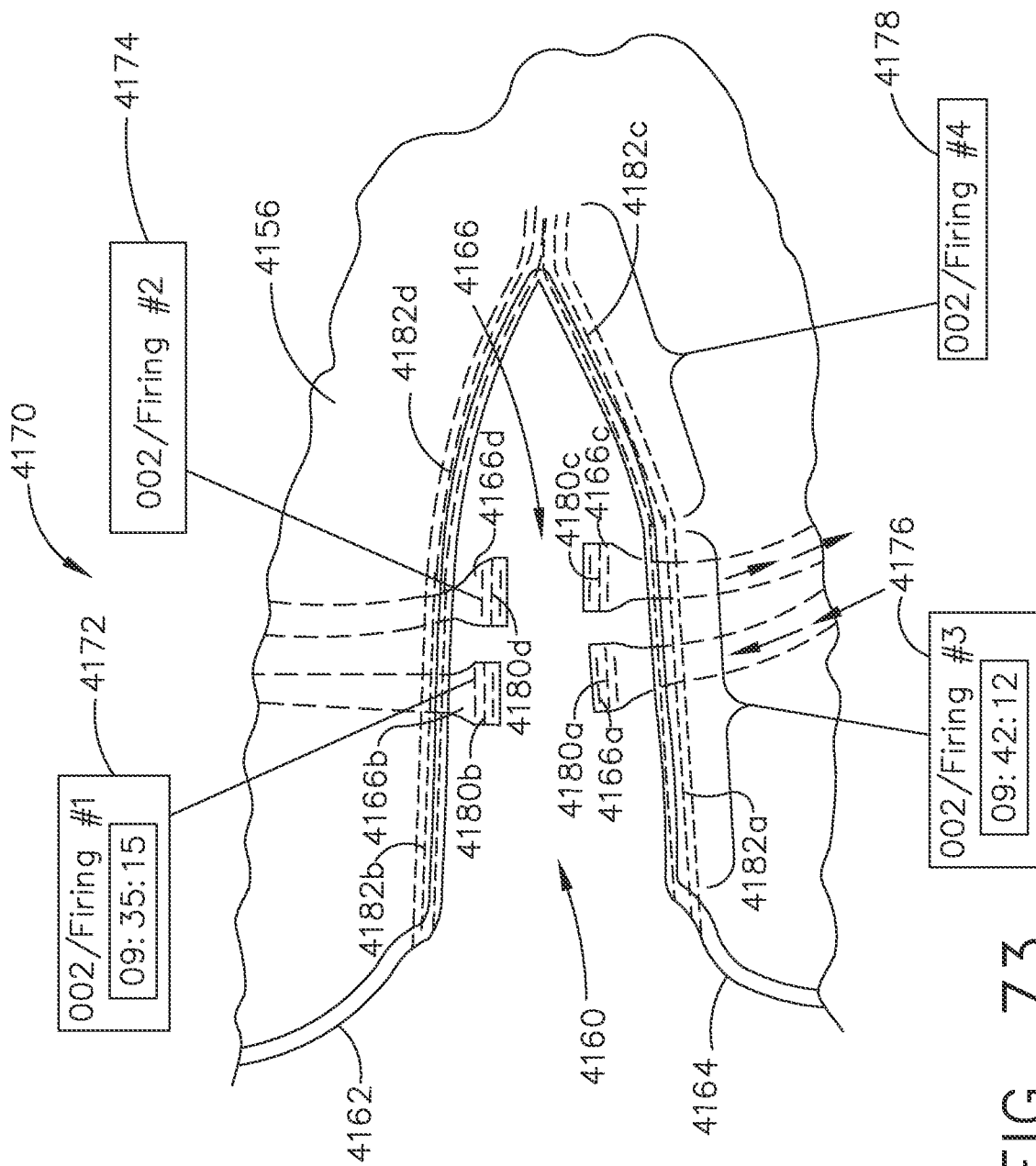
FIG. 73 is a diagram of a lung tumor resection surgical procedure including four separate firings of a surgical stapler to seal and cut bronchial vessels exposed in the fissure leading to and from the upper and lower lobes of the right lung shown in FIG. 72, in accordance with at least one aspect of the present disclosure.

FIG. 73 is a diagram 4170 of a lung tumor resection surgical procedure including four separate firings of a surgical stapler device 235 to seal and cut bronchial vessels 4166 exposed in the fissure 4160 leading to and from the upper and lower lobes 4162, 4164 of the right lung 4156 shown in FIG. 72, according to one aspect of the present disclosure. The surgical stapler device 235 is identified by a Device ID "002". The data from each firing of the surgical stapler device 235 is recorded and formed into a data packet 4100 comprising self-describing data as shown in FIG. 70. The self-describing data packet 4100 shown in FIG. 70 is representative of the first firing of device "002" having a staple cartridge serial number of ESN736, for example. In the following description, reference also is made to FIGS. 12-19 for descriptions of various architectures of instruments/devices 235 that include a processor or a control circuit coupled to a memory for recording (e.g., saving or storing) data collected during a surgical procedure.

Figure 74:
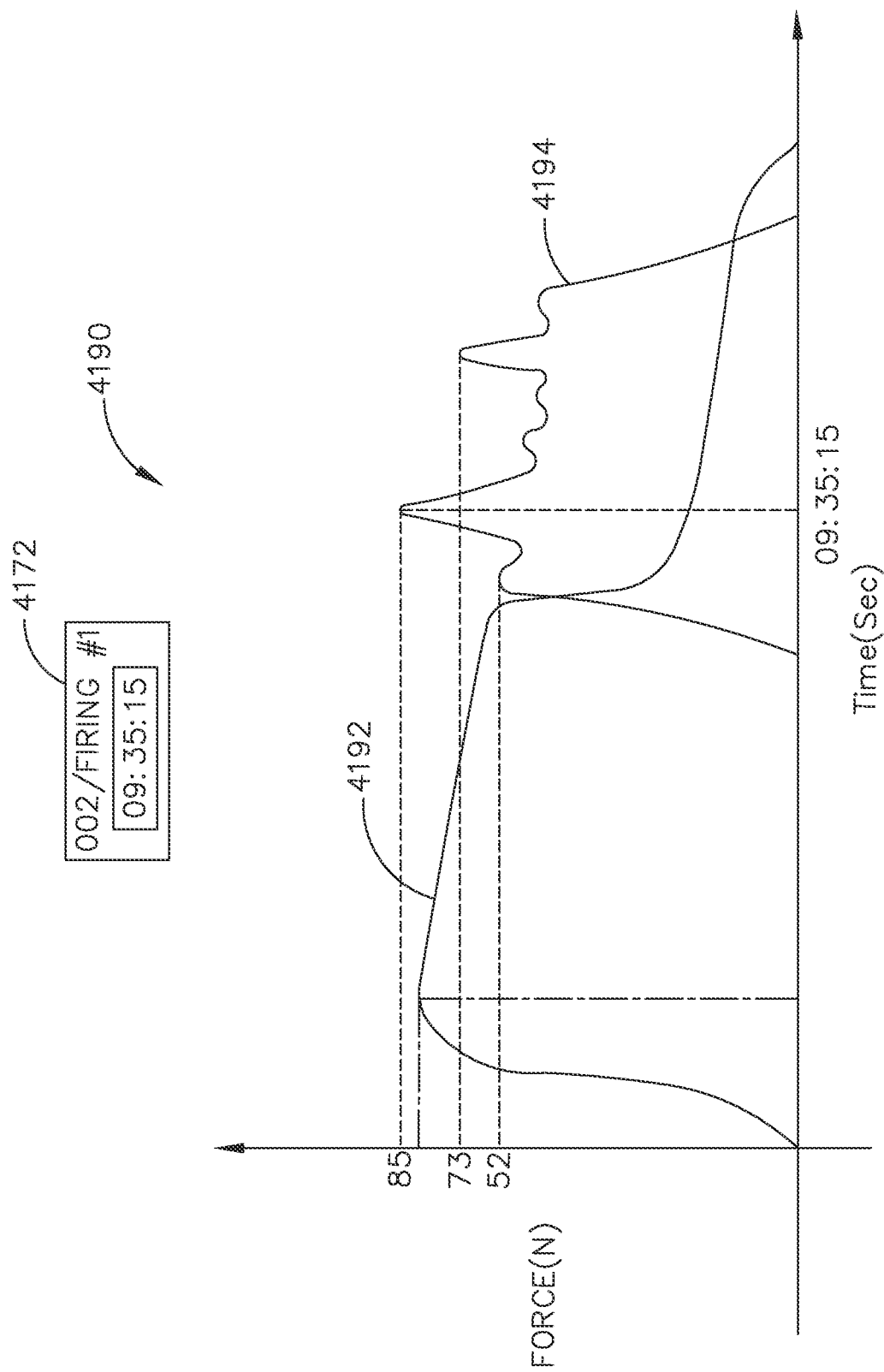
FIG. 74 is a graphical illustration of a force-to-close (FTC) versus time curve and a force-to-fire (FTF) versus time curve characterizing the first firing of device 002 as shown in FIG. 72, in accordance with at least one aspect of the present disclosure.

The first firing 4172 is recorded at anonymous time 09:35:15. The first firing 4172 seals and severs a first bronchial vessel 4166 leading to and from the middle lobe 4164 and the upper lobe 4162 of the right lung 4156 into a first portion 4166a and a second portion 4166b, where each portion 4166a, 4166b is sealed by respective first and second staple lines 4180a, 4180b. Information associated with the first firing 4172, for example the information described in connection with FIG. 70, is recorded in the surgical stapler device 235 memory and is used to build a first self-describing data packet 4100 described in connection with FIGS. 69-71. The first self-describing packet 4100 may be transmitted upon completion of the first firing 4172 or may be kept stored in the surgical stapler device 235 memory until the surgical procedure is completed. Once transmitted by the surgical stapler device 235, the first self-describing data packet 4100 is received by the surgical hub 206. The first self-describing data packet 4100 is anonymized by stripping and time stamping 4038 the data, as discussed, for example, in connection with FIG. 63. After the lung resection surgical is completed, the integrity of the seals of the first and second staple lines 4182a, 4182b will be evaluated as shown in FIG. 74, for example, and the results of the evaluation will be paired with information associated with the first firing 4172.

The second firing 4174 seals and severs a second bronchial vessel of the bronchial vessels 4166 leading to and from the middle lobe 4164 and the upper lobe 4162 of the right lung 4156 into a first portion 4166c and a second portion 4166d, where each portion 4166c, 4166d is sealed by first and second staple lines 4180c, 4180d. Information associated with the second firing 4174, for example the information described in connection with FIGS. 69-71, is recorded in the surgical stapler device 235 memory and is used to build a second self-describing data packet 4100 described in connection with FIGS. 69-71. The second self-describing data packet 4100 may be transmitted upon completion of the second firing 4174 or may be kept stored in the surgical stapler device 235 memory until the surgical procedure is completed. Once transmitted by the surgical stapler device 235, the second self-describing data packet 4100 is received by the surgical hub 206. The second self-describing data packet 4100 is anonymized by stripping and time stamping 4038 the data as discussed, for example, in connection with FIG. 63. After the lung resection surgical is completed, the integrity of the seals of the first and second staple lines 4182c, 4182d will be evaluated as shown in FIG. 74, for example, and the results of the evaluation will be paired with information associated with the second firing 4174.

The third firing 4176 is recorded at anonymous time 09:42:12. The third firing 4176 seals and severs an outer portion of the upper and middle lobes 4162, 4164 of the right lung 4156. First and second staple lines 4182a, 4182b are used to seal the outer portion of the upper and middle lobes 4162, 4162. Information associated with the third firing 4176, for example the information described in connection with FIGS. 69-71, is recorded in the surgical stapler device 235 memory and is used to build a third self-describing data packet 4100 described in connection with FIGS. 69-71. The third self-describing packet 4100 may be transmitted upon completion of the third firing 4176 or may be kept stored in the surgical stapler device 235 memory until the surgical procedure is completed. Once transmitted by the surgical stapler device 235, the third self-describing data packet 4100 is received by the surgical hub 206. The third self-describing data packet 4100 is anonymized by stripping and time stamping 4038 the data, as discussed, for example, in connection with FIG. 63. After the lung resection surgical is completed, the integrity of the seals of the first and second staple lines 4180a, 4180b will be evaluated as shown in FIG. 74, for example, and the results of the evaluation will be paired with information associated with the third firing 4172.

The fourth firing 4178 seals and severs an inner portion of the upper and middle lobes 4162, 4162 of the right lung 4156. First and second staple lines 4182c, 4182d are used to seal the inner portions of the upper and middle lobes 4162, 4164. Information associated with the fourth firing 4178, for example the information described in connection with FIG. 70, is recorded in the surgical stapler device 235 memory and is used to build a fourth self-describing data packet 4100 described in connection with FIGS. 69-71. The fourth self-describing packet 4100 may be transmitted upon completion of the fourth firing 4178 or may be kept stored in the surgical stapler device 235 memory until the surgical procedure is completed. Once transmitted by the surgical stapler device 235, the fourth self-describing data packet 4100 is received by the surgical hub 206. The fourth self-describing data packet 4100 is anonymized by stripping and time stamping 4038 the data, as discussed, for example, in connection with FIG. 63. After the lung resection surgical is completed, the integrity of the seals of the first and second staple lines 4182a, 4182b will be evaluated as shown in FIG. 74, for example, and the results of the evaluation will be paired with information associated with the fourth firing 4172.

FIG. 74 is a graphical illustration 4190 of a force-to-close (FTC) versus time curve 4192 and a force-to-fire (FTF) versus time curve 4194 characterizing the first firing 4172 of device 002 shown in FIG. 73, according to one aspect of the present disclosure. The surgical stapler device 235 is identified as 002 with a 30 mm staple cartridge S/N ESN736 with a PVS shaft S/N M3615N (Shaft ID W30). The surgical stapler device 235 was used for the first firing 4172 to complete the lung resection surgical procedure shown in FIG. 73. As shown in FIG. 74, the peak force-to-fire force of 85 N, is recorded at anonymous time 09:35:15. Algorithms in the surgical stapler device 235 determine a tissue thickness of about 1.1 mm. As described hereinbelow, the FTC versus time curve 4192 and the FTF versus time curve 4194 characterizing the first firing 4172 of the surgical device 235 identified by ID 002 will be paired with the outcome of the lung resection surgical procedure, transmitted to the surgical hub 206, anonymized, and either stored in the surgical hub 206 or transmitted to the cloud 204 for aggregation, further processing, analysis, etc.

Figure 75:
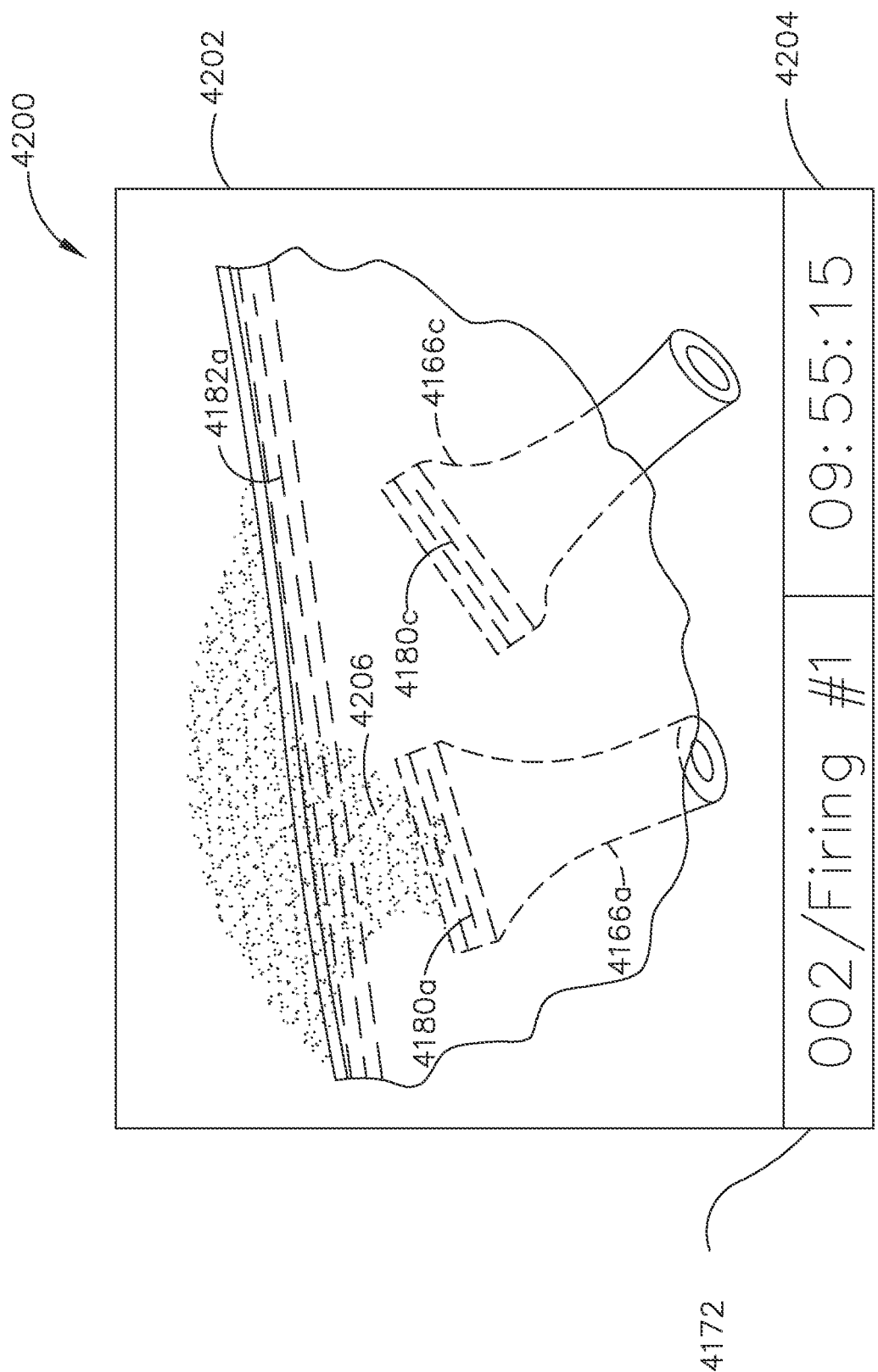
FIG. 75 is a diagram of a staple line visualization laser Doppler to evaluate the integrity of staple line seals by monitoring bleeding of a vessel after a firing of a surgical stapler, in accordance with at least one aspect of the present disclosure.

FIG. 75 is a diagram 4200 illustrating a staple line visualization laser Doppler to evaluate the integrity of staple line seals by monitoring bleeding of a vessel after a firing of a surgical stapler, according to one aspect of the present disclosure. A laser Doppler technique is described in above under the heading "Advanced Imaging Acquisition Module." in U.S. Provisional Patent Application Ser. No. 62/611, 341, filed Dec. 28, 2017, and titled INTERACTIVE SURGICAL PLATFORM, which is hereby incorporated by reference herein in its entirety. The laser Doppler provides an image 4202 suitable for inspecting seals along the staple lines 4180a, 4180b, 4182a and for visualizing bleeding 4206 of any defective seals. Laser Doppler inspection of the first firing 4172 of device 002 shows a defective seal at the first staple line 4180a of the first portion 4166a of the bronchial vessel sealed during the first firing 4172. The staple line 4180a seal is bleeding 4206 out at a volume of 0.5 cc. The image 4202 is recorded at anonymous time 09:55:15 4204 and is paired with the force-to-close curve 4192 and force-to-fire curve 4194 shown in FIG. 74. The data pair set is grouped by surgery and is stored locally in the surgical hub 206 storage 248 and/or remotely to the cloud 204 storage 205 for aggregation, processing, and analysis, for example. For example, the cloud 204 analytics engine associates the information contained in the first self-describing packet 4100 associated with the first firing 4172 and indicate that a defective seal was produced at the staple line 4166a. Over time, this information can be aggregated, analyzed, and used to improve outcomes of the surgical procedure, such as, resection of a lung tumor, for example.

Figure 76:
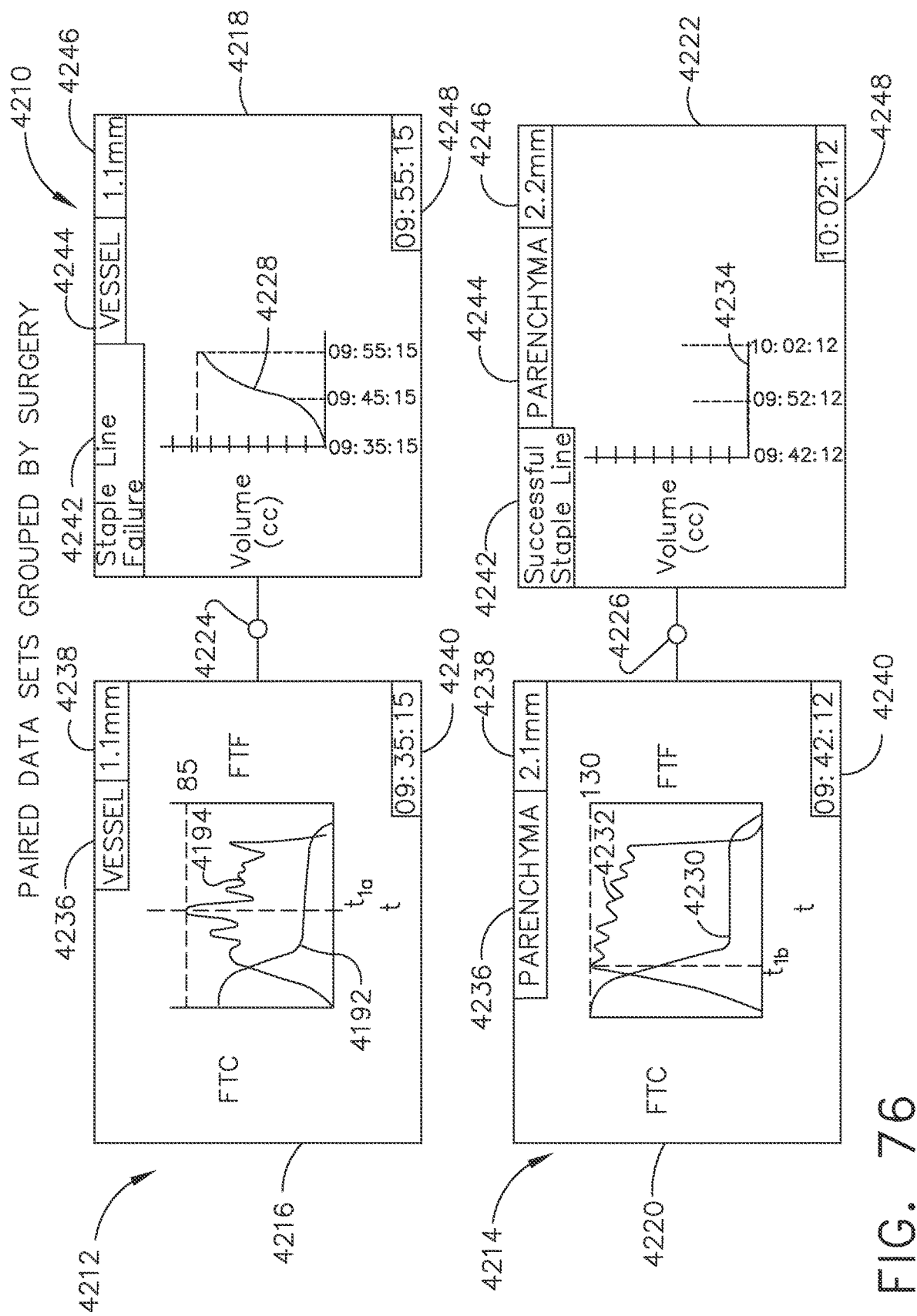
FIG. 76 illustrates a paired data set grouped by surgery, in accordance with at least one aspect of the present disclosure.

FIG. 76 illustrates two paired data sets 4210 grouped by surgery, according to one aspect of the present disclosure. The upper paired data set 4212 is grouped by one surgery and a lower paired data set 4214 grouped by another surgery. The upper paired data set 4212, for example, is grouped by the lung tumor resection surgery discussed in connection with FIGS. 73-76. Accordingly, the rest of the description of FIG. 76 will reference information described in FIGS. 32-35 as well as FIGS. 1-21 to show interaction with an interactive surgical system 100 environment including a surgical hub 106, 206. The lower paired data set 4214 is grouped by a liver tumor resection surgical procedure where the surgeon treated parenchyma tissue. The upper paired data set is associated with a failed staple line seal and the bottom paired data set is associated with a successful staple line seal. The upper and lower paired data sets 4212, 4214 are sampled by the instrument device 235 and each sample formed into a self-describing data packet 4100 which is transmitted to the surgical hub 206 and eventually is transmitted from the surgical hub 206 to the cloud 204. The samples may be stored locally in the instrument device 235 prior to packetizing or may be transmitted on the fly. Sampling rate and transmission rate are dictated by communication traffic in the surgical hub 206 and may be adjusted dynamically to accommodate current bandwidth limitations.

The upper paired data set 4212 includes a left data set 4216 recorded by the instrument/device 235 during the first firing 4172 linked 4224 to a right data set 4218 recorded at the time the staple line seal 4180a of the first bronchial vessel 4166a was evaluated. The left data set 4216 indicates a "Vessel" tissue type 4236 having a thickness 4238 of 1.1 mm. Also included in the left data set 4216 is the force-to-close curve 4192 and force-to-fire curve 4194 versus time (anonymous real time) recorded during the first firing 4172 of the lung tumor resection surgical procedure. The left data set 4216 shows that the force-to-fire peaked at 85 Lbs. and recorded at anonymous real time 4240 $t_{1a}$ (09:35:15). The right data set 4218 depicts the staple line visualization curve 4228 depicting leakage versus time. The right data set 4218 indicates that a "Vessel" tissue type 4244 having a thickness 4246 of 1.1 mm experienced a staple line 4180a seal failure 4242. The staple line visualization curve 4228 depicts leakage volume (cc) versus time of the staple line 4180a seal. The staple line visualization curve 4228 shows that the leakage volume reached 0.5 cc, indicating a failed staple line 4180a seal of the bronchial vessel 4166a, recorded at anonymous time 4248 (09:55:15).

The lower paired data set 4214 includes a left data set 4220 recorded by the instrument/device 235 during a firing linked 4226 to a right data set 4222 recorded at the time the staple line seal of the parenchyma tissue was evaluated. The left data set 4220 indicates a "Parenchyma" tissue type 4236 having a thickness 4238 of 2.1 mm. Also included in the left data set 4220 is the force-to-close curve 4230 and force-to-fire curve 4232 versus time (anonymous real time) recorded during the first firing of the liver tumor resection surgical procedure. The left data set 4220 shows that the force-to-fire peaked at 100 Lbs. and recorded at anonymous real time 4240 $t_{1b}$ (09:42:12). The right data set 4222 depicts the staple line visualization curve 4228 depicting leakage versus time. The right data set 4234 indicates that a "Parenchyma" tissue type 4244 having a thickness 4246 of 2.2 mm experienced a successful staple line seal. The staple line visualization curve 4234 depicts leakage volume (cc) versus time of the staple line seal. The staple line visualization curve 4234 shows that the leakage volume was 0.0 cc, indicating a successful staple line seal of the parenchyma tissue, recorded at anonymous time 4248 (10:02:12).

The paired date sets 4212, 4214 grouped by surgery are collected for many procedures and the data contained in the paired date sets 4212, 4214 is recorded and stored in the cloud 204 storage 205 anonymously to protect patient privacy, as described in connection with FIGS. 62-69. In one aspect, the paired date sets 4212, 4214 data are transmitted from the instrument/device 235, or other modules coupled to the surgical hub 206, to the surgical hub 206 and to the cloud 204 in the form of the self-describing packet 4100 as described in connection with FIGS. 71 and 72 and surgical procedure examples described in connection with FIGS. 72-76. The paired date sets 4212, 4214 data stored in the cloud 204 storage 205 is analyzed in the cloud 204 to provide feedback to the instrument/device 235, or other modules coupled to the surgical hub 206, notifying a surgical robot coupled to the robot hub 222, or the surgeon, that the conditions identified by the left data set ultimately lead to either a successful or failed seal. As described in connection with FIG. 76, the upper left data set 4216 led to a failed seal and the bottom left data set 4220 led to a successful seal. This is advantageous because the information provided in a paired data set grouped by surgery can be used to improve resection, transection, and creation of anastomosis in a variety of tissue types. The information can be used to avoid pitfalls that may lead to a failed seal.

FIG. 77 is a diagram of the right lung 4156 and FIG. 78 is a diagram of the bronchial tree 4250 including the trachea 4252 and the bronchi 4254, 4256 of the lungs. As shown in FIG. 77, the right lung 4156 is composed of three lobes divided into the upper lobe 4162, the middle lobe 4160, and the lower lobe 4165 separated by the oblique fissure 4167 and horizontal fissure 4160. The left lung is composed of only two smaller lobes due to the position of heart. As shown in FIG. 78, inside each lung, the right bronchus 4254 and the left bronchus 4256 divide into many smaller airways called bronchioles 4258, greatly increasing surface area. Each bronchiole 4258 terminates with a cluster of air sacs called alveoli 4260, where gas exchange with the bloodstream occurs.

Figure 79:
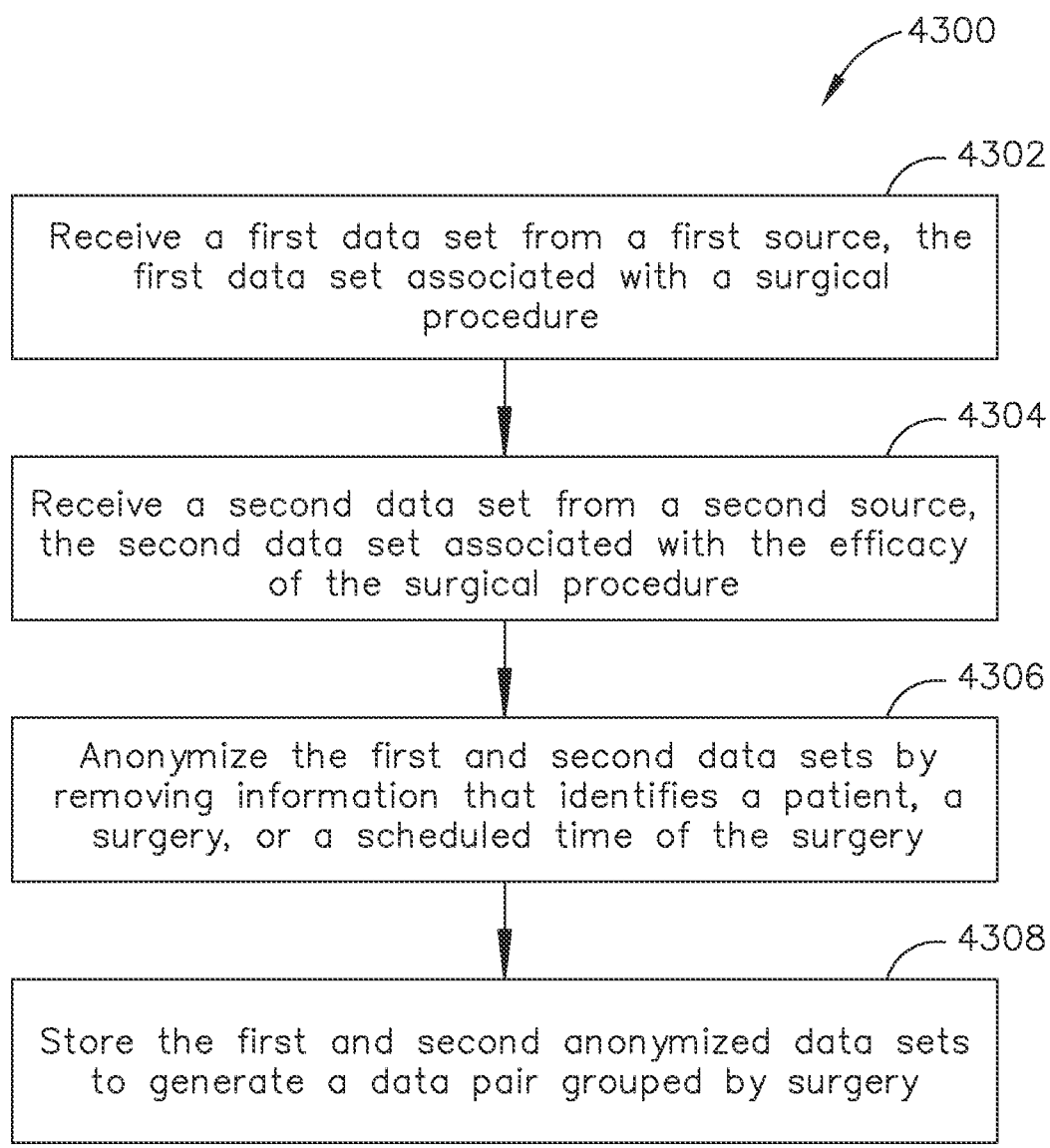
FIG. 79 is a logic flow diagram of a process depicting a control program or a logic configuration for storing paired anonymous data sets grouped by surgery, in accordance with at least one aspect of the present disclosure.

FIG. 79 is a logic flow diagram 4300 of a process depicting a control program or a logic configuration for storing paired anonymous data sets grouped by surgery, according to one aspect of the present disclosure. With reference to FIGS. 1-79, in one aspect, the present disclosure provides a surgical hub 206 configured to communicate with a surgical instrument 235. The surgical hub 206 comprises a processor 244 and a memory 249 coupled to the processor 244. The memory 249 storing instructions executable by the processor 244 to receive 4302 a first data set from a first source, the first data set associated with a surgical procedure, receive 4304 a second data set from a second source, the second data set associated with the efficacy of the surgical procedure, anonymize 4306 the first and second data sets by removing information that identifies a patient, a surgery, or a scheduled time of the surgery, and store 4308 the first and second anonymized data sets to generate a data pair grouped by surgery. The first data set is generated at a first time, the second data set is generated at a second time, and the second time is separate and distinct from the first time.

In another aspect, the memory 249 stores instructions executable by the processor 244 to reconstruct a series of chronological events based on the data pair. In another aspect, the memory 249 stores instructions executable by the processor 244 to reconstruct a series of coupled but unconstrained data sets based on the data pair. In another aspect, the memory 249 stores instructions executable by the processor 244 to encrypt the data pair, define a backup format for the data pair, and mirror the data pair to a cloud 204 storage device 205.

Determination of Data to Transmit to Cloud Based Medical Analytics

In one aspect, the present disclosure provides a communication hub and storage device for storing parameters and status of a surgical device what has the ability to determine when, how often, transmission rate, and type of data to be shared with a cloud based analytics system. The disclosure further provides techniques to determine where the analytics system communicates new operational parameters for the hub and surgical devices.

In a surgical hub environment, large amounts of data can be generated rather quickly and may cause storage and communication bottlenecks in the surgical hub network. One solution may include local determination of when and what data is transmitted for to the cloud-based medical analytics system for further processing and manipulation of surgical hub data. The timing and rate at which the surgical hub data is exported can be determined based on available local data storage capacity. User defined inclusion or exclusion of specific users, patients, or procedures enable data sets to be included for analysis or automatically deleted. The time of uploads or communications to the cloud-based medical analytics system may be determined based on detected surgical hub network down time or available capacity.

With reference to FIGS. 1-79, in one aspect, the present disclosure provides a surgical hub 206 comprising a storage device 248, a processor 244 coupled to the storage device 248, and a memory 249 coupled to the processor 244. The memory 249 stores instructions executable by the processor 244 to receive data from a surgical instrument 235, determine a rate at which to transfer the data to a remote cloud-based medical analytics network 204 based on available storage capacity of the storage device 248, determine a frequency at which to transfer the data to the remote cloud-based medical analytics network 204 based on the available storage capacity of the storage device 248 or detected surgical hub network 206 down time, and determine a type of data to transfer the data to a remote cloud-based medical analytics network 204 based on inclusion or exclusion of data associated with a users, patient, or surgical procedure.

In another aspect, the memory 249 stores instructions executable by the processor 244 to receive new operational parameters for the surgical hub 206 or the surgical instrument 235.

In various aspects, the present disclosure provides a control circuit to determine, rate, frequency and type of data to transfer the data to the remote cloud-based medical analytics network as described above. In various aspects, the present disclosure provides a non-transitory computer-readable medium storing computer readable instructions which, when executed, causes a machine to determine, rate, frequency and type of data to transfer to the remote cloud-based medical analytics network.

In one aspect, the surgical hub 206 is configured to determine what data to transmit to the cloud based analytics system 204. For example, a surgical hub 206 modular device 235 that includes local processing capabilities may determine the rate, frequency, and type of data to be transmitted to the cloud based analytics system 204 for analysis and processing.

In one aspect, the surgical hub 206 comprises a modular communication hub 203 and storage device 248 for storing parameters and status of a device 235 that has the ability to determine when and how often data can be shared with a cloud based analytics system 204, the transmission rate and the type of data that can be shared with the cloud based analytics system 204. In another aspect, the cloud analytics system 204 communicates new operational parameters for the surgical hub 206 and surgical devices 235 coupled to the surgical hub 206. A cloud based analytics system 204 is described in commonly-owned U.S. Provisional Patent Application Ser. No. 62/611,340, filed Dec. 28, 2017, and titled CLOUD-BASED MEDICAL ANALYTICS, which is incorporated herein by reference in its entirety.

In one aspect, a device 235 coupled to a local surgical hub 206 determines when and what data is transmitted to the cloud analytics system 204 for company analytic improvements. In one example, the available local data storage capacity remaining in the storage device 248 controls the timing and rate at which the data is exported. In another example, user defined inclusion or exclusion of specific users, patients, or procedures allows data sets to be included for analysis or automatically deleted. In yet another example, detected network down time or available capacity determines the time of uploads or communications.

In another aspect, transmission of data for diagnosis of failure modes is keyed by specific incidents. For example, user defined failure of a device, instrument, or tool within a procedure initiates archiving and transmission of data recorded with respect to that instrument for failure modes analysis. Further, when a failure event is identified, all the data surrounding the event is archived and packaged for sending back for predictive informatics (PI) analytics. Data that is part of a PI failure is flagged for storage and maintenance until either the hospital or the cloud based analytics system releases the hold on the data.

Catastrophic failures of instruments may initiate an automatic archive and submission of data for implications analysis. Detection of a counterfeit component or adapter on an original equipment manufacturer (OEM) device initiates documentation of the component and recording of the results and outcome of its use.

Figure 80:
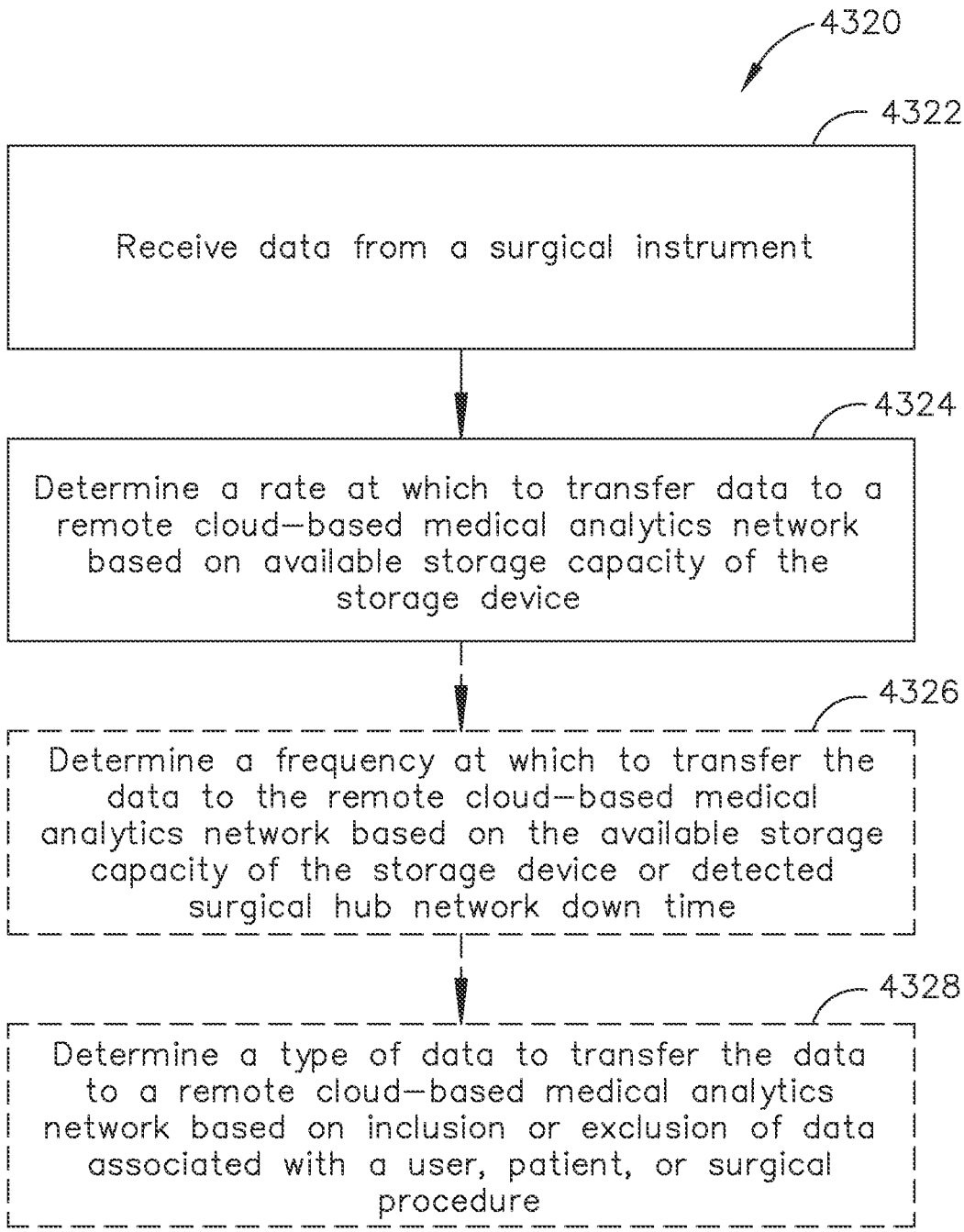
FIG. 80 is a logic flow diagram of a process depicting a control program or a logic configuration for determining rate, frequency, and type of data to transfer to a remote cloud-based analytics network, in accordance with at least one aspect of the present disclosure.

FIG. 80 is a logic flow diagram 4320 of a process depicting a control program or a logic configuration for determining rate, frequency, and type of data to transfer to a remote cloud-based analytics network, according to one aspect of the present disclosure. With reference to FIGS. 1-80, in one aspect, the present disclosure provides a surgical hub 206 comprising a storage device 248, a processor 244 coupled to the storage device 248, and a memory 249 coupled to the processor 244. The memory 249 stores instructions executable by the processor 244 to receive 4322 data from a surgical instrument 235, determine 4324 a rate at which to transfer the data to a remote cloud-based medical analytics network 204 based on available storage capacity of the storage device 248. Optionally, the memory 249 stores instructions executable by the processor 244 to determine 4326 a frequency at which to transfer the data to the remote cloud-based medical analytics network 204 based on the available storage capacity of the storage device 248. Optionally, the memory 249 stores instructions executable by the processor 244 to detect surgical hub network downtime and to determine 4326 a frequency at which to transfer the data to the remote cloud-based medical analytics network 204 based on the detected surgical hub network 206 down time. Optionally, the memory 249 stores instructions executable by the processor 244 to determine 4328 a type of data to transfer the data to a remote cloud-based medical analytics network 204 based on inclusion or exclusion of data associated with a users, patient, or surgical procedure.

In another aspect, the memory 249 stores instructions executable by the processor 244 to receive new operational parameters for the surgical hub 206 or the surgical instrument 235.

In one aspect, the present disclosure provides a surgical hub, comprising: a processor; and a memory coupled to the processor, the memory storing instructions executable by the processor to: interrogate a surgical instrument, wherein the surgical instrument is a first source of patient data; retrieve a first data set from the surgical instrument, wherein the first data set is associated with a patient and a surgical procedure; interrogate a medical imaging device, wherein the medical imaging device is a second source of patient data; retrieve a second data set from the medical imaging device, wherein the second data set is associated with the patient and an outcome of the surgical procedure; associate the first and second data sets by a key; and transmit the associated first and second data sets to remote network outside of the surgical hub. The present disclosure further provides, a surgical hub wherein the memory stores instructions executable by the processor to: retrieve the first data set using the key; anonymize the first data set by removing its association with the patient; retrieve the second data set using the key; anonymize the second data set by removing its association with the patient; pair the anonymized first and second data sets; and determine success rates of surgical procedures grouped by the surgical procedure based on the anonymized paired first and second data sets. The present disclosure further provides a surgical hub, wherein the memory stores instructions executable by the processor to: retrieve the anonymized first data set; retrieve the anonymized second data set; and reintegrate the anonymized first and second data sets using the key. The present disclosure further provides a surgical hub, wherein the first and second data sets define first and second data payloads in respective first and second data packets. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub, comprising: a processor; and a memory coupled to the processor, the memory storing instructions executable by the processor to: receive a first data packet from a first source, the first data packet comprising a first preamble, a first data payload, a source of the first data payload, and a first encryption certificate, wherein the first preamble defines the first data payload and the first encryption certificate verifies the authenticity of the first data packet; receive a second data packet from a second source, the second data packet comprising a second preamble, a second data payload, a source of the second data payload, and a second encryption certificate, wherein the second preamble defines the second data payload and the second encryption certificate verifies the authenticity of the second data packet; associate the first and second data packets; and generate a third data packet comprising the first and second data payloads. The present disclosure further provides a surgical hub, wherein the memory stores instructions executable by the processor to: determine that a data payload is from a new source; verify the new source of the data payload; and alter a data collection process at the surgical hub to receive subsequent data packets from the new source. The present disclosure further provides a surgical, wherein the memory stores instructions executable by the processor to associate the first and second data packets based on a key. The present disclosure further provides a surgical hub, wherein the memory stores instructions executable by the processor to anonymize the data payload of the third data packet. The present disclosure further provides a surgical hub, wherein the memory stores instructions executable by the processor to receive an anonymized third data packet and reintegrate the anonymized third data packet into the first and second data packets using the key. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub configured to communicate with a surgical instrument, the surgical hub comprising: a processor; and a memory coupled to the processor, the memory storing instructions executable by the processor to: receive a first data set associated with a surgical procedure, wherein the first data set is generated at a first time; receive a second data set associated with the efficacy of the surgical procedure, wherein the second data set is generated at a second time, wherein the second time is separate and distinct from the first time; anonymize the first and second data sets by removing information that identifies a patient, a surgery, or a scheduled time of the surgery; and store the first and second anonymized data sets to generate a data pair grouped by surgery. The present disclosure further provides a surgical hub, wherein the memory stores instructions executable by the processor to reconstruct a series of chronological events based on the data pair. The present disclosure further provides a surgical hub, wherein the memory stores instructions executable by the processor to reconstruct a series of coupled but unconstrained data sets based on the data pair. The present disclosure further provides a surgical hub, wherein the memory stores instructions executable by the processor to: encrypt the data pair; define a backup format for the data pair; and mirror the data pair to a cloud storage device. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub comprising: a storage device; a processor coupled to the storage device; and a memory coupled to the processor, the memory storing instructions executable by the processor to: receive data from a surgical instrument; determine a rate at which to transfer the data to a remote cloud-based medical analytics network based on available storage capacity of the storage device; determine a frequency at which to transfer the data to the remote cloud-based medical analytics network based on the available storage capacity of the storage device or detected surgical hub network down time; and determine a type of data to transfer the data to a remote cloud-based medical analytics network based on inclusion or exclusion of data associated with a users, patient, or surgical procedure. The present disclosure further provides a surgical hub, wherein the memory stores instructions executable by the processor to receive new operational parameters for the surgical hub or the surgical instrument. The present disclosure further provides a control circuit to perform any one of the above recited functions and/or a non-transitory computer readable medium storing computer readable instructions which, when executed, causes a machine to perform any one of the above recited functions.

In another aspect, the present disclosure provides a surgical hub comprising: a control configured to: receive data from a surgical instrument; determine a rate at which to transfer the data to a remote cloud-based medical analytics network based on available storage capacity of the storage device; determine a frequency at which to transfer the data to the remote cloud-based medical analytics network based on the available storage capacity of the storage device or detected surgical hub network down time; and determine a type of data to transfer the data to a remote cloud-based medical analytics network based on inclusion or exclusion of data associated with a users, patient, or surgical procedure.

Surgical Hub Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 81:
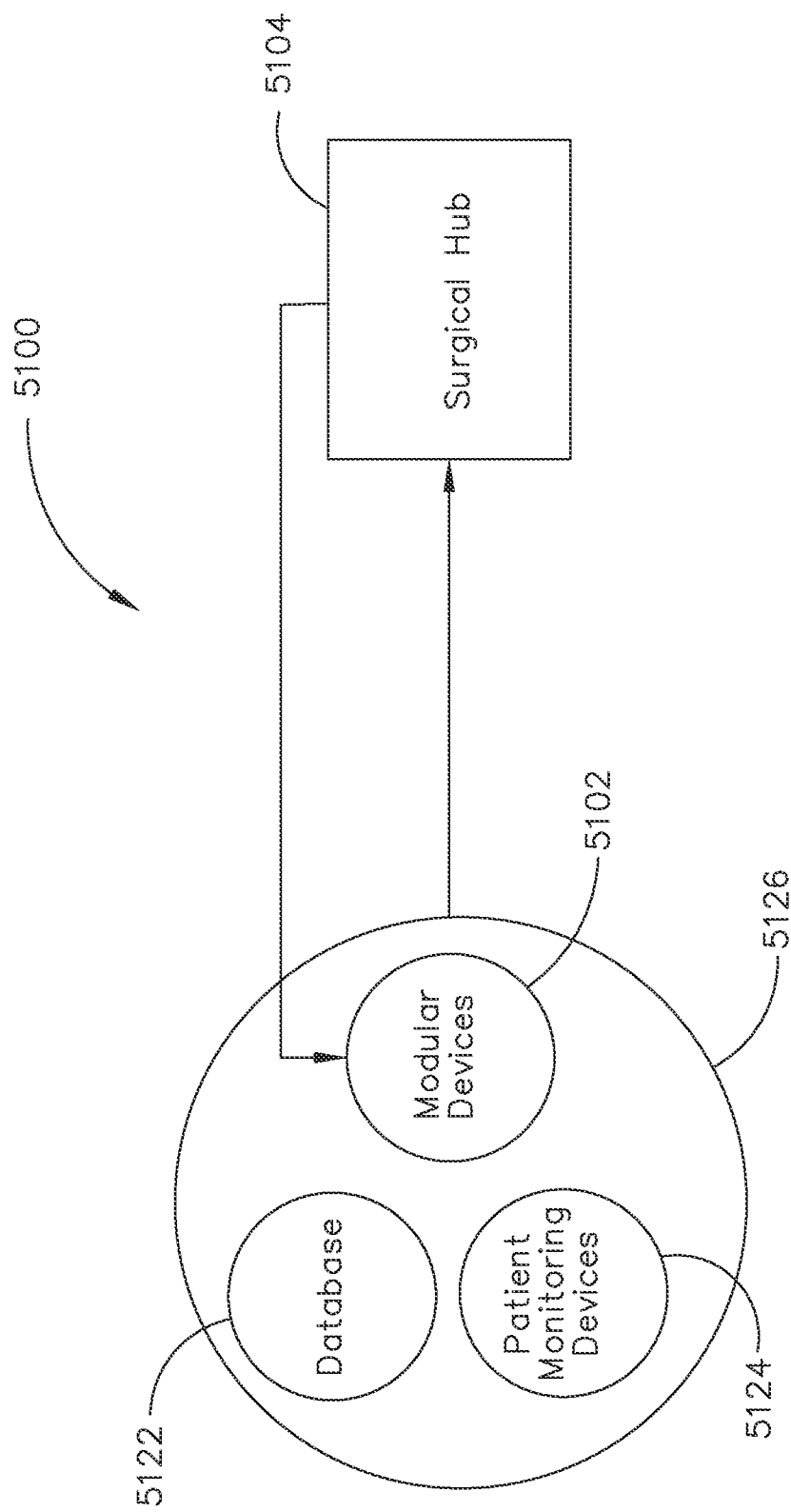
FIG. 81 illustrates a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 81 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiogram monitor). The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view.

The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure (scanned by the scanner 5132 depicted in FIG. 85B, for example) and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

Figure 82A:
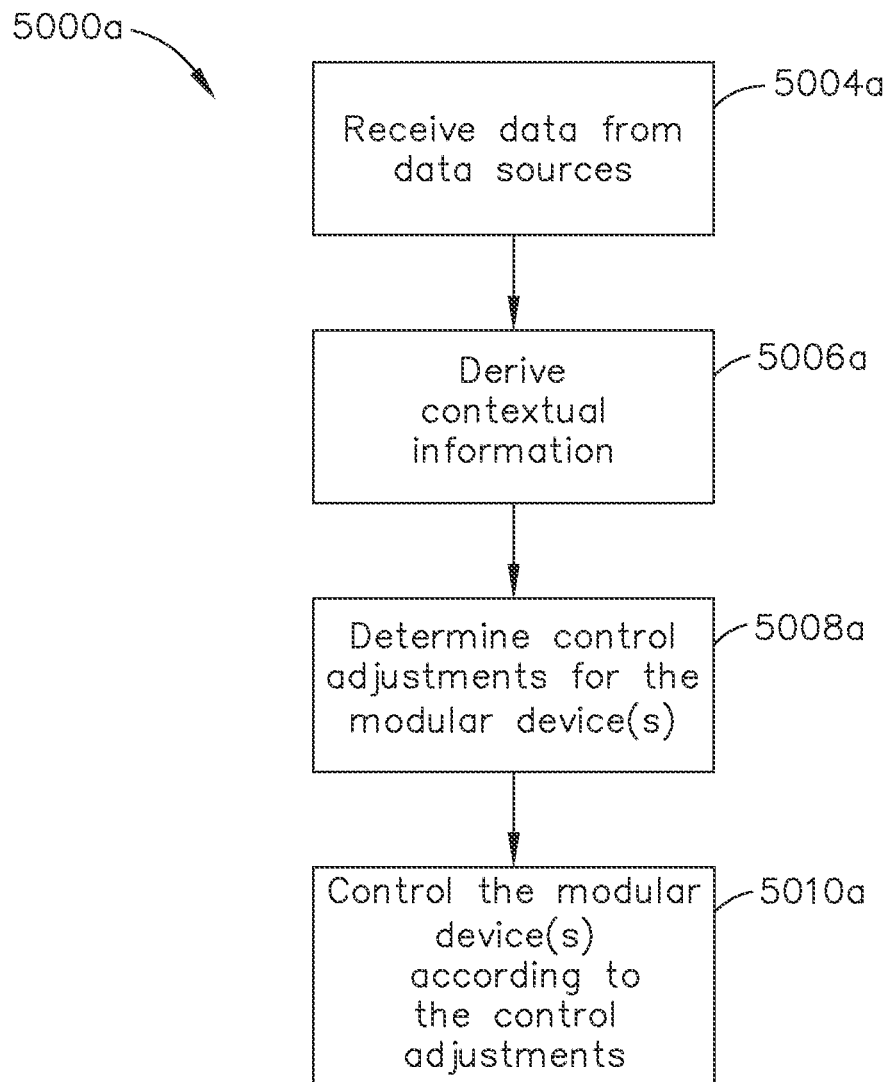
FIG. 82A illustrates a logic flow diagram of a process for controlling a modular device according to contextual information derived from received data, in accordance with at least one aspect of the present disclosure.

FIG. 82A illustrates a logic flow diagram of a process 5000a for controlling a modular device 5102 according to contextual information derived from received data, in accordance with at least one aspect of the present disclosure. In other words, a situationally aware surgical hub 5104 can execute the process 5000a to determine appropriate control adjustments for modular devices 5102 paired with the surgical hub 5104 before, during, or after a surgical procedure as dictated by the context of the surgical procedure. In the following description of the process 5000a, reference should also be made to FIG. 81. In one exemplification, the process 5000a can be executed by a control circuit of a surgical hub 5104, as depicted in FIG. 10 (processor 244). In another exemplification, the process 5000a can be executed by a cloud computing system 104, as depicted in FIG. 1. In yet another exemplification, the process 5000a can be executed by a distributed computing system including at least one of the aforementioned cloud computing system 104 and/or a control circuit of a surgical hub 5104 in combination with a control circuit of a modular device, such as the microcontroller 461 of the surgical instrument depicted in FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5000a will be described as being executed by the control circuit of a surgical hub 5104; however, it should be understood that the description of the process 5000a encompasses all of the aforementioned exemplifications.

Figure 85A:
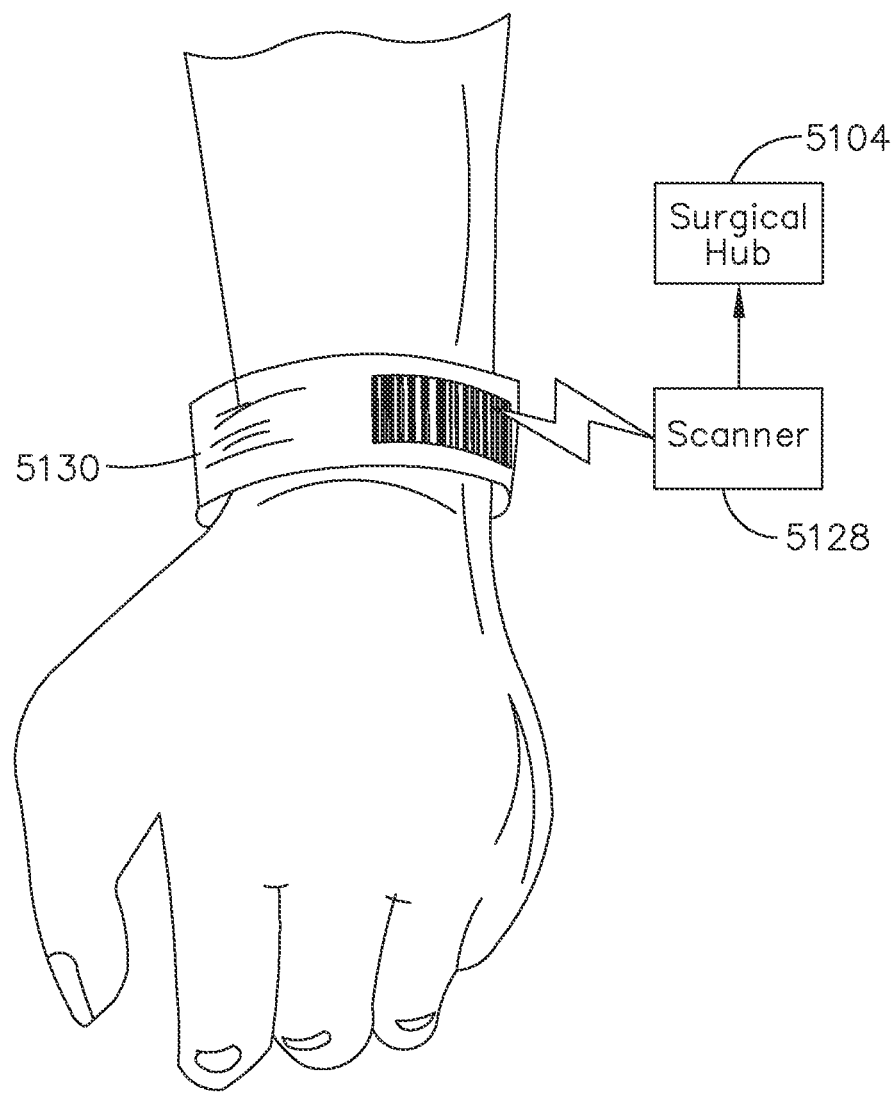
FIG. 85A illustrates a scanner coupled to a surgical hub for scanning a patient wristband, in accordance with at least one aspect of the present disclosure.

The control circuit of the surgical hub 5104 executing the process 5000a receives 5004a data from one or more data sources 5126 to which the surgical hub 5104 is communicably connected. The data sources 5126 include, for example, databases 5122, patient monitoring devices 5124, and modular devices 5102. In one exemplification, the databases 5122 can include a patient EMR database associated with the medical facility at which the surgical procedure is being performed. The data received 5004a from the data sources 5126 can include perioperative data, which includes preoperative data, intraoperative data, and/or postoperative data associated with the given surgical procedure. The data received 5004a from the databases 5122 can include the type of surgical procedure being performed or the patient's medical history (e.g., medical conditions that may or may not be the subject of the present surgical procedure). In one exemplification depicted in FIG. 83A, the control circuit can receive 5004a the patient or surgical procedure data by querying the patient EMR database with a unique identifier associated with the patient. The surgical hub 5104 can receive the unique identifier from, for example, a scanner 5128 for scanning the patient's wristband 5130 encoding the unique identifier associated with the patient when the patient enters the operating theater, as depicted in FIG. 85A. In one exemplification, the patient monitoring devices 5124 include BP monitors, EKG monitors, and other such devices that are configured to monitor one or more parameters associated with a patient. As with the modular devices 5102, the patient monitoring devices 5124 can be paired with the surgical hub 5104 such that the surgical hub 5104 receives 5004a data therefrom. In one exemplification, the data received 5004*a* from the modular devices 5102 that are paired with (i.e., communicably coupled to) the surgical hub 5104 includes, for example, activation data (i.e., whether the device is powered on or in use), data of the internal state of the modular device 5102 (e.g., force to fire or force to close for a surgical cutting and stapling device, pressure differential for an insufflator or smoke evacuator, or energy level for an RF or ultrasonic surgical instrument), or patient data (e.g., tissue type, tissue thickness, tissue mechanical properties, respiration rate, or airway volume).

As the process 5000*a* continues, the control circuit of the surgical hub 5104 can derive 5006*a* contextual information from the data received 5004*a* from the data sources 5126. The contextual information can include, for example, the type of procedure being performed, the particular step being performed in the surgical procedure, the patient's state (e.g., whether the patient is under anesthesia or whether the patient is in the operating room), or the type of tissue being operated on. The control circuit can derive 5006*a* contextual information according to data from ether an individual data source 5126 or combinations of data sources 5126. Further, the control circuit can derive 5006*a* contextual information according to, for example, the type(s) of data that it receives, the order in which the data is received, or particular measurements or values associated with the data. For example, if the control circuit receives data from an RF generator indicating that the RF generator has been activated, the control circuit could thus infer that the RF electrosurgical instrument is now in use and that the surgeon is or will be performing a step of the surgical procedure utilizing the particular instrument. As another example, if the control circuit receives data indicating that a laparoscope imaging device has been activated and an ultrasonic generator is subsequently activated, the control circuit can infer that the surgeon is on a laparoscopic dissection step of the surgical procedure due to the order in which the events occurred. As yet another example, if the control circuit receives data from a ventilator indicating that the patient's respiration is below a particular rate, then the control circuit can determine that the patient is under anesthesia.

The control circuit can then determine 5008*a* what control adjustments are necessary (if any) for one or more modular devices 5102 according to the derived 5006*a* contextual information. After determining 5008*a* the control adjustments, the control circuit of the surgical hub 5104 can then control 5010*a* the modular devices according to the control adjustments (if the control circuit determined 5008*a* that any were necessary). For example, if the control circuit determines that an arthroscopic procedure is being performed and that the next step in the procedure utilizes an RF or ultrasonic surgical instrument in a liquid environment, the control circuit can determine 5008*a* that a control adjustment for the generator of the RF or ultrasonic surgical instrument is necessary to preemptively increase the energy output of the instrument (because such instruments require increased energy in liquid environments to maintain their effectiveness). The control circuit can then control 5010*a* the generator and/or the RF or ultrasonic surgical instrument accordingly by causing the generator to increase its output and/or causing the RF or ultrasonic surgical instrument to increase the energy drawn from the generator. The control circuit can control 5010*a* the modular devices 5102 according to the determined 5008*a* control adjustment by, for example, transmitting the control adjustments to the particular modular device to update the modular device's 5102 programming. In another exemplification wherein the modular device(s) 5102 and the surgical hub 5104 are executing a distributed computing architecture, the control circuit can control 5010*a* the modular device 5102 according to the determined 5008*a* control adjustments by updating the distributed program.

Figure 82B:
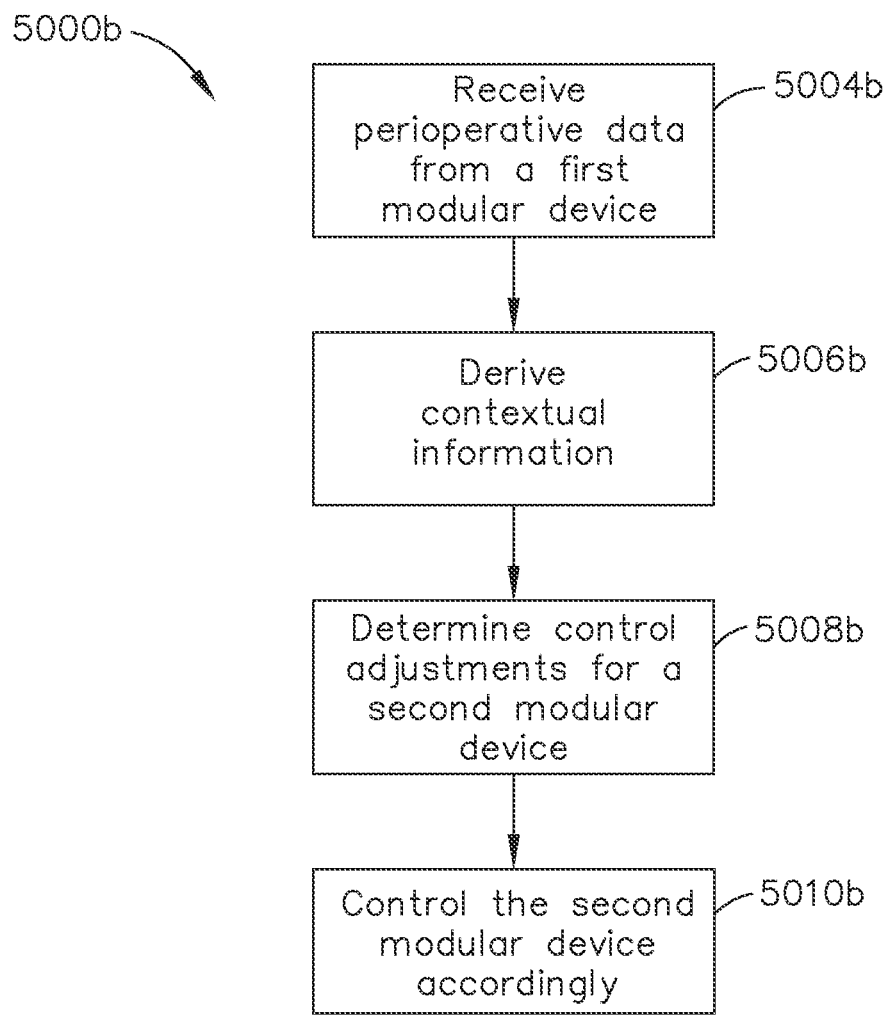
FIG. 82B illustrates a logic flow diagram of a process for controlling a second modular device according to contextual information derived from perioperative data received from a first modular device, in accordance with at least one aspect of the present disclosure.
Figure 82C:
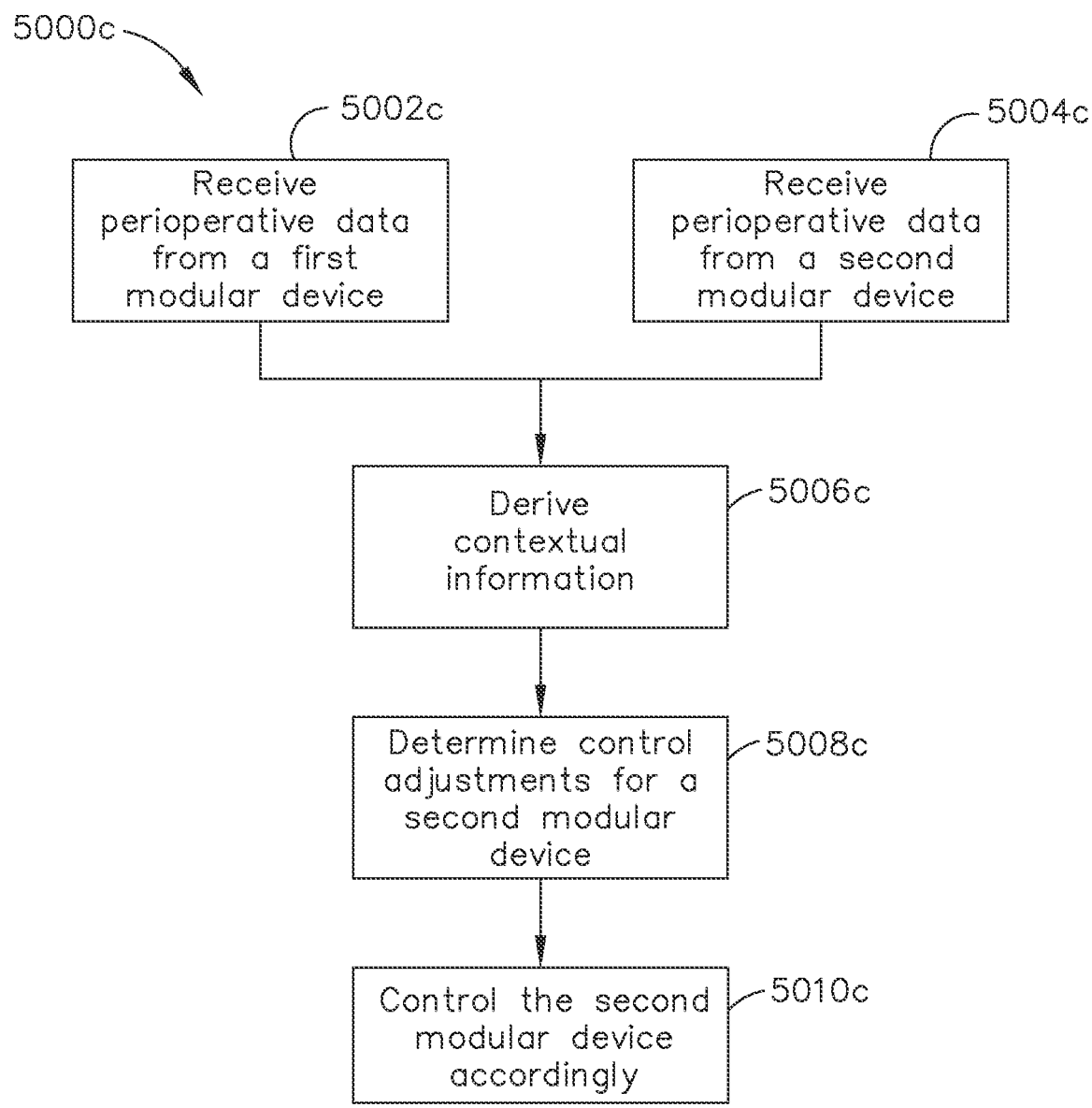
FIG. 82C illustrates a logic flow diagram of a process for controlling a second modular device according to contextual information derived from perioperative data received from a first modular device and the second modular device, in accordance with at least one aspect of the present disclosure.
Figure 82D:
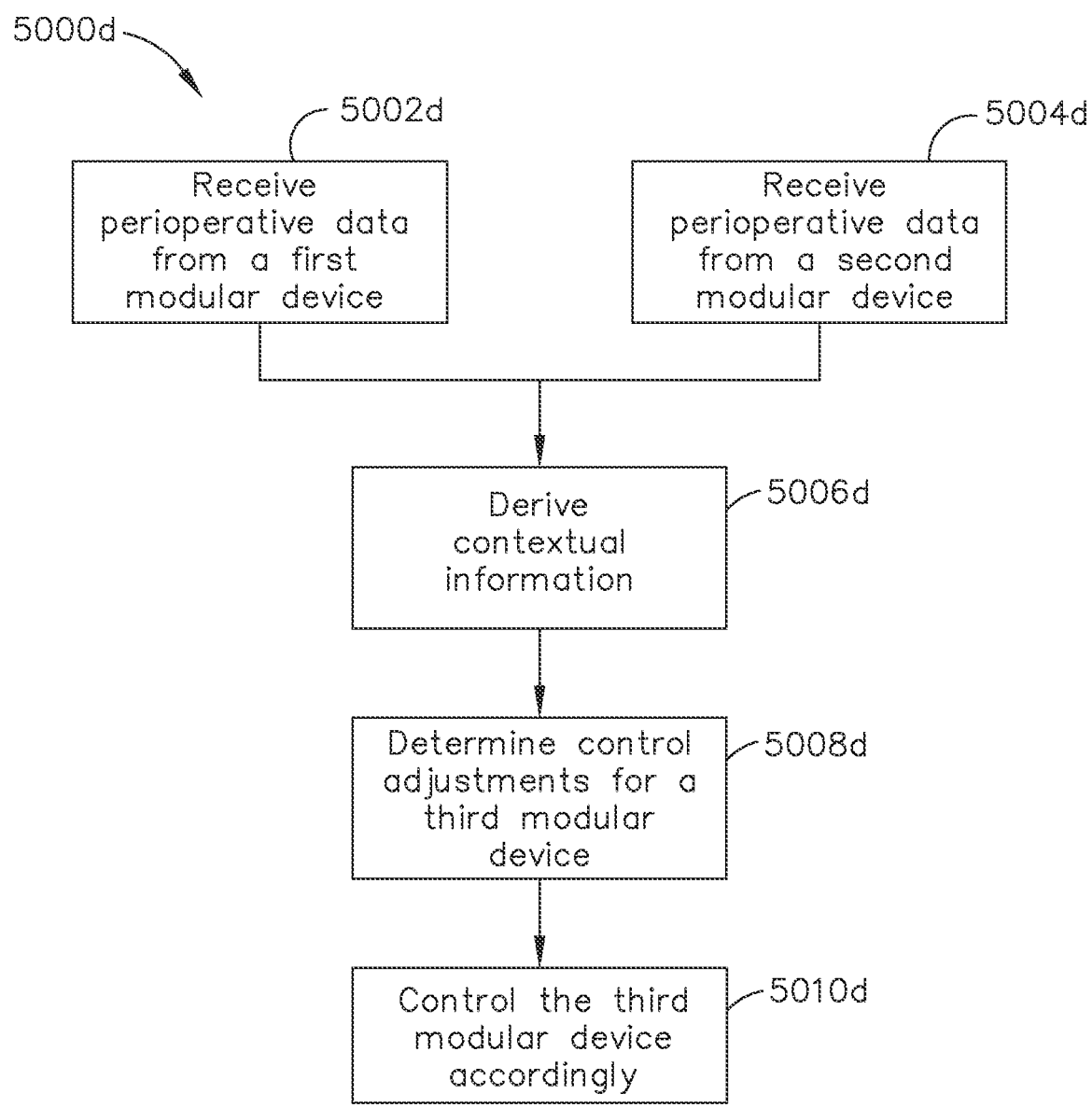
FIG. 82D illustrates a logic flow diagram of a process for controlling a third modular device according to contextual information derived from perioperative data received from a first modular device and a second modular device, in accordance with at least one aspect of the present disclosure.

FIGS. 82B-D illustrate representative implementations of the process 5000*a* depicted in FIG. 82A. As with the process 5000*a* depicted in FIG. 82A, the processes illustrated in FIGS. 82B-D can, in one exemplification, be executed by a control circuit of the surgical hub 5104. FIG. 82B illustrates a logic flow diagram of a process 5000*b* for controlling a second modular device according to contextual information derived from perioperative data received from a first modular device, in accordance with at least one aspect of the present disclosure. In the illustrated exemplification, the control circuit of the surgical hub 5104 receives 5004*b* perioperative data from a first modular device. The perioperative data can include, for example, data regarding the modular device 5102 itself (e.g., pressure differential, motor current, internal forces, or motor torque) or data regarding the patient with which the modular device 5102 is being utilized (e.g., tissue properties, respiration rate, airway volume, or laparoscopic image data). After receiving 5004*b* the perioperative data, the control circuit of the surgical hub 5104 derives 5006*b* contextual information from the perioperative data. The contextual information can include, for example, the procedure type, the step of the procedure being performed, or the status of the patient. The control circuit of the surgical hub 5104 then determines 5008*b* control adjustments for a second modular device based upon the derived 5006*b* contextual information and then controls 5010*b* the second modular device accordingly. For example, the surgical hub 5104 can receive 5004*b* perioperative data from a ventilator indicating that the patient's lung has been deflated, derive 5006*b* the contextual information therefrom that the subsequent step in the particular procedure type utilizes a medical imaging device (e.g., a scope), determine 5008*b* that the medical imaging device should be activated and set to a particular magnification, and then control 5010*b* the medical imaging device accordingly.

FIG. 82C illustrates a logic flow diagram of a process 5000*c* for controlling a second modular device according to contextual information derived from perioperative data received from a first modular device and the second modular device. In the illustrated exemplification, the control circuit of the surgical hub 5104 receives 5002*c* perioperative data from a first modular device and receives 5004*c* perioperative data from a second modular device. After receiving 5002*c*, 5004*c* the perioperative data, the control circuit of the surgical hub 5104 derives 5006*c* contextual information from the perioperative data. The control circuit of the surgical hub 5104 then determines 5008*c* control adjustments for the second modular device based upon the derived 5006*c* contextual information and then controls 5010*c* the second modular device accordingly. For example, the surgical hub 5104 can receive 5002*c* perioperative data from a RF electrosurgical instrument indicating that the instrument has been fired, receive 5004*c* perioperative data from a surgical stapling instrument indicating that the instrument has been fired, derive 5006*c* the contextual information therefrom that the subsequent step in the particular procedure type requires that the surgical stapling instrument be fired with a particular force (because the optimal force to fire can vary according to the tissue type being operated on), determine 5008*c* the particular force thresholds that should be applied to the surgical stapling instrument, and then control 5010*c* the surgical stapling instrument accordingly.

FIG. 82D illustrates a logic flow diagram of a process 5000d for controlling a third modular device according to contextual information derived from perioperative data received from a first modular device and a second modular device. In the illustrated exemplification, the control circuit of the surgical hub 5104 receives 5002d perioperative data from a first modular device and receives 5004d perioperative data from a second modular device. After receiving 5002d, 5004d the perioperative data, the control circuit of the surgical hub 5104 derives 5006d contextual information from the perioperative data. The control circuit of the surgical hub 5104 then determines 5008d control adjustments for a third modular device based upon the derived 5006d contextual information and then controls 5010d the third modular device accordingly. For example, the surgical hub 5104 can receive 5002d, 5004d perioperative data from an insufflator and a medical imaging device indicating that both devices have been activated and paired to the surgical hub 5104, derive 5006d the contextual information therefrom that a video-assisted thoracoscopic surgery (VATS) procedure is being performed, determine 5008d that the displays connected to the surgical hub 5104 should be set to display particular views or information associated with the procedure type, and then control 5010d the displays accordingly.

Figure 83A:
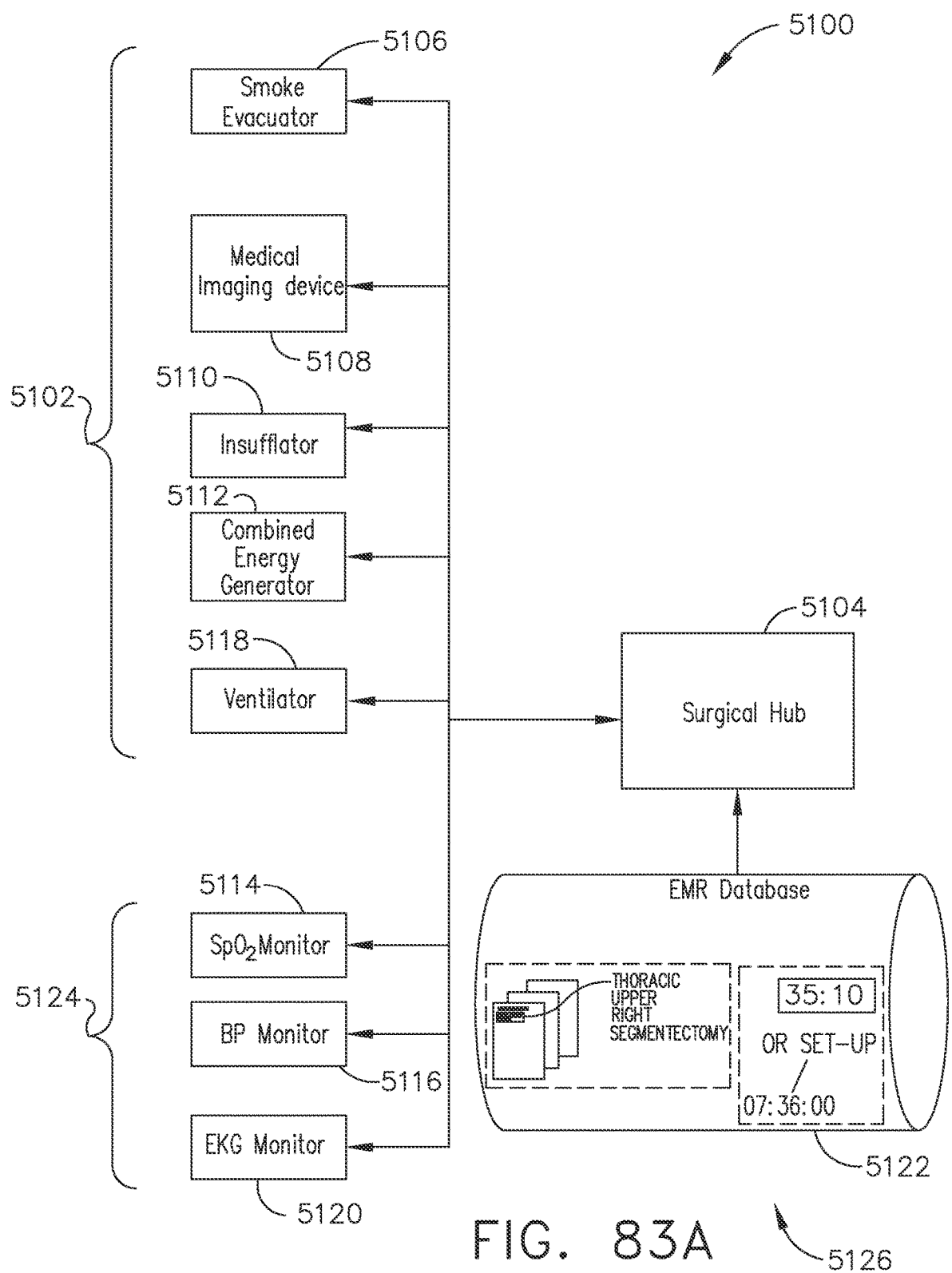
FIG. 83A illustrates a diagram of a surgical hub communicably coupled to a particular set of modular devices and an Electronic Medical Record (EMR) database, in accordance with at least one aspect of the present disclosure.

FIG. 83A illustrates a diagram of a surgical system 5100 including a surgical hub 5104 communicably coupled to a particular set of data sources 5126. A surgical hub 5104 including a situational awareness system can utilize the data received from the data sources 5126 to derive contextual information regarding the surgical procedure that the surgical hub 5104, the modular devices 5102 paired to the surgical hub 5104, and the patient monitoring devices 5124 paired to the surgical hub 5104 are being utilized in connection with. The inferences (i.e., contextual information) that one exemplification of the situational awareness system can derive from the particular set of data sources 5126 are depicted in dashed boxes extending from the data source(s) 5126 from which they are derived. The contextual information derived from the data sources 5126 can include, for example, what step of the surgical procedure is being performed, whether and how a particular modular device 5102 is being used, and the patient's condition.

In the example illustrated in FIG. 83A, the data sources 5126 include a database 5122, a variety of modular devices 5102, and a variety of patient monitoring devices 5124. The surgical hub 5104 can be connected to various databases 5122 to retrieve therefrom data regarding the surgical procedure that is being performed or is to be performed. In one exemplification of the surgical system 5100, the databases 5122 include an EMR database of a hospital. The data that can be received by the situational awareness system of the surgical hub 5104 from the databases 5122 can include, for example, start (or setup) time or operational information regarding the procedure (e.g., a segmentectomy in the upper right portion of the thoracic cavity). The surgical hub 5104 can derive contextual information regarding the surgical procedure from this data alone or from the combination of this data and data from other data sources 5126.

The surgical hub 5104 can also be connected to (i.e., paired with) a variety of patient monitoring devices 5124. In one exemplification of the surgical system 5100, the patient monitoring devices 5124 that can be paired with the surgical hub 5104 can include a pulse oximeter ($SpO_2$ monitor) 5114, a BP monitor 5116, and an EKG monitor 5120. The perioperative data that can be received by the situational awareness system of the surgical hub 5104 from the patient monitoring devices 5124 can include, for example, the patient's oxygen saturation, blood pressure, heart rate, and other physiological parameters. The contextual information that can be derived by the surgical hub 5104 from the perioperative data transmitted by the patient monitoring devices 5124 can include, for example, whether the patient is located in the operating theater or under anesthesia. The surgical hub 5104 can derive these inferences from data from the patient monitoring devices 5124 alone or in combination with data from other data sources 5126 (e.g., the ventilator 5118).

The surgical hub 5104 can also be connected to (i.e., paired with) a variety of modular devices 5102. In one exemplification of the surgical system 5100, the modular devices 5102 that can be paired with the surgical hub 5104 can include a smoke evacuator 5106, a medical imaging device 5108, an insufflator 5110, a combined energy generator 5112 (for powering an ultrasonic surgical instrument and/or an RF electrosurgical instrument), and a ventilator 5118.

The medical imaging device 5108 includes an optical component and an image sensor that generates image data. The optical component includes a lens or a light source, for example. The image sensor includes a charge-coupled device (CCD) or a complementary metal-oxide-semiconductor (CMOS), for example. In various exemplifications, the medical imaging device 5108 includes an endoscope, a laparoscope, a thoracoscope, and other such imaging devices. Various additional components of the medical imaging device 5108 are described above. The perioperative data that can be received by the surgical hub 5104 from the medical imaging device 5108 can include, for example, whether the medical imaging device 5108 is activated and a video or image feed. The contextual information that can be derived by the surgical hub 5104 from the perioperative data transmitted by the medical imaging device 5108 can include, for example, whether the procedure is a VATS procedure (based on whether the medical imaging device 5108 is activated or paired to the surgical hub 5104 at the beginning or during the course of the procedure). Furthermore, the image or video data from the medical imaging device 5108 (or the data stream representing the video for a digital medical imaging device 5108) can processed by a pattern recognition system or a machine learning system to recognize features (e.g., organs or tissue types) in the field of view (FOV) of the medical imaging device 5108, for example. The contextual information that can be derived by the surgical hub 5104 from the recognized features can include, for example, what type of surgical procedure (or step thereof) is being performed, what organ is being operated on, or what body cavity is being operated in.

Figure 83B:
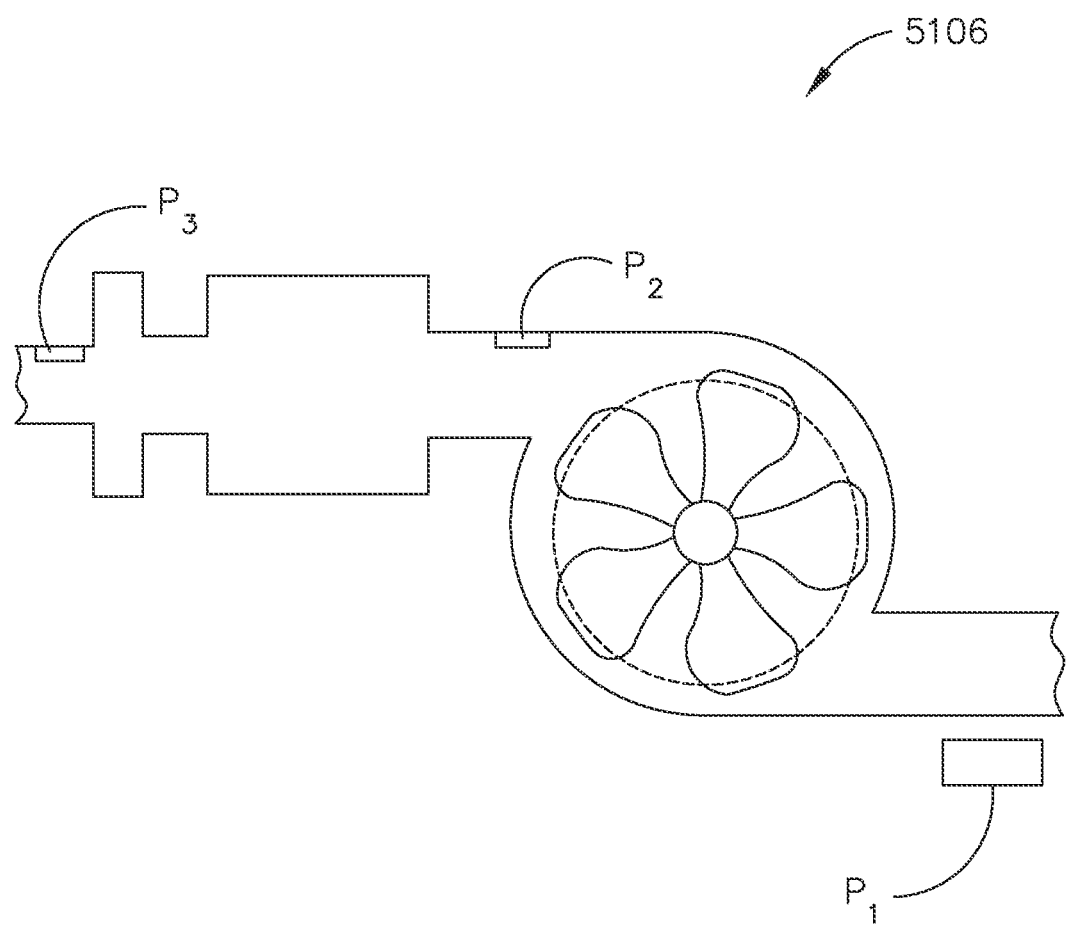
FIG. 83B illustrates a diagram of a smoke evacuator including pressure sensors, in accordance with at least one aspect of the present disclosure.

In one exemplification depicted in FIG. 83B, the smoke evacuator 5106 includes a first pressure sensor $P_1$ configured to detect the ambient pressure in the operating theater, a second pressure sensor $P_2$ configured to detect the internal downstream pressure (i.e., the pressure downstream from the inlet), and a third pressure sensor $P_3$ configured to detect the internal upstream pressure. In one exemplification, the first pressure sensor $P_1$ can be a separate component from the smoke evacuator 5106 or otherwise located externally to the smoke evacuator 5106. The perioperative data that can be received by the surgical hub 5104 from the smoke evacuator 5106 can include, for example, whether the smoke evacuator 5106 is activated, pressure readings from each of the sensors $P_1$, $P_2$, $P_3$, and pressure differentials between pairs of the sensors $P_1$, $P_2$, $P_3$. The perioperative data can also include, for example, the type of tissue being operated on (based upon the chemical composition of the smoke being evacuated) and the amount of tissue being cut. The contextual information that can be derived by the surgical hub 5104 from the perioperative data transmitted by the smoke evacuator 5106 can include, for example, whether the procedure being performed is utilizing insufflation. The smoke evacuator 5106 perioperative data can indicate whether the procedure is utilizing insufflation according to the pressure differential between $P_3$ and $P_1$. If the pressure sensed by $P_3$ is greater than the pressure sensed by $P_1$ (i.e., $P_3-P_1>0$), then the body cavity to which the smoke evacuator 5106 is connected is insufflated. If the pressure sensed by $P_3$ is equal to the pressure sensed by $P_1$ (i.e., $P_3-P_1=0$), then the body cavity is not insufflated. When the body cavity is not insufflated, the procedure may be an open type of procedure.

The insufflator 5110 can include, for example, pressure sensors and current sensors configured to detect internal parameters of the insufflator 5110. The perioperative data that can be received by the surgical hub 5104 from the insufflator can include, for example, whether the insufflator 5110 is activated and the electrical current drawn by the insufflator's 5110 pump. The surgical hub 5104 can determine whether the insufflator 5110 is activated by, for example, directly detecting whether the device is powered on, detecting whether there is a pressure differential between an ambient pressure sensor and a pressure sensor internal to the surgical site, or detecting whether the pressure valves of the insufflator 5110 are pressurized (activated) or non-pressurized (deactivated). The contextual information that can be derived by the surgical hub 5104 from the perioperative data transmitted by the insufflator 5110 can include, for example, the type of procedure being performed (e.g., insufflation is utilized in laparoscopic procedures, but not arthroscopic procedures) and what body cavity is being operated in (e.g., insufflation is utilized in the abdominal cavity, but not in the thoracic cavity). In some exemplifications, the inferences derived from the perioperative data received from different modular devices 5102 can be utilized to confirm and/or increase the confidence of prior inferences. For example, if the surgical hub 5104 determines that the procedure is utilizing insufflation because the insufflator 5110 is activated, the surgical hub 5104 can then confirm that inference by detecting whether the perioperative data from the smoke evacuator 5106 likewise indicates that the body cavity is insufflated.

The combined energy generator 5112 supplies energy to one or more ultrasonic surgical instruments or RF electrosurgical instruments connected thereto. The perioperative data that can be received by the surgical hub 5104 from the combined energy generator 5112 can include, for example, the mode that the combined energy generator 5112 is set to (e.g., a vessel sealing mode or a cutting/coagulation mode). The contextual information that can be derived by the surgical hub 5104 from the perioperative data transmitted by the combined energy generator 5112 can include, for example, the surgical procedural type (based on the number and types of surgical instruments that are connected to the energy generator 5112) and the procedural step that is being performed (because the particular surgical instrument being utilized or the particular order in which the surgical instruments are utilized corresponds to different steps of the surgical procedure). Further, the inferences derived by the surgical hub 5104 can depend upon inferences and/or perioperative data previously received by the surgical hub 5104. Once the surgical hub 5104 has determined the general category or specific type of surgical procedure being performed, the surgical hub 5104 can determine or retrieve an expected sequence of steps for the surgical procedure and then track the surgeon's progression through the surgical procedure by comparing the detected sequence in which the surgical instruments are utilized relative to the expected sequence.

The perioperative data that can be received by the surgical hub 5104 from the ventilator 5118 can include, for example, the respiration rate and airway volume of the patient. The contextual information that can be derived by the surgical hub 5104 from the perioperative data transmitted by the ventilator 5118 can include, for example, whether the patient is under anesthesia and whether the patient's lung is deflated. In some exemplifications, certain contextual information can be inferred by the surgical hub 5104 based on combinations of perioperative data from multiple data sources 5126. For example, the situational awareness system of the surgical hub 5104 can be configured to infer that the patient is under anesthesia when the respiration rate detected by the ventilator 5118, the blood pressure detected by the BP monitor 5116, and the heart rate detected by the EKG monitor 5120 fall below particular thresholds. For certain contextual information, the surgical hub 5104 can be configured to only derive a particular inference when the perioperative data from a certain number or all of the relevant data sources 5126 satisfy the conditions for the inference.

As can be seen from the particular exemplified surgical system 5100, the situational awareness system of a surgical hub 5104 can derive a variety of contextual information regarding the surgical procedure being performed from the data sources 5126. The surgical hub 5104 can utilize the derived contextual information to control the modular devices 5102 and make further inferences about the surgical procedure in combination with data from other data sources 5126. It should be noted that the inferences depicted in FIG. 83A and described in connection with the depicted surgical system 5100 are merely exemplary and should not be interpreted as limiting in any way. Furthermore, the surgical hub 5104 can be configured to derive a variety of other inferences from the same (or different) modular devices 5102 and/or patient monitoring devices 5124. In other exemplifications, a variety of other modular devices 5102 and/or patient monitoring devices 5124 can be paired to the surgical hub 5104 in the operating theater and data received from those additional modular devices 5102 and/or patient monitoring devices 5124 can be utilized by the surgical hub 5104 to derive the same or different contextual information about the particular surgical procedure being performed.

Figure 84A:
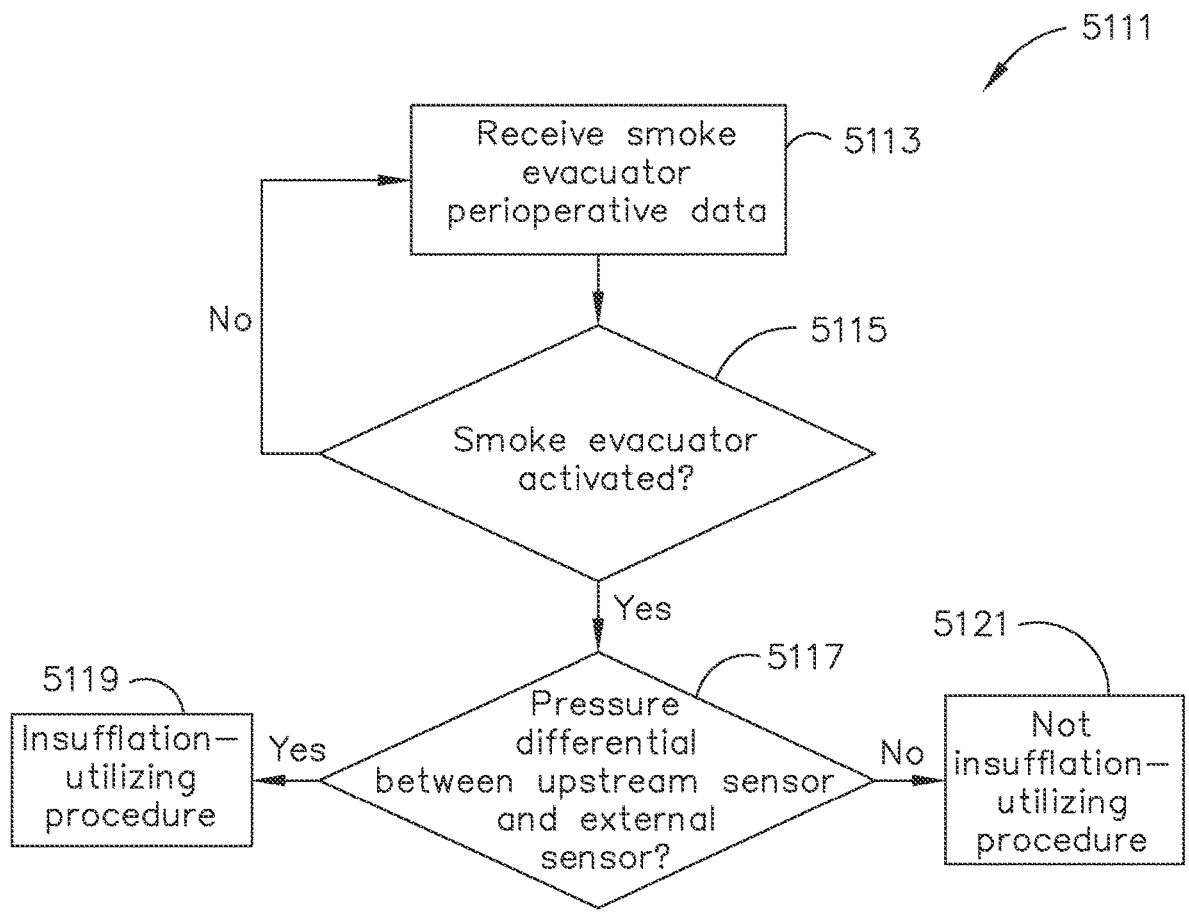
FIG. 84A illustrates a logic flow diagram of a process for determining a procedure type according to smoke evacuator perioperative data, in accordance with at least one aspect of the present disclosure.
Figure 84B:
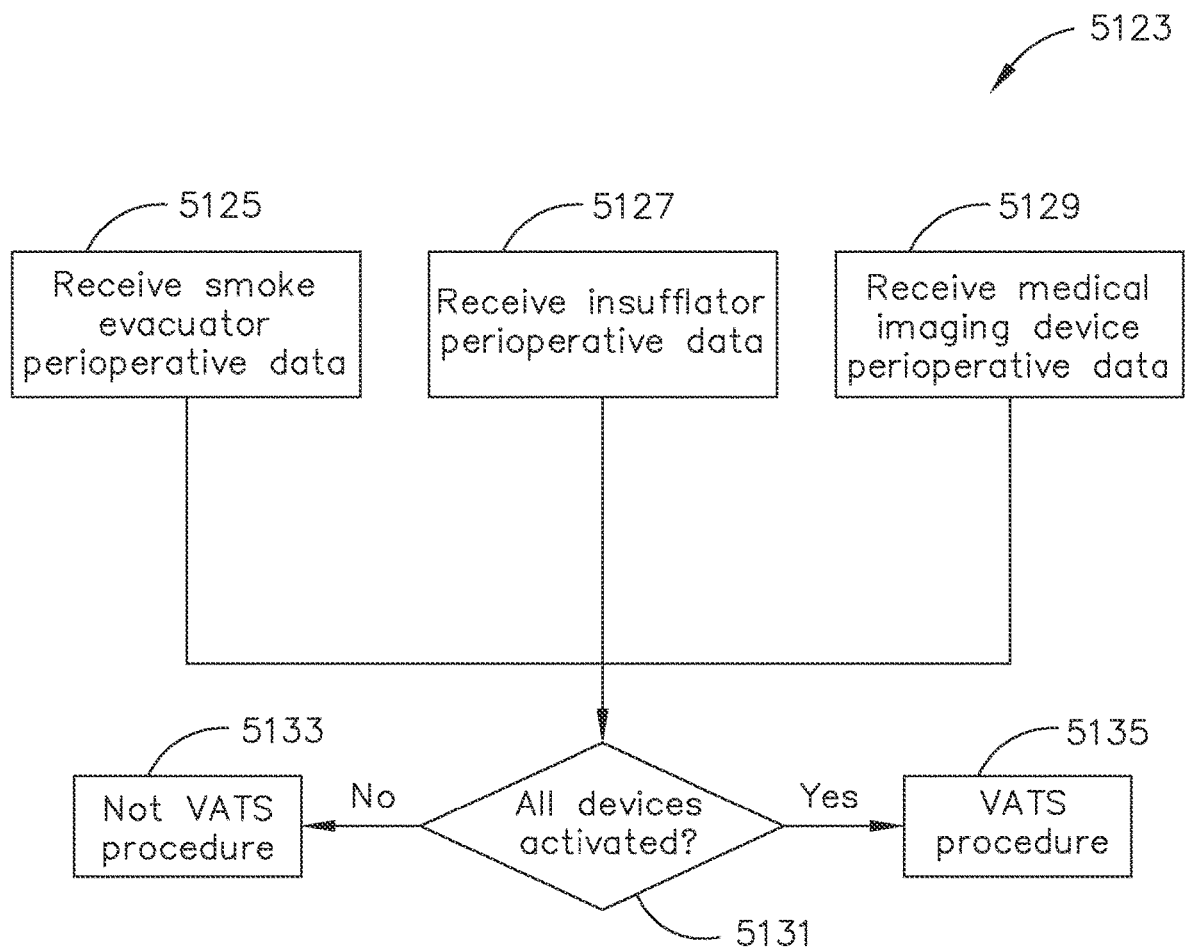
FIG. 84B illustrates a logic flow diagram of a process for determining a procedure type according to smoke evacuator, insufflator, and medical imaging device perioperative data, in accordance with at least one aspect of the present disclosure.
Figure 84C:
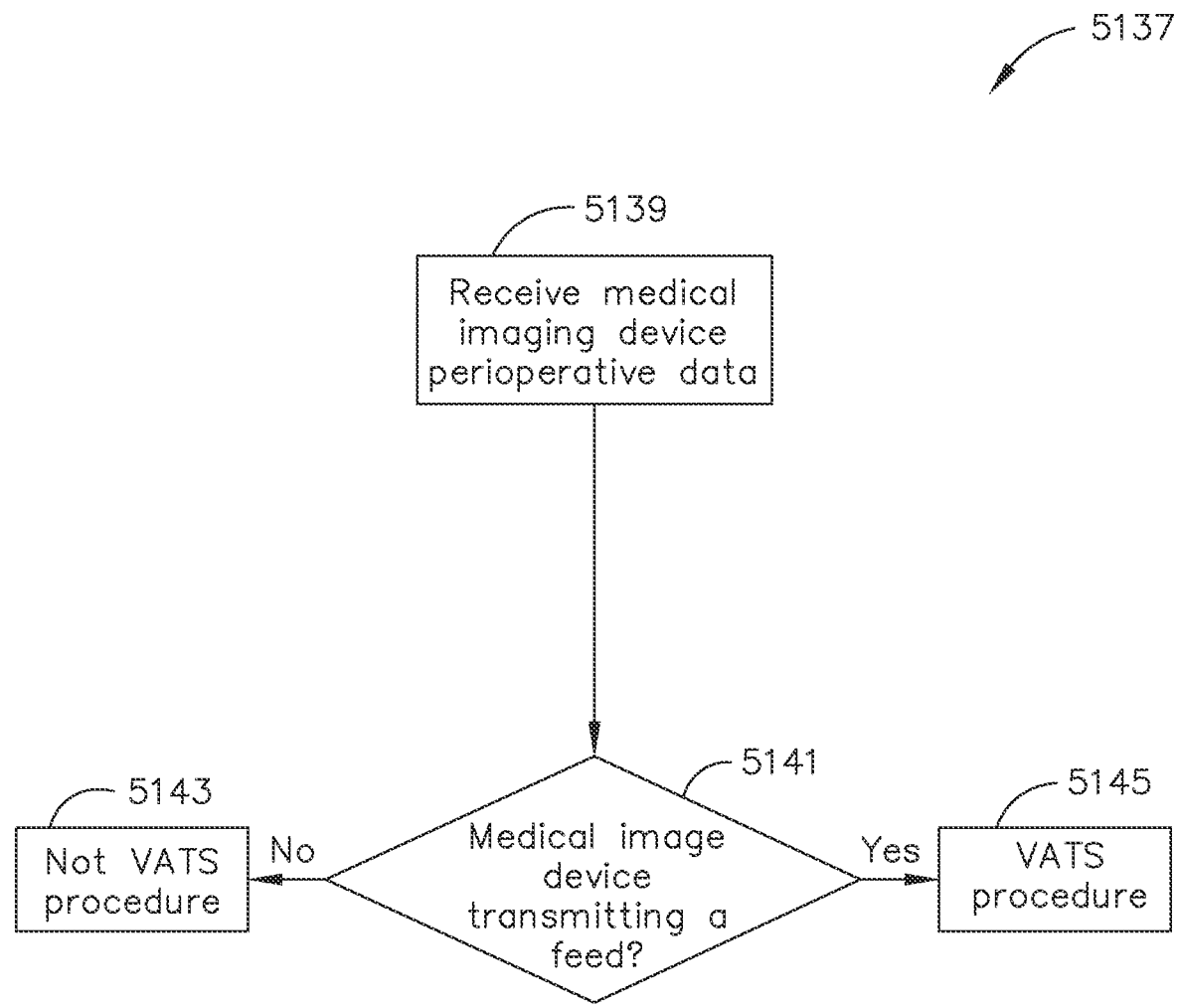
FIG. 84C illustrates a logic flow diagram of a process for determining a procedure type according to medical imaging device perioperative data, in accordance with at least one aspect of the present disclosure.
Figure 84D:
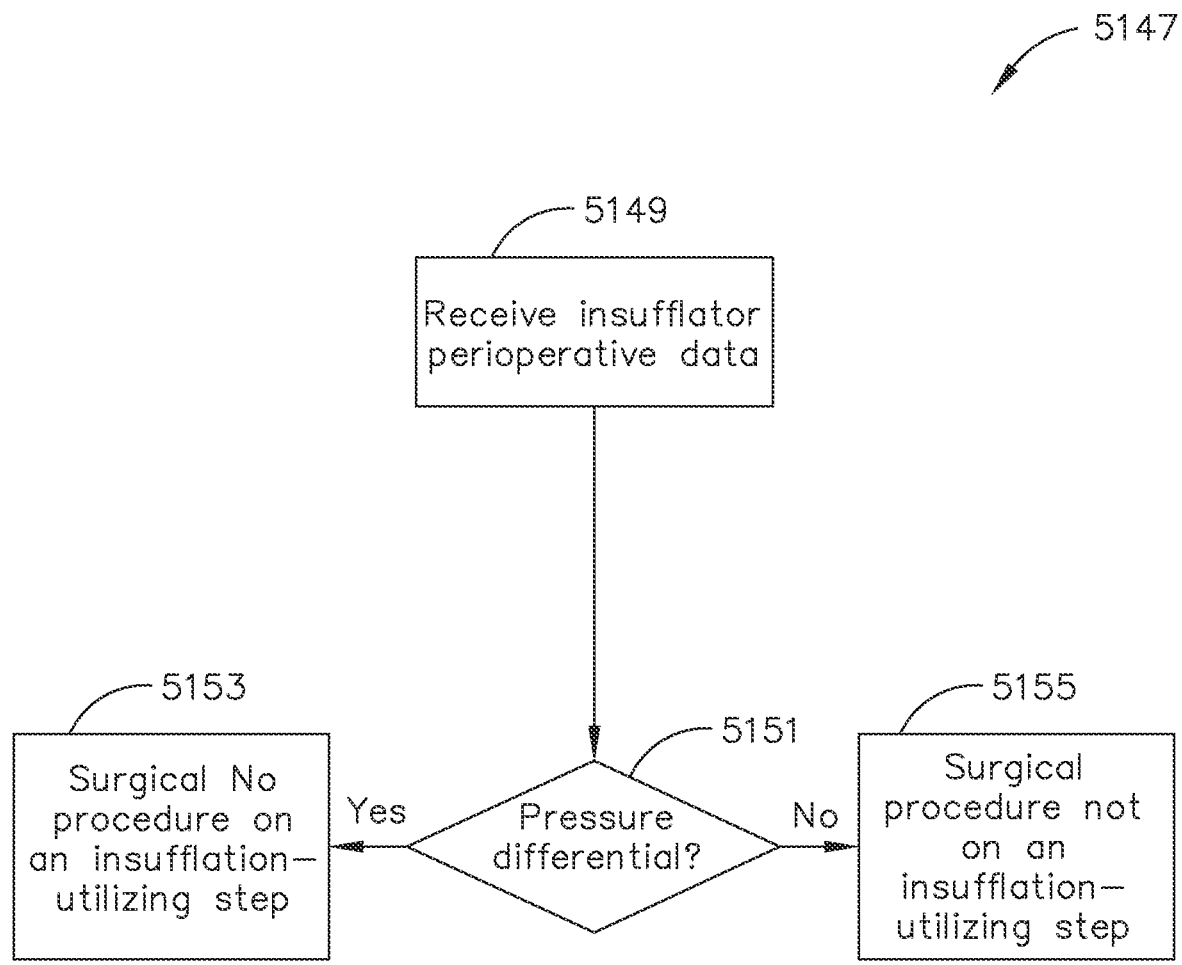
FIG. 84D illustrates a logic flow diagram of a process for determining a procedural step according to insufflator perioperative data, in accordance with at least one aspect of the present disclosure.
Figure 84E:
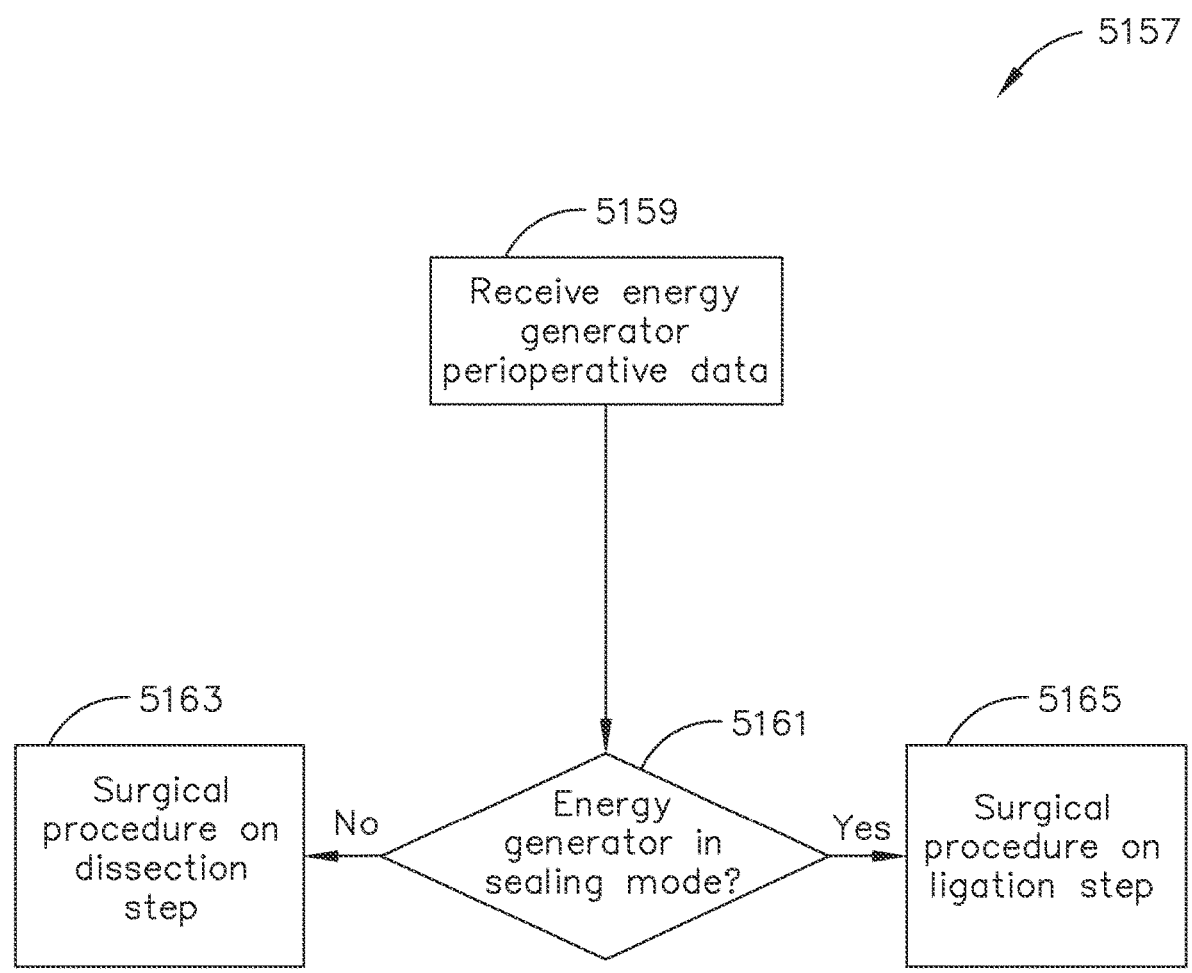
FIG. 84E illustrates a logic flow diagram of a process for determining a procedural step according to energy generator perioperative data, in accordance with at least one aspect of the present disclosure.
Figure 84F:
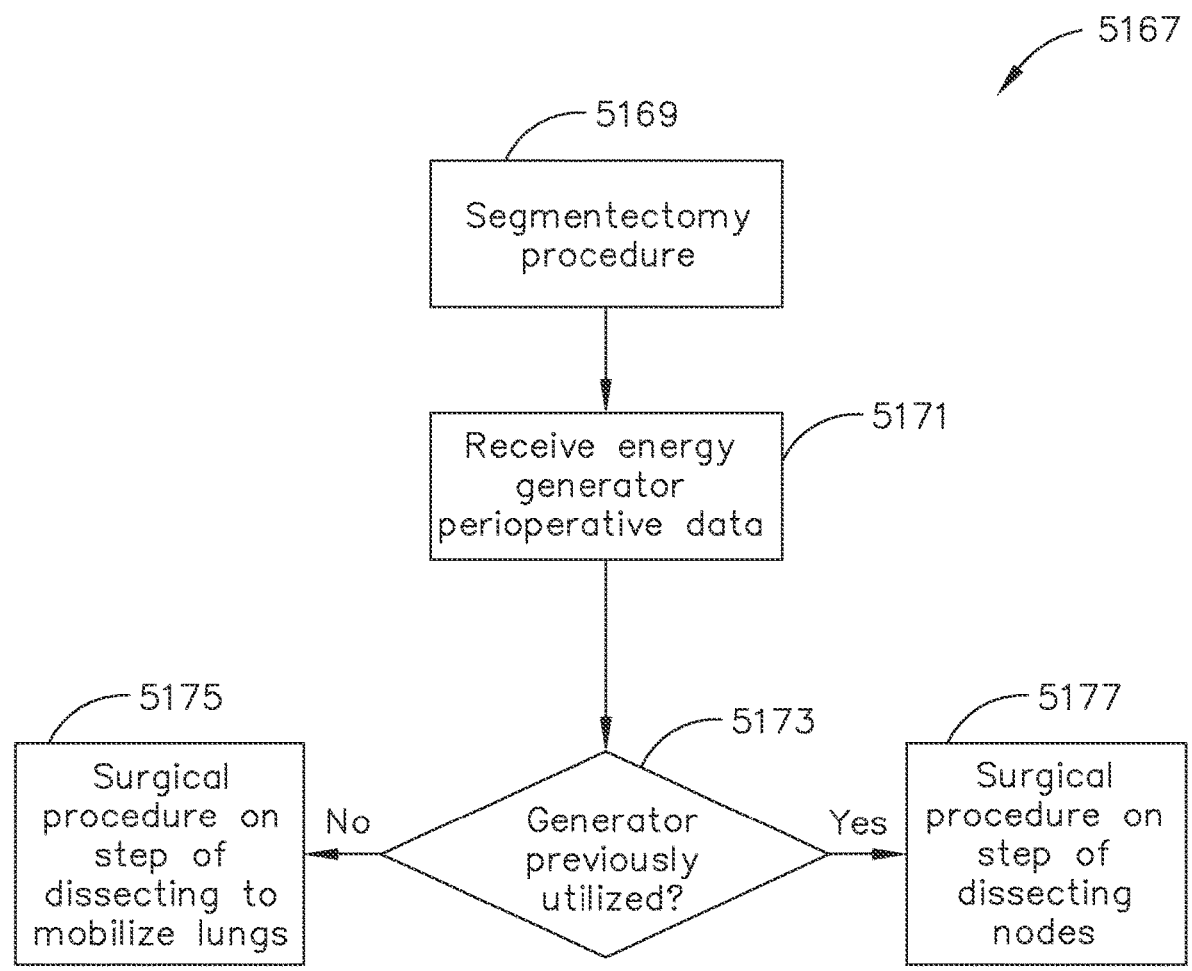
FIG. 84F illustrates a logic flow diagram of a process for determining a procedural step according to energy generator perioperative data, in accordance with at least one aspect of the present disclosure.
Figure 84G:
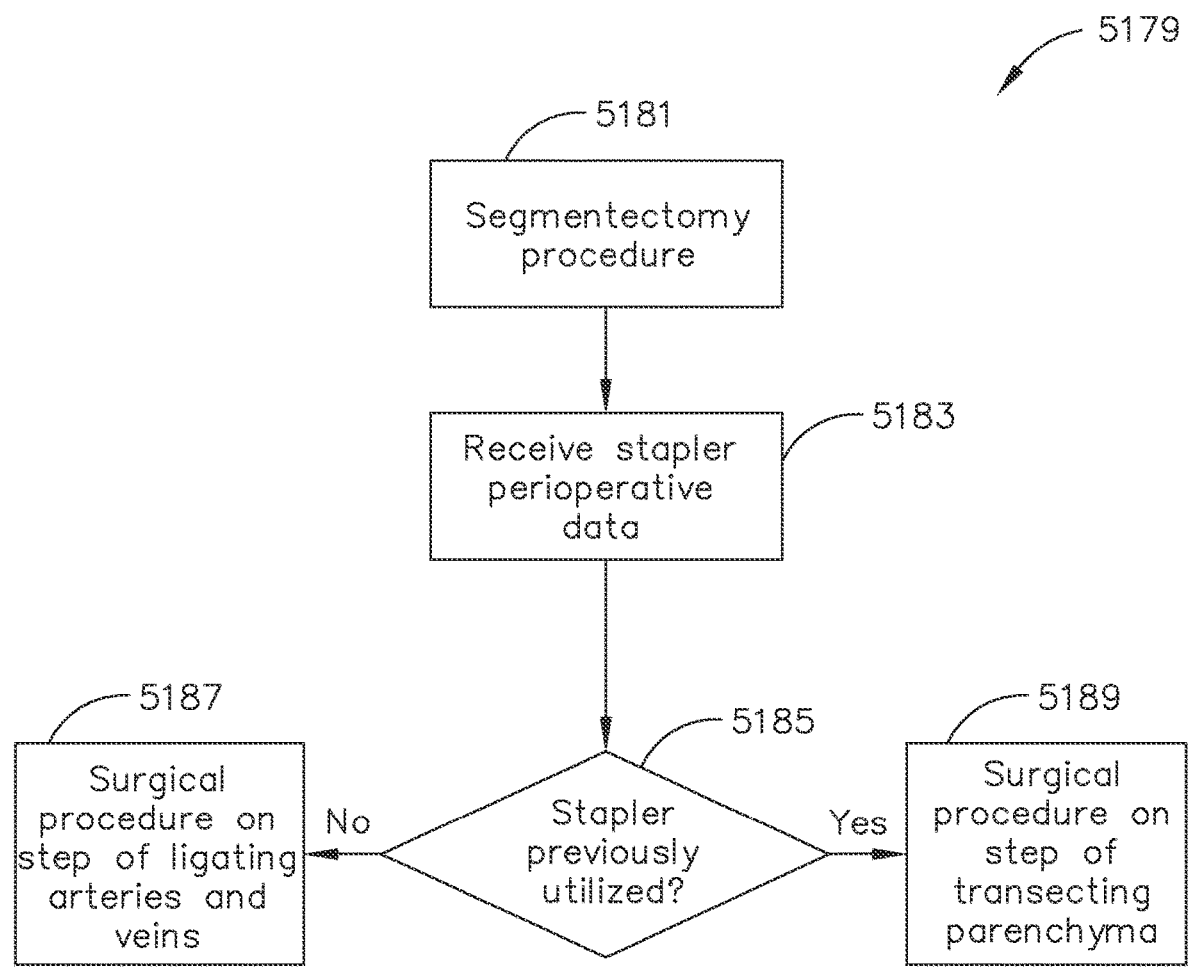
FIG. 84G illustrates a logic flow diagram of a process for determining a procedural step according to stapler perioperative data, in accordance with at least one aspect of the present disclosure.
Figure 84H:
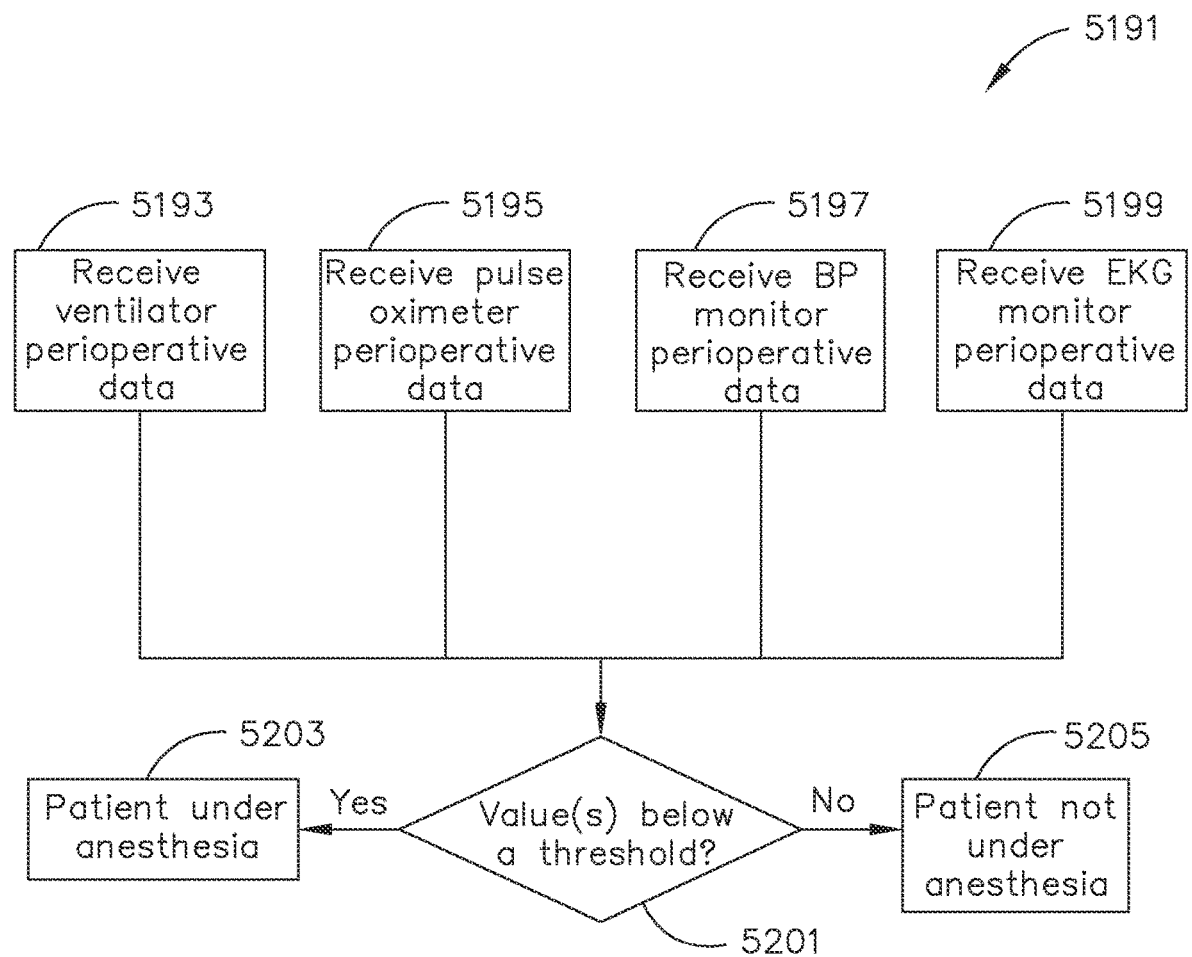
FIG. 84H illustrates a logic flow diagram of a process for determining a patient status according to ventilator, pulse oximeter, blood pressure monitor, and/or EKG monitor perioperative data, in accordance with at least one aspect of the present disclosure.
Figure 841:
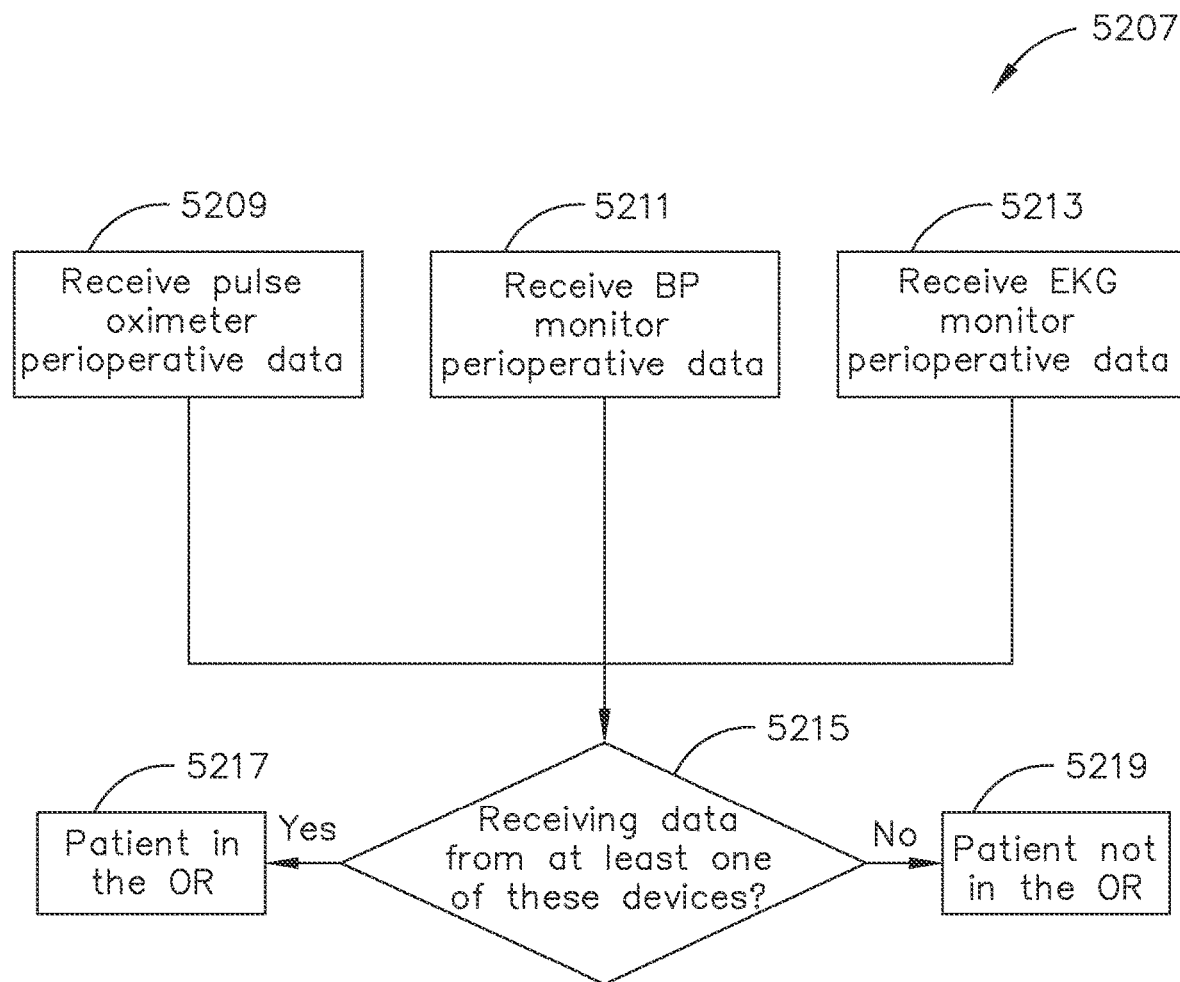
Figure 84J:
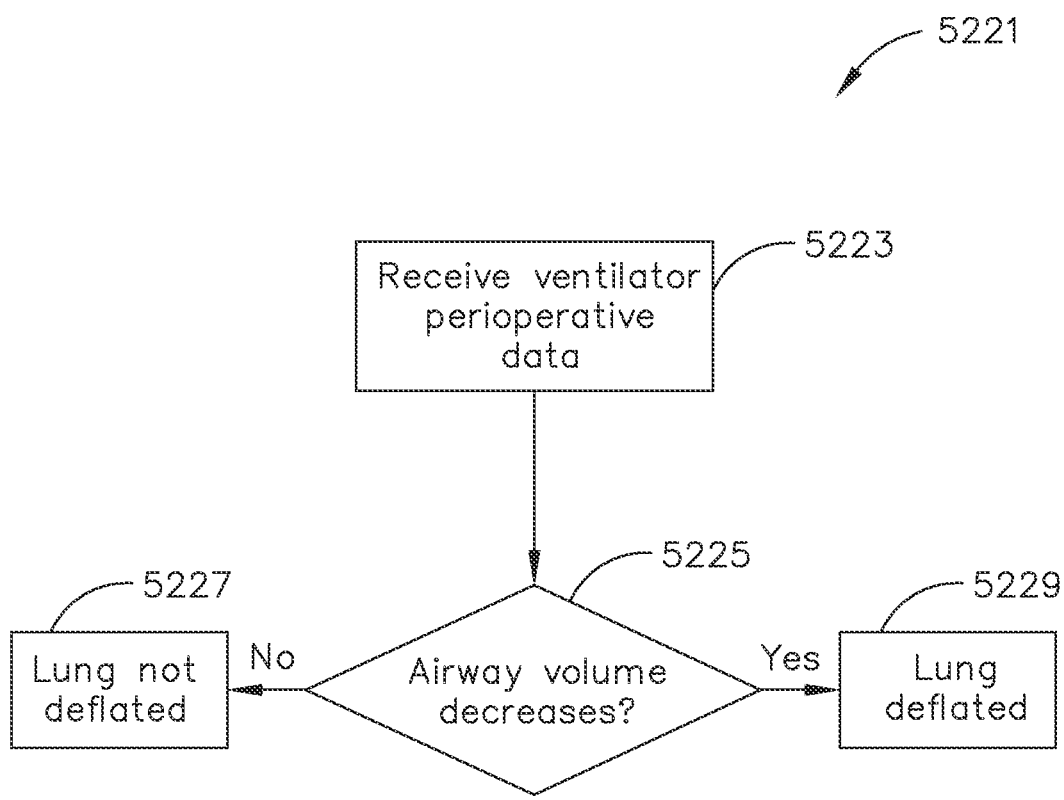
FIG. 84J illustrates a logic flow diagram of a process for determining a patient status according to ventilator perioperative data, in accordance with at least one aspect of the present disclosure.

FIGS. 84A-J depict logic flow diagrams for processes for deriving 5008*a*, 5008*b*, 5008*c*, 5008*d* contextual information from various modular devices, as discussed above with respect to the processes 5000*a*, 5000*b*, 5000*c*, 5000*d* depicted in FIGS. 82A-D. The derived contextual information in FIGS. 84A-C is the procedure type. The procedure type can correspond to techniques utilized during the surgical procedure (e.g., a segmentectomy), the category of the surgical procedure (e.g., a laparoscopic procedure), the organ, tissue, or other structure being operated on, and other characteristics to identify the particular surgical procedure (e.g., the procedure utilizes insufflation). The derived contextual information in FIGS. 84D-G is the particular step of the surgical procedure that is being performed. The derived contextual information in FIGS. 84H-J is the patient's status. It can be noted that the patient's status can also correspond to the particular step of the surgical procedure that is being performed (e.g., determining that the patient's status has changed from not being under anesthesia to being under anesthesia can indicate that the step of the surgical procedure of placing the patient under anesthesia was carried out by the surgical staff). As with the process 5000a depicted in FIG. 82A, the processes illustrated in FIGS. 84A-J can, in one exemplification, be executed by a control circuit of the surgical hub 5104. In the following descriptions of the processes illustrated in FIGS. 84A-J, reference should also be made to FIG. 83A.

FIG. 84A illustrates a logic flow diagram of a process 5111 for determining a procedure type according to smoke evacuator 5106 perioperative data. In this exemplification, the control circuit of the surgical hub 5104 executing the process 5111 receives 5113 perioperative data from the smoke evacuator 5106 and then determines 5115 whether the smoke evacuator 5106 is activated based thereon. If the smoke evacuator 5106 is not activated, then the process 5111 continues along the NO branch and the control circuit of the surgical hub 5104 continues monitoring for the receipt of smoke evacuator 5106 perioperative data. If the smoke evacuator 5106 is activated, then the process 5111 continues along the YES branch and the control circuit of the surgical hub 5104 determines 5117 whether there is a pressure differential between an internal upstream pressure sensor $P_3$ (FIG. 83B) and an external or ambient pressure sensor $P_1$ (FIG. 83B). If there is a pressure differential (i.e., the internal upstream pressure of the smoke evacuator 5106 is greater then the ambient pressure of the operating theater), then the process 5111 continues along the YES branch and the control circuit determines 5119 that the surgical procedure is an insufflation-utilizing procedure. If there is not a pressure differential, then the process 5111 continues along the NO branch and the control circuit determines 5121 that the surgical procedure is not an insufflation-utilizing procedure.

FIG. 84B illustrates a logic flow diagram of a process 5123 for determining a procedure type according to smoke evacuator 5106, insufflator 5110, and medical imaging device 5108 perioperative data. In this exemplification, the control circuit of the surgical hub 5104 executing the process 5123 receives 5125, 5127, 5129 perioperative data from the smoke evacuator 5106, insufflator 5110, and medical imaging device 5108 and then determines 5131 whether all of the devices are activated or paired with the surgical hub 5104. If all of these devices are not activated or paired with the surgical hub 5104, then the process 5123 continues along the NO branch and the control circuit determines 5133 that the surgical procedure is not a VATS procedure. If all of the aforementioned devices are activated or paired with the surgical hub 5104, then the process 5123 continues along the YES branch and the control circuit determines 5135 that the surgical procedure is a VATS procedure. The control circuit can make this determination based upon the fact that al of these devices are required for a VATS procedure; therefore, if not all of these devices are being utilized in the surgical procedure, it cannot be a VATS procedure.

FIG. 84C illustrates a logic flow diagram of a process 5137 for determining a procedure type according to medical imaging device 5108 perioperative data. In this exemplification, the control circuit of the surgical hub 5104 executing the process 5137 receives 5139 perioperative data from the medical imaging device 5108 and then determines 5141 whether the medical imaging device 5108 is transmitting an image or video feed. If the medical imaging device 5108 is not transmitting an image or video feed, then the process 5137 continues along the NO branch and the control circuit determines 5143 that the surgical procedure is not a VATS procedure. If the medical imaging device 5108 is not transmitting an image or video feed, then the process 5137 continues along the YES branch and the control circuit determines 5145 that the surgical procedure is a VATS procedure. In one exemplification, the control circuit of the surgical hub 5104 can execute the process 5137 depicted in FIG. 84C in combination with the process 5123 depicted in FIG. 84B in order to confirm or increase the confidence in the contextual information derived by both processes 5123, 5137. If there is a discontinuity between the determinations of the processes 5123, 5137 (e.g., the medical imaging device 5108 is transmitting a feed, but not all of the requisite devices are paired with the surgical hub 5104), then the surgical hub 5104 can execute additional processes to come to a final determination that resolves the discontinuities between the processes 5123, 5137 or display an alert or feedback to the surgical staff as to the discontinuity.

FIG. 84D illustrates a logic flow diagram of a process 5147 for determining a procedural step according to insufflator 5110 perioperative data. In this exemplification, the control circuit of the surgical hub 5104 executing the process 5147 receives 5149 perioperative data from the insufflator 5110 and then determines 5151 whether there is a pressure differential between the surgical site and the ambient environment of the operating theater. In one exemplification, the insufflator 5110 perioperative data can include a surgical site pressure (e.g., the intra-abdominal pressure) sensed by a first pressure sensor associated with the insufflator 5110, which can be compared against a pressure sensed by a second pressure sensor configured to detect the ambient pressure. The first pressure sensor can be configured to detect an intra-abdominal pressure between 0-10 mmHg, for example. If there is a pressure differential, then the process 5147 continues along the YES branch and the control circuit determines 5153 that an insufflation-utilizing step of the surgical procedure is being performed. If there is not a pressure differential, then the process 5147 continues along the NO branch and the control circuit determines 5155 that an insufflation-utilizing step of the surgical procedure is not being performed.

FIG. 84E illustrates a logic flow diagram of a process 5157 for determining a procedural step according to energy generator 5112 perioperative data. In this exemplification, the control circuit of the surgical hub 5104 executing the process 5157 receives 5159 perioperative data from the energy generator 5112 and then determines 5161 whether the energy generator 5112 is in the sealing mode. In various exemplifications, the energy generator 5112 can include two modes: a sealing mode corresponding to a first energy level and a cut/coagulation mode corresponding to a second energy level. If the energy generator 5112 is not in the sealing mode, then the process 5157 proceeds along the NO branch and the control circuit determines 5163 that a dissection step of the surgical procedure is being performed. The control circuit can make this determination 5163 because if the energy generator 5112 is not on the sealing mode, then it must thus be on the cut/coagulation mode for energy generators 5112 having two modes of operation. The cut/coagulation mode of the energy generator 5112 corresponds to a dissection procedural step because it provides an appropriate degree of energy to the ultrasonic surgical instrument or RF electrosurgical instrument to dissect tissue. If the energy generator 5112 is in the sealing mode, then the process 5157 proceeds along the YES branch and the control circuit determines 5165 that a ligation step of the surgical procedure is being performed. The sealing mode of the energy generator 5112 corresponds to a ligation procedural step because it provides an appropriate degree of energy to the ultrasonic surgical instrument or RF electrosurgical instrument to ligate vessels.

FIG. 84F illustrates a logic flow diagram of a process 5167 for determining a procedural step according to energy generator 5112 perioperative data. In various aspects, previously received perioperative data and/or previously derived contextual information can also be considered by processes in deriving subsequent contextual information. This allows the situational awareness system of the surgical hub 5104 to derive additional and/or increasingly detailed contextual information about the surgical procedure as the procedure is performed. In this exemplification, the process 5167 determines 5169 that a segmentectomy procedure is being performed. This contextual information can be derived by this process 5167 or other processes based upon other received perioperative data and/or retrieved from a memory. Subsequently, the control circuit receives 5171 perioperative data from the energy generator 5112 indicating that a surgical instrument is being fired and then determines 5173 whether the energy generator 5112 was utilized in a previous step of the procedure to fire the surgical instrument. The control circuit can determine 5173 whether the energy generator 5112 was previously utilized in a prior step of the procedure by retrieving a list of the steps that have been performed in the current surgical procedure from a memory, for example. In such exemplifications, when the surgical hub 5104 determines that a step of the surgical procedure has been performed or completed by the surgical staff, the surgical hub 5104 can update a list of the procedural steps that have been performed, which can then be subsequently retrieved by the control circuit of the surgical hub 5104. In one exemplification, the surgical hub 5104 can distinguish between sequences of firings of the surgical instrument as corresponding to separate steps of the surgical procedure according to the time delay between the sequences of firings, whether any intervening actions were taken or modular devices 5102 were utilized by the surgical staff, or other factors that the situational awareness system can detect. If the energy generator 5112 has not been previously utilized during the course of the segmentectomy procedure, the process 5167 proceeds along the NO branch and the control circuit determines 5175 that the step of dissecting tissue to mobilize the patient's lungs is being performed by the surgical staff. If the energy generator 5112 has been previously utilized during the course of the segmentectomy procedure, the process 5167 proceeds along the YES branch and the control circuit determines 5177 that the step of dissecting nodes is being performed by the surgical staff. An ultrasonic surgical instrument or RF electrosurgical instrument is utilized twice during the course of an example of a segmentectomy procedure (e.g., FIG. 86); therefore, the situational awareness system of the surgical hub 5104 executing the process 5167 can distinguish between which step the utilization of the energy generator 5112 indicates is currently being performed based upon whether the energy generator 5112 was previously utilized.

FIG. 84G illustrates a logic flow diagram of a process 5179 for determining a procedural step according to stapler perioperative data. As described above with respect to the process 5167 illustrated in FIG. 84F, the process 5179 utilizes previously received perioperative data and/or previously derived contextual information in deriving subsequent contextual information. In this exemplification, the process 5179 determines 5181 that a segmentectomy procedure is being performed. This contextual information can be derived by this process 5179 or other processes based upon other received perioperative data and/or retrieved from a memory. Subsequently, the control circuit receives 5183 perioperative data from the surgical stapling instrument (i.e., stapler) indicating that the surgical stapling instrument is being fired and then determines 5185 whether the surgical stapling instrument was utilized in a previous step of the surgical procedure. As described above, the control circuit can determine 5185 whether the surgical stapling instrument was previously utilized in a prior step of the procedure by retrieving a list of the steps that have been performed in the current surgical procedure from a memory, for example. If the surgical stapling instrument has not been utilized previously, then the process 5179 proceeds along the NO branch and the control circuit determines 5187 that the step of ligating arteries and veins is being performed by the surgical staff. If the surgical stapling instrument has been previously utilized during the course of the segmentectomy procedure, the process 5179 proceeds along the YES branch and the control circuit determines 5189 that the step of transecting parenchyma is being performed by the surgical staff. A surgical stapling instrument is utilized twice during the course of an example of a segmentectomy procedure (e.g., FIG. 86); therefore, the situational awareness system of the surgical hub 5104 executing the process 5179 can distinguish between which step the utilization of the surgical stapling instrument indicates is currently being performed based upon whether the surgical stapling instrument was previously utilized.

FIG. 84H illustrates a logic flow diagram of a process 5191 for determining a patient status according to ventilator 5110, pulse oximeter 5114, BP monitor 5116, and/or EKG monitor 5120 perioperative data. In this exemplification, the control circuit of the surgical hub 5104 executing the process 5191 receives 5193, 5195, 5197, 5199 perioperative data from each of the ventilator 5110, pulse oximeter 5114, BP monitor 5116, and/or EKG monitor 5120 and then determines whether one or more values of the physiological parameters sensed by each of the devices fall below a threshold for each of the physiological parameters. The threshold for each physiological parameter can correspond to a value that corresponds to a patient being under anesthesia. In other words, the control circuit determines 5201 whether the patient's respiration rate, oxygen saturation, blood pressure, and/or heart rate indicate that the patient is under anesthesia according data sensed by the respective modular device 5102 and/or patient monitoring devices 5124. In one exemplification, if the all of the values from the perioperative data are below their respective thresholds, then the process 5191 proceeds along the YES branch and the control circuit determines 5203 that the patient is under anesthesia. In another exemplification, the control circuit can determine 5203 that the patient is under anesthesia if a particular number or ratio of the monitored physiological parameters indicate that the patient is under anesthesia. Otherwise, the process 5191 proceeds along the NO branch and the control circuit determines 5205 that the patient is not under anesthesia.

FIG. 84I illustrates a logic flow diagram of a process 5207 for determining a patient status according to pulse oximeter 5114, BP monitor 5116, and/or EKG monitor 5120 perioperative data. In this exemplification, the control circuit of the surgical hub 5104 executing the process 5207 receives 5209, 5211, 5213 (or attempts to receive) perioperative data the pulse oximeter 5114, BP monitor 5116, and/or EKG monitor 5120 and then determines 5215 whether at least one of the devices is paired with the surgical hub 5104 or the surgical hub 5104 is otherwise receiving data therefrom. If the control circuit is receiving data from at least one of these patient monitoring devices 5124, the process 5207 proceeds along the YES branch and the control circuit determines 5217 that the patient is in the operating theater. The control circuit can make this determination because the patient monitoring devices 5214 connected to the surgical hub 5104 must be in the operating theater and thus the patient must likewise be in the operating theater. If the control circuit is not receiving data from at least one of these patient monitoring devices 5124, the process 5207 proceeds along the NO branch and the control circuit determines 5219 that the patient is not in the operating theater.

FIG. 84J illustrates a logic flow diagram of a process 5221 for determining a patient status according to ventilator 5110 perioperative data. In this exemplification, the control circuit of the surgical hub 5104 executing the process 5221 receives 5223 perioperative data from the ventilator 5110 and then determines 5225 whether the patient's airway volume has decreased or is decreasing. In one exemplification, the control circuit determines 5225 whether the patient's airway volume falls below a particular threshold value indicative of a lung having collapsed or been deflated. In another exemplification, the control circuit determines 5225 whether the patient's airway volume falls below an average or baseline level by a threshold amount. If the patient's airway volume has not decreased sufficiently, the process 5221 proceeds along the NO branch and the control circuit determines 5227 that the patient's lung is not deflated. If the patient's airway volume has decreased sufficiently, the process 5221 proceeds along the YES branch and the control circuit determines 5229 that the patient's lung is not deflated.

Figure 85B:
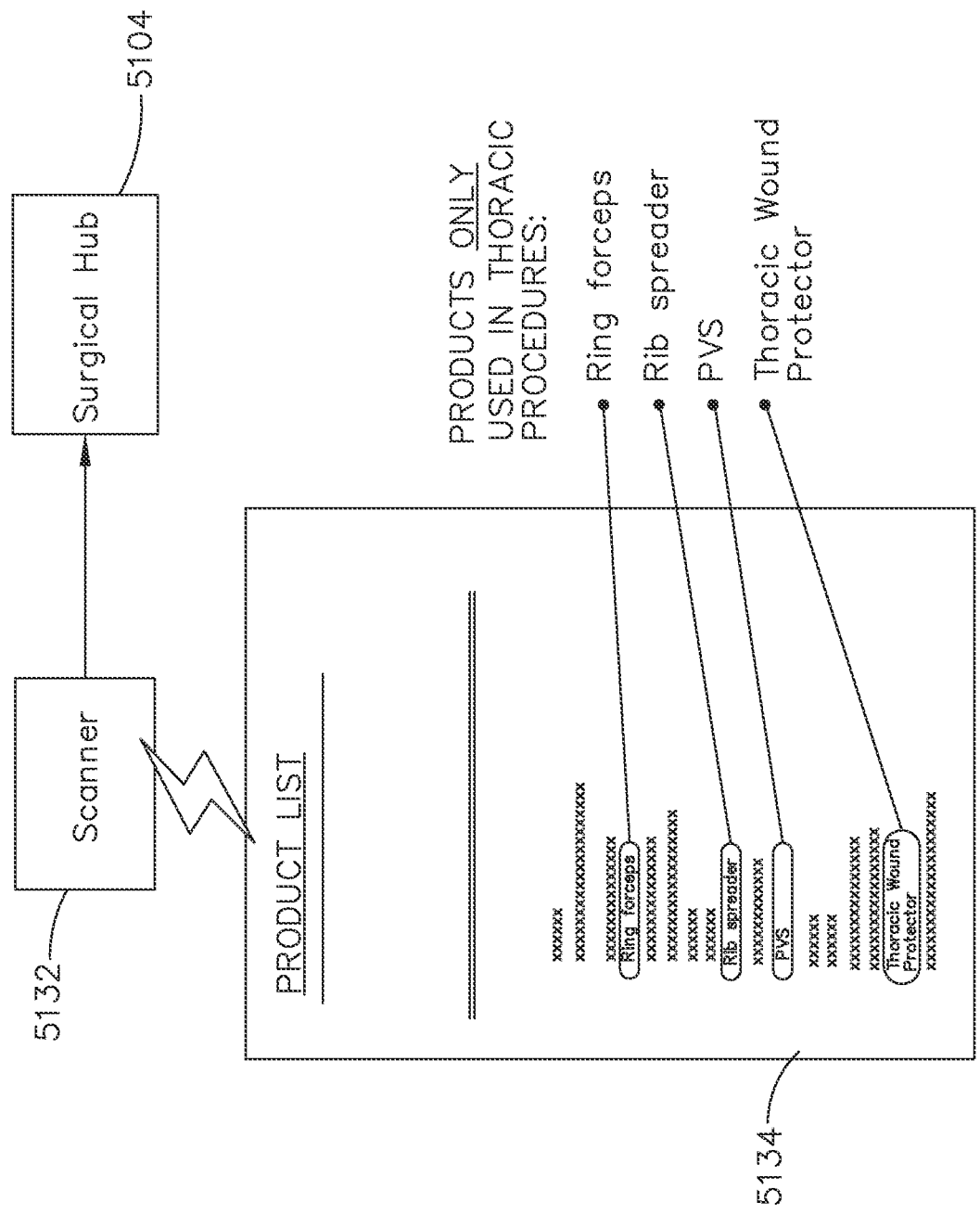
FIG. 85B illustrates a scanner coupled to a surgical hub for scanning a list of surgical items, in accordance with at least one aspect of the present disclosure.

In one exemplification, the surgical system 5100 can further include various scanners that can be paired with the surgical hub 5104 to detect and record objects and individuals that enter and exit the operating theater. FIG. 85A illustrates a scanner 5128 paired with a surgical hub 5104 that is configured to scan a patient wristband 5130. In one aspect, the scanner 5128 includes, for example, a barcode reader or a radio-frequency identification (RFID) reader that is able to read patient information from the patient wristband 5130 and then transmit that information to the surgical hub 5104. The patient information can include the surgical procedure to be performed or identifying information that can be cross-referenced with the hospital's EMR database 5122 by the surgical hub 5104, for example. FIG. 85B illustrates a scanner 5132 paired with a surgical hub 5104 that is configured to scan a product list 5134 for a surgical procedure. The surgical hub 5104 can utilize data from the scanner 5132 regarding the number, type, and mix of items to be used in the surgical procedure to identify the type of surgical procedure being performed. In one exemplification, the scanner 5132 includes a product scanner (e.g., a barcode reader or an RFID reader) that is able to read the product information (e.g., name and quantity) from the product itself or the product packaging as the products are brought into the operating theater and then transmit that information to the surgical hub 5104. In another exemplification, the scanner 5132 includes a camera (or other visualization device) and associated optical character recognition software that is able to read the product information from a product list 5134. The surgical hub 5104 can be configured to cross-reference the list of items indicated by the received data with a lookup table or database of items utilized for various types of surgical procedures in order to infer the particular surgical procedure that is to be (or was) performed. As shown in FIG. 85B, the illustrative product list 5134 includes ring forceps, rib spreaders, a powered vascular stapler (PVS), and a thoracic wound protector. In this example, the surgical hub 5104 can infer that the surgical procedure is a thoracic procedure from this data since these products are only utilized in thoracic procedures. In sum, the scanner(s) 5128, 5132 can provide serial numbers, product lists, and patient information to the surgical hub 5104. Based on this data regarding what devices and instruments are being utilized and the patient's medical information, the surgical hub 5104 can determine additional contextual information regarding the surgical procedure.

Situational Awareness

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

In order to assist in the understanding of the process 5000a illustrated in FIG. 82A and the other concepts discussed above, FIG. 86 illustrates a timeline 5200 of an illustrative surgical procedure and the contextual information that a surgical hub 5104 can derive from the data received from the data sources 5126 at each step in the surgical procedure. In the following description of the timeline 5200 illustrated in FIG. 86, reference should also be made to FIG. 81. The timeline 5200 depicts the typical steps that would be taken by the nurses, surgeons, and other medical personnel during the course of a lung segmentectomy procedure, beginning with setting up the operating theater and ending with transferring the patient to a post-operative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports (e.g., see FIGS. 90-101), verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

As the first step 5202 in this illustrative procedure, the hospital staff members retrieve the patient's EMR from the hospital's EMR database. Based on select patient data in the EMR, the surgical hub 5104 determines that the procedure to be performed is a thoracic procedure. Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure (e.g., as depicted in FIG. 85B). Further, the surgical hub 5104 is also able to determine that the procedure is not a wedge procedure (because the incoming supplies either lack certain supplies that are necessary for a thoracic wedge procedure or do not otherwise correspond to a thoracic wedge procedure). Third 5206, the medical personnel scan the patient band (e.g., as depicted in FIG. 85A) via a scanner 5128 that is communicably connected to the surgical hub 5104. The surgical hub 5104 can then confirm the patient's identity based on the scanned data. Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing. Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater, as described in the process 5207 depicted in FIG. 84I, for example. Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations thereof, as described in the process 5191 depicted in FIG. 84H, for example. Upon completion of the sixth step 5212, the pre-operative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed, as described in the process 5221 depicted in FIG. 84J, for example. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure. Eighth 5216, the medical imaging device 5108 (e.g., a scope) is inserted and video from the medical imaging device is initiated. The surgical hub 5104 receives the medical imaging device data (i.e., video or image data) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step 5204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step. Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process. Eleventh 5222, the segmentectomy portion of the procedure is performed. The surgical hub 5104 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 5104 to infer that the segmentectomy portion of the procedure is being performed. Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example. Lastly, the fourteenth step 5228 is that the medical personnel remove the various patient monitoring devices 5124 from the patient. The surgical hub 5104 can thus infer that the patient is being transferred to a recovery room when the hub loses EKG, BP, and other data from the patient monitoring devices 5124. As can be seen from the description of this illustrative procedure, the surgical hub 5104 can determine or infer when each step of a given surgical procedure is taking place according to data received from the various data sources 5126 that are communicably coupled to the surgical hub 5104.

Figure 86:
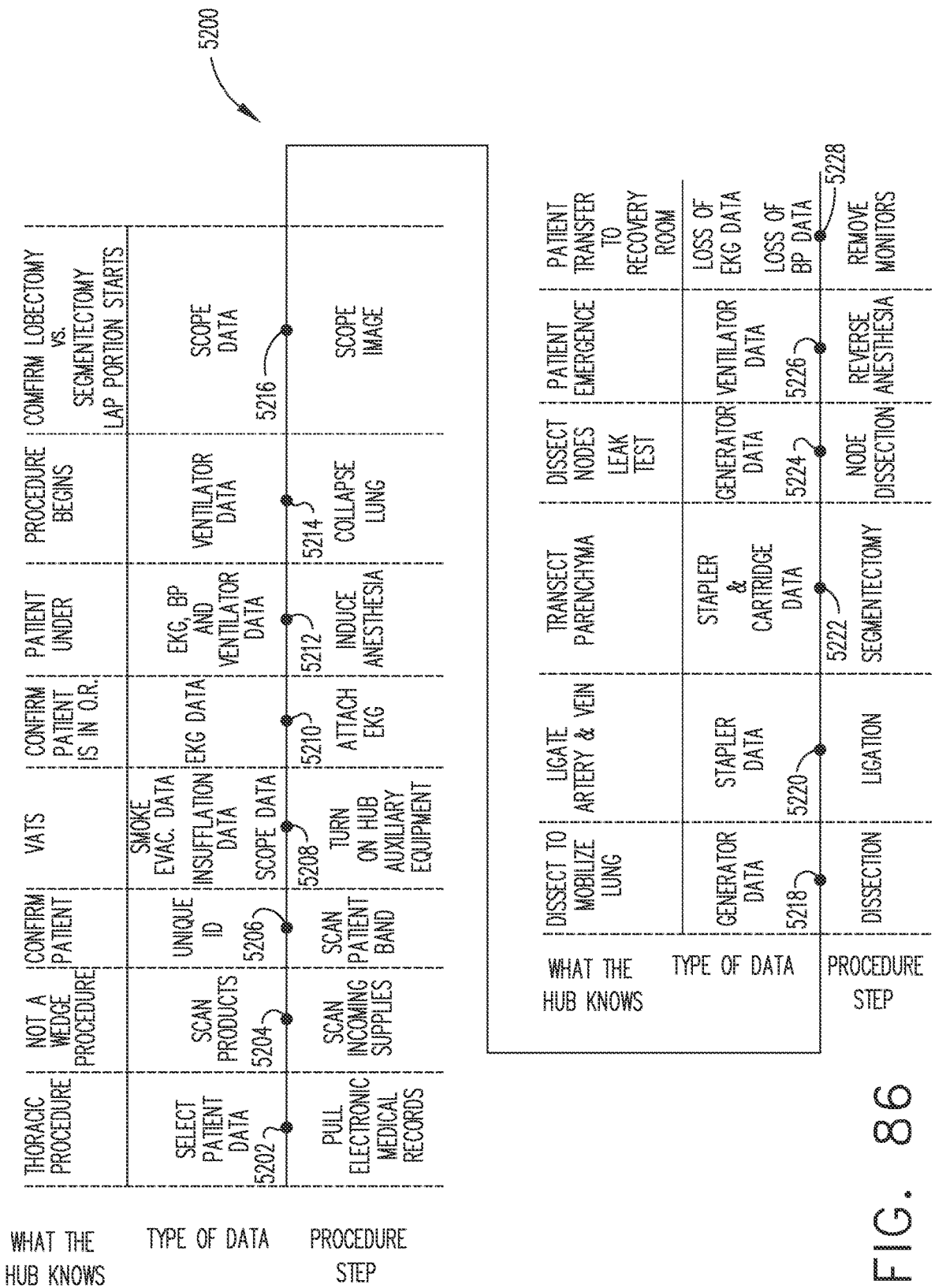
FIG. 86 illustrates a timeline of an illustrative surgical procedure and the inferences that the surgical hub can make from the data detected at each step in the surgical procedure, in accordance with at least one aspect of the present disclosure.
Figure 87A:
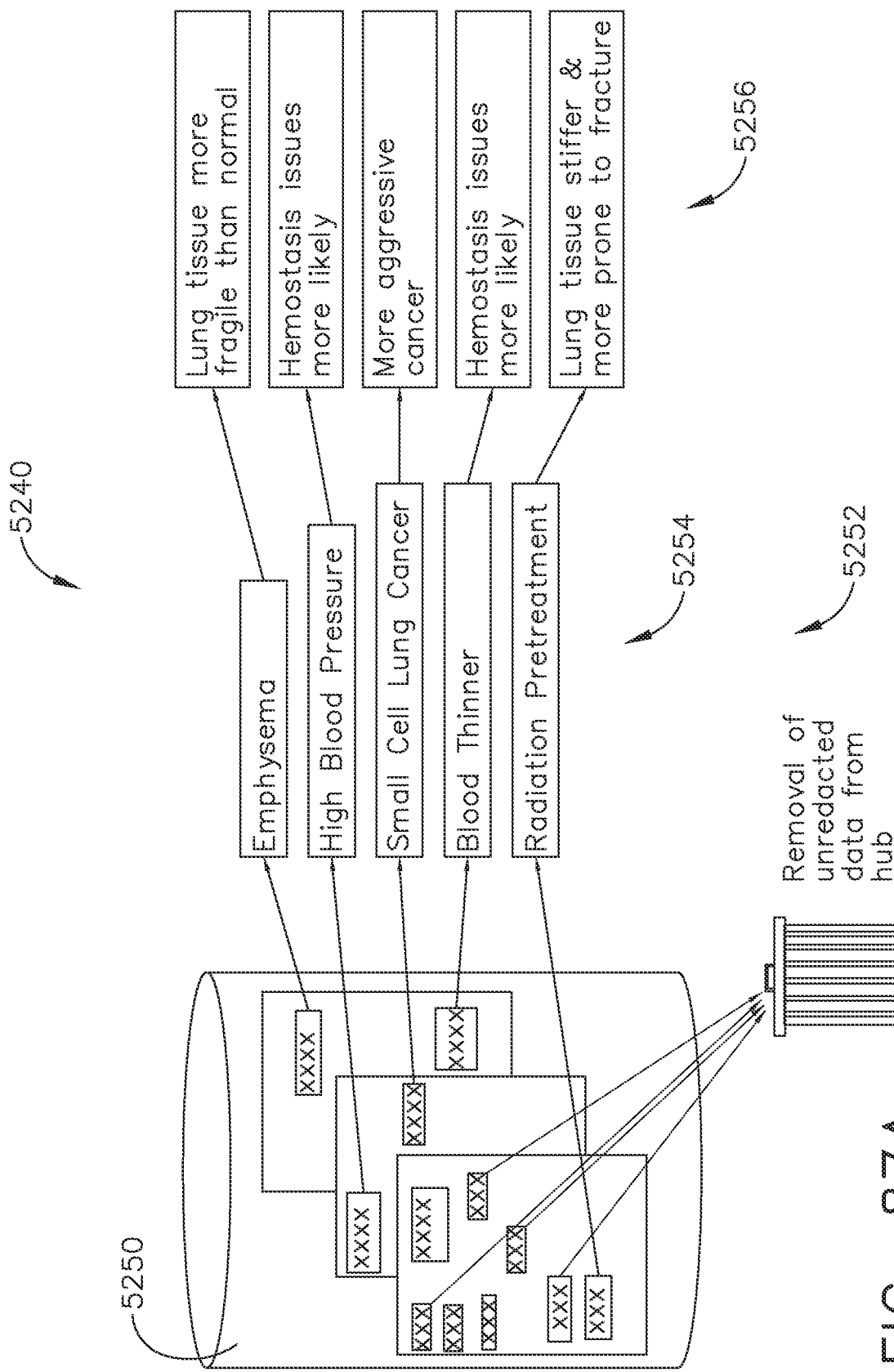
FIG. 87A illustrates a flow diagram depicting the process of importing patient data stored in an EMR database and deriving inferences therefrom, in accordance with at least one aspect of the present disclosure.
Figure 87B:
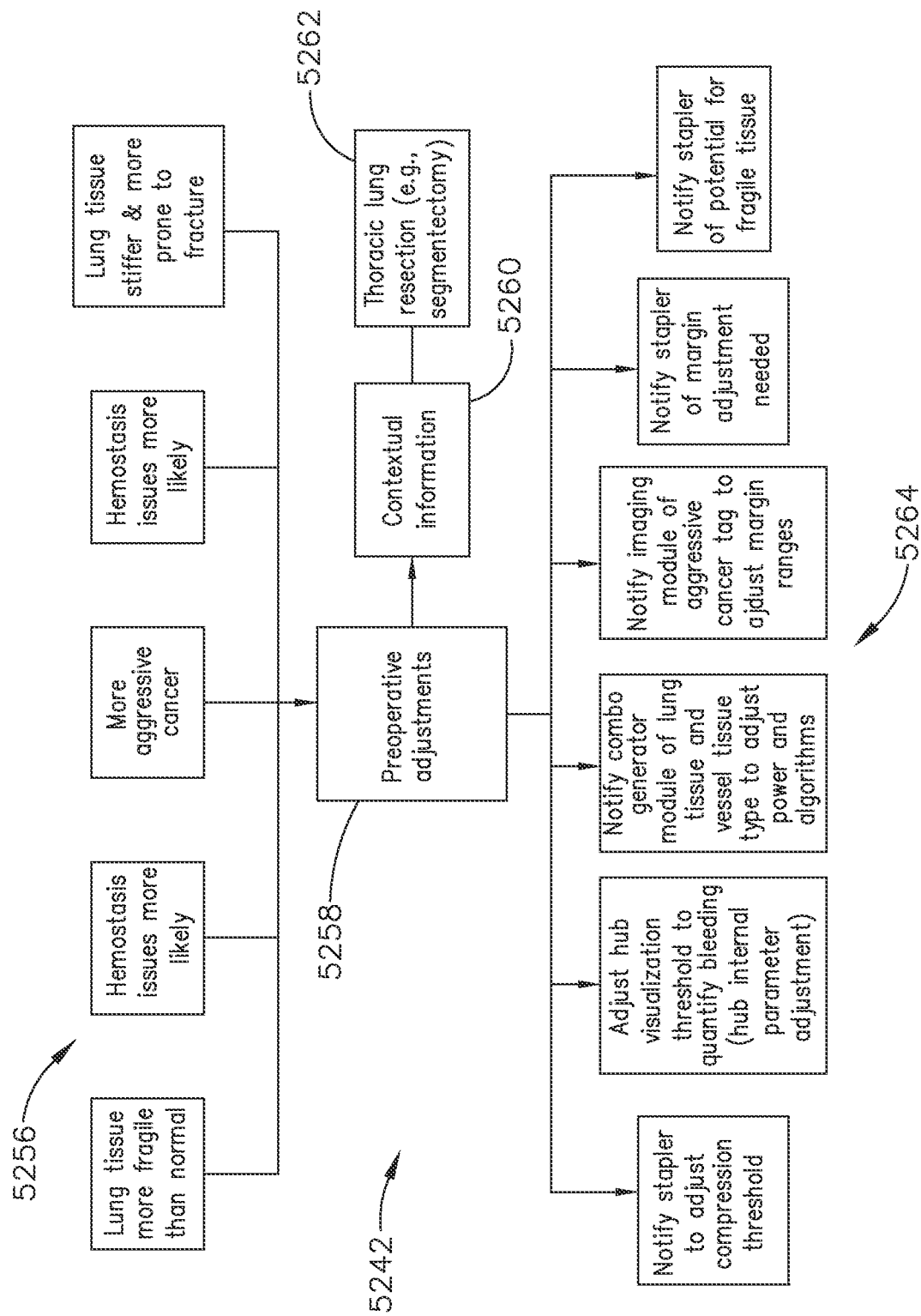
FIG. 87B illustrates a flow diagram depicting the process of determining control adjustments corresponding to the derived inferences from FIG. 87A, in accordance with at least one aspect of the present disclosure.

In addition to utilizing the patient data from EMR database(s) to infer the type of surgical procedure that is to be performed, as illustrated in the first step 5202 of the timeline 5200 depicted in FIG. 86, the patient data can also be utilized by a situationally aware surgical hub 5104 to generate control adjustments for the paired modular devices 5102. FIG. 87A illustrates a flow diagram depicting the process 5240 of importing patient data stored in an EMR database 5250 and deriving inferences 5256 therefrom, in accordance with at least one aspect of the present disclosure. Further, FIG. 87B illustrates a flow diagram depicting the process 5242 of determining control adjustments 5264 corresponding to the derived inferences 5256 from FIG. 87A, in accordance with at least one aspect of the present disclosure. In the following description of the processes 5240, 5242, reference should also be made to FIG. 81.

As shown in FIG. 87A, the surgical hub 5104 retrieves the patient information (e.g., EMR) stored in a database 5250 to which the surgical hub 5104 is communicably connected. The unredacted portion of the patient data is removed 5252 from the surgical hub 5104, leaving anonymized, stripped patient data 5254 related to the patient's condition and/or the surgical procedure to be performed. The unredacted patient data is removed 5252 in order to maintain patient anonymity for the processing of the data (including if the data is uploaded to the cloud for processing and/or data tracking for reports). The stripped patient data 5254 can include any medical conditions that the patient is suffering from, the patient's medical history (including previous treatments or procedures), medication that the patient is taking, and other such medically relevant details. The control circuit of the surgical hub 5104 can then derive various inferences 5256 from the stripped patient data 5254, which can in turn be utilized by the surgical hub 5104 to derive various control adjustments for the paired modular devices 5102. The derived inferences 5256 can be based upon individual pieces of data or combinations of pieces of data. Further, the derived inferences 5256 may, in some cases, be redundant with each other as some data may lead to the same inference. By integrating each patient's stripped patient data 5254 into the situational awareness system, the surgical hub 5104 is thus able to generate pre-procedure adjustments to optimally control each of the modular devices 5102 based on the unique circumstances associated with each individual patient. In the illustrated example, the stripped patient data 5254 includes that (i) the patient is suffering from emphysema, (ii) has high blood pressure, (iii) is suffering from a small cell lung cancer, (iv) is taking warfarin (or another blood thinner), and/or (v) has received radiation pretreatment. In the illustrated example, the inferences 5256 derived from the stripped patient data 5254 include that (i) the lung tissue will be more fragile than normal lung tissue, (ii) hemostasis issues are more likely, (iii) the patient is suffering from a relatively aggressive cancer, (iv) hemostasis issues are more likely, and (v) the lung tissue will be stiffer and more prone to fracture, respectively.

After the control circuit of the surgical hub 5104 receives or identifies the implications 5256 that are derived from anonymized patient data, the control circuit of the surgical hub 5104 is configured to execute a process 5242 to control the modular devices 5102 in a manner consistent with the derived implications 5256. In the example shown in FIG. 87B, the control circuit of the surgical hub 5104 interprets how the derived implications 5256 impacts the modular devices 5102 and then communicates corresponding control adjustments to each of the modular devices 5102. In the example shown in FIG. 87B, the control adjustments include (i) adjusting the compression rate threshold parameter of the surgical stapling and cutting instrument, (ii) adjusting the visualization threshold value of the surgical hub 5104 to quantify bleeding via the visualization system 108 (FIG. 2) (this adjustment can apply to the visualization system 108 itself or as an internal parameter of the surgical hub 5104), (iii) adjusts the power and control algorithms of the combo generator module 140 (FIG. 3) for the lung tissue and vessel tissue types, (iv) adjusts the margin ranges of the medical imaging device 124 (FIG. 2) to account for the aggressive cancer type, (v) notifies the surgical stapling and cutting instrument of the margin parameter adjustment needed (the margin parameter corresponds to the distance or amount of tissue around the cancer that will be excised), and (vi) notifies the surgical stapling and cutting instrument that the tissue is potentially fragile, which causes the control algorithm of the surgical stapling and cutting instrument to adjust accordingly. Furthermore, the data regarding the implications 5256 derived from the anonymized patient data 5254 is considered by the situational awareness system to infer contextual information 5260 regarding the surgical procedure being performed. In the example shown in FIG. 87B, the situational awareness system further infers that the procedure is a thoracic lung resection 5262, e.g., segmentectomy.

Determining where inefficiencies or ineffectiveness may reside in a medical facility's practice can be challenging because medical personnel's efficiency in completing a surgical procedure, correlating positive patient outcomes with particular surgical teams or particular techniques in performing a type of surgical procedure, and other performance measures are not easily quantified using legacy systems. As one solution, the surgical hubs can be employed to track and store data pertaining to the surgical procedures that the surgical hubs are being utilized in connection with and generate reports or recommendations related to the tracked data. The tracked data can include, for example, the length of time spent during a particular procedure, the length of time spent on a particular step of a particular procedure, the length of downtime between procedures, modular device(s) (e.g., surgical instruments) utilized during the course of a procedure, and the number and type of surgical items consumed during a procedure (or step thereof). Further, the tracked data can include, for example, the operating theater in which the surgical hub is located, the medical personnel associated with the particular event (e.g., the surgeon or surgical team performing the surgical procedure), the day and time at which the particular event(s) occurred, and patient outcomes. This data can be utilized to create performance metrics, which can be utilized to detect and then ultimately address inefficiencies or ineffectiveness within a medical facility's practice. In one exemplification, the surgical hub includes a situational awareness system, as described above, that is configured to infer or determine information regarding a particular event (e.g., when a particular step of a surgical procedure is being performed and/or how long the step took to complete) based on data received from data sources connected to the surgical hub (e.g., paired modular devices). The surgical hub can then store this tracked data to provide reports or recommendations to users.

Aggregation and Reporting of Surgical Hub Data

Figure 88:
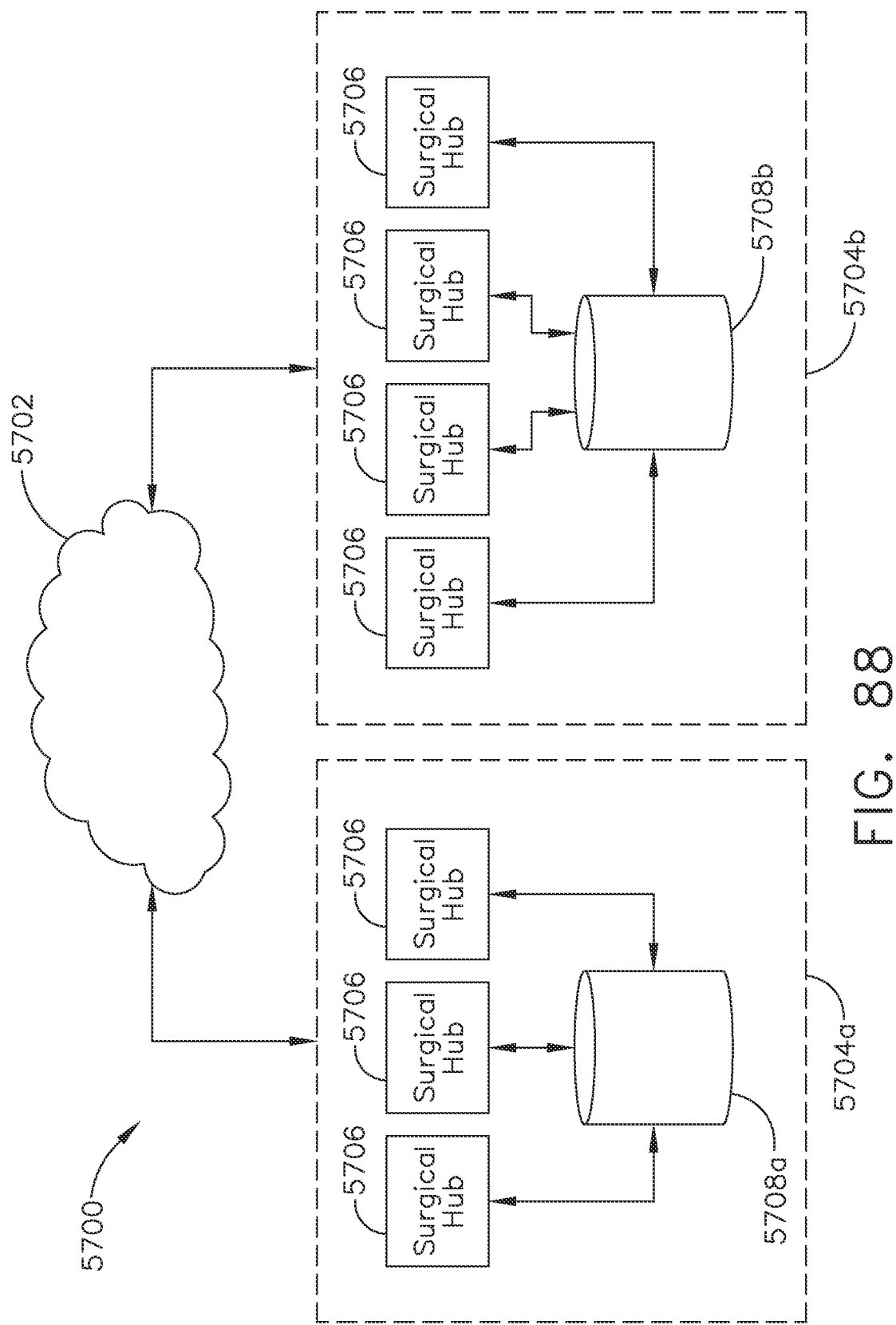
FIG. 88 illustrates a block diagram of a computer-implemented interactive surgical system, in accordance with at least one aspect of the present disclosure.

FIG. 88 illustrates a block diagram of a computer-implemented interactive surgical system 5700, in accordance with at least one aspect of the present disclosure. The system 5700 includes a number of surgical hubs 5706 that, as described above, are able to detect and track data related to surgical procedures that the surgical hubs 5706 (and the modular devices paired to the surgical hubs 5706) are utilized in connection with. In one exemplification, the surgical hubs 5706 are connected to form local networks such that the data being tracked by the surgical hubs 5706 is aggregated together across the network. The networks of surgical hubs 5706 can be associated with a medical facility, for example. The data aggregated from the network of surgical hubs 5706 can be analyzed to provide reports on data trends or recommendations. For example, the surgical hubs 5706 of a first medical facility 5704*a* are communicably connected to a first local database 5708*a* and the surgical hubs 5706 of a second medical facility 5704*b* are communicably connected to a second local database 5708*b*. The network of surgical hubs 5706 associated with the first medical facility 5704*a* can be distinct from the network of surgical hubs 5706 associated with the second medical facility 5704*b*, such that the aggregated data from each network of surgical hubs 5706 corresponds to each medical facility 5704*a*, 5704*b* individually. A surgical hub 5706 or another computer terminal communicably connected to the database 5708*a*, 5708*b* can be configured to provide reports or recommendations based on the aggregated data associated with the respective medical facility 5704*a*, 5704*b*. In this exemplification, the data tracked by the surgical hubs 5706 can be utilized to, for example, report whether a particular incidence of a surgical procedure deviated from the average in-network time to complete the particular procedure type.

In another exemplification, each surgical hub 5706 is configured to upload the tracked data to the cloud 5702, which then processes and aggregates the tracked data across multiple surgical hubs 5706, networks of surgical hubs 5706, and/or medical facilities 5704*a*, 5704*b* that are connected to the cloud 5702. Each surgical hub 5706 can then be utilized to provide reports or recommendations based on the aggregated data. In this exemplification, the data tracked by the surgical hubs 5706 can be utilized to, for example, report whether a particular incidence of a surgical procedure deviated from the average global time to complete the particular procedure type.

In another exemplification, each surgical hub 5706 can further be configured to access the cloud 5702 to compare locally tracked data to global data aggregated from all of the surgical hubs 5706 that are communicably connected to the cloud 5702. Each surgical hub 5706 can be configured to provide reports or recommendations based on the comparison between the tracked local data relative to local (i.e., in-network) or global norms. In this exemplification, the data tracked by the surgical hubs 5706 can be utilized to, for example, report whether a particular incidence of a surgical procedure deviated from either the average in-network time or the average global time to complete the particular procedure type.

In one exemplification, each surgical hub 5706 or another computer system local to the surgical hub 5706 is configured to locally aggregate the data tracked by the surgical hubs 5706, store the tracked data, and generate reports and/or recommendations according to the tracked data in response to queries. In cases where the surgical hub 5706 is connected to a medical facility network (which may include additional surgical hubs 5706), the surgical hub 5706 can be configured to compare the tracked data with the bulk medical facility data. The bulk medical facility data can include EMR data and aggregated data from the local network of surgical hubs 5706. In another exemplification, the cloud 5702 is configured to aggregate the data tracked by the surgical hubs 5706, store the tracked data, and generate reports and/or recommendations according to the tracked data in response to queries.

Each surgical hub 5706 can provide reports regarding trends in the data and/or provide recommendations on improving the efficiency or effectiveness of the surgical procedures being performed. In various exemplifications, the data trends and recommendations can be based on data tracked by the surgical hub 5706 itself, data tracked across a local medical facility network containing multiple surgical hubs 5706, or data tracked across a number of surgical hubs 5706 communicably connected to a cloud 5702. The recommendations provided by the surgical hub 5706 can describe, for example, particular surgical instruments or product mixes to utilize for particular surgical procedures based on correlations between the surgical instruments/product mixes and patient outcomes and procedural efficiency. The reports provided by the surgical hub 5706 can describe, for example, whether a particular surgical procedure was performed efficiently relative to local or global norms, whether a particular type of surgical procedure being performed at the medical facility is being performed efficiently relative to global norms, and the average time taken to complete a particular surgical procedure or step of a surgical procedure for a particular surgical team.

Figure 90:
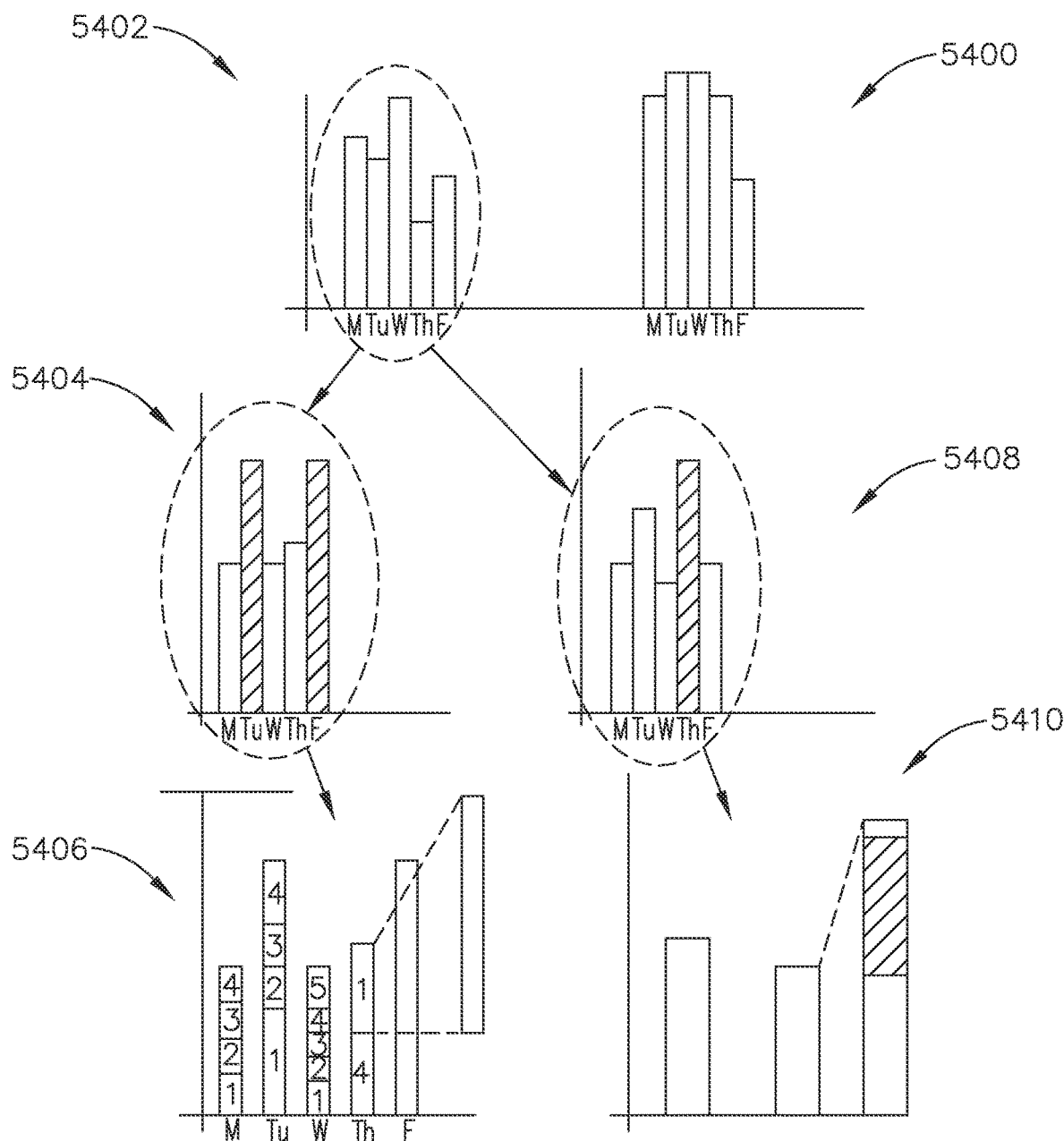
FIG. 90 illustrates a diagram depicting how the data tracked by the surgical hub can be parsed to provide increasingly detailed metrics, in accordance with at least one aspect of the present disclosure.

In one exemplification, each surgical hub 5706 is configured to determine when operating theater events occur (e.g., via a situational awareness system) and then track the length of time spent on each event. An operating theater event is an event that a surgical hub 5706 can detect or infer the occurrence of. An operating theater event can include, for example, a particular surgical procedure, a step or portion of a surgical procedure, or downtime between surgical procedures. The operating theater events can be categorized according to an event type, such as a type of surgical procedure being performed, so that the data from individual procedures can be aggregated together to form searchable data sets. FIG. 90 illustrates an example of a diagram 5400 depicting the data tracked by the surgical hubs 5706 being parsed to provide increasingly detailed metrics related to surgical procedures or the use of the surgical hub 5706 (as depicted further in FIGS. 91-95) for an illustrative data set. In one exemplification, the surgical hub 5706 is configured to determine whether a surgical procedure is being performed and then track both the length of time spent between procedures (i.e., downtime) and the time spent on the procedures themselves. The surgical hub 5706 can further be configured to determine and track the time spent on each of the individual steps taken by the medical personnel (e.g., surgeons, nurses, orderlies) either between or during the surgical procedures. The surgical hub can determine when surgical procedures or different steps of surgical procedures are being performed via a situational awareness system, which is described in further detail above.

Figure 89:
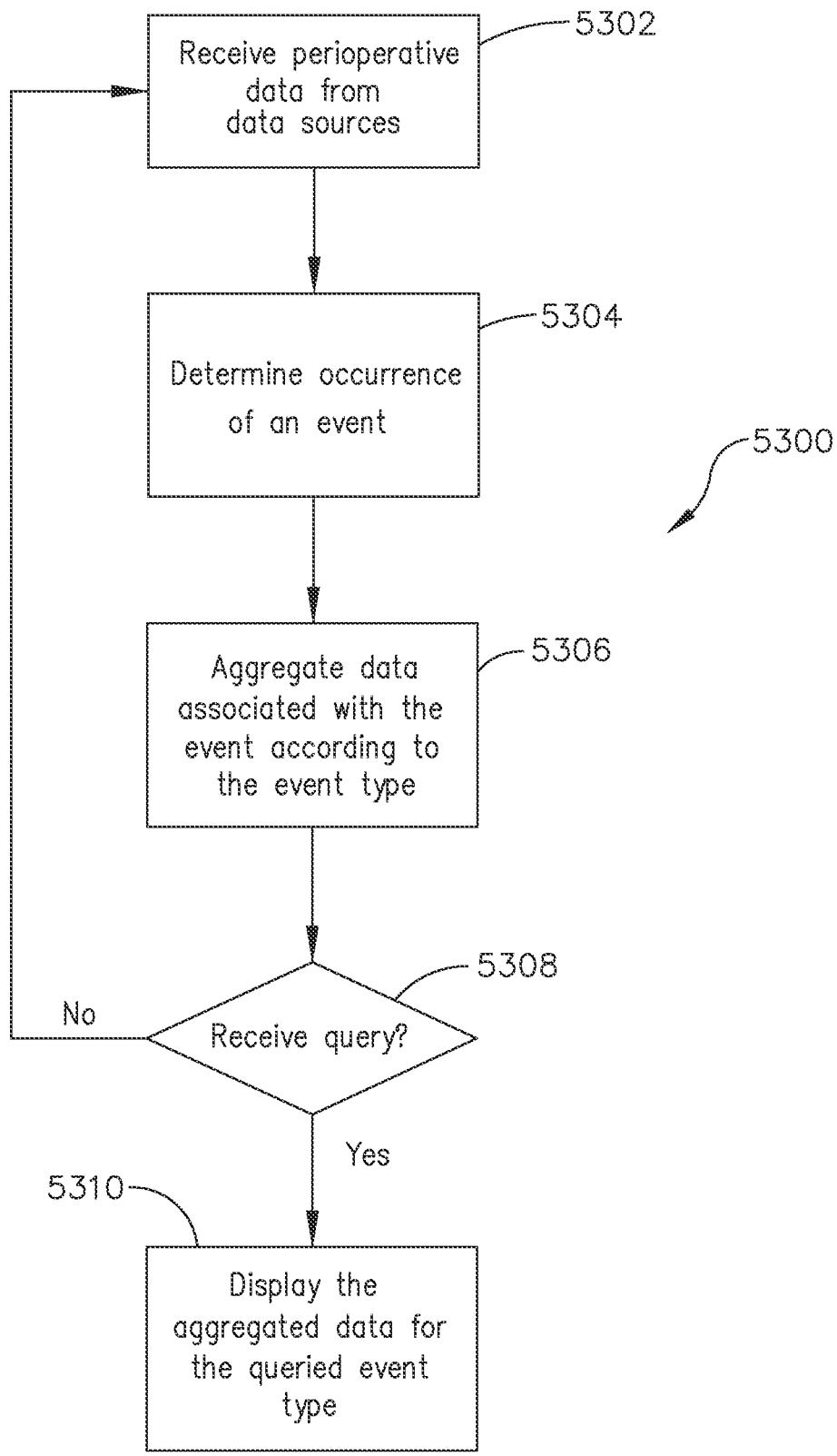
FIG. 89 illustrates a logic flow diagram of tracking data associated with an operating theater event, in accordance with at least one aspect of the present disclosure.

FIG. 89 illustrates a logic flow diagram of a process 5300 for tracking data associated with an operating theater event. In the following description, description of the process 5300, reference should also be made to FIG. 88. In one exemplification, the process 5300 can be executed by a control circuit of a surgical hub 206, as depicted in FIG. 10 (processor 244). In yet another exemplification, the process 5300 can be executed by a distributed computing system including a control circuit of a surgical hub 206 in combination with a control circuit of a modular device, such as the microcontroller 461 of the surgical instrument depicted FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5300 will be described as being executed by the control circuit of a surgical hub 5706; however, it should be understood that the description of the process 5300 encompasses all of the aforementioned exemplifications.

The control circuit of the surgical hub 5706 executing the process 5300 receives 5302 perioperative data from the modular devices and other data sources (e.g., databases and patient monitoring devices) that are communicably coupled to the surgical hub 5706. The control circuit then determines 5304 whether an event has occurred via, for example, a situational awareness system that derives contextual information from the received 5302 data. The event can be associated with an operating theater in which the surgical hub 5706 in being used. The event can include, for example, a surgical procedure, a step or portion of a surgical procedure, or downtime between surgical procedures or steps of a surgical procedure. Furthermore, the control circuit tracks data associated with the particular event, such as the length of time of the event, the surgical instruments and/or other medical products utilized during the course of the event, and the medical personnel associated with the event. The surgical hub 5706 can further determine this information regarding the event via, for example, the situational awareness system.

For example, the control circuit of a situationally aware surgical hub 5706 could determine that anesthesia is being induced in a patient through data received from one or more modular devices 5102 (FIG. 81) and/or patient monitoring devices 5124 (FIG. 81). The control circuit could then determine that the operative portion of the surgical procedure has begun upon detecting that an ultrasonic surgical instrument or RF electrosurgical instrument has been activated. The control circuit could thus determine the length of time for the anesthesia inducement step according to the difference in time between the beginning of that particular step and the beginning of the first step in the operative portion of the surgical procedure. Likewise, the control circuit could determine how long the particular operative step in the surgical procedure took according to when the control circuit detects the subsequent step in the procedure begins. Further, the control circuit could determine how long the overall operative portion of the surgical procedure took according to when the control circuit detects that the final operative step in the procedure ends. The control circuit can also determine what surgical instruments (and other modular devices 5102) are being utilized during the course of each step in the surgical procedure by tracking the activation and/or use of the instruments during each of the steps. The control circuit can also detect the completion of the surgical procedure by, for example, detecting when the patient monitoring devices 5124 have been removed from the patient (as in step fourteen 5228 of FIG. 86). The control circuit can then track the downtime between procedures according to when the control circuit infers that the subsequent surgical procedure has begun.

The control circuit executing the process 5300 then aggregates 5306 the data associated with the event according to the event type. In one exemplification, the aggregated 5306 data can be stored in a memory 249 (FIG. 10) of the surgical hub 5706. In another exemplification, the control circuit is configured to upload the data associated with the event to the cloud 5702, whereupon the data is aggregated 5306 according to the event type for all of the data uploaded by each of the surgical hubs 5706 connected to the cloud 5702. In yet another exemplification, the control circuit is configured to upload the data associated with the event to a database associated with a local network of the surgical hubs 5706, whereupon the data is aggregated 5306 according to the event type for all of the data uploaded across the local network of surgical hubs 5706.

In one exemplification, the control circuit is further configured to compare the data associated with the event type to baseline data associated with the event type. The baseline data can correspond to, for example, average values associated with the particular event type for a particular hospital, network of hospitals, or across the entirety of the cloud 5702. The baseline data can be stored on the surgical hub 5706 or retrieved by the surgical 5706 as the perioperative data is received 5302 thereby.

Aggregating 5306 the data from each of the events according to the event type allows individual incidents of the event type to thereafter be compared against the historical or aggregated data to determine when deviations from the norm for an event type occur. The control circuit further determines 5308 whether it has received a query. If the control circuit does not receive a query, then the process 5300 continues along the NO branch and loops back to continue receiving 5302 data from the data sources. If the control circuit does receive a query for a particular event type, the process 5300 continues along the YES branch and the control circuit then retrieves the aggregated data for the particular event type and displays 5310 the appropriate aggregated data corresponding to the query. In various exemplifications, the control circuit can retrieve the appropriate aggregated data from the memory of the surgical hub 5706, the cloud 5702, or a local database 5708*a*, 5708*b*.

In one example, the surgical hub 5706 is configured to determine a length of time for a particular procedure via the aforementioned situational awareness system according to data received from one or more modular devices utilized in the performance of the surgical procedure (and other data sources). Each time a surgical procedure is completed, the surgical hub 5706 uploads or stores the length of time required to complete the particular type of surgical procedure, which is then aggregated with the data from every other instance of the type of procedure. In some aspects, the surgical hub 5706, cloud 5702, and/or local database 5708*a*, 5708*b* can then determine an average or expected procedure length for the particular type of procedure from the aggregated data. When the surgical hub 5706 receives a query as to the particular type of procedure thereafter, the surgical hub 5706 can then provide feedback as to the average (or expected) procedure length or compare an individual incidence of the procedure type to the average procedure length to determine whether the particular incidence deviates therefrom.

In some aspects, the surgical hub 5706 can be configured to automatically compare each incidence of an event type to average or expected norms for the event type and then provide feedback (e.g., display a report) when a particular incidence of the event type deviates from the norm. For example, the surgical hub 5706 can be configured to provide feedback whenever a surgical procedure (or a step of the surgical procedure) deviates from the expected length of time to complete the surgical procedure (or the step of the surgical procedure) by more than a set amount.

Referring back to FIG. 90, the surgical hub 5706 could be configured to track, store, and display data regarding the number of patients operated on (or procedures completed) per day per operating theater (bar graph 5402 depicted further in FIG. 91), for example. The surgical hub 5706 could be configured to further parse the number of patients operated on (or procedures completed) per day per operating theater and can be further parsed according to the downtime between the procedures on a given day (bar graph 5404 depicted further in FIG. 92) or the average procedure length on a given day (bar graph 5408 depicted further in FIG. 94). The surgical hub 5706 can be further configured to provide a detailed breakdown of the downtime between procedures according to, for example, the number and length of the downtime time periods and the subcategories of the actions or steps during each time period (bar graph 5406 depicted further in FIG. 93). The surgical hub 5706 can be further configured to provide a detailed breakdown of the average procedure length on a given day according to each individual procedure and the subcategory of actions or steps during each procedure (bar graph 5410 depicted further in FIG. 95). The various graphs shown in FIGS. 90-95 can represent data tracked by the surgical hub 5706 and can further be generated automatically or displayed by the surgical hub 5706 in response to queries submitted by users.

Figure 91:
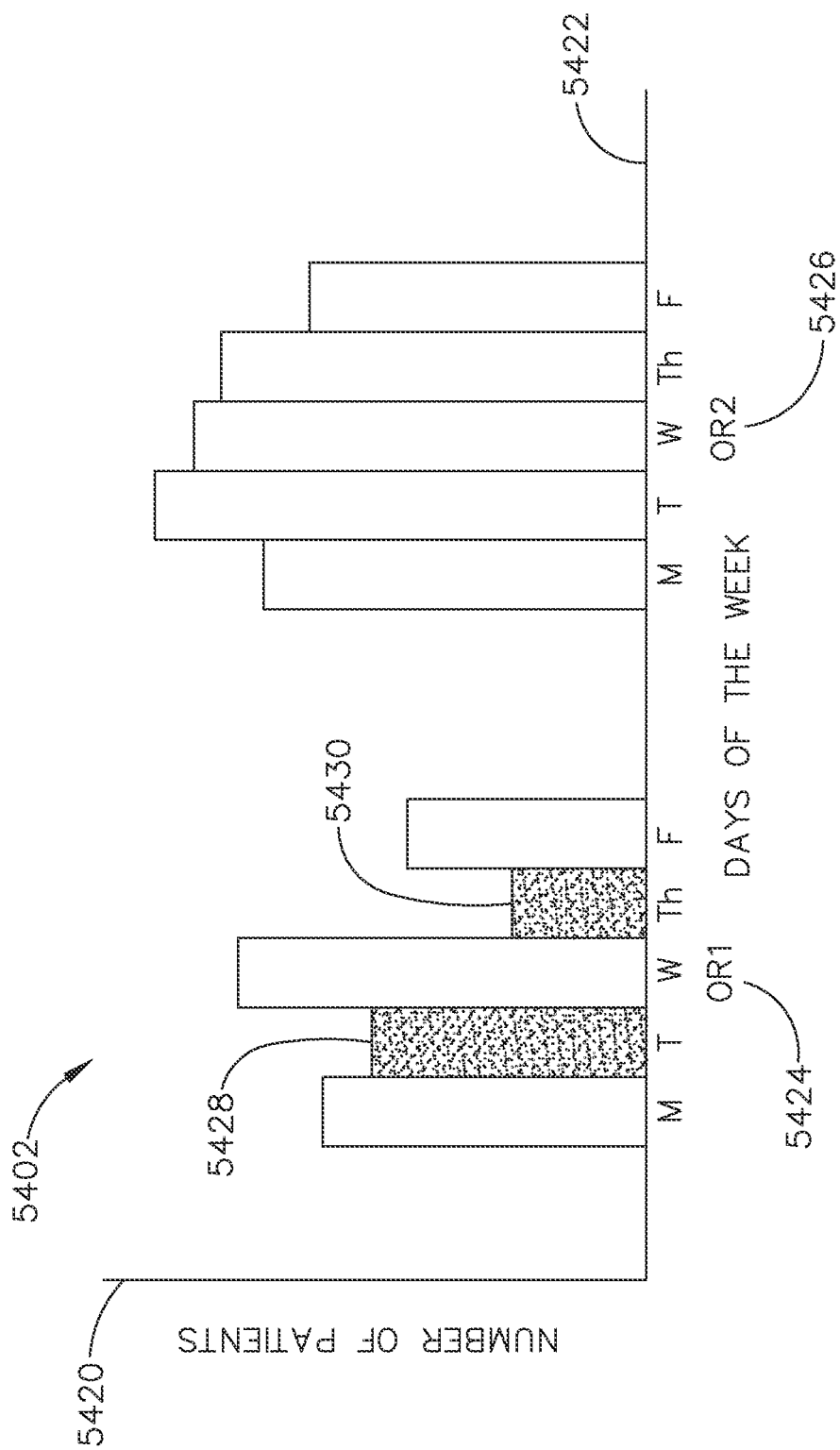
FIG. 91 illustrates a bar graph depicting the number of patients operated on relative to the days of a week for different operating rooms, in accordance with at least one aspect of the present disclosure.

FIG. 91 illustrates an example bar graph 5402 depicting the number of patients 5420 operated on relative to the days of the week 5422 for different operating rooms 5424, 5426. The surgical hub 5706 can be configured to provide (e.g., via a display) the number of patients 5420 operated on or procedures that are completed in connection with each surgical hub 5706, which can be tracked through a situational awareness system or accessing the hospital's EMR database, for example. In one exemplification, the surgical hub 5706 can further be configured to collate this data from different surgical hubs 5706 within the medical facility that are communicably connected together, which allows each individual surgical hub to present the aggregated data of the medical facility on a hub-by-hub or operating theater-by-theater basis. In one exemplification, the surgical hub 5706 can be configured to compare one or more tracked metrics to a threshold value (which may be unique to each tracked metric). When at least one of the tracked metrics exceeds the threshold value (i.e., either increases above or drops below the threshold value, as appropriate for the particular tracked metric), then the surgical hub 5706 provides a visual, audible, or tactile alert to notify a user of such. For example, the surgical hub 5706 can be configured to indicate when the number of patients or procedures deviates from an expected, average, or threshold value. For example, FIG. 91 depicts the number of patients on Tuesday 5428 and Thursday 5430 for a first operating theater 5424 as being highlighted for being below expectation. Conversely, no days are highlighted for a second operating theater 5426 for this particular week, which means in this context that the number of patients for each day falls within expectations.

Figure 92:
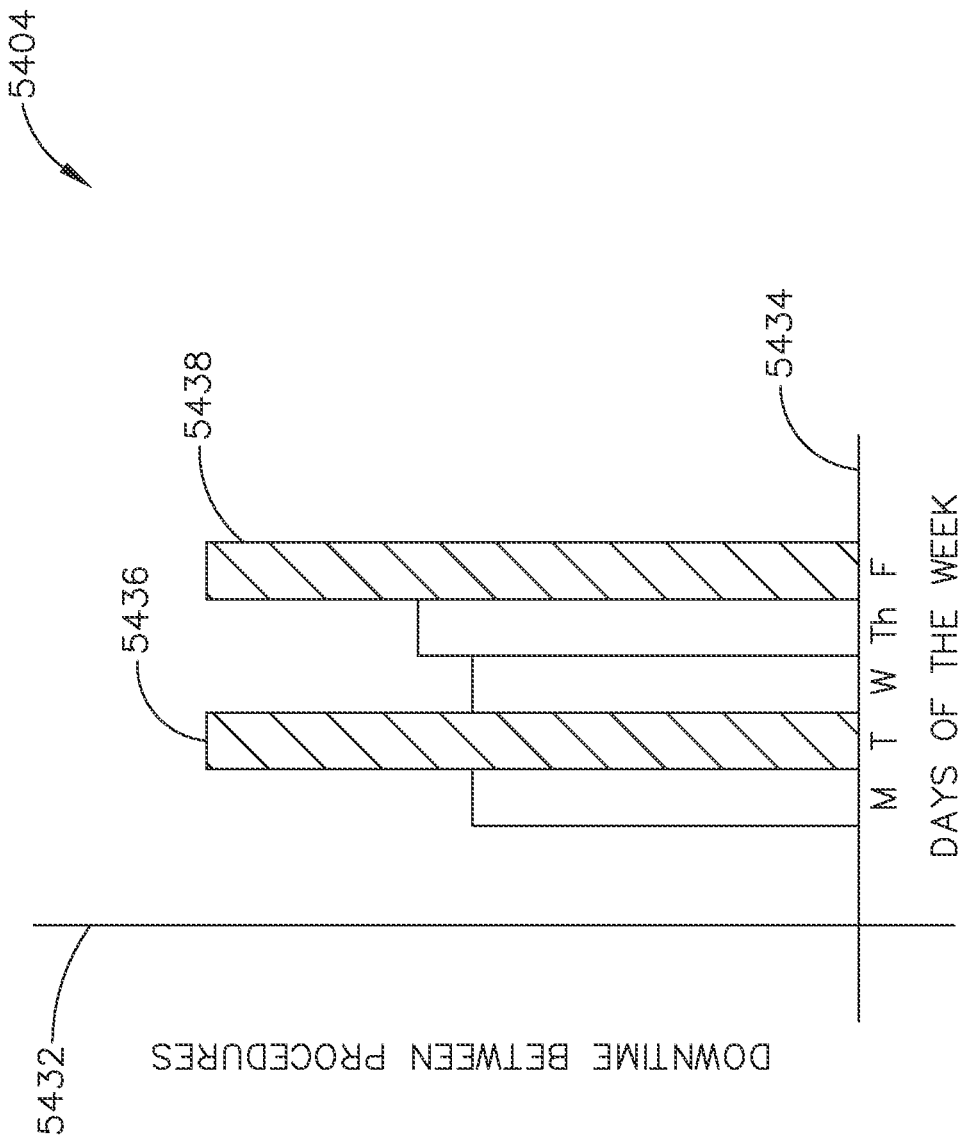
FIG. 92 illustrates a bar graph depicting the total downtime between procedures relative to the days of a week for a particular operating room, in accordance with at least one aspect of the present disclosure.

FIG. 92 illustrates a bar graph 5404 depicting the total downtime between procedures 5432 relative to the days of a week 5434 for a particular operating room. The surgical hub 5706 can be configured to track the length of downtime between surgical procedures through a situational awareness system, for example. The situational awareness system can detect or infer when each particular downtime instance is occurring and then track the length of time for each instance of downtime. The surgical hub 5706 can thereby determine the total downtime 5432 for each day of the week 5434 by summing the downtime instances for each particular day. In one exemplification, the surgical hub 5706 can be configured to provide an alert when the total length of downtime on a given day (or another unit of time) deviates from an expected, average, or threshold value. For example, FIG. 92 depicts the total downtime 5432 on Tuesday 5436 and Friday 5438 as being highlighted for deviating from an expected length of time.

Figure 93:
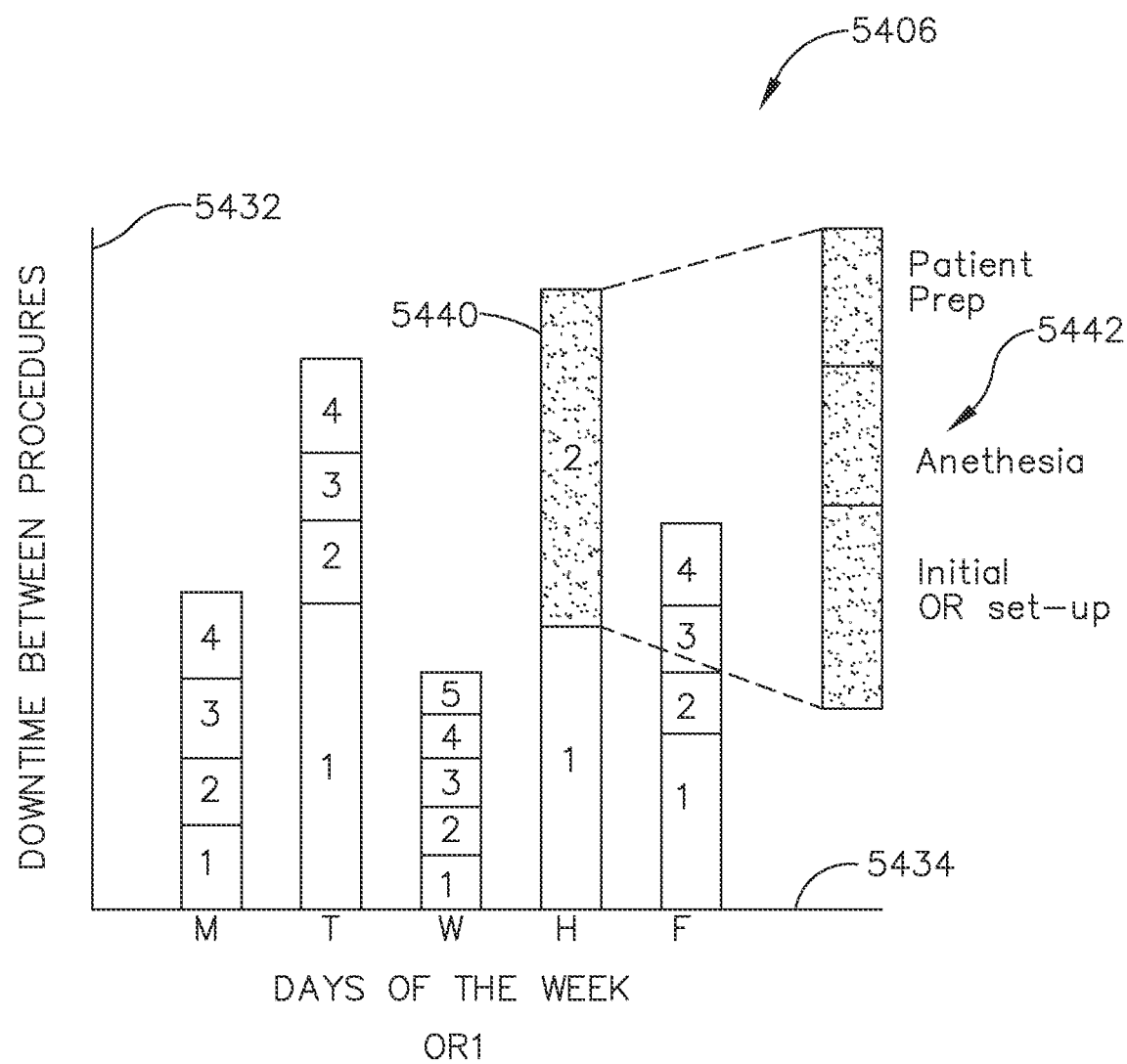
FIG. 93 illustrates a bar graph depicting the total downtime per day of the week depicted in FIG. 92 broken down according to each individual downtime instance, in accordance with at least one aspect of the present disclosure.

FIG. 93 illustrates a bar graph 5406 depicting the total downtime 5432 per day of the week 5434 as depicted in FIG. 92 broken down according to each individual downtime instance. The number of downtime instances and the length of time for each downtime instance can be represented within each day's total downtime. For example, on Tuesday in the first operating theater (OR1) there were four instances of downtime between procedures and the magnitude of the first downtime instance indicates that it was longer than the other three instances. In one exemplification, the surgical hub 5706 is configured to further indicate the particular actions or steps taken during a selected downtime instance. For example, in FIG. 93. Thursday's second downtime instance 5440 has been selected, which then causes a callout 5442 to be displayed indicating that this particular downtime instance consisted of performing the initial set-up of the operating theater, administering anesthesia, and prepping the patient. As with the downtime instances themselves, the relative size or length of the actions or steps within the callout 5442 can correspond to the length of time for each particular action or step. The detail views for the downtime instances can be displayed when a user selects the particular instance, for example.

Figure 94:
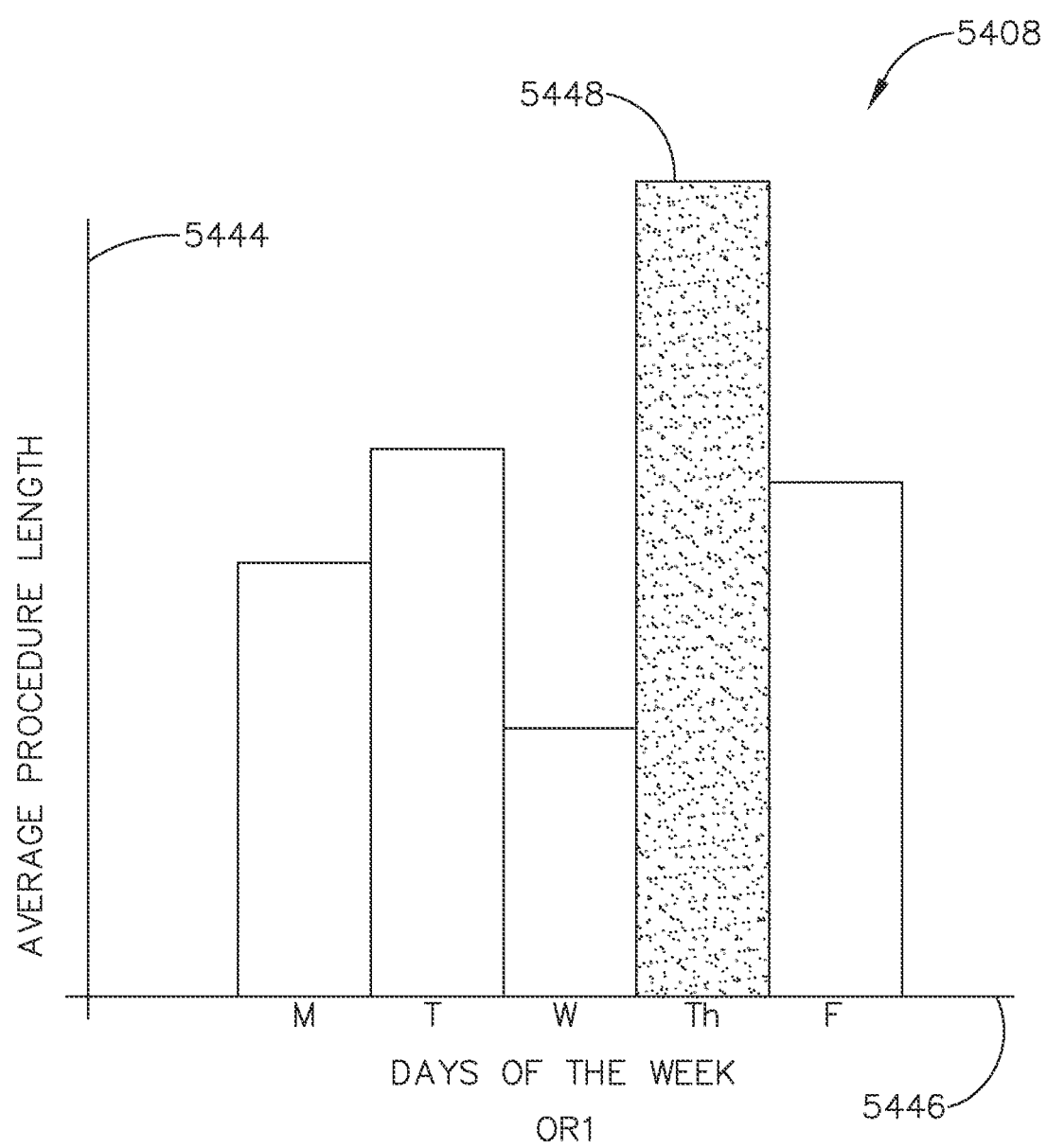
FIG. 94 illustrates a bar graph depicting the average procedure length relative to the days of a week for a particular operating room, in accordance with at least one aspect of the present disclosure.

FIG. 94 illustrates a bar graph 5408 depicting the average procedure length 5444 relative to the days of a week 5446 for a particular operating theater. The surgical hub 5706 can be configured to track the average procedure length through a situational awareness system, for example. The situational awareness system can detect or infer when each particular step of a surgical procedure is occurring (see FIG. 86, for example) and then track the length of time for each of the steps. The surgical hub 5706 can thereby determine the total downtime 5432 for each day of the week 5434 by summing the lengths of the downtime instances for the particular day. In one exemplification, the surgical hub 5706 can be configured to indicate when the average procedure length deviates from an expected value. For example, FIG. 94 depicts Thursday's average procedure length 5448 for the first operating room (OR1) as being highlighted for deviating from an expected length of time.

Figure 95:
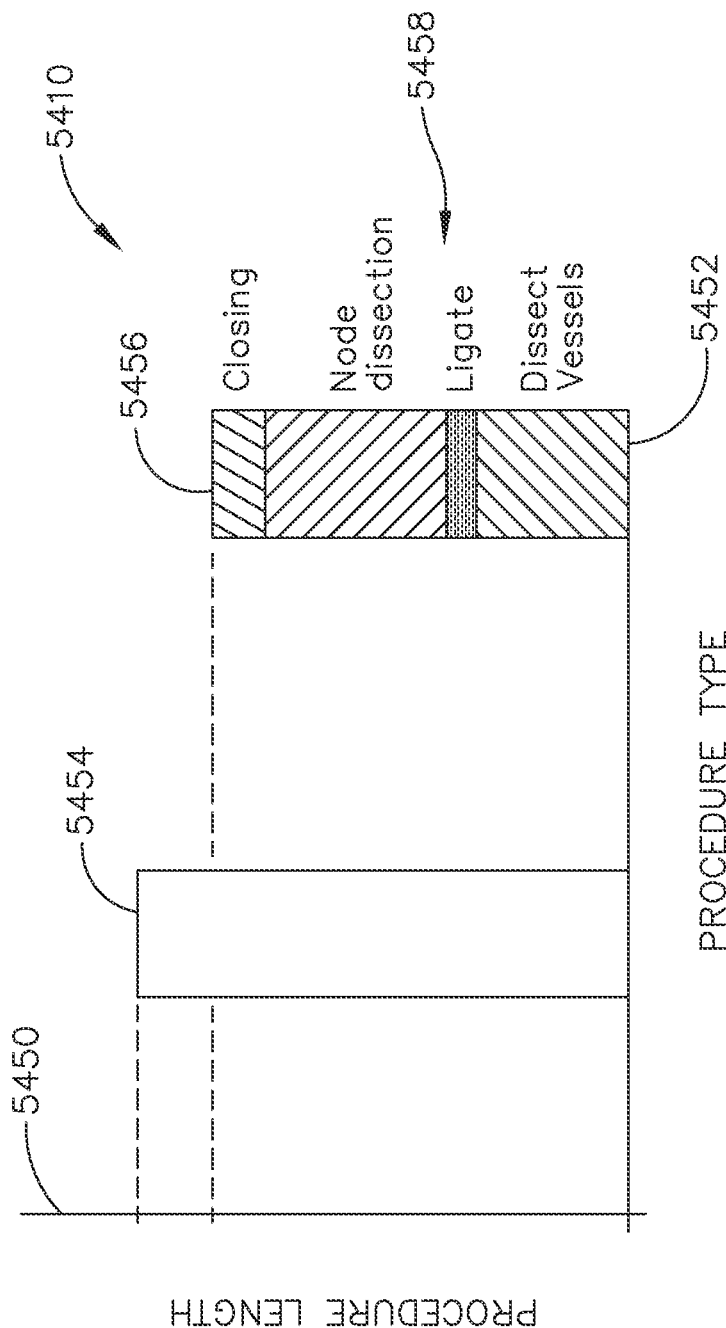
FIG. 95 illustrates a bar graph depicting procedure length relative to procedure type, in accordance with at least one aspect of the present disclosure.

FIG. 95 illustrates a bar graph 5410 depicting the procedure lengths 5450 relative to procedure types 5452. The depicted procedure lengths 5450 can either represent the average procedure lengths for particular types of procedures or the procedure lengths for each individual procedure performed on a given day in a given operating theater. The procedure lengths 5450 for different procedure types 5452 can then be compared. Further, the average lengths for the steps in a procedure type 5452 or the length for each particular step in a particular procedure can be displayed when a procedure is selected. Further, the procedure types 5452 can be tagged with various identifiers for parsing and comparing different data sets. For example, in FIG. 95 the first procedure 5454 corresponds to a colorectal procedure (specifically, a low anterior resection) where there was a preoperative identification of abdominal adhesions. The second procedure 5456 corresponds to a thoracic procedure (specifically, a segmentectomy). It should be noted again that the procedures depicted in FIG. 95 can represent the lengths of time for individual procedures or the average lengths of time for all of the procedures for the given procedure types. Each of the procedures can further be broken down according to the length of time for each step in the procedure. For example, FIG. 95 depicts the second procedure 5456 (a thoracic segmentectomy) as including an icon or graphical representation 5458 of the length of time spent on the dissect vessels, ligate (the vessels), nodal dissection, and closing steps of the surgical procedure. As with the procedure lengths themselves, the relative size or length of the steps within the graphical representation 5442 can correspond to the length of time for each particular step of the surgical procedure. The detail views for the steps of the surgical procedures can be displayed when a user selects the particular procedure, for example. In one exemplification, the surgical hub 5706 can be configured to identify when a length of time to complete a given step in the procedure deviates from an expected length of time. For example, FIG. 95 depicts the nodal dissection step as being highlighted for deviating from an expected length of time.

In one exemplification, an analytics package of the surgical hub 5706 can be configured to provide the user with usage data and results correlations related to the surgical procedures (or downtime between procedures). For example, the surgical hub 5706 can be configured to display methods or suggestions to improve the efficiency or effectiveness of a surgical procedure. As another example, the surgical hub 5706 can be configured to display methods to improve cost allocation. FIGS. 96-101 depict examples of various metrics that can be tracked by the surgical hub 5706, which can then be utilized to provide medical facility personnel suggestions for inventory utilization or technique outcomes. For example, a surgical hub 5706 could provide a surgeon with a suggestion pertaining to a particular technique outcome prior to or at the beginning of a surgical procedure based on the metrics tracked by the surgical hub 5706.

Figure 96:
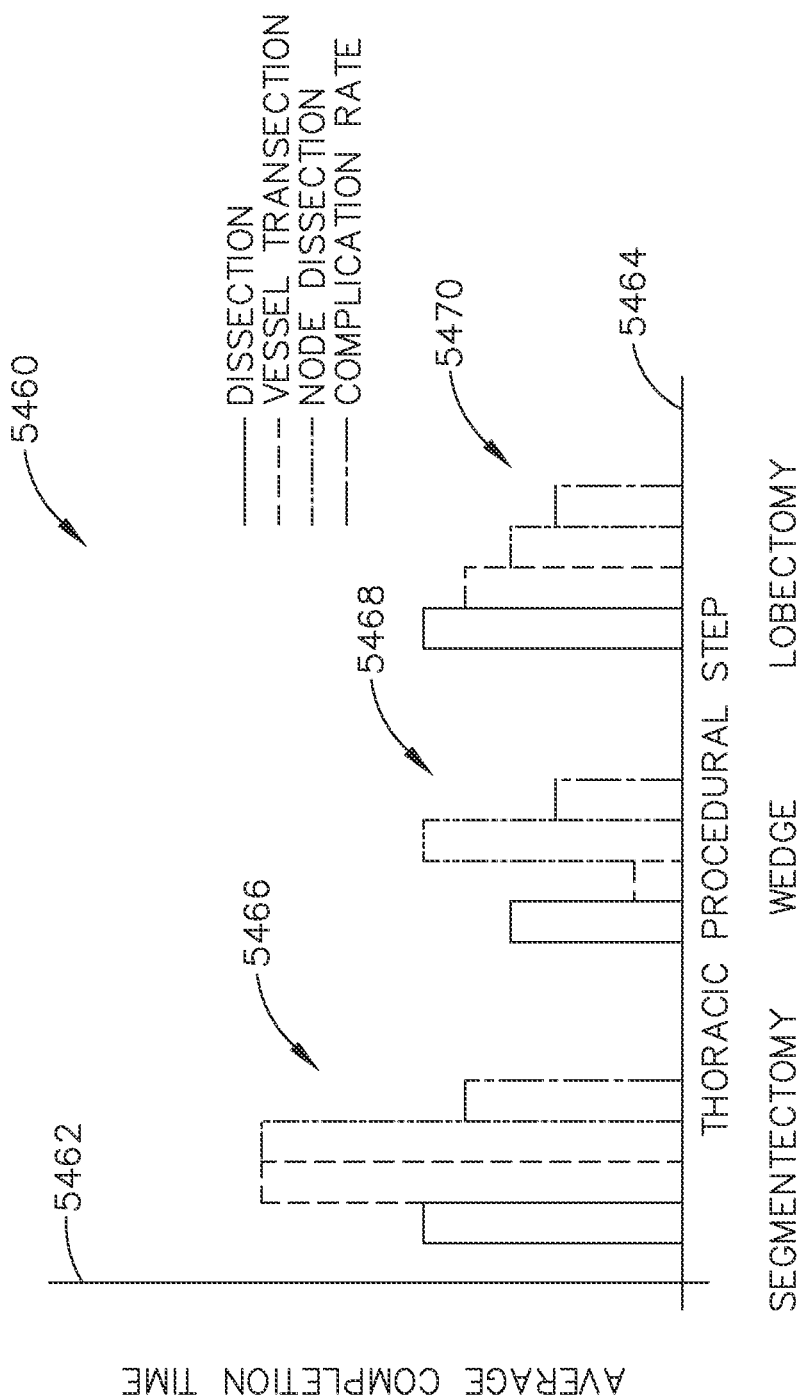
FIG. 96 illustrates a bar graph depicting the average completion time for particular procedural steps for different types of thoracic procedures, in accordance with at least one aspect of the present disclosure.

FIG. 96 illustrates a bar graph 5460 depicting the average completion time 5462 for particular procedural steps 5464 for different types of thoracic procedures. The surgical hub 5706 can be configured to track and store historical data for different types of procedures and calculate the average time to complete the procedure (or an individual step thereof). For example, FIG. 96 depicts the average completion time 5462 for thoracic segmentectomy 5466, wedge 5468, and lobectomy 5470 procedures. For each type of procedure, the surgical hub 5706 can track the average time to complete each step thereof. In this particular example, the dissection, vessel transection, and node dissection steps are indicated for each type of procedure. In addition to tracking and providing the average time for the steps of the procedure types, the surgical hub 5706 can additionally track other metrics or historical data, such as the complication rate for each procedure type (i.e., the rate of procedures having at least one complication as defined by the surgical hub 5706 or the surgeon). Additional tracked metrics for each procedure type, such as the complication rate, can also be depicted for comparison between the different procedure types.

Figure 97:
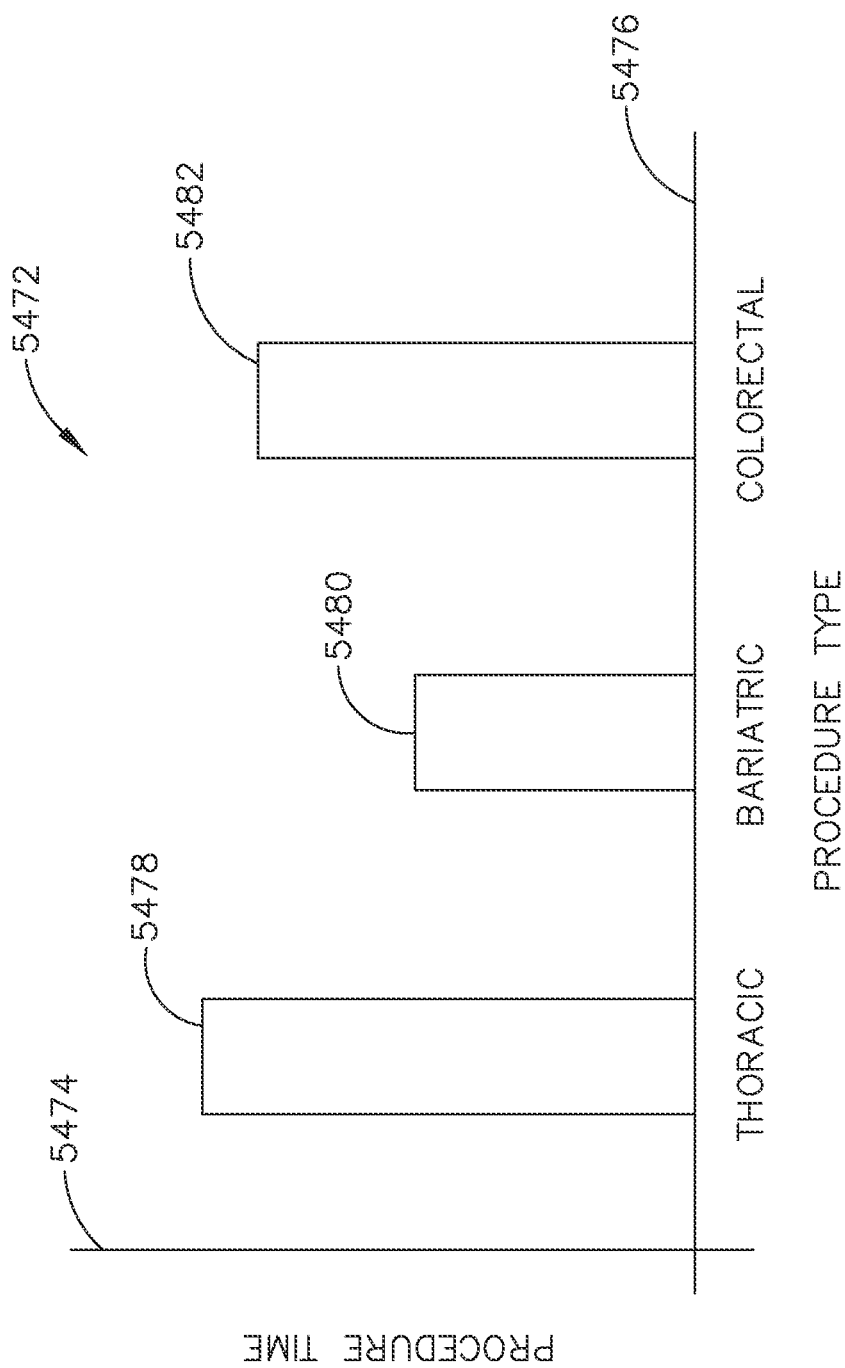
FIG. 97 illustrates a bar graph depicting procedure time relative to procedure types, in accordance with at least one aspect of the present disclosure.

FIG. 97 illustrates a bar graph 5472 depicting the procedure time 5474 relative to procedure types 5476. The surgical hub 5706 can be configured to track and store historical data or metrics for different procedure types 5476 or classes, which can encompass multiple subtypes of procedures. For example, FIG. 97 depicts the procedure time 5474 for surgical procedures classified as a thoracic 5478, bariatric 5480, or colorectal 5482 procedure. In various exemplifications, the surgical hub 5706 can output the procedure time 5474 for the procedure classifications expressed in terms of either the total length of time or the average time spent on the given procedure types 5476. The analytics package of the surgical hub 5706 can, for example, provide this data to the surgeons, hospital officials, or medical personnel to track the efficiency of the queried procedures. For example, FIG. 97 depicts bariatric procedures 5480 as taking a lower average time (i.e., being more time efficient) than either thoracic procedures 5478 or colorectal procedures 5482.

Figure 98:
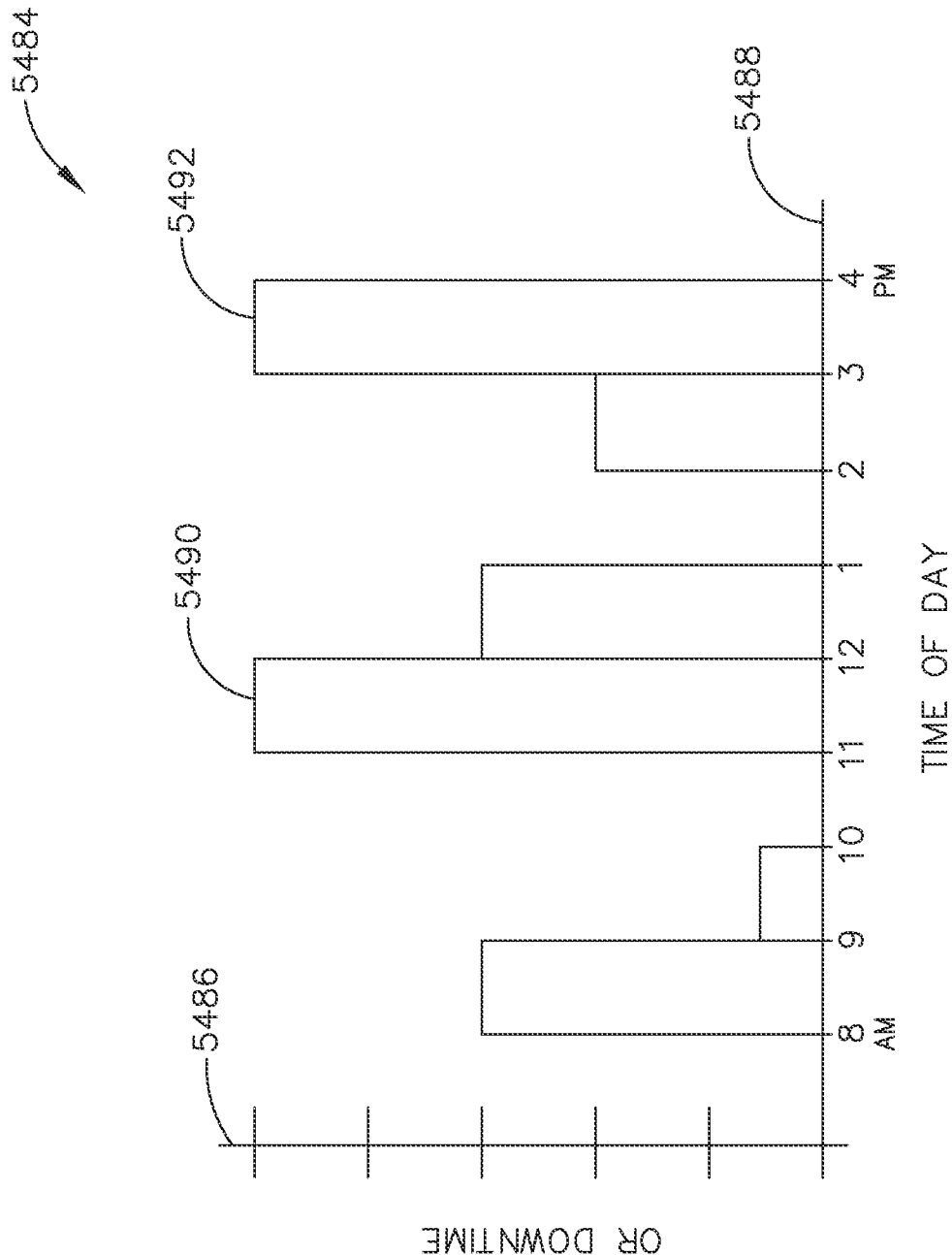
FIG. 98 illustrates a bar graph depicting operating room downtime relative to the time of day, in accordance with at least one aspect of the present disclosure.
Figure 99:
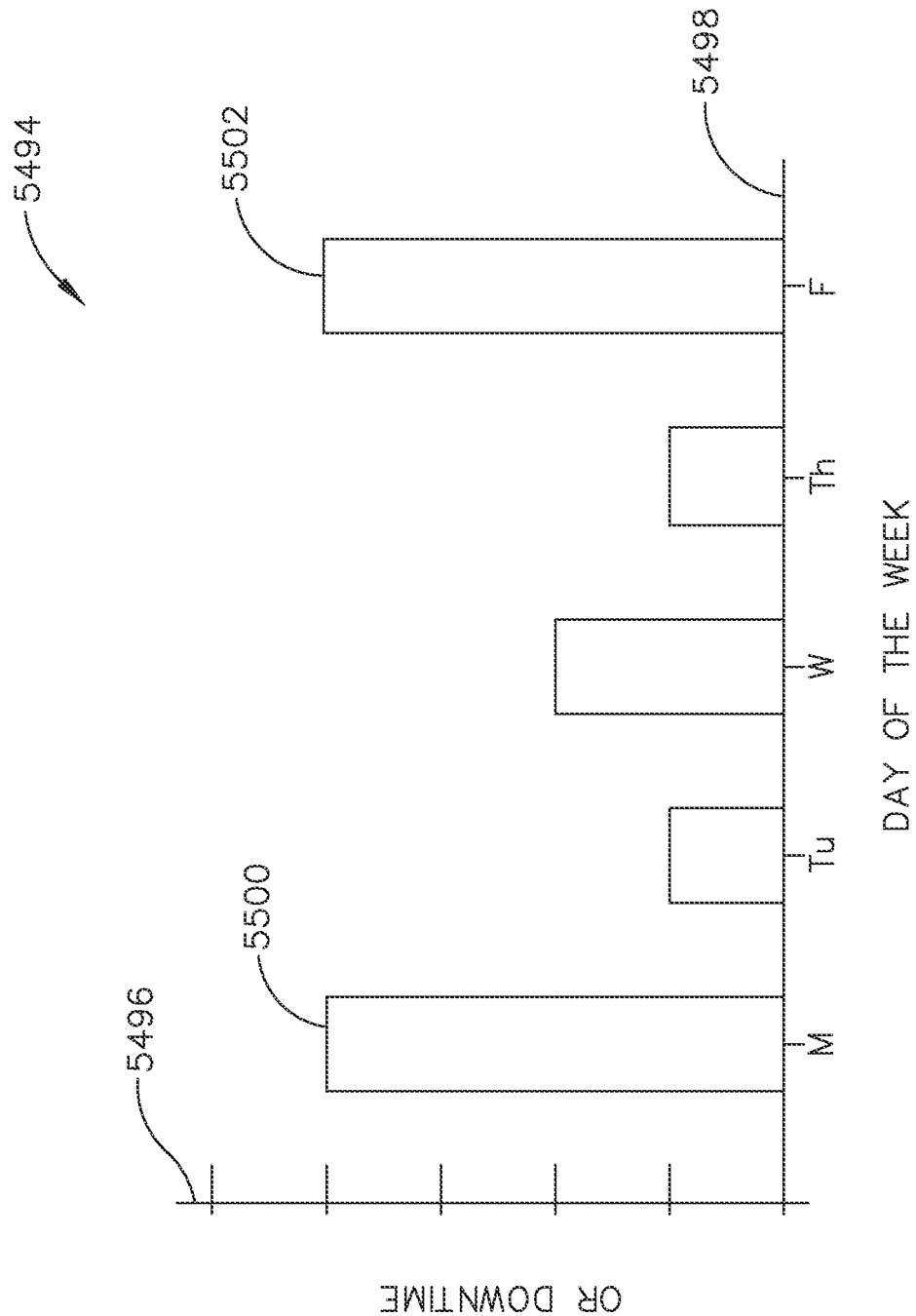
FIG. 99 illustrates a bar graph depicting operating room downtime relative to the day of the week, in accordance with at least one aspect of the present disclosure.

FIG. 98 illustrates a bar graph 5484 depicting operating room downtime 5486 relative to the time of day 5488. Relatedly, FIG. 99 illustrates a bar graph 5494 depicting operating room downtime 5496 relative to the day of the week 5498. Operating room downtime 5486, 5496 can be expressed in, for example, a length of a unit of time or relative utilization (i.e., percentage of time that the operating room is in use). The operating room downtime data can encompass an individual operating room or an aggregation of multiple operating rooms at a medical facility. As discussed above, a surgical hub 5706 can be configured to track whether a surgical procedure is being performed in the operating theater associated with the surgical hub 5706 (including the length of time that a surgical procedure is or is not being performed) utilizing a situational awareness system, for example. As shown in FIGS. 98 and 99, the surgical hub 5706 can provide an output (e.g., bar graphs 5484, 5494 or other graphical representations of data) depicting the tracked data pertaining to when the operating room is being utilized (i.e., when a surgical procedure is being performed) and/or when there is downtime between procedures. Such data can be utilized to identify ineffectiveness or inefficiencies in performing surgical procedures, cleaning or preparing operating theaters for surgery, scheduling, and other metrics associated with operating theater use. For example, FIG. 98 depicts a comparative increase in operating room downtime 5486 at a first instance 5490 from 11:00 a.m.-12:00 p.m. and a second instance 5492 from 3:00-4:00 p.m. As another example, FIG. 99 depicts a comparative increase in operating room downtime 5496 on Mondays 5500 and Fridays 5502. In various exemplifications, the surgical hub 5706 can provide operating theater downtime data for a particular instance (i.e., a specific time, day, week, etc.) or an average operating theater downtime data for a category of instances (i.e., aggregated data for a day, time, week, etc.). Hospital officials or other medical personnel thus could use this data to identify specific instances where an inefficiency may have occurred or identify trends in particular days and/or times of day where there may be inefficiencies. From such data, the hospital officials or other medical personnel could then investigate to identify the specific reasons for these increased downtimes and take corrective action to address the identified reason.

Figure 100:
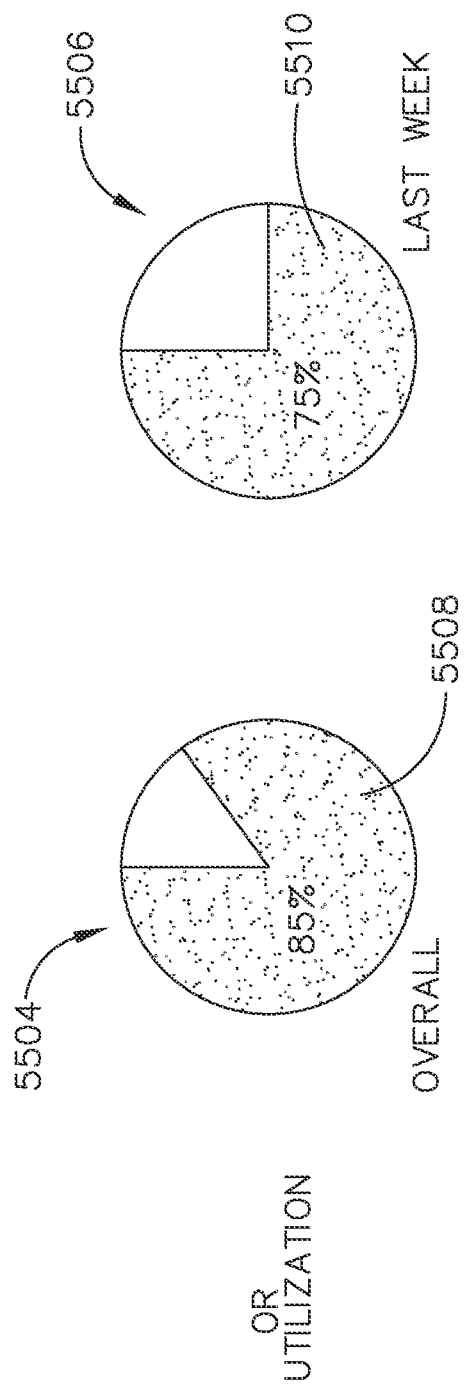
FIG. 100 illustrates a pair of pie charts depicting the percentage of time that the operating theater is utilized, in accordance with at least one aspect of the present disclosure.

In various exemplifications, the surgical hub 5706 can be configured to display data in response to queries in a variety of different formats (e.g., bar graphs, pie graphs, infographics). FIG. 100 illustrates a pair of pie charts depicting the percentage of time that the operating theater is utilized. The operating theater utilization percentage can encompass an individual operating theater or an aggregation of multiple operating theaters (e.g., the operating rooms at a medical facility or every operating room for all medical facilities having surgical hubs 5706 connected to the cloud 5702). As discussed above, a surgical hub 5706 can be configured to determine when a surgical procedure is or is not being performed (i.e., whether the operating theater associated with the surgical hub 5706 is being utilized) using a situational awareness system, for example. In addition to expressing operating theater utilization in terms of an average or absolute amount for different time periods (as depicted in FIGS. 98-99), the surgical hub 5706 can additionally express operating theater utilization in terms of a percentage or relative amount compared to a maximum possible utilization. As above, the operating theater utilization can be parsed for particular time periods, including the overall utilization (i.e., the total historical percentage of time in use) for the particular operating theater (or groups of operating theaters) or the utilization over the span of a particular time period. As shown in FIG. 100, a first pie chart 5504 depicts the overall operating theater utilization 5508 (85%) and a second pie chart 5506 depicts the operating theater utilization for the prior week 5510 (75%). Hospital officials and other medical personnel could use this data to identify that there may have been some inefficiency that occurred in the prior week that caused the particular operating theater (or group of operating theaters) to be utilized less efficiently compared to the historical average so that further investigations can be carried out to identify the specific reasons for this decreased utilization.

Figure 101:
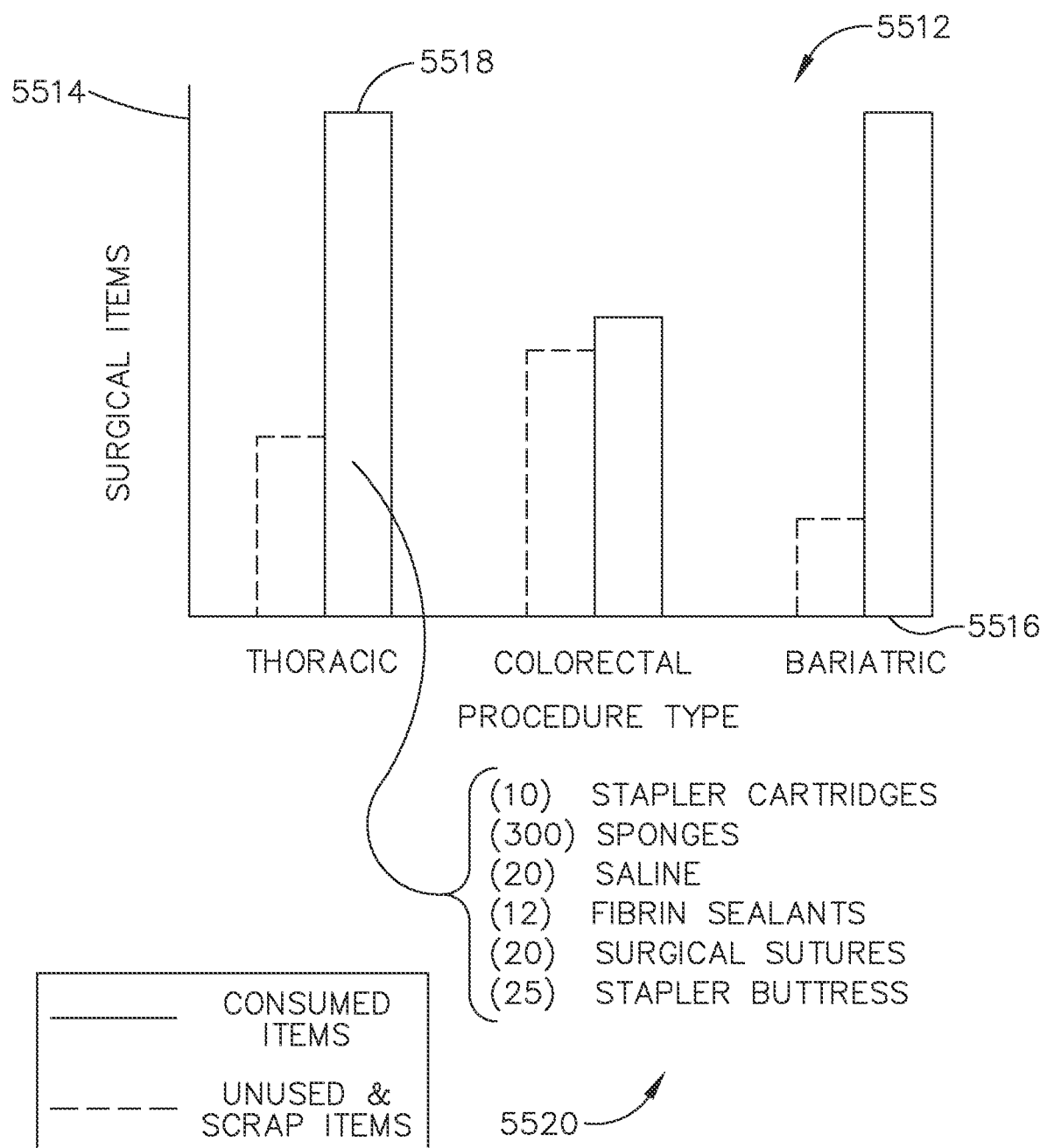
FIG. 101 illustrates a bar graph depicting consumed and unused surgical items relative to procedure type, in accordance with at least one aspect of the present disclosure.

In some exemplifications, the surgical hub 5706 is configured to track detect and track the number of surgical items that are utilized during the course of a surgical procedure. This data can then be aggregated and displayed (either automatically or in response to a query) according to, for example, a particular time period (e.g., per day or per week) or for a particular surgical procedure type (e.g., thoracic procedures or abdominal procedures). FIG. 101 illustrates a bar graph 5512 depicting consumed and unused surgical items 5514 relative to procedure type 5516. The surgical hub 5706 can be configured to determine or infer what surgical items are being consumed during the course of each surgical procedure via a situational awareness system. The situational awareness system can determine or receive the list of surgical items to be used in a procedure (e.g., see FIG. 85B), determine or infer when each procedure (and steps thereof) begins and ends, and determine when a particular surgical item is being utilized according to the procedural step being performed. The inventory of surgical items that are consumed or unused during the course of a surgical procedure can be represented in terms of the total number of surgical items or the average number of surgical items per procedure type 5516, for example. The consumed surgical items can include non-reusable items that are utilized during the course of a surgical procedure. The unused surgical items can include additional items that are not utilized during the procedure(s) or scrap items. The procedure type can correspond to broad classifications of procedures or a specific procedure type or technique for performing a procedure type. For example, in FIG. 101 the procedure types 5516 being compared are thoracic, colorectal, and bariatric procedures. For each of these procedure types 5516, the average number of consumed and unused surgical items 5514 are both provided. In one aspect, the surgical hub 5706 can be configured to further parse the consumed and/or unused surgical items 5514 by the specific item type. In one exemplification, the surgical hub 5706 can provide a detailed breakdown of the surgical items 5514 making up each item category for each surgical procedure type 5516 and graphically represent the different categories of surgical items 5514. For example, in FIG. 101, the unused surgical items are depicted in dashed lines and the consumed surgical items are depicted in solid lines. In one exemplification, the surgical hub 5706 is configured to further indicate the specific within a category for a particular procedure type 5516. For example, in FIG. 93, the consumed items category for the thoracic procedure type has been selected, which then causes a callout 5520 to be displayed listing the particular surgical items in the category: stapler cartridges, sponges, saline, fibrin sealants, surgical sutures, and stapler buttress material. Furthermore, the callout 5520 can be configured to provide the quantities of the listed items in the category, which may be the average or absolute quantities of the items (either consumed or unused) for the particular procedure type.

In one exemplification, the surgical hub 5706 can be configured to aggregate tracked data in a redacted format (i.e., with any patient-identifying information stripped out). Such bulk data can be utilized for academic or business analysis purposes. Further, the surgical hub 5706 can be configured to upload the redacted or anonymized data to a local database of the medical facility in which the surgical hub 5706 is located, an external database system, or the cloud 5702, whereupon the anonymized data can be accessed by user/client applications on demand. The anonymized data can be utilized to compare outcomes and efficiencies within a hospital or between geographic regions, for example.

The process 5300 depicted in FIG. 89 improves scheduling efficiency by allowing the surgical hubs 5706 to automatically store and provide granular detail on correlations between lengths of time required for various procedures according to particular days, particular types of procedures, particular hospital staff members, and other such metrics. This process 5300 also reduces surgical item waste by allowing the surgical hubs 5706 to provide alerts when the amount of surgical items being consumed, either on a per-procedure basis or as a category, are deviating from the expected amounts. Such alerts can be provided either automatically or in response to receiving a query.

Figure 102:
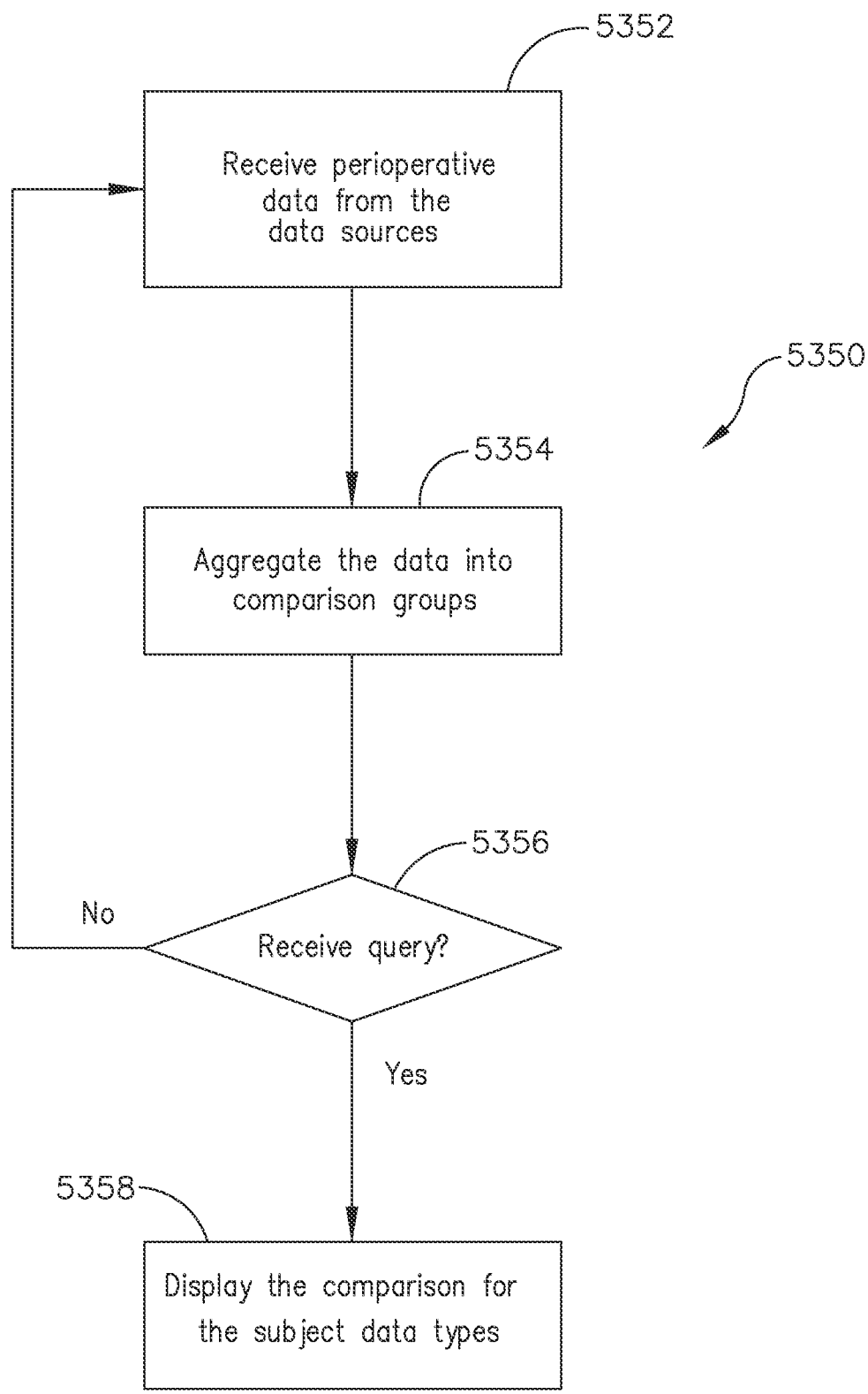
FIG. 102 illustrates a logic flow diagram of a process for storing data from the modular devices and patient information database for comparison, in accordance with at least one aspect of the present disclosure.

FIG. 102 illustrates a logic flow diagram of a process 5350 for storing data from the modular devices and patient information database for comparison. In the following description, description of the process 5350, reference should also be made to FIG. 88. In one exemplification, the process 5350 can be executed by a control circuit of a surgical hub 206, as depicted in FIG. 10 (processor 244). In yet another exemplification, the process 5350 can be executed by a distributed computing system including a control circuit of a surgical hub 206 in combination with a control circuit of a modular device, such as the microcontroller 461 of the surgical instrument depicted FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5350 will be described as being executed by the control circuit of a surgical hub 5706; however, it should be understood that the description of the process 5350 encompasses all of the aforementioned exemplifications.

The control circuit executing the process 5350 receives data from the data sources, such as the modular device(s) and the patient information database(s) (e.g., EMR databases) that are communicably coupled to the surgical hub 5706. The data from the modular devices can include, for example, usage data (e.g., data pertaining to how often the modular device has been utilized, what procedures the modular device has been utilized in connection with, and who utilized the modular devices) and performance data (e.g., data pertaining to the internal state of the modular device and the tissue being operated on). The data from the patient information databases can include, for example, patient data (e.g., data pertaining to the patient's age, sex, and medical history) and patient outcome data (e.g., data pertaining to the outcomes from the surgical procedure). In some exemplifications, the control circuit can continuously receive 5352 data from the data sources before, during, or after a surgical procedure.

As the data is received 5352, the control circuit aggregates 5354 the data in comparison groups of types of data. In other words, the control circuit causes a first type of data to be stored in association with a second type of data. However, more than two different types of data can be aggregated 5354 together into a comparison group. For example, the control circuit could store a particular type of performance data for a particular type of modular device (e.g., the force to fire for a surgical cutting and stapling instrument or the characterization of the energy expended by an RF or ultrasonic surgical instrument) in association with patient data, such as sex, age (or age range), a condition (e.g., emphysema) associated with the patient. In one exemplification, when the data is aggregated 5354 into comparison groups, the data is anonymized such that all patient-identifying information is removed from the data. This allows the data aggregated 5354 into comparison groups to be utilized for studies, without compromising confidential patient information. The various types of data can be aggregated 5354 and stored in association with each other in lookup tables, arrays, and other such formats. In one exemplification, the received 5352 data is automatically aggregated 5354 into comparison groups. Automatically aggregating 5354 and storing the data allows the surgical hub 5706 to quickly return results for queries and the groups of data to be exported for analysis according to specifically desired data types.

When the control circuit receives 5356 a query for a comparison between two or more of the tracked data types, the process 5350 proceeds along the YES branch. The control circuit then retrieves the particular combination of the data types stored in association with each other and then displays 5358 a comparison (e.g., a graph or other graphical representation of the data) between the subject data types. If the control circuit does not receive 5356 a query, the process 5350 continues along the NO branch and the control circuit continues receiving 5352 data from the data sources.

In one exemplification, the control circuit can be configured to automatically quantify a correlation between the received 5352 data types. In such aspects, the control circuit can calculate a correlation coefficient (e.g., the Pearson's coefficient) between pairs of data types. In one aspect, the control circuit can be configured to automatically display a report providing suggestions or other feedback if the quantified correlation exceeds a particular threshold value. In one aspect, the control circuit of the surgical hub 5706 can be configured to display a report on quantified correlations exceeding a particular threshold value upon receiving a query or request from a user.

In one exemplification, a surgical hub 5706 can compile information on procedures that the surgical hub 5706 was utilized in the performance of, communicate with other surgical hubs 5706 within its network (e.g., a local network of a medical facility or a number of surgical hubs 5706 connected by the cloud 5702), and compare results between type of surgical procedures or particular operating theaters, doctors, or departments. Each surgical hub 5706 can calculate and analyze utilization, efficiency, and comparative results (relative to all surgical hubs 5706 across a hospital network, a region, etc.). For example, the surgical hub 5706 can display efficiency and comparative data, including operating theater downtime, operating theater clean-up and recycle time, step-by-step completion timing for procedures (including highlighting which procedural steps take the longest, for example), average times for surgeons to complete procedures (including parsing the completion times on a procedure-by-procedure basis), historical completion times (e.g., for completing classes of procedures, specific procedures, or specific steps within a procedure), and/or operating theater utilization efficiency (i.e., the time efficiency from a procedure to a subsequent procedure). The data that is accessed and shared across networks by the surgical hubs 5706 can include the anonymized data aggregated into comparison groups, as discussed above.

For example, the surgical hub 5706 can be utilized to perform studies of performance by instrument type or cartridge type for various procedures. As another example, the surgical hub 5706 can be utilized to perform studies on the performance of individual surgeons. As yet another example, the surgical hub 5706 can be utilized to perform studies on the effectiveness of different surgical procedures according to patients' characteristics or disease states.

In another exemplification, a surgical hub 5706 can provide suggestions on streamlining processes based on tracked data. For example, the surgical hub 5706 can suggest different product mixes according to the length of certain procedures or steps within a procedure (e.g., suggest a particular item that is more appropriate for long procedure steps), suggest more cost effective product mixes based on the utilization of items, and/or suggest kitting or pre-grouping certain items to lower set-up time. In another exemplification, a surgical hub 5706 can compare operating theater utilization across different surgical groups in order to better balance high volume surgical groups with surgical groups that have more flexible bandwidth. In yet another aspect, the surgical hub 5706 could be put in a forecasting mode that would allow the surgical hub 5706 to monitor upcoming procedure preparation and scheduling, then notify the administration or department of upcoming bottlenecks or allow them to plan for scalable staffing. The forecasting mode can be based on, for example, the anticipated future steps of the current surgical procedure that is being performed using the surgical hub 5706, which can be determined by a situational awareness system.

In another exemplification, a surgical hub 5706 can be utilized as a training tool to allow users to compare their procedure timing to other types of individuals or specific individuals within their department (e.g., a resident could compare his or her timing to a particular specialist or the average time for a specialist within the hospital) or the department average times. For example, users could identify what steps of a surgical procedure they are spending an inordinate amount of time on and, thus, what steps of the surgical procedure that they need to improve upon.

In one exemplification, all processing of stored data is performed locally on each surgical hub 5706. In another exemplification, each surgical hub 5706 is part of a distributed computing network, wherein each individual surgical hub 5706 compiles and analyzes its stored data and then communicates the data to the requesting surgical hub 5706. A distributed computing network could permit fast parallel processing. In another exemplification, each surgical hub 5706 is communicably connected to a cloud 5702, which can be configured to receive the data from each surgical hub 5706 and then perform the necessary processing (data aggregation, calculations, and so on) on the data.

The process 5350 depicted in FIG. 102 improves the ability to determine when procedures are being performed inefficiently by allowing the surgical hubs 5706 to provide alerts when particular procedures, either on a per-procedure basis or as category, are deviating from the expected times to complete the procedures. Such alerts can be provided either automatically or in response to receiving a query. This process 5350 also improves the ability to perform studies on what surgical instruments and surgical procedure techniques provide the best patient outcomes by automatically tracking and indexing such data in easily-retrievable and reportable formats.

Some systems described herein offload the data processing that controls the modular devices (e.g., surgical instruments) from the modular devices themselves to an external computing system (e.g., a surgical hub) and/or a cloud. However in some exemplifications, some modular devices can sample data (e.g., from the sensors of the surgical instruments) at a faster rate that the rate at which the data can be transmitted to and processed by a surgical hub. As one solution, the surgical hub and the surgical instruments (or other modular devices) can utilize a distributed computing system where at least a portion of the data processing is performed locally on the surgical instrument. This can avoid data or communication bottlenecks between the instrument and the surgical hub by allowing the onboard processor of the surgical instrument to handle at least some of the data processing when the data sampling rate is exceeding the rate at which the data can be transmitted to the surgical hub. In some exemplifications, the distributed computing system can cease distributing the processing between the surgical hub and the surgical instrument and instead have the processing be executed solely onboard the surgical instrument. The processing can be executed solely by the surgical instrument in situations where, for example, the surgical hub needs to allocate its processing capabilities to other tasks or the surgical instrument is sampling data at a very high rate and it has the capabilities to execute all of the data processing itself.

Similarly, the data processing for controlling the modular devices, such as surgical instruments, can be taxing for an individual surgical hub to perform. If the surgical hub's processing of the control algorithms for the modular devices cannot keep pace with the use of the modular devices, then the modular devices will not perform adequately because their control algorithms will either not be updated as needed or the updates to the control algorithms will lag behind the actual use of the instrument. As one solution, the surgical hubs can be configured to utilize a distributed computing system where at least a portion of the processing is performed across multiple separate surgical hubs. This can avoid data or communication bottlenecks between the modular devices and the surgical hub by allowing each surgical hub to utilize the networked processing power of multiple surgical hubs, which can increase the rate at which the data is processed and thus the rate at which the control algorithm adjustments can be transmitted by the surgical hub to the paired modular devices. In addition to distributing the computing associated with controlling the various modular devices connected to the surgical hubs, a distributed computing system can also dynamically shift computing resources between multiple surgical hubs in order to analyze tracked data in response to queries from users and perform other such functions. The distributed computing system for the surgical hubs can further be configured to dynamically shift data processing resources between the surgical hubs when any particular surgical hub becomes overtaxed.

The modular devices that are communicably connectable to the surgical hub can include sensors, memories, and processors that are coupled to the memories and configured to receive and analyze data sensed by the sensors. The surgical hub can further include a processor coupled to a memory that is configured to receive (through the connection between the modular device and the surgical hub) and analyze the data sensed by the sensors of the modular device. In one exemplification, the data sensed by the modular device is processed externally to the modular device (e.g., external to a handle assembly of a surgical instrument) by a computer that is communicably coupled to the modular device. For example, the advanced energy algorithms for controlling the operation of a surgical instrument can be processed by an external computing system, rather than on a controller embedded in the surgical instrument (such as instrument using an Advanced RISC Machine (ARM) processor). The external computer system processing the data sensed by the modular devices can include the surgical hub to which the modular devices are paired and/or a cloud computing system. In one exemplification, data sampled at a particular rate (e.g., 20 Ms/sec) and a particular resolution (e.g., 12 bits resolution) by a surgical instrument is decimated and then transmitted over a link to the surgical hub to which the surgical instrument is paired. Based on this received data, the control circuit of the surgical hub then determines the appropriate control adjustments for the surgical instrument, such as controlling power for an ultrasonic surgical instrument or RF electrosurgical instrument, setting motor termination points for a motor-driven surgical instrument, and so on. The control adjustments are then transmitted to the surgical instrument for application thereon.

Distributed Processing

Figure 103:
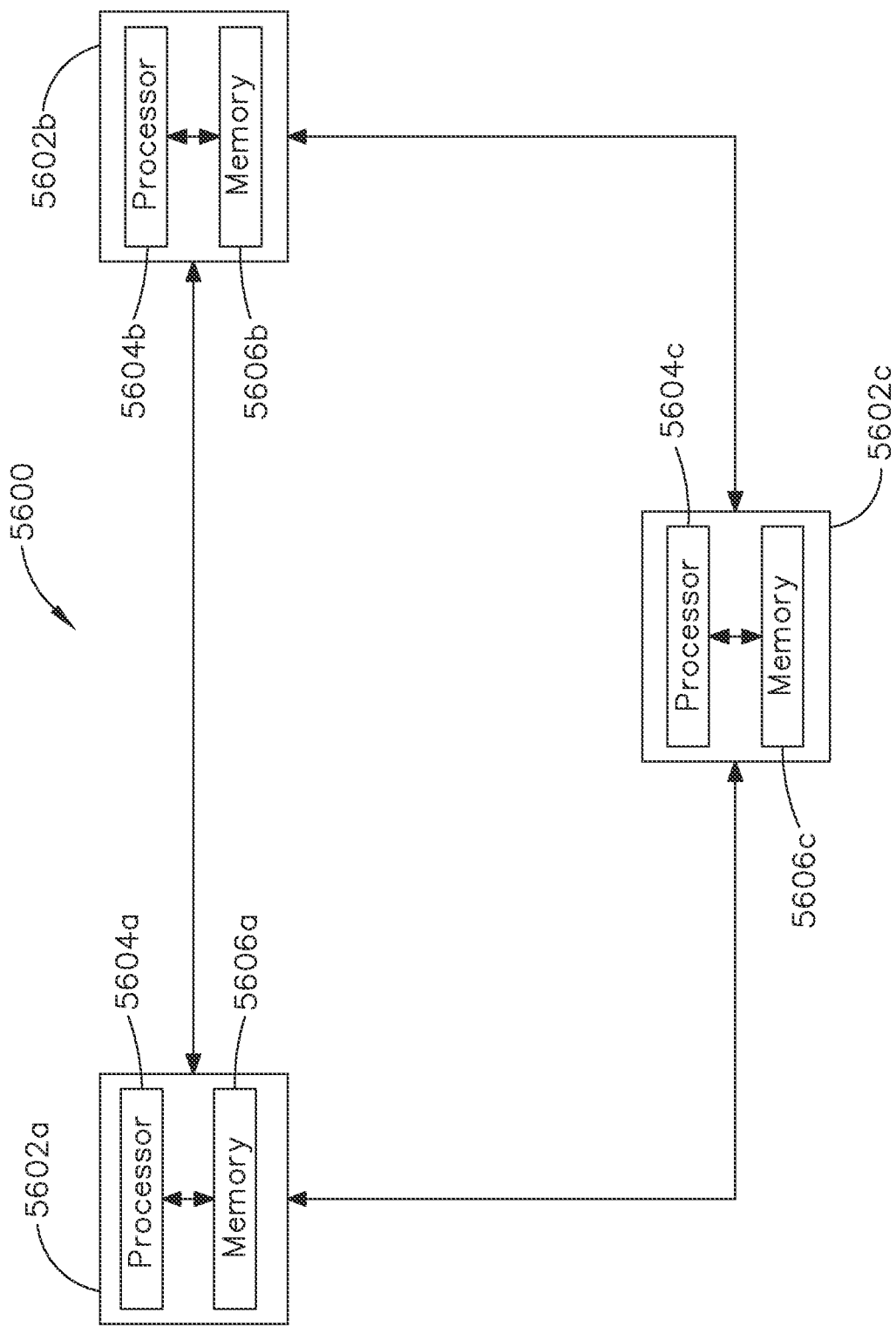
FIG. 103 illustrates a diagram of a distributed computing system, in accordance with at least one aspect of the present disclosure.

FIG. 103 illustrates a diagram of a distributed computing system 5600. The distributed computing system 5600 includes a set of nodes 5602a, 5602b, 5602c that are communicably coupled by a distributed multi-party communication protocol such that they execute a shared or distributed computer program by passing messages therebetween. Although three nodes 5602a, 5602b, 5602c are depicted, the distributed computing system 5600 can include any number of nodes 5602a, 5602b, 5602c that are communicably connected together. Each of the nodes 5602a, 5602b, 5602c comprises a respective memory 5606a, 5606b, 5606c and processor 5604a, 5604b, 5604c coupled thereto. The processors 5604a, 5604b, 5604c execute the distributed multi-party communication protocol, which is stored at least partially in the memories 5606a, 5606b, 5606c. Each node 5602a, 5602b, 5602c can represent either a modular device or a surgical hub. Therefore, the depicted diagram represents aspects wherein various combinations of surgical hubs and/or modular devices are communicably coupled. In various exemplifications, the distributed computing system 5600 can be configured to distribute the computing associated with controlling the modular device(s) (e.g., advanced energy algorithms) over the modular device(s) and/or the surgical hub(s) to which the modular device(s) are connected. In other words, the distributed computing system 5600 embodies a distributed control system for controlling the modular device(s) and/or surgical hub(s).

In some exemplifications, the modular device(s) and surgical hub(s) utilize data compression for their communication protocols. Wireless data transmission over sensor networks can consume a significant amount of energy and/or processing resources compared to data computation on the device itself. Thus data compression can be utilized to reduce the data size at the cost of extra processing time on the device. In one exemplification, the distributed computing system 5600 utilizes temporal correlation for sensing data, data transformation from one dimension to two dimension, and data separation (e.g., upper 8 bit and lower 8 bit data). In another exemplification, the distributed computing system 5600 utilizes a collection tree protocol for data collection from different nodes 5602a, 5602b, 5602c having sensors (e.g., modular devices) to a root node. In yet another aspect, the distributed computing system 5600 utilizes first-order prediction coding to compress the data collected by the nodes 5602a, 5602b, 5602c having sensors (e.g., modular devices), which can minimize the amount of redundant information and greatly reduce the amount of data transmission between the nodes 5602a, 5602b, 5602c of the network. In yet another exemplification, the distributed computing system 5600 is configured to transmit only the electroencephalogram (EEG) features. In still yet another exemplification, the distributed computing system 5600 can be configured to transmit only the complex data features that are pertinent to the surgical instrument detection, which can save significant power in wireless transmission. Various other exemplifications can utilize combinations of the aforementioned data compression techniques and/or additional techniques of data compression.

Figure 104:
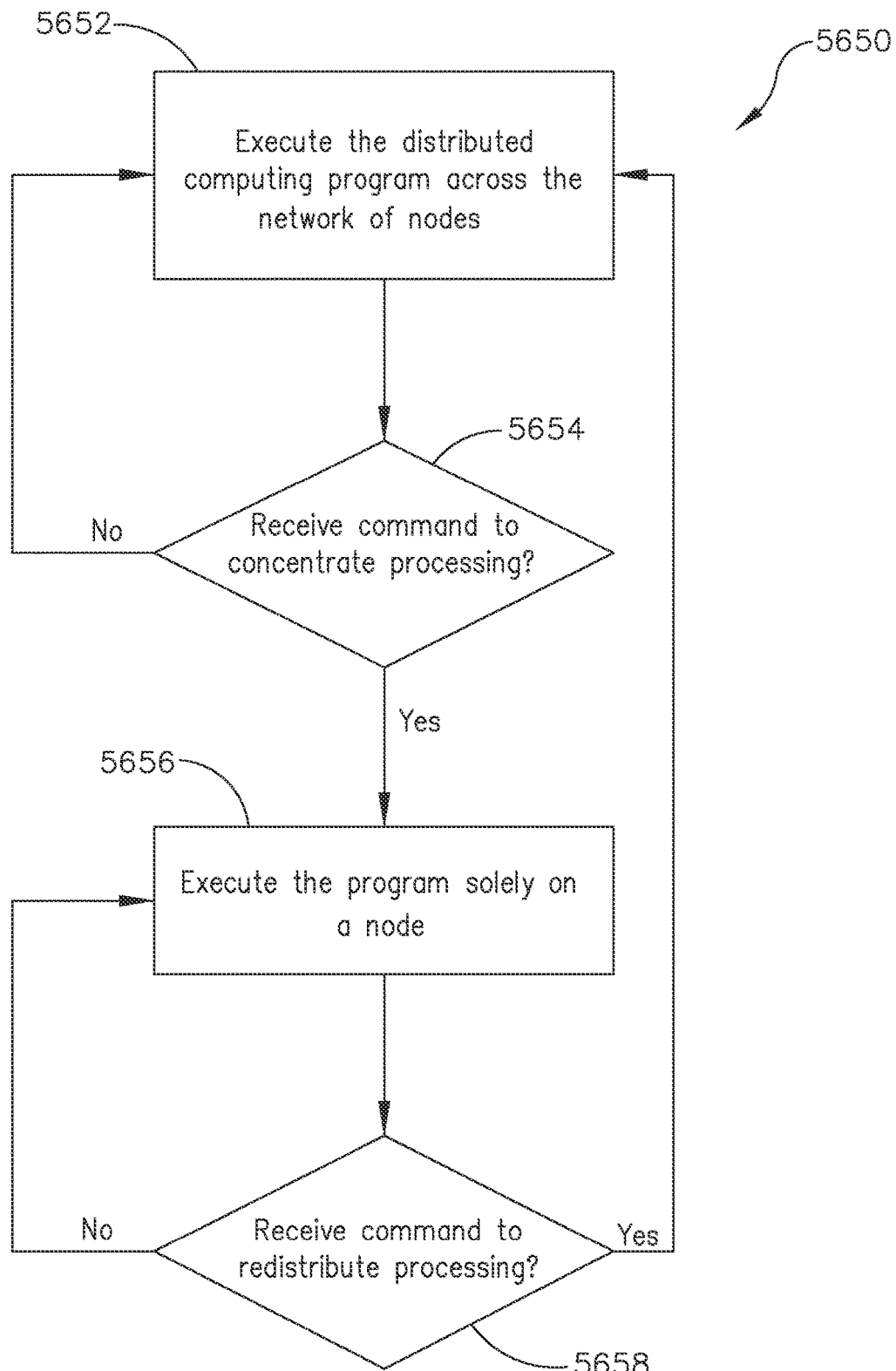
FIG. 104 illustrates a logic flow diagram of a process for shifting distributed computing resources, in accordance with at least one aspect of the present disclosure.

FIG. 104 illustrates a logic flow diagram of a process 5650 for shifting distributed computing resources. In the following description of the 5650, reference should also be made to FIG. 103. In one exemplification, the process 5650 can be executed by a distributed computing system including a control circuit of a surgical hub 206, as depicted in FIG. 10 (processor 244), in combination with a control circuit of a second surgical hub 206 and/or a control circuit of a modular device, such as the microcontroller 461 of the surgical instrument depicted FIG. 12, the microcontroller 620 of the surgical instrument depicted in FIG. 16, the control circuit 710 of the robotic surgical instrument 700 depicted in FIG. 17, the control circuit 760 of the surgical instruments 750, 790 depicted in FIGS. 18 and 19, or the controller 838 of the generator 800 depicted in FIG. 20. For economy, the following description of the process 5650 will be described as being executed by the control circuits of one or more nodes; however, it should be understood that the description of the process 5650 encompasses all of the aforementioned exemplifications.

The control circuits of each node execute 5652 a distributed control program in synchrony. As the distributed control program is being executed across the network of nodes, at least one of the control circuits monitors for a command instructing the distributed computing system to shift from a first mode, wherein the distributed computing program is executed across the network of nodes, to a second mode, wherein the control program is executed by a single node. In one exemplification, the command can be transmitted by a surgical hub in response to the surgical hub's resources being needed for an alternative computing task. In another exemplification, the command can be transmitted by a modular device in response to the rate at which the data is sampled by the modular device outpacing the rate at which the sampled data can be communicated to the other nodes in the network. If a control circuit determines that an appropriate command has been received 5654, the process 5650 continues along the YES branch and the distributed computing system 5600 shifts to a single node executing 5656 the program. For example, the distributed computing system 5600 shifts the distributed computing program from being executed by both a modular device and a surgical hub to being executed solely by the modular device. As another example, the distributed computing system 5600 shifts the distributed computing program from being executed by both a first surgical hub and a second surgical hub to being executed solely by the first surgical hub. If no control circuit determines that an appropriate command has been received 5654, the process continues along the NO branch and the control circuits of the network of nodes continues executing 5652 the distributed computing program across the network of nodes.

In the event that the program has been shifted to being executed 5656 by a single node, the control circuit of the particular node solely executing the distributed program and/or a control circuit of another node within the network (which previously was executing the distributed program) monitors for a command instructing the node to re-distribute the processing of the program across the distributed computing system. In other words, the node monitors for a command to re-initiate the distributed computing system. In one exemplification, the command to re-distribute the processing across the network can be generated when the sampling rate of the sensor is less than the data communication rate between the modular device and the surgical hub. If a control circuit receives 5658 an appropriate command to re-distribute the processing, then the process 5650 proceeds along the YES branch and the program is once again executed 5652 across the node network. If a control circuit has not received 5658 an appropriate command, then the node continues singularly executing 5656 the program.

The process 5650 depicted in FIG. 104 eliminates data or communication bottlenecks in controlling modular devices by utilizing a distributed computing architecture that can shift computing resources either between the modular devices and surgical hubs or between the surgical hubs as needed. This process 5650 also improves the modular devices' data processing speed by allowing the processing of the modular devices' control adjustments to be executed at least in part by the modular devices themselves. This process 5650 also improves the surgical hubs' data processing speed by allowing the surgical hubs to shift computing resources between themselves as necessary.

It can be difficult during video-assisted surgical procedures, such as laparoscopic procedures, to accurately measure sizes or dimensions of features being viewed through a medical imaging device due to distortive effects caused by the device's lens. Being able to accurately measure sizes and dimensions during video-assisted procedures could assist a situational awareness system for a surgical hub by allowing the surgical hub to accurately identify organs and other structures during video-assisted surgical procedures. As one solution, a surgical hub could be configured to automatically calculate sizes or dimensions of structures (or distances between structures) during a surgical procedure by comparing the structures to markings affixed to devices that are intended to be placed within the FOV of the medical imaging device during a surgical procedure. The markings can represent a known scale, which can then be utilized to make measurements by comparing the unknown measured length to the known scale.

In one exemplification, the surgical hub is configured to receive image or video data from a medical imaging device paired with the surgical hub. When a surgical instrument bearing a calibration scale is within the FOV of the medical imaging device, the surgical hub is able to measure organs and other structures that are likewise within the medical imaging device's FOV by comparing the structures to the calibration scale. The calibration scale can be positioned on, for example, the distal end of a surgical instrument.

Figure 105:
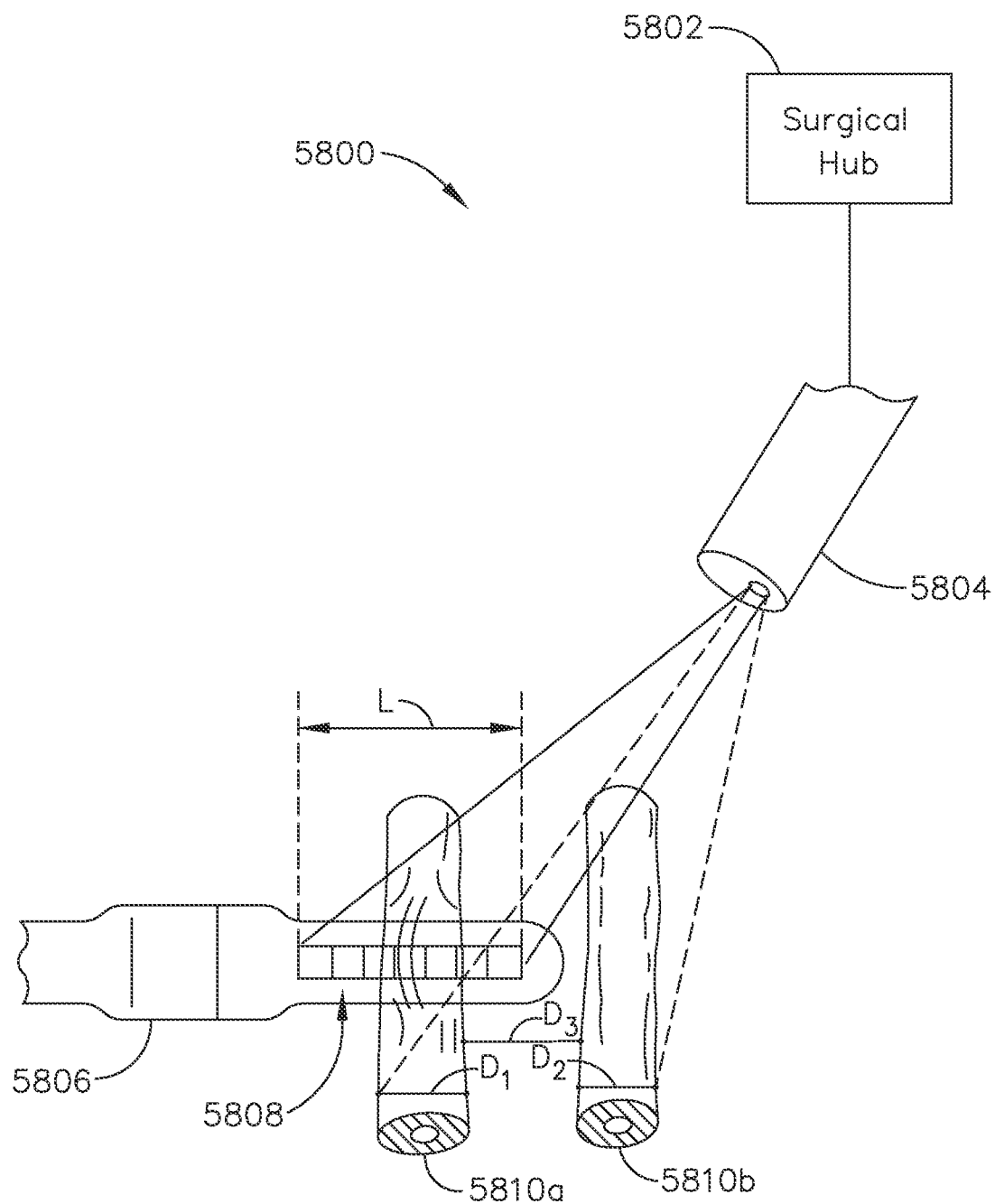
FIG. 105 illustrates a diagram of an imaging system and a surgical instrument bearing a calibration scale, in accordance with at least one aspect of the present disclosure.

FIG. 105 illustrates a diagram of an imaging system 5800 and a surgical instrument 5806 bearing a calibration scale 5808. The imaging system 5800 includes a medical imaging device 5804 that is paired with a surgical hub 5802. The surgical hub 5802 can include a pattern recognition system or a machine learning system configured to recognize features in the FOV from image or video data received from the medical imaging device 5804. In one exemplification, a surgical instrument 5806 (e.g., a surgical cutting and stapling instrument) that is intended to enter the FOV of the medical imaging device 5804 during a surgical procedure includes a calibration scale 5808 affixed thereon. The calibration scale 5808 can be positioned on the exterior surface of the surgical instrument 5806, for example. In aspects wherein the surgical instrument 5806 is a surgical cutting and stapling instrument, the calibration scale 5808 can be positioned along the exterior surface of the anvil. The calibration scale 5808 can include a series of graphical markings separated at fixed and/or known intervals. The distance between the end or terminal markings of the calibration scale 5808 can likewise be a set distance L (e.g., 35 mm). In one exemplification, the end markings (e.g., the most proximal marking and the most distal marking) of the calibration scale 5808 are differentiated from the intermediate markings in size, shape, color, or another such fashion. This allows the image recognition system of the surgical hub 5802 to identify the end markings separately from the intermediate markings. The distance(s) between the markings can be stored in a memory or otherwise retrieved by the surgical hub 5802. The surgical hub 5802 can thus measure lengths or sizes of structures relative to the provided calibration scale 5808. In FIG. 105, for example, the surgical hub 5802 can calculate that the artery 5810*a* has a diameter or width of D1 (e.g., 17.0 mm), the vein 5810*b* has a diameter or width of D2 (e.g., 17.5 mm), and the distance between the vessels is D3 (e.g., 20 mm) by comparing the visualizations of these distances D1, D2, D3 to the known length L of the calibration scale 5808 positioned on the surgical instrument 5806 within the FOV of the medical imaging device 5804. The surgical hub 5802 can recognize the presence of the vessels 5810*a*, 5810*b* via an image recognition system. In some exemplifications, the surgical hub 5802 can be configured to automatically measure and display the size or dimension of detected features within the FOV of the medical imaging device 5804. In some exemplifications, the surgical hub 5802 can be configured to calculate the distance between various points selected by a user on an interactive display that is paired with the surgical hub 5802.

The imaging system 5800 configured to detect and measure sizes according to a calibration scale 5808 affixed to surgical instruments 5806 provides the ability to accurately measure sizes and distances during video-assisted procedures. This can make it easier for surgeons to precisely perform video-assisted procedures by compensating for the optically distortive effects inherent in such procedures.

User Feedback Methods

The present disclosure provides user feedback techniques. In one aspect, the present disclosure provides a display of images through a medical imaging device (e.g., laparoscope, endoscope, thoracoscope, and the like). A medical imaging device comprises an optical component and an image sensor. The optical component may comprise a lens and a light source, for example. The image sensor may be implemented as a charge coupled device (CCD) or complementary oxide semiconductor (CMOS). The image sensor provides image data to electronic components in the surgical hub. The data representing the images may be transmitted by wired or wireless communication to display instrument status, feedback data, imaging data, and highlight tissue irregularities and underlining structures. In another aspect, the present disclosure provides wired or wireless communication techniques for communicating user feedback from a device (e.g., instrument, robot, or tool) to the surgical hub. In another aspect, the present disclosure provides identification and usage recording and enabling. Finally, in another aspect, the surgical hub may have a direct interface control between the device and the surgical hub.

Through Laparoscope Monitor Display of Data

In various aspects, the present disclosure provides through laparoscope monitor display of data. The through laparoscope monitor display of data may comprise displaying a current instrument alignment to adjacent previous operations, cooperation between local instrument displays and paired laparoscope display, and display of instrument specific data needed for efficient use of an end-effector portion of a surgical instrument. Each of these techniques is described hereinbelow.

Display of Current Instrument Alignment to Adjacent Previous Operations

In one aspect, the present disclosure provides alignment guidance display elements that provide the user information about the location of a previous firing or actuation and allow them to align the next instrument use to the proper position without the need for seeing the instrument directly. In another aspect, the first device and second device and are separate; the first device is within the sterile field and the second is used from outside the sterile field.

During a colorectal transection using a double-stapling technique it is difficult to align the location of an anvil trocar of a circular stapler with the center of an overlapping staple line. During the procedure, the anvil trocar of the circular stapler is inserted in the rectum below the staple line and a laparoscope is inserted in the peritoneal cavity above the staple line. Because the staple line seals off the colon, there is no light of sight to align the anvil trocar using the laparoscope to optically align the anvil trocar insertion location relative to the center of the staple line overlap.

One solution provides a non-contact sensor located on the anvil trocar of the circular stapler and a target located at the distal end of the laparoscope. Another solution provides a non-contact sensor located at the distal end of the laparoscope and a target located on the anvil trocar of the circular stapler.

A surgical hub computer processor receives signals from the non-contact sensor and displays a centering tool on a screen indicating the alignment of the anvil trocar of the circular stapler and the overlap portion at the center of staple line. The screen displays a first image of the target staple line with a radius around the staple line overlap portion and a second image of the projected anvil trocar location. The anvil trocar and the overlap portion at the center of staple line are aligned when the first and second images overlap.

In one aspect, the present disclosure provides a surgical hub for aligning a surgical instrument. The surgical hub comprises a processor and a memory coupled to the processor. The memory stores instructions executable by the processor to receive image data from an image sensor, generate a first image based on the image data, display the first image on a monitor coupled to the processor, receive a signal from a non-contact sensor, generate a second image based on the position of the surgical device, and display the second image on the monitor. The first image data represents a center of a staple line seal. The first image represents a target corresponding to the center of the staple line. The signal is indicative of a position of a surgical device relative to the center of the staple line. The second image represents the position of the surgical device along a projected path of the surgical device toward the center of the staple line.

In one aspect, the center of the staple line is a double-staple overlap portion zone. In another aspect, the image sensor receives an image from a laparoscope. In another aspect, the surgical device is a circular stapler comprising an anvil trocar and the non-contact sensor is configured to detect the location of the anvil trocar relative to the center of the staple line seal. In another aspect, the non-contact sensor is an inductive sensor. In another aspect, the non-contact sensor is a capacitive sensor.

In various aspects, the present disclosure provides a control circuit to align the surgical instrument as described above. In various aspects, the present disclosure provides a non-transitory computer readable medium storing computer readable instructions which, when executed, causes a machine to align the surgical instrument as described above.

This technique provides better alignment of a surgical instrument such as a circular stapler about the overlap portion of the staple line to produce a better seal and cut after the circular stapler is fired.

In one aspect, the present disclosure provides a system for displaying the current instrument alignment relative to prior adjacent operations. The instrument alignment information may be displayed on a monitor or any suitable electronic device suitable for the visual presentation of data whether located locally on the instrument or remotely from the instrument through the modular communication hub. The system may display the current alignment of a circular staple cartridge to an overlapping staple line, display the current alignment of a circular staple cartridge relative to a prior linear staple line, and/or show the existing staple line of the linear transection and an alignment circle indicating an appropriately centered circular staple cartridge. Each of these techniques is described hereinbelow.

In one aspect, the present disclosure provides alignment guidance display elements that provide the user information about the location of a previous firing or actuation of a surgical instrument (e.g., surgical stapler) and allows the user to align the next instrument use (e.g., firing or actuation of the surgical stapler) to the proper position without the need for seeing the instrument directly. In another aspect, the present disclosure provides a first device and a second device that is separate from the first device. The first device is located within a sterile field and the second is located outside the sterile field. The techniques described herein may be applied to surgical staplers, ultrasonic instruments, electrosurgical instruments, combination ultrasonic/electrosurgical instruments, and/or combination surgical stapler/electrosurgical instruments.

Figure 106:
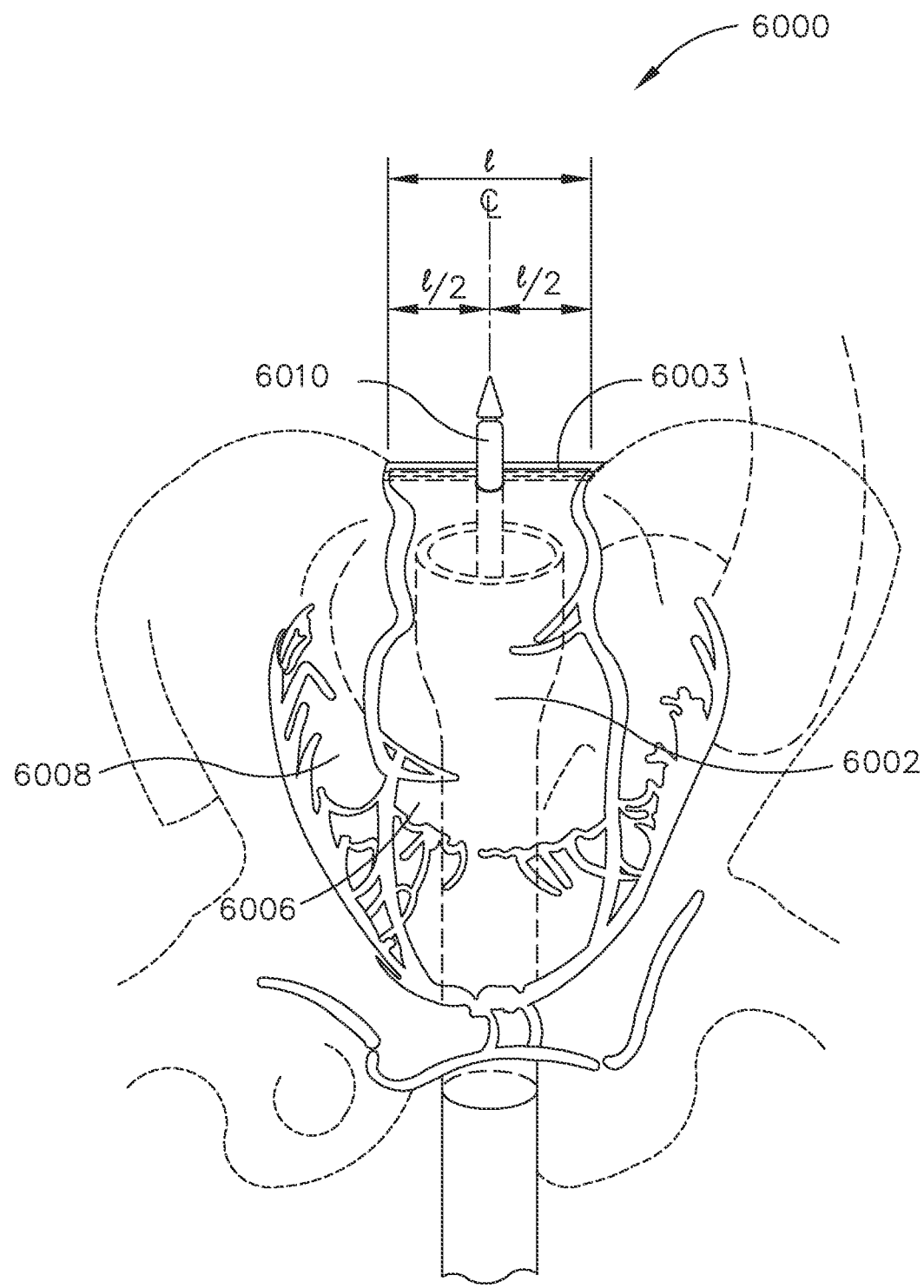
FIG. 106 illustrates a diagram of a surgical instrument centered on a linear staple transection line using the benefit of centering tools and techniques described in connection with FIGS. 107-119, in accordance with at least one aspect of the present disclosure.

FIG. 106 illustrates a diagram 6000 of a surgical instrument 6002 centered on a staple line 6003 using the benefit of centering tools and techniques described in connection with FIGS. 23-33, according to one aspect of the present disclosure. As used in the following description of FIGS. 107-117 a staple line may include multiple rows of staggered staples and typically includes two or three rows of staggered staples, without limitation. The staple line may be a double staple line 6004 formed using a double-stapling technique as described in connection with FIGS. 107-111 or may be a linear staple line 6052 formed using a linear transection technique as described in connection with FIGS. 112-117. The centering tools and techniques described herein can be used to align the instrument 6002 located in one part of the anatomy with either the staple line 6003 or with another instrument located in another part of the anatomy without the benefit of a line of sight. The centering tools and techniques include displaying the current alignment of the instrument 6002 adjacent to previous operations. The centering tool is useful, for example, during laparoscopic-assisted rectal surgery that employ a double-stapling technique, also referred to as an overlapping stapling technique. In the illustrated example, during a laparoscopic-assisted rectal surgical procedure, a circular stapler 6002 is positioned in the rectum 6006 of a patient within the pelvic cavity 6008 and a laparoscope is positioned in the peritoneal cavity.

During the laparoscopic-assisted rectal surgery, the colon is transected and sealed by the staple line 6003 having a length "1." The double-stapling technique uses the circular stapler 6002 to create an end-to-end anastomosis and is currently used widely in laparoscopic-assisted rectal surgery. For a successful formation of an anastomosis using a circular stapler 6002, the anvil trocar 6010 of the circular stapler 6002 should be aligned with the center "½" of the staple line 6003 transection before puncturing through the center "½" of the staple line 6003 and/or fully clamping on the tissue before firing the circular stapler 6002 to cut out the staple overlap portion 6012 and forming the anastomosis. Misalignment of the anvil trocar 6010 to the center of the staple line 6003 transection may result in a high rate of anastomotic failures. This technique may be applied to ultrasonic instruments, electrosurgical instruments, combination ultrasonic/electrosurgical instruments, and/or combination surgical stapler/electrosurgical instruments. Several techniques are now described for aligning the anvil trocar 6010 of the circular stapler 6002 to the center "½" of the staple line 6003.

In one aspect, as described in FIGS. 107-109 and with reference also to FIGS. 1-11 to show interaction with an interactive surgical system 100 environment including a surgical hub 106, 206, the present disclosure provides an apparatus and method for detecting the overlapping portion of the double staple line 6004 in a laparoscopic-assisted rectal surgery colorectal transection using a double stapling technique. The overlapping portion of the double staple line 6004 is detected and the current location of the anvil trocar 6010 of the circular stapler 6002 is displayed on a surgical hub display 215 coupled to the surgical hub 206. The surgical hub display 215 displays the alignment of a circular stapler 6002 cartridge relative to the overlapping portion of the double staple line 6004, which is located at the center of the double staple line 6004. The surgical hub display 215 displays a circular image centered around the overlapping double staple line 6004 region to ensure that the overlapping portion of the double staple line 6004 is contained within the knife of the circular stapler 6002 and therefore removed following the circular firing. Using the display, the surgeon aligns the anvil trocar 6010 with the center of the double staple line 6004 before puncturing through the center of the double staple line 6004 and/or fully clamping on the tissue before firing the circular stapler 6002 to cut out the staple overlap portion 6012 and form the anastomosis.

FIGS. 107-109 illustrate a process of aligning an anvil trocar 6010 of a circular stapler 6022 to a staple overlap portion 6012 of a double staple line 6004 created by a double-stapling technique, according to one aspect of the present disclosure. The staple overlap portion 6012 is centered on the double staple line 6004 formed by a double-stapling technique. The circular stapler 6002 is inserted into the colon 6020 below the double staple line 6004 and a laparoscope 6014 is inserted through the abdomen above the double staple line 6004. A laparoscope 6014 and a non-contact sensor 6022 are used to determine an anvil trocar 6010 location relative to the staple overlap portion 6012 of the double staple line 6004. The laparoscope 6014 includes an image sensor to generate an image of the double staple line 6004. The image sensor image is transmitted to the surgical hub 206 via the imaging module 238. The sensor 6022 generates a signal 6024 that detects the metal staples using inductive or capacitive metal sensing technology. The signal 6024 varies based on the position of the anvil trocar 6010 relative to the staple overlap portion 6004. A centering tool 6030 presents an image 6038 of the double staple line 6004 and a target alignment ring 6032 circumscribing the image 6038 of the double staple line 6004 centered about an image 6040 of the staple overlap portion 6012 on the surgical hub display 215. The centering tool 6030 also presents a projected cut path 6034 of an anvil knife of the circular stapler 6002. The alignment process includes displaying an image 6038 of the double staple line 6004 and a target alignment ring 6032 circumscribing the image 6038 of the double staple line 6004 centered on the image 6040 of the staple overlap portion 6012 to be cut out by the circular knife of the circular stapler 6002. Also displayed is an image of a crosshair 6036 (X) relative to the image 6040 of the staple overlap portion 6012.

FIG. 107 illustrates an anvil trocar 6010 of a circular stapler 6002 that is not aligned with a staple overlap portion 6012 of a double staple line 6004 created by a double-stapling technique. The double staple line 6004 has a length "l" and the staple overlap portion 6012 is located midway along the double staple line 6004 at "½." As shown in FIG. 107, the circular stapler 6002 is inserted into a section of the colon 6020 and is positioned just below the double staple line 6004 transection. A laparoscope 6014 is positioned above the double staple line 6004 transection and feeds an image of the double staple line 6004 and staple overlap portion 6012 within the field of view 6016 of the laparoscope 6014 to the surgical hub display 215. The position of the anvil trocar 6010 relative to the staple overlap portion 6012 is detected by a sensor 6022 located on the circular stapler 6002. The sensor 6022 also provides the position of the anvil trocar 6010 relative to the staple overlap portion 6012 to the surgical hub display 215.

As shown in In FIG. 107, the projected path 6018 of the anvil trocar 6010 is shown along a broken line to a position marked by an X. As shown in FIG. 107, the projected path 6018 of the anvil trocar 6010 is not aligned with the staple overlap portion 6012. Puncturing the anvil trocar 6010 through the double staple line 6004 at a point off the staple overlap portion 6012 could lead to an anastomotic failure. Using the anvil trocar 6010 centering tool 6030 described in FIG. 109, the surgeon can align the anvil trocar 6010 with the staple overlap portion 6012 using the images displayed by the centering tool 6030. For example, in one implementation, the sensor 6022 is an inductive sensor. Since the staple overlap portion 6012 contains more metal than the rest of the lateral portions of the double staple line 6004, the signal 6024 is maximum when the sensor 6022 is aligned with and proximate to the staple overlap portion 6012. The sensor 6022 provides a signal to the surgical hub 206 that indicates the location of the anvil trocar 6010 relative to the staple overlap portion 6012. The output signal is converted to a visualization of the location of the anvil trocar 6010 relative to the staple overlap portion 6012 that is displayed on the surgical hub display 215.

As shown in FIG. 108, the anvil trocar 6010 is aligned with the staple overlap portion 6012 at the center of the double staple line 6004 created by a double-stapling technique. The surgeon can now puncture the anvil trocar 6010 through the staple overlap portion 6012 of the double staple line 6004 and/or fully clamp on the tissue before firing the circular stapler 6002 to cut out the staple overlap portion 6012 and form an anastomosis.

FIG. 109 illustrates a centering tool 6030 displayed on a surgical hub display 215, the centering tool providing a display of a staple overlap portion 6012 of a double staple line 6004 created by a double-staling technique, where the anvil trocar 6010 is not aligned with the staple overlap portion 6012 of the double staple line 6004 as shown in FIG. 107. The centering tool 6030 presents an image 6038 on the surgical hub display 215 of the double staple line 6004 and an image 6040 of the staple overlap portion 6012 received from the laparoscope 6014. A target alignment ring 6032 centered about the image 6040 of the staple overlap portion 6012 circumscribes the image 6038 of the double staple line 6004 to ensure that the staple overlap portion 6012 is located within the circumference of the projected cut path 6034 of the circular stapler 6002 knife when the projected cut path 6034 is aligned to the target alignment ring 6032. The crosshair 6036 (X) represents the location of the anvil trocar 6010 relative to the staple overlap portion 6012. The crosshair 6036 (X) indicates the point through the double staple line 6004 where the anvil trocar 6010 would puncture if it were advanced from its current location.

As shown in FIG. 109, the anvil trocar 6010 is not aligned with the desired puncture through location designated by the image 6040 of the staple overlap portion 6012. To align the anvil trocar 6010 with the staple overlap portion 6012 the surgeon manipulates the circular stapler 6002 until the projected cut path 6034 overlaps the target alignment ring 6032 and the crosshair 6036 (X) is centered on the image 6040 of the staple overlap portion 6012. Once alignment is complete, the surgeon punctures the anvil trocar 6010 through the staple overlap portion 6012 of the double staple line 6004 and/or fully clamps on the tissue before firing the circular stapler 6002 to cut out the staple overlap portion 6012 and form the anastomosis.

As discussed above, the sensor 6022 is configured to detect the position of the anvil trocar 6010 relative to the staple overlap portion 6012. Accordingly, the location of the crosshair 6036 (X) presented on the surgical hub display 215 is determined by the surgical stapler sensor 6022. In another aspect, the sensor 6022 may be located on the laparoscope 6014, where the sensor 6022 is configured to detect the tip of the anvil trocar 6010. In other aspects, the sensor 6022 may be located either on the circular stapler 6022 or the laparoscope 6014, or both, to determine the location of the anvil trocar 6010 relative to the staple overlap portion 6012 and provide the information to the surgical hub display 215 via the surgical hub 206.

FIGS. 110 and 111 illustrate a before image 6042 and an after image 6043 of a centering tool 6030, according to one aspect of the present disclosure. FIG. 110 illustrates an image of a projected cut path 6034 of an anvil trocar 6010 and circular knife before alignment with the target alignment ring 6032 circumscribing the image 6038 of the double staple line 6004 over the image 6040 of the staple overlap portion 6040 presented on a surgical hub display 215. FIG. 111 illustrates an image of a projected cut path 6034 of an anvil trocar 6010 and circular knife after alignment with the target alignment ring 6032 circumscribing the image 6038 of the double staple line 6004 over the image 6040 of the staple overlap portion 6040 presented on a surgical hub display 215. The current location of the anvil trocar 6010 is marked by the crosshair 6036 (X), which as shown in FIG. 110, is positioned below and to the left of center of the image 6040 of the staple overlap portion 6040. As shown in FIG. 111, as the surgeon moves the anvil trocar 6010 of the along the projected path 6046, the projected cut path 6034 aligns with the target alignment ring 6032. The target alignment ring 6032 may be displayed as a greyed out alignment circle overlaid over the current position of the anvil trocar 6010 relative to the center of the double staple line 6004, for example. The image may include indication marks to assist the alignment process by indication which direction to move the anvil trocar 6010. The target alignment ring 6032 may be shown in bold, change color or may be highlighted when it is located within a predetermined distance of center within acceptable limits.

In another aspect, the sensor 6022 may be configured to detect the beginning and end of a linear staple line in a colorectal transection and to provide the position of the current location of the anvil trocar 6010 of the circular stapler 6002. In another aspect, the present disclosure provides a surgical hub display 215 to present the circular stapler 6002 centered on the linear staple line, which would create even dog ears, and to provide the current position of the anvil trocar 6010 to allow the surgeon to center or align the anvil trocar 6010 as desired before puncturing and/or fully clamping on tissue prior to firing the circular stapler 6002.

In another aspect, as described in FIGS. 112-114 and with reference also to FIGS. 1-11 to show interaction with an interactive surgical system 100 environment including a surgical hub 106, 206, in a laparoscopic-assisted rectal surgery colorectal transection using a linear stapling technique, the beginning and end of the linear staple line 6052 is detected and the current location of the anvil trocar 6010 of the circular stapler 6002 is displayed on a surgical hub display 215 coupled to the surgical hub 206. The surgical hub display 215 displays a circular image centered on the double staple line 6004, which would create even dog ears and the current position of the anvil trocar 6002 is displayed to allow the surgeon to center or align the anvil trocar 6010 before puncturing through the linear staple line 6052 and/or fully clamping on the tissue before firing the circular stapler 6002 to cut out the center 6050 of the linear staple line 6052 to form an anastomosis.

FIGS. 112-114 illustrate a process of aligning an anvil trocar 6010 of a circular stapler 6022 to a center 6050 of a linear staple line 6052 created by a linear stapling technique, according to one aspect of the present disclosure. FIGS. 112 and 113 illustrate a laparoscope 6014 and a sensor 6022 located on the circular stapler 6022 to determine the location of the anvil trocar 6010 relative to the center 6050 of the linear staple line 6052. The anvil trocar 6010 and the sensor 6022 is inserted into the colon 6020 below the linear staple line 6052 and the laparoscope 6014 is inserted through the abdomen above the linear staple line 6052.

FIG. 112 illustrates the anvil trocar 6010 out of alignment with the center 6050 of the linear staple line 6052 and FIG. 113 illustrates the anvil trocar 6010 in alignment with the center 6050 of the linear staple line 6052. The sensor 6022 is used to detect the center 6050 of the linear staple line 6052 to align the anvil trocar 6010 with the center of the staple line 6052. In one aspect, the center 6050 of the linear staple line 6052 may be located by moving the circular stapler 6002 until one end of the linear staple line 6052 is detected. An end may be detected when there are no more staples in the path of the sensor 6022. Once one of the ends is reached, the circular stapler 6002 is moved along the linear staple line 6053 until the opposite end is detected and the length "l" of the linear staple line 6052 is determined by measurement or by counting individual staples by the sensor 6022. Once the length of the linear staple line 6052 is determined, the center 6050 of the linear staple line 6052 can be determined by dividing the length by two "½."

FIG. 114 illustrates a centering tool 6054 displayed on a surgical hub display 215, the centering tool providing a display of a linear staple line 6052, where the anvil trocar 6010 is not aligned with the staple overlap portion 6012 of the double staple line 6004 as shown in FIG. 112. The surgical hub display 215 presents a standard reticle field of view 6056 of the laparoscopic field of view 6016 of the linear staple line 6052 and a portion of the colon 6020. The surgical hub display 215 also presents a target ring 6062 circumscribing the image center of the linear staple line and a projected cut path 6064 of the anvil trocar and circular knife. The crosshair 6066 (X) represents the location of the anvil trocar 6010 relative to the center 6050 of the linear staple line 6052. The crosshair 6036 (X) indicates the point through the linear staple line 6052 where the anvil trocar 6010 would puncture if it were advanced from its current location.

As shown in FIG. 114, the anvil trocar 6010 is not aligned with the desired puncture through location designated by the offset between the target ring 6062 and the projected cut path 6064. To align the anvil trocar 6010 with the center 6050 of the linear staple line 6052 the surgeon manipulates the circular stapler 6002 until the projected cut path 6064 overlaps the target alignment ring 6062 and the crosshair 6066 (X) is centered on the image 6040 of the staple overlap portion 6012. Once alignment is complete, the surgeon punctures the anvil trocar 6010 through the center 6050 of the linear staple line 6052 and/or fully clamps on the tissue before firing the circular stapler 6002 to cut out the staple overlap portion 6012 and forming the anastomosis.

In one aspect, the present disclosure provides an apparatus and method for displaying an image of an linear staple line 6052 using a linear transection technique and an alignment ring or bullseye positioned as if the anvil trocar 6010 of the circular stapler 6022 were centered appropriately along the linear staple line 6052. The apparatus displays a greyed out alignment ring overlaid over the current position of the anvil trocar 6010 relative to the center 6050 of the linear staple line 6052. The image may include indication marks to assist the alignment process by indication which direction to move the anvil trocar 6010. The alignment ring may be bold, change color or highlight when it is located within a predetermined distance of centered.

With reference now to FIGS. 112-115, FIG. 115 is an image 6080 of a standard reticle field view 6080 of a linear staple line 6052 transection of a surgical as viewed through a laparoscope 6014 displayed on the surgical hub display 215, according to one aspect of the present disclosure. In a standard reticle view 6080, it is difficult to see the linear staple line 6052 in the standard reticle field of view 6056. Further, there are no alignment aids to assist with alignment and introduction of the anvil trocar 6010 to the center 6050 of the linear staple line. This view does not show an alignment circle or alignment mark to indicate if the circular stapler is centered appropriately and does not show the projected trocar path. In this view it also difficult to see the staples because there is no contrast with the background image.

With reference now to FIGS. 112-116, FIG. 116 is an image 6082 of a laser-assisted reticle field of view 6072 of the surgical site shown in FIG. 115 before the anvil trocar 6010 and circular knife of the circular stapler 6002 are aligned to the center 6050 of the linear staple line 6052, according to one aspect of the present disclosure. The laser-assisted reticle field of view 6072 provides an alignment mark or crosshair 6066 (X), currently positioned below and to the left of center of the linear staple line 6052 showing the projected path of the anvil trocar 6010 to assist positioning of the anvil trocar 6010. In addition to the projected path marked by the crosshair 6066 (X) of the anvil trocar 6010, the image 6082 displays the staples of the linear staple line 6052 in a contrast color to make them more visible against the background. The linear staple line 6052 is highlighted and a bullseye target 6070 is displayed over the center 6050 of the linear staple line 6052. Outside of the laser-assisted reticle field of view 6072, the image 6082 displays a status warning box 6068, a suggestion box 6074, a target ring 6062, and the current alignment position of the anvil trocar 6010 marked by the crosshair 6066 (X) relative to the center 6050 of the linear staple line 6052. As shown in FIG. 116, the status warning box 6068 indicates that the trocar is "MISALIGNED" and the suggestion box 6074 states "Adjust trocar to center staple line."

With reference now to FIGS. 112-117, FIG. 117 is an image 6084 of a laser-assisted reticle field of view 6072 of the surgical site shown in FIG. 116 after the anvil trocar 6010 and circular knife of the circular stapler 6002 are aligned to the center 6050 of the linear staple line 6052, according to one aspect of the present disclosure. The laser-assisted reticle field of view 6072 provides an alignment mark or crosshair 6066 (X), currently positioned below and to the left of center of the linear staple line 6052 showing the projected path of the anvil trocar 6010 to assist positioning of the anvil trocar 6010. In addition to the projected path marked by the crosshair 6066 (X) of the anvil trocar 6010, the image 6082 displays the staples of the linear staple line 6052 in a contrast color to make them more visible against the background. The linear staple line 6052 is highlighted and a bullseye target 6070 is displayed over the center 6050 of the linear staple line 6052. Outside of the laser-assisted reticle field of view 6072, the image 6082 displays a status warning box 6068, a suggestion box 6074, a target ring 6062, and the current alignment position of the anvil trocar 6010 marked by the crosshair 6066 (X) relative to the center 6050 of the linear staple line 6052. As shown in FIG. 116, the status warning box 6068 indicates that the trocar is "MISALIGNED" and the suggestion box 6074 states "Adjust trocar to center staple line."

FIG. 117 is a laser assisted view of the surgical site shown in FIG. 116 after the anvil trocar 6010 and circular knife are aligned to the center of the staple line 6052. In this view, inside the field of view 6072 of the laser-assisted reticle, the alignment mark crosshair 6066 (X) is positioned over the center of the staple line 6052 and the highlighted bullseye target to indicate alignment of the trocar to the center of the staple line. Outside the field of view 6072 of the laser-assisted reticle, the status warning box indicates that the trocar is "ALIGNED" and the suggestion is "Proceed trocar introduction."

FIG. 118 illustrates a non-contact inductive sensor 6090 implementation of the non-contact sensor 6022 to determine an anvil trocar 6010 location relative to the center of a staple line transection (the staple overlap portion 6012 of the double staple line 6004 shown in FIGS. 107-108 or the center 6050 of the linear staple line 6052 shown in FIGS. 112-113, for example), according to one aspect of the present disclosure. The non-contact inductive sensor 6090 includes an oscillator 6092 that drives an inductive coil 6094 to generate an electromagnetic field 6096. As a metal target 6098, such as a metal staple, is introduced into the electromagnetic field 6096, eddy currents 6100 induced in the target 6098 oppose the electromagnetic field 6096 and the reluctance shifts and the amplitude of the oscillator voltage 6102 drops. An amplifier 6104 amplifies the oscillator voltage 6102 amplitude as it changes.

With reference now to FIGS. 1-11 to show interaction with an interactive surgical system 100 environment including a surgical hub 106, 206 and also to FIGS. 106-117, the inductive sensor 6090 is a non-contact electronic sensor. It can be used for positioning and detecting metal objects such as the metal staples in the staple lines 6003, 6004, 6052 described above. The sensing range of the inductive sensor 6090 is dependent on the type of metal being detected. Because the inductive sensor 6090 is a non-contact sensor, it can detect metal objects across a stapled tissue barrier. The inductive sensor 6090 can be located either on the circular stapler 6002 to detect staples in the staple lines 6003, 6004, 6052, detect the location of the distal end of the laparoscope 6014, or it may be located on the laparoscope 6014 to detect the location of the anvil trocar 6010. A processor or control circuit located either in the circular stapler 6002, laparoscope 6014, or coupled to the surgical hub 206 receives signals from the inductive sensors 6090 and can be employed to display the centering tool on the surgical hub display 215 to determine the location of the anvil trocar 6010 relative to either staple overlap portion 6012 of a double staple line 6004 or the center 6050 of a linear staple line 6052.

In one aspect, the distal end of the laparoscope 6014 may be detected by the inductive sensor 6090 located on the circular stapler 6002. The inductive sensor 6090 may detect a metal target 6098 positioned on the distal end of the laparoscope 6014. Once the laparoscope 6014 is aligned with the center 6050 of the linear staple line 6052 or the staple overlap portion 6012 of the double staple line 6004, a signal from the inductive sensor 6090 is transmitted to circuits that convert the signals from the inductive sensor 6090 to present an image of the relative alignment of the laparoscope 6014 with the anvil trocar 6010 of the circular stapler 6002.

FIGS. 119A and 119B illustrate one aspect of a non-contact capacitive sensor 6110 implementation of the non-contact sensor 6022 to determine an anvil trocar 6010 location relative to the center of a staple line transection (the staple overlap portion 6012 of the double staple line 6004 shown in FIGS. 107-108 or the center 6050 of the linear staple line 6052 shown in FIGS. 112-113, for example), according to one aspect of the present disclosure. FIG. 119A shows the non-contact capacitive sensor 6110 without a nearby metal target and FIG. 119B shows the non-contact capacitive sensor 6110 near a metal target 6112. The non-contact capacitive sensor 6110 includes capacitor plates 6114, 6116 housed in a sensing head and establishes field lines 6118 when energized by an oscillator waveform to define a sensing zone. FIG. 119A shows the field lines 6118 when no target is present proximal to the capacitor plates 6114, 6116. FIG. 119B shows a ferrous or nonferrous metal target 6120 in the sensing zone. As the metal target 6120 enters the sensing zone, the capacitance increases causing the natural frequency to shift towards the oscillation frequency causing amplitude gain. Because the capacitive sensor 6110 is a non-contact sensor, it can detect metal objects across a stapled tissue barrier. The capacitive sensor 6110 can be located either on the circular stapler 6002 to detect the staple lines 6004, 6052 or the location of the distal end of the laparoscope 6014 or the capacitive sensor 6110 may be located on the laparoscope 6014 to detect the location of the anvil trocar 6010. A processor or control circuit located either in the circular stapler 6002, the laparoscope 6014, or coupled to the surgical hub 206 receives signals from the capacitive sensor 6110 to present an image of the relative alignment of the laparoscope 6014 with the anvil trocar 6010 of the circular stapler 6002.

FIG. 120 is a logic flow diagram 6130 of a process depicting a control program or a logic configuration for aligning a surgical instrument, according to one aspect of the present disclosure. With reference to FIGS. 1-11 to show interaction with an interactive surgical system 100 environment including a surgical hub 106, 206 and also to FIGS. 106-119, the surgical hub 206 comprises a processor 244 and a memory 249 coupled to the processor 244. The memory 249 stores instructions executable by the processor 244 to receive 6132 image data from a laparoscope image sensor, generate 6134 a first image based on the image data, display 6136 the first image on a surgical hub display 215 coupled to the processor 244, receive 6138 a signal from a non-contact sensor 6022, the signal indicative of a position of a surgical device, generate a second image based on the signal indicative of the position of the surgical device, e.g., the anvil trocar 6010 and display 6140 the second image on the surgical hub display 215. The first image data represents a center 6044, 6050 of a staple line 6004, 6052 seal. The first image represents a target corresponding to the center 6044, 6050 of the staple line 6004, 6052 seal. The signal is indicative of a position of a surgical device, e.g., an anvil trocar 6010, relative to the center 6044, 6050 of the staple line 6004, 6052 seal. The second image represents the position of the surgical device, e.g., an anvil trocar 6010, along a projected path 6018 of the surgical device, e.g., an anvil trocar 6010, toward the center 6044, 6050 of the staple line 6004, 6052 seal.

In one aspect, the center 6044 of the double staple line 6004 seal defines a staple overlap portion 6012. In another aspect, an image sensor receives an image from a medical imaging device. In another aspect, the surgical device is a circular stapler 6002 comprising an anvil trocar 6010 and the non-contact sensor 6022 is configured to detect the location of the anvil trocar 6010 relative to the center 6044 of the double staple line 6004 seal. In another aspect, the non-contact sensor 6022 is an inductive sensor 6090. In another aspect, the non-contact sensor 6022 is a capacitive sensor 6110. In one aspect, the staple line may be a linear staple line 6052 formed using a linear transection technique.

Cooperation Between Local Instrument Displays And Paired Imaging Device Display

In one aspect, the present disclosure provides an instrument including a local display, a hub having an operating room (OR), or operating theater, display separate from the instrument display. When the instrument is linked to the surgical hub, the secondary display on the device reconfigures to display different information than when it is independent of the surgical hub connection. In another aspect, some portion of the information on the secondary display of the instrument is then displayed on the primary display of the surgical hub. In another aspect, image fusion allowing the overlay of the status of a device, the integration landmarks being used to interlock several images and at least one guidance feature are provided on the surgical hub and/or instrument display. Techniques for overlaying or augmenting images and/or text from multiple image/text sources to present composite images on a single display are described hereinbelow in connection with FIGS. 129-137 and FIGS. 147-151.

In another aspect, the present disclosure provides cooperation between local instrument displays and a paired laparoscope display. In one aspect, the behavior of a local display of an instrument changes when it senses the connectable presence of a global display coupled to the surgical hub. In another aspect, the present disclosure provides 360° composite top visual field of view of a surgical site to avoid collateral structures. Each of these techniques is described hereinbelow.

During a surgical procedure, the surgical site is displayed on a remote "primary" surgical hub display. During a surgical procedure, surgical devices track and record surgical data and variables (e.g., surgical parameters) that are stored in the instrument (see FIGS. 12-19 for instrument architectures comprising processors, memory, control circuits, storage, etc.). The surgical parameters include force-to-fire (FTF), force-to-close (FTC), firing progress, tissue gap, power level, impedance, tissue compression stability (creep), and the like. Using conventional techniques during the procedure the surgeon needs to watch two separate displays. Providing image/text overlay is thus advantageous because during the procedure the surgeon can watch a single display presenting the overlaid image/text information.

One solution detects when the surgical device (e.g., instrument) is connected to the surgical hub and then display a composite image on the primary display that includes a field of view of the surgical site received from a first instrument (e.g., medical imaging device such as, e.g., laparoscope, endoscope, thoracoscope, and the like) augmented by surgical data and variables received from a second instrument (e.g., a surgical stapler) to provide pertinent images and data on the primary display.

During a surgical procedure the surgical site is displayed as a narrow field of view of a medical imaging device on the primary surgical hub display. Items outside the current field of view, collateral structures, cannot be viewed without moving the medical imaging device.

One solution provides a narrow field of view of the surgical site in a first window of the display augmented by a wide field of view of the surgical site in a separate window of the display. This provides a composite over head field of view mapped using two or more imaging arrays to provide an augmented image of multiple perspective views of the surgical site.

In one aspect, the present disclosure provides a surgical hub, comprising a processor and a memory coupled to the processor. The memory stores instructions executable by the processor to detect a surgical device connection to the surgical hub, transmit a control signal to the detected surgical device to transmit to the surgical hub surgical parameter data associated with the detected device, receive the surgical parameter data, receive image data from an image sensor, and display, on a display coupled to the surgical hub, an image received from the image sensor in conjunction with the surgical parameter data received from the surgical device.

In another aspect, the present disclosure provides a surgical hub, comprising a processor and a memory coupled to the processor. The memory stores instructions executable by the processor to receive first image data from a first image sensor, receive second image data from a second image sensor, and display, on a display coupled to the surgical hub, a first image corresponding to the first field of view and a second image corresponding to the second field of view. The first image data represents a first field of view and the second image data represents a second field of view.

In one aspect, the first field of view is a narrow angle field of view and the second field of view is a wide angle field of view. In another aspect, the memory stores instructions executable by the processor to augment the first image with the second image on the display. In another aspect, the memory stores instructions executable by the processor to fuse the first image and the second image into a third image and display a fused image on the display. In another aspect, the fused image data comprises status information associated with a surgical device, an image data integration landmark to interlock a plurality of images, and at least one guidance parameter. In another aspect, the first image sensor is the same as the same image sensor and wherein the first image data is captured as a first time and the second image data is captured at a second time.

In another aspect, the memory stores instructions executable by the processor to receive third image data from a third image sensor, wherein the third image data represents a third field of view, generate composite image data comprising the second and third image data, display the first image in a first window of the display, wherein the first image corresponds to the first image data, and display a third image in a second window of the display, wherein the third image corresponds to the composite image data.

In another aspect, the memory stores instructions executable by the processor to receive third image data from a third image sensor, wherein the third image data represents a third field of view, fuse the second and third image data to generate fused image data, display the first image in a first window of the display, wherein the first image corresponds to the first image data, and display a third image in a second window of the display, wherein the third image corresponds to the fused image data.

In various aspects, the present disclosure provides a control circuit to perform the functions described above. In various aspects, the present disclosure provides a non-transitory computer readable medium storing computer readable instructions, which when executed, causes a machine to perform the functions described above.

By displaying endoscope images augmented with surgical device images on one primary surgical hub display, enables the surgeon to focus on one display to obtain a field of view of the surgical site augmented with surgical device data associated with the surgical procedure such as force-to-fire, force-to-close, firing progress, tissue gap, power level, impedance, tissue compression stability (creep), and the like.

Displaying a narrow field of view image in a first window of a display and a composite image of several other perspectives such as wider fields of view enables the surgeon to view a magnified image of the surgical site simultaneously with wider fields of view of the surgical site without moving the scope.

In one aspect, the present disclosure provides both global and local display of a device, e.g., a surgical instrument, coupled to the surgical hub. The device displays all of its relevant menus and displays on a local display until it senses a connection to the surgical hub at which point a sub-set of the information is displayed only on the monitor through the surgical hub and that information is either mirrored on the device display or is no longer accessible on the device detonated screen. This technique frees up the device display to show different information or display larger font information on the surgical hub display.

In one aspect, the present disclosure provides an instrument having a local display, a surgical hub having an operating theater (e.g., operating room or OR) display that is separate from the instrument display. When the instrument is linked to the surgical hub, the instrument local display becomes a secondary display and the instrument reconfigures to display different information than when it is operating independent of the surgical hub connection. In another aspect, some portion of the information on the secondary display is then displayed on the primary display in the operating theater through the surgical hub.

FIG. 121 illustrates a primary display 6200 of the surgical hub 206 comprising a global display 6202 and a local instrument display 6204, according to one aspect of the present disclosure. With continued reference to FIGS. 1-11 to show interaction with an interactive surgical system 100 environment including a surgical hub 106, 206 and FIGS. 12-21 for surgical hub connected instruments together with FIG. 121, the local instrument display 6204 behavior is displayed when the instrument 235 senses the connectable presence of a global display 6202 through the surgical hub 206. The global display 6202 shows a field of view 6206 of a surgical site 6208, as viewed through a medical imaging device such as, for example, a laparoscope/endoscope 219 coupled to an imaging module 238, at the center of the surgical hub display 215, referred to herein also as a monitor, for example. The end effector 6218 portion of the connected instrument 235 is shown in the field of view 6206 of the surgical site 6208 in the global display 6202. The images shown on the display 237 located on an instrument 235 coupled to the surgical hub 206 is shown, or mirrored, on the local instrument display 6204 located in the lower right corner of the monitor 6200 as shown in FIG. 121, for example. During operation, all relevant instrument and information and menus are displayed on the display 237 located on the instrument 235 until the instrument 235 senses a connection of the instrument 235 to the surgical hub 206 at which point all or some sub-set of the information presented on the instrument display 237 is displayed only on the local instrument display 6204 portion of the surgical hub display 6200 through the surgical hub 206. The information displayed on the local instrument display 6204 may be mirrored on the display 237 located on the instrument 235 or may be no longer accessible on the instrument display 237 detonated screen. This technique frees up the instrument 235 to show different information or to show larger font information on the surgical hub display 6200. Several techniques for overlaying or augmenting images and/or text from multiple image/text sources to present composite images on a single display are described hereinbelow in connection with FIGS. 129-137 and FIGS. 147-151.

The surgical hub display 6200 provides perioperative visualization of the surgical site 6208. Advanced imaging identifies and visually highlights 6222 critical structures such as the ureter 6220 (or nerves, etc.) and also tracks instrument proximity displays 6210 and shown on the left side of the display 6200. In the illustrated example, the instrument proximity displays 6210 show instrument specific settings. For example the top instrument proximity display 6212 shows settings for a monopolar instrument, the middle instrument proximity display 6214 shows settings for a bipolar instrument, and the bottom instrument proximity display 6212 shows settings for an ultrasonic instrument.

In another aspect, independent secondary displays or dedicated local displays can be linked to the surgical hub 206 to provide both an interaction portal via a touchscreen display and/or a secondary screen that can display any number of surgical hub 206 tracked data feeds to provide a clear non-confusing status. The secondary screen may display force to fire (FTF), tissue gap, power level, impedance, tissue compression stability (creep), etc., while the primary screen may display only key variables to keep the feed free of clutter. The interactive display may be used to move the display of specific information to the primary display to a desired location, size, color, etc. In the illustrated example, the secondary screen displays the instrument proximity displays 6210 on the left side of the display 6200 and the local instrument display 6204 on the bottom right side of the display 6200. The local instrument display 6204 presented on the surgical hub display 6200 displays an icon of the end effector 6218, such as the icon of a staple cartridge 6224 currently in use, the size 6226 of the staple cartridge 6224 (e.g., 60 mm), and an icon of the current position of the knife 6228 of the end effector.

In another aspect, the display 237 located on the instrument 235 displays the wireless or wired attachment of the instrument 235 to the surgical hub 206 and the instrument's communication/recording on the surgical hub 206. A setting may be provided on the instrument 235 to enable the user to select mirroring or extending the display to both monitoring devices. The instrument controls may be used to interact with the surgical hub display of the information being sourced on the instrument. As previously discussed, the instrument 235 may comprise wireless communication circuits to communicate wirelessly with the surgical hub 206.

In another aspect, a first instrument coupled to the surgical hub 206 can pair to a screen of a second instrument coupled to the surgical hub 206 allowing both instruments to display some hybrid combination of information from the two devices of both becoming mirrors of portions of the primary display. In yet another aspect, the primary display 6200 of the surgical hub 206 provides a 360° composite top visual view of the surgical site 6208 to avoid collateral structures. For example, a secondary display of the end-effector surgical stapler may be provided within the primary display 6200 of the surgical hub 206 or on another display in order to provide better perspective around the areas within a current the field of view 6206. These aspects are described hereinbelow in connection with FIGS. 122-124.

FIGS. 122-124 illustrate a composite overhead views of an end-effector 6234 portion of a surgical stapler mapped using two or more imaging arrays or one array and time to provide multiple perspective views of the end-effector 6234 to enable the composite imaging of an overhead field of view. The techniques described herein may be applied to ultrasonic instruments, electrosurgical instruments, combination ultrasonic/electrosurgical instruments, and/or combination surgical stapler/electrosurgical instruments. Several techniques for overlaying or augmenting images and/or text from multiple image/text sources to present composite images on a single display are described hereinbelow in connection with FIGS. 129-137 and FIGS. 147-151.

FIG. 122 illustrates a primary display 6200 of the surgical hub 206, according to one aspect of the present disclosure. A primary window 6230 is located at the center of the screen shows a magnified or exploded narrow angle view of a surgical field of view 6232. The primary window 6230 located in the center of the screen shows a magnified or narrow angle view of an end-effector 6234 of the surgical stapler grasping a vessel 6236. The primary window 6230 displays knitted images to produce a composite image that enables visualization of structures adjacent to the surgical field of view 6232. A second window 6240 is shown in the lower left corner of the primary display 6200. The second window 6240 displays a knitted image in a wide angle view at standard focus of the image shown in the primary window 6230 in an overhead view. The overhead view provided in the second window 6240 enables the viewer to easily see items that are out of the narrow field surgical field of view 6232 without moving the laparoscope, or other imaging device 239 coupled to the imaging module 238 of the surgical hub 206. A third window 6242 is shown in the lower right corner of the primary display 6200 shows an icon 6244 representative of the staple cartridge of the end-effector 6234 (e.g., a staple cartridge in this instance) and additional information such as "4 Row" indicating the number of staple rows 6246 and "35 mm" indicating the distance 6248 traversed by the knife along the length of the staple cartridge. Below the third window 6242 is displayed an icon 6258 of a frame of the current state of a clamp stabilization sequence 6250 (FIG. 123) that indicates clamp stabilization.

FIG. 123 illustrates a clamp stabilization sequence 6250 over a five second period, according to one aspect of the present disclosure. The clamp stabilization sequence 6250 is shown over a five second period with intermittent displays 6252, 6254, 6256, 6258, 6260 spaced apart at one second intervals 6268 in addition to providing the real time 6266 (e.g., 09:35:10), which may be a pseudo real time to preserve anonymity of the patient. The intermittent displays 6252, 6254, 6256, 6258, 6260 show elapsed by filling in the circle until the clamp stabilization period is complete. At that point, the last display 6260 is shown in solid color. Clamp stabilization after the end effector 6234 clamps the vessel 6236 enables the formation of a better seal.

FIG. 124 illustrates a diagram 6270 of four separate wide angle view images 6272, 6274, 6276, 6278 of a surgical site at four separate times during the procedure, according to one aspect of the present disclosure. The sequence of images shows the creation of an overhead composite image in wide and narrow focus over time. A first image 6272 is a wide angle view of the end-effector 6234 clamping the vessel 6236 taken at an earlier time to (e.g., 09:35:09). A second image 6274 is another wide angle view of the end-effector 6234 clamping the vessel 6236 taken at the present time $t_1$ (e.g., 09:35:13). A third image 6276 is a composite image of an overhead view of the end-effector 6234 clamping the vessel 6236 taken at present time $t_1$. The third image 6276 is displayed in the second window 6240 of the primary display 6200 of the surgical hub 206 as shown in FIG. 122. A fourth image 6278 is a narrow angle view of the end-effector 6234 clamping the vessel 6236 at present time $t_1$ (e.g., 09:35:13). The fourth image 6278 is the narrow angle view of the surgical site shown in the primary window 6230 of the primary display 6200 of the surgical hub 206 as shown in FIG. 122.

Display of Instrument Specific Data Needed for Efficient Use of the End-Effector In one aspect, the present disclosure provides a surgical hub display of instrument specific data needed for efficient use of a surgical instrument, such as a surgical stapler. The techniques described herein may be applied to ultrasonic instruments, electrosurgical instruments, combination ultrasonic/electrosurgical instruments, and/or combination surgical stapler/electrosurgical instruments. In one aspect, a clamp time indicator based on tissue properties is shown on the display. In another aspect, a 360° composite top visual view is shown on the display to avoid collateral structures as shown and described in connection with FIGS. 121-124 is incorporated herein by reference and, for conciseness and clarity of disclosure, the description of FIGS. 121-124 will not be repeated here.

In one aspect, the present disclosure provides a display of tissue creep to provide the user with in-tissue compression/tissue stability data and to guide the user making an appropriate choice of when to conduct the next instrument action. In one aspect, an algorithm calculates a constant advancement of a progressive time based feedback system related to the viscoelastic response of tissue. These and other aspects are described hereinbelow.

FIG. 125 is a graph 6280 of tissue creep clamp stabilization curves 6282, 6284 for two tissue types, according to one aspect of the present disclosure. The clamp stabilization curves 6284, 6284 are plotted as force-to-close (FTC) as a function of time, where FTC (N) is displayed along the vertical axis and Time, t, (Sec) is displayed along the horizontal axis. The FTC is the amount of force exerted to close the clamp arm on the tissue. The first clamp stabilization curve 6282 represents stomach tissue and the second clamp stabilization curve 6284 represents lung tissue. In one aspect, the FTC along the vertical axis is scaled from 0-180 N. and the horizontal axis is scaled from 0-5 Sec. As shown, the FTC as a different profile over a five second clamp stabilization period (e.g., as shown in FIG. 123).

With reference to the first clamp stabilization curve 6282, as the stomach tissue is clamped by the end-effector 6234, the force-to-close (FTC) applied by the end-effector 6234 increases from 0 N to a peak force-to-close of ~180 N after ~1 Sec. While the end-effector 6234 remains clamped on the stomach tissue, the force-to-close decays and stabilizes to ~150 N over time due to tissue creep.

Similarly, with reference to the second clamp stabilization curve 6284, as the lung tissue is clamped by the end-effector 6234, the force-to-close applied by the end-effector 6234 increases from 0 N to a peak force-to-close of ~90 N after just less than ~1 Sec. While the end-effector 6234 remains clamped on the lung tissue, the force-to-close decays and stabilizes to ~60 N over time due to tissue creep.

The end-effector 6234 clamp stabilization is monitored as described above in connection with FIGS. 122-124 and is displayed every second corresponding the sampling times $t_1$, $t_2$, $t_3$, $t_4$, $t_5$ of the force-to-close to provide user feedback regarding the state of the clamped tissue. FIG. 125 shows an example of monitoring tissue stabilization for the lung tissue by sampling the force-to-close every second over a 5 seconds period. At each sample time $t_1$, $t_2$, $t_3$, $t_4$, $t_5$, the instrument 235 or the surgical hub 206 calculates a corresponding vector tangent 6288, 6292, 6294, 6298, 6302 to the second clamp stabilization curve 6284. The vector tangent 6288, 6292, 6294, 6298, 6302 is monitored until its slope drops below a threshold to indicate that the tissue creep is complete and the tissue is ready to sealed and cut. As shown in FIG. 125, the lung tissue is ready to be sealed and cut after ~5 Sec. clamp stabilization period, where a solid gray circle is shown at sample time 6300. As shown, the vector tangent 6302 is less than a predetermined threshold.

The equation of a vector tangent 6288, 6292, 6294, 6298, 6302 to the clamp stabilization curve 6284 may be calculated using differential calculus techniques, for example. In one aspect, at a given point on the clamp stabilization curve 6284, the gradient of the curve 6284 is equal to the gradient of the tangent to the curve 6284. The derivative (or gradient function) describes the gradient of the curve 6284 at any point on the curve 6284. Similarly, it also describes the gradient of a tangent to the curve 6284 at any point on the curve 6284. The normal to the curve 6284 is a line perpendicular to the tangent to the curve 6284 at any given point. To determine the equation of a tangent to a curve find the derivative using the rules of differentiation. Substitute the x coordinate (independent variable) of the given point into the derivative to calculate the gradient of the tangent. Substitute the gradient of the tangent and the coordinates of the given point into an appropriate form of the straight line equation. Make the y coordinate (dependent variable) the subject of the formula.

FIG. 126 is a graph 6310 of time dependent proportionate fill of a clamp force stabilization curve, according to one aspect of the present disclosure. The graph 6310 includes clamp stabilization curves 6312, 6314, 6316 for standard thick stomach tissue, thin stomach tissue, and standard lung tissue. The vertical axis represents FTC (N) scaled from 0-240 N and the horizontal axis represents Time, t, (Sec) scaled from 0-15 Sec. As shown, the standard thick stomach tissue curve 6316 is the default force decay stability curve. All three clamp stabilization curves 6312, 6314, 6316 FTC profiles reach a maximum force shortly after clamping on the tissue and then the FTC decreases over time until it eventually stabilizes due to the viscoelastic response of the tissue. As shown the standard lung tissue clamp stabilization curve 6312 stabilizes after a period of ~5 Sec., the thin stomach tissue clamp stabilization curve 6314 stabilizes after a period of ~10 Sec., and the thick stomach tissue clamp stabilization curve 6316 stabilizes after a period of ~15 Sec.

FIG. 127 is a graph 6320 of the role of tissue creep in the clamp force stabilization curve 6322, according to one aspect of the present disclosure. The vertical axis represents force-to-close FTC (N) and the horizontal axis represents Time, t, (Sec) in seconds. Vector tangent angles $d\theta_1$, $d\theta_2 \ldots d\theta_n$ are measured at each force-to-close sampling ($t_0$, $t_1$, $t_2$, $t_3$, $t_4$, etc.) times. The vector tangent angle $d\theta_n$ is used to determine when the tissue has reached the creep termination threshold, which indicates that the tissue has reached creep stability.

FIGS. 128A and 128B illustrate two graphs 6330, 6340 for determining when the clamped tissue has reached creep stability, according to one aspect of the present disclosure. The graph 6330 in FIG. 128A illustrates a curve 6332 that represents a vector tangent angle dθ as a function of time. The vector tangent angle dθ is calculated as discussed in FIG. 127. The horizontal line 6334 is the tissue creep termination threshold. The tissue creep is deemed to be stable at the intersection 6336 of the vector tangent angle dθ curve 6332 and the tissue creep termination threshold 6334. The graph 6340 in FIG. 128B illustrates a ΔFTC curve 6342 that represents ΔFTC as a function of time. The ΔFTC curve 6342 illustrates the threshold 6344 to 100% complete tissue creep stability meter. The tissue creep is deemed to be stable at the intersection 6346 of the ΔFTC curve 6342 and the threshold 6344.

Communication Techniques

With reference to FIGS. 1-11 to show interaction with an interactive surgical system 100 environment including a surgical hub 106, 206, and in particular, FIGS. 9-10, in various aspects, the present disclosure provides communications techniques for exchanging information between an instrument 235, or other modules, and the surgical hub 206. In one aspect, the communications techniques include image fusion to place instrument status and analysis over a laparoscope image, such as a screen overlay of data, within and around the perimeter of an image presented on a surgical hub display 215, 217. In another aspect, the communication techniques include combining an intermediate short range wireless, e.g., Bluetooth, signal with the image, and in another aspect, the communication techniques include applying security and identification of requested pairing. In yet another aspect, the communication techniques include an independent interactive headset worn by a surgeon that links to the hub with audio and visual information that avoids the need for overlays, but allows customization of displayed information around periphery of view. Each of these communication techniques is discussed hereinbelow.

Screen Overlay of Data within and Around the Perimeter of the Displayed Image

In one aspect, the present disclosure provides image fusion allowing the overlay of the status of a device, the integration landmarks being used to interlock several images, and at least one guidance feature. In another aspect, the present disclosure provides a technique for screen overlay of data within and around the perimeter of displayed image. Radiographic integration may be employed for live internal sensing and pre-procedure overlay. Image fusion of one source may be superimposed over another. Image fusion may be employed to place instrument status and analysis on a medical imaging device (e.g., laparoscope, endoscope, thoracoscope, etc.) image. Image fusion allows the overlay of the status of a device or instrument, integration landmarks to interlock several images, and at least one guidance feature.

FIG. 129 illustrates an example of an augmented video image 6350 comprising a pre-operative video image 6352 augmented with data 6354, 6356, 6358 identifying displayed elements. An augmented reality vision system may be employed in surgical procedures to implement a method for augmenting data onto a pre-operative image 6352. The method includes generating a pre-operative image 6352 of an anatomical section of a patient and generating an augmented video image of a surgical site within the patient. The augmented video image 6350 includes an image of at least a portion of a surgical tool 6354 operated by a user 6456. The method further includes processing the pre-operative image 6352 to generate data about the anatomical section of the patient. The data includes a label 6358 for the anatomical section and a peripheral margin of at least a portion of the anatomical section. The peripheral margin is configured to guide a surgeon to a cutting location relative to the anatomical section, embedding the data and an identity of the user 6356 within the pre-operative image 6350 to display an augmented video image 6350 to the user about the anatomical section of the patient. The method further includes sensing a loading condition on the surgical tool 6354, generating a feedback signal based on the sensed loading condition, and updating, in real time, the data and a location of the identity of the user operating the surgical tool 6354 embedded within the augmented video image 6350 in response to a change in a location of the surgical tool 6354 within the augmented video image 6350. Further examples are disclosed in U.S. Pat. No. 9,123,155, titled APPARATUS AND METHOD FOR USING AUGMENTED REALITY VISION SYSTEM IN SURGICAL PROCEDURES, which issued on Sep. 1, 2015, which is herein incorporated by reference in its entirety.

In another aspect, radiographic integration techniques may be employed to overlay the pre-operative image 6352 with data obtained through live internal sensing or pre-procedure techniques. Radiographic integration may include marker and landmark identification using surgical landmarks, radiographic markers placed in or outside the patient, identification of radio-opaque staples, clips or other tissue-fixated items. Digital radiography techniques may be employed to generate digital images for overlaying with a pre-operative image 6352. Digital radiography is a form of X-ray imaging that employs a digital image capture device with digital X-ray sensors instead of traditional photographic film. Digital radiography techniques provide immediate image preview and availability for overlaying with the pre-operative image 6352. In addition, special image processing techniques can be applied to the digital X-ray mages to enhance the overall display quality of the image.

Digital radiography techniques employ image detectors that include flat panel detectors (FPDs), which are classified in two main categories indirect FPDs and direct FPDs. Indirect FPDs include amorphous silicon (a-Si) combined with a scintillator in the detector's outer layer, which is made from cesium iodide (CsI) or gadolinium oxy-sulfide (Gd2O2S), converts X-rays to light. The light is channeled through the a-Si photodiode layer where it is converted to a digital output signal. The digital signal is then read out by thin film transistors (TFTs) or fiber-coupled charge coupled devices (CCDs). Direct FPDs include amorphous selenium (a-Se) FPDs that convert X-ray photons directly into charge. The outer layer of a flat panel in this design is typically a high-voltage bias electrode. X-ray photons create electron-hole pairs in a-Se, and the transit of these electrons and holes depends on the potential of the bias voltage charge. As the holes are replaced with electrons, the resultant charge pattern in the selenium layer is read out by a TFT array, active matrix array, electrometer probes or micro plasma line addressing. Other direct digital detectors are based on CMOS and CCD technology. Phosphor detectors also may be employed to record the X-ray energy during exposure and is scanned by a laser diode to excite the stored energy which is released and read out by a digital image capture array of a CCD.

FIG. 130 is a logic flow diagram 6360 of a process depicting a control program or a logic configuration to display images, according to one aspect of the present disclosure. With reference also to FIGS. 1-11 to show interaction with an interactive surgical system 100 environment including a surgical hub 106, 206, the present disclosure provides, in one aspect, a surgical hub 206, comprising a processor 244 and a memory 249 coupled to the processor 244. The memory 249 stores instructions executable by the processor 244 to receive 6362 first image data from a first image sensor, receive 6364 second image data from a second image sensor, and display 6366, on a display 217 coupled to the surgical hub 206, a first image corresponding to the first field of view and a second image corresponding to the second field of view. The first image data represents a first field of view and the second image data represents a second field of view.

In one aspect, the first field of view is a narrow angle field of view and the second field of view is a wide angle field of view. In another aspect, the memory 249 stores instructions executable by the processor 244 to augment the first image with the second image on the display. In another aspect, the memory 249 stores instructions executable by the processor 244 to fuse the first image and the second image into a third image and display a fused image on the display 217. In another aspect, the fused image data comprises status information associated with a surgical device 235, an image data integration landmark to interlock a plurality of images, and at least one guidance parameter. In another aspect, the first image sensor is the same as the same image sensor and wherein the first image data is captured as a first time and the second image data is captured at a second time.

In another aspect, the memory 249 stores instructions executable by the processor 244 to receive third image data from a third image sensor, wherein the third image data represents a third field of view, generate composite image data comprising the second and third image data, display the first image in a first window of the display, wherein the first image corresponds to the first image data, and display a third image in a second window of the display 215, wherein the third image corresponds to the composite image data.

In another aspect, the memory 249 stores instructions executable by the processor 244 to receive third image data from a third image sensor, wherein the third image data represents a third field of view, fuse the second and third image data to generate fused image data, display the first image in a first window of the display 217, wherein the first image corresponds to the first image data, and display a third image in a second window of the display 217, wherein the third image corresponds to the fused image data.

Intermediate Short Range Wireless (e.g., Bluetooth) Signal Combiner

An intermediate short range wireless, e.g., Bluetooth, signal combiner may comprise a wireless heads-up display adapter placed into the communication path of the monitor to a laparoscope console allowing the surgical hub to overlay data onto the screen. Security and identification of requested pairing may augment the communication techniques.

FIG. 131 illustrates a communication system 6370 comprising an intermediate signal combiner 6372 positioned in the communication path between an imaging module 238 and a surgical hub display 217, according to one aspect of the present disclosure. The signal combiner 6372 receives image data from an imaging module 238 in the form of short range wireless or wired signals. The signal combiner 6372 also receives audio and image data form a headset 6374 and combines the image data from the imaging module 238 with the audio and image data from the headset 6374. The surgical hub 206 receives the combined data from the combiner 6372 and overlays the data provided to the display 217, where the overlaid data is displayed. The signal combiner 6372 may communicate with the surgical hub 206 via wired or wireless signals. The headset 6374 receives image data from an imaging device 6376 coupled to the headset 6374 and receives audio data from an audio device 6378 coupled to the headset 6374. The imaging device 6376 may be a digital video camera and the audio device 6378 may be a microphone. In one aspect, the signal combiner 6372 may be an intermediate short range wireless, e.g., Bluetooth, signal combiner. The signal combiner 6374 may comprise a wireless heads-up display adapter to couple to the headset 6374 placed into the communication path of the display 217 to a console allowing the surgical hub 206 to overlay data onto the screen of the display 217. Security and identification of requested pairing may augment the communication techniques. The imaging module 238 may be coupled to a variety if imaging devices such as an endoscope 239, laparoscope, etc., for example.

Independent Interactive Headset

FIG. 132 illustrates an independent interactive headset 6380 worn by a surgeon 6382 to communicate data to the surgical hub, according to one aspect of the present disclosure. Peripheral information of the independent interactive headset 6380 does not include active video. Rather, the peripheral information includes only device settings, or signals that do not have same demands of refresh rates. Interaction may augment the surgeon's 6382 information based on linkage with preoperative computerized tomography (CT) or other data linked in the surgical hub 206. The independent interactive headset 6380 can identify structure—ask whether instrument is touching a nerve, vessel, or adhesion, for example. The independent interactive headset 6380 may include pre-operative scan data, an optical view, tissue interrogation properties acquired throughout procedure, and/or processing in the surgical hub 206 used to provide an answer. The surgeon 6382 can dictate notes to the independent interactive headset 6380 to be saved with patient data in the hub storage 248 for later use in report or in follow up.

In one aspect, the independent interactive headset 6380 worn by the surgeon 6382 links to the surgical hub 206 with audio and visual information to avoid the need for overlays, and allows customization of displayed information around periphery of view. The independent interactive headset 6380 provides signals from devices (e.g., instruments), answers queries about device settings, or positional information linked with video to identify quadrant or position. The independent interactive headset 6380 has audio control and audio feedback from the headset 6380. The independent interactive headset 6380 is still able to interact with all other systems in the operating theater (e.g., operating room), and have feedback and interaction available wherever the surgeon 6382 is viewing.

Identification and Usage Recording

In one aspect, the present disclosure provides a display of the authenticity of reloads, modular components, or loading units. FIG. 133 illustrates a method 6390 for controlling the usage of a device 6392. A device 6392 is connected to an energy source 6394. The device 6392 includes a memory device 6396 that includes storage 6398 and communication 6400 devices. The storage 6398 includes data 6402 that may be locked data 6404 or unlocked data 6406. Additionally, the storage 6398 includes an error-detecting code 6408 such as a cyclic redundancy check (CRC) value and a sterilization indicator 6410. The energy source 6394 includes a reader 6412, display 6414, a processor 6416, and a data port 6418 that couples the energy source 6394 to a network 6420. The network 6420 is coupled to a central server 6422, which is coupled to a central database 6424. The network 6420 also is coupled to a reprocessing facility 6426. The reprocessing facility 6426 includes a reprocessing data reader/writer 6428 and a sterilizing device 6430.

The method comprises connecting the device to an energy source 6394. Data is read from a memory device 6396 incorporated in the device 6392. The data including one or more of a unique identifier (UID), a usage value, an activation value, a reprocessing value, or a sterilization indicator. The usage value is incremented when the device 6392 is connected to the energy source 6394. The activation value is incremented when the device 6392 is activated permitting energy to flow from the energy source 6394 to an energy consuming component of the device 6392. Usage of the device 6392 may be prevented if: the UID is on a list of prohibited UIDs, the usage value is not lower than a usage limitation value, the reprocessing value is equal to a reprocessing limitation value, the activation value is equal to an activation limitation value, and/or the sterilization indicator does not indicate that the device has been sterilized since its previous usage. Further examples are disclosed in U.S. Patent Application Publication No. 2015/0317899, titled SYSTEM AND METHOD FOR USING RFID TAGS TO DETERMINE STERILIZATION OF DEVICES, which published on Nov. 5, 2015, which is herein incorporated by reference in its entirety.

FIG. 134 provides a surgical system 6500 in accordance with the present disclosure and includes a surgical instrument 6502 that is in communication with a console 6522 or a portable device 6526 through a local area network 6518 or a cloud network 6520 via a wired or wireless connection. In various aspects, the console 6522 and the portable device 6526 may be any suitable computing device. The surgical instrument 6502 includes a handle 6504, an adapter 6508, and a loading unit 6514. The adapter 6508 releasably couples to the handle 6504 and the loading unit 6514 releasably couples to the adapter 6508 such that the adapter 6508 transmits a force from a drive shaft to the loading unit 6514. The adapter 6508 or the loading unit 6514 may include a force gauge (not explicitly shown) disposed therein to measure a force exerted on the loading unit 6514. The loading unit 6514 includes an end effector 6530 having a first jaw 6532 and a second jaw 6534. The loading unit 6514 may be an in-situ loaded or multi-firing loading unit (MFLU) that allows a clinician to fire a plurality of fasteners multiple times without requiring the loading unit 6514 to be removed from a surgical site to reload the loading unit 6514.

The first and second jaws 6532, 6534 are configured to clamp tissue therebetween, fire fasteners through the clamped tissue, and sever the clamped tissue. The first jaw 6532 may be configured to fire at least one fastener a plurality of times, or may be configured to include a replaceable multi-fire fastener cartridge including a plurality of fasteners (e.g., staples, clips, etc.) that may be fired more that one time prior to being replaced. The second jaw 6534 may include an anvil that deforms or otherwise secures the fasteners about tissue as the fasteners are ejected from the multi-fire fastener cartridge.

The handle 6504 includes a motor that is coupled to the drive shaft to affect rotation of the drive shaft. The handle 6504 includes a control interface to selectively activate the motor. The control interface may include buttons, switches, levers, sliders, touchscreen, and any other suitable input mechanisms or user interfaces, which can be engaged by a clinician to activate the motor.

The control interface of the handle 6504 is in communication with a controller 6528 of the handle 6504 to selectively activate the motor to affect rotation of the drive shafts. The controller 6528 is disposed within the handle 6504 and is configured to receive input from the control interface and adapter data from the adapter 6508 or loading unit data from the loading unit 6514. The controller 6528 analyzes the input from the control interface and the data received from the adapter 6508 and/or loading unit 6514 to selectively activate the motor. The handle 6504 may also include a display that is viewable by a clinician during use of the handle 6504. The display is configured to display portions of the adapter or loading unit data before, during, or after firing of the instrument 6502.

The adapter 6508 includes an adapter identification device 6510 disposed therein and the loading unit 6514 includes a loading unit identification device 6516 disposed therein. The adapter identification device 6510 is in communication with the controller 6528, and the loading unit identification device 6516 is in communication with the controller 6528. It will be appreciated that the loading unit identification device 6516 may be in communication with the adapter identification device 6510, which relays or passes communication from the loading unit identification device 6516 to the controller 6528.

The adapter 6508 may also include a plurality of sensors 6512 (one shown) disposed thereabout to detect various conditions of the adapter 6508 or of the environment (e.g., if the adapter 6508 is connected to a loading unit, if the adapter 6508 is connected to a handle, if the drive shafts are rotating, the torque of the drive shafts, the strain of the drive shafts, the temperature within the adapter 6508, a number of firings of the adapter 6508, a peak force of the adapter 6508 during firing, a total amount of force applied to the adapter 6508, a peak retraction force of the adapter 6508, a number of pauses of the adapter 6508 during firing, etc.). The plurality of sensors 6512 provides an input to the adapter identification device 6510 in the form of data signals. The data signals of the plurality of sensors 6512 may be stored within, or be used to update the adapter data stored within, the adapter identification device 6510. The data signals of the plurality of sensors 6512 may be analog or digital. The plurality of sensors 6512 may include a force gauge to measure a force exerted on the loading unit 6514 during firing.

The handle 6504 and the adapter 6508 are configured to interconnect the adapter identification device 6510 and the loading unit identification device 6516 with the controller 6528 via an electrical interface. The electrical interface may be a direct electrical interface (i.e., include electrical contacts that engage one another to transmit energy and signals therebetween). Additionally or alternatively, the electrical interface may be a non-contact electrical interface to wirelessly transmit energy and signals therebetween (e.g., inductively transfer). It is also contemplated that the adapter identification device 6510 and the controller 6528 may be in wireless communication with one another via a wireless connection separate from the electrical interface.

The handle 6504 includes a transmitter 6506 that is configured to transmit instrument data from the controller 6528 to other components of the system 6500 (e.g., the LAN 6518, the cloud 6520, the console 6522, or the portable device 6526). The transmitter 6506 also may receive data (e.g., cartridge data, loading unit data, or adapter data) from the other components of the system 6500. For example, the controller 6528 may transmit instrument data including a serial number of an attached adapter (e.g., adapter 6508) attached to the handle 6504, a serial number of a loading unit (e.g., loading unit 6514) attached to the adapter, and a serial number of a multi-fire fastener cartridge (e.g., multi-fire fastener cartridge), loaded into the loading unit, to the console 6528. Thereafter, the console 6522 may transmit data (e.g., cartridge data, loading unit data, or adapter data) associated with the attached cartridge, loading unit, and adapter, respectively, back to the controller 6528. The controller 6528 can display messages on the local instrument display or transmit the message, via transmitter 6506, to the console 6522 or the portable device 6526 to display the message on the display 6524 or portable device screen, respectively.

Multi-Functional Surgical Control System and Switching Interface for Verbal Control of Imaging Device FIG. 135 illustrates a verbal AESOP camera positioning system. Further examples are disclosed in U.S. Pat. No. 7,097,640, titled MULTI-FUNCTIONAL SURGICAL CONTROL SYSTEM AND SWITCHING INTERFACE, which issued on Aug. 29, 2006, which is herein incorporated by reference in its entirety. FIG. 135 shows a surgical system 6550 that may be coupled to surgical hub 206, described in connection with FIGS. 1-11. The system 6550 allows a surgeon to operate a number of different surgical devices 6552, 6554, 6556, and 6558 from a single input device 6560. Providing a single input device reduces the complexity of operating the various devices and improves the efficiency of a surgical procedure performed by a surgeon. The system 6550 may be adapted and configured to operate a positioning system for an imaging device such as a camera or endoscope using verbal commands.

The surgical device 6552 may be a robotic arm which can hold and move a surgical instrument. The arm 6552 may be a device such as that sold by Computer Motion, Inc. of Goleta, Calif. under the trademark AESOP, which is an acronym for Automated Endoscopic System for Optimal Positioning. The arm 6552 is commonly used to hold and move an endoscope within a patient. The system 6550 allows the surgeon to control the operation of the robotic arm 6552 through the input device 6560.

The surgical device 6554 may be an electrocautery device. Electrocautery devices typically have a bi-polar tip which carries a current that heats and denatures tissue. The device is typically coupled to an on-off switch to actuate the device and heat the tissue. The electrocautery device may also receive control signals to vary its power output. The system 6550 allows the surgeon to control the operation of the electrocautery device through the input device 6560.

The surgical device 6556 may be a laser. The laser 6556 may be actuated through an on-off switch. Additionally, the power of the laser 6556 may be controlled by control signals. The system 6550 allows the surgeon to control the operation of the laser 6556 through the input device 6560.

The device 6558 may be an operating table. The operating table 6558 may contain motors and mechanisms which adjust the position of the table. The present invention allows the surgeon to control the position of the table 6558 through the input device 6560. Although four surgical devices 6552, 6554, 6556, and 6558 are described, it is to be understood that other functions within the operating room may be controlled through the input device 6560. By way of example, the system 6560 may allow the surgeon to control the lighting and temperature of the operating room through the input device 6560.

The input device 6560 may be a foot pedal which has a plurality of buttons 6562, 6564, 6565, 6566, and 6568 that can be depressed by the surgeon. Each button is typically associated with a specific control command of a surgical device. For example, when the input device 6560 is controlling the robotic arm 6552, depressing the button 6562 may move the arm in one direction and depressing the button 6566 may move the arm in an opposite direction. Likewise, when the electrocautery device 6554 or the laser 6556 is coupled to the input device 6560, depressing the button 6568 may energize the devices, and so forth and so on. Although a foot pedal is shown and described, it is to be understood that the input device 6560 may be a hand controller, a speech interface which accepts voice commands from the surgeon, a cantilever pedal or other input devices which may be well known in the art of surgical device control. Using the speech interface, the surgeon is able to position a camera or endoscope connected to the robotic arm 6552 using verbal commands. The imaging device, such as a camera or endoscope, may be coupled to the robotic arm 6552 positioning system that be controlled through the system 6550 using verbal commands.

The system 6550 has a switching interface 6570 which couples the input device 6560 to the surgical devices 6552, 6554, 6556, and 6558. The interface 6570 has an input channel 6572 which is connected to the input device 6560 by a bus 6574. The interface 6570 also has a plurality of output channels 6576, 6578, 6580, and 6582 that are coupled to the surgical devices by busses 6584, 6586, 6588, 6590, 6624, 6626, 6628 and which may have adapters or controllers disposed in electrical communication therewith and therebetween. Such adapters and controllers will be discussed in more detail hereinbelow.

Because each device 6552, 6554, 6556, 6558 may require specifically configured control signals for proper operation, adapters 6620, 6622 or a controller 6618 may be placed intermediate and in electrical communication with a specific output channel and a specific surgical device. In the case of the robotic arm system 6552, no adapter is necessary and as such, the robotic arm system 6552 may be in direct connection with a specific output channel. The interface 6570 couples the input channel 6572 to one of the output channels 6576, 6578, 6580, and 6582.

The interface 6570 has a select channel 6592 which can switch the input channel 6572 to a different output channel 6576, 6578, 6580, or 6582 so that the input device 6560 can control any of the surgical devices. The interface 6570 may be a multiplexor circuit constructed as an integrated circuit and placed on an ASIC. Alternatively, the interface 6570 may be a plurality of solenoid actuated relays coupled to the select channel by a logic circuit. The interface 6570 switches to a specific output channel in response to an input signal or switching signal applied on the select channel 6592.

As depicted in FIG. 135, there may be several inputs to the select channel 6592. Such inputs originate from the foot pedal 6560, the speech interface 6600 and the CPU 6662. The interface 6570 may have a multiplexing unit such that only one switching signal may be received at the select channel 6592 at any one time, thus ensuring no substantial hardware conflicts. The prioritization of the input devices may be configured so the foot pedal has highest priority followed by the voice interface and the CPU. This is intended for example as the prioritization scheme may be employed to ensure the most efficient system. As such other prioritization schemes may be employed. The select channel 6592 may sequentially connect the input channel to one of the output channels each time a switching signal is provided to the select channel 6592. Alternatively, the select channel 6592 may be addressable so that the interface 6570 connects the input channel to a specific output channel when an address is provided to the select channel 6592. Such addressing is known in the art of electrical switches.

The select channel 6592 may be connected by line 6594 to a dedicated button 6596 on the foot pedal 6560. The surgeon can switch surgical devices by depressing the button 6596. Alternatively, the select channel 6592 may be coupled by line 6598 to a speech interface 6600 which allows the surgeon to switch surgical devices with voice commands.

The system 6550 may have a central processing unit (CPU) 6602 which receives input signals from the input device 6560 through the interface 6570 and a bus 6585. The CPU 6602 receives the input signals, and can ensure that no improper commands are being input at the controller. If this occurs, the CPU 6602 may respond accordingly, either by sending a different switching signal to select channel 6592, or by alerting the surgeon via a video monitor or speaker.

The CPU 6602 can also provide output commands for the select channel 6592 on the bus 6608 and receives input commands from the speech interface 6600 on the same bi-directional bus 6608. The CPU 6602 may be coupled to a monitor 6610 and/or a speaker 6612 by buses 6614 and 6616, respectively. The monitor 6610 may provide a visual indication of which surgical device is coupled to the input device 6560. The monitor may also provide a menu of commands which can be selected by the surgeon either through the speech interface 6600 or button 6596. Alternatively, the surgeon could switch to a surgical device by selecting a command through a graphic user interface. The monitor 6610 may also provide information regarding improper control signals sent to a specific surgical device 6552, 6554, 6556, 6558 and recognized by the CPU 6602. Each device 6552, 6554, 6556, 6558 has a specific appropriate operating range, which is well known to the skilled artisan. As such, the CPU 6602 may be programmed to recognize when the requested operation from the input device 6560 is inappropriate and will then alert the surgeon either visually via the monitor 6610 or audibly via the speaker 6612. The speaker 6612 may also provide an audio indication of which surgical device is coupled to the input device 6560.

The system 6550 may include a controller 6618 which receives the input signals from the input device 6560 and provides corresponding output signals to control the operating table 6558. Likewise, the system may have adapters 6620, 6622 which provide an interface between the input device 6560 and the specific surgical instruments connected to the system.

In operation, the interface 6570 initially couples the input device 6560 to one of the surgical devices. The surgeon can control a different surgical device by generating an input command that is provided to the select channel 6592. The input command switches the interface 6570 so that the input device 6560 is coupled to a different output channel and corresponding surgical device or adapter. What is thus provided is an interface 6570 that allows a surgeon to select, operate and control a plurality of different surgical devices through a common input device 6560.

FIG. 136 illustrates a multi-functional surgical control system 6650 and switching interface for virtual operating room integration. A virtual control system for controlling surgical equipment in an operating room while a surgeon performs a surgical procedure on a patient, comprising: a virtual control device including an image of a control device located on a surface and a sensor for interrogating contact interaction of an object with the image on the surface, the virtual control device delivering an interaction signal indicative of the contact interaction of the object with the image; and a system controller connected to receive the interaction signal from the virtual control device and to deliver a control signal to the surgical equipment in response to the interaction signal to control the surgical equipment in response to the contact interaction of the object with the image. Further examples are disclosed in U.S. Pat. No. 7,317,955, titled VIRTUAL OPERATING ROOM INTEGRATION, which issued on Jan. 8, 2008, which is herein incorporated by reference in its entirety.

As shown in FIG. 136, communication links 6674 are established between the system controller 6676 and the various components and functions of the virtual control system 6650. The communication links 6674 are preferably optical paths, but the communication links may also be formed by radio frequency transmission and reception paths, hardwired electrical connections, or combinations of optical, radio frequency and hardwired connection paths as may be appropriate for the type of components and functions obtained by those components. The arrows at the ends of the links 6674 represent the direction of primary information flow.

The communication links 6674 with the surgical equipment 6652, a virtual control panel 6556, a virtual foot switch 6654 and patient monitoring equipment 6660 are bidirectional, meaning that the information flows in both directions through the links 6674 connecting those components and functions. For example, the system controller 6676 supplies signals which are used to create a control panel image from the virtual control panel 6656 and a foot switch image from the virtual foot switch 6654. The virtual control panel 6656 and the virtual foot switch 6654 supply information to the system controller 6676 describing the physical interaction of the surgeon's finger and foot relative to a projected control panel image and the projected foot switch image. The system controller 6676 responds to the information describing the physical interaction with the projected image, and supplies control signals to the surgical equipment 6652 and patient monitoring equipment 6660 to control functionality of those components in response to the physical interaction information. The control, status and functionality information describing the surgical equipment 6652 and patient monitoring equipment 6660 flows to the system controller 6676, and after that information is interpreted by the system controller 6676, it is delivered to a system display 6670, a monitor 6666, and/or a heads up display 6668 for presentation.

The communication links 6674 between the system controller 6676 and the system display 6670, the heads up display 6668, the monitor 6666, a tag printer 6658 and output devices 6664 are all uni-directional, meaning that the information flows from the system controller 6676 to those components and functions. In a similar manner, the communication links 6674 between the system controller 6676 and a scanner 6672 and the input devices 6662 are also unidirectional, but the information flows from the components 6662, 6672 to the system controller 6676. In certain circumstances, certain control and status information may flow between the system controller 6676 and the components 6658, 6660, 6662, 6664, 6666, 6668, 6670, 6672 in order to control the functionality of the those components.

Each communication link 6674 preferably has a unique identity so that the system controller 6676 can individually communicate with each of the components of the virtual control system 6650. The unique identity of each communication link is preferable when some or all of the communication links 6674 are through the same medium, as would be the case of optical and radio frequency communications. The unique identity of each communication link 6674 assures that the system controller 6676 has the ability to exercise individual control over each of the components and functions on a very rapid and almost simultaneous manner. The unique identity of each communication link 6674 can be achieved by using different frequencies for each communication link 6674 or by using unique address and identification codes associated with the communications transferred over each communication link 6674.

In one aspect, the present disclosure provides illustrates a surgical communication and control headset that interfaces with the surgical hub 206 described in connection with FIGS. 1-11. Further examples are disclosed in U.S. Patent Application Publication No. 2009/0046146, titled SURGICAL COMMUNICATION AND CONTROL SYSTEM, which published on Feb. 19, 2009, which is herein incorporated by reference in its entirety. FIG. 137 illustrates a diagram 6680 of a beam source and combined beam detector system utilized as a device control mechanism in an operating theater. The system 6680 is configured and wired to allow for device control with the overlay generated on the primary procedural display. The footswitch shows a method to allow the user to click on command icons that would appear on the screen while the beam source is used to aim at the particular desired command icon to be clicked. The control system graphic user interface (GUI) and device control processor communicate and parameters are changed using the system. The system 6680 includes a display 6684 coupled to a beam detecting sensor 6682 and a head mounted source 6686. The beam detecting sensor 6682 is in communication with a control system GUI overlay processor and beam source processor 6688. The surgeon operates a footswitch 6692 or other adjunctive switch, which provides a signal to a device control interface unit 6694.

The system 6680 will provide a means for a sterile clinician to control procedural devices in an easy and quick, yet hands free and centralized fashion. The ability to maximize the efficiency of the operation and minimize the time a patient is under anesthesia is important to the best patient outcomes. It is common for surgeons, cardiologists or radiologists to verbally request adjustments be made to certain medical devices and electronic equipment used in the procedure outside the sterile field. It is typical that he or she must rely on another staff member to make the adjustments he or she needs to settings on devices such as cameras, bovies, surgical beds, shavers, insufflators, injectors, to name a few. In many circumstances, having to command a staff member to make a change to a setting can slow down a procedure because the non-sterile staff member is busy with another task. The sterile physician cannot adjust non-sterile equipment without compromising sterility, so he or she must often wait for the non-sterile staff member to make the requested adjustment to a certain device before resuming the procedure.

The system 6680 allows a user to use a beam source and beam detector to regenerate a pointer overlay coupled with a GUI and a concurrent switching method (i.e., a foot switch, etc.) to allow the clinician to click through commands on the primary display. In one aspect, a GUI could appear on the procedural video display when activated, such as when the user tilts his or her head twice to awaken it or steps on a foot switch provided with the system. Or it is possible that a right head tilt wakes up the system, and a left head tilt simply activates the beam source. When the overlay (called device control GUI overlay) appears on the screen it shows button icons representing various surgical devices and the user can use the beam source, in this case a laser beam, to aim at the button icons. Once the laser is over the proper button icon, a foot switch, or other simultaneous switch method can be activated, effectively acting like a mouse click on a computer. For example a user can "wake up" the system, causing a the device control GUI overlay to pop up that lists button icons on the screen, each one labeled as a corresponding procedural medical device. The user can point the laser at the correct box or device and click a foot pedal (or some other concurrent control-like voice control, waistband button, etc.) to make a selection, much like clicking a mouse on a computer. The sterile physician can then select "insufflator, for example" The subsequent screen shows arrow icons that can be clicked for various settings for the device that need to be adjusted (pressure, rate, etc.). In one iteration, the user can then can point the laser at the up arrow and click the foot pedal repeatedly until the desired setting is attained.

In one aspect, components of the system 6680 could be coupled with existing robotic endoscope holders to "steer" a rigid surgical endoscopic camera by sending movement commands to the robotic endoscope holding arm (provided separately, i.e., AESOP by Computer Motion). The endoscope is normally held by an assistant nurse or resident physician. There are robotic and mechanical scope holders currently on the market and some have even had been introduced with voice control. However, voice control systems have often proven cumbersome, slow and inaccurate. This aspect would employ a series of software and hardware components to allow the overlay to appear as a crosshair on the primary procedural video screen. The user could point the beam source at any part of the quadrant and click a simultaneous switch, such as a foot pedal, to send movement commands to the existing robotic arm, which, when coupled with the secondary trigger (i.e., a foot switch, waist band switch, etc.) would send a command to adjust the arm in minute increments in the direction of the beam source. It could be directed by holding down the secondary trigger until the desired camera angle and position is achieved and then released. This same concept could be employed for surgical bed adjustments by having the overlay resemble the controls of a surgical bed. The surgical bed is commonly adjusted during surgery to allow better access to the anatomy. Using the combination of the beam source, in this case a laser, a beam detecting sensor such as a camera, a control system GUI overlay processing unit and beam source processor, and a device control interface unit, virtually any medical device could be controlled through this system. Control codes would be programmed into the device control interface unit, and most devices can be connected using an RS-232 interface, which is a standard for serial binary data signals connecting between a DTE (Data Terminal Equipment) and a DCE (Data Circuit-terminating Equipment). The present invention while described with reference to application in the medical field can be expanded/modified for use in other fields. Another use of this invention could be in helping those who are without use of their hands due to injury or handicap or for professions where the hands are occupied and hands free interface is desired.

Surgical Hub with Direct Interface Control with Secondary Surgeon Display Units Designed to be within the Sterile Field and Accessible for Input and Display by the Surgeon In one aspect, the surgical hub 206 provides a secondary user interface that enables display and control of surgical hub 206 functions from with the sterile field. The secondary display could be used to change display locations, what information is displayed where, pass off control of specific functions or devices.

During a surgical procedure, the surgeon may not have a user interface device accessible for interactive input by the surgeon and display within the sterile field. Thus, the surgeon cannot interface with the user interface device and the surgical hub from within the sterile field and cannot control other surgical devices through the surgical hub from within the sterile field.

One solution provides a display unit designed to be used within the sterile field and accessible for input and display by the surgeon to allow the surgeon to have interactive input control from the sterile field to control other surgical devices coupled to the surgical hub. The display unit is sterile and located within the sterile field to allow the surgeons to interface with the display unit and the surgical hub to directly interface and configure instruments as necessary without leaving the sterile field. The display unit is a master device and may be used for display, control, interchanges of tool control, allowing feeds from other surgical hubs without the surgeon leaving the sterile field.

In one aspect, the present disclosure provides a control unit, comprising an interactive touchscreen display, an interface configured to couple the interactive touchscreen display to a surgical hub, a processor, and a memory coupled to the processor. The memory stores instructions executable by the processor to receive input commands from the interactive touchscreen display located inside a sterile field and transmits the input commands to a surgical hub to control devices coupled to the surgical hub located outside the sterile field.

In another aspect, the present disclosure provides a control unit, comprising an interactive touchscreen display, an interface configured to couple the interactive touchscreen display to a surgical hub, and a control circuit configured to receive input commands from the interactive touchscreen display located inside a sterile field and transmit the input commands to a surgical hub to control devices coupled to the surgical hub located outside the sterile field.

In another aspect, the present disclosure provides a non-transitory computer readable medium storing computer readable instructions which, when executed, causes a machine to receive input commands from an interactive touchscreen display located inside a sterile field and transmit the input commands to a surgical hub through an interface configured to couple the interactive touchscreen display to the surgical hub to control devices coupled to the surgical hub located outside the sterile field.

Providing a display unit designed to be used within the sterile field and accessible for input and display by the surgeon provides the surgeon interactive input control from the sterile field to control other surgical devices coupled to the surgical hub.

This display unit within the sterile field is sterile and allows the surgeons to interface with it and the surgical hub. This gives the surgeon control of the instruments coupled to the surgical hub and allows the surgeon to directly interface and configure the instruments as necessary without leaving the sterile field. The display unit is a master device and may be used for display, control, interchanges of tool control, allowing feeds from other surgical hubs without the surgeon leaving the sterile field.

In various aspects, the present disclosure provides a secondary user interface to enable display and control of surgical hub functions from within a sterile field. This control could be a display device like an I-pad, e.g., a portable interactive touchscreen display device configured to be introduced into the operating theater in a sterile manner. It could be paired like any other device or it could be location sensitive. The display device would be allowed to function in this manner whenever the display device is placed over a specific location of the draped abdomen of the patient during a surgical procedure. In other aspects, the present disclosure provides a smart retractor and a smart sticker. These and other aspects are described hereinbelow.

In one aspect, the present disclosure provides a secondary user interface to enable display and control of surgical hub functions from within the sterile field. In another aspect, the secondary display could be used to change display locations, determine what information and where the information is displayed, and pass off control of specific functions or devices.

There are four types of secondary surgeon displays in two categories. One type of secondary surgeon display units is designed to be used within the sterile field and accessible for input and display by the surgeon within the sterile field interactive control displays. Sterile field interactive control displays may be shared or common sterile field input control displays.

A sterile field display may be mounted on the operating table, on a stand, or merely laying on the abdomen or chest of the patient. The sterile field display is sterile and allows the surgeons to interface with the sterile field display and the surgical hub. This gives the surgeon control of the system and allows them to directly interface and configure the sterile field display as necessary. The sterile field display may be configured as a master device and may be used for display, control, interchanges of tool control, allowing feeds from other surgical hubs, etc.

In one aspect, the sterile field display may be employed to re-configure the wireless activation devices within the operating theater (OR) and their paired energy device if a surgeon hands the device to another. FIGS. 138A-138E illustrate various types of sterile field control and data input consoles 6700, 6702, 6708, 6712, 6714 according to various aspects of the present disclosure. Each of the disclosed sterile field control and data input consoles 6700, 6702, 6708, 6712, 6714 comprise at least one touchscreen 6701, 6704/6706, 6709, 6713, 6716 input/output device layered on the top of an electronic visual display of an information processing system. The sterile field control and data input consoles 6700, 6702, 6708, 6712, 6714 may include batteries as a power source. Some include a cable 6710 to connect to a separate power source or to recharge the batteries. A user can give input or control the information processing system through simple or multi-touch gestures by touching the touchscreen 6701, 6704/6706, 6709, 6713, 6716 with a stylus, one or more fingers, or a surgical tool. The sterile field control and data input consoles 6700, 6702, 6708, 6712, 6714 may be used to re-configure wireless activation devices within the operating theater and a paired energy device if a surgeon hands the device to another surgeon. The sterile field control and data input consoles 6700, 6702, 6708, 6712, 6714 may be used to accept consult feeds from another operating theater where it would then configure a portion of the operating theater screens or all of them to mirror the other operating theater so the surgeon is able to see what is needed to help. The sterile field control and data input consoles 6700, 6702, 6708, 6712, 6714 are configured to communicate with the surgical hub 206. Accordingly, the description of the surgical hub 206 discussed in connection with FIGS. 1-11 is incorporated in this section by reference.

FIG. 138A illustrates a single zone sterile field control and data input console 6700, according to one aspect of the present disclosure. The single zone console 6700 is configured for use in a single zone within a sterile field. Once deployed in a sterile field, the single zone console 6700 can receive touchscreen inputs from a user in the sterile field. The touchscreen 6701 enables the user to interact directly with what is displayed, rather than using a mouse, touchpad, or other such devices (other than a stylus or surgical tool). The single zone console 6700 includes wireless communication circuits to communicate wirelessly to the surgical hub 206.

FIG. 138B illustrates a multi zone sterile field control and data input console 6702, according to one aspect of the present disclosure. The multi zone console 6702 comprises a first touchscreen 6704 to receive an input from a first zone of a sterile field and a second touchscreen 6706 to receive an input from a second zone of a sterile field. The multi zone console 6702 is configured to receive inputs from multiple users in a sterile field. The multi zone console 6702 includes wireless communication circuits to communicate wirelessly to the surgical hub 206. Accordingly, the multi zone sterile field control and data input console 6702 comprises an interactive touchscreen display with multiple input and output zones.

FIG. 138C illustrates a tethered sterile field control and data input console 6708, according to one aspect of the present disclosure. The tethered console 6708 includes a cable 6710 to connect the tethered console 6708 to the surgical hub 206 via a wired connection. The cable 6710 enables the tethered console 6708 to communicate over a wired link in addition to a wireless link. The cable 6710 also enables the tethered console 6708 to connect to a power source for powering the console 6708 and/or recharging the batteries in the console 6708.

FIG. 138D illustrates a battery operated sterile field control and data input console 6712, according to one aspect of the present disclosure. The sterile field console 6712 is battery operated and includes wireless communication circuits to communicate wirelessly with the surgical hub 206. In particular, in one aspect, the sterile field console 6712 is configured to communicate with any of the modules coupled to the hub 206 such as the generator module 240. Through the sterile field console 6712, the surgeon can adjust the power output level of a generator using the touchscreen 6713 interface. One example is described below in connection with FIG. 138E.

FIG. 138E illustrates a battery operated sterile field control and data input console 6714, according to one aspect of the present disclosure. The sterile field console 6714 includes a user interface displayed on the touchscreen of a generator. The surgeon can thus control the output of the generator by touching the up/down arrow icons 6718A, 6718B that increase/decrease the power output of the generator module 240. Additional icons 6719 enable access to the generator module settings 6174, volume 6178 using the +/− icons, among other features directly from the sterile field console 6714. The sterile field console 6714 may be employed to adjust the settings or reconfigure other wireless activations devices or modules coupled to the hub 206 within the operating theater and their paired energy device when the surgeon hands the sterile field console 6714 to another.

FIGS. 139A-139B illustrate a sterile field console 6700 in use in a sterile field during a surgical procedure, according to one aspect of the present disclosure. FIG. 139A shows the sterile field console 6714 positioned in the sterile field near two surgeons engaged in an operation. In FIG. 139B, one of the surgeons is shown tapping the touchscreen 6701 of the sterile field console with a surgical tool 6722 to adjust the output of a modular device coupled to the surgical hub 206, reconfigure the modular device, or an energy device paired with the modular device coupled to the surgical hub 206.

In another aspect, the sterile field display may be employed to accept consult feeds from another operating room (OR), such as another operating theater or surgical hub 206, where it would then configure a portion of the OR screens or all of them to mirror the other ORs so the surgeon could see what is needed to help. FIG. 140 illustrates a process 6750 for accepting consult feeds from another operating room, according to one aspect of the present disclosure. The sterile field control and data input consoles 6700, 6702, 6708, 6712, 6714 shown in FIGS. 138A-138E, 139A-139B may be used as an interact-able scalable secondary display allowing the surgeon to overlay other feeds or images from laser Doppler image scanning arrays or other image sources. The sterile field control and data input consoles 6700, 6702, 6708, 6712, 6714 may be used to call up a pre-operative scan or image to review. Laser Doppler techniques are described in U.S. Provisional Patent Application No. 62/611,341, filed Dec. 28, 2017, and titled INTERACTIVE SURGICAL PLATFORM, which is incorporated herein by reference in its entirety.

It is recognized that the tissue penetration depth of light is dependent on the wavelength of the light used. Thus, the wavelength of the laser source light may be chosen to detect particle motion (such a blood cells) at a specific range of tissue depth. A laser Doppler employs means for detecting moving particles such as blood cells based at a variety of tissue depths based on the laser light wavelength. A laser source may be directed to a surface of a surgical site. A blood vessel (such as a vein or artery) may be disposed within the tissue at some depth δ from the tissue surface. Red laser light (having a wavelength in the range of about 635 nm to about 660 nm) may penetrate the tissue to a depth of about 1 mm. Green laser light (having a wavelength in the range of about 520 nm to about 532 nm) may penetrate the tissue to a depth of about 2-3 mm. Blue laser light (having a wavelength in the range of about 405 nm to about 445 nm) may penetrate the tissue to a depth of about 4 mm or greater. A blood vessel may be located at a depth of about 2-3 mm below the tissue surface. Red laser light will not penetrate to this depth and thus will not detect blood cells flowing within this vessel. However, both green and blue laser light can penetrate this depth. Therefore, scattered green and blue laser light from the blood cells will result in an observed Doppler shift in both the green and blue.

In some aspects, a tissue may be probed by red, green, and blue laser illumination in a sequential manner and the effect of such illumination may be detected by a CMOS imaging sensor over time. It may be recognized that sequential illumination of the tissue by laser illumination at differing wavelengths may permit a Doppler analysis at varying tissue depths over time. Although red, green, and blue laser sources may be used to illuminate the surgical site, it may be recognized that other wavelengths outside of visible light (such as in the infrared or ultraviolet regions) may be used to illuminate the surgical site for Doppler analysis. The imaging sensor information may be provided to the sterile field control and data input consoles 6700, 6702, 6708, 6712, 6714.

The sterile field control and data input consoles 6700, 6702, 6708, 6712, 6714 provide access to past recorded data. In one operating theater designated as OR1, the sterile field control and data input consoles 6700, 6702, 6708, 6712, 6714 may be configured as "consultants" and to erase all data when the consultation is complete. In another operating theater designated as OR3 (operating room 3), the sterile field control and data input consoles 6700, 6702, 6708, 6712, 6714 may be configured as a "consultees" and are configured to record all data received from operating theater OR1 (operating room 1) sterile field control and data input consoles 6700, 6702, 6708, 6712, 6714. These configurations are summarized in TABLE 2 below:

TABLE 2

| Sterile Field Control And Data Input Console In OR1 | Sterile Field Control And Data Input Console In OR3 |
|---|---|
| Access to past recorded data OR1 Consultant Erase data when done | OR 3 Consultee Record all data |

In one implementation of the process 6750, operating theater OR1 receives 6752 a consult request from OR3. Data is transferred to the OR1 sterile field control and data input console 6700, for example. The data is temporarily stored 6754. The data is backed up in time and the OR1 view 6756 of the temporary data begins on the OR1 sterile field control and data input console 6700 touchscreen 6701. When the view is complete, the data is erased 6758 and control returns 6760 to OR1. The data is then erased 6762 from the OR1 sterile field control and data input console 6700 memory.

In yet another aspect, the sterile field display may be employed as an interactable scalable secondary display allowing the surgeon to overlay other feeds or images like laser Doppler scanning arrays. In yet another aspect, the sterile field display may be employed to call up a preoperative scan or image to review. Once vessel path and depth and device trajectory are estimated, the surgeon employs a sterile field interactable scalable secondary display allowing the surgeon to overlay other feeds or images.

FIG. 141 is a diagram 6770 that illustrates a technique for estimating vessel path, depth, and device trajectory. Prior to dissecting a vessel 6772, 6774 located below the surface of the tissue 6775 using a standard approach, the surgeon estimates the path and depth of the vessel 6772, 6774 and a trajectory 6776 of a surgical device 6778 will take to reach the vessel 6772, 6774. It is often difficult to estimate the path and depth 6776 of a vessel 6772, 6774 located below the surface of the tissue 6775 because the surgeon cannot accurately visualize the location of the vessel 6772, 6774 path and depth 6776.

FIGS. 142A-142D illustrate multiple real time views of images of a virtual anatomical detail for dissection including perspective views (FIGS. 142A, 142C) and side views (FIGS. 142B, 142D). The images are displayed on a sterile field display of tablet computer or sterile field control and data input console employed as an interactable scalable secondary display allowing the surgeon to overlay other feeds or images, according to one aspect of the present disclosure. The images of the virtual anatomy enable the surgeon to more accurately predict the path and depth of a vessel 6772, 6774 located below the surface of the tissue 6775 as shown in FIG. 141 and the best trajectory 6776 of the surgical device 6778.

FIG. 142A is a perspective view of a virtual anatomy 6780 displayed on a tablet computer or sterile field control and data input console. FIG. 142B is a side view of the virtual anatomy 6780 shown in FIG. 142A, according to one aspect of the present disclosure. With reference to FIGS. 142A-142B, in one aspect, the surgeon uses a smart surgical device 6778 and a tablet computer to visualize the virtual anatomy 6780 in real time and in multiple views. The three dimensional perspective view includes a portion of tissue 6775 in which the vessels 6772, 6774 are located below surface. The portion of tissue is overlaid with a grid 6786 to enable the surgeon to visualize a scale and gauge the path and depth of the vessels 6772, 6774 at target locations 6782, 6784 each marked by an X. The grid 6786 also assists the surgeon determine the best trajectory 6776 of the surgical device 6778. As illustrated, the vessels 6772, 6774 have an unusual vessel path.

FIG. 142C illustrates a perspective view of the virtual anatomy 6780 for dissection, according to one aspect of the present disclosure. FIG. 142D is a side view of the virtual anatomy 6780 for dissection, according to one aspect of the present disclosure. With reference to FIGS. 142C-142D, using the tablet computer, the surgeon can zoom and pan 360° to obtain an optimal view of the virtual anatomy 6780 for dissection. The surgeon then determines the best path or trajectory 6776 to insert the surgical device 6778 (e.g., a dissector in this example). The surgeon may view the anatomy in a three-dimensional perspective view or any one of six views. See for example the side view of the virtual anatomy in FIG. 142D and the insertion of the surgical device 6778 (e.g., the dissector).

In another aspect, a sterile field control and data input console may allow live chatting between different departments, such as, for example, with the oncology or pathology department, to discuss margins or other particulars associated with imaging. The sterile field control and data input console may allow the pathology department to tell the surgeon about relationships of the margins within a specimen and show them to the surgeon in real time using the sterile field console.

In another aspect, a sterile field control and data input console may be used to change the focus and field of view of its own image or control that of any of the other monitors coupled to the surgical hub.

In another aspect, a sterile field control and data input console may be used to display the status of any of the equipment or modules coupled to the surgical hub 206. Knowledge of which device coupled to the surgical hub 206 is being used may be obtained via information such as the device is not on the instrument pad or on-device sensors. Based on this information, the sterile field control and data input console may change display, configurations, switch power to drive one device, and not another, one cord from capital to instrument pad and multiple cords from there. Device diagnostics may obtain knowledge that the device is inactive or not being used. Device diagnostics may be based on information such as the device is not on the instrument pad or based on-device sensors.

In another aspect, a sterile field control and data input console may be used as a learning tool. The console may display checklists, procedure steps, and/or sequence of steps. A timer/clock may be displayed to measure time to complete steps and/or procedures. The console may display room sound pressure level as indicator for activity, stress, etc.

FIGS. 143A-143B illustrate a touchscreen display 6890 that may be used within the sterile field, according to one aspect of the present disclosure. Using the touchscreen display 6890, a surgeon can manipulate images 6892 displayed on the touchscreen display 6890 using a variety of gestures such as, for example, drag and drop, scroll, zoom, rotate, tap, double tap, flick, drag, swipe, pinch open, pinch close, touch and hold, two-finger scroll, among others.

FIG. 143A illustrates an image 6892 of a surgical site displayed on a touchscreen display 6890 in portrait mode. FIG. 143B shows the touchscreen display 6890 rotated 6894 to landscape mode and the surgeon uses his index finger 6896 to scroll the image 6892 in the direction of the arrows. FIG. 143C shows the surgeon using his index finger 6896 and thumb 6898 to pinch open the image 6892 in the direction of the arrows 6899 to zoom in. FIG. 143D shows the surgeon using his index finger 6896 and thumb 6898 to pinch close the image 6892 in the direction of the arrows 6897 to zoom out. FIG. 143E shows the touchscreen display 6890 rotated in two directions indicated by arrows 6894, 6896 to enable the surgeon to view the image 6892 in different orientations.

Outside the sterile field, control and static displays are used that are different from the control and static displays used inside the sterile field. The control and static displays located outside the sterile field provide interactive and static displays for operating theater (OR) and device control. The control and static displays located outside the sterile field may include secondary static displays and secondary touchscreens for input and output.

Secondary static non-sterile displays 107, 109, 119 (FIG. 2) for used outside the sterile field include monitors placed on the wall of the operating theater, on a rolling stand, or on capital equipment. A static display is presented with a feed from the control device to which they are attached and merely displays what is presented to it.

Secondary touch input screens located outside the sterile field may be part of the visualization system 108 (FIG. 2), part of the surgical hub 108 (FIG. 2), or may be fixed placement touch monitors on the walls or rolling stands. One difference between secondary touch input screens and static displays is that a user can interact with a secondary touch input screen by changing what is displayed on that specific monitor or others. For capital equipment applications, it could be the interface to control the setting of the connected capital equipment. The secondary touch input screens and the static displays outside the sterile field can be used to preload the surgeon's preferences (instrumentation settings and modes, lighting, procedure and preferred steps and sequence, music, etc.)

Secondary surgeon displays may include personal input displays with a personal input device that functions similarly to the common sterile field input display device but it is controlled by a specific surgeon. Personal secondary displays may be implemented in many form factors such as, for example, a watch, a small display pad, interface glasses, etc. A personal secondary display may include control capabilities of a common display device and since it is located on or controlled by a specific surgeon, the personal secondary display would be keyed to him/her specifically and would indicate that to others and itself. Generally speaking, a personal secondary display would normally not be useful to exchanging paired devices because they are not accessible to more than one surgeon. Nevertheless, a personal secondary display could be used to grant permission for release of a device.

A personal secondary display may be used to provide dedicated data to one of several surgical personnel that wants to monitor something that the others typically would not want to monitor. In addition, a personal secondary display may be used as the command module. Further, a personal secondary display may be held by the chief surgeon in the operating theater and would give the surgeon the control to override any of the other inputs from anyone else. A personal secondary display may be coupled to a short range wireless, e.g., Bluetooth, microphone and earpiece allowing the surgeon to have discrete conversations or calls or the personal secondary display may be used to broadcast to all the others in the operating theater or other department.

FIG. 144 illustrates a surgical site 6900 employing a smart surgical retractor 6902 comprising a direct interface control to a surgical hub 206 (FIGS. 1-11), according to one aspect of the present disclosure. The smart surgical retractor 6902 helps the surgeon and operating room professionals hold an incision or wound open during surgical procedures. The smart surgical retractor 6902 aids in holding back underlying organs or tissues, allowing doctors/nurses better visibility and access to the exposed area. With reference also to FIGS. 1-11, the smart surgical retractor 6902 may comprise an input display 6904 operated by the smart surgical retractor 6902. The smart surgical retractor 6902 may comprise a wireless communication device to communicate with a device connected to a generator module 240 coupled to the surgical hub 206. Using the input display 6904 of the smart surgical retractor 6902, the surgeon can adjust power level or mode of the generator module 240 to cut and/or coagulate tissue. If using automatic on/off for energy delivery on closure of an end effector on the tissue, the status of automatic on/off may be indicated by a light, screen, or other device located on the smart retractor 6902 housing. Power being used may be changed and displayed.

In one aspect, the smart surgical retractor 6902 can sense or know what device/instrument 235 the surgeon is using, either through the surgical hub 206 or RFID or other device placed on the device/instrument 235 or the smart surgical retractor 6902, and provide an appropriate display. Alarm and alerts may be activated when conditions require. Other features include displaying the temperature of the ultrasonic blade, nerve monitoring, light source 6906 or fluorescence. The light source 6906 may be employed to illuminate the surgical field of view 6908 and to charge photocells 6918 on single use sticker display that stick onto the smart retractor 6902 (see FIG. 145, for example). In another aspect, the smart surgical retractor 6902 may include an augmented reality projected on the patient's anatomy (e.g., like a vein viewer).

FIG. 145 illustrates a surgical site 6910 with a smart flexible sticker display 6912 attached to the body/skin 6914 of a patient, according to one aspect of the present disclosure. As shown, the smart flexible sticker display 6912 is applied to the body/skin 6914 of a patient between the area exposed by the surgical retractors 6916. In one aspect, the smart flexible sticker display 6912 may be powered by light, an on board battery, or a ground pad. The flexible sticker display 6912 may communicate via short range wireless (e.g., Bluetooth) to a device, may provide readouts, lock power, or change power. The smart flexible sticker display 6912 also comprises photocells 6918 to power the smart flexible sticker display 6912 using ambient light energy. The flexible sticker display 6912 includes a display of a control panel 6920 user interface to enable the surgeon to control devices 235 or other modules coupled to the surgical hub 206 (FIGS. 1-11).

FIG. 146 is a logic flow diagram 6920 of a process depicting a control program or a logic configuration to communicate from inside a sterile field to a device located outside the sterile field, according to one aspect of the present disclosure. In one aspect, a control unit comprises an interactive touchscreen display, an interface configured to couple the interactive touchscreen display to a surgical hub, a processor, and a memory coupled to the processor. The memory stores instructions executable by the processor to receive 6922 input commands from the interactive touch-screen display located inside a sterile field and transmits 6924 the input commands to a surgical hub to control devices coupled to the surgical hub located outside the sterile field.

FIG. 147 illustrates a system for performing surgery. The system comprises a control box which includes internal circuitry; a surgical instrument including a distal element and techniques for sensing a position or condition of said distal element; techniques associated with said surgical instrument for transmitting said sensed position or condition to said internal circuitry of said control box; and for transmitting said sensed position or condition from said internal circuitry of said control box to a video monitor for display thereon, wherein said sensed position or condition is displayed on said video monitor as an icon or symbol, further comprising a voltage source for generating a voltage contained entirely within said surgical instrument. Further examples are disclosed in U.S. Pat. No. 5,503,320, titled SURGICAL APPARATUS WITH INDICATOR, which issued on Apr. 2, 1996, which is herein incorporated by reference in its entirety.

FIG. 147 shows schematically a system whereby data is transmitted to a video monitor for display, such data relating to the position and/or condition of one or more surgical instruments. As shown in FIG. 147, a laparoscopic surgical procedure is being performed wherein a plurality of trocar sleeves 6930 are inserted through a body wall 6931 to provide access to a body cavity 6932. A laparoscope 6933 is inserted through one of the trocar sleeves 6930 to provide illumination (light cable 6934 is shown leading toward a light source, not pictured) to the surgical site and to obtain an image thereof. A camera adapter 6935 is attached at the proximal end of laparoscope 6933 and image cable 6936 extends therefrom to a control box 6937 discussed in more detail below. Image cable inputs to image receiving port 416 on control box 6937.

Additional surgical instruments 6939, 6940 are inserted through additional trocar sleeves 6900 which extend through body wall 6931. In FIG. 147, instrument 6939 schematically illustrates an endoscopic stapling device, e.g., an Endo GIA® instrument manufactured by the assignee of this application, and instrument 6940 schematically illustrates a hand instrument, e.g., an Endo Grasp® device also manufactured by the present assignee. Additional and/or alternative instruments may also be utilized according to the present invention; the illustrated instruments are merely exemplary of surgical instruments which may be utilized according to the present invention.

Instruments 6939, 6940 include adapters 6941, 6942 associated with their respective handle portions. The adapters electronically communicate with conductive mechanisms (not pictured). These mechanisms, which include electrically conductive contact members electrically connected by wires, cables and the like, are associated with the distal elements of the respective instruments, e.g., the anvil 6943 and cartridge 6944 of the Endo GIA® instrument, the jaws 6945, 6946 of the Endo Grasp® device, and the like. The mechanisms are adapted to interrupt an electronic circuit when the distal elements are in a first position or condition and to complete the electronic circuit when the distal elements are in a second position or condition. A voltage source for the electronic circuit may be provided in the surgical instrument, e.g., in the form of a battery, or supplied from control box 6937 through cables 6947, 6948.

Control box 6937 includes a plurality of jacks 6949 which are adapted to receive cables 6947, 6948 and the like. Control box 6937 further includes an outgoing adapter 6950 which is adapted to cooperate with a cable 6951 for transmitting the laparoscopic image obtained by the laparoscope 6933 together with data concerning surgical instruments 6939, 6940 to video monitor 6952. Circuitry within control box 6937 is provided for converting the presence of an interrupted circuit, e.g., for the electronics within cable 6947 and the mechanism associated with the distal elements of instrument 6939, to an icon or symbol for display on video monitor 6952. Similarly, the circuitry within control box 6937 is adapted to provide a second icon or symbol to video monitor 6952 when a completed circuit exists for cable 6947 and the associated mechanism.

Illustrative icons/symbols 6953, 6954 are shown on video monitor 6952. Icon 6953 shows a surgical staple and could be used to communicate to the surgeon that the cartridge 6944 and anvil 6943 of instrument 6939 are properly positioned to form staples in tissue 6955. Icon 6953 could take another form when the cartridge 6944 and anvil 6943 are not properly positioned for forming staples, thereby interrupting the circuit. Icon 6954 shows a hand instrument with jaws spread apart, thereby communicating to the surgeon that the jaws 6945, 6946 of instrument 6940 are open. Icon 6954 could take another form when jaws 6945, 6946 are closed, thereby completing the circuit.

FIG. 148 illustrates a second layer of information overlaying a first layer of information. The second layer of information includes a symbolic representation of the knife overlapping the detected position of the knife in the DLU depicted in the first layer of information. Further examples are disclosed in U.S. Pat. No. 9,283,054, titled SURGICAL APPARATUS WITH INDICATOR, which issued on Mar. 15, 2016, which is herein incorporated by reference in its entirety.

Referring to FIG. 148, the second layer of information 6963 can overlay at least a portion of the first layer of information 6962 on the display 6960. Furthermore, the touch screen 6961 can allow a user to manipulate the second layer of information 6963 relative to the video feedback in the underlying first layer of information 6962 on the display 6960. For example, a user can operate the touch screen 6961 to select, manipulate, reformat, resize, and/or otherwise modify the information displayed in the second layer of information 6963. In certain aspects, the user can use the touch screen 6961 to manipulate the second layer of information 6963 relative to the surgical instrument 6964 depicted in the first layer of information 6962 on the display 6960. A user can select a menu, category and/or classification of the control panel 6967 thereof, for example, and the second layer of information 6963 and/or the control panel 6967 can be adjusted to reflect the user's selection. In various aspects, a user may select a category from the instrument feedback category 6969 that corresponds to a specific feature or features of the surgical instrument 6964 depicted in the first layer of information 6962. Feedback corresponding to the user-selected category can move, locate itself, and/or "snap" to a position on the display 6960 relative to the specific feature or features of the surgical instrument 6964. For example, the selected feedback can move to a position near and/or overlapping the specific feature or features of the surgical instrument 6964 depicted in the first layer of information 6962.

The instrument feedback menu 6969 can include a plurality of feedback categories, and can relate to the feedback data measured and/or detected by the surgical instrument 6964 during a surgical procedure. As described herein, the surgical instrument 6964 can detect and/or measure the position 6970 of a moveable jaw between an open orientation and a closed orientation, the thickness 6973 of clamped tissue, the clamping force 6976 on the clamped tissue, the articulation 6974 of the DLU 6965, and/or the position 6971, velocity 6972, and/or force 6975 of the firing element, for example. Furthermore, the feedback controller in signal communication with the surgical instrument 6964 can provide the sensed feedback to the display 6960, which can display the feedback in the second layer of information 6963. As described herein, the selection, placement, and/or form of the feedback data displayed in the second layer of information 6963 can be modified based on the user's input to the touch screen 6961, for example.

When the knife of the DLU 6965 is blocked from view by the end effector jaws 6966 and/or tissue T, for example, the operator can track and/or approximate the position of the knife in the DLU 6964 based on the changing value of the feedback data and/or the shifting position of the feedback data relative to the DLU 6965 depicted in the underlying first layer of information 6962.

In various aspects, the display menu 6977 of the control panel 6967 can relate to a plurality of categories, such as unit systems 6978 and/or data modes 6979, for example. In certain aspects, a user can select the unit systems category 6978 to switch between unit systems, such as between metric and U.S. customary units, for example. Additionally, a user can select the data mode category 6979 to switch between types of numerical representations of the feedback data and/or types of graphical representations of the feedback data, for example. The numerical representations of the feedback data can be displayed as numerical values and/or percentages, for example. Furthermore, the graphical representations of the feedback data can be displayed as a function of time and/or distance, for example. As described herein, a user can select the instrument controller menu 6980 from the control panel 6967 to input directives for the surgical instrument 6964, which can be implemented via the instrument controller and/or the microcontroller, for example. A user can minimize or collapse the control panel 6967 by selecting the minimize/maximize icon 6968, and can maximize or un-collapse the control panel 6967 by re-selecting the minimize/maximize icon 6968.

FIG. 149 depicts a perspective view of a surgeon using a surgical instrument that includes a handle assembly housing and a wireless circuit board during a surgical procedure, with the surgeon wearing a set of safety glasses. The wireless circuit board transmits a signal to a set of safety glasses worn by a surgeon using the surgical instrument during a procedure. The signal is received by a wireless port on the safety glasses. One or more lighting devices on a front lens of the safety glasses change color, fade, or glow in response to the received signal to indicate information to the surgeon about the status of the surgical instrument. The lighting devices are disposable on peripheral edges of the front lens to not distract the direct line of vision of the surgeon. Further examples are disclosed in U.S. Pat. No. 9,011,427, titled SURGICAL INSTRUMENT WITH SAFETY GLASSES, which issued on Apr. 21, 2015, which is herein incorporated by reference in its entirety.

FIG. 149 shows a version of safety glasses 6991 that may be worn by a surgeon 6992 during a surgical procedure while using a medical device. In use, a wireless communications board housed in a surgical instrument 6993 may communicate with a wireless port 6994 on safety glasses 6991. Exemplary surgical instrument 6993 is a battery-operated device, though instrument 6993 could be powered by a cable or otherwise. Instrument 6993 includes an end effector. Particularly, wireless communications board 6995 transmits one or more wireless signals indicated by arrows (B, C) to wireless port 6994 of safety glasses 6991. Safety glasses 6991 receive the signal, analyze the received signal, and display indicated status information received by the signal on lenses 6996 to a user, such as surgeon 6992, wearing safety glasses 6991. Additionally or alternatively, wireless communications board 6995 transmits a wireless signal to surgical monitor 6997 such that surgical monitor 6997 may display received indicated status information to surgeon 6992, as described above.

A version of the safety glasses 6991 may include lighting device on peripheral edges of the safety glasses 6991. A lighting device provides peripheral-vision sensory feedback of instrument 6993, with which the safety glasses 6991 communicate to a user wearing the safety glasses 6991. The lighting device may be, for example, a light-emitted diode ("LED"), a series of LEDs. or any other suitable lighting device known to those of ordinary skill in the art and apparent in view of the teachings herein.

LEDs may be located at edges or sides of a front lens of the safety glasses 6991 so not to distract from a user's center of vision while still being positioned within the user's field of view such that the user does not need to look away from the surgical site to see the lighting device. Displayed lights may pulse and/or change color to communicate to the wearer of the safety glasses 6991 various aspects of information retrieved from instrument 6993, such as system status information or tissue sensing information (i.e., whether the end effector has sufficiently severed and sealed tissue). Feedback from housed wireless communications board 6995 may cause a lighting device to activate, blink, or change color to indicate information about the use of instrument 6993 to a user. For example, a device may incorporate a feedback mechanism based on one or more sensed tissue parameters. In this case, a change in the device output(s) based on this feedback in synch with a tone change may submit a signal through wireless communications board 6995 to the safety glasses 6991 to trigger activation of the lighting device. Such described means of activation of the lighting device should not be considered limiting as other means of indicating status information of instrument 6993 to the user via the safety glasses 6991 are contemplated. Further, the safety glasses 6991 may be single-use or reusable eyewear. Button-cell power supplies such as button-cell batteries may be used to power wireless receivers and LEDs of versions of safety glasses 6991, which may also include a housed wireless board and tri-color LEDs. Such button-cell power supplies may provide a low-cost means of providing sensory feedback of information about instrument 6993 when in use to surgeon 6992 wearing safety glasses 6991.

FIG. 150 is a schematic diagram of a feedback control system for controlling a surgical instrument. The surgical instrument includes a housing and an elongated shaft that extends distally from the housing and defines a first longitudinal axis. The surgical instrument also includes a firing rod disposed in the elongated shaft and a drive mechanism disposed at least partially within the housing. The drive mechanism mechanically cooperates with the firing rod to move the firing rod. A motion sensor senses a change in the electric field (e.g., capacitance, impedance, or admittance) between the firing rod and the elongated shaft. The measurement unit determines a parameter of the motion of the firing rod, such as the position, speed, and direction of the firing rod, based on the sensed change in the electric field. A controller uses the measured parameter of the motion of the firing rod to control the drive mechanism. Further examples are disclosed in U.S. Pat. No. 8,960,520, titled METHOD AND APPARATUS FOR DETERMINING PARAMETERS OF LINEAR MOTION IN A SURGICAL INSTRUMENT, which issued on Feb. 24, 2015, which is herein incorporated by reference in its entirety.

With reference to FIG. 150, aspects of the present disclosure may include a feedback control system 6150. The system 6150 includes a feedback controller 6152. The surgical instrument 6154 is connected to the feedback controller 6152 via a data port, which may be either wired (e.g., FireWire®, USB, Serial RS232, Serial RS485, USART, Ethernet, etc.) or wireless (e.g., Bluetooth®, ANT3®, KNX®, Z-Wave X10®, Wireless USB®, Wi-Fi®, IrDAR, nano NET®, TinyOS®, ZigBee®, 802.11 IEEE, and other radio, infrared, UHF, VHF communications and the like). The feedback controller 6152 is configured to store the data transmitted to it by the surgical instrument 6154 as well as process and analyze the data. The feedback controller 6152 is also connected to other devices, such as a video display 6154, a video processor 6156 and a computing device 6158 (e.g., a personal computer, a PDA, a smartphone, a storage device, etc.). The video processor 6156 is used for processing output data generated by the feedback controller 6152 for output on the video display 6154. The computing device 6158 is used for additional processing of the feedback data. In one aspect, the results of the sensor feedback analysis performed by a microcontroller may be stored internally for later retrieval by the computing device 6158.

FIG. 151 illustrates a feedback controller 6152 including an on-screen display (OSD) module and a heads-up-display (HUD) module. The modules process the output of a microcontroller for display on various displays. More specifically, the OSD module overlays text and/or graphical information from the feedback controller 6152 over other video images received from the surgical site via cameras disposed therein. The modified video signal having overlaid text is transmitted to the video display allowing the user to visualize useful feedback information from the surgical instrument 6154 and/or feedback controller 6152 while still observing the surgical site. The feedback controller 6152 includes a data port 6160 coupled to a microcontroller which allows the feedback controller 6152 to be connected to the computing device 6158 (FIG. 150). The data port 6160 may provide for wired and/or wireless communication with the computing device 6158 providing for an interface between the computing device 6158 and the feedback controller 6152 for retrieval of stored feedback data, configuration of operating parameters of the feedback controller 6152 and upgrade of firmware and/or other software of the feedback controller 6152.

The feedback controller 6152 includes a housing 6162 and a plurality of input and output ports, such as a video input 6164, a video output 6166, and a HUD display output 6168. The feedback controller 6152 also includes a screen for displaying status information concerning the feedback controller 6152. Further examples are disclosed in U.S. Pat. No. 8,960,520, titled METHOD AND APPARATUS FOR DETERMINING PARAMETERS OF LINEAR MOTION IN A SURGICAL INSTRUMENT, which issued on Feb. 24, 2015, which is herein incorporated by reference in its entirety.

EXAMPLES

Various aspects of the subject matter described herein are set out in the following numbered examples:

Example 1: A method, comprising detecting a modular surgical device within bounds of a surgical operating room, connecting the modular surgical device to a surgical hub, connecting the surgical hub to a cloud-based system, transmitting surgical data associated with a surgical procedure being performed in the surgical operating room from the modular surgical device to the surgical hub, and transmitting the surgical data from the surgical hub to the cloud-based system.

Example 2: The method of Example 1, wherein the modular surgical device is a first modular surgical device, and wherein the method further comprises detecting a second modular surgical device within the bounds of the surgical operating room.

Example 3: The method of Example 2, further comprising connecting the second modular surgical device to the surgical hub.

Example 4: The method of Example 3, further comprising controlling the first modular surgical device with the second modular surgical device.

Example 5: The method of any one of Examples 1-4, further comprising inferring progression of the surgical procedure from the surgical data.

Example 6: A method, comprising detecting a medical imaging device within bounds of a surgical operating room, connecting the medical imaging device to a surgical hub including an imaging module, transmitting a livestream of a surgical site in the surgical operating room from the medical imaging device to the imaging module, capturing, by the imaging module, at least one image frame from the livestream, deriving information relevant to the surgical site from data extracted from the at least one image frame, transmitting the information from the surgical hub to the medical imaging device, and overlaying the information onto the livestream.

Example 7: The method of Example 6, further comprising detecting a modular surgical device within the bounds of the surgical operating room.

Example 8: The method of Example 7, further comprising connecting the modular surgical device to the surgical hub.

Example 9: The method of Example 8, further comprising assessing a surgical activity performed by an end effector of the modular surgical device at the surgical site from the data extracted from the at least one image frame.

Example 10: The method of any one of Examples 6-9, further comprising connecting the surgical hub to a cloud-based control system.

Example 11: The method of Example 10, further comprising transmitting the information from the surgical hub to the cloud-based control system.

Example 12: A method, comprising detecting a modular surgical device within bounds of a surgical operating room, connecting the modular surgical device to a surgical hub, transmitting a livestream of a surgical site in the surgical operating room to an imaging module of the surgical hub, capturing, by the imaging module, at least one image frame from the livestream, and assessing a surgical activity performed by an end effector of the modular surgical device at the surgical site from data extracted from the at least one image frame.

Example 13: The method of Example 12, further comprising inferring progression of the surgical activity from the data.

Example 14: The method of Example 13, further comprising connecting the surgical hub to a cloud-based control system.

Example 15: The method of Example 14, further comprising transmitting the data from the surgical hub to the cloud-based control system.

Various additional aspects of the subject matter described herein are set out in the following numbered examples:

Example 1: A surgical hub configured to transmit generator data associated with a surgical procedure from a generator of the surgical hub to a cloud-based system communicatively coupled to a plurality of surgical hubs, the surgical hub, comprising: a processor; and a memory coupled to the processor, the memory storing instructions executable by the processor to: receive generator data from the generator, wherein the generator data is structured into a data packet comprising at least two of the following fields: a field that indicates a source of the data; a unique time stamp; a field indicating an energy mode of the generator; a field indicating a power output of the generator; and a field indicating a duration of the power output of the generator; encrypt the generator data; generate a message authentication code based on the generator data; generate a datagram comprising the encrypted generator data, the generated message authentication code, a source identifier and a destination identifier; and transmit the datagram to a cloud-based system, wherein the datagram allows for the cloud-based system to: decrypt the encrypted generator data of the transmitted datagram; verify the integrity of the generator data based on the message authentication code; authenticate the surgical hub as the source of the datagram; and validate a transmission path followed by the datagram between the surgical hub and the cloud-based system.

Example 2: The surgical hub of Example 1, wherein generating the datagram comprises: generating a datagram header, wherein the datagram header is structured to comprise: a field indicating an IP address associated with the surgical hub; and a field indicating an IP address associated with the cloud-based system; and generating a datagram payload, wherein the datagram payload is structured to comprise the encrypted generator data and the generated message authentication code.

Example 3: The surgical hub of Examples 2, wherein the datagram header is further structured to comprise: a field indicating a transmission path designating at least one IP address associated with at least one intermediate network component through which the datagram is to pass as the datagram is transmitted from the IP address associated with the surgical hub to the IP address associated with the cloud-based system.

Example 4: The surgical hub of any one of Examples 1-3, wherein the instructions are further executable by the processor to: receive a receipt message from the cloud-based system in response to the transmitted datagram, wherein the receipt message indicates at least one of: the integrity of the generator data, decrypted from the transmitted datagram, has been verified by the cloud-based system; the surgical hub has been authenticated as the source of the datagram by the cloud-based system; or the transmission path followed by the transmitted datagram between the surgical hub and the cloud-based system has been validated by the cloud-based system.

Example 5: The surgical hub of any one of Examples 1-4, wherein the instructions are further executable by the processor to: send a message to the cloud-based system, wherein the message requests recommendation generator data associated with a particular surgical procedure; receive a response datagram from the cloud-based system, wherein the response datagram comprises encrypted recommendation generator data and a response message authentication code; decrypt the encrypted recommendation generator data of the response datagram, wherein the recommendation generator data is structured into a response data packet comprising at least one of the following fields: a field indicating an energy mode of the generator for the particular surgical procedure; a field indicating a power output of the generator for the particular surgical procedure; or a field indicating a duration of the power output of the generator for the particular surgical procedure; verify the integrity of the recommendation generator data based on the response message authentication code; and send the recommendation generator data to the generator for implementation, via a generator module, during the particular surgical procedure.

Example 6: The surgical hub of Example 5, wherein the recommendation generator data is based on generator data associated with the particular surgical procedure as securely transmitted by the plurality of surgical hubs to the cloud-based system over time.

Example 7: The surgical hub of Example 1, wherein generating the message authentication code comprises: calculating the message authentication code based on a key, a hash function and one of the received generator data or the encrypted generator data.

Example 8: The surgical hub of Example 7, wherein the key is a secret key and the hash algorithm is a message authentication code algorithm, and wherein calculating the message authentication code comprises processing the encrypted generator data through the message authentication code algorithm using the secret key.

Example 9: The surgical hub of any one of Examples 7-8, wherein the key is a secret key and the hash algorithm is a message authentication code algorithm, and wherein calculating the message authentication code comprises processing the received generator data through the message authentication code algorithm using the secret key.

Example 10: The surgical hub of Example 1, wherein encrypting the generator data comprises encrypting the received generator data using a shared secret or a public key associated with the cloud-based system.

Example 11: A surgical hub configured to transmit generator data associated with a surgical procedure from a generator of the surgical hub to a cloud-based system communicatively coupled to a plurality of surgical hubs, the surgical hub, comprising: a control circuit configured to: receive generator data from the generator, wherein the generator data is structured into a data packet comprising at least two of the following fields: a field that indicates a source of the data; a unique time stamp; a field indicating an energy mode of the generator; a field indicating a power output of the generator; and a field indicating a duration of the power output of the generator; encrypt the generator data; generate a message authentication code based on the generator data; generate a datagram comprising the encrypted generator data, the generated message authentication code, a source identifier and a destination identifier; and transmit the datagram to a cloud-based system, wherein the datagram allows for the cloud-based system to: decrypt the encrypted generator data of the transmitted datagram; verify the integrity of the generator data based on the message authentication code; authenticate the surgical hub as the source of the datagram; and validate a transmission path followed by the datagram between the surgical hub and the cloud-based system.

Example 12: The surgical hub of Example 11, wherein the control circuit is further configured to: send a message to the cloud-based system, wherein the message requests recommendation generator data associated with a particular surgical procedure; receive a response datagram from the cloud-based system, wherein the response datagram comprises encrypted recommendation generator data and a response message authentication code; decrypt the encrypted recommendation generator data of the response datagram, wherein the recommendation generator data is structured into a response data packet comprising at least one of the following fields: a field indicating an energy mode of the generator for the particular surgical procedure; a field indicating a power output of the generator for the particular surgical procedure; or a field indicating a duration of the power output of the generator for the particular surgical procedure; verify the integrity of the recommendation generator data based on the response message authentication code; and send the recommendation generator data to the generator for implementation, via a generator module, during the particular surgical procedure.

Example 13: The surgical hub of any one of Examples 11-12, wherein the recommendation generator data is based on generator data associated with the particular surgical procedure as securely transmitted by the plurality of surgical hubs to the cloud-based system over time.

Example 14: A surgical hub configured to prioritize surgical data associated with a surgical procedure from a surgical device of the surgical hub to a cloud-based system communicatively coupled to a plurality of surgical hubs, the surgical hub comprising: a processor; and a memory coupled to the processor, the memory storing instructions executable by the processor to: capture surgical data, wherein the surgical data comprises data associated with the surgical device; time-stamp the captured surgical data; identify a failure event; identify a time period associated with the failure event; isolate failure event surgical data from surgical data not associated with the failure event based on the identified time period; chronologize the failure event surgical data by time-stamp; encrypt the chronologized failure event surgical data; generate a datagram comprising the encrypted failure event surgical data, wherein the datagram is structured to include a field which includes a flag that prioritizes the encrypted failure event surgical data over other encrypted data of the datagram; transmit the datagram to the cloud-based system, wherein the datagram allows for the cloud-based system to: decrypt the encrypted failure event surgical data; focus analysis on the failure event surgical data rather than surgical data not associated with the failure event; and flag the surgical device associated with the failure event for at least one of: removal from an operating room; return to a manufacturer; future inoperability in the cloud-based system; or a download update to prevent failure events.

Example 15: The surgical hub of Example 14, wherein the surgical device comprises an end effector including a staple cartridge, wherein the captured surgical data comprises snapshots taken via an endoscope of the surgical hub during a stapling portion of a surgical procedure, and wherein identifying the failure event comprises comparing, via an imaging module of the surgical hub, the snapshots to images conveying correctly fired staples to detect at least one of a misfired staple or evidence of a misfired staple.

Example 16: The surgical hub of any one of Examples 14-15, wherein the instructions are further executable by the processor to: download a program from the cloud-based system for execution by the surgical device, wherein execution of the program modifies the surgical device to prevent misfired staples.

Example 17: The surgical hub of any one of Examples 14-16, wherein the surgical device comprises an end effector including a temperature sensor, wherein the captured surgical data comprises at least one temperature detected by the temperature sensor during a tissue sealing portion of a surgical procedure, and wherein identifying the failure event comprises comparing the at least one detected temperature to a temperature or a range of temperatures associated with that surgical procedure to detect an inadequate sealing temperature.

Example 18: The surgical hub of Example 17, wherein the instructions are further executable by the processor to: download a program from the cloud-based system for execution by the surgical device, wherein execution of the program modifies the surgical device to prevent inadequate sealing temperatures.

Example 19: The surgical hub of Example 14, wherein the identified time period includes a period of time prior to the failure event being identified.

Example 20: The surgical hub of any one of Examples 14-18, wherein the instructions are further executable by the processor to: receive an action message from the cloud-based system, wherein the action message indicates the surgical device as flagged for at least one of: removal from the operating room; return to the manufacturer; future inoperability in the cloud-based system; or the download update to prevent failure events; and provide a notification, via at least one of a user interface of the surgical hub or a user interface of the surgical device, to perform an action associated with the action message.

Various additional aspects of the subject matter described herein are set out in the following numbered examples:

Example 1: A surgical hub configured to authenticate data communications with surgical devices, the surgical hub comprising: a processor; and a memory coupled to the processor, the memory storing instructions executable by the processor to: detect that a surgical device is communicatively coupled to the surgical hub; transmit a public key associated with the surgical hub to the surgical device; receive a message from the surgical device, wherein the message is encrypted using the public key associated with the surgical hub, wherein the encrypted message comprises a shared secret associated with the surgical device and a checksum function associated with the shared secret, and wherein the shared secret comprises an identifier assigned to the surgical device; decrypt the encrypted message, using a private key associated with the transmitted public key, to reveal the shared secret and the checksum function; receive data communications from the surgical device, wherein each data communication is encrypted using the shared secret received from the surgical device, and wherein each data communication comprises a checksum value, derived via the checksum function, based on the data of each received communication; and decrypt each data communication using the shared secret until the surgical device is decoupled from the surgical hub, wherein the integrity of each data communication is verifiable based on its associated checksum value.

Example 2: The surgical hub of Example 1, wherein the identifier assigned to the surgical device comprises a unique serial number of the surgical device.

Example 3: The surgical hub of any one of Examples 1-2, wherein the instructions are further executable by the processor to: transmit a message to a cloud-based system communicatively coupled to a plurality of surgical hubs, wherein the message is encrypted using the public key associated with the cloud-based system, wherein the encrypted message comprises the shared secret associated with the surgical device, and wherein the shared secret comprises the identifier assigned to the surgical device; and transmit each data communication received from the surgical device to the cloud-based system, wherein each data communication is encrypted using the shared secret received from the surgical device to allow the cloud-based system to decrypt each data communication using the shared secret until the surgical device is decoupled from the surgical hub.

Example 4: The surgical hub of any one of Examples 1-3, wherein the instructions are further executable by the processor to: detect that a multi-component surgical device comprising a plurality of sub-components is communicatively coupled to the surgical hub, wherein each sub-component is associated with an identifier; transmit a public key associated with the surgical hub to the multi-component surgical device; receive a message from the multi-component surgical device, wherein the message is encrypted using the public key associated with the surgical hub, wherein the encrypted message comprises a shared secret associated with the multi-component surgical device and a checksum function associated with the shared secret, and wherein the shared secret comprises a unique string of the identifiers associated with the plurality of sub-components that combine to form the multi-component surgical device; decrypt the encrypted message, using a private key associated with the transmitted public key, to reveal the shared secret and the checksum function; receive data communications from the multi-component surgical device, wherein each data communication is encrypted using the shared secret received from the multi-component surgical device, and wherein each data communication comprises a checksum value, derived via the checksum function, based on the data of each received communication; and decrypt each data communication using the shared secret until the multi-component surgical device is decoupled from the surgical hub, wherein the integrity of each data communication is verifiable based on its associated checksum value.

Example 5: The surgical hub of Example 4, wherein the unique string of the identifiers associated with the plurality of sub-components that combine to form the multi-component surgical device comprises a random ordering of the identifiers associated with the plurality of sub-components.

Example 6: The surgical hub of Example 5, wherein each identifier of the unique string of identifiers comprises a unique serial number associated with each respective sub-component of the multi-component surgical device.

Example 7: A surgical hub configured to authenticate data communications with surgical devices, the surgical hub comprising a control circuit configured to: detect that a surgical device is communicatively coupled to the surgical hub; transmit a public key associated with the surgical hub to the surgical device; receive a message from the surgical device, wherein the message is encrypted using the public key associated with the surgical hub, wherein the encrypted message comprises a shared secret associated with the surgical device and a checksum function associated with the shared secret, and wherein the shared secret comprises an identifier assigned to the surgical device; decrypt the encrypted message, using a private key associated with the transmitted public key, to reveal the shared secret and the checksum function; receive data communications from the surgical device, wherein each data communication is encrypted using the shared secret received from the surgical device, and wherein each data communication comprises a checksum value, derived via the checksum function, based on the data of each received communication; and decrypt each data communication using the shared secret until the surgical device is decoupled from the surgical hub, wherein the integrity of each data communication is verifiable based on its associated checksum value.

Example 8: A surgical hub configured to authenticate surgical devices coupled to the surgical hub, the surgical hub comprising: a processor; and a memory coupled to the processor, the memory storing instructions executable by the processor to: detect that a surgical device is communicatively coupled to the surgical hub; receive an encrypted identifier and a source ID from the surgical device; transmit a first message from the surgical hub to a server of a surgical device manufacturer associated with the source ID, wherein the first message comprises the encrypted identifier, and wherein the first message is encrypted using a public key associated with the surgical device manufacturer; receive a second message from the server of the surgical device manufacturer, wherein the second message is encrypted using a public key associated with the surgical hub, and wherein the encrypted second message comprises a shared secret associated with the encrypted identifier of the surgical device; decrypt the encrypted second message using a private key associated with the public key used to encrypt the second message to reveal the shared secret associated with the encrypted identifier of the surgical device; and decrypt the encrypted identifier of the surgical device using the shared secret to reveal the identifier to authenticate the surgical device and its manufacturer.

Example 9: The surgical hub of any one of Example 8, wherein the identifier comprises a unique serial number of the surgical device.

Example 10: The surgical hub of any one of Examples 8-9, wherein the instructions are further executable by the processor to: compare the decrypted identifier to a list of authorized identifiers; and permit use of the surgical device based on a match of the decrypted identifier to an authorized identifier in the list.

Example 11: The surgical hub of Example 10, wherein the instructions are further executable by the processor to: download the list of authorized identifiers from a cloud-based system communicatively coupled to a plurality of surgical hubs.

Example 12: The surgical hub of any one of Examples 8-11, wherein receiving the encrypted identifier and the source ID from the surgical device comprises: reading the encrypted identifier and the source ID from a memory device of the surgical device.

Example 13: The surgical hub of any one of Examples 8-12, wherein the instructions are further executable by the processor to: read usage data from a memory device of the coupled surgical device; store at least a portion of the read usage data each time the surgical device is coupled to the surgical hub; compare the read usage data to previously stored usage data to identify a discrepancy in the usage data; and prevent usage of the surgical device with the surgical hub based on an identified discrepancy.

Example 14: The surgical hub of any one of Examples 8-13, wherein the instructions are further executable by the processor to: transmit a record of the coupling of the surgical device and the surgical hub to at least one of a cloud-based system or a plurality of other surgical hubs communicatively coupled to the cloud-based system in a surgical system, wherein the record links the unique identifier assigned to the surgical device to a unique identifier assigned to the surgical hub.

Example 15: The surgical hub of any one of Examples 8-14, wherein the unique identifier assigned to the surgical device comprises a serial number.

Example 16: The surgical hub of any one of Examples 8-15, wherein the instructions are further executable by the processor to: store the record of the coupling of the surgical device and the surgical hub as a genesis record, wherein the genesis record comprises a timestamp.

Example 17: The surgical hub of any one of Examples 8-16, wherein the instructions are further executable by the processor to: store a new record for each subsequent coupling of the surgical device to the surgical hub, wherein each new record in a chain of records associated with the surgical device comprises a cryptographic hash of the most recent record, the linkage of the unique identifier assigned to the surgical device to the unique identifier assigned to the surgical hub, and a timestamp.

Example 18: The surgical hub of any one of Examples 8-17, wherein the instructions are further executable by the processor to: receive a record of a coupling of the surgical device to one of the plurality of other surgical hubs communicatively coupled to the cloud-based system; and store a new record for the coupling of the surgical device to the one of the plurality of other surgical hubs, wherein the new record in a chain of records associated with the surgical device comprises a cryptographic hash of the most recent record, a linkage of the unique identifier assigned to the surgical device to a unique identifier assigned to the one of the plurality of other surgical hubs, and a timestamp.

Example 19: The surgical hub of Example 18, wherein the instructions are further executable by the processor to: trace couplings of the surgical device to the surgical hub and the plurality of other surgical hubs in the surgical system back to the genesis record.

Example 20: The surgical hub of Example 19, wherein the instructions are further executable by the processor to: analyze the traced couplings to determine whether past usage of the surgical device contributed to or caused a failure event.

Various additional aspects of the subject matter described herein are set out in the following numbered examples:

Example 1: A surgical hub for use with a surgical system in a surgical procedure performed in an operating room, wherein the surgical hub comprises a control circuit configured to: pair the surgical hub with a first device of the surgical system; assign a first identifier to the first device; pair the surgical hub with a second device of the surgical system; assign a second identifier to the second device; and selectively pair the first device with the second device based on perioperative data.

Example 2: The surgical hub of Example 1, further comprising a storage medium, wherein the control circuit is further configured to store a record indicative of the pairing between the first device and the second device in the storage medium.

Example 3: The surgical hub of any one of Examples 1-2, wherein the pairing between the first device and the second device defines a communication pathway therebetween.

Example 4: The surgical hub of any one of Examples 1-3, wherein the pairing between the first device and the second device defines a control pathway for transmitting control actions from the second device to the first device.

Example 5: The surgical hub of any one of Examples 1-4, wherein the control circuit is further configured to: pair the surgical hub with a third device of the surgical system; assign a third identifier to the third device; sever the pairing between the first device and the second device; and selectively pair the first device with the third device.

Example 6: The surgical hub of any one of Examples 1-5, wherein the control circuit is further configured to store a record indicative of the pairing between the first device and the third device in the storage medium.

Example 7: The surgical hub of any one of Examples 1-6, wherein the pairing between the first device and the third device defines a communication pathway therebetween.

Example 8: The surgical hub of any one of Examples 1-7, wherein the pairing between the first device and the third device defines a control pathway for transmitting control actions from the third device to the first device.

Example 9: A surgical hub for use with a surgical system in a surgical procedure performed in an operating room, wherein the surgical hub comprises: a processor; and a memory coupled to the processor, the memory storing instructions executable by the processor to: pair the surgical hub with a first device of the surgical system; assign a first identifier to the first device; pair the surgical hub with a second device of the surgical system; assign a second identifier to the second device; and selectively pair the first device with the second device based on perioperative data.

Example 10: The surgical hub of Example 9, a record indicative of the pairing between the first device and the second device is stored in the memory.

Example 11: The surgical hub of any one of Examples 9-10, wherein the pairing between the first device and the second device defines a communication pathway therebetween.

Example 12: The surgical hub of any one of Examples 9-11, wherein the pairing between the first device and the second device defines a control pathway for transmitting control actions from the second device to the first device.

Example 13: The surgical hub of any one of Examples 9-12, wherein the control circuit is further configured to: pair the surgical hub with a third device of the surgical system; assign a third identifier to the third device; sever the pairing between the first device and the second device; and selectively pair the first device with the third device.

Example 14: The surgical hub of any one of Examples 9-13, wherein a record indicative of the pairing between the first device and the third device is stored in the memory.

Example 15: The surgical hub of any one of Examples 9-14, wherein the pairing between the first device and the third device defines a communication pathway therebetween.

Example 16: The surgical hub of any one of Examples 9-15, wherein the pairing between the first device and the third device defines a control pathway for transmitting control actions from the third device to the first device.

Example 17: A non-transitory computer readable medium storing computer readable instructions which, when executed, causes a machine to: pair a surgical hub with a first device of a surgical system; assign a first identifier to the first device; pair the surgical hub with a second device of the surgical system; assign a second identifier to the second device; and selectively pair the first device with the second device based on perioperative data.

Example 18: The non-transitory computer readable medium of Example 17, wherein the pairing between the first device and the second device defines a control pathway for transmitting control actions from the second device to the first device.

Example 19: The non-transitory computer readable medium of any one of Examples 17-18, wherein the computer readable instructions, when executed, further cause a machine to: pair the surgical hub with a third device of the surgical system; assign a third identifier to the third device;

sever the pairing between the first device and the second device; and selectively pair the first device with the third device.

Example 20: The non-transitory computer readable medium of any one of Examples 17-19, wherein the pairing between the first device and the third device defines a control pathway for transmitting control actions from the third device to the first device.

Various additional aspects of the subject matter described herein are set out in the following numbered examples:

Example 1: A surgical hub for use with a surgical system in a surgical procedure performed in an operating room, wherein the surgical hub comprises a control circuit configured to: determine bounds of the operating room; determine devices of the surgical system located within the bounds of the operating room; and pair the surgical hub with the devices of the surgical system located within the bounds of the operating room.

Example 2: The surgical hub of any one of Example 1, wherein the step of determining devices of the surgical system comprises: detecting a potential device of the surgical system; and assessing whether the potential device of the surgical system is within the bounds of the operating room or outside the bounds of the operating room.

Example 3: The surgical hub of any one of Examples 1-2, wherein the control circuit is configured to determine the bounds of the operating room after activation of the surgical hub.

Example 4: The surgical hub of any one of Examples 1-3, wherein the control circuit is configured to redetermine the bounds of the operating room after determining that the surgical hub has been moved.

Example 5: The surgical hub of any one of Examples 1-4, wherein the control circuit is configured to redetermine the bounds of the operating room after a potential device of the surgical system is detected.

Example 6: The surgical hub of any one of Examples 1-5, wherein the control circuit is configured to periodically determine the bounds of the operating room.

Example 7: The surgical hub of any one of Examples 1-6, comprising non-contact sensors configured to measure the bounds of the operating room.

Example 8: A surgical hub for use with a surgical system in a surgical procedure performed in an operating room, wherein the surgical hub comprises: a processor; and a memory coupled to the processor, the memory storing instructions executable by the processor to: determine bounds of the operating room; determine devices of the surgical system located within the bounds of the operating room; and pair the surgical hub with the devices of the surgical system located within the bounds of the operating room.

Example 9: The surgical hub of Example 8, wherein the step of determining devices of the surgical system comprises: detecting a potential device of the surgical system; and assessing whether the potential device of the surgical system is within the bounds of the operating room or outside the bounds of the operating room.

Example 10: The surgical hub of any one of Examples 8-9, wherein the memory further stores instructions executable by the processor to determine the bounds of the operating room after activation of the surgical hub.

Example 11: The surgical hub of any one of Examples 8-10, wherein the memory further stores instructions executable by the processor to redetermine the bounds of the operating room after determining that the surgical hub has been moved.

Example 12: The surgical hub of any one of Examples 8-11, wherein the memory further stores instructions executable by the processor to redetermine the bounds of the operating room after a potential device of the surgical system is detected.

Example 13: The surgical hub of any one of Examples 8-12, wherein the memory further stores instructions executable by the processor to periodically determine the bounds of the operating room.

Example 14: The surgical hub of any one of Examples 8-13, comprising non-contact sensors configured to measure the bounds of the operating room.

Example 15: A non-transitory computer readable medium storing computer readable instructions which, when executed, cause a machine to: determine bounds of an operating room; determine devices of a surgical system located within the bounds of the operating room; and pair a surgical hub with the devices of the surgical system located within the bounds of the operating room.

Example 16: The non-transitory computer readable medium of Example 15, wherein the step of determining devices of the surgical system comprises: detecting a potential device of the surgical system; and assessing whether the potential device of the surgical system is within the bounds of the operating room or outside the bounds of the operating room.

Example 17: The non-transitory computer readable medium of any one of Examples 15-16, wherein the computer readable instructions, when executed, further cause a machine to determine the bounds of the operating room after activation of the surgical hub.

Example 18: The non-transitory computer readable medium of any one of Examples 15-17, wherein the computer readable instructions, when executed, further cause a machine to redetermine the bounds of the operating room after determining that the surgical hub has been moved.

Example 19: The non-transitory computer readable medium of any one of Examples 15-18, wherein the computer readable instructions, when executed, further cause a machine to redetermine the bounds of the operating room after a potential device of the surgical system is detected.

Example 20: The non-transitory computer readable medium of any one of Examples 15-19, wherein the computer readable instructions, when executed, further cause a machine to periodically determine the bounds of the operating room.

Various additional aspects of the subject matter described herein are set out in the following numbered examples:

Example 1: A surgical hub for use with a medical imaging device at a remote surgical site in a surgical procedure, wherein the surgical hub comprises a circuit configured to: receive a livestream of the surgical site from the medical imaging device; capture an image frame of a surgical step of the surgical procedure from the livestream; derive information relevant to the surgical step from data extracted from the image frame; and overlay the information onto the livestream.

Example 2: The surgical hub of Example 1, wherein the information is regarding completion of the surgical step.

Example 3: The surgical hub of any one of Examples 1-2, wherein the surgical step comprises deploying staples from a staple cartridge into tissue at the surgical site.

Example 4: The surgical hub of any one of Examples 1-3, wherein the information identifies the staple cartridge.

Example 5: The surgical hub of any one of Examples 1-4, wherein the information comprises a serial number of the staple cartridge.

Example 6: The surgical hub of any one of Examples 1-5, wherein the information identifies a leak at the surgical site.

Example 7: The surgical hub of any one of Examples 1-7, wherein the information identifies the surgical step.

Example 8: A surgical hub for use with a medical imaging device at a remote surgical site in a surgical procedure including surgical steps, wherein the surgical hub comprises a circuit configured to: receive a livestream of the surgical site from the medical imaging device; capture image frames of the surgical steps of the surgical procedure from the livestream; and differentiate among the surgical steps based on data extracted from the image frames.

Example 9: The surgical hub of Example 8, derive information regarding completion of the surgical steps from the data extracted from the image frames.

Example 10: The surgical hub of any one of Examples 8-9, wherein one of the surgical steps comprises deploying staples from a staple cartridge into tissue at the surgical site.

Example 11: The surgical hub of any one of Examples 8-10, wherein the information identifies the staple cartridge.

Example 12: The surgical hub of any one of Examples 8-11, wherein the information comprises a serial number of the staple cartridge.

Example 13: The surgical hub of any one of Examples 8-12, wherein the information identifies a leak at the surgical site.

Example 14: The surgical hub of any one of Examples 8-10, wherein another one of the surgical steps comprises applying energy to tissue at the surgical site.

Example 15: A surgical hub for use with a medical imaging device at a remote surgical site in a surgical procedure, wherein the surgical hub comprises a circuit configured to: receive a livestream of the surgical site from the medical imaging device; capture an image frame from the livestream; detect a staple pattern in the image frame, wherein the staple pattern is defined by staples deployed from a staple cartridge into tissue at the surgical site; and identify the staple cartridge based on the staple pattern.

Example 16: The surgical hub of Example 15, wherein the staple pattern corresponds to a serial number of the staple cartridge.

Example 17: The surgical hub of any one of Examples 15-16, wherein the staples comprise a first staple and a second staple different than the first staple.

Example 18: The surgical hub of any one of Examples 15-17, wherein the first staple is comprised of a non-ionized material.

Example 19: The surgical hub of any one of Examples 15-18, wherein the second staple is comprised of an ionized material.

Example 20: The surgical hub of any one of Examples 15-19, wherein the staple pattern is defined in a plurality of rows of staples.

Various additional aspects of the subject matter described herein are set out in the following numbered examples:

Example 1: A surgical hub for use with a surgical system in a surgical procedure performed in an operating room, wherein the surgical hub comprises: non-contact sensors; and a control circuit configured to: determine bounds of the operating room based on measurements performed by the non-contact sensors; and establish a control arrangement with a detected surgical hub located within the bounds of the operating room.

Example 2: The surgical hub of Example 1, wherein the control arrangement is a master-slave arrangement.

Example 3: The surgical hub of any one of Examples 1-2, wherein the control circuit is configured to select one of a master mode of operation or a slave mode of operation in the master-slave arrangement.

Example 4: The surgical hub of any one of Examples 1-3, wherein the control circuit is configured to surrender control of at least one surgical instrument to the detected surgical hub in the slave mode of operation.

Example 5: The surgical hub of any one of Examples 1, wherein the control arrangement is a peer-to-peer arrangement.

Example 6: The surgical hub of Example 1-5, wherein the non-contact sensors are ultrasonic sensors.

Example 7: The surgical hub of Example 1-5, wherein the non-contact sensors are laser sensors.

Example 8: A surgical hub for use with a surgical system in a surgical procedure performed in an operating room, wherein the surgical hub comprises: non-contact sensors; a processor; and a memory coupled to the processor, the memory storing instructions executable by the processor to: determine bounds of the operating room based on measurements performed by the non-contact sensors; and establish a control arrangement with a detected surgical hub located within the bounds of the operating room.

Example 9: The surgical hub of Example 8, wherein the control arrangement is a master-slave arrangement.

Example 10: The surgical hub of Example 9, wherein the control circuit is configured to select one of a master mode of operation or a slave mode of operation in the master-slave arrangement.

Example 11: The surgical hub of Example 10, wherein the control circuit is configured to surrender control of at least one surgical instrument to the detected surgical hub in the slave mode of operation.

Example 12: The surgical hub of Example 11, wherein the control arrangement is a peer-to-peer arrangement.

Example 13: The surgical hub of anyone of Examples 8-12, wherein the non-contact sensors are ultrasonic sensors.

Example 14: The surgical hub of Example 8, wherein the non-contact sensors are laser sensors.

Example 15: A non-transitory computer readable medium storing computer readable instructions which, when executed, causes a machine to: determine bounds of an operating room; and establish a control arrangement with a detected surgical hub located within the bounds of the operating room.

Example 16: The non-transitory computer readable medium of Example 15, wherein the control arrangement is a master-slave arrangement.

Example 17: The non-transitory computer readable medium of any one of Examples 15-16, wherein the computer readable instructions, when executed, further causes the machine to select one of a master mode of operation or a slave mode of operation in the master-slave arrangement.

Example 18: The non-transitory computer readable medium of any one of Examples 15-17, wherein the computer readable instructions, when executed, further causes the machine to surrender control of at least one surgical instrument to the detected surgical hub in the slave mode of operation.

Example 19: The non-transitory computer readable medium of any one of Examples 15-18, wherein the control arrangement is a peer-to-peer arrangement.

Various additional aspects of the subject matter described herein are set out in the following numbered examples:

Example 1: A surgical hub, comprising: a processor; a memory coupled to the processor, the memory storing instructions executable by the processor to: interrogate a modular device coupled to the processor via a modular communication hub, wherein the modular device is a source of data sets that include patient identity data and surgical procedure data; receive a data set from the modular device; discard the patient identity data and any portion of the surgical procedure data that identifies the patient from the data set; extract anonymous data from the data set and create an anonymized data set; and configure operation of the surgical hub or the modular device based on the anonymized data set.

Example 2: The surgical hub of Example 1, wherein the anonymized data set includes catastrophic failure of a modular device, and wherein the memory stores instructions executable by the processor to initiate automatic archive and submission of data for implications analysis based on the catastrophic failure of the modular device.

Example 3: The surgical hub of any one of Examples 1-2, wherein the memory stores instructions executable by the processor to detect counterfeit component information from the anonymized data set.

Example 4: The surgical hub of any one of Examples 1-3, wherein the memory stores instructions executable by the processor to derive implications of the modular device from the anonymized data set.

Example 5: The surgical hub of any one of Examples 1-4, wherein the memory stores instructions executable by the processor to configure the modular device to operate based on the derived implications.

Example 6: The surgical hub of any one of Examples 1-5, wherein the memory stores instructions executable by the processor to configure the surgical hub based on the derived implications.

Example 7: The surgical hub of any one of Examples 1-6, wherein the memory stores instructions executable by the processor to conglomerate the anonymized data.

Example 8: The surgical hub of any one of Examples 1-7, wherein the memory stores instructions executable by the processor to extract the anonymized data prior to storing the received data in a storage device coupled to the surgical hub.

Example 9: The surgical hub of any one of Examples 1-8, wherein the memory stores instructions executable by the processor to: transmit the anonymized data to a remote network outside of the surgical hub; compile the anonymized data at the remote network; and store a copy of the data set from the modular device in a patient electronic medical records database.

Example 10: The surgical hub of any one of Examples 1-9, comprising a modular communication hub coupled to the processor, the modular communication hub configured to connect modular devices located in one or more operating theaters to the surgical hub.

Example 11: A method of stripping data originating from a modular device coupled to a surgical hub by a communication hub, the surgical hub comprising a processor and a memory coupled to the processor, the memory storing instructions executable by the processor, the method comprising: interrogating, by a processor, a modular device coupled to the processor via a modular communication hub, wherein the modular communication hub is configured to connect modular devices located in one or more operating theaters to a surgical hub, wherein the modular device is a source of data sets that include patient identity data and surgical procedure data; receiving, by the processor, a data set from the modular device by the processor via the communication hub; discarding, by the processor, the patient identity data and any portion of the surgical procedure data that identifies the patient from the data set; extracting, by the processor, anonymous data from the data set and create an anonymized data set; and configuring, by the processor, operation of the surgical hub or the modular device based on the anonymized data set.

Example 12: The method of Example 11, comprising: initiating, by the processor, automatic archive and submission of data for implications analysis based on the catastrophic failure of the modular device wherein the anonymized data set includes catastrophic failure of a modular device.

Example 13: The method of any one of Examples 11-12, comprising by the processor, detecting counterfeit component information from the anonymized data set.

Example 14: The method of any one of Examples 11-13, comprising deriving implications of the modular device from the anonymized data set.

Example 15: The method of Example 14, comprising configuring, by the processor, the modular device to operate based on the derived implications.

Example 16: The method of any one of Examples 14-15, comprising configuring, by the processor, the surgical hub based on the derived implications.

Example 17: The method of any one of Examples 14-16, comprising, conglomerating by the processor, the anonymized data.

Example 18: The method of Example 11, extracting, by the processor, the anonymized data prior to storing the received data in a storage device coupled to the surgical hub.

Example 19: The method of Example 11, comprising: transmitting, by the processor, the anonymized data to a remote network outside of the surgical hub; compiling, by a server at the remote network, the anonymized data at the remote network; and storing, by the processor, a copy of the data set from the modular device in a patient electronic medical records database.

Example 20: A non-transitory computer readable medium storing computer readable instructions which, when executed, causes a machine to: interrogate a modular device coupled to the processor via the modular communication hub, wherein the modular device is a source of data sets that include patient identity data and surgical procedure data; receive a data set from the modular device; discard the patient identity data and any portion of the surgical procedure data that identifies the patient from the data set; extract anonymous data from the data set and create an anonymized data set; and configure operation of the surgical hub or the modular device based on the anonymized data set.

Example 21: The non-transitory computer readable medium of Example 20, storing computer readable instructions which, when executed, causes a machine to derive implications of the modular device from the anonymized data set.

Various additional aspects of the subject matter described herein are set out in the following numbered examples:

Example 1: A surgical hub comprising: a storage device; a processor coupled to the storage device; and a memory coupled to the processor, the memory storing instructions executable by the processor to: receive data from a surgical instrument coupled to the surgical hub; and determine a rate at which to transfer the data from the surgical hub to a remote cloud-based medical analytics network based on available storage capacity of the storage device.

Example 2: The surgical hub of Example 1, wherein the memory stores instructions executable by the processor to determine a frequency at which to transfer the data from the surgical hub to the remote cloud-based medical analytics network based on the available storage capacity of the storage device.

Example 3: The surgical hub of any one of Examples 1-2, wherein the memory stores instructions executable by the processor to: detect surgical hub network down time; and determine a frequency at which to transfer the data from the surgical hub to the remote cloud-based medical analytics network based on the detected surgical hub network down time.

Example 4: The surgical hub of any one of Examples 1-3, wherein the memory stores instructions executable by the processor to determine a type of data to transfer from the surgical hub to the remote cloud-based medical analytics network based on inclusion or exclusion of data associated with a users, patient, or surgical procedure.

Example 5: The surgical hub of any one of Examples 1-4, wherein the memory stores instructions executable by the processor to determine when to transfer data from the surgical hub to the remote cloud-based medical analytics network.

Example 6: The surgical hub of any one of Examples 1-5, wherein the memory stores instructions executable by the processor to receive new operational parameters for the surgical hub from the remote cloud-based medical analytics network.

Example 7: The surgical hub of any one of Examples 1-6, wherein the memory stores instructions executable by the processor to receive new operational parameters for the surgical instrument from the remote cloud-based medical analytics network.

Example 8: A method of transmitting data from a surgical hub to a remote cloud-based medical analytics network, the surgical hub comprising a storage device, a processor coupled to the storage device, and a memory coupled to the processor, the memory storing instructions executable by the processor, the method comprising: receiving, by a processor, data from a surgical instrument coupled to the surgical hub; and determining, by the processor, a rate at which to transfer the data from the surgical hub to the remote cloud-based medical analytics network based on available storage capacity of a storage device coupled to the surgical hub.

Example 9: The method of Example 8, comprising determining, by the processor, a frequency at which to transfer the data from the surgical hub to the remote cloud-based medical analytics network based on the available storage capacity of the storage device Example 10: The method of any one of Examples 8-9, comprising: detecting, by the processor, surgical hub network down time; and determining, by the processor, a frequency at which to transfer the data from the surgical hub to the remote cloud-based medical analytics network based on the detected surgical hub network down time.

Example 11: The method of any one of Examples 8-10, comprising determining, by the processor, a type of data to transfer from the surgical hub to the remote cloud-based medical analytics network based on inclusion or exclusion of data associated with a users, patient, or surgical procedure.

Example 12: The method of any one of Examples 8-11, comprising determining, by the processor, when to transfer the data from the surgical hub to the remote cloud-based medical analytics network.

Example 13: The method of any one of Examples 8-12, comprising receiving, by the processor, new operational parameters for the surgical hub from the remote cloud-based medical analytics network.

Example 14: The method of any one of Examples 8-13, comprising receiving, by the processor, new operational parameters for the surgical instrument from the remote cloud-based medical analytics network.

Example 15: A non-transitory computer readable medium storing computer readable instructions which, when executed, causes a machine to: receive data from a surgical instrument coupled to the surgical hub; and determine a rate at which to transfer the data from the surgical hub to a remote cloud-based medical analytics network based on available storage capacity of the storage device.

Example 16: The non-transitory computer readable medium of Example 15, storing computer readable instructions which, when executed, causes a machine to determine a frequency at which to transfer the data from the surgical hub to the remote cloud-based medical analytics network based on the available storage capacity of the storage device.

Example 17: The non-transitory computer readable medium of any one of Examples 15-16, storing computer readable instructions which, when executed, causes a machine to: detect surgical hub network down time; and determine a frequency at which to transfer the data from the surgical hub to the remote cloud-based medical analytics network based on the detected surgical hub network down time.

Example 18: The non-transitory computer readable medium of any one of Examples 15-17, storing computer readable instructions which, when executed, causes a machine to determine a type of data to transfer from the surgical hub to the remote cloud-based medical analytics network based on inclusion or exclusion of data associated with a users, patient, or surgical procedure.

Example 19: The non-transitory computer readable medium of any one of Examples 15-18, storing computer readable instructions which, when executed, causes a machine to determine when to transfer data from the surgical hub to the remote cloud-based medical analytics network.

Example 20: The non-transitory computer readable medium of any one of Examples 15-19, storing computer readable instructions which, when executed, causes a machine to receive new operational parameters for the surgical hub from the remote cloud-based medical analytics network.

Example 21: The non-transitory computer readable medium of any one of Examples 15-20, storing computer readable instructions which, when executed, causes a machine to receive new operational parameters for the surgical instrument from the remote cloud-based medical analytics network.

Various additional aspects of the subject matter described herein are set out in the following numbered examples:

Example 1: A surgical hub, comprising: a processor; and a memory coupled to the processor, the memory storing instructions executable by the processor to: receive a first self-describing data packet from a first data source, the first self-describing data packet comprising a first preamble, a first data payload, a source of the first data payload, and a first encryption certificate, wherein the first preamble defines the first data payload and the first encryption certificate verifies the authenticity of the first data packet; parse the received first preamble; and interpret the first data payload based on the first preamble.

Example 2: The surgical hub of Example 1, wherein the memory stores instructions executable by the processor to: receive a second self-describing data packet from a second data source, the second self-describing data packet comprising a second preamble, a second data payload, a source of the second data payload, and a second encryption certificate, wherein the second preamble defines the second data payload and the second encryption certificate verifies the authenticity of the second data packet; parse the received second preamble; interpret the second data payload based on the second preamble; associate the first and second self-describing data packets; and generate a third self-describing data packet comprising the first and second data payloads.

Example 3: The surgical hub of any one of Examples 1-2, wherein the memory stores instructions executable by the processor to anonymize the data payload of the third self-describing data packet.

Example 4: The surgical hub of any one of Examples 1-3, wherein the memory stores instructions executable by the processor to: determine that a data payload was generated by a new data source; verify the new data source of the data payload; and alter a data collection process at the surgical hub to receive subsequent data packets from the new data source.

Example 5: The surgical hub of any one of Examples 1-4, wherein the memory stores instructions executable by the processor to associate the first and second self-describing data packets based on a key.

Example 6: The surgical hub of any one of Examples 1-5, wherein the memory stores instructions executable by the processor to: receive an anonymized third self-describing data packet; and reintegrate the anonymized third self-describing data packet into the first and second self-describing data packets using the key.

Example 7: A surgical hub, comprising: a control circuit configured to: receive a first self-describing data packet from a first data source, the first self-describing data packet comprising a first preamble, a first data payload, a source of the first data payload, and a first encryption certificate, wherein the first preamble defines the first data payload and the first encryption certificate verifies the authenticity of the first data packet; parse the received first preamble; and interpret the first data payload based on the first preamble.

Example 8: The surgical hub of Example 7, wherein the control circuit is further configured: receive a second self-describing data packet from a second data source, the second self-describing data packet comprising a second preamble, a second data payload, a source of the second data payload, and a second encryption certificate, wherein the second preamble defines the second data payload and the second encryption certificate verifies the authenticity of the second data packet; parse the received second preamble; interpret the second data payload based on the second preamble; associate the first and second self-describing data packets; and generate a third self-describing data packet comprising the first and second data payloads.

Example 9: The surgical hub of any one of Examples 7-8, wherein the control circuit is further configured to anonymize the data payload of the third self-describing data packet.

Example 10: The surgical hub of any one of Examples 7-9, wherein the control circuit is further configured to: determine that a data payload was generated by a new data source; verify the new data source of the data payload; and alter a data collection process at the surgical hub to receive subsequent data packets from the new data source.

Example 11: The surgical hub of any one of Examples 7-10, wherein the control circuit is further configured to associate the first and second self-describing data packets based on a key.

Example 12: The surgical hub of any one of Examples 7-11, wherein the control circuit is further configured to: receive an anonymized third self-describing data packet; and reintegrate the anonymized third self-describing data packet into the first and second self-describing data packets using the key.

Example 13: A non-transitory computer readable medium storing computer readable instructions which, when executed, causes a machine to: receive a first self-describing data packet from a first data source, the first self-describing data packet comprising a first preamble, a first data payload, a source of the first data payload, and a first encryption certificate, wherein the first preamble defines the first data payload and the first encryption certificate verifies the authenticity of the first data packet; parse the received first preamble; and interpret the first data payload based on the first preamble.

Example 14: The non-transitory computer-readable medium of Example 13, storing computer readable instructions which, when executed, causes a machine to: receive a second self-describing data packet from a second data source, the second self-describing data packet comprising a second preamble, a second data payload, a source of the second data payload, and a second encryption certificate, wherein the second preamble defines the second data payload and the second encryption certificate verifies the authenticity of the second data packet; parse the received second preamble; interpret the second data payload based on the second preamble; associate the first and second self-describing data packets; and generate a third self-describing data packet comprising the first and second data payloads.

Example 15: The non-transitory computer-readable medium of any one of Examples 13-14, storing computer readable instructions to anonymize the data payload of the third self-describing data packet.

Example 16: The non-transitory computer-readable medium of any one of Examples 13-15, storing computer readable instructions to: determine that a data payload was generated by a new data source; verify the new data source of the data payload; and alter a data collection process at the surgical hub to receive subsequent data packets from the new data source.

Example 17: The non-transitory computer-readable medium of any one of Examples 13-16, storing computer readable instructions to associate the first and second self-describing data packets based on a key.

Example 18: The non-transitory computer-readable medium of any one of Examples 13-17, storing computer readable instructions to: receive an anonymized third self-describing data packet; and reintegrate the anonymized third self-describing data packet into the first and second self-describing data packets using the key.

Various additional aspects of the subject matter described herein are set out in the following numbered examples:

Example 1: A surgical hub configured to communicate with a surgical instrument, the surgical hub comprising: a processor; and a memory coupled to the processor, the memory storing instructions executable by the processor to: receive a first data set associated with a surgical procedure, wherein the first data set is generated at a first time; receive a second data set associated with the efficacy of the surgical procedure, wherein the second data set is generated at a second time, wherein the second time is separate and distinct from the first time; anonymize the first and second data sets by removing information that identifies a patient, a surgery, or a scheduled time of the surgery; and store the first and second anonymized data sets to generate a data pair grouped by surgery.

Example 2: The surgical hub of Example 1, wherein the memory stores instructions executable by the processor to reconstruct a series of chronological events based on the data pair.

Example 3: The surgical hub of any one of Examples 1-2, wherein the memory stores instructions executable by the processor to reconstruct a series of coupled but unconstrained data sets based on the data pair.

Example 4: The surgical hub of any one of Examples 1-3, wherein the memory stores instructions executable by the processor to: encrypt the data pair; define a backup format for the data pair; and mirror the data pair to a cloud storage device.

Example 5: A surgical hub configured to communicate with a surgical instrument, the surgical hub comprising: a control circuit configured to: receive a first data set associated with a surgical procedure, wherein the first data set is generated at a first time; receive a second data set associated with the efficacy of the surgical procedure, wherein the second data set is generated at a second time, wherein the second time is separate and distinct from the first time; anonymize the first and second data sets by removing information that identifies a patient, a surgery, or a scheduled time of the surgery; and store the first and second anonymized data sets to generate a data pair grouped by surgery.

Example 6: The surgical hub of Example 5, wherein the control circuit is further configured to reconstruct a series of chronological events based on the data pair.

Example 7: The surgical hub of any one of Examples 5-6, wherein the control circuit is further configured to reconstruct a series of coupled but unconstrained data sets based on the data pair.

Example 8: The surgical hub of any one of Examples 5-7, wherein the control circuit is further configured to: encrypt the data pair; define a backup format for the data pair; and mirror the data pair to a cloud storage device.

Example 9: A non-transitory computer readable medium storing computer readable instructions which, when executed, causes a machine to: receive a first data set associated with a surgical procedure, wherein the first data set is generated at a first time; receive a second data set associated with the efficacy of the surgical procedure, wherein the second data set is generated at a second time, wherein the second time is separate and distinct from the first time; anonymize the first and second data sets by removing information that identifies a patient, a surgery, or a scheduled time of the surgery; and store the first and second anonymized data sets to generate a data pair grouped by surgery.

Example 10: The non-transitory computer-readable medium of Example 9, storing computer readable instructions which, when executed, causes a machine to reconstruct a series of chronological events based on the data pair.

Example 11: The surgical hub of any one of Examples 9-10, storing computer readable instructions which, when executed, causes a machine to reconstruct a series of coupled but unconstrained data sets based on the data pair.

Example 12: The surgical hub of any one of any one of Examples 9-11, storing computer readable instructions which, when executed, causes a machine to: encrypt the data pair; define a backup format for the data pair; and mirror the data pair to a cloud storage device.

Example 13: A surgical hub, comprising: a processor; and a memory coupled to the processor, the memory storing instructions executable by the processor to: interrogate a surgical instrument, wherein the surgical instrument is a first source of patient data; retrieve a first data set from the surgical instrument, wherein the first data set is associated with a patient and a surgical procedure; interrogate a medical imaging device, wherein the medical imaging device is a second source of patient data; retrieve a second data set from the medical imaging device, wherein the second data set is associated with the patient and an outcome of the surgical procedure; associate the first and second data sets by a key; and transmit the associated first and second data sets to remote network outside of the surgical hub.

Example 14: The surgical hub of Example 13, wherein the memory stores instructions executable by the processor to: retrieve the first data set using the key; anonymize the first data set by removing patient information from the first data set; retrieve the second data set using the key; anonymize the second data set by removing patient information from the second data set; pair the anonymized first and second data sets; and determine success rates of surgical procedures grouped by the surgical procedure based on the anonymized paired first and second data sets.

Example 15: The surgical hub of any one of Examples 13-14, wherein the memory stores instructions executable by the processor to: retrieve the anonymized first data set; retrieve the anonymized second data set; and reintegrate the anonymized first and second data sets using the key.

Example 16: The surgical hub of any one of Examples 13-15, wherein the first and second data sets define first and second data payloads in respective first and second data packets.

Example 17: The surgical hub of any one of Examples 13-16, wherein the memory stores instructions executable by the processor to retrieve information from an electronic medical records database.

Example 18: The surgical hub of any one of Examples 13-17, wherein the memory stores instructions executable by the processor to anonymize the information retrieved from the electronic medical records database by removing patient information from the information retrieved from the electronic medical records database.

Various additional aspects of the subject matter described herein are set out in the following numbered examples:

Example 1: A surgical hub configured to communicably couple to a data source and a modular device, the surgical hub comprising: a processor; and a memory coupled to the processor, the memory storing instructions that, when executed by the processor, cause the surgical hub to: receive perioperative data from the data source, wherein the perioperative data comprises data detected by the data source during the course of a surgical procedure; determine contextual information regarding the surgical procedure according to the perioperative data; determine control adjustments for the modular device according to the contextual information; and control the modular device according to the control adjustments.

Example 2: The surgical hub of any one of Example 1, wherein the data source comprises a first modular device and the modular device comprises a second modular device.

Example 3: The surgical hub of any one of Examples 1-2, wherein the data source comprises a patient monitoring device.

Example 4: The surgical hub of any one of Examples 1-3, wherein the contextual information comprises a procedural type of the surgical procedure.

Example 5: The surgical hub of any one of Examples 1-4, wherein the contextual information comprises a procedural step of the surgical procedure.

Example 6: The surgical hub of any one of Examples 1-5, wherein the perioperative data comprises a parameter associated with the modular device.

Example 7: The surgical hub of any one of Examples 1-6, wherein the perioperative data comprises a parameter associated with a patient.

Example 8: A surgical hub configured to communicably couple to a data source and a modular device, the surgical hub comprising a control circuit configured to receive perioperative data from the data source, wherein the perioperative data comprises data detected by the data source during the course of a surgical procedure; determine contextual information regarding the surgical procedure according to the perioperative data; determine control adjustments for the modular device according to the contextual information; and control the modular device according to the control adjustments.

Example 9: The surgical hub of any one of Example 8, wherein the data source comprises a first modular device and the modular device comprises a second modular device.

Example 10: The surgical hub of any one of Examples 8-9, wherein the data source comprises a patient monitoring device.

Example 11: The surgical hub of any one of Examples 8-10, wherein the contextual information comprises a procedural type of the surgical procedure.

Example 12: The surgical hub of any one of Examples 8-11, wherein the contextual information comprises a procedural step of the surgical procedure.

Example 13: The surgical hub of any one of Examples 8-12, wherein the perioperative data comprises a parameter associated with the modular device.

Example 14: The surgical hub of any one of Examples 8-13, wherein the perioperative data comprises a parameter associated with a patient.

Example 15: A non-transitory computer readable medium storing computer readable instructions thereon that, when executed by a surgical hub configured to communicably couple to a data source and a modular device, causes the surgical hub to receive perioperative data from the data source, wherein the perioperative data comprises data detected by the data source during the course of a surgical procedure; determine contextual information regarding the surgical procedure according to the perioperative data; determine control adjustments for the modular device according to the contextual information; and control the modular device according to the control adjustments.

Example 16: The surgical hub of any one of Examples 15, wherein the data source comprises a first modular device and the modular device comprises a second modular device.

Example 17: The surgical hub of any one of Examples 15-16, wherein the data source comprises a patient monitoring device.

Example 18: The surgical hub of any one of Examples 15-17, wherein the contextual information comprises a procedural type of the surgical procedure.

Example 19: The surgical hub of any one of Examples 15-18, wherein the contextual information comprises a procedural step of the surgical procedure.

Example 20: The surgical hub of any one of Examples 15-19, wherein the perioperative data comprises a parameter associated with the modular device.

Example 21: The surgical hub of any one of Examples 15-20, wherein the perioperative data comprises a parameter associated with a patient.

Various additional aspects of the subject matter described herein are set out in the following numbered examples:

Example 1: A system comprising a surgical hub configured to communicably couple to a modular device comprising a sensor configured to detect data associated with the modular device and a device processor, the surgical hub comprising: a hub processor; and a hub memory coupled to the hub processor; and a distributed control system executable at least in part by each of the device processor and the hub processor, the distributed control system configured to: receive the data detected by the sensor; determine control adjustments for the modular device according to the data; and control the modular device according to the control adjustments; wherein in a first mode the distributed control system is executed by both the hub processor and the device processor, and in a second mode the distributed control system is executed solely by the device processor.

Example 2: The system of any one of Examples 1, wherein the distributed control system is configured to shift from the first mode to the second mode when a sampling rate of the sensor is greater than a data transmission rate from the modular device to the surgical hub.

Example 3: The system of any one of Examples 1-2, wherein the distributed control system is configured to shift from the second mode to the first mode when a sampling rate of the sensor is less than a data transmission rate from the modular device to the surgical hub.

Example 4: The system of any one of Examples 1-3, wherein the modular device comprises a radiofrequency (RF) electrosurgical instrument and the distributed control system is configured to control an energy level of the RF electrosurgical instrument.

Example 5: The system of any one of Examples 1-4, wherein the modular device comprises a surgical cutting and stapling instrument and the distributed control system is configured to control a rate at which a motor of the surgical cutting and stapling instrument drives a knife.

Example 6: A system comprising: a modular device configured to communicably couple to a surgical hub comprising a hub processor, the modular device comprising: a sensor configured to detect data associated with the modular device; a device memory; and a device processor coupled to the device memory and the sensor; and a distributed control system executable at least in part by each of the device processor and the hub processor, the distributed control system configured to: receive the data detected by the sensor; determine control adjustments for the modular device according to the data; and control the modular device according to the control adjustments; wherein in a first mode the distributed control system is executed by both the hub processor and the device processor, and in a second mode the distributed control system is executed solely by the device processor.

Example 7: The system of any one of Examples 6, wherein the distributed control system is configured to shift from the first mode to the second mode when a sampling rate of the sensor is greater than a data transmission rate from the modular device to the surgical hub.

Example 8: The system of any one of Examples 6-7, wherein the distributed control system is configured to shift from the second mode to the first mode when a sampling rate of the sensor is less than a data transmission rate from the modular device to the surgical hub.

Example 9: The system of any one of Examples 6-8, wherein the modular device comprises a radiofrequency (RF) electrosurgical instrument and the distributed control system is configured to control an energy level of the RF electrosurgical instrument.

Example 10: The system of any one of Examples 6-9, wherein the modular device comprises a surgical cutting and stapling instrument and the distributed control system is configured to control a rate at which a motor of the surgical cutting and stapling instrument drives a knife.

Example 11: A system configured to control a modular device comprising a sensor configured to detect data associated with the modular device, the system comprising: a first surgical hub configured to communicably couple to the modular device and to a second surgical hub comprising a second processor, the first surgical hub comprising: a memory; and a first processor coupled to the memory; and a distributed control system executable at least in part by each of the first processor and the second processor, the distributed control system configured to: receive the data detected by the sensor; determine control adjustments for the modular device according to the data; and control the modular device according to the control adjustments.

Example 12: The system of any one of Examples 11, wherein the distributed control system is transitionable between a first mode, where the distributed control system is executed by both the first processor and the second processor, and a second mode, where the distributed control system is executed solely by the first processor.

Example 13: The system of any one of Examples 11-12, wherein the distributed control system is configured to shift between the first mode and the second mode upon receiving a command.

Example 14: The system of any one of Examples 11-13, wherein the modular device comprises a radiofrequency (RF) electrosurgical instrument and the distributed control system is configured to control an energy level of the RF electrosurgical instrument.

Example 15: The system of any one of Examples 11-14, wherein the modular device comprises a surgical cutting and stapling instrument and the distributed control system is configured to control a rate at which a motor of the surgical cutting and stapling instrument drives a knife.

Various additional aspects of the subject matter described herein are set out in the following numbered examples:

Example 1: A surgical hub, comprising: a processor; and a memory coupled to the processor, the memory storing instructions executable by the processor to: receive first image data from a first image sensor, wherein the first image data represents a first field of view; receive second image data from a second image sensor, wherein the second image data represents a second field of view; and display, on a display coupled to the processor, a first image rendered from the first image data corresponding to the first field of view and a second image rendered from the second image data corresponding to the second field of view.

Example 2: The surgical hub of Example 1, wherein the first field of view is a narrow angle field of view.

Example 3: The surgical hub of any one of Examples 1-2, wherein the first field of view is a wide angle field of view.

Example 4: The surgical hub of any one of Examples 1-3, wherein the memory stores instructions executable by the processor to augment the first image with the second image on the display.

Example 5: The surgical hub of any one of Examples 1-4, wherein the memory stores instructions executable by the processor to fuse the first image and the second image into a third image and display a fused image on the display.

Example 6: The surgical hub of any one of Examples 1-5, wherein the fused image data comprises status information associated with a surgical device, an image data integration landmark to interlock a plurality of images, and at least one guidance parameter.

Example 7: The surgical hub of any one of Examples 1-6, wherein the first image sensor is the same as the second image sensor and wherein the first image data is captured as a first time by the first image sensor and the second image data is captured at a second time by the first image sensor.

Example 8: The surgical hub of any one of Examples 1-7, wherein the memory stores instructions executable by the processor to: receive third image data from a third image sensor, wherein the third image data represents a third field of view; generate composite image data comprising the second and third image data; display the first image in a first window of the display, wherein the first image corresponds to the first image data; and display a third image in a second window of the display, wherein the third image corresponds to the composite image data.

Example 9: The surgical hub of any one of Examples 1-8, wherein the memory stores instructions executable by the processor to: receive third image data from a third image sensor, wherein the third image data represents a third field of view; fuse the second and third image data to generate fused image data; display the first image in a first window of the display, wherein the first image corresponds to the first image data; and display a third image in a second window of the display, wherein the third image corresponds to the fused image data.

Example 10: A surgical hub, comprising: a processor; and a memory coupled to the processor, the memory storing instructions executable by the processor to: detect a surgical device connection to the surgical hub; transmit a control signal to the detected surgical device to transmit to the surgical hub surgical parameter data associated with the detected surgical device; receive the surgical parameter data from the detected surgical device; receive image data from an image sensor; and display, on a display coupled to the surgical hub, an image rendered based on the image data received from the image sensor in conjunction with the surgical parameter data received from the surgical device.

Example 11: The surgical hub of Example 10, wherein the surgical device comprises a local display that is separate from the display coupled to the surgical hub.

Example 12: The surgical hub of any one of Examples 10-11, wherein the surgical device connected to the surgical hub is configured to reconfigure the local display to present information that is different from information presented when the surgical device is not connected to the surgical hub.

Example 13: The surgical hub of any one of Examples 10-12, wherein a portion of information displayed on the local display is displayed on the display coupled to the surgical hub.

Example 14: The surgical hub of any one of Examples 10-13, wherein information displayed on the display coupled to the surgical hub is mirrored on the local display of the surgical device.

Example 15: A surgical hub, comprising: a control circuit configured to: detect a surgical device connection to the surgical hub; transmit a control signal to the detected surgical device to transmit to the surgical hub surgical parameter data associated with the detected surgical device; receive the surgical parameter data from the detected surgical device; receive image data from an image sensor; and display, on a display coupled to the surgical hub, an image received from the image sensor in conjunction with the surgical parameter data received from the surgical device.

Example 16: The surgical hub of Example 15, wherein the surgical device comprises a local display that is separate from the display coupled to the surgical hub.

Example 17: The surgical hub of any one of Examples 15-16, wherein the surgical device connected to the surgical hub is configured to reconfigure the local display to present information that is different from information presented when the surgical device is not connected to the surgical hub.

Example 18: The surgical hub of any one of Examples 15-17, wherein a portion of information displayed on the local display is displayed on the display coupled to the surgical hub.

Example 19: The surgical hub of any one of Examples 15-18, wherein information displayed on the display coupled to the surgical hub is mirrored on the local display of the surgical device.

Example 20: A non-transitory computer readable medium storing computer readable instructions which, when executed, causes a machine to: detect a surgical device connection to the surgical hub; transmit a control signal to the detected surgical device to transmit to the surgical hub surgical parameter data associated with the detected surgical device; receive the surgical parameter data from the detected surgical device; receive image data from an image sensor; and display, on a display coupled to the surgical hub, an image received from the image sensor in conjunction with the surgical parameter data received from the surgical device.

Example 21: A non-transitory computer readable medium storing computer readable instructions which, when executed, causes a machine to: receive first image data from a first image sensor, wherein the first image data represents a first field of view; receive second image data from a second image sensor, wherein the second image data represents a second field of view; and display, on a display coupled to the surgical hub, a first image corresponding to the first field of view and a second image corresponding to the second field of view.

Various additional aspects of the subject matter described herein are set out in the following numbered examples:

Example 1: A surgical hub, comprising: a processor; and a memory coupled to the processor, the memory storing instructions executable by the processor to: receive image data from an image sensor; generate a first image based on the image data; display the first image on a surgical hub display coupled to the processor; receive a signal from a non-contact sensor, the signal indicative of a position of a surgical device; generate a second image based on the signal indicative of the position of the surgical device; and display the second image on the surgical hub display coupled to the processor.

Example 2: The surgical hub of Example 1, wherein the first image data represents a center of a staple line.

Example 3: The surgical hub of any one of Examples 1-2, wherein the first image represents a target corresponding to the center of the staple line.

Example 4: The surgical hub of any one of Examples 1-3, wherein the signal is indicative of the position of the surgical device relative to the center of the staple line.

Example 5: The surgical hub of any one of Examples 1-4, wherein the second image represents the position of the surgical device along a projected path of the surgical device toward the center of the staple line.

Example 6: The surgical hub of Example 1, wherein the staple line is a double staple line defining a staple overlap portion.

Example 7: The surgical hub of Example 6, wherein the surgical device is a circular stapler comprising an anvil trocar and the non-contact sensor is configured to detect the location of the anvil trocar relative to the staple overlap portion.

Example 8: The surgical hub of Example 1, wherein the staple line is a linear staple line formed using a linear transection technique.

Example 9: The surgical hub of Example 8, wherein a center of the linear staple line is located halfway between one end of the linear staple line and an opposite end of the linear staple line.

Example 10: The surgical hub of any one of Examples 1-9, wherein the image sensor is coupled to a medical imaging device.

Example 11: The surgical hub of any one of Examples 1-10, wherein the image sensor and the surgical device are separate devices.

Example 12: The surgical hub of Example 1, wherein the non-contact sensor is an inductive sensor.

Example 13: The surgical hub of Example 1, wherein the non-contact sensor is a capacitive sensor.

Example 14: A method of aligning a surgical instrument coupled to a surgical hub, the method comprising: receiving image data by a processor from an image sensor; generating a first image by the processor based on the image data; displaying the first image on a surgical hub display coupled to the processor; receiving a signal by the processor from a non-contact sensor, the signal indicative of a position of a surgical device; generating a second image by the processor based on the signal indicative of the position of the surgical device; and displaying the second image on the surgical hub display coupled to the processor.

Example 15: The method of Example 14, comprising displaying, on the surgical hub display coupled to the processor, an indication when the second image is not aligned with the first image.

Example 16: The method of any one of Examples 14-15, comprising displaying, on the surgical hub display coupled to the processor, an indication when the second image is aligned with the first image.

Example 17: The method of any one of Examples 14-16, comprising displaying, on the surgical hub display coupled to the processor, a projected path of the surgical device as the second image moves towards the first image.

Example 18: The method of any one of Examples 14-17, comprising displaying, on the surgical hub display coupled to the processor, the position of the surgical device along the projected path of the surgical device toward the center of the staple line.

Example 19: A non-transitory computer readable medium storing computer readable instructions which, when executed, causes a machine to: receive image data by a processor from an image sensor; generate a first image by the processor based on the image data; display the first image on a surgical hub display coupled to the processor; receive a signal by the processor from a non-contact sensor, the signal indicative of a position of a surgical device; generate a second image by the processor based on the signal indicative of the position of the surgical device; and display the second image on the surgical hub display coupled to the processor.

Example 20: The non-transitory computer readable medium of any one of Example 19, storing computer readable instructions which, when executed, causes a machine to display, on the surgical hub display coupled to the processor, an indication when the second image is not aligned with the first image.

Example 21: The non-transitory computer readable medium of any one of Examples 19-20, storing computer readable instructions which, when executed, causes a machine to display, on the surgical hub display coupled to the processor, an indication when the second image is aligned with the first image.

Example 22: The non-transitory computer readable medium of any one of Examples 19-21, storing computer readable instructions which, when executed, causes a machine to display, on the surgical hub display coupled to the processor, a projected path of the surgical device as the second image moves towards the first image.

Example 23: The non-transitory computer readable medium of any one of Examples 19-22, storing computer readable instructions which, when executed, causes a machine to display, on the surgical hub display coupled to the processor, the position of the surgical device along the projected path of the surgical device toward the center of the staple line.

Example 24: A surgical hub for aligning a surgical instrument, the surgical hub comprising: a processor; and a memory coupled to the processor, the memory storing instructions executable by the processor to: receive image data from an image sensor, wherein the first image data represents a center of a staple line; generate a first image based on the image data; display the first image on a monitor coupled to the processor, wherein the first image represents a target corresponding to the center of the staple line; receive a signal from a non-contact sensor, the signal indicative of a position of a surgical device relative to the center of the staple line; and generate a second image based on the position of the surgical device; display the second image on the monitor, wherein the second image represents the position of the surgical device along a projected path of the surgical device toward the center of the staple line.

Example 25: The surgical hub of Example 24, wherein the center of the staple line is a double-staple overlap portion zone.

Example 26: The surgical hub of any one of Examples 24-25, wherein the image sensor receives an image from a medical imaging device.

Example 27: The surgical hub of any one of Examples 24-26, wherein the surgical device is a circular stapler comprising an anvil trocar and the non-contact sensor is configured to detect the location of the anvil trocar relative to the center of the staple line.

Example 28: The surgical hub of Example 24, wherein the non-contact sensor is an inductive sensor.

Example 29: The surgical hub of Example 24, wherein the non-contact sensor is a capacitive sensor.

Example 30: A non-transitory computer readable medium storing computer readable instructions which, when executed, causes a machine to: receive image data from an image sensor, wherein the first image data represents a center of a staple line; generate a first image based on the image data; display the first image on a monitor coupled to the processor, wherein the first image represents a target corresponding to the center of the staple line; receive a signal from a non-contact sensor, wherein the signal is indicative of a position of a surgical device relative to the center of the staple line; generate a second image based on the position of the surgical device; and display the second image on the monitor, wherein the second image represents the position of the surgical device along a projected path of the surgical device toward the center of the staple line.

Various additional aspects of the subject matter described herein are set out in the following numbered examples:

Example 1: An interactive control unit, comprising: an interactive touchscreen display; an interface configured to couple the control unit to a surgical hub; a processor; and a memory coupled to the processor, the memory storing instructions executable by the processor to: receive input commands from the interactive touchscreen display located inside a sterile field; and transmit the input commands to the surgical hub to control devices coupled to the surgical hub located outside the sterile field.

Example 2: The interactive control unit of Example 1, wherein the processor is configured to receive an image array from a scanning device and display the image on the interactive touchscreen display.

Example 3: The interactive control unit of any one of Examples 1-2, wherein the processor is configured to display on the interactive touchscreen display an image of a virtual anatomy based on the received image array.

Example 4: The interactive control unit of any one of Examples 1-3, wherein the processor is configured to receive an image array from a laser Doppler scanning device.

Example 5: The interactive control unit of any one of Examples 1-4, wherein the processor is configured to re-configure wireless devices coupled to the surgical hub from control inputs received via the interactive touchscreen display.

Example 6: The interactive control unit of any one of Examples 1-5, wherein the interactive touchscreen display comprises multiple input and output zones.

Example 7: An interactive control unit, comprising: an interactive touchscreen display; an interface configured to couple the control unit to a first surgical hub; a processor; and a memory coupled to the processor, the memory storing instructions executable by the processor to: receive input commands from the interactive touchscreen display located inside a sterile field; transmit the input commands to the first surgical hub to control devices coupled to the first surgical hub located outside the sterile field; receive a consult request from a second surgical hub; and configure a portion of the interactive touchscreen display to display information received from the second surgical hub after receiving the consult request.

Example 8: The interactive control unit of Example 7, wherein the processor is configured to temporarily store data associated with the interactive touchscreen display.

Example 9: The interactive control unit of any one of Examples 7-8, wherein the processor is configured to back up the data in time.

Example 10: The interactive control unit of any one of Examples 7-9, wherein the processor is configured to view the information received from the second surgical hub.

Example 11: The interactive control unit of any one of Examples 7-10, wherein the processor is configured to delete the information received from the second surgical hub.

Example 12: The interactive control unit of any one of Examples 7-11, wherein the processor is configured to return control to the interactive surgical touchscreen in the first surgical hub.

Example 13: An interactive control unit, comprising: an interactive touchscreen display; an interface configured to couple the control unit to a surgical hub; and a control circuit to: receive input commands from the interactive touchscreen display located inside a sterile field; and transmit the input commands to the surgical hub to control devices coupled to the surgical hub located outside the sterile field.

Example 14: The interactive control unit of Example 13, wherein the control circuit is configured to receive an image array from a scanning device and display the image on the interactive touchscreen display.

Example 15: The interactive control unit of any one of Examples 13-14, wherein the control circuit is configured to display on the interactive touchscreen display an image of a virtual anatomy based on the received image array.

Example 16: The interactive control unit of any one of Examples 13-15, wherein the control circuit is configured to receive an image array from a laser Doppler scanning device.

Example 17: The interactive control unit of any one of Examples 13-16, wherein the control circuit is configured to re-configure wireless devices coupled to the surgical hub from control inputs received via the interactive touchscreen display.

Example 18: The interactive control unit of any one of Examples 13-17, wherein the interactive touchscreen display comprises multiple input and output zones.

Various additional aspects of the subject matter described herein are set out in the following numbered examples:

Example 1: A surgical hub for use with a surgical instrument configured to deliver therapeutic energy to tissue at a surgical site of a surgical procedure, wherein the surgical hub comprises: a hub enclosure, comprising a docking station including a docking port comprising data and power contacts; and a combo generator module removably retainable in the docking station, wherein the combo generator module comprises: an ultrasonic energy generator component; a radio frequency (RF) energy generator component; a smoke evacuation component; a connection port, wherein at least one of the ultrasonic energy generator component and the radio frequency (RF) generator component is couplable to the surgical instrument through the connection port; and at least one smoke evacuation component configured to evacuate smoke generated by an application of therapeutic energy to the tissue by the surgical instrument.

Example 2: The surgical hub of Example 1, wherein the docking station is a first docking station, wherein the docking port is a first docking port, and wherein the hub enclosure comprises a second docking station comprising a second docking port that has data and power contacts.

Example 3: The surgical hub of Example 2, further comprising a suction and irrigation module removably retainable in the second docking station.

Example 4: The surgical hub of Example 3, wherein the combo generator module comprises a third docking port connectable to the first docking port of the first docking station.

Example 5: The surgical hub of Example 4, wherein the suction and irrigation module comprises a fourth docking port connectable to the second docking port of the second docking station.

Example 6: The surgical hub of Example 5, wherein the hub enclosure comprises a communication link between the second docking port and the first docking port.

Example 7: The surgical hub of any of Examples 1-6, wherein the combo generator module comprises a fluid line extendable to the remote surgical site for passing the smoke evacuated from the remote surgical site to the combo generator module.

Example 8: The surgical hub of any one of Examples 1-7, wherein the docking station comprises brackets configured to slidably receive and guide the combo generator module into a working connection with the power and data contacts of the docking port.

Example 9: The surgical hub of any one of Examples 1-8, wherein the combo generator module comprises side brackets configured to movably engage the brackets of the docking station.

Example 10: A modular surgical hub for use with a surgical instrument configured to deliver therapeutic energy to tissue at a surgical site of a surgical procedure, wherein the modular surgical enclosure comprises: a first energy-generator module configured to generate a first therapeutic energy for application to the tissue; a first docking station comprising a first docking port that includes first data and power contacts, wherein the first energy-generator module is slidably movable into an electrical engagement with the first data and power contacts, and wherein the first energy-generator module is slidably movable out of the electrical engagement with the first data and power contacts; a second energy-generator module configured to generate a second therapeutic energy, different than the first therapeutic energy, for application to the tissue; a second docking station comprising a second docking port that includes second data and power contacts, wherein the second energy-generator module is slidably movable into an electrical engagement with the second data and power contacts, and wherein the second energy-generator module is slidably movable out of the electrical engagement with the second data and power contacts; and a communication bus between the first docking port and the second docking port configured to facilitate communication between the first energy-generator module and the second energy-generator module.

Example 11: The modular surgical hub of Example 10, wherein the first docking station comprises brackets configured to slidably receive and guide the first energy-generator module into the electrical engagement with the first data and power contacts.

Example 12: The modular surgical hub of Example 11, wherein the second docking station comprises brackets configured to slidably receive and guide the second energy-generator module into the electrical engagement with the second data and power contacts.

Example 13: The modular surgical hub of any one of Examples 10-12, wherein the first therapeutic energy is an ultrasonic energy.

Example 14: The modular surgical hub of any one of Exampled 10-12, wherein the second therapeutic energy is a radio frequency (RF) energy.

Example 15: The modular surgical hub of any one of Examples 10-14, further comprising a smoke evacuation module configured to evacuate smoke generated at the remote surgical site by application of the first therapeutic energy to the tissue.

Example 16: The modular surgical hub of Example 15, further comprising a third docking station comprising a third docking port that includes third data and power contacts.

Example 17: The modular surgical hub of Example 16, further comprising a suction and irrigation module slidably movable into an electrical engagement with the third data and power contacts, and wherein the suction and irrigation module is slidably movable out of the electrical engagement with the third data and power contacts.

Example 18: A surgical hub for use with a surgical instrument configured to deliver therapeutic energy to tissue at a surgical site of a surgical procedure, wherein the surgical hub comprises: a hub enclosure, comprising docking stations including docking ports comprising data and power contacts; a combo generator module slidably receivable in a first of the docking stations, wherein the combo generator module comprises: an ultrasonic energy generator component; a radio frequency (RF) energy generator component; and a connection port, wherein at least one of the ultrasonic energy generator component and the radio frequency (RF) generator component is couplable to the surgical instrument through the connection port; a smoke evacuation module slidably receivable in a second one of the docking stations, wherein the smoke evacuation module is configured to evacuate smoke generated by an application of the therapeutic energy to the tissue by the surgical instrument; a processing module slidably receivable in a third one of the docking stations; a memory module slidably receivable in a fourth one of the docking stations; and an operating-room mapping module slidably receivable in a fifth one of the docking stations.

Example 19: The surgical hub of Example 18, wherein the docking stations comprise brackets configured to slidably guide the modules into electrical engagements with the power and data contacts of the docking ports.

Example 20: The surgical hub of any one of Examples 18-19, comprising a display.

Various additional aspects of the subject matter described herein are set out in the following numbered examples:

Example 1: A surgical image acquisition system comprising: a plurality of illumination sources wherein each illumination source is configured to emit light having a specified central wavelength; a light sensor configured to receive a portion of the light reflected from a tissue sample when illuminated by the one or more of the plurality of illumination sources; and a computing system, wherein the computing system is configured to: receive data from the light sensor when the tissue sample is illuminated by each of the plurality of illumination sources; determine a depth location of a structure within the tissue sample based on the data received by the light sensor when the tissue sample is illuminated by each of the plurality of illumination sources; and calculate visualization data regarding the structure and the depth location of the structure, wherein the visualization data have a data format that may be used by a display system, and wherein the structure comprises one or more vascular tissues.

Example 2: The surgical image acquisition system of any one of Example 1, wherein the plurality of illumination sources comprises an illumination source having a central wavelength in a range between 635 nm and 660 nm, inclusive.

Example 3: The surgical image acquisition system of any one of Examples 1-2, wherein the plurality of illumination sources comprises an illumination source having a central wavelength in a range between 750 nm and 3000 nm.

Example 4: The surgical image acquisition system of any one of Examples 1-3, wherein the plurality of illumination sources comprises an illumination source configured to emit a broad spectral range of illumination.

Example 5: The surgical image acquisition system of any one of Examples 1-4, wherein the plurality of illumination sources comprises a laser illumination source.

Example 6: A surgical image acquisition system comprising: a processor; and a memory coupled to the processor, the memory storing instructions executable by the processor to: control the operation of a plurality of illumination sources of a tissue sample wherein each illumination source is configured to emit light having a specified central wavelength; receive data from a light sensor when the tissue sample is illuminated by each of the plurality of illumination sources; determine a depth location of a structure within the tissue sample based on the data received by the light sensor when the tissue sample is illuminated by each of the plurality of illumination sources; and calculate visualization data regarding the structure and the depth location of the structure, wherein the visualization data have a data format that may be used by a display system, and wherein the structure comprises one or more vascular tissues.

Example 7: The surgical image acquisition system of any one of Example 6, wherein the instruction, executable by the processor, to determine a depth location of a structure within the tissue sample based on the data received by the light sensor when the tissue sample is illuminated by each of the plurality of illumination sources comprises an instruction to determine a depth location of a structure within the tissue sample based on a central wavelength of light emitted by at least one of the plurality of illumination sources.

Example 8: The surgical image acquisition system of any one of Examples 6-7, wherein the instructions, executable by the processor, further comprise an instruction to calculate a flow of a material through the one or more vascular tissues.

Example 9: The surgical image acquisition system of any one of Example 8, wherein the instruction, executable by the processor, to calculate visualization data regarding the structure and the depth location of the structure further includes an instruction, executable by the processor, to calculate visualization data including data representative of the flow of material through the one or more vascular tissues.

Example 10: A surgical image acquisition system comprising: a control circuit configured to: control the operation of a plurality of illumination sources of a tissue sample wherein each illumination source is configured to emit light having a specified central wavelength; receive data from a light sensor when the tissue sample is illuminated by each of the plurality of illumination sources; determine a depth location of a structure within the tissue sample based on the data received by the light sensor when the tissue sample is illuminated by each of the plurality of illumination sources; and calculate visualization data regarding the structure and the depth location of the structure, wherein the visualization data have a data format that may be used by a display system, and wherein the structure comprises one or more vascular tissues.

Example 11: The surgical image acquisition system of any one of Example 10, wherein the control circuit configured to control the operation of a plurality of illumination sources of a tissue sample comprises a control circuit configured to sequentially actuate each of the plurality of illumination sources to illuminate the tissue sample.

Example 12: The surgical image acquisition system of any one of Examples 10-11, wherein the control circuit configured to determine a depth location of a structure within the tissue sample comprises a control circuit configured to determine the depth location of the structure based on a penetration depth of illumination sourced by each of the plurality of illumination sources.

Example 13: The surgical image acquisition system of any one of Example 12, wherein the structure comprises a surface structure within the tissue sample.

Example 14: The surgical image acquisition system of any one of Examples 10-13, wherein the control circuit configured to control the operation of a plurality of illumination sources of a tissue sample comprises a control circuit configured to operate at least one of a red light illumination source, a green light illumination source, and a blue light illumination source.

Example 15: The surgical image acquisition system of any one of Examples 10-14, wherein the control circuit configured to control the operation of a plurality of illumination sources of a tissue sample comprises a control circuit configured to operate at least one of an infrared light illumination source and an ultraviolet light illumination source.

Example 16: The surgical image acquisition system of any one of Examples 10-15, wherein the control circuit is further configured to determine a flow of material through the one or more vascular tissues.

Example 17: The surgical image acquisition system of any one of Example 16, wherein the control circuit configured to determine a flow of material through the one or more vascular tissues comprises a control circuit configured to analyze the data received from the light sensor when the tissue sample is illuminated by each of the plurality of illumination sources for a Doppler shift in wavelength of light emitted by each of the plurality of illumination sources.

Example 18: A non-transitory computer readable medium storing computer readable instructions which, when executed, causes a machine to: control the operation of a plurality of illumination sources of a tissue sample wherein each illumination source is configured to emit light having a specified central wavelength; receive data from a light sensor when the tissue sample is illuminated by each of the plurality of illumination sources; determine a depth location of a structure within the tissue sample based on the data received by the light sensor when the tissue sample is illuminated by each of the plurality of illumination sources; and calculate visualization data regarding the structure and the depth location of the structure, wherein the visualization data have a data format that may be used by a display system, and wherein the structure comprises one or more vascular tissues.

Example 19: The non-transitory computer readable medium of any one of Example 18, wherein the computer readable instructions, when executed, further cause the machine to: control the operation of an additional illumination source wherein the additional illumination source is a white light source; and receive data from the light sensor when the tissue sample is illuminated by the white light source.

Example 20: The non-transitory computer readable medium of any one of Example 19, wherein the computer readable instructions, when executed, that cause the machine to calculate visualization data regarding the structure and the depth location of the structure further cause the machine to calculate visualization data based on the data received from the light sensor when the tissue sample is illuminated by the white light source.

Various additional aspects of the subject matter described herein are set out in the following numbered examples:

Example 1: A surgical image acquisition system comprising: a plurality of illumination sources wherein each illumination source is configured to emit light having a specified central wavelength; a light sensor configured to receive a portion of the light reflected from a tissue sample when illuminated by the one or more of the plurality of illumination sources; and a computing system, wherein the computing system is configured to: receive data from the light sensor when the tissue sample is illuminated by each of the plurality of illumination sources; calculate structural data related to a characteristic of a structure within the tissue sample based on the data received by the light sensor when the tissue sample is illuminated by each of the illumination sources; and transmit the structural data related to the characteristic of the structure to be received by a smart surgical device, wherein the characteristic of the structure is a surface characteristic or a structure composition.

Example 2: The surgical image acquisition system of any one of Example 1, wherein the plurality of illumination sources comprises at least one of a red light illumination source, a green light illumination source, and a blue light illumination source.

Example 3: The surgical image acquisition system of any one of Examples 1-2, wherein the plurality of illumination sources comprises at least one of an infrared light illumination source and an ultraviolet light illumination source.

Example 4: The surgical image acquisition system of any one of Examples 1-3, wherein the computing system, configured to calculate structural data related to a characteristic of a structure within the tissue, comprises a computing system configured to calculate structural data related to a composition of a structure within the tissue.

Example 5: The surgical image acquisition system of any one of Examples 1-4, wherein the computing system, configured to calculate structural data related to a characteristic of a structure within the tissue, comprises a computing system configured to calculate structural data related to a surface roughness of a structure within the tissue.

Example 6: A surgical image acquisition system comprising: a processor; and a memory coupled to the processor, the memory storing instructions executable by the processor to: control the operation of a plurality of illumination sources of a tissue sample wherein each illumination source is configured to emit light having a specified central wavelength; receive data from the light sensor when the tissue sample is illuminated by each of the plurality of illumination sources; calculate structural data related to a characteristic of a structure within the tissue sample based on the data received by the light sensor when the tissue sample is illuminated by each of the illumination sources; and transmit the structural data related to the characteristic of the structure to be received by a smart surgical device, wherein the characteristic of the structure is a surface characteristic or a structure composition.

Example 7: The surgical image acquisition system of any one of Example 6, wherein the instructions executable by the processor to control the operation of a plurality of illumination sources comprise one or more instructions to illuminate the tissue sample sequentially by each of the plurality of illumination sources.

Example 8: The surgical image acquisition system of any one of Examples 6-Example 7 wherein the instructions executable by the processor to calculate structural data related to a characteristic of a structure within the tissue sample based on the data received by the light sensor comprise one or more instructions to calculate structural data related to a characteristic of a structure within the tissue sample based on a phase shift in the illumination reflected by the tissue sample.

Example 9: The surgical image acquisition system of any one of Examples 6-8, wherein the structure composition comprises a relative composition of collagen and elastin in a tissue.

Example 10: The surgical image acquisition system of any one of Examples 6-9, wherein the structure composition comprises an amount of hydration of a tissue.

Example 11: A surgical image acquisition system comprising: a control circuit configured to: control the operation of a plurality of illumination sources of a tissue sample wherein each illumination source is configured to emit light having a specified central wavelength; receive data from the light sensor when the tissue sample is illuminated by each of the plurality of illumination sources; calculate structural data related to a characteristic of a structure within the tissue sample based on the data received by the light sensor when the tissue sample is illuminated by each of the illumination sources; and transmit the structural data related to the characteristic of the structure to be received by a smart surgical device, wherein the characteristic of the structure is a surface characteristic or a structure composition.

Example 12: The surgical image acquisition system of any one of Example 11, wherein the control circuit is configured to transmit the structural data related to the characteristic of the structure to be received by a smart surgical device wherein the smart surgical device is a smart surgical stapler.

Example 13: The surgical image acquisition system of any one of Example 12, wherein the control circuit is further configured to transmit data related to an anvil pressure based on the characteristic of the structure to be received by the smart surgical stapler.

Example 14: The surgical image acquisition system of any one of Examples 11-13, wherein the control circuit is configured to transmit the structural data related to the characteristic of the structure to be received by a smart surgical device wherein the smart surgical device is a smart surgical RF sealing device.

Example 15: The surgical image acquisition system of any one of Example 14, wherein the control circuit is further configured to transmit data related to an amount of RF power based on the characteristic of the structure to be received by the smart RF sealing device.

Example 16: The surgical image acquisition system of any one of Examples 11-15, wherein the control circuit is configured to transmit the structural data related to the characteristic of the structure to be received by a smart surgical device wherein the smart surgical device is a smart ultrasound cutting device.

Example 17: The surgical image acquisition system of any one of Example 16, wherein the control circuit is further configured to transmit data related to an amount of power provided to an ultrasonic transducer or a driving frequency of the ultrasonic transducer based on the characteristic of the structure to be received by the ultrasound cutting device.

Example 18: A non-transitory computer readable medium storing computer readable instructions which, when executed, causes a machine to: control the operation of a plurality of illumination sources of a tissue sample wherein each illumination source is configured to emit light having a specified central wavelength; receive data from the light sensor when the tissue sample is illuminated by each of the plurality of illumination sources; calculate structural data related to a characteristic of a structure within the tissue sample based on the data received by the light sensor when the tissue sample is illuminated by each of the illumination sources; and transmit the structural data related to the characteristic of the structure to be received by a smart surgical device, wherein the characteristic of the structure is a surface characteristic or a structure composition.

Various additional aspects of the subject matter described herein are set out in the following numbered examples:

Example 1: A minimally invasive image acquisition system comprising: a plurality of illumination sources wherein each illumination source is configured to emit light having a specified central wavelength; a first light sensing element having a first field of view and configured to receive illumination reflected from a first portion of a surgical site when the first portion of the surgical site is illuminated by at least one of the plurality of illumination sources; a second light sensing element having a second field of view and configured to receive illumination reflected from a second portion of the surgical site when the second portion of the surgical site is illuminated by at least one of the plurality of illumination sources, wherein the second field of view overlaps at least a portion of the first field of view; and a computing system, wherein the computing system is configured to: receive data from the first light sensing element, receive data from the second light sensing element, compute imaging data based on the data received from the first light sensing element and the data received from the second light sensing element, and transmit the imaging data for receipt by a display system.

Example 2: The minimally invasive image acquisition system of any one of Example 1, wherein the first field of view has a first angle and the second field of view has a second angle and the first angle is the same as the second angle.

Example 3: The minimally invasive image acquisition system of any one of Examples 1-2, wherein the first field of view has a first angle and the second field of view has a second angle and the first angle differs from the second angle.

Example 4: The minimally invasive image acquisition system of any one of Examples 1-3, wherein the first light sensing element has an optical component configured to adjust the first field of view.

Example 5: The minimally invasive image acquisition system of any one of Examples 1-4, wherein the second light sensing element has an optical component configured to adjust the second field of view.

Example 6: The minimally invasive image acquisition system of any one of Examples 1-5, wherein the second field of view overlaps all of the first field of view.

Example 7: The minimally invasive image acquisition system of any one of Examples 1-6, wherein the first field of view is completely enclosed by the second field of view.

Example 8: The minimally invasive image acquisition system of any one of Examples 1-7, wherein the first light sensing element and the second light sensing element are at least partially disposed within an elongated camera probe.

Example 9: The minimally invasive image acquisition system of any one of Examples 1-8, wherein each of the plurality of illumination source is configured to emit light having a specified central wavelength within a visible spectrum.

Example 10: The minimally invasive image acquisition system of any one of Examples 1-9, wherein at least one of the plurality of illumination source is configured to emit light having a specified central wavelength outside of a visible spectrum.

Example 11: The minimally invasive image acquisition system of any one of Example 10, wherein the specified central wavelength outside of the visible spectrum is within an ultra-violet range.

Example 12: The minimally invasive image acquisition system of any one of Examples 10-11, wherein the specified central wavelength outside of the visible spectrum is within an infrared range.

Example 13: The minimally invasive image acquisition system of any one of Examples 1-12, wherein the computing system configured to compute imaging data based on the data received from the first light sensing element and the data received from the second light sensing element comprises a computing system configured to perform a first data analysis on the data received from the first light sensing element and a second data analysis on the data received from the second light sensing element.

Example 14: The minimally invasive image acquisition system of any one of Example 13, wherein the first data analysis differs from the second data analysis.

Example 15: A minimally invasive image acquisition system comprising: a processor; and a memory coupled to the processor, the memory storing instructions executable by the processor to: control an operation of a plurality of illumination sources of a tissue sample wherein each illumination source is configured to emit light having a specified central wavelength; receive, from a first light sensing element, first data related to illumination reflected from a first portion of a surgical site when the first portion of the surgical site is illuminated by at least one of the plurality of illumination source, receive, from a second light sensing element, second data related to illumination reflected from a second portion of the surgical site when the second portion of the surgical site is illuminated by at least one of the plurality of illumination sources, wherein the second field of view overlaps at least a portion of the first field of view, compute imaging data based on the first data received from the first light sensing element and the second data received from the second light sensing element, and transmit the imaging data for receipt by a display system.

Example 16: The minimally invasive image acquisition system of any one of Example 15, wherein the memory coupled to the processor further stores instructions executable by the processor to receive, from a surgical instrument, operational data related to a function or status of the surgical instrument.

Example 17: The minimally invasive image acquisition system of any one of Example 16, wherein the memory coupled to the processor further stores instructions executable by the processor to compute imaging data based on the first data received from the first light sensing element, the second data received from the second light sensing element, and the operational data related to the function or status of the surgical instrument.

Example 18: A minimally invasive image acquisition system comprising: a control circuit configured to: control an operation of a plurality of illumination sources of a tissue sample wherein each illumination source is configured to emit light having a specified central wavelength; receive, from a first light sensing element, first data related to illumination reflected from a first portion of a surgical site when the first portion of the surgical site is illuminated by at least one of the plurality of illumination source, receive, from a second light sensing element, second data related to illumination reflected from a second portion of the surgical site when the second portion of the surgical site is illuminated by at least one of the plurality of illumination sources, wherein the second field of view overlaps at least a portion of the first field of view, compute imaging data based on the first data received from the first light sensing element and the second data received from the second light sensing element, and transmit the imaging data for receipt by a display system.

Example 19: A non-transitory computer readable medium storing computer readable instructions which, when executed, causes a machine to: control an operation of a plurality of illumination sources of a tissue sample wherein each illumination source is configured to emit light having a specified central wavelength; receive, from a first light sensing element, first data related to illumination reflected from a first portion of a surgical site when the first portion of the surgical site is illuminated by at least one of the plurality of illumination source, receive, from a second light sensing element, second data related to illumination reflected from a second portion of the surgical site when the second portion of the surgical site is illuminated by at least one of the plurality of illumination sources, wherein the second field of view overlaps at least a portion of the first field of view, compute imaging data based on the first data received from the first light sensing element and the second data received from the second light sensing element, and transmit the imaging data for receipt by a display system.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skilled in the art in light of this disclosure. In addition, those skilled in the art will appreciate that the mechanisms of the subject matter described herein are capable of being distributed as one or more program products in a variety of forms and that an illustrative form of the subject matter described herein applies regardless of the particular type of signal-bearing medium used to actually carry out the distribution.

Instructions used to program logic to perform various disclosed aspects can be stored within a memory in the system, such as DRAM, cache, flash memory, or other storage. Furthermore, the instructions can be distributed via a network or by way of other computer-readable media. Thus a machine-readable medium may include any mechanism for storing or transmitting information in a form readable by a machine (e.g., a computer), but is not limited to, floppy diskettes, optical disks, CD-ROMs, magnetooptical disks, ROM, RAM, EPROM, EEPROM, magnetic or optical cards, flash memory, or tangible, machine-readable storage used in the transmission of information over the Internet via electrical, optical, acoustical, or other forms of propagated signals (e.g., carrier waves, infrared signals, digital signals). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, DSP, PLD, programmable logic array (PLA), or FPGA), state machine circuitry, firmware that stores instructions executed by programmable circuitry, and any combination thereof. The control circuit may, collectively or individually, be embodied as circuitry that forms part of a larger system, for example, an integrated circuit, an application-specific integrated circuit (ASIC), a system on-chip (SoC), desktop computers, laptop computers, tablet computers, servers, smart phones, etc. Accordingly, as used herein, "control circuit" includes, but is not limited to, electrical circuitry having at least one discrete electrical circuit, electrical circuitry having at least one integrated circuit, electrical circuitry having at least one application-specific integrated circuit, electrical circuitry forming a general-purpose computing device configured by a computer program (e.g., a general-purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein the term "logic" may refer to an app, software, firmware, and/or circuitry configured to perform any of the aforementioned operations. Software may be embodied as a software package, code, instructions, instruction sets, and/or data recorded on non-transitory computer-readable storage medium. Firmware may be embodied as code, instructions, instruction sets, and/or data that are hard-coded (e.g., non-volatile) in memory devices.

As used in any aspect herein, the terms "component," "system," "module," and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet-switched network. The communication devices may be capable of communicating with each other using a selected packet-switched network communications protocol. One example communications protocol may include an Ethernet communications protocol which may be capable permitting communication using a Transmission Control Protocol/IP. The Ethernet protocol may comply or be compatible with the Ethernet standard published by the Institute of Electrical and Electronics Engineers (IEEE) titled "IEEE 802.3 Standard." published in December 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum, titled "ATM-MPLS Network Interworking 2.0." published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining." "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission, or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components, inactive-state components, and/or standby-state components, unless context requires otherwise.

The terms "proximal" and "distal" are used herein with reference to a clinician manipulating the handle portion of the surgical instrument. The term "proximal" refers to the portion closest to the clinician, and the term "distal" refers to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims), are generally intended as "open" terms (e.g., the term "including" should be interpreted as "including, but not limited to"; the term "having" should be interpreted as "having at least"; the term "includes" should be interpreted as "includes, but is not limited to"). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"): the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations." without other modifiers, typically means at least two recitations or two or more recitations). Furthermore, in those instances where a convention analogous to "at least one of A, B, and C, etc.," is used, in general, such a construction is intended in the sense that one having skill in the art would understand the convention (e.g., "a system having at least one of A, B, and C" would include, but not be limited to, systems that have A alone, B alone, C alone, A and B together, A and C together, B and C together, and/or A, B, and C together). In those instances where a convention analogous to "at least one of A, B, or C, etc." is used, in general, such a construction is intended in the sense that one having skill in the art would understand the convention (e.g., "a system having at least one of A, B, or C" would include, but not be limited to, systems that have A alone. B alone. C alone. A and B together, A and C together, B and C together, and/or A, B, and C together). It will be further understood by those within the art that typically a disjunctive word and/or phrase presenting two or more alternative terms, whether in the description, claims, or drawings, should be understood to contemplate the possibilities of including one of the terms, either of the terms, or both terms, unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures, or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials are not inconsistent herewith. As such, and to the extent necessary, the disclosure as explicitly set forth herein supersedes any conflicting material incorporated herein by reference. Any material, or portion thereof, that is said to be incorporated by reference herein but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:
1. A surgical system comprising:
 a plurality of modular surgical devices; and
 a surgical hub comprising:
  a control circuit configured to:
   determine bounds of an operating room in which the surgical hub is located;
   adjust a wireless pairing distance of the surgical hub based on the bounds of the operating room;
   detect each modular surgical device of the plurality of modular surgical devices;
   determine which of the plurality of modular surgical devices are within the bounds of the operating room;
   wirelessly pair the surgical hub with each modular surgical device determined to be within the bounds of the operating room, wherein the pairing establishes at least one of a communication link or a control link between the surgical hub and each wirelessly paired modular surgical device, and wherein each wirelessly paired modular surgical device is assigned, by the surgical hub, a unique identifier; and
   determine a location of each wirelessly paired modular surgical device.

2. The surgical system of claim 1, wherein at least one of the plurality of modular surgical devices comprises a medical imaging device wirelessly paired with the surgical hub, and wherein the surgical hub further comprises an imaging module configured to:

receive, from the medical imaging device, a livestream of a surgical procedure;
capture at least one image frame from the livestream of the surgical procedure;
extract data from the at least one image frame; and
differentiate between a plurality of surgical steps performed by at least one modular surgical device wirelessly paired with the surgical hub based on the data extracted from the at least one image frame.

3. The surgical system of claim 1, wherein the surgical hub further comprises a room-mapping module comprising a plurality of non-contact sensors, and wherein determining the bounds of the operating room comprises assessing, via the plurality of non-contact sensors, a distance between the surgical hub and one or more walls of the operating room.

4. The surgical system of claim 1, wherein the control circuit is further configured to:
reevaluate, on a periodic basis, the bounds of the operating room; and
detect a movement of the surgical hub based on the reevaluation.

5. The surgical system of claim 1, wherein the control circuit is further configured to detect a triggering event and reevaluate the bounds of the operating room based on the triggering event.

6. The surgical system of claim 5, wherein the control circuit is further configured to continuously monitor each modular surgical device previously determined to be within the operating room, and wherein the triggering event comprises detecting a change in modular surgical devices previously determined to be within the bounds of the operating room.

7. The surgical system of claim 6, wherein the change in modular surgical devices previously determined to be within the bounds of the operating room comprises at least one of a detection of a new modular surgical device not previously determined to be within the bounds of the operating room or a detection of a disappearance, disconnection, or un-pairing of a modular surgical device that was previously determined to be within the bounds of the operating room.

8. A surgical system comprising:
a plurality of modular surgical devices; and
a surgical hub comprising:
a control circuit configured to:
determine bounds of an operating room in which the surgical hub is located;
detect each modular surgical device of the plurality of modular surgical devices;
determine which of the plurality of modular surgical devices are within the bounds of the operating room;
wirelessly pair the surgical hub with each modular surgical device within the bounds of the operating room, wherein the wireless pairing establishes at least one of a communication link or a control link between the surgical hub and each wirelessly paired modular surgical device;
receive perioperative data from a first wirelessly paired modular surgical device;
derive contextual information from the received perioperative data;
determine one or more control adjustments for a second wirelessly paired modular surgical device based on the derived contextual information; and
control the second wirelessly paired modular surgical device based on the one or more control adjustments.

9. The surgical system of claim 8, wherein at least one of the plurality of modular surgical devices comprises a medical imaging device wirelessly paired with the surgical hub, and wherein the surgical hub further comprises an imaging module configured to:
receive, from the medical imaging device, a livestream of a surgical procedure;
capture at least one image frame from the livestream of the surgical procedure;
extract data from the at least one image frame; and
differentiate between a plurality of surgical steps performed by at least one modular surgical device wirelessly paired with the surgical hub based on the data extracted from the at least one image frame.

10. The surgical system of claim 8, wherein the surgical hub further comprises a room-mapping module comprising a plurality of non-contact sensors, and wherein determining the bounds of the operating room comprises assessing, via the plurality of non-contact sensors, a distance between the surgical hub and one or more walls of the operating room.

11. The surgical system of claim 8, wherein the control circuit is further configured to:
reevaluate, on a periodic basis, the bounds of the operating room; and
detect a movement of the surgical hub based on the reevaluation.

12. The surgical system of claim 8, wherein the control circuit is further configured to detect a triggering event and reevaluate the bounds of the operating room based on the triggering event.

13. The surgical system of claim 12, wherein the control circuit is further configured to continuously monitor each modular surgical device previously determined to be within the operating room, and wherein the triggering event comprises detecting a change in modular surgical devices previously determined to be within the bounds of the operating room.

14. The surgical system of claim 13, wherein the change in modular surgical devices previously determined to be within the bounds of the operating room comprises at least one of a detection of a new modular surgical device not previously determined to be within the bounds of the operating room or a detection of a disappearance, disconnection, or un-pairing of a modular surgical device that was previously determined to be within the bounds of the operating room.

15. A method comprising:
determining, by a control circuit of a surgical hub of a surgical system, bounds of an operating room in which the surgical hub is located;
detecting, by the control circuit, each modular surgical device of a plurality of modular surgical devices of the surgical system;
determining, by the control circuit, which of the plurality of modular surgical devices are within the bounds of the operating room;
wirelessly pairing, by the control circuit, each of the modular surgical devices within the bounds of the operating room, wherein the wireless pairing establishes at least one of a communication link or a control link between the surgical hub and each wirelessly paired modular surgical device;
receiving, by the control circuit, perioperative data from a first wirelessly paired modular surgical device;
deriving, by the control circuit, contextual information from the received perioperative data;

determining, by the control circuit, one or more control adjustments for a second wirelessly paired modular surgical device based on the derived contextual information; and controlling, by the control circuit, the second wirelessly paired modular surgical device based on the one or more control adjustments.

16. The method of claim 15, further comprising:

receiving, by an imaging module of the surgical hub, a livestream of a surgical procedure from a wirelessly paired medical imaging device;

capturing, by the imaging module, at least one image frame from the livestream of the surgical procedure;

extracting, by the imaging module, data from the at least one image frame; and differentiating, by the imaging module, between a plurality of surgical steps performed by at least one modular surgical device wirelessly paired with the surgical hub based on the data extracted from the at least one image frame.

17. The method of claim 15, further comprising:

determining, by a room-mapping module of the surgical hub, the bounds of the operating room, wherein the room-mapping module comprises a plurality of non-contact sensors, and wherein the determining the bounds of the operating room comprises assessing, by the plurality of non-contact sensors, a distance between the surgical hub and one or more walls of the operating room.

18. The method of claim 15, further comprising:

reevaluating, by the control circuit, the bounds of the operating room on a periodic basis; and detecting, by the control circuit, a movement of the surgical hub based on the reevaluating.

19. The method of claim 15, further comprising:

detecting, by the control circuit, a triggering event; and reevaluating, by the control circuit, the bounds of the operating room based on the triggering event.

20. The method of claim 19, further comprising:

continuously monitoring, by the control circuit, each modular surgical device previously determined to be within the operating room; and detecting, by the control circuit, a change in modular surgical devices previously determined to be within the bounds of the operating room.

\* \* \* \* \*